(12) United States Patent
Ruminski et al.

(10) Patent No.: US 9,085,606 B2
(45) Date of Patent: Jul. 21, 2015

(54) BETA AMINO ACID DERIVATIVES AS INTEGRIN ANTAGONISTS

(71) Applicant: Saint Louis University, St. Louis, MO (US)

(72) Inventors: Peter Ruminski, Wildwood, MO (US); David Griggs, Ballwin, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 13/944,599

(22) Filed: Jul. 17, 2013

(65) Prior Publication Data

US 2014/0038910 A1 Feb. 6, 2014

Related U.S. Application Data

(60) Provisional application No. 61/673,058, filed on Jul. 18, 2012, provisional application No. 61/764,443, filed on Feb. 13, 2013.

(51) Int. Cl.
| | |
|---|---|
| C07K 5/06 | (2006.01) |
| C07D 403/12 | (2006.01) |
| C07D 309/06 | (2006.01) |
| C07D 309/08 | (2006.01) |
| C07C 279/18 | (2006.01) |
| C07D 233/50 | (2006.01) |
| C07D 401/12 | (2006.01) |
| C07D 239/16 | (2006.01) |
| C07D 405/12 | (2006.01) |
| C07D 211/72 | (2006.01) |

(52) U.S. Cl.
CPC ............. *C07K 5/06* (2013.01); *C07C 279/18* (2013.01); *C07D 211/72* (2013.01); *C07D 233/50* (2013.01); *C07D 239/16* (2013.01); *C07D 309/06* (2013.01); *C07D 309/08* (2013.01); *C07D 401/12* (2013.01); *C07D 403/12* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 5,602,155 | A | 2/1997 | Ruminski |
| 5,639,765 | A | 6/1997 | Ruminski |
| 5,681,820 | A | 10/1997 | Ruminski |
| 5,773,646 | A | 6/1998 | Chandrakumar et al. |
| 5,798,370 | A | 8/1998 | Ruminski |
| 5,840,961 | A | 11/1998 | Behling et al. |
| 5,852,210 | A | 12/1998 | Chen et al. |
| 6,013,651 | A | 1/2000 | Rogers et al. |
| 6,028,223 | A | 2/2000 | Ruminski et al. |
| 6,372,719 | B1 | 4/2002 | Cunningham et al. |
| 6,414,180 | B1 | 7/2002 | Colson et al. |
| 6,689,787 | B1 | 2/2004 | McKearn et al. |
| 6,933,304 | B2 | 8/2005 | Nagarajan et al. |
| 7,119,098 | B2 | 10/2006 | Nagarajan et al. |

FOREIGN PATENT DOCUMENTS

| | | |
|---|---|---|
| EP | 1667668 | 7/2008 |
| WO | WO 96/23771 | 8/1996 |
| WO | WO 97/08145 | 3/1997 |
| WO | WO 97/36859 | 10/1997 |
| WO | WO 97/36860 | 10/1997 |
| WO | WO 97/36862 | 10/1997 |
| WO | WO 99/44994 | 9/1999 |
| WO | WO 99/44996 | 9/1999 |
| WO | WO 99/52896 | 10/1999 |
| WO | WO 00/51686 | 9/2000 |
| WO | WO 2004/060376 | 7/2004 |
| WO | WO 2008/018827 | 2/2008 |
| WO | WO 2010/010184 | 1/2010 |

(Continued)

OTHER PUBLICATIONS

Abdollahi et al., "Inhibition of alpha(v)beta3 integrin survival signaling enhances antiangiogenic and antitumor effects of radiotherapy," *Clin. Cancer Res.*, 11:6270-6279, 2005.

Adachi et al., "Significance of integrin alpha5 gene expression as a prognostic factor in node-negative non-small cell lung cancer," *Clin. Cancer Res.*, 6(1):96-101, 2000.

Asano et al., "Increased expression of integrin alpha(v)beta3 contributes to the establishment of autocrine TGF-beta signaling in scleroderma fibroblasts," *J. Immunol.*, 175(11):7708-7718, 2005.

(Continued)

*Primary Examiner* — Thomas S Heard
(74) *Attorney, Agent, or Firm* — Parker Highlander PLLC

(57) ABSTRACT

Disclosed herein are novel pharmaceutical agents which are useful as integrin receptor antagonists that mediate the pathologic processes of angiogenesis and fibrosis and as such are useful in pharmaceutical compositions and in methods for treating conditions mediated by these integrins by inhibiting or antagonizing these integrins. The novel pharmaceutical agents include those of the formula:

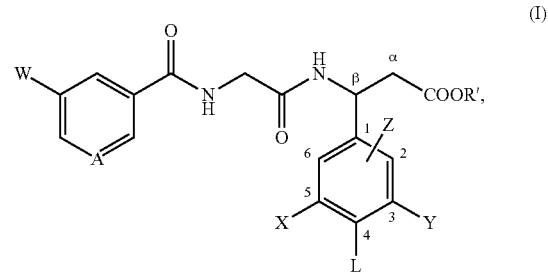

wherein the variables are defined herein. Also provided are pharmaceutical compositions, kits and articles of manufacture comprising such pharmaceutical agents. Methods and intermediates useful for making the pharmaceutical agents and methods of using the pharmaceutical agents are also provided.

18 Claims, No Drawings

(56) References Cited

FOREIGN PATENT DOCUMENTS

| WO | WO 2010/104933 | 9/2010 |
|----|----------------|--------|
| WO | WO 2011/025927 | 3/2011 |
| WO | WO 2012/027322 | 3/2012 |

OTHER PUBLICATIONS

Avraamides et al., "Integrins in angiogenesis and lymphangiogenesis," *Nat. Rev. Cancer*, 8(8):604-617, 2008.
Awasthi et al., "Practical enantioselective synthesis of β-substituted-β-amino esters," *J. Org. Chem.*, 70:5387-5397, 2005.
Babadzhanova et al., "Convenient syntheses of 1,1,1,3,3,3-hexafluoro-2-organyl-propan-2-ols and the corresponding trimethylsilyl ethers," *Tetrahedron*, 61(7):1813-1819, 2005.
Bax et al., "Cell adhesion to fibrillin-1 molecules and microfibrils is mediated by alpha 5 beta 1 and alpha v beta 3 integrins," *J. Biol. Chem.*, 278(36):34605-34616, 2003.
Becker et al., "An expedient synthesis of 3-amino-5-hydroxybenzoic acid and its n-alkyl analogues," *Tetrahedron*, 39:4189-4192, 1983.
Bhaskar et al., "A function blocking anti-mouse integrin alpha5beta1 antibody inhibits angiogenesis and impedes tumor growth in vivo," *J. Transl. Med.*, 5:61, 2007.
Blase et al., "The capacity of human malignant B-lymphocytes to disseminate in SCID mice is correlated with functional expression of the fibronectin receptor alpha 5 beta 1 (CD49e/CD29)," *Int. J. Cancer*, 60(6):860-866, 1995.
Carron et al., "A peptidomimetic antagonist of the integrin avb3 inhibits Leydig cell tumor growth and the development of hypercalcemia of malignancy," *Cancer Res.*, 58:1930-1935, 1998.
Carron et al., "Peptidomimetic antagonists of avb3 inhibit bone resorption by inhibiting osteoclast bone resorptive activity, not osteoclast adhesion to b one," *J. Endocrinol.*, 165:587-598, 2000.
Chai et al., "αv and β1 integrins regulate dynamic compression-induced proteoglycan synthesis in 3D gel culture by distinct complementary pathways," *Osteoarthritis and Cartilage*, 18:249-256, 2009.
Clark, et al., "Pilot Plant Preparation of an αvβ3 Integrin Antagonist. Part 1. Process Research and Development of a (S)-β-Amino Acid Ester Intermediate: Synthesis via a Scalable, Diastereoselective Imino-Reformatsky Reaction," *Organic Process Research & Development*, 8:51-61, 2004.
Clark, et al., "Pilot-Plant Preparation of an αvβ3 Integrin Antagonist. Part 2. Synthesis of N-[2-(5-Hydroxy-4,6-tetrahydropyrimidine)]-3-amino-5-hydroxybenzoic Acid," *Organic Process Research & Development*, 8:571-575, 2004.
Collo, "Endothelial cell integrin alpha5beta1 expression is modulated by cytokines and during migration in vitro," *J. Cell Sci.*, 112(Pt 4):569-578, 1999.
Cue et al., "A nonpeptide integrin antagonist can inhibit epithelial cell ingestion of *Streptococcus pyogenes* by blocking formation of integrin alpha 5beta 1-fibronectin-M1 protein complexes," *Proc Natl Acad Sci USA*, 97(6):2858-2863, 2000.
Danen et al., "Emergence of alpha 5 beta 1 fibronectin- and alpha v beta 3 vitronectin-receptor expression in melanocytic tumour progression," *Histopathology*, 24(3):249-256, 1994.
Database Registry, Chemical Abstracts Service, Database accession No. 773126-23-1, retrieved from STN, 2004.
Database Registry, Chemical Abstracts Service, Database accession No. 682803-43-6, retrieved from STN, 2011.
Database Registry, Chemical Abstracts Service, Database accession No. 1270085-65-8, retrieved from STN, 2011.
Duggan et al., "Ligands to the integrin receptor alphavbeta3," *Expert Opinion on Therapeutic Patents*, 10(9):1367-1383, 2000.
Edward, "Integrins and other adhesion molecules involved in melanocytic tumor progression." *Curr. Opin. Oncol.*, 7(2):185-191, 1995.
Engleman et al., "A peptidomimetic antagonist of the avb3 integrin inhibits bone resorption in vitro and prevents osteoporosis in vivo," *J. Clin. Invest.*, 99:2284-2292, 1997.

Faulconbridge et al., "Preparation of enantiomerically enriched aromatic β-amino acids via enzymatic resolution," *Tetrahedron Lett.*, 41:2679-2681, 2000.
Ferrari et al., "VEGF, a prosurvival factor, acts in concert with TGF-beta1 to induce endothelial cell apoptosis," *Proc Natl Acad Sci USA*, 103(46):17260-17265, 2006.
Gao and Brigstock, "A novel integrin alpha5beta1 binding domain in module 4 of connective tissue growth factor (CCN2/CTGF) promotes adhesion and migration of activated pancreatic stellate cells." *Gut*, 55:856-862, 2006.
Gisch et al., "Enzymatically Activated cycloSal-d4T-monophosphates: The Third Generation of cycloSal-Pronucleotides," *J. Med. Chem.*, 50:1658-1667, 2007.
Gisch et al., "Studies on Enzyme-Cleavable Dialkoxymethyl-cycloSaligenyl-2',3'-dideoxy-2',3'-didehydrothymidine Monophosphates," *J. Med. Chem.*, 51:6752-6760, 2008.
Goodman et al., "Nanomolar small molecule inhibitors for alphav(beta)6, alphav(beta)5, and alphav(beta)3 integrins," *J Med Chem.*, 45(5):1045-1051, 2002.
Griggs et al., "Characteristics of cation binding to the I domains of LFA-1 and MAC-1," *J. Biol. Chem.*, 273:22113-22119, 1998.
Griggs et al., "Promoter elements determining weak expression of the GAL4 regulatory gene of *Saccharomyces cerevisiae*," *Mol. Cell. Biol.*, 13(8):4999-5009, 1993.
Griggs et al., "Regulated expression of the GAL4 activator gene in yeast provides a sensitive genetic switch for glucose repression," *Proc. Natl. Acad. Sci.*, 88:8597-8601, 1991.
Harms et al., "A small molecule antagonist of the αvβ3 integrin suppresses MDA-MB-435 skeletal metastasis," *Clin. Exp. Metastasis*, 21:119-128, 2004.
Heckman et al., "Probing integrin selectivity: rational design of highly active and selective ligands for the alpha5beta1 and alphavbeta3 integrin receptor," *Angew Chem Int Ed Engl.*, 46(19):3571-3574, 2007.
Heckman et al., "Rational design of highly active and selective ligands for the alpha5beta1 integrin receptor," *Chembiochem.*, 9(9):1397-1407, 2008.
Henderson et al., "Selective αav integrin deletion identifies a core, targetable molecular pathway that regulates fibrosis across solid organs," *Nature Medicine*, in press, 2013.
Herlt et al., "Synthesis of unlabeled and carboxyl-labelled 3-amino-5-hydroxybenzoic acid," *Austr. J. Chem.*, 34(6):1319-1324, 1981.
Hippenmeyer et al., "Adenovirus inhibition by peptidomimetic integrin antagonists," *Antiviral Res.*, 55:169-178, 2002.
Horan et al., "Partial inhibition of integrin alpha(v)beta6 prevents pulmonary fibrosis without exacerbating inflammation." *Am. J. Respir. Crit. Care Med.*, 177(1):56-65, 2008.
Huang, et al., "Direct Trifluoromethylation of Nitriles Promoted by Tetrabutylammonium Bifluoride," *Synlett*, 15:2518-2520, 2009.
Jørgensen, et al., "Efficient Synthesis of α-Aryl Esters by Room-Temperature Palladium-Catalyzed Coupling of Aryl Halides with Ester Enolates," *J. Am. Chem. Soc.*, 124(42):12557-12565, 2002.
Kapp et al., "Integrin modulators: a patent review." *Institute for Advanced Study and Center for Integrated Protein Science.* Oct. 2013: 23(10): 1273-95.
Kim et al., "Regulation of angiogenesis in vivo by ligation of integrin alpha5beta1 with the central cell-binding domain of fibronectin." *Am. J. Pathol.*, 156(4):1345-1362, 2000.
Kurahashi et al., "One-Electron Oxidation of Electronically Diverse Manganese(III) and Nickel(II) Salen Complexes: Transition from Localized to Delocalized Mixed-Valence Ligand Radicals," *J. Am. Chem. Soc.*, 133(21):8307-8316, 2011.
Landis et al., "Kinetic Resolution of β-Amino Esters by Acylation Using Immobilized Penicillin Amidohydrolase," *Organic Process Research & Development*, 6:539-546, 2002.
Li et al., "Integrin alpha5beta1 mediates attachment, migration, and proliferation in human retinal pigment epithelium: relevance for proliferative retinal disease." *Invest. Ophthalmol. Vis. Sci.*, 50(12):5988-5996, 2009.
Livant et al., "The PHSRN sequence induces extracellular matrix invasion and accelerates wound healing in obese diabetic mice." *J. Clin. Invest.*, 105(11):1537-1545, 2000.

(56) References Cited

OTHER PUBLICATIONS

Lobert et al., "Ubiquitination of alpha 5 beta 1 integrin controls fibroblast migration through lysosomal degradation of fibronectin-integrin complexes." *Dev. Cell*, 19(1):148-159, 2010.

Malfait et al., "Proprotein convertase activation of accrecanases in cartilage in situ," *Arch. Biochem. Biophys.*, 478:43-51, 2008.

Melton et al., "Expression of αvβ8 integrin on dendritic cells regulates Th17 cell development and experimental autoimmune encephalomyelitis in mice." *J. Clin. Invest.*, 120(12):4436-4444, 2010.

Millard et al., "Integrin targeted therapeutics." *Theranostics*, 1:154-88, 2011.

Mu et al., "The integrin alpha(v)beta8 mediates epithelial homeostasis through MT1-MMP-dependent activation of TGF-beta1." *Cell Biol.*, 157(3):493-507, 2002.

Munger et al., "Interactions between growth factors and integrins: latent forms of transforming growth factor-beta are ligands for the integrin alphavbeta1." *Mol. Biol. Cell*, 9:2627-2638, 1998.

Munger et al., The integrin alpha v beta 6 binds and activates latent TGF beta1: a mechanism for regulating pulmonary inflammation and fibrosis. *Cell.*, 96(3):319-328, 1999.

Nagarajan et al., "Discovery of diphenylmethanepropionic and dihydrostilbeneacetic acids as antagonists of the integrin αvβ3," *Chem. Biol. Drug Des.*, 67:177-181, 2006.

Nagarajan et al., "R-isomers of Arg-Gly-Asp (RGD) mimics as potent alphavbeta3 inhibitors," *Bioorganic & Medicinal Chemistry*, 15(11):3783-3800, 2007.

Nandrot et al., "Novel role for alphavbeta5-integrin in retinal adhesion and its diurnal peak," *Am J Physiol Cell Physiol*, 290(4):C1256-C1262, 2006.

Nishimura, "Integrin-mediated transforming growth factor-beta activation, a potential therapeutic target in fibrogenic disorders." *Am. J. Pathol.*, 175(4):1362-1370, 2009.

Nomura et al., "Stereoselective Ring-Opening Polymerization of a Racemic Lactide by Using Achiral Salen- and Homosalen-Aluminum Complexes," *Chemistry—A Europ. J.*, 13(16):4433-4451, 2007.

PCT International Search Report issued in International Application No. PCT/US2013/050917, mailed Sep. 23, 2013.

Perdih, "Small molecule antagonists of integrin receptors." *Curr. Med. Chem.*, 17(22):2371-2392, 2010.

Popov et al., "Integrin alphavbeta6 is a marker of the progression of biliary and portal liver fibrosis and a novel target for antifibrotic therapies." *J. Hepatol.*, 48(3):453-464, 2008.

Rico, "Synthesis of novel β-amino acid precursors: β-amino-hydrocoumarins as unusual aspartic acid mimetics used in fibrinogen receptor antagonists," *Tett. Let.*, 35:6599-6602, 1994.

Schmidt et al., "Characterization of spontaneous metastasis in an aggressive breast carcinoma model using flow cytometry," *Clin. Exp. Metastasis*, 17:537-544, 1999.

Scotton et al., "Increased local expression of coagulation factor X contributes to the fibrotic response in human and murine lung injury," *J Clin Invest.*, 119(9):2550-2563, 2009.

Shannon et al., "Anti-metastatic properties of RGD-peptidomimetic agents S137 and S247," *Clin. Exp. Metastasis*, 21:129-138, 2004.

Song et al., "Aggrecan degradation in human articular cartilage explants is mediated by both ADAMTS-4 and ADAMTS-5," *Arthritis Rheum.*, 56:575-585, 2007.

Stragies et al., "Design and synthesis of a new class of selective integrin alpha5beta1 antagonists," *J Med Chem.*, 50(16):3786-3794, 2007.

Suehiro et al., "Fibrinogen binds to integrin alpha(5)beta(1) via the carboxyl terminal RGD site of the Aalpha-chain" *J. Biochem.*, 128(4):705-710, 2000.

Tanaka and Shishido, "Synthesis of aromatic compounds containing a 1,1-dialkyl-2-trifluoromethyl group, a bioisostere of the tert-alkyl moiety," *Bioorg. Med. Chem. Lett.*, 17(22):6079-6085, 2007.

Wan, et al., "Synthesis of Potent and Orally Efficacious 11β-Hydroxysteroid Dehydrogenase Type 1 Inhibitor HSD-016," *J. Org. Chem.* 76(17):7048-7055, 2011.

Wipff et al., "Myofibroblast contraction activates latent TGF-beta1 from the extracellular matrix." *J. Cell Biol.*, 179(6):1311-1323, 2007.

Wong et al., "$α_v$ Integrins mediate adhesion and migration of breast carcinoma cell lines," *Clin. Exp. Metastasis*, 16:50-61, 1998.

Wu, et al., "Mild Palladium-Catalyzed Selective Monoarylation of Nitriles," *J. Am. Chem. Soc.*, 127(45):15824-15832, 2005.

Yang et al., "Embryonic mesodermal defects in alpha 5 integrin-deficient mice." *Development*, 119(4):1093-1105, 1993.

Yoshimura and Muto, "TGF-β function in immune suppression," *Curr Top Microbiol Immunol.*, 350:127-147, 2011.

Zack et al., "ADAM-8 isolated from human osteoarthritic chondrocytes is capable of cleaving fibronectin at Ala271," *Arthritis Rheum.*, 60:2704-2713, 2009.

Zahn et al., "Assessment of the integrin alpha5beta1 antagonist JSM6427 in proliferative vitreoretinopathy using in vitro assays and a rabbit model of retinal detachment." *Invest. Ophthalmol. Vis. Sci.*, 51(2):1028-1035, 2010.

Zahn et al., "Preclinical evaluation of the novel small-molecule integrin alpha5beta1 inhibitor JSM6427 in monkey and rabbit models of choroidal neovascularization." *Arch. Ophthalmol.*, 127(10):1329-1335, 2009.

BETA AMINO ACID DERIVATIVES AS INTEGRIN ANTAGONISTS

PRIORITY CLAIM

This application claims the benefit of U.S. Provisional Applications Nos. 61/673,058 filed Jul. 18, 2012 and 61/764,443 filed Feb. 13, 2013, both of which are incorporated herein by reference in their entirely.

BACKGROUND OF THE INVENTION

I. Field of the Invention

The present invention relates to the fields of pharmaceuticals, medicine and cell biology. More specifically, it relates to pharmaceutical agents (compounds) which are useful as integrin receptor antagonists, with particularly exceptional biological activity as antagonists of a group of integrins that mediate the pathologic processes of angiogenesis and fibrosis. As such, these compounds are useful in pharmaceutical compositions and in methods for treating conditions mediated by such integrins by inhibiting or antagonizing these integrins.

II. Description of Related Art

Integrins are a family of integral cytoplasmic membrane proteins that mediate cell interactions with other cells and with the extracellular matrix. Approximately one third of the members of the integrin family directly bind to a specific amino acid motif, arginine-glycine-asparate (RGD), that is contained within the sequence of their cognate protein ligands. It has been established in the art that peptides containing the RGD sequence, and synthetic small molecule compounds that mimic the RGD sequence, are capable of binding to these integrin receptors with varying degrees of specificity, and thereby inhibit the binding to normal physiologic ligands (Millard et al., 2011.). The biological effects of treatment with such agents is dependent on intrinsic molecular properties, reflected in the structure, that determine to what degree a particular integrin, or combination of integrins, is inhibited in a body tissue over a period of time.

Many human diseases are characterized by either or both of two common contributing pathological mechanisms: angiogenesis and fibrosis. Different subsets of the RGD-binding integrins have predominant roles in driving these dual processes, so that simultaneous antagonism of angiogenesis and fibrosis requires agents capable of binding potently to several target integrins. This contrasts with agents designed specifically for binding to a single integrin which may be less effective in some applications due to their more restricted mechanism of action.

Integrins which have been shown to have a role in promoting angiogenesis include, $\alpha v \beta 3$, $\alpha v \beta 5$, and $\alpha 5 \beta 1$. $\alpha v \beta 3$ and $\alpha v \beta 5$ were initially described as mediators of bFGF- and VEGF-induced angiogenesis, respectively, in corneal or choriallantoic models. More recently, data from studies using mice lacking these integrins also support an important functional role for $\alpha 5 \beta 1$. The integrin $\alpha 5 \beta 1$ (also known as VLA-5) is often referred to as the 'classic fibronectin receptor' reflecting its well characterized interaction with this extracellular matrix protein. Cells expressing $\alpha 5 \beta 1$ bind to fibronectin in a region that incorporates the ninth and tenth type III fibronectin repeats, the latter of which contains the RGD motif critical for integrin binding. In addition to fibronectin, $\alpha 5 \beta 1$ has been reported to interact with other RGD-containing extracellular matrix proteins including fibrinogen, denatured collagen, and fibrillin-1 (Bax et al., 2003; Perdih, 2010; Suchiro et al., 2000). These ligands are components of the provisional matrix that is laid down by cells as part of the wound healing response in tissues. Key components of this response are angiogenesis (new blood vessel formation) and fibrosis (scar formation) which are beneficial for healing of acute injuries, but can be deleterious in many disease contexts.

Antagonists of RGD-binding integrins should be useful for treatment of human diseases having angiogenesis or fibrosis as a principal part of their pathology. In particular, the important role of $\alpha 5 \beta 1$ in angiogenesis is supported by numerous studies. For example, mice lacking this integrin exhibit embryonic lethality at day 10-11 with a phenotype that includes defects in both the embryonic and extraembryonic vasculature (Yang et al., 1993). Angiogenic cytokines such as bFGF, IL-8, TGFβ, and TNFα upregulate $\alpha 5 \beta 1$ expression on endothelial cells in vitro and in vivo, and immunohistochemistry shows coordinated increases in both $\alpha 5 \beta 1$ and fibronectin staining in blood vessels from various types of human tumor biopsies and xenograft tumors in animals (Collo, 1999; Kim et al., 2000). Monoclonal antibodies that specifically inhibit $\alpha 5 \beta 1$, and compounds that have been described as $\alpha 5 \beta 1$ inhibitors, significantly reduce angiogenesis in a number of experimental models (Kim et al., 2000; Bhaskar et al., 2007; Livant et al., 2000; Zahn et al., 2009).

Because $\alpha 5 \beta 1$ expression is not confined to the endothelium, it has other functional roles in addition to angiogenesis. It is expressed to varying degrees in many cell types including fibroblasts, hematopoietic and immune cells, smooth muscle cells, epithelial cells, and tumor cells. Expression on tumor cells has been implicated in the progression of tumor growth and metastasis (Adachi et al., 2000; Blasé et al., 1995; Danen et al., 1994; Edward, 1995). In human fibroblasts, $\alpha 5 \beta 1$ promotes motility and survival (Lobert et al., 2010). In pancreatic stellate cells, it interacts with connective tissue growth factor to stimulate adhesion, migration, and fibrogenesis (Gao and Brigstock, 2006). It has been shown that pharmacologic antagonism of $\alpha 5 \beta 1$ inhibits the attachment migration, and proliferation of human retinal epithelial cells in vitro, and reduces retinal cell proliferation and scarring when administered intravitreally to rabbits with retinal detachment (Li et al., 2009; Zahn et al., 2010).

Multiple RGD-binding integrins of the alpha v family have been implicated in promoting the biological activation of the latent pro-fibrotic cytokine TGFβ. This is mediated by binding to the latency associated peptide (LAP), particularly by $\alpha v \beta 6$ and $\alpha v \beta 8$, but also by $\alpha v \beta 1$, $\alpha v \beta 3$, and $\alpha v \beta 5$. These integrin interactions are all critically dependent upon the amino acid sequence arg-gly-asp (RGD) contained in LAP. Indeed, mice containing a mutation in the RGD sequence are incapable of cytokine activation and phenocopy TGFβ-null mice. It is anticipated that simultaneous inhibition of multiple integrins with the potential to activate TGFβ may have particular utility to prevent or treat a range of fibrotic conditions. In addition, such broad spectrum integrin antagonists may be particularly useful for simultaneous modulation of both angiogenesis and fibrosis.

SUMMARY OF THE INVENTION

The present disclosure provides novel integrin receptor antagonists, pharmaceutical compositions, and methods for their manufacture, and methods for their use.

In some aspects, the present invention provides a compound of the formula:

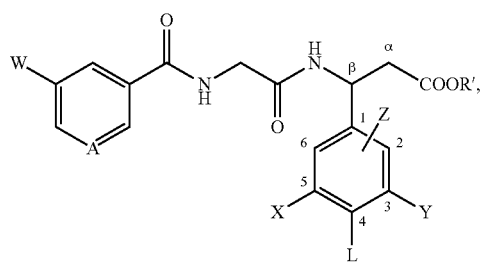

(I)

wherein: W is

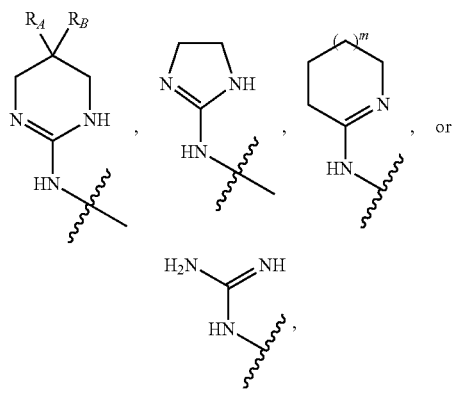

wherein: $R_A$ is —H or —F; $R_B$ is —H, —OH, —NH$_2$, —F, —CN, or alkoxy$_{(C\leq 8)}$, wherein if $R_A$ is —F, then $R_B$ is —H or —F; and m is 0-3; A is C—R" or N, wherein: R" is —H, —OH, —CO$_2$R$_1$, —C(=O)R$_2$, or —N(R$_1$)(C=O)R$_3$, or alkoxy$_{(C\leq 8)}$, acyloxy$_{(C\leq 8)}$, alkylamino$_{(C\leq 8)}$, dialkylamino$_{(C\leq 8)}$, or a substituted version of any of the groups, wherein: $R_1$ is —H, alkyl$_{(C\leq 8)}$ or substituted alkyl$_{(C\leq 8)}$; $R_2$ is alkylamino$_{(C\leq 8)}$, dialkylamino$_{(C\leq 8)}$, heterocycloalkyl$_{(C\leq 8)}$, heteroaryl$_{(C\leq 8)}$, or a substituted version of any of the groups; $R_3$ is alkyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, or a substituted version of any of the groups; R' is —H, alkyl$_{(C\leq 8)}$ or substituted alkyl$_{(C\leq 8)}$; X is: hydrogen, halo, or cyano; alkyl$_{(C\leq 12)}$, alkoxy$_{(C\leq 12)}$, aryl$_{(C\leq 12)}$, aralkyl$_{(C\leq 12)}$, heteroaryl$_{(C\leq 8)}$, heterocycloalkyl$_{(C\leq 12)}$, aryloxy$_{(C\leq 12)}$, acyloxy$_{(C\leq 12)}$, or a substituted version of any of the groups; —(CH$_2$)$_{n'}$—CO$_2$-alkyl$_{(C\leq 6)}$, wherein, n' is 0-3;

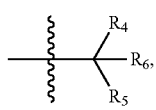

wherein $R_4$ and $R_5$ are each independently alkyl$_{(C\leq 8)}$, substituted alkyl$_{(C\leq 8)}$, or —CH$_2$O-alkyl$_{(C\leq 8)}$; $R_6$ is —OH, —CN, —NH$_2$, —CF$_3$, —CF$_2$H, —CH$_2$F, —CO$_2$H, —CO$_2$-alkyl$_{(C\leq 8)}$, —C(=O)NH$_2$, —CH$_2$OH, —CH$_2$O-alkyl$_{(C\leq 8)}$, or alkoxy$_{(C\leq 8)}$, provided that where $R_4$ and $R_5$ are each —CF$_3$, then $R_6$ is —OH, alkoxy$_{(C\leq 8)}$ or —NH$_2$;

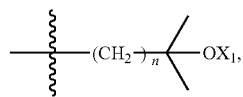

wherein n is 1 or 2 and $X_1$ is —H or alkyl$_{(C\leq 8)}$; or

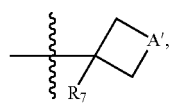

wherein: A' is a covalent bond, thereby forming a cyclopropane ring, —CF$_2$—, —O—, alkanediyl$_{(C\leq 6)}$ or alkoxydiyl$_{(C\leq 8)}$; and $R_7$ is —OH, —CN, —NH$_2$, —CO$_2$H, —CO$_2$-alkyl$_{(C\leq 8)}$, —C(=O)NH$_2$, —CF$_3$, —CF$_2$H, —CH$_2$F, —CH$_2$OH, —CH$_2$O-alkyl$_{(C\leq 8)}$, alkyl$_{(C\leq 8)}$ or alkoxy$_{(C\leq 8)}$; Y is: t-butyl, neopentyl, norbornyl, or adamantyl;

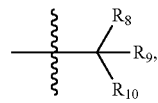

wherein $R_8$ and $R_9$ are each independently alkyl$_{(C\leq 8)}$, substituted alkyl$_{(C\leq 8)}$, or —CH$_2$O-alkyl$_{(C\leq 8)}$; $R_{10}$ is —OH, —CN, —NH$_2$, —CF$_3$, —CF$_2$H, —CFH$_2$, —CO$_2$H, —CO$_2$-alkyl$_{(C\leq 8)}$, —C(=O)NH$_2$, —CH$_2$OH, —CH$_2$O-alkyl$_{(C\leq 8)}$, or alkoxy$_{(C\leq 8)}$, provided that where $R_8$ and $R_9$ are each —CF$_3$, then $R_{10}$ is —OH, alkoxy$_{(C\leq 8)}$ or —NH$_2$;

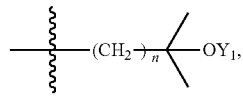

wherein n" is 1 or 2 and $Y_1$ is —H or alkyl$_{(C\leq 8)}$; or

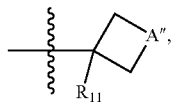

wherein: A" is a covalent bond, thereby forming a cyclopropane ring, —O—, —CF$_2$—, alkanediyl$_{(C\leq 6)}$ or alkoxydiyl$_{(C\leq 8)}$; and $R_{11}$ is —OH, —CN, —NH$_2$, —CO$_2$H, —CO$_2$-alkyl$_{(C\leq 8)}$, —C(=O)NH$_2$, —CF$_3$, —CF$_2$F, —CH$_2$OH, —CH$_2$O-alkyl$_{(C\leq 8)}$, alkyl$_{(C\leq 8)}$ or alkoxy$_{(C\leq 8)}$; L is hydrogen, hydroxy or alkoxy$_{(C\leq 8)}$; and Z is hydrogen, fluorine, or hydroxy and is attached to either carbon atom 2 or 6; provided that if W is

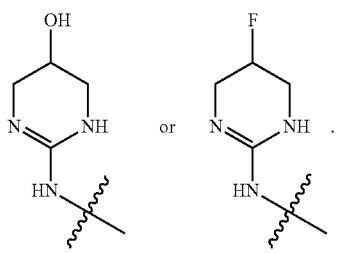 [SMILES: *NC1=NCC(O)CN1 ; *NC1=NCC(F)CN1]

then X and Y are not both each t-butyl; and further provided that if W is

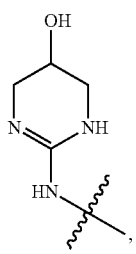 [SMILES: *NC1=NCC(O)CN1]

A is C—OH, Z is hydrogen, and X is bromo or iodo, then Y is not t-butyl; or a pharmaceutically acceptable salt or tautomer thereof. In some embodiments, the compound is further defined as:

(IA)

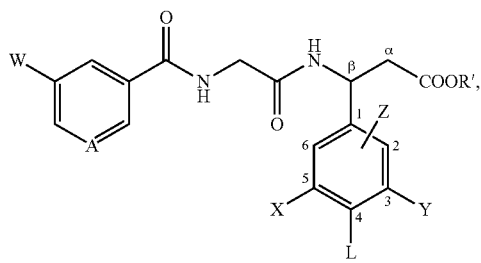

wherein: W is

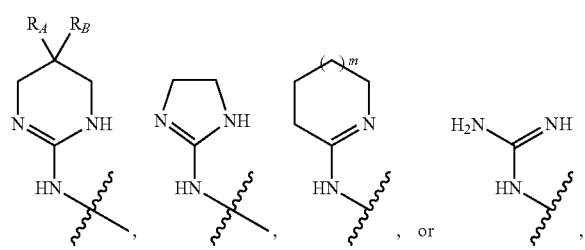

wherein: $R_A$ is —H or —F; $R_B$ is —H, —OH, —NH$_2$, —F, —CN, or alkoxy$_{(C \leq 8)}$, wherein if $R_A$ is —F, then $R_B$ is —H or —F; and m is 0-3; A is C—R" or N, wherein: R" is —H, —OH, —CO$_2$R$_1$, —C(=O)R$_2$, or —N(R$_1$)(C=O)R$_3$, or alkoxy$_{(C \leq 8)}$, acyloxy$_{(C \leq 8)}$, alkylamino$_{(C \leq 8)}$, dialkylamino$_{(C \leq 8)}$, or a substituted version of any of the groups, wherein: $R_1$ is —H, alkyl$_{(C \leq 8)}$ or substituted alkyl$_{(C \leq 8)}$; $R_2$ is alkylamino$_{(C \leq 8)}$, dialkylamino$_{(C \leq 8)}$, heterocycloalkyl$_{(C \leq 8)}$, heteroaryl$_{(C \leq 8)}$, or a substituted version of any of the groups; $R_3$ is alkyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, or a substituted version of any of the groups; R' is —H, alkyl$_{(C \leq 8)}$ or substituted alkyl$_{(C \leq 8)}$; X is: hydrogen, halo, or cyano; alkyl$_{(C \leq 12)}$, alkoxy$_{(C \leq 12)}$, aryl$_{(C \leq 12)}$, aralkyl$_{(C \leq 12)}$, heteroaryl$_{(C \leq 8)}$, heterocycloalkyl$_{(C \leq 12)}$, aryloxy$_{(C \leq 12)}$, acyloxy$_{(C \leq 12)}$, or a substituted version of any of the groups; —(CH$_2$)$_{n'}$—CO$_2$-alkyl$_{(C \leq 6)}$, wherein, n' is 0-3;

wherein $R_4$ and $R_5$ are each independently alkyl$_{(C \leq 8)}$ or substituted alkyl$_{(C \leq 8)}$; $R_6$ is —OH, —CN, —NH$_2$, —CF$_3$, —CF$_2$H, —CO$_2$H, —CO$_2$-alkyl$_{(C \leq 8)}$, —C(=O)NH$_2$, —CH$_2$OH, or alkoxy$_{(C \leq 8)}$, provided that where $R_4$ and $R_5$ are each CF$_3$, then $R_6$ is OH;

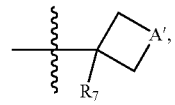

wherein n is 1 or 2; or

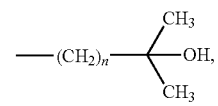

wherein: A' is a covalent bond, thereby forming a cyclopropane ring, alkanediyl$_{(C \leq 6)}$ or alkoxydiyl$_{(C \leq 8)}$; and $R_7$ is —OH, —CN, —NH$_2$, —CO$_2$H, —CO$_2$-alkyl$_{(C \leq 8)}$, —C(=O)NH$_2$, —CF$_3$, —CF$_2$H, or alkoxy$_{(C \leq 8)}$; Y is: t-butyl, neopentyl, norbornyl, or adamantyl;

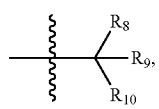

wherein $R_8$ and $R_9$ are each independently alkyl$_{(C \leq 8)}$ or substituted alkyl$_{(C \leq 8)}$; $R_{10}$ is —OH, —CN, —NH$_2$, —CF$_3$, —CF$_2$H, —CO$_2$H, —CO$_2$-alkyl$_{(C \leq 8)}$, —C(=O)NH$_2$, —CH$_2$OH, or alkoxy$_{(C \leq 8)}$, provided that where $R_8$ and $R_9$ are each CF$_3$, then $R_{10}$ is OH;

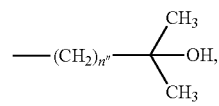

wherein n" is 1 or 2; or

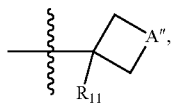

wherein: A" is a covalent bond, thereby forming a cyclopropane ring, alkanediyl$_{(C \leq 6)}$ or alkoxydiyl$_{(C \leq 8)}$; and R$_{11}$ is —OH, —CN, —NH$_2$, —CO$_2$H, —CO$_2$-alkyl$_{(C \leq 8)}$, —C(=O)NH$_2$, —CF$_3$, —CF$_2$H, or alkoxy$_{(C \leq 8)}$; L is hydrogen, hydroxy or alkoxy$_{(C \leq 8)}$; and Z is hydrogen or hydroxy and is attached to either carbon atom 2 or 6; provided that if W is

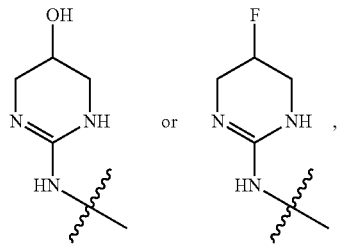 [SMILES: *NC1=NCC(O)CN1 ; *NC1=NCC(F)CN1]

then X and Y are not both each t-butyl; and further provided that if W is

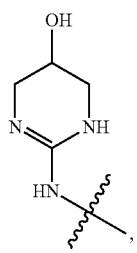 [SMILES: *NC1=NCC(O)CN1]

A is C—OH, Z is hydrogen, and X is bromo or iodo, then Y is not t-butyl; or a pharmaceutically acceptable salt or tautomer thereof. In some embodiments, the compound is further defined as:

(II)

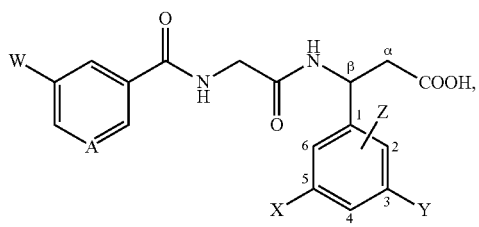

wherein: W is

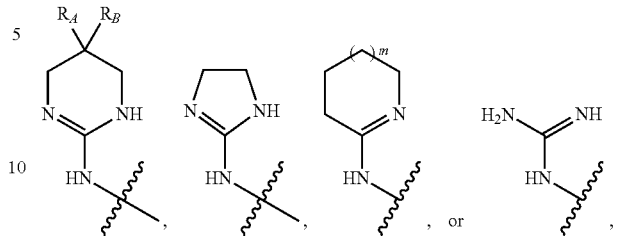

wherein: R$_A$ is —H or —F; R$_B$ is —H, —OH, —NH$_2$, —F, —CN, or alkoxy$_{(C \leq 8)}$, wherein if R$_A$ is —F, then R$_B$ is —H or —F; and m is 0-3; A is C—R" or N, wherein: R" is —H, —OH, —CO$_2$R$_1$, —C(=O)R$_2$, or —N(R$_1$)(C=O)R$_3$, or alkoxy$_{(C \leq 8)}$, acyloxy$_{(C \leq 8)}$, alkylamino$_{(C \leq 8)}$, dialkylamino$_{(C \leq 8)}$, or a substituted version of any of the groups, wherein: R$_1$ is —H, alkyl$_{(C \leq 8)}$ or substituted alkyl$_{(C \leq 8)}$; R$_2$ is alkylamino$_{(C \leq 8)}$, dialkylamino$_{(C \leq 8)}$, heterocycloalkyl$_{(C \leq 8)}$, heteroaryl$_{(C \leq 8)}$, or a substituted version of any of the groups; R$_3$ is alkyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, or a substituted version of any of the groups; X is: hydrogen, halo, or cyano; alkyl$_{(C \leq 12)}$, alkoxy$_{(C \leq 12)}$, aryl$_{(C \leq 12)}$, aralkyl$_{(C \leq 12)}$, heteroaryl$_{(C \leq 8)}$, heterocycloalkyl$_{(C \leq 12)}$, aryloxy$_{(C \leq 12)}$, acyloxy$_{(C \leq 12)}$, or a substituted version of any of the groups; —(CH$_2$)$_{n'}$—CO$_2$-alkyl$_{(C \leq 6)}$, wherein, n' is 0-3;

wherein R$_4$ and R$_5$ are each independently alkyl$_{(C \leq 8)}$, substituted alkyl$_{(C \leq 8)}$, or —CH$_2$O-alkyl$_{(C \leq 8)}$; R$_6$ is —OH, —CN, —NH$_2$, —CF$_3$, —CF$_2$H, —CH$_2$F, —CO$_2$H, —CO$_2$-alkyl$_{(C \leq 8)}$, —C(=O)NH$_2$, —CH$_2$OH, —CH$_2$O-alkyl$_{(C \leq 8)}$, or alkoxy$_{(C \leq 8)}$, provided that where R$_4$ and R$_5$ are each —CF$_3$, then R$_6$ is —OH, alkoxy$_{(C \leq 8)}$ or —NH$_2$;

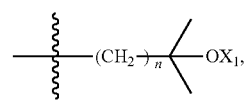

wherein n is 1 or 2 and X$_1$ is —H or alkyl$_{(C \leq 8)}$; or

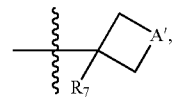

wherein: A' is a covalent bond, thereby forming a cyclopropane ring, —CF$_2$—, —O—, alkanediyl$_{(C \leq 6)}$ or alkoxydiyl$_{(C \leq 8)}$; and R$_7$ is —OH, —CN, —NH$_2$, —CO$_2$H, —CO$_2$-alkyl$_{(C \leq 8)}$, —C(=O)NH$_2$, —CF$_3$, —CF$_2$H, —CH$_2$F, —CH$_2$OH, —CH$_2$O-alkyl$_{(C \leq 8)}$, alkyl$_{(C \leq 8)}$ or alkoxy$_{(C \leq 8)}$; Y is: t-butyl;

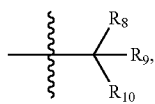

wherein $R_8$ and $R_9$ are each independently alkyl$_{(C\leq 8)}$, substituted alkyl$_{(C\leq 8)}$, or —CH$_2$O-alkyl$_{(C\leq 8)}$; $R_{10}$ is —OH, —CN, —NH$_2$, —CF$_3$, —CF$_2$H, —CFH$_2$, —CO$_2$H, —CO$_2$-alkyl$_{(C\leq 8)}$, —C(=O)NH$_2$, —CH$_2$OH, —CH$_2$O-alkyl$_{(C\leq 8)}$, or alkoxy$_{(C\leq 8)}$, provided that where $R_8$ and $R_9$ are each —CF$_3$, then $R_{10}$ is —OH, alkoxy$_{(C\leq 8)}$ or —NH$_2$;

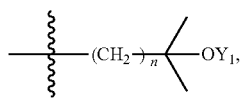

wherein n is 1 or 2 and $Y_1$ is —H or alkyl$_{(C\leq 8)}$; or

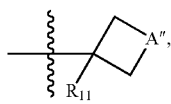

wherein: A″ is a covalent bond, thereby forming a cyclopropane ring, —O—, —CF$_2$—, alkanediyl$_{(C\leq 6)}$ or alkoxydiyl$_{(C\leq 8)}$; and $R_{11}$ is —OH, —CN, —NH$_2$, —CO$_2$H, —CO$_2$-alkyl$_{(C\leq 8)}$, —C(=O)NH$_2$, —CF$_3$, —CF$_2$H, —CH$_2$F, —CH$_2$OH, —CH$_2$O-alkyl$_{(C\leq 8)}$, alkyl$_{(C\leq 8)}$ or alkoxy$_{(C\leq 8)}$; and Z is hydrogen, fluorine, or hydroxy and is attached to either carbon atom 2 or 6; provided that if W is

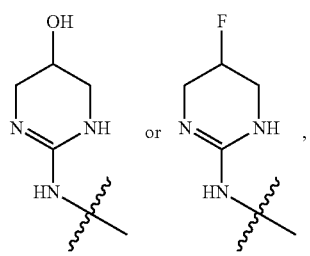 [SMILES: *NC1=NCC(O)CN1 ; *NC1=NCC(F)CN1]

then X and Y are not both each t-butyl; and further provided that if W is

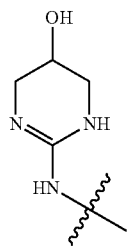

A is C—OH, Z is hydrogen, and X is bromo or iodo, then Y is not t-butyl; or a pharmaceutically acceptable salt or tautomer thereof. In some embodiments, the compound is further defined as:

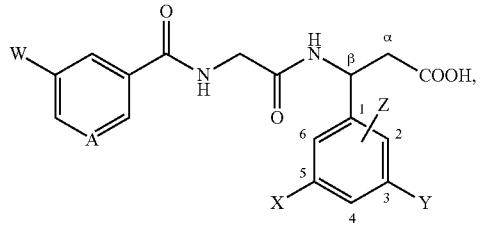

wherein: W is

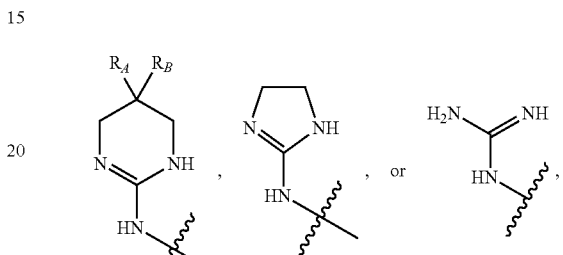

wherein: $R_A$ is —H or —F; $R_B$ is —H, —OH, —F, wherein if $R_A$ is —F, then $R_B$ is —H or —F; A is C—R″ or N, wherein: R″ is —H, —OH, X is: halo, t-butyl, CF$_3$, CF$_2$H or cyano;

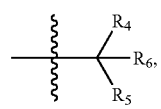

wherein $R_4$ and $R_5$ are each independently alkyl$_{(C\leq 8)}$ or substituted alkyl$_{(C\leq 8)}$; $R_6$ is —OH, —CN, —NH$_2$, —CF$_3$, —CF$_2$H, —CO$_2$H, —CO$_2$-alkyl$_{(C\leq 8)}$, —C(=O)NH$_2$, —CH$_2$OH, or alkoxy$_{(C\leq 8)}$, provided that where $R_4$ and $R_5$ are each CF$_3$, then $R_6$ is OH;

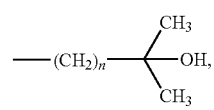

wherein n is 1 or 2; or

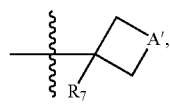

wherein: A′ is a covalent bond, thereby forming a cyclopropane ring, alkanediyl$_{(C\leq 6)}$ or alkoxydiyl$_{(C\leq 8)}$; and $R_7$ is —OH, —CN, —NH$_2$, —CO$_2$H, —CO$_2$-alkyl$_{(C\leq 8)}$, —C(=O)NH$_2$, —CF$_3$, —CF$_2$H, or alkoxy$_{(C\leq 8)}$; Y is: t-butyl;

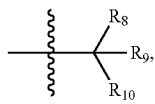

wherein $R_8$ and $R_9$ are each independently alkyl$_{(C\leq8)}$ or substituted alkyl$_{(C\leq8)}$; $R_{10}$ is —OH, —CN, —NH$_2$, —CF$_3$, —CF$_2$H, —CO$_2$H, —CO$_2$-alkyl$_{(C\leq8)}$, —C(=O)NH$_2$, —CH$_2$OH, or alkoxy$_{(C\leq8)}$, provided that where $R_8$ and $R_9$ are each CF$_3$, then $R_{10}$ is OH;

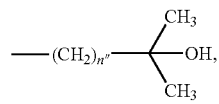

wherein n" is 1 or 2; or

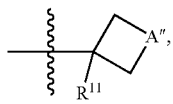

wherein: A" is a covalent bond, thereby forming a cyclopropane ring, alkanediyl$_{(C\leq6)}$ or alkoxydiyl$_{(C\leq8)}$; and $R_{11}$ is —OH, —CN, —NH$_2$, —CO$_2$H, —CO$_2$-alkyl$_{(C\leq8)}$, —C(=O)NH$_2$, —CF$_3$, —CF$_2$H, or alkoxy$_{(C\leq8)}$; and Z is hydrogen or hydroxy and is attached to either carbon atom 2 or 6; provided that if W is

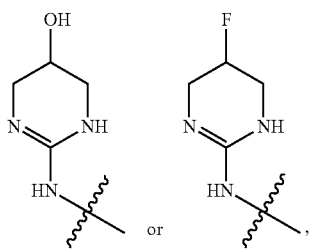 [SMILES: *NC1=NCC(O)CN1 ; *NC1=NCC(F)CN1]

then X and Y are not both each t-butyl; and further provided that if W is

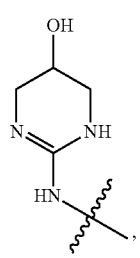

A is C—OH, Z is hydrogen, and X is bromo or iodo, then Y is not t-butyl; or a pharmaceutically acceptable salt or tautomer thereof. In some embodiments, the carbon atom labeled β is in the R configuration. In other embodiments, the carbon atom labeled β is in the S configuration. In some embodiments, Y is:

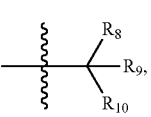

wherein: $R_8$ and $R_9$ are each independently alkyl$_{(C\leq8)}$, substituted alkyl$_{(C\leq8)}$, or —CH$_2$O-alkyl$_{(C\leq8)}$; and $R_{10}$ is —OH, —CF$_3$, —CF$_2$H, —CFH$_2$, —CO$_2$-alkyl$_{(C\leq8)}$, —CH$_2$OH, —CH$_2$O-alkyl$_{(C\leq8)}$, or alkoxy$_{(C\leq8)}$, provided that where $R_8$ and $R_9$ are each —CF$_3$, then $R_{10}$ is —OH, alkoxy$_{(C\leq8)}$ or —NH$_2$.

In some embodiments, W is

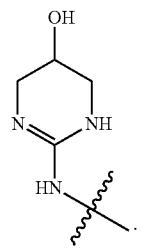

In some embodiments, A is C—OH. In other embodiments, A is N. In some embodiments, X is halo. In some embodiments, X is bromo. In other embodiments, X is chloro. In other embodiments, X is alkyl$_{(C\leq8)}$ or substituted alkyl$_{(C\leq8)}$. In some embodiments, X is t-butyl. In other embodiments, X is 2-hydroxy-isopropyl. In other embodiments, X is —CF$_3$. In other embodiments, X is cyano. In other embodiments, X is heteroaryl. In some embodiments, X is pyrimidyl. In other embodiments, X is pyridyl. In some embodiments, L is hydrogen. In some embodiments, Y is t-butyl. In other embodiments, Y is 2-hydroxy-isopropyl. In other embodiments, Y is

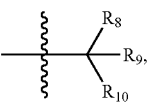

wherein $R_8$ and $R_9$ are each independently alkyl$_{(C\leq8)}$, substituted alkyl$_{(C\leq8)}$, or —CH$_2$O-alkyl$_{(C\leq8)}$; $R_{10}$ is —OH, —CN, —NH$_2$, —CF$_3$, —CF$_2$H, —CFH$_2$, —CO$_2$H, —CO$_2$-alkyl$_{(C\leq8)}$, —C(=O)NH$_2$, —CH$_2$OH, —CH$_2$O-alkyl$_{(C\leq8)}$, or alkoxy$_{(C\leq8)}$, provided that where $R_8$ and $R_9$ are each —CF$_3$, then $R_{10}$ is —OH, alkoxy$_{(C\leq8)}$ or —NH$_2$. In some embodiments, $R_8$ and $R_9$ are alkyl$_{(C\leq8)}$. In some embodiments, $R_8$ and $R_9$ are methyl. In some embodiments, $R_{10}$ is —CN, —CH$_2$OH, —CH$_2$O-alkyl$_{(C\leq8)}$, or —CF$_3$. In other embodiments, wherein $R_{10}$ is —CH$_2$O—CH$_3$. In other embodiments, Y is

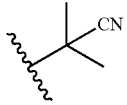

In other embodiments, Y is

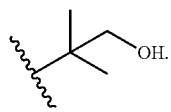 [SMILES: *C(C)(C)CO]

In other embodiments, Y is

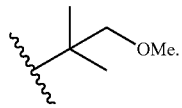 [SMILES: *C(C)(C)COC]

In other embodiments, Y is

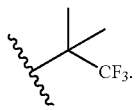

In other embodiments, $R_8$ is alkyl$_{(C \leq 8)}$. In other embodiments, $R_8$ is methyl. In other embodiments, $R_9$ is substituted alkyl$_{(C \leq 8)}$. In other embodiments, $R_9$ is —CF$_3$. In other embodiments, $R_{10}$ is —OH. In other embodiments, Y is

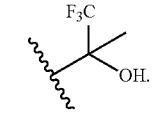

In other embodiments, Y is

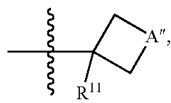

wherein: A" is a covalent bond, thereby form a cyclopropane ring, —O—, —CF$_2$—, alkanediyl$_{(C \leq 6)}$ or alkoxydiyl$_{(C \leq 8)}$; and $R_{11}$ is —OH, —CN, —NH$_2$, —CO$_2$H, —CO$_2$-alkyl$_{(C \leq 8)}$, —C(=O)NH$_2$, —CF$_3$, —CF$_2$H, —CH$_2$F, —CH$_2$OH, —CH$_2$O-alkyl$_{(C \leq 8)}$, alkyl$_{(C \leq 8)}$ or alkoxy$_{(C \leq 8)}$. In some embodiments, A" is a covalent bond. In other embodiments, A" is alkoxydiyl$_{(C \leq 8)}$. In some embodiments, A" is —CH$_2$OCH$_2$—. In other embodiments, A" is alkanediyl$_{(C \leq 6)}$. In some embodiments, A" is —CH$_2$—. In other embodiments, $R_{11}$ is —CN, —CH$_2$OH, —CH$_2$O-alkyl$_{(C \leq 8)}$, —CF$_2$H, or —CFH$_2$. In some embodiments, $R_{11}$ is —CH$_2$OCH$_3$. In other embodiments, Y is

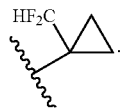

In other embodiments, Y is

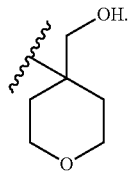 [SMILES: *C1(CO)CCOCC1]

In other embodiments, Y is

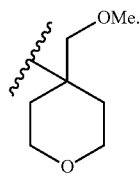 [SMILES: *C1(COC)CCOCC1]

In other embodiments, Y is

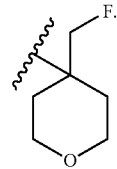

In other embodiments, Y is

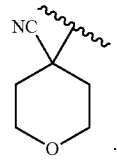

In other embodiments, Y is

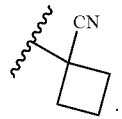

In some embodiments, Z is hydrogen. In other embodiments, Z is hydroxy and attached to carbon atom 2. In other embodiments, Z is hydroxy and attached to carbon atom 6. In other embodiments, Z is fluoride and attached to carbon atom 2. In other embodiments, Z is fluoride and attached to carbon atom 6. In some embodiments, R' is hydrogen.

In other embodiments, W is

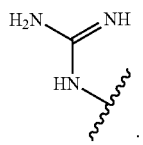

In some embodiments, A is C—OH. In other embodiments, A is C—H. In other embodiments, A is N. In some embodiments, R' is hydrogen. In some embodiments, L is hydrogen. In some embodiments, Z is hydrogen. In some embodiments, Y is alkyl$_{(C\leq 8)}$. In some embodiments, Y is t-butyl. In some embodiments, X is halo. In some embodiments, X is bromo. In other embodiments, X is alkyl$_{(C\leq 8)}$. In other embodiments, X is t-butyl.

In some embodiments, W is

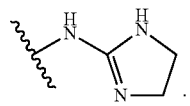

In some embodiments, A is C—OH. In other embodiments, A is C—H. In some embodiments, R' is hydrogen. In some embodiments, L is hydrogen. In some embodiments, Z is hydrogen. In some embodiments, Y is alkyl$_{(C\leq 8)}$. In some embodiments, Y is t-butyl. In some embodiments, X is halo. In some embodiments, X is bromo.

In some embodiments, the compound is further defined as:

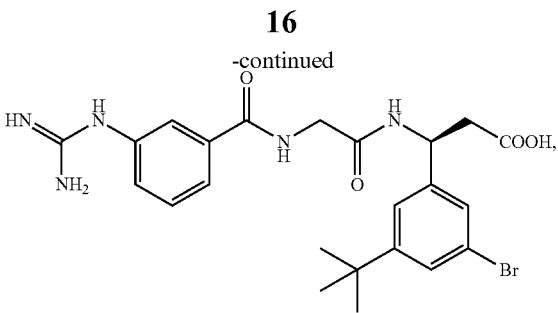

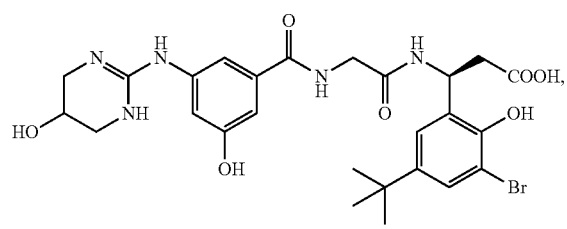

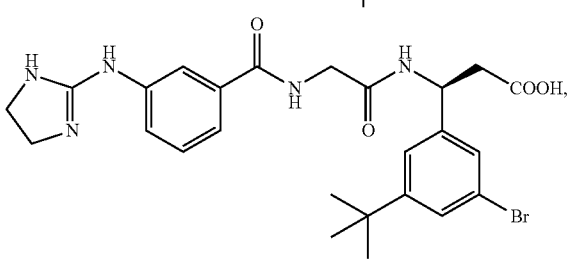

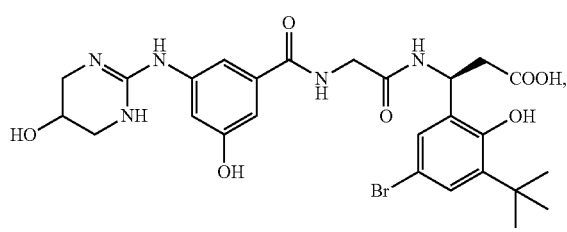

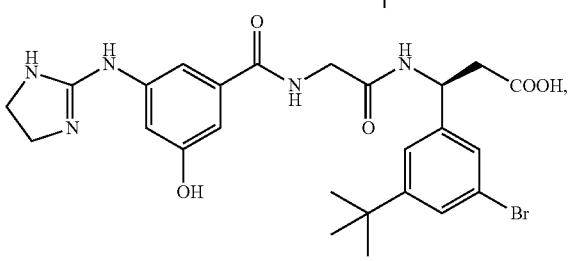

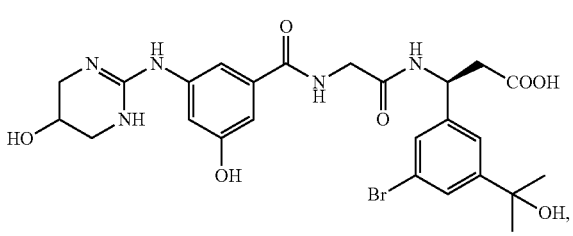

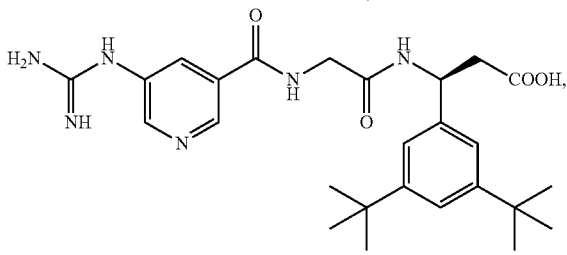

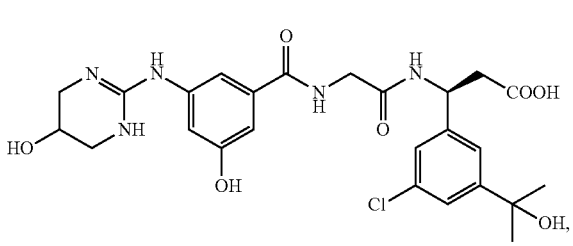

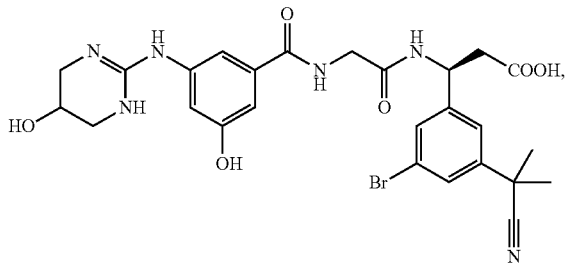

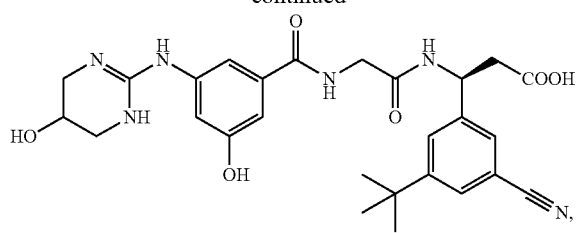
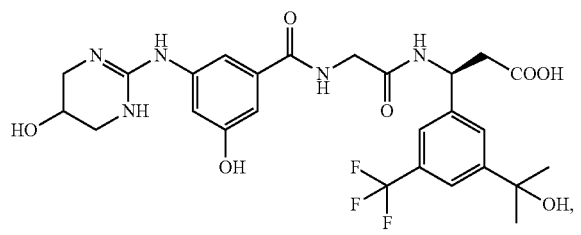
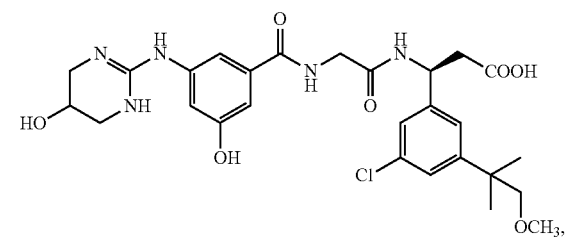
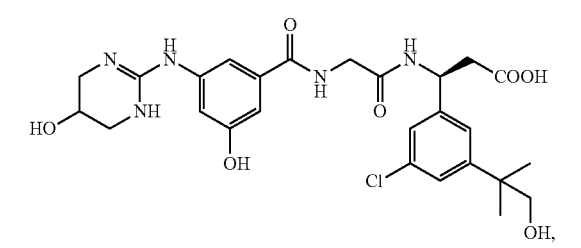
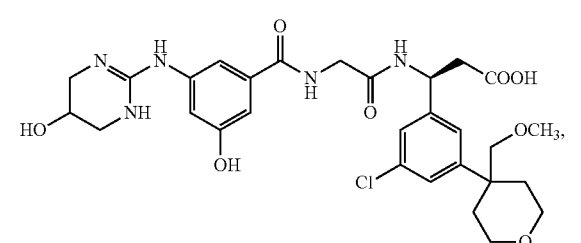
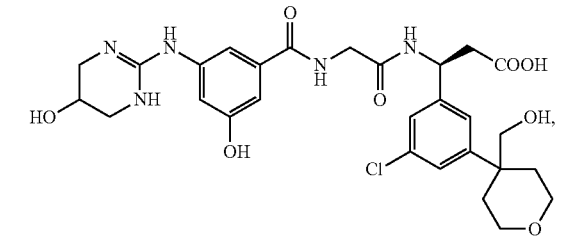
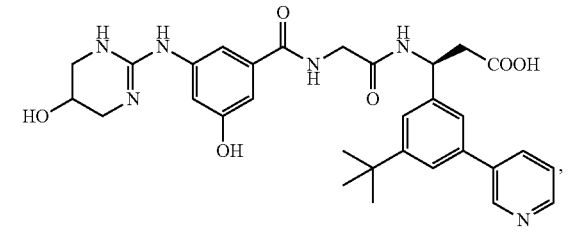
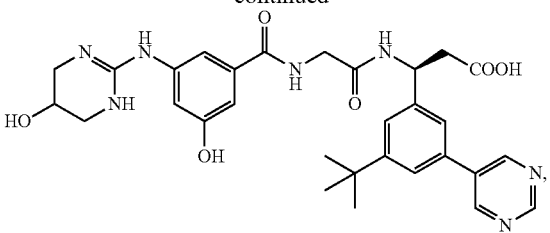
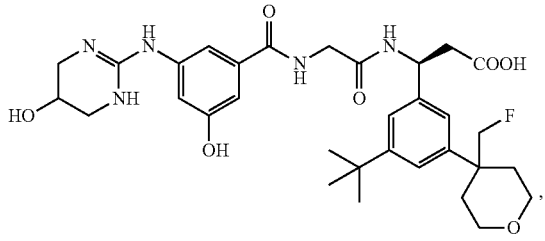
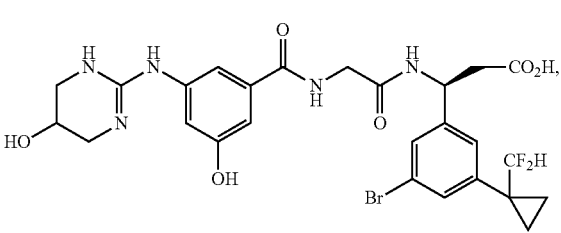
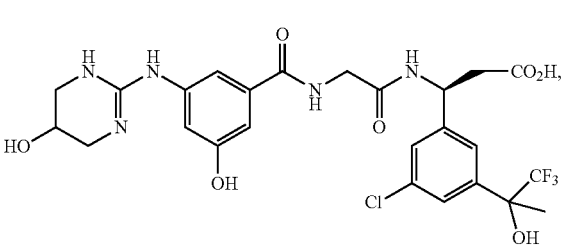
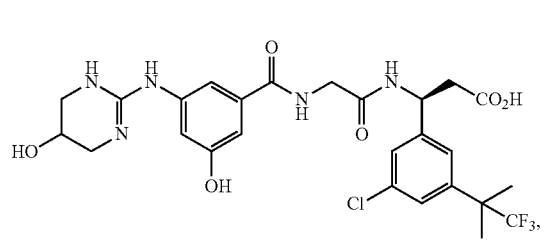
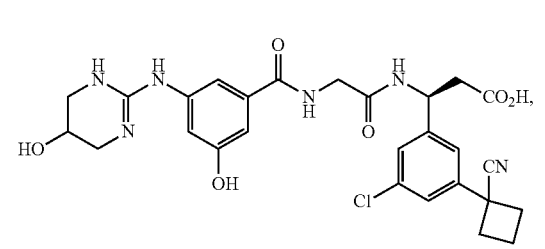
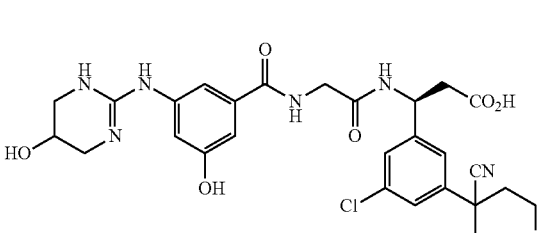

-continued
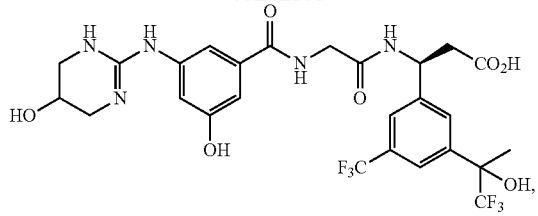
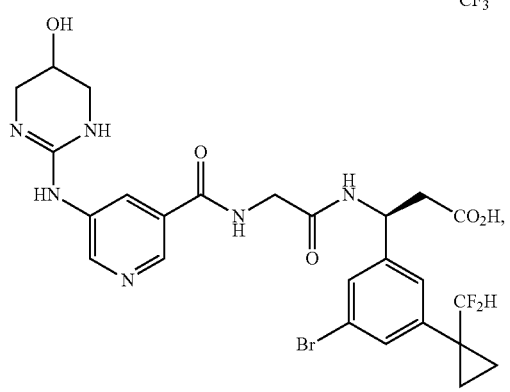
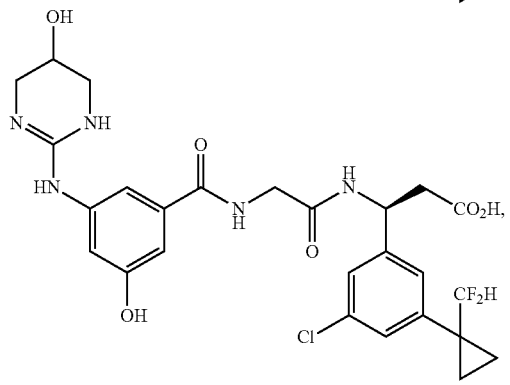
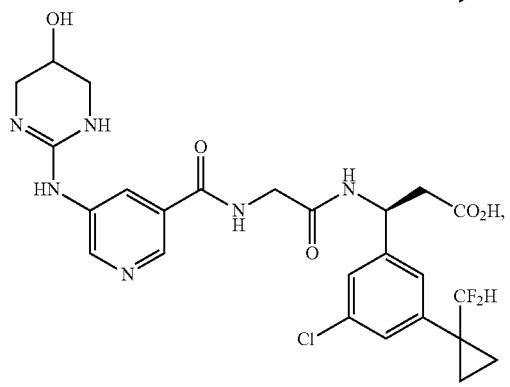
-continued
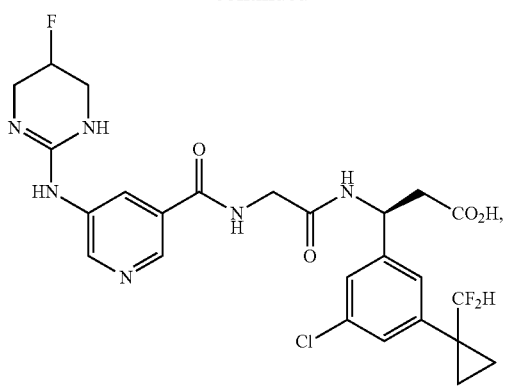
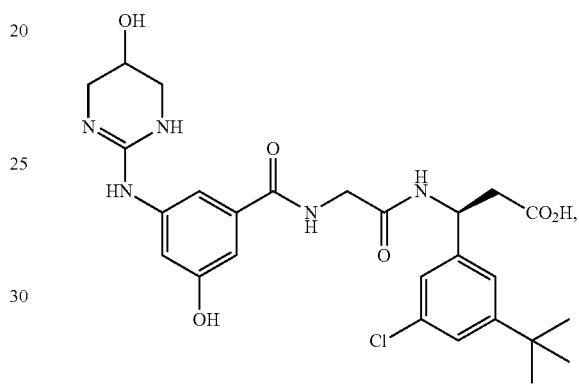
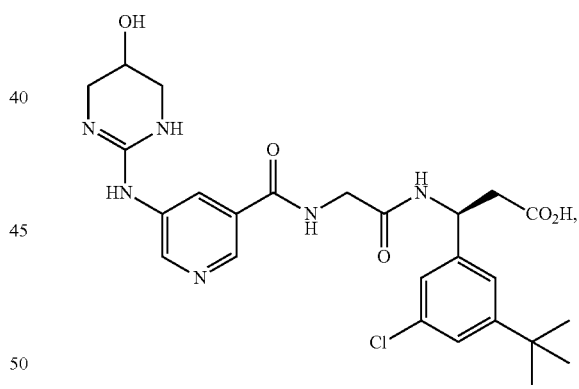
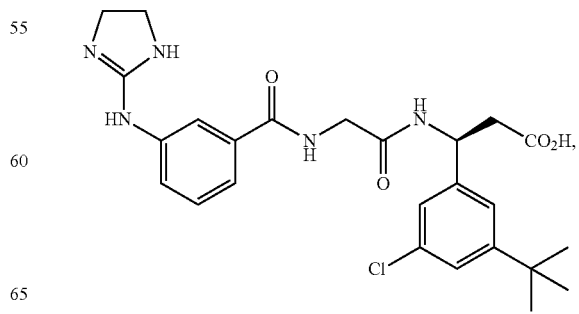

-continued
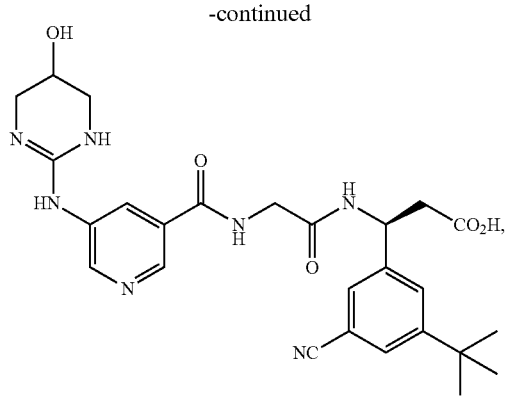
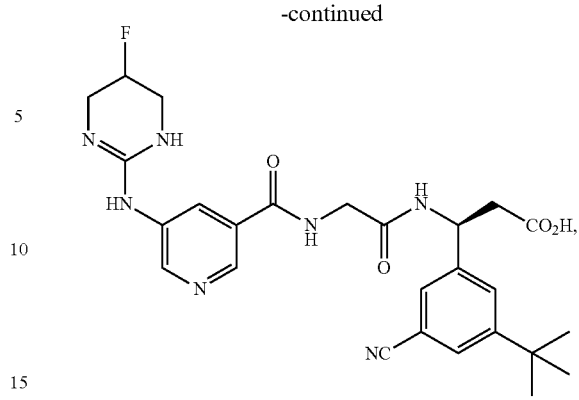
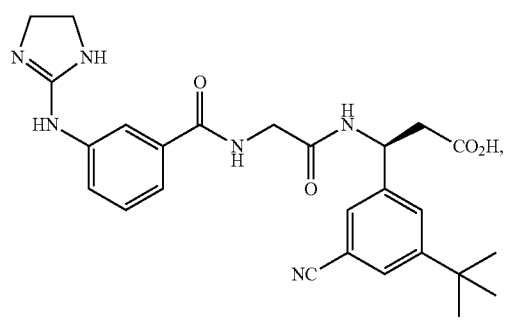
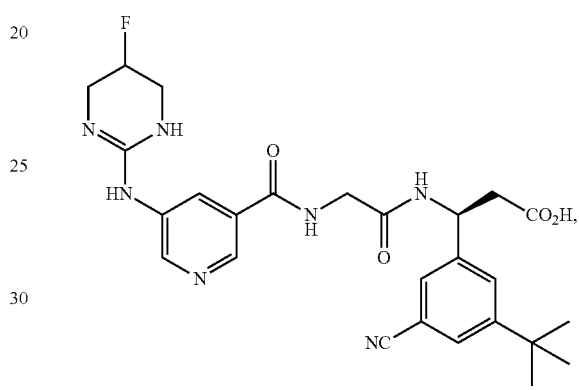
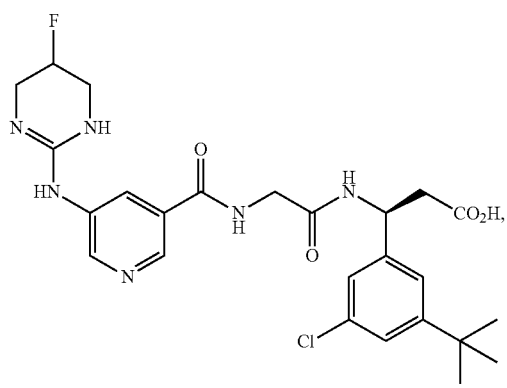
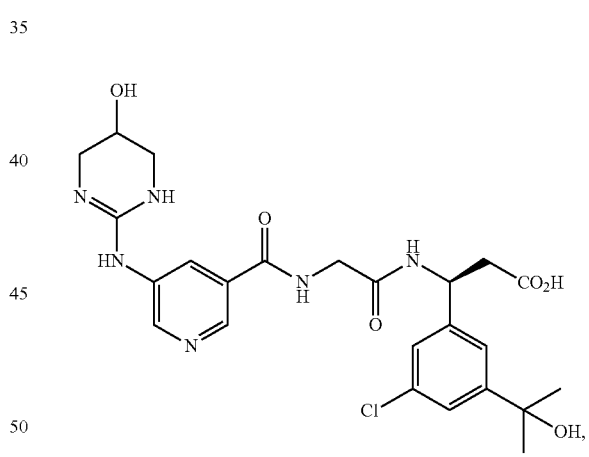
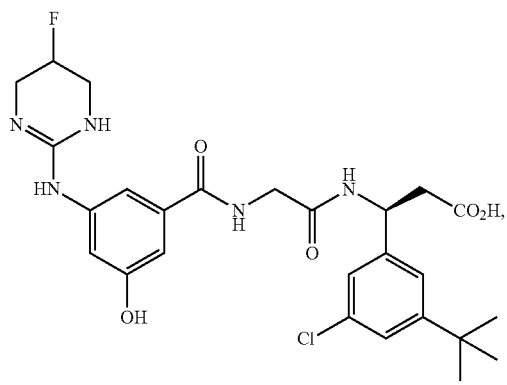
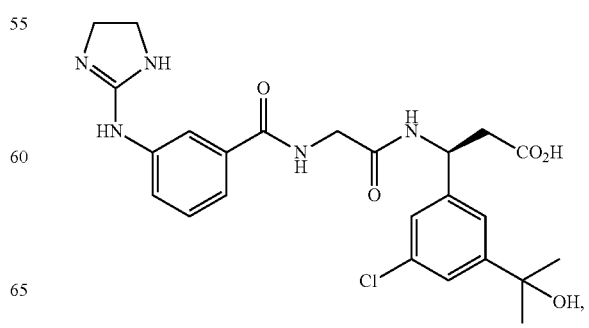

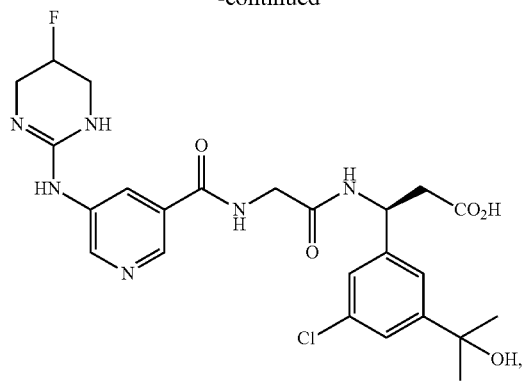
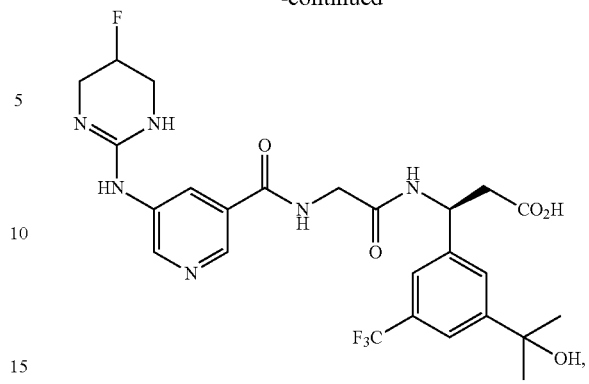
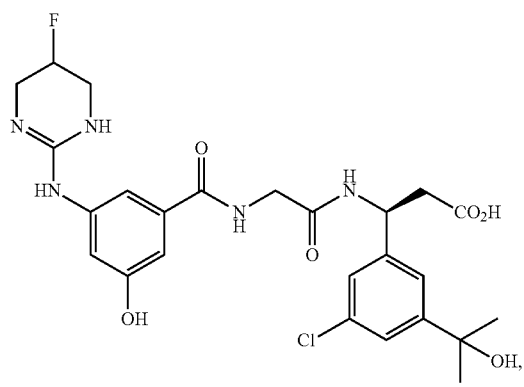
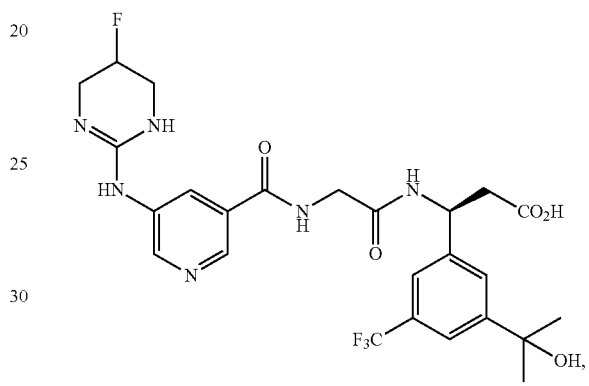
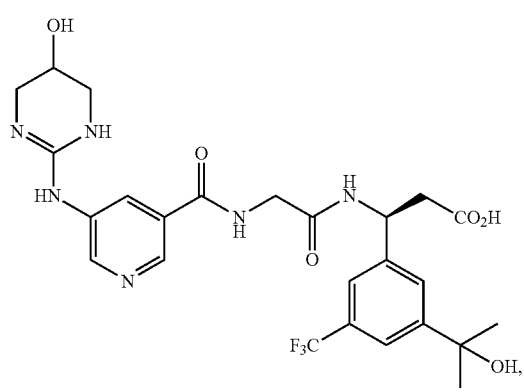
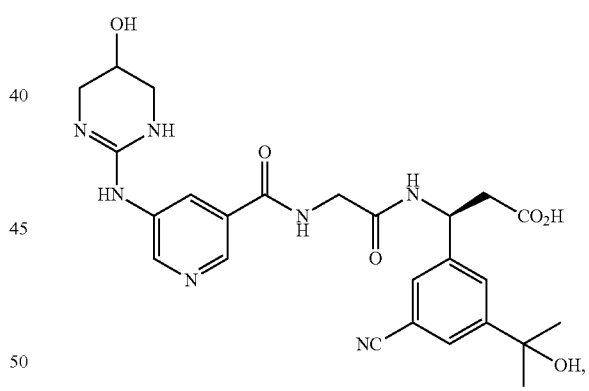
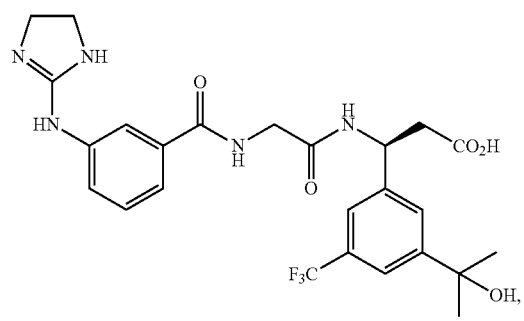
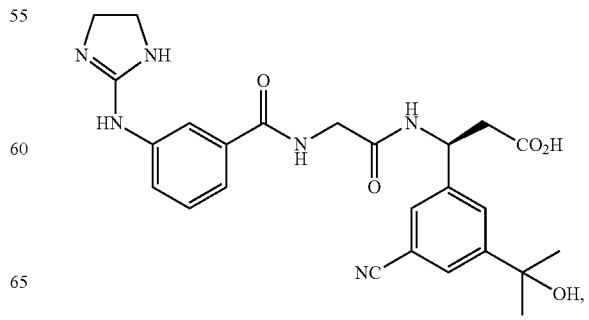

25
-continued
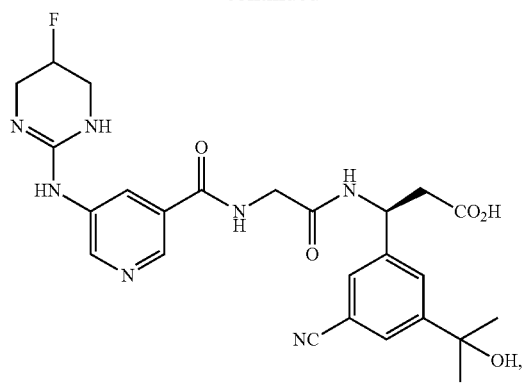
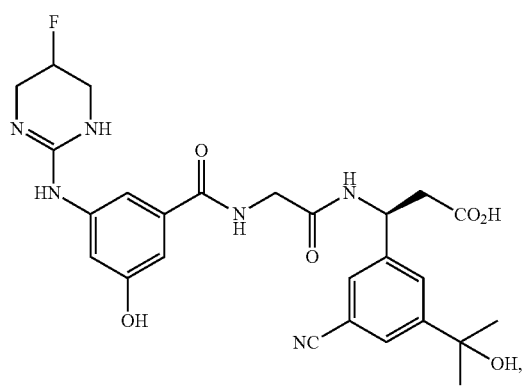
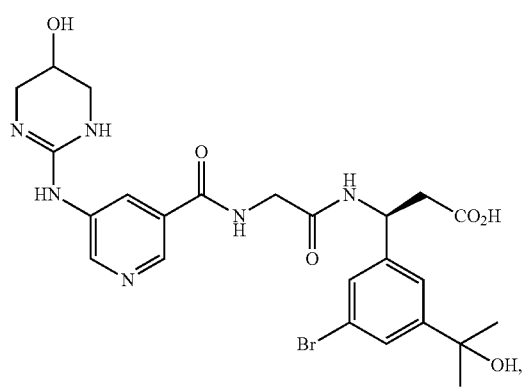
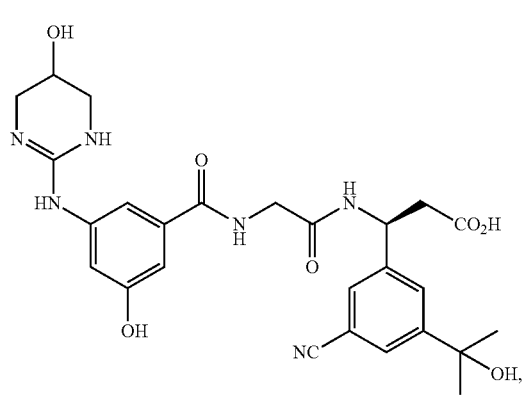
26
-continued
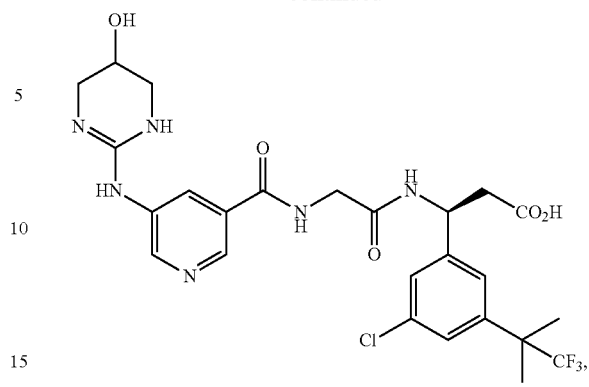
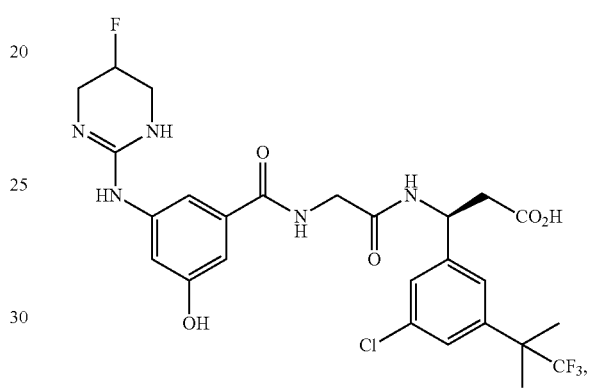
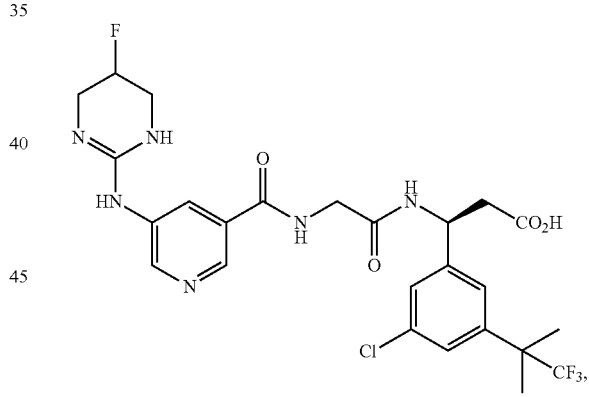
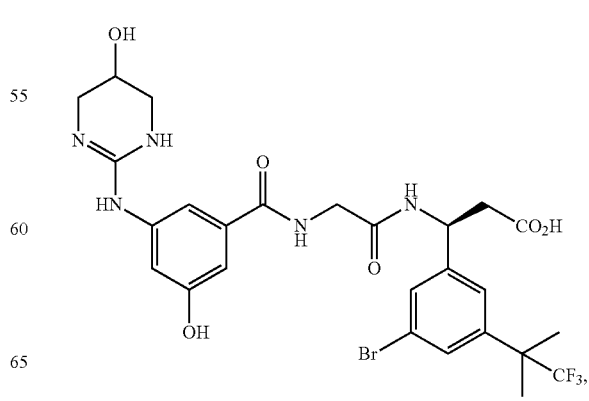

27
-continued
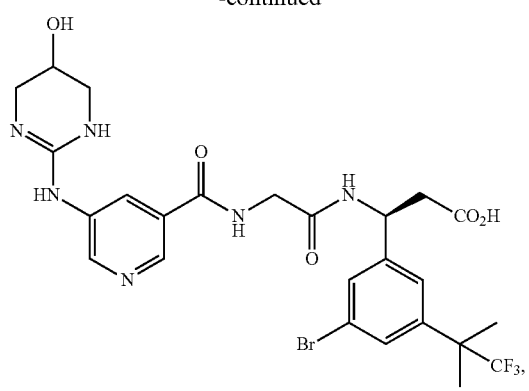
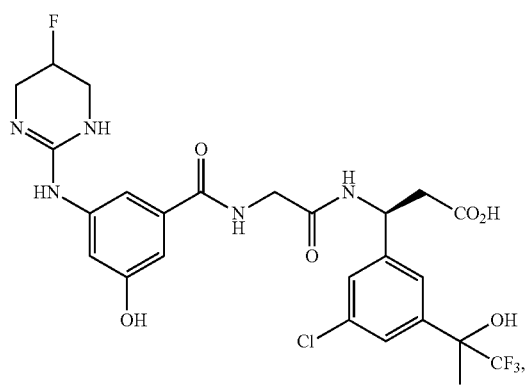
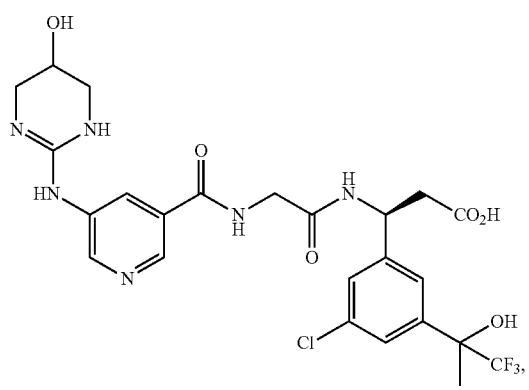
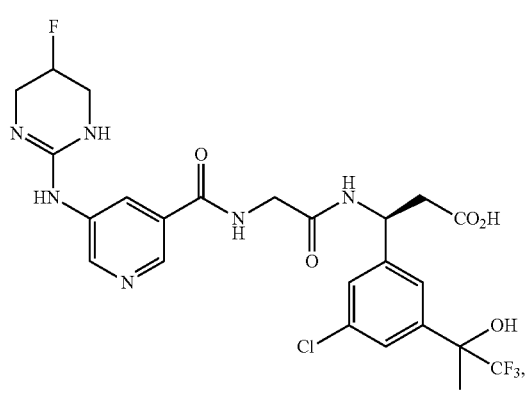
28
-continued
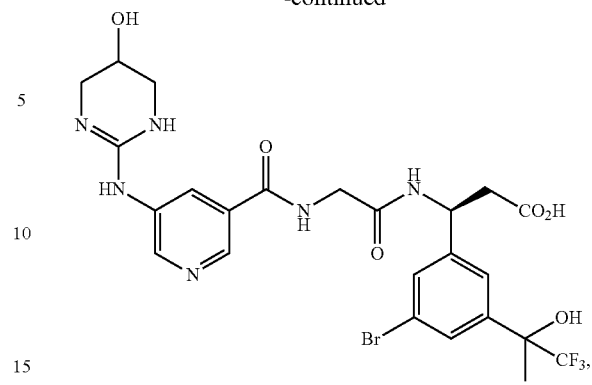
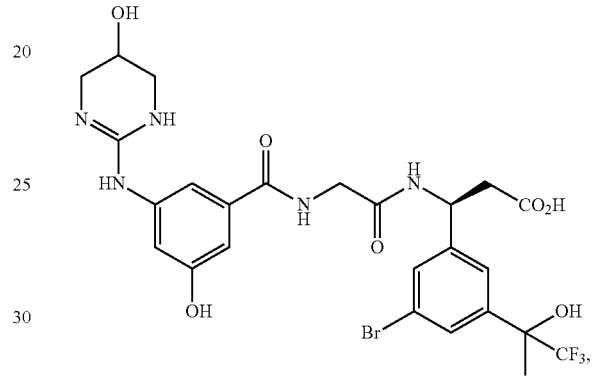
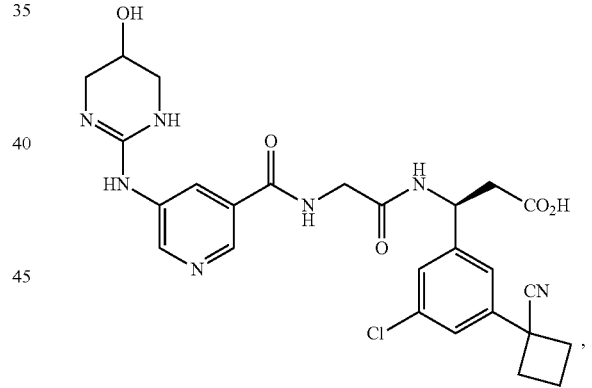
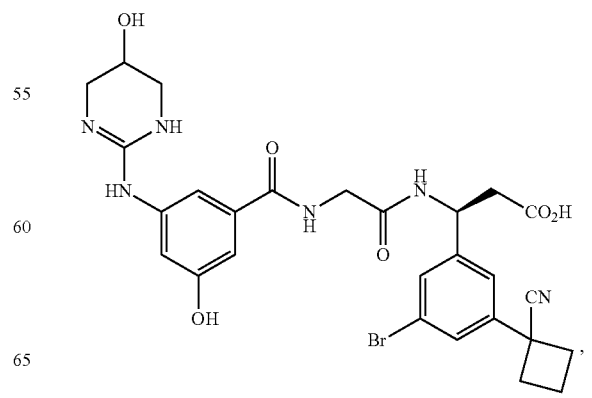

-continued
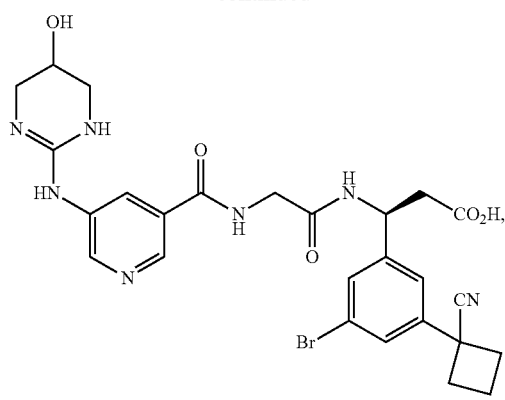
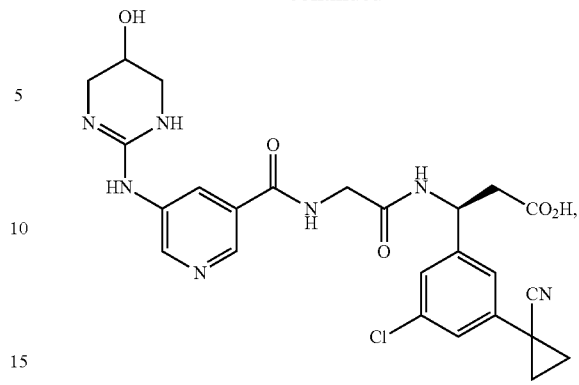
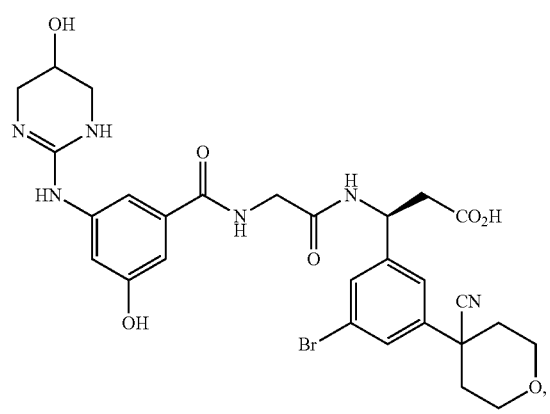
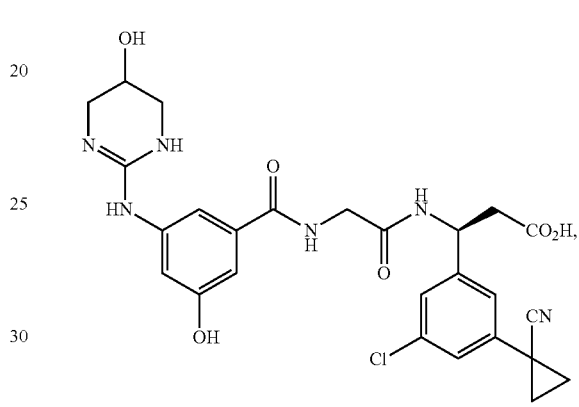
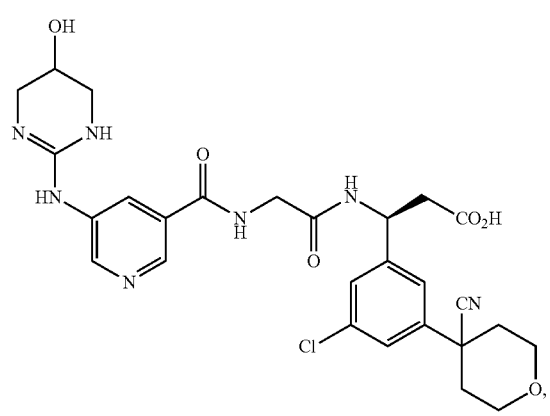
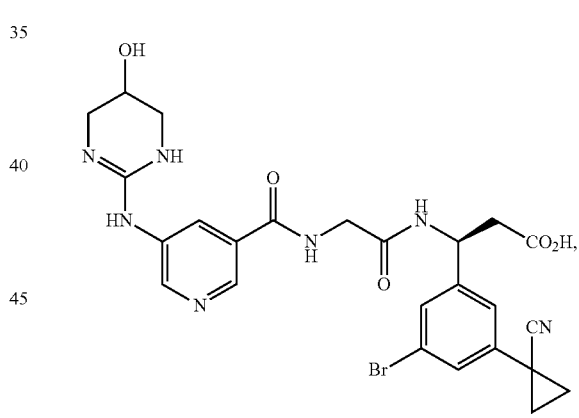
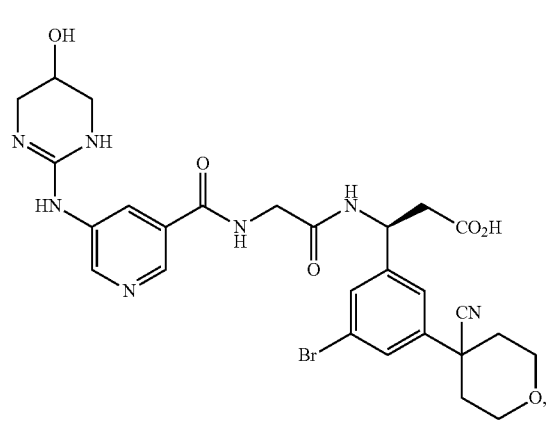
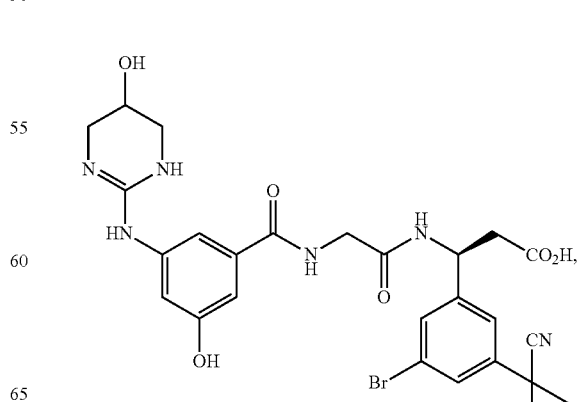

-continued
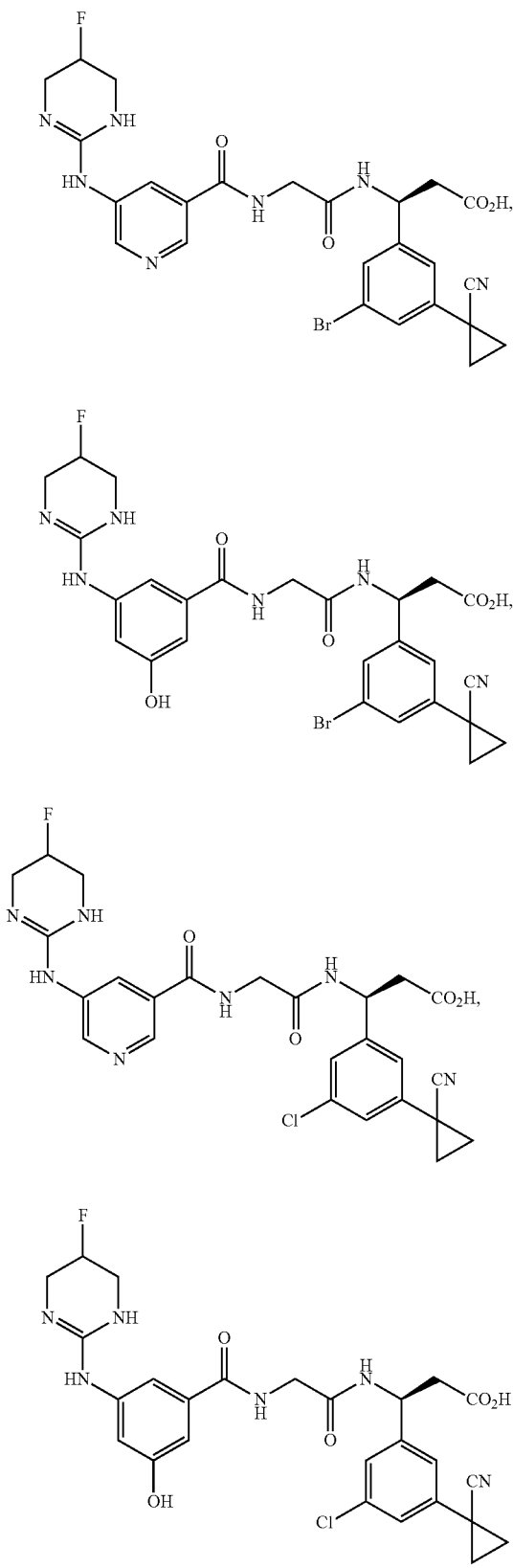
or a pharmaceutically acceptable salt or tautomer thereof.
In other embodiments, the compound is further defined as:
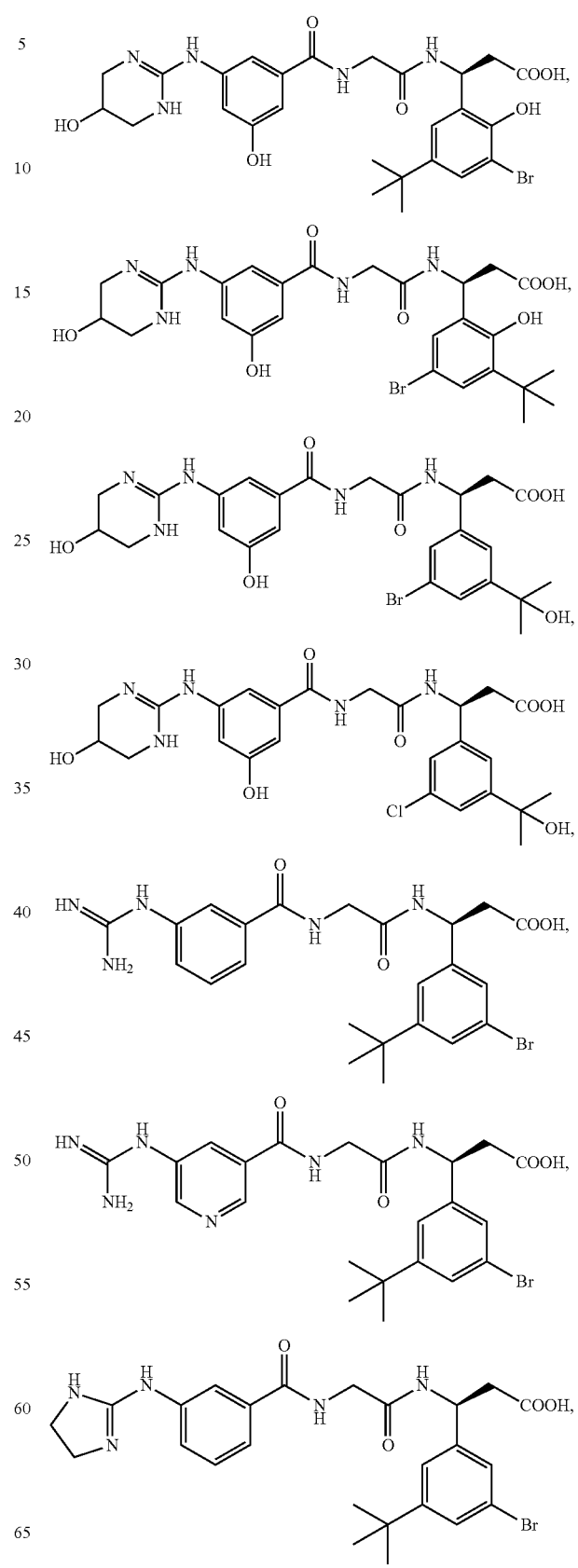
and 33
-continued
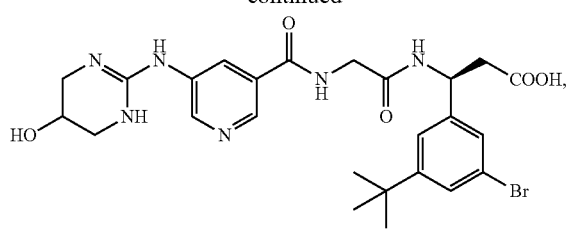
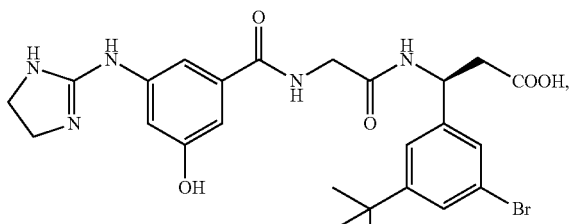
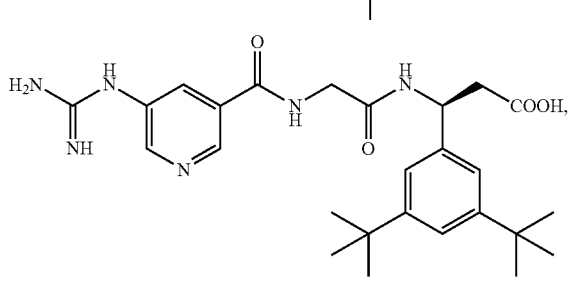
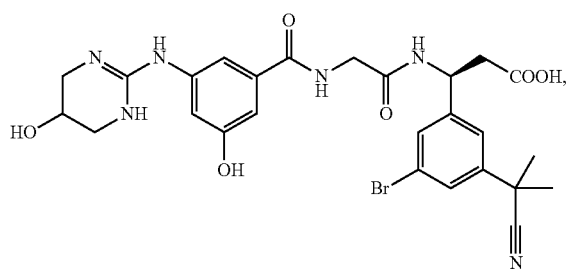
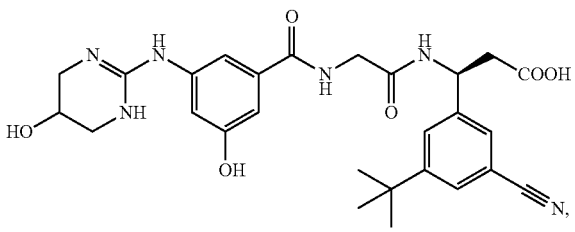
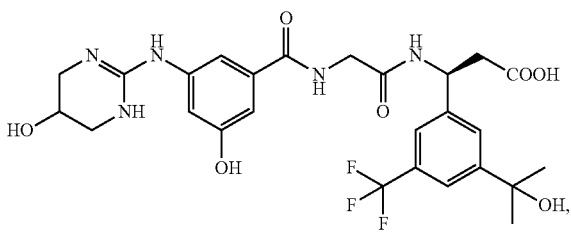
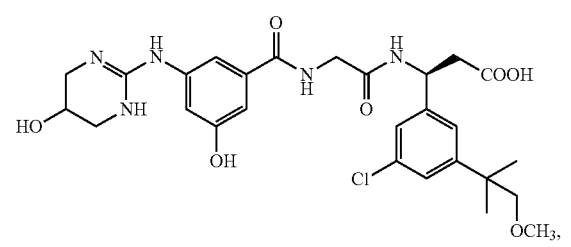
34
-continued
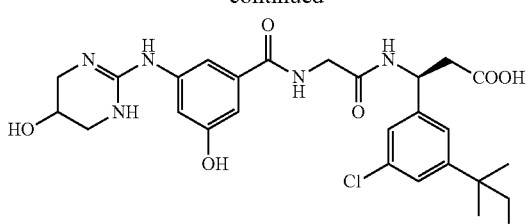
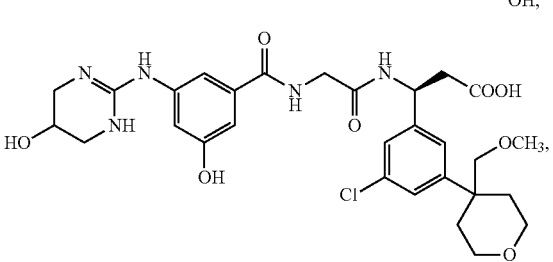
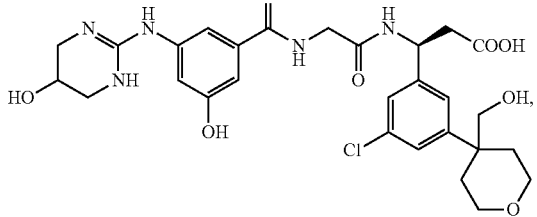
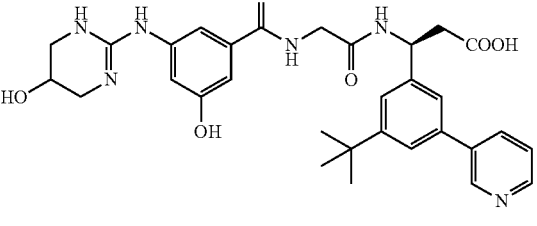
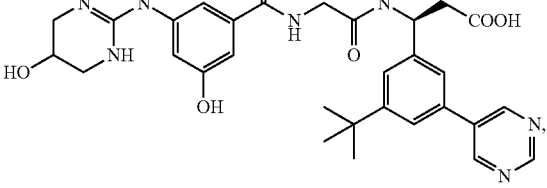
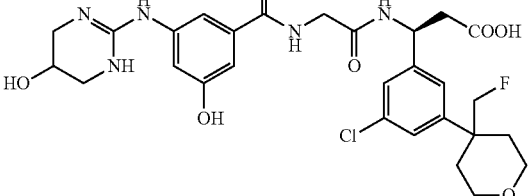
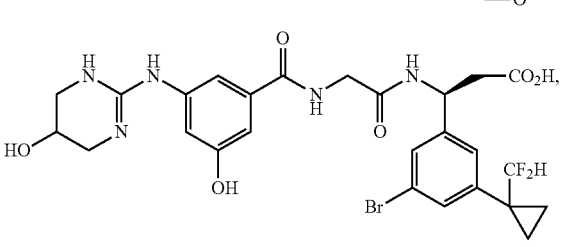

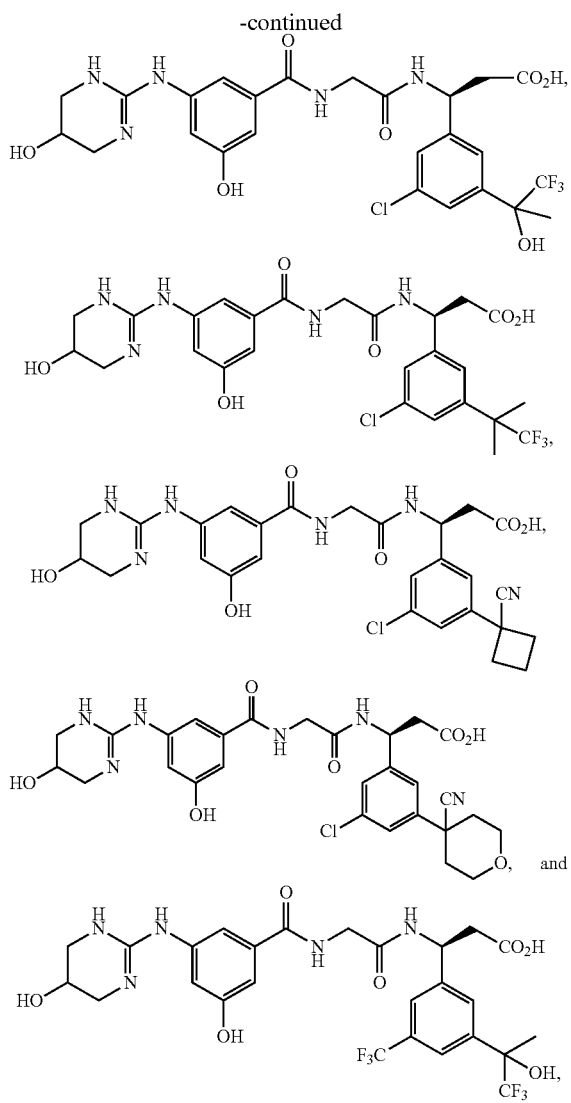

or a pharmaceutically acceptable salt or tautomer thereof.

In some embodiments, the compound of claim 1 of the formula shown in Table A or a pharmaceutically acceptable salt or tautomer thereof.

In another aspect, the present invention provides a pharmaceutical composition comprising: a) the compound of the present invention; and b) an excipient.

In yet another aspect, the present invention provides a method of treating and/or preventing a disease or a disorder in a patient in need thereof, comprising administering to the patient a compound of the present invention in an amount sufficient to treat and/or prevent the disease or disorder. In some embodiments, the disease or disorder is associated with angiogenesis. In other embodiments, the disease or disorder is associated with fibrosis. In other embodiments, the disease or disorder is associated with fibrosis and/or angiogenesis. In other embodiments, the disease or disorder is pulmonary, liver, renal, cardiac, and pancreatic fibrosis, scleroderma, scarring, retinopathy of prematurity, familial exudative vitreoretinopathy, proliferative vitreoretinopathies, macular degeneration, diabetic retinopathy, cancer, osteoporosis, autoimmune diseases, humoral hypercalcemia of malignancy, Paget's disease, periodontal disease, psoriasis, arthritis, restenosis, and infection. In other embodiments, the disease or disorder is pulmonary fibrosis. In other embodiments, the disease or disorder is liver fibrosis. In other embodiments, the disease or disorder is cardiac fibrosis. In other embodiments, the disease or disorder is renal fibrosis. In other embodiments, the disease or disorder is pancreatic fibrosis. In other embodiments, the disease or disorder is scleroderma. In other embodiments, the disease or disorder is scarring. In some embodiments, the scarring is dermal scarring. In other embodiments, the scarring is retinal scarring. In other embodiments, wherein the scarring is corneal scarring. In other embodiments, the disease or disorder is retinopathy of prematurity. In other embodiments, the disease or disorder is familial exudative vitreoretinopathy. In other embodiments, the disease or disorder is proliferative vitreoretinopathies. In other embodiments, the disease or disorder is macular degeneration. In other embodiments, the disease or disorder is diabetic retinopathy. In other embodiments, the disease or disorder is cancer. In some embodiments, the cancer includes solid tumor growth or neoplasia. In other embodiments, the cancer includes tumor metathesis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma. In other embodiments, the disease or disorder is osteoporosis. In other embodiments, the disease or disorder is an autoimmune disease. In some embodiments, the autoimmune disorder is multiple sclerosis. In other embodiments, the disease or disorder is humoral hypercalcemia of malignancy. In other embodiments, the disease or disorder is Paget's disease. In other embodiments, the disease or disorder is periodontal disease. In other embodiments, the disease or disorder is psoriasis. In other embodiments, the disease or disorder is arthritis. In some embodiments, the arthritis is rheumatoid arthritis. In other embodiments, the disease or disorder is restenosis. In other embodiments, the disease or disorder is an infection. In some embodiments, the patient is a human, monkey, cow, horse, sheep, goat, dog, cat, mouse, rat, guinea pig, or transgenic species thereof. In other embodiments, the patient is a monkey, cow, horse, sheep, goat, dog, cat, mouse, rat, or guinea pig. In other embodiments, the patient is a human.

In another aspect, the present invention provides a compound of the formula:

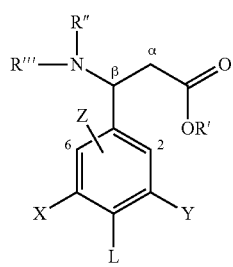

wherein: R' is —H, alkyl$_{(C \leq 8)}$ substituted alkyl$_{(C \leq 8)}$, alkylaryl$_{(C \leq 12)}$, and silyl; R" and R''' are each independently —H, alkyl$_{(C \leq 8)}$ substituted alkyl$_{(C \leq 8)}$, alkylaryl$_{(C \leq 12)}$, substituted alkylaryl$_{(C \leq 12)}$, acyl, tert-butyloxycarbonyl, 9-fluorenylmethyloxycarbonyl, carbamate, carbobenzyloxy, or benzoyl; X is: hydrogen, halo, or cyano; alkyl$_{(C \leq 12)}$, alkoxy$_{(C \leq 12)}$, aryl$_{(C \leq 12)}$, aralkyl$_{(C \leq 12)}$, heteroaryl$_{(C \leq 8)}$, heterocycloalkyl$_{(C \leq 12)}$, aryloxy$_{(C \leq 12)}$, acyloxy$_{(C \leq 12)}$, or a substituted version of any of the groups; —(CH$_2$)$_{n'}$—CO$_2$-alkyl$_{(C \leq 6)}$, wherein, n' is 0-3;

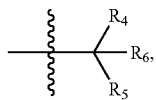

wherein R$_4$ and R$_5$ are each independently alkyl$_{(C \leq 8)}$, substituted alkyl$_{(C \leq 8)}$, or —CH$_2$O-alkyl$_{(C \leq 8)}$; R$_6$ is —OH, —CN, —NH$_2$, —CF$_3$, —CF$_2$H, —CH$_2$F, —CO$_2$H, —CO$_2$-alkyl$_{(C \leq 8)}$, —C(=O)NH$_2$, —CH$_2$OH, —CH$_2$O-alkyl$_{(C \leq 8)}$, or alkoxy$_{(C \leq 8)}$, provided that where R$_4$ and R$_5$ are each —CF$_3$, then R$_6$ is —OH, alkoxy$_{(C \leq 8)}$ or —NH$_2$;

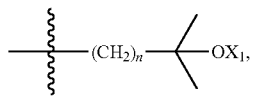

wherein n is 1 or 2 and X$_1$ is —H or alkyl$_{(C \leq 8)}$; or

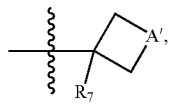

wherein: A' is a covalent bond, thereby forming a cyclopropane ring, —CF$_2$—, —O—, alkanediyl$_{(C \leq 6)}$ or alkoxydiyl$_{(C \leq 8)}$; and R$_7$ is —OH, —CN, —NH$_2$, —CO$_2$H, —CO$_2$-alkyl$_{(C \leq 8)}$, —C(=O)NH$_2$, —CF$_3$, —CF$_2$H, —CH$_2$F, —CH$_2$OH, —CH$_2$O-alkyl$_{(C \leq 8)}$, alkyl$_{(C \leq 8)}$ or alkoxy$_{(C \leq 8)}$; Y is: t-butyl, neopentyl, norbornyl, or adamantyl;

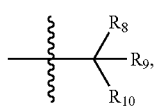

wherein R$_8$ and R$_9$ are each independently alkyl$_{(C \leq 8)}$, substituted alkyl$_{(C \leq 8)}$, or —CH$_2$O-alkyl$_{(C \leq 8)}$; R$_{10}$ is —OH, —CN, —NH$_2$, —CF$_3$, —CF$_2$H, —CFH$_2$, —CO$_2$H, —CO$_2$-alkyl$_{(C \leq 8)}$, —C(=O)NH$_2$, —CH$_2$OH, —CH$_2$O-alkyl$_{(C \leq 8)}$, or alkoxy$_{(C \leq 8)}$, provided that where R$_8$ and R$_9$ are each —CF$_3$, then R$_{10}$ is —OH, alkoxy$_{(C \leq 8)}$ or —NH$_2$;

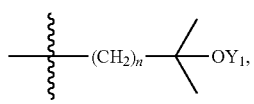

wherein n" is 1 or 2 and Y$_1$ is —H or alkyl$_{(C \leq 8)}$; or

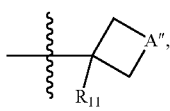

wherein: A" is a covalent bond, thereby forming a cyclopropane ring, —O—, —CF$_2$—, alkanediyl$_{(C \leq 6)}$ or alkoxydiyl$_{(C \leq 8)}$; and R$_{11}$ is —OH, —CN, —NH$_2$, —CO$_2$H, —CO$_2$-alkyl$_{(C \leq 8)}$, —C(=O)NH$_2$, —CF$_3$, —CF$_2$H, —CH$_2$F, —CH$_2$OH, —CH$_2$O-alkyl$_{(C \leq 8)}$, alkyl$_{(C \leq 8)}$ or alkoxy$_{(C \leq 8)}$; L is hydrogen, hydroxy or alkoxy$_{(C \leq 8)}$; and Z is hydrogen, fluorine, or hydroxy and is attached to either carbon atom 2 or 6; or a salt or tautomer thereof. In other embodiments, the present invention provides a compound of the formula:

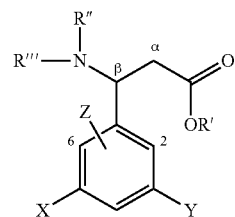

wherein: R' is —H, alkyl$_{(C \leq 8)}$ substituted alkyl$_{(C \leq 8)}$, alkylaryl$_{(C \leq 12)}$, and silyl; R" and R''' are each independently —H, alkyl$_{(C \leq 8)}$ substituted alkyl$_{(C \leq 8)}$, alkylaryl$_{(C \leq 12)}$, substituted alkylaryl$_{(C \leq 12)}$, acyl, tert-butyloxycarbonyl, 9-fluorenylmethyloxycarbonyl, carbamate, carbobenzyloxy, or benzoyl; X is: hydrogen, halo, or cyano; alkyl$_{(C \leq 12)}$, alkoxy$_{(C \leq 12)}$, aryl$_{(C \leq 12)}$, aralkyl$_{(C \leq 12)}$, heteroaryl$_{(C \leq 8)}$, heterocycloalkyl$_{(C \leq 12)}$, aryloxy$_{(C \leq 12)}$, acyloxy$_{(C \leq 12)}$, or a substituted version of any of the groups; —(CH$_2$)$_{n'}$—CO$_2$-alkyl$_{(C \leq 6)}$, wherein, n' is 0-3;

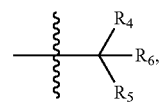

wherein R$_4$ and R$_5$ are each independently alkyl$_{(C \leq 8)}$, substituted alkyl$_{(C \leq 8)}$, or —CH$_2$O-alkyl$_{(C \leq 8)}$; R$_6$ is —OH, —CN, —NH$_2$, —CF$_3$, —CF$_2$H, —CH$_2$F, —CO$_2$H, —CO$_2$-alkyl$_{(C \leq 8)}$, —C(=O)NH$_2$, —CH$_2$OH, —CH$_2$O-alkyl$_{(C \leq 8)}$, or alkoxy$_{(C \leq 8)}$, provided that where R$_4$ and R$_5$ are each —CF$_3$, then R$_6$ is —OH, alkoxy$_{(C \leq 8)}$ or —NH$_2$;

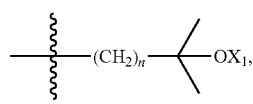

wherein n is 1 or 2 and X$_1$ is —H or alkyl$_{(C \leq 8)}$; or

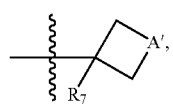

wherein: A' is a covalent bond, thereby forming a cyclopropane ring, —CF$_2$—, —O—, alkanediyl$_{(C \leq 6)}$ or alkoxydiyl$_{(C \leq 8)}$; and R$_7$ is —OH, —CN, —NH$_2$, —CO$_2$H, —CO$_2$-alkyl$_{(C \leq 8)}$, —C(=O)NH$_2$, —CF$_3$, —CF$_2$H, —CH$_2$F, —CH$_2$OH, —CH$_2$O-alkyl$_{(C \leq 8)}$, alkyl$_{(C \leq 8)}$ or alkoxy$_{(C \leq 8)}$; Y is: t-butyl, neopentyl, norbornyl, or adamantyl;

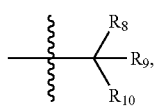

wherein $R_8$ and $R_9$ are each independently alkyl$_{(C\le8)}$, substituted alkyl$_{(C\le8)}$, or —CH$_2$O-alkyl$_{(C\le8)}$; $R_{10}$ is —OH, —CN, —NH$_2$, —CF$_3$, —CF$_2$H, —CFH$_2$, —CO$_2$H, —CO$_2$-alkyl$_{(C\le8)}$, —C(=O)NH$_2$, —CH$_2$OH, —CH$_2$O-alkyl$_{(C\le8)}$, or alkoxy$_{(C\le8)}$, provided that where $R_8$ and $R_9$ are each —CF$_3$, then $R_{10}$ is —OH, alkoxy$_{(C\le8)}$ or —NH$_2$;

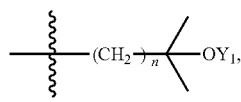

wherein n″ is 1 or 2 and $Y_1$ is —H or alkyl$_{(C\le8)}$; or

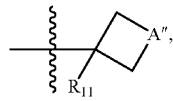

wherein: A″ is a covalent bond, thereby forming a cyclopropane ring, —O—, —CF$_2$—, alkanediyl$_{(C\le6)}$ or alkoxydiyl$_{(C\le8)}$; and $R_{11}$ is —OH, —CN, —NH$_2$, —CO$_2$H, —CO$_2$-alkyl$_{(C\le8)}$, —C(=O)NH$_2$, —CF$_3$, —CF$_2$H, —CH$_2$F, —CH$_2$OH, —CH$_2$O-alkyl$_{(C\le8)}$, alkyl$_{(C\le8)}$ or alkoxy$_{(C\le8)}$; L is hydrogen, hydroxy or alkoxy$_{(C\le8)}$; and Z is hydrogen, fluorine, or hydroxy and is attached to either carbon atom 2 or 6; or a salt or tautomer thereof. In some embodiments, the compound is limited by the proviso that X and Y are not both each t-butyl; and further provided that Z is hydrogen, and X is bromo or iodo, then Y is not t-butyl. In some embodiments, the carbon atom labeled β is in the R configuration. In other embodiments, the carbon atom labeled β is in the S configuration. In some embodiments, R' is —H. In other embodiments, R' is alkyl$_{(C\le8)}$. In some embodiments, R' is ethyl. In some embodiments, R″ is —H. In some embodiments, R‴ is —H. In other embodiments, R″ and R‴ are both —H. In some embodiments, L is hydrogen. In some embodiments, Z is hydrogen. In other embodiments, Z is hydroxy. In other embodiments, Z is hydroxyl and attached to the carbon labeled 2. In other embodiments, Z is hydroxyl and attached to the carbon labeled 6. In some embodiments, X is halo. In some embodiments, X is chloro. In other embodiments, X is bromo. In other embodiments, X is alkyl$_{(C\le12)}$ or substituted alkyl$_{(C\le12)}$. In some embodiments, X is alkyl$_{(C\le12)}$. In some embodiments, X is t-butyl. In other embodiments, X is substituted alkyl$_{(C\le12)}$. In some embodiments, X is trifluoromethyl. In other embodiments, X is heteroaryl$_{(C\le8)}$. In some embodiments, X is 3-pyridinyl. In other embodiments, X is 3-pyrimidyl. In other embodiments, X is cyano. In some embodiments, Y is t-butyl. In other embodiments, Y is

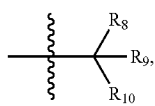

wherein $R_8$ and $R_9$ are each independently alkyl$_{(C\le8)}$, substituted alkyl$_{(C\le8)}$, or —CH$_2$O-alkyl$_{(C\le8)}$ and $R_{10}$ is —OH, —CN, —NH$_2$, —CF$_3$, —CF$_2$H, —CFH$_2$, —CO$_2$H, —CO$_2$-alkyl$_{(C\le8)}$, —C(=O)NH$_2$, —CH$_2$OH, —CH$_2$O-alkyl$_{(C\le8)}$, or alkoxy$_{(C\le8)}$, provided that where $R_8$ and $R_9$ are each —CF$_3$, then $R_{10}$ is —OH, alkoxy$_{(C\le8)}$ or —NH$_2$. In other embodiments, $R_8$ is alkyl$_{(C\le8)}$. In some embodiments, $R_8$ is methyl. In some embodiments, $R_9$ is alkyl$_{(C\le8)}$ or substituted alkyl$_{(C\le8)}$. In some embodiments, $R_9$ is alkyl$_{(C\le8)}$. In some embodiments, $R_9$ is methyl. In other embodiments, $R_9$ is substituted alkyl$_{(C\le8)}$. In some embodiments, $R_9$ is trifluoromethyl. In some embodiments, $R_{10}$ is —OH, —CN, —CF$_3$, —CH$_2$OH, or —CH$_2$O-alkyl$_{(C\le8)}$. In some embodiments, $R_{10}$ is —OH. In other embodiments, $R_{10}$ is —CN. In other embodiments, $R_{10}$ is —CH$_2$OH. In other embodiments, $R_{10}$ is —CF$_3$. In other embodiments, $R_{10}$ is —CH$_2$O-alkyl$_{(C\le8)}$. In other embodiments, $R_{10}$ is —CH$_2$O—CH$_3$. In other embodiments, Y is 2-hydroxy-isopropyl. In other embodiments, Y is

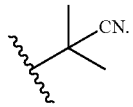 [SMILES: *C(C)(C)C#N]

In other embodiments, Y is

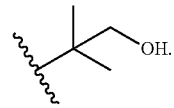 [SMILES: *C(C)(C)CO]

In other embodiments, Y is

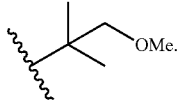

In other embodiments, Y is

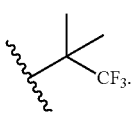

In other embodiments, Y is

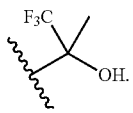

In other embodiments, Y is

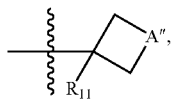

wherein: A" is a covalent bond, thereby forming a cyclopropane ring, —O—, —CF$_2$, alkanediyl$_{(C\leq6)}$ or alkoxydiyl$_{(C\leq8)}$; and R$_{11}$ is —OH, —CN, —NH$_2$, —CO$_2$H, —CO$_2$-alkyl$_{(C\leq8)}$, —C(=O)NH$_2$, —CF$_3$, —CF$_2$H, —CH$_2$F, —CH$_2$OH, —CH$_2$O-alkyl$_{(C\leq8)}$, alkyl$_{(C\leq8)}$ or alkoxy$_{(C\leq8)}$. In some embodiments, A" is a covalent bond, thereby forming a cyclopropane ring. In other embodiments, A" is alkanediyl$_{(C\leq6)}$. In some embodiments, A" is —CH$_2$—. In other embodiments, A" is alkoxydiyl$_{(C\leq8)}$. In some embodiments, A" is —CH$_2$—O—CH$_2$—. In some embodiments, R$_{11}$ is —CN. In other embodiments, R$_{11}$ is —CHF$_2$. In other embodiments, R$_{11}$ is —CH$_2$F. In other embodiments, R$_{11}$ is —CH$_2$OH. In other embodiments, R$_{11}$ is —CH$_2$O-alkyl$_{(C\leq8)}$. In other embodiments, R$_H$ is —CH$_2$O—CH$_3$. In other embodiments, Y is

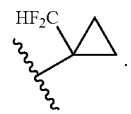

In other embodiments, Y is

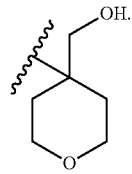

In other embodiments, Y is

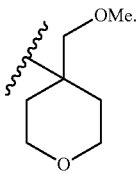

In other embodiments, Y is

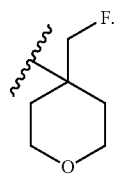

In other embodiments, Y is

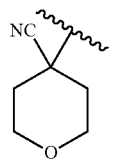

In other embodiments, Y is

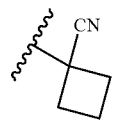

In some embodiments, the compound is further defined as:

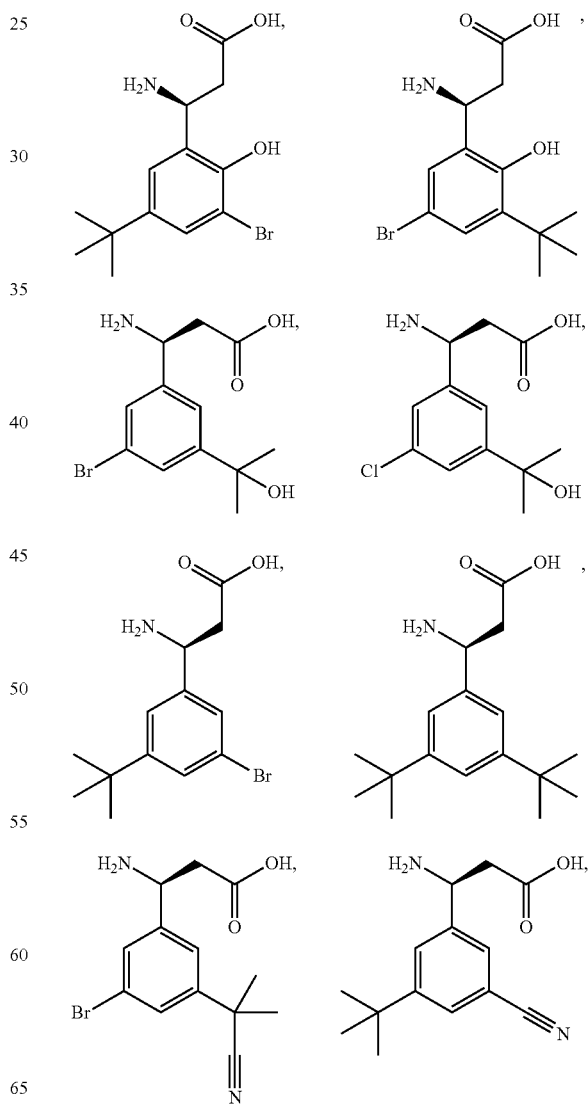

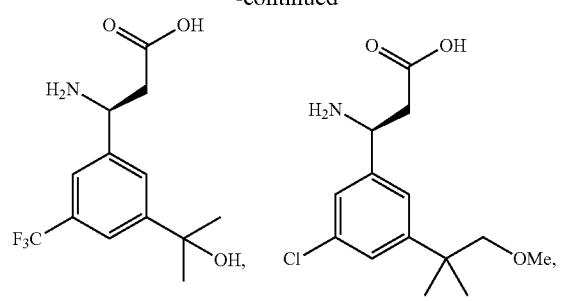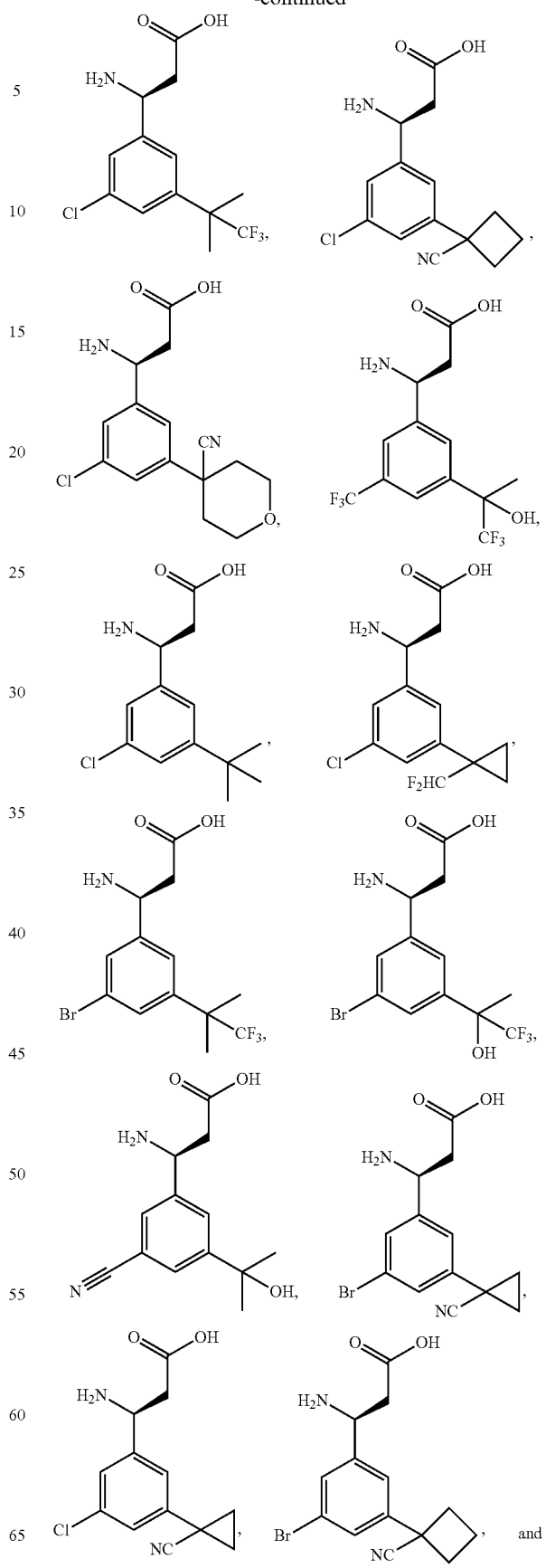

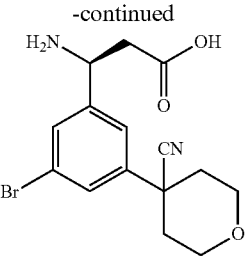
or a salt or tautomer thereof. In other embodiments, the compound is further defined as:
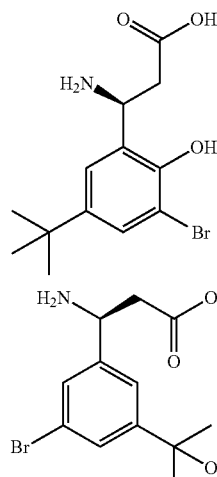 
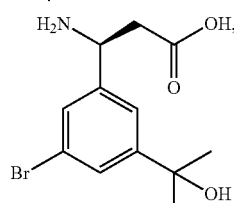 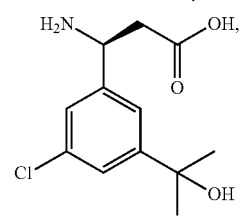
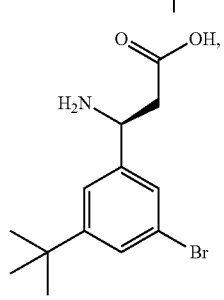 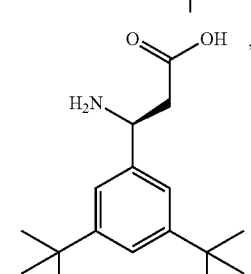
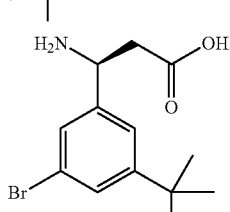 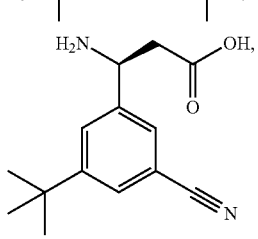
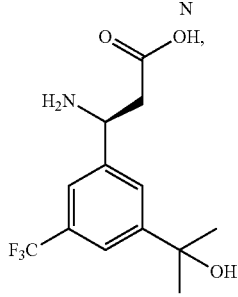 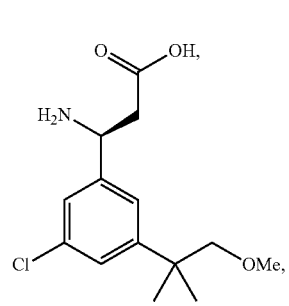
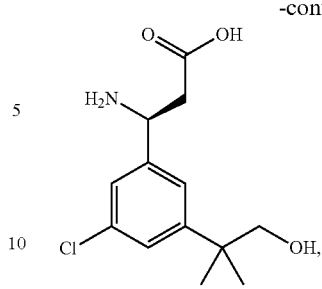
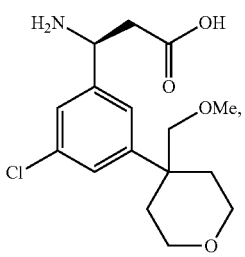
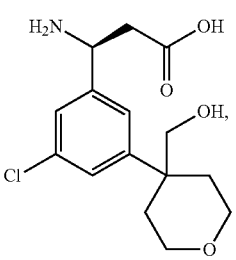 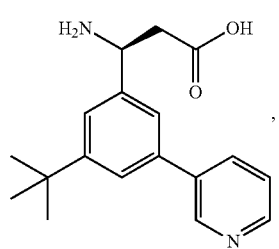
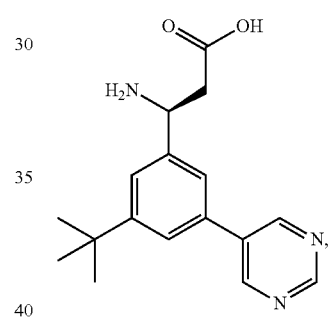 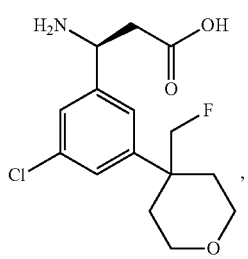
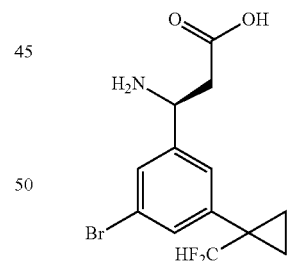 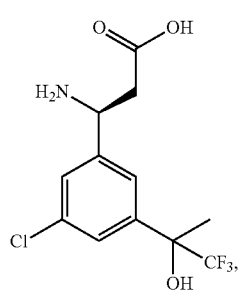
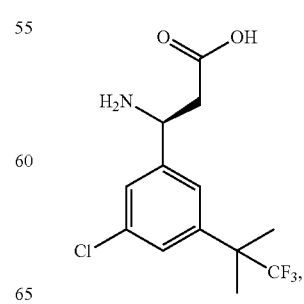 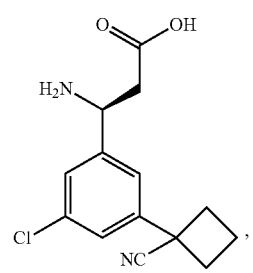

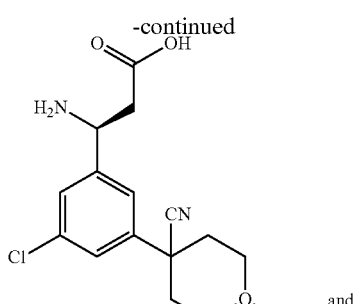
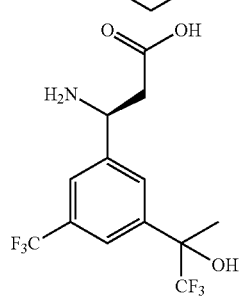
or a salt or tautomer thereof. In other embodiments, the compound is further defined as:
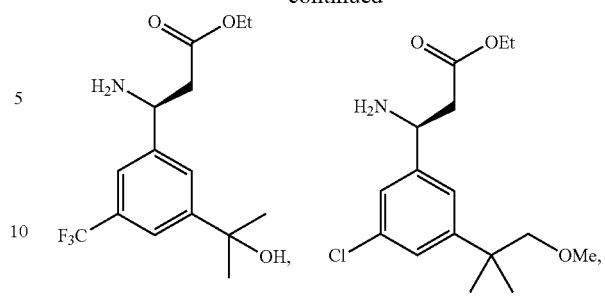
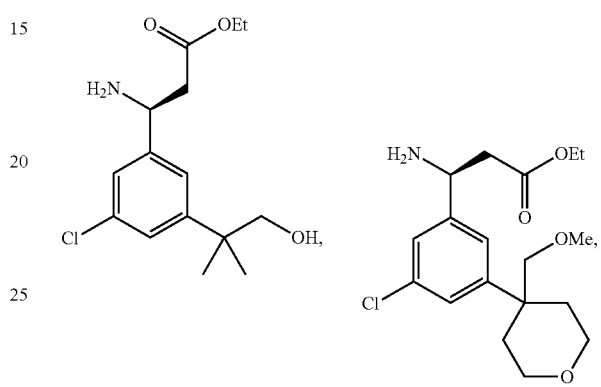
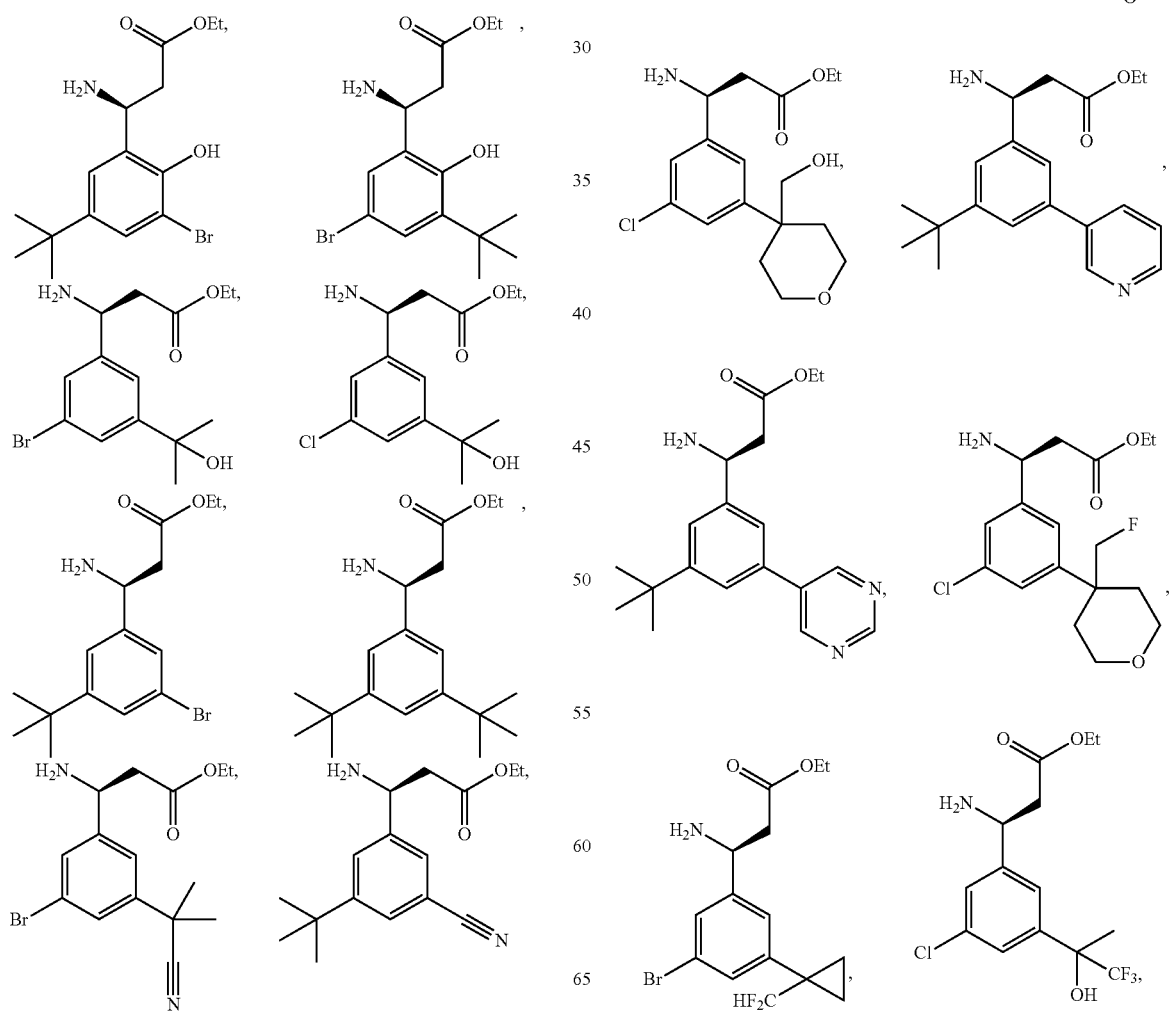

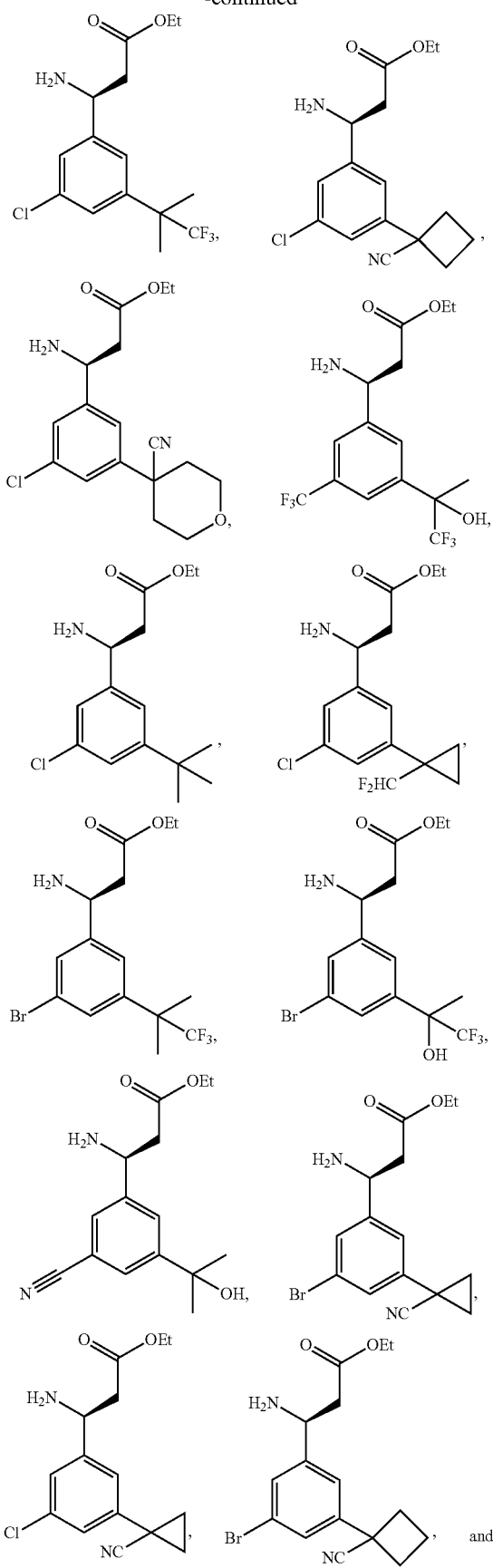
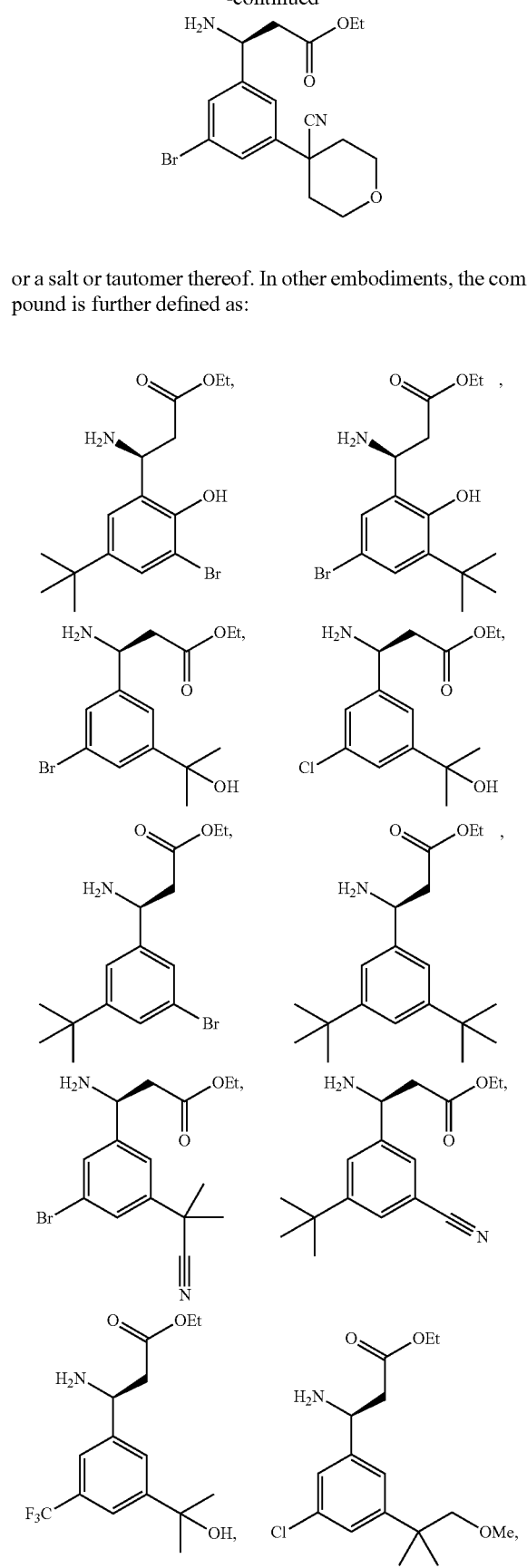
or a salt or tautomer thereof. In other embodiments, the compound is further defined as:

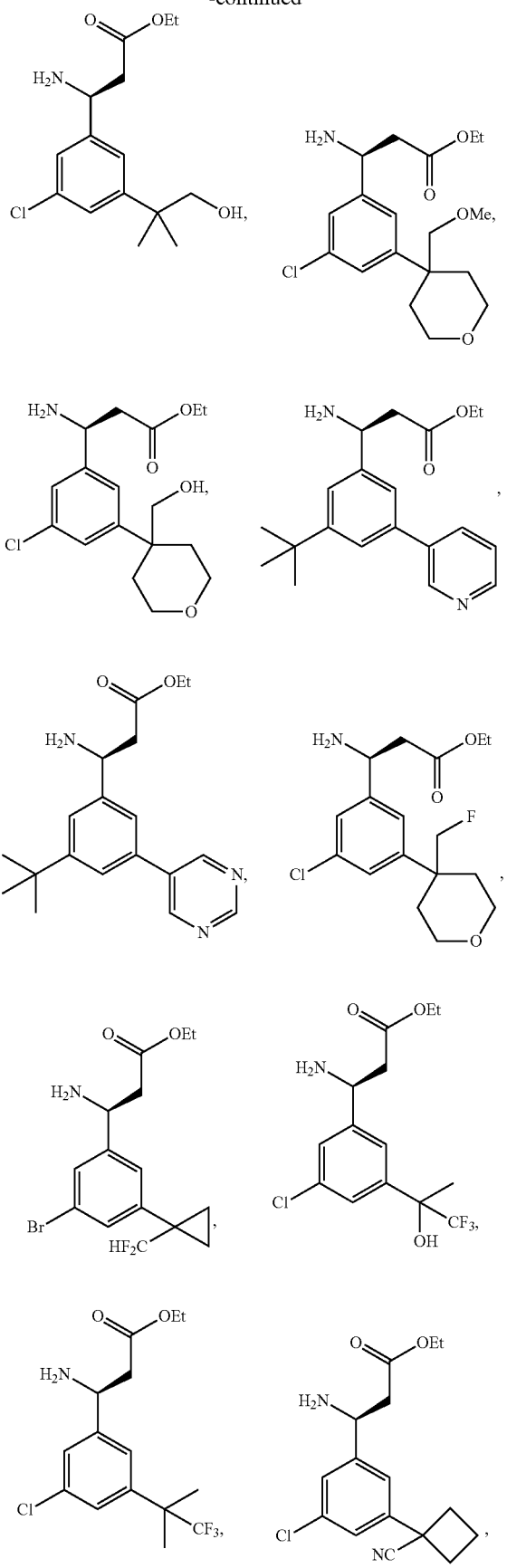

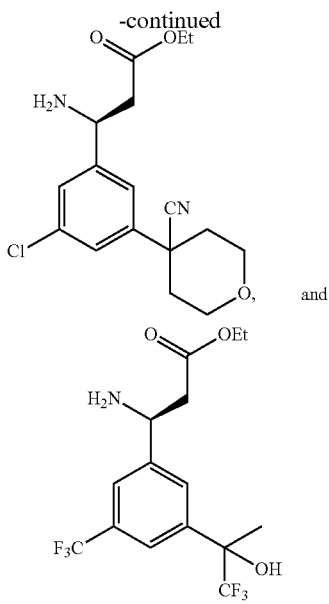

or a salt or tautomer thereof.

In some aspects, the present disclosure contemplates the fact that the bond between the phenyl ring and the amino acid backbone on the β-amino acid is freely rotating. As such, in some aspects, it is contemplated that the structure may rotate such that the X group is on the oriented towards the backbone and the Y is oriented away form the backbone as well as the manner drawn in most commonly in the specification showing the X group on the oriented towards the backbone and the Y oriented away from the backbone as shown in the structures below. The structure:

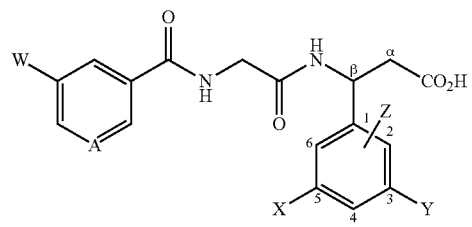

is equivalent to the structure:

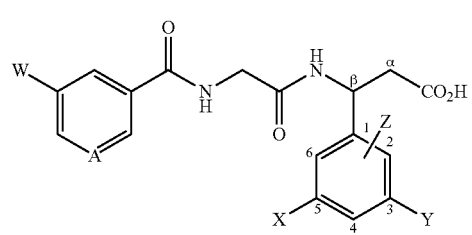

given the free rotation of the bond joining the carbon label β in the backbone and the carbon labeled 1 in the aromatic ring.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with integrin receptor antagonists properties, methods for their manufacture, and methods for their use, including for the treatment and/or prevention of disease.

I. Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol "⹀" represents a single bond or a double bond. Thus, for example, the structure

includes the structures

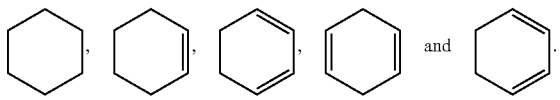

As will be understood by a person of skill in the art, no one such ring atom forms part of more than one double bond. The symbol "⌒", when drawn perpendicularly across a bond indicates a point of attachment of the group. It is noted that the point of attachment is typically only identified in this manner for larger groups in order to assist the reader in rapidly and unambiguously identifying a point of attachment. The symbol "◄▬" means a single bond where the group attached to the thick end of the wedge is "out of the page." The symbol "⫶⫶⫶⫶" means a single bond where the group attached to the thick end of the wedge is "into the page". The symbol "⌒" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

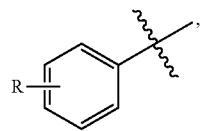

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

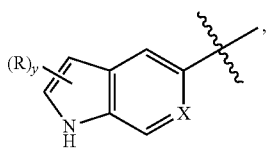

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$(Me), —CH$_2$CH$_3$(Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (Methylene), —CH$_2$CH$_2$—, —CH$_2$C(CH$_3$)$_2$CH$_2$—, —CH$_2$CH$_2$CH$_2$—, and

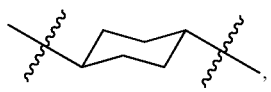 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one non-aromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

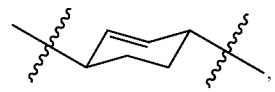 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl) phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

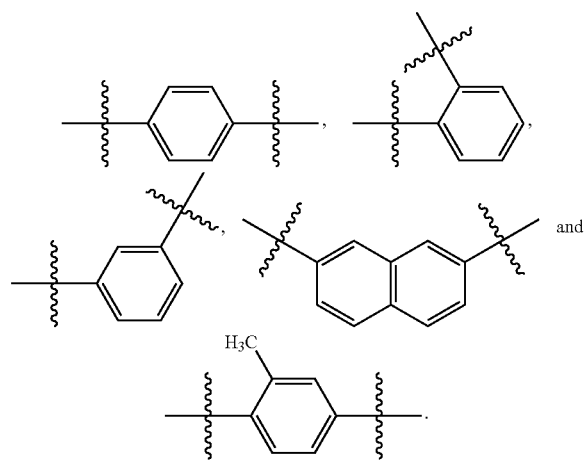

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

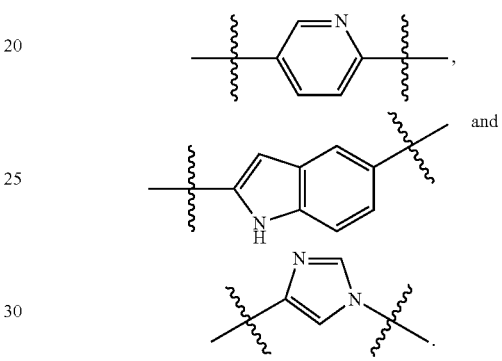

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (Methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (Methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, pig, dog, cat, mouse, rat, guinea pig, or transgenic species thereof. In some embodiments, the patient may also comprise avian, reptilian, amphibian, fish, and insect animals. In other embodiments, the patient may also comprise a zoo animal or an animal raised as a pet such as a dog, cat, mouse, rat, guinea pig, lizard, snake, bird, turtle, frog, or fish. Non-limiting examples of avian subjects include chickens, turkeys, ducks, geese, game birds such as quail and pheasants, and pet birds, such as parakeets, cockatiel, lovebirds, parrots, and macaws. Turtles, terrapins, tortoises, snakes and lizards represent non-limiting examples of reptilian subjects or patients. Frogs, toads, newts and salamanders represent non-limiting examples of amphibian subjects In certain embodiments, the fish subject is represented by the following non-limiting examples: freshwater fish such as tilapia, salmon, catfish, carp, eel, and trout, marine fish such as tuna, cod, herring, sardine, anchovy, flounder, sole, and shark, as well as mollusk and crustacean such as shrimp, prawn, octopus, squid, lobsters, crabs, oysters, hill, and mussels. In certain embodiments, the patient is an insect including the non-limiting examples of honey bees. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylenebis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, ACN or $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, ml is milliliter, mL is milliliter, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methylpyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, and Δ is heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure may be made using the methods outlined below and further described in the Examples section. General synthetic sequences for preparing the compounds useful in the present invention are outlined in Schemes I-XIV. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention. Starting materials and equipment employed were either commercially available prepared by methods previously reported and readily duplicated by those skilled in the art.

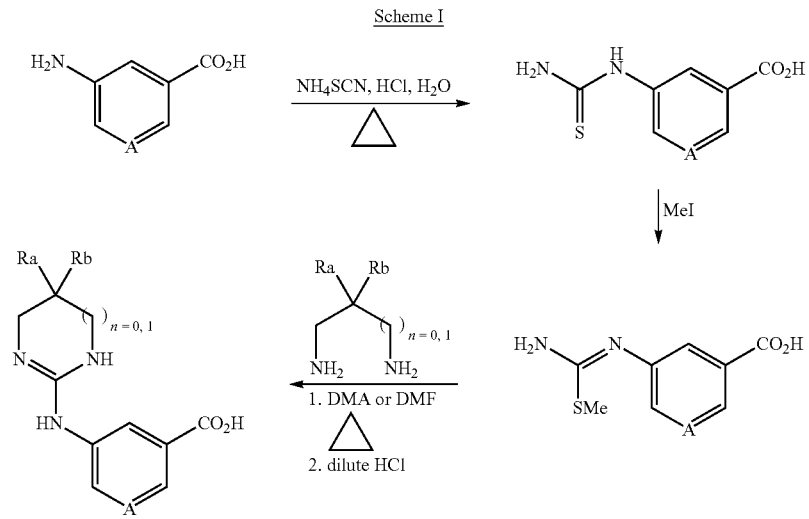

Scheme I

Scheme I illustrates general methodology useful for preparing the cyclic guanidine substituted left hand side aromatic acid portion of Formula I of the present invention which can then be coupled to a gly-β-amino acid ester, or to gly ester first, followed by (after ester hydrolysis) coupling to the appropriate β-amino acid ester. Briefly, in Scheme I, the appropriate amino benzoic (or pyridine) acid is reacted with ammonium thiocyanate in hot dilute hydrochloric to give the resulting 3-thiourea benzoic (or pyridine) acid after normal work-up. The starting amino benzoic (or pyridine) acids are either commercially available or can be converted to such amino benzoic (or pyridine) acids via reduction of the corresponding nitro benzoic (or pyridine) acid, which can be obtained commercially or synthesized by nitration of the appropriate benzoic (or pyridine) acid, followed by reduction to the desired amino benzoic (or pyridine) acid, or by other reported methodologies that are known to those skilled in the art. This thiourea intermediate is converted to the S-methyl derivative by reaction with methyl iodide in ethanol at reflux. The appropriate 1,3-diamino-2-substituted propane, or ethylene diamine, is reacted with this resulting intermediate in hot DMA (or DMF). Upon cooling, a precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5-7 where zwitterionic product precipitates and is isolated by filtration. The HCl salt may be obtained as previously stated or by simply dissolving in dilute hydrochloric acid and concentrating to a solid and drying.

(after ester hydrolysis) coupling to the appropriate β-amino acid ester. This can also be accomplished using other appropriate guanidating reagents known to those skilled in the art, for example using pyrazole-carboxamidine. HCl. The methodology of Scheme IA can be modified using conventional techniques and methods to prepare alternate compounds useful for coupling to the β-amino acids.

Briefly, in Scheme IA, to 3,5-dimethylpyrazole-1-carboxamidine nitrate in dioxane/water and DIEA, is added the appropriate 3-aminobenzoic (or pyridine) acid. The mixture is stirred at reflux, the precipitate filtered, washed and dried. The precipitate is then further slurried in water, acidified with HCl and concentrated. The solvent is removed and the residue slurried in ether and dried to yield the appropriate 3-guanidinobenzoic (or pyridine) acid hydrochloride.

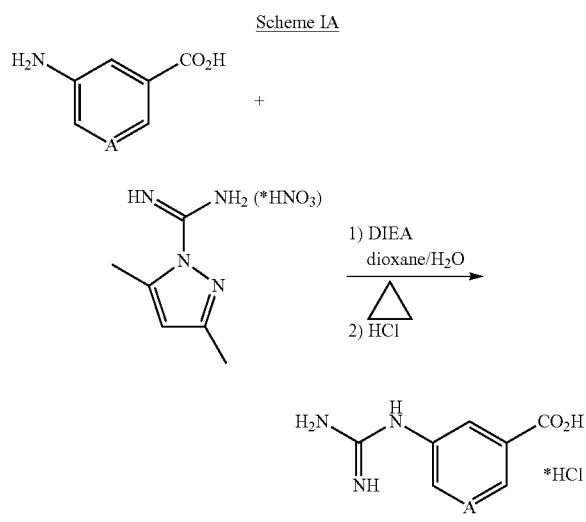

Scheme IA

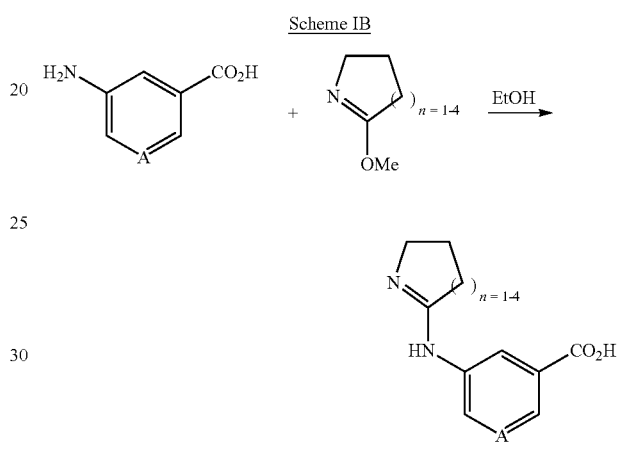

Scheme IB

Scheme IB is illustrative of methodology useful for preparing a cyclic amidine substituted left hand side aromatic acid portion of Formula I, which can then be coupled to a gly-β-amino acid ester, or to gly ester first, followed by (after ester hydrolysis) coupling to the appropriate β-amino acid ester.

Scheme IA is illustrative of methodology useful for preparing the simple guanidine substituted left hand side aromatic acid portion of Formula I, which can then be coupled to a gly-β-amino acid ester, or to gly ester first, followed by Together, Schemes I, IA and IB illustrate general methodologies for the synthesis of left hand side benzoic and pyridine acids consisting of the varied substituents defined for W and Z in Formula I and II.

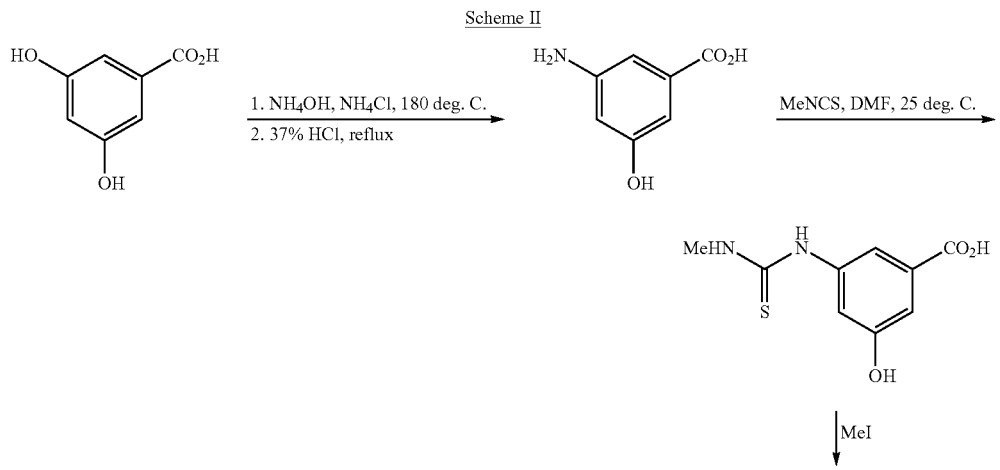

Scheme II

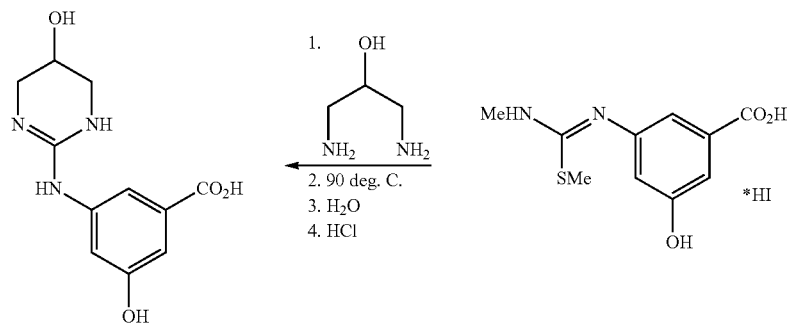

Scheme II illustrates methodology useful for preparing a preferred tetrahydropyrimidinobenzoic acid portion of Formula I or II of the present invention which can then be coupled to a gly-β-amino acid ester, or to gly ester first, followed by (after ester hydrolysis) coupling to the appropriate β-amino acid ester. Briefly, in Scheme II, 3,5-dihydroxybenzoic acid is converted to 3-amino-5-hydroxy-benzoic acid using the procedure described in *Austr. J. Chem.* (1981) or Becker et al., (1983), which are incorporated herein by reference. The product is reacted with methyl isothiocyanate in DMF at room temperature taught by *Organic Process Research & Development*, 2004, which is incorporated herein by reference, to give 3-N'-methyl thiourea-5-hydroxybenzoic acid after normal work-up. This thiourea intermediate is converted to the S-methyl derivative by reaction with methyl iodide neat at below 40° C. 1,3-diamino-2-hydroxypropane is reacted with this resulting intermediate in hot DMA (or DMF). Upon cooling, a precipitate forms and the zwitterionic product is isolated by filtration. The HCl salt may be obtained by lyophilizing from dilute hydrochloric acid. Alternatively, the product may be isolated from the original reaction mixture by removing volatiles and concentrating. The resulting product is taken up in water and pH adjusted to about 5-7 where zwitterionic product precipitates and is isolated by filtration. The HCl salt may be obtained as previously stated or by simply dissolving in dilute hydrochloric acid and concentrating to a solid and drying.

Scheme III

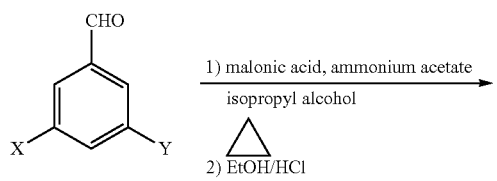

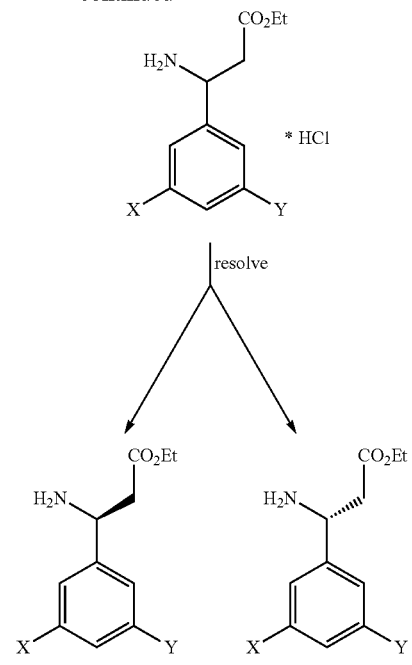

Scheme III illustrates a general methodology for the synthesis of the beta amino acid ester portion of Formula I or II of the present invention when Z=H, starting from an appropriate benzaldehyde. This beta amino acid ester can then be coupled to Boc-glycine followed by (after removal of the Boc protecting group) coupling to the appropriate benzoic acid described in Schemes I and II, or to the benzoic acid that has been coupled to glycine. Briefly in Scheme III, to the appropriate benzaldehyde in isopropanol is added ammonium acetate followed by malonic acid. The reaction mixture is stirred at reflux, the resulting precipitate filtered and washed with hot isopropanol and dried to yield the desired racemic beta amino acid. The ethyl ester is synthesized by heating this acid in excess ethanol in the presence of excess HCl gas. These racemic beta amino acid esters can be resolved into the (R) and the preferred (S) enantiomers via chiral chromatographic separation, or via enzymatic resolution as described in Faulconbridge et al. (2000) or Landis et al. (2002), which are incorporated herein by reference.

Scheme IV

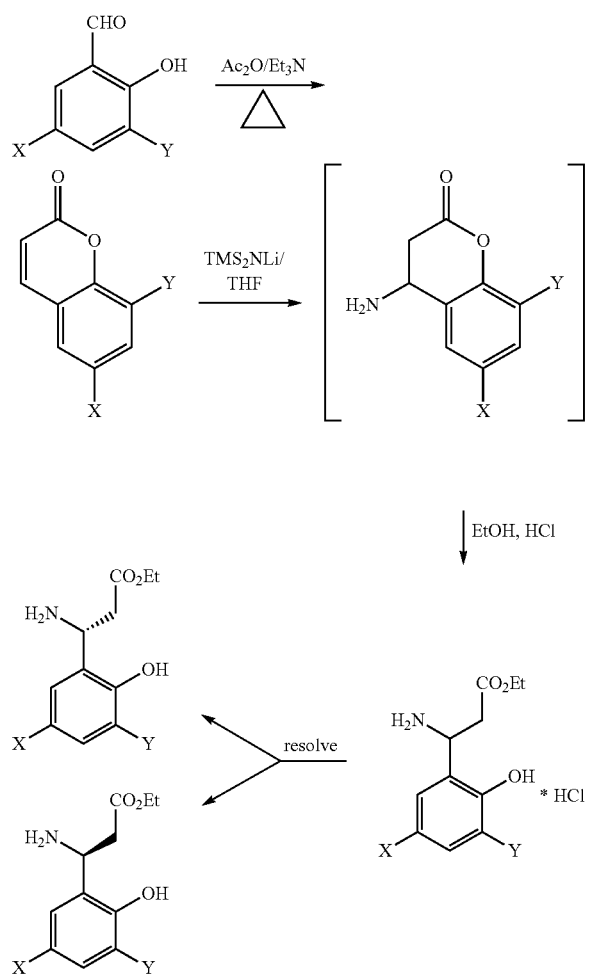

Scheme V

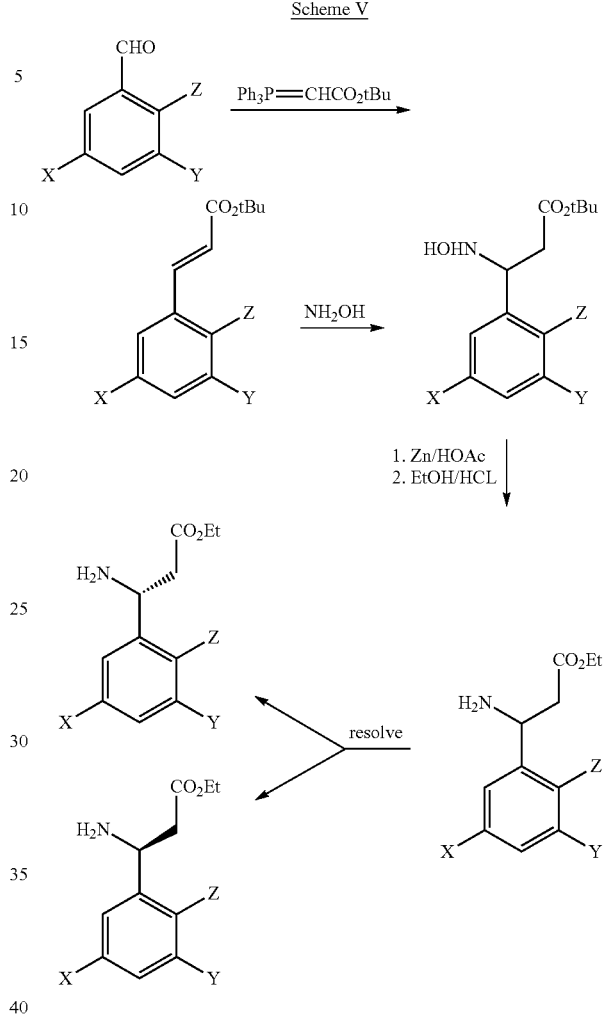

Scheme IV illustrates a general methodology for the synthesis of the beta amino acid ester portion of Formula I or II of the present invention, wherein Z=OH, starting from an appropriate benzaldehyde. This beta amino acid ester can then be coupled to Boc-glycine followed by (after removal of the Boc protecting group) coupling to the appropriate benzoic acid described in Schemes I and II (preferred method), or to the benzoic acid that has been coupled to glycine. Briefly, coumarins are readily prepared from salicylaldehydes using a modified Perkin reaction taught for example by Vogel's Textbook of Practical Organic Chemistry, 1989, which is incorporated herein by reference. The appropriately substituted coumarins are converted to 3-aminohydrocoumarins similarly to Rico (1994) which is incorporated herein by reference, which are readily opened in acidic alcohol to give 3-amino-3-(3,5-substituted-2-hydroxy)phenyl propanoic acid esters. These racemic beta amino acid esters can be resolved into the (R) and the preferred (S) enantiomers via chiral chromatographic separation (for example, via the CBZ derivative of the racemic ester, which is separated on a reverse phase chiral column, providing, after deprotection with, for example, TMSI, the pure (S) and (R) beta amino acid ester enantiomers) or via enzymatic resolution as described in Faulconbridge et al. (2000) or Landis et al. (2002), which are incorporated herein by reference.

Scheme V illustrates an alternate general methodology for the synthesis of the beta amino acid ester portion of Formula I or II of the present invention, starting from an appropriate benzaldehyde. This beta amino acid ester can then be coupled to Boc-glycine followed by (after removal of the Boc protecting group) coupling to the appropriate benzoic acid described in Schemes I and II, or to the benzoic acid that has been coupled to glycine. Briefly, the appropriate benzaldehyde is converted to the corresponding cinnamate via the Wittig reaction. Michael addition of hydroxylamine to the resulting cinnamate affords the N-hydroxylated beta-amino acid ester. Reduction of the N-hydroxy-beta-amino acid ester with Zn/acetic acid gives, after conversion to the corresponding ethyl ester in EtOH/HCl, the desired beta amino acid ester as a racemate. As in Scheme IV, these racemic beta amino acid esters can be resolved into the (R) and the preferred (S) enantiomers via chiral chromatographic separation (for example, via the CBZ derivative of the racemic ester, which is separated on a reverse phase chiral column, providing, after deprotection with, for example, TMSI, the pure (S) and (R) beta amino acid ester enantiomers) or via enzymatic resolution as described in Faulconbridge et al. (2000) or Landis et al. (2002), which are incorporated herein by reference.

Scheme VI

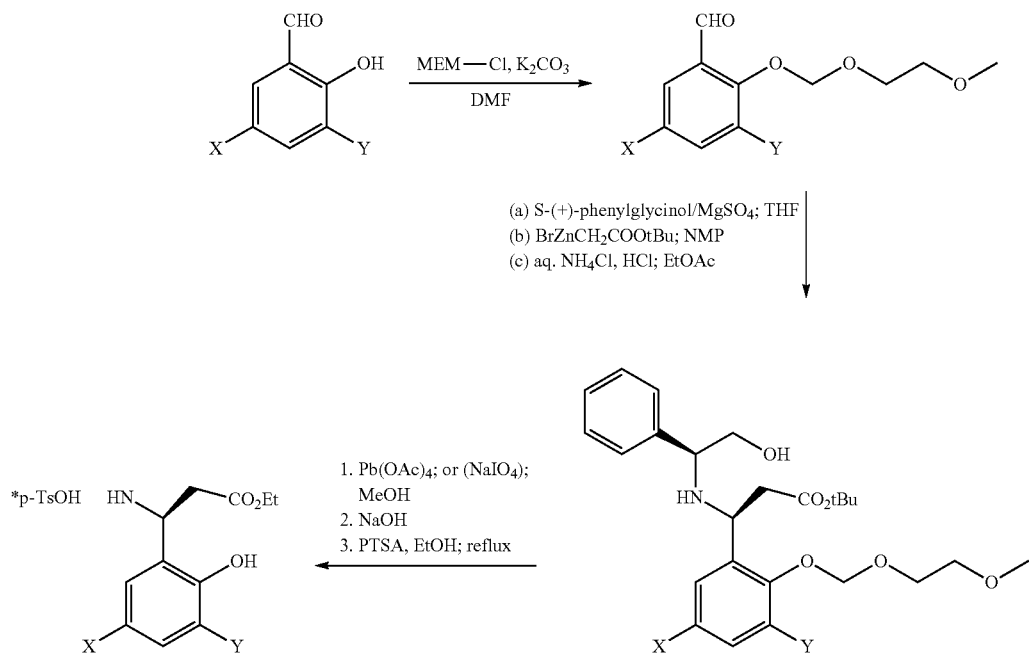

Scheme VI illustrates an alternate general methodology for the chiral synthesis of the beta amino acid ester portion of Formula I or II of the present invention, wherein Z is OH, starting from an appropriate benzaldehyde, and using a chiral auxiliary. This beta amino acid ester can then be coupled to Boc-glycine followed by (after removal of the Boc protecting group) coupling to the appropriate benzoic acid described in Schemes I and II (particular method), or to the benzoic acid that has been coupled to glycine. As described, Scheme VI illustrates the chiral synthesis of the preferred (S) enantiomer of the desired beta amino acid ester using S-phenylglycinol as the chiral auxiliary (synthesis of the (R) isomer is afforded by utilizing R-phenylglycinol instead). Literature references describing such reactions include: *Organic Process Research & Development* (2004); Awasthi et al. (2005); U.S. Pat. No. 6,414,180; U.S. Pat. No. 5,840,961, which are incorporated herein by reference. Briefly, the appropriate salicylaldehyde is first treated with MEM chloride and potassium carbonate to afford the MEM protected salicylaldehyde. The MEM ether protected salicylaldehyde is then reacted with S-phenylglycinol in the presence of magnesium sulfate in THF to afford the imine. The Reformatsky reagent, tert-butyl zinc bromoacetate, is then added to the imine in N-methylpyrrolidine. The chiral auxiliary of the resulting beta amino acid ester is cleaved off by treatment with lead tetraacetate. Basic workup of the reaction mixture followed by heating at reflux with p-toluenesulfonic acid in ethanol affords the desired PTSA salt of the (S)-beta amino acid ester.

Scheme VII

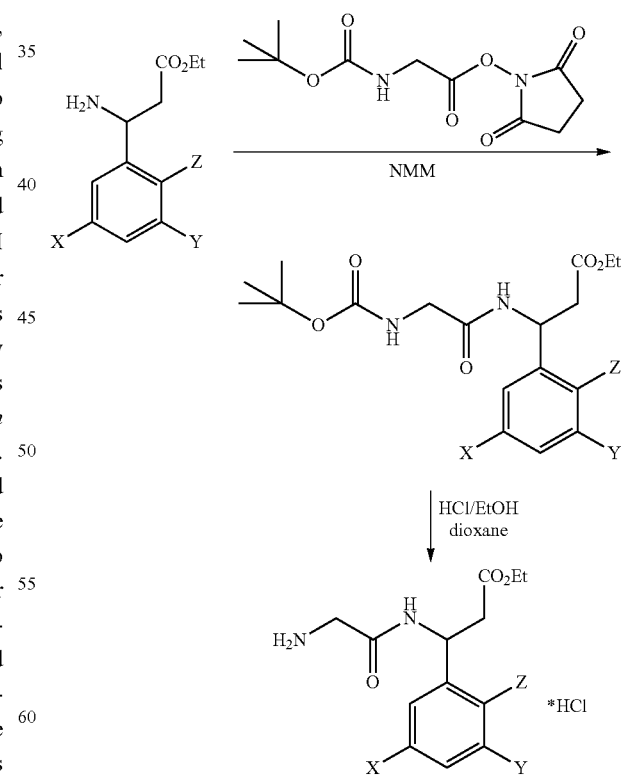

Scheme VII illustrates a general methodology for preparing the ethyl-N-gly-beta amino acid portion of Formula I of the present invention, which can be coupled to the benzoic acid portion of Formula I or II described in Schemes I and II). This method describes coupling a beta amino acid ester to glycine. Briefly, the desired beta amino acid ester (example methodologies described in Schemes III-VI above) is treated with activated Boc glycine. Removal of the Boc protective group (by treatment with ethanol/HCl, for example) affords the glycine amide of the corresponding beta amino acid ester (the preferred (S) enantiomer is afforded by utilizing the (S)-beta amino acid ester, described in the above schemes).

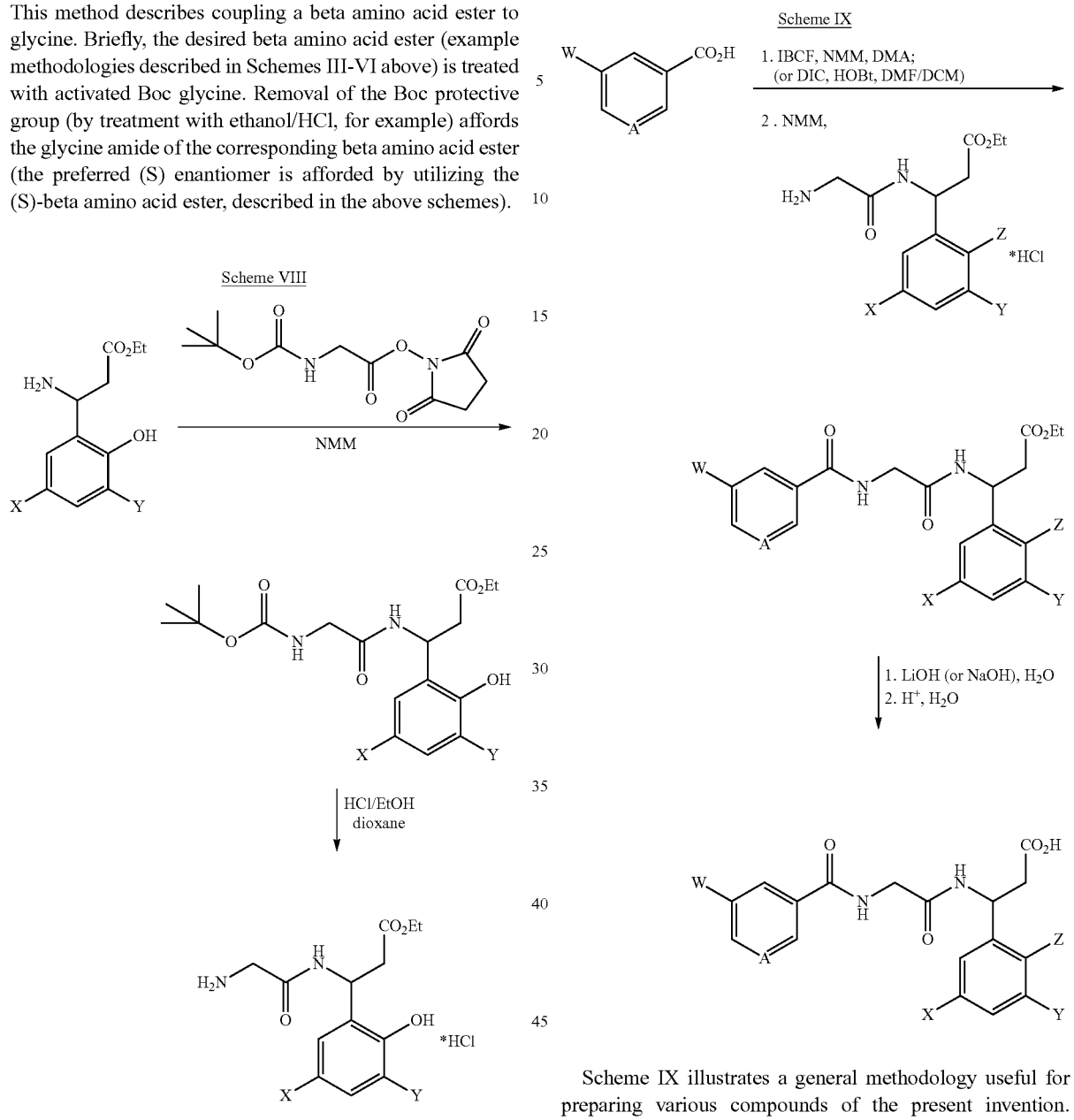

Scheme VIII illustrates a general methodology for preparing the ethyl-N-gly-beta amino acid portion of Formula I or II of the present invention when Z=OH, which can be coupled to the benzoic acid portion of Formula I described in Schemes I and II). This method describes coupling a beta amino acid ester (where Z=OH) to glycine. Briefly, the desired beta amino acid ester (example methodologies described in Schemes III-VI above) is treated with activated Boc glycine. Removal of the Boc protective group (by treatment with ethanol/HCl, for example) affords the glycine amide of the corresponding beta amino acid ester (the preferred (S) enantiomer is afforded by utilizing the (S)-beta amino acid ester, described in the above schemes). Scheme VIII is a preferred method for the synthesis of compounds of formula I when Z=OH.

Scheme IX illustrates a general methodology useful for preparing various compounds of the present invention. Briefly, the appropriate left hand side aromatic acid (described for example in Schemes I, IA, IB, and II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added the gly-β-amino acid ester and NMM. Upon completion of the reaction the product is purified by prep HPLC and the ester hydrolyzed to the acid by treating with a base, such as LiOH in a suitable solvent (dioxane/water or acetonitrile/water). Alternatively, a suitable acid, such as TFA can be used. The product is isolated by prep HPLC or by isolating the zwitterion at pH 5-7 and converting to the desired salt by standard procedures. (The preferred (S) enantiomer is afforded by utilizing the (S)-beta amino acid ester, described in the above schemes).

Scheme X

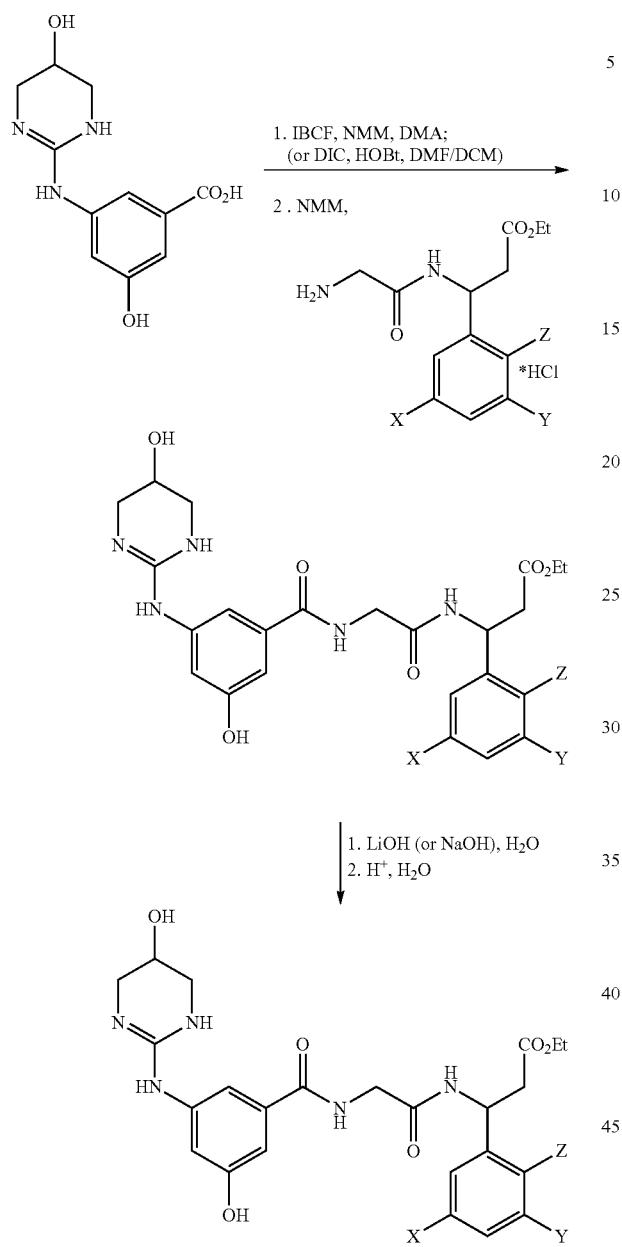

Scheme X illustrates a general methodology useful for preparing various compounds of the present invention. Briefly, 3-Hydroxy-5-[(1,4,5,6-tetrahydro-5-hydroxy-2-pyrimidinyl)amino]benzoic acid (described for example in Scheme II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added the gly-β-amino acid ester and NMM. Upon completion of the reaction the product is purified by prep HPLC and the ester hydrolyzed to the acid by treating with a base, such as LiOH in a suitable solvent (dioxane/water or acetonitrile/water). Alternatively, a suitable acid, such as TFA can be used. The product is isolated by prep HPLC or by isolating the zwitterion at pH 5-7 and converting to the desired salt by standard procedures. (The preferred (S) enantiomer is afforded by utilizing the (S)-beta amino acid ester, described in the above schemes).

Scheme XI

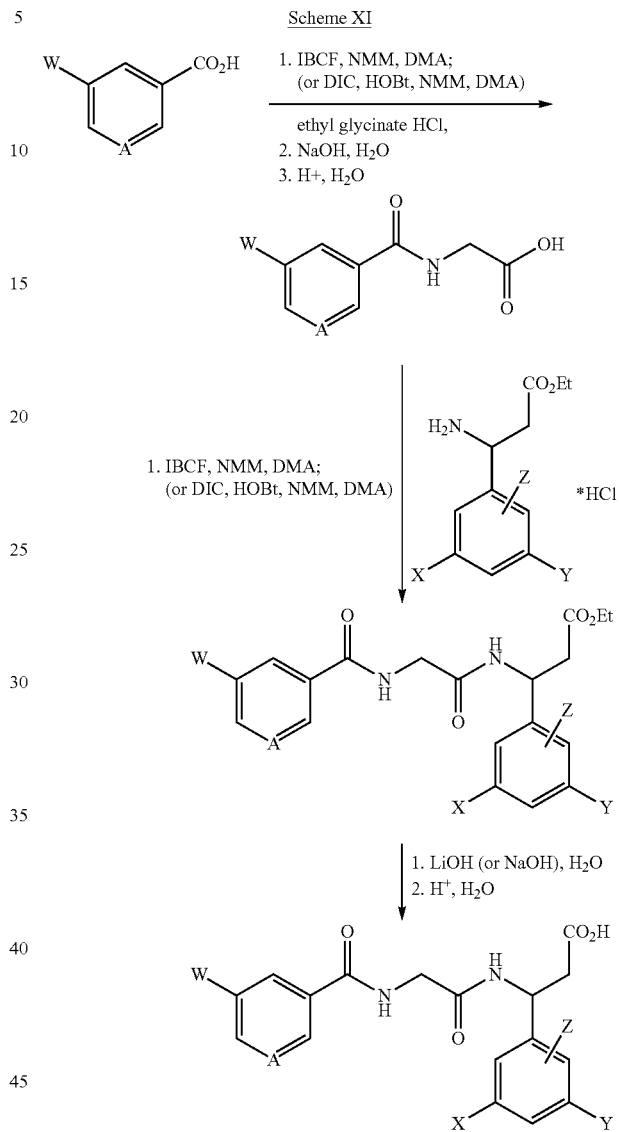

Scheme XI illustrates a general methodology useful for preparing various compounds of the present invention. Briefly, the appropriate left hand side aromatic acid (described for example in Schemes I, IA, IB and II) is activated for coupling using known methods. Thus, after dissolving in a suitable solvent such as DMA an equivalent of NMM is added. The reaction mixture is cooled to ice-bath temperatures and IBCF added. To the mixed anhydride intermediate is added ethyl glycinate HCl and NMM. Upon completion of the reaction the product is purified by prep HPLC and the ester hydrolyzed to the acid by treating with a base, such as NaOH in a suitable solvent (water, dioxane/water or acetonitrile/water), followed by acidification. This gly adduct is then activated for coupling using known methods. Thus, after dissolving in a suitable solvent such as DMA an equivalent of NMM is added. The reaction mixture is cooled to ice-bath temperatures and IBCF added. To the mixed anhydride intermediate is added the appropriate beta amino acid ester salt (described, for example, in Schemes III-VI above) and NMM. Upon completion of the reaction the product is purified by prep HPLC and the ester hydrolyzed to the acid by treating with a base, such as LiOH in a suitable solvent (dioxane/water or acetonitrile/water). Alternatively, a suitable acid, such as TFA can be used. The product is isolated by prep HPLC or by isolating the zwitterion at pH 5-7 and converting to the desired salt by standard procedures (the particular (S) enantiomer is afforded by utilizing the (S)-beta amino acid ester, described in the above schemes).

Scheme XII

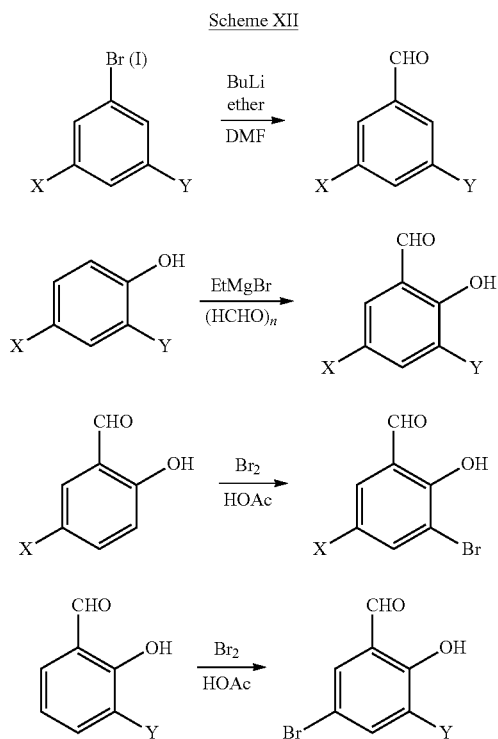

Scheme XII illustrates general synthetic methodologies for benzaldehyde starting materials that may not be readily available from commercial sources and that are useful for preparing various compounds of the present invention as described in the previous schemes. In the bottom two examples above, known methods of aromatic chlorination can be substituted for the bromination reactions depicted, thus yielding the corresponding chlorine substituted benzaldehydes. Such methods are well known in the art. See Kurahashi et al. (2011) in the supporting information section; Nomura et al. (2007); and *March's Advanced Organic Chemistry: Reactions, Mechanisms, and Structure* (2007), which are all incorporated by reference herein.

Scheme XIII

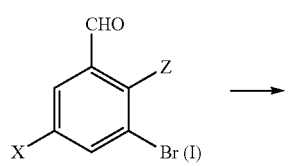

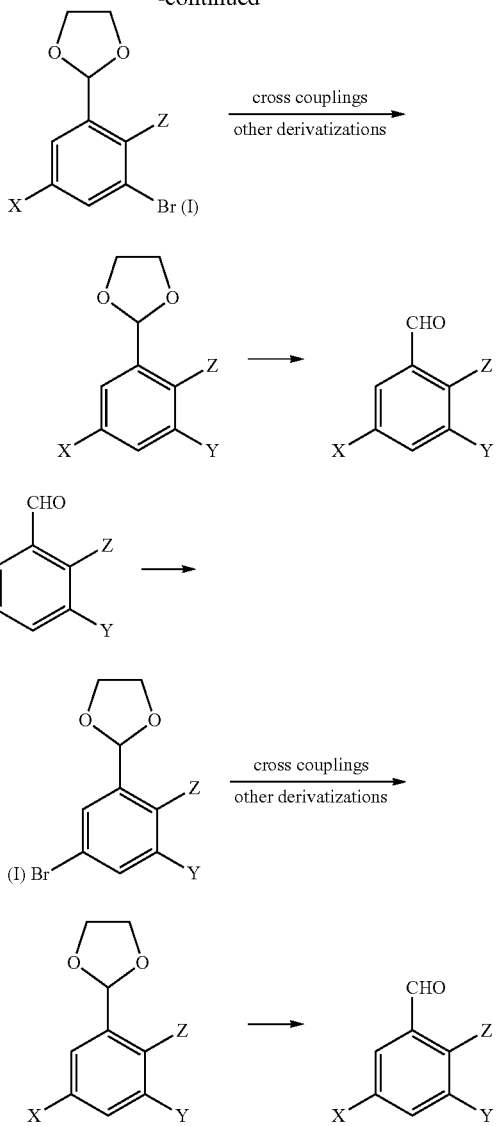

Scheme XIII illustrates general synthetic methodologies for benzaldehyde starting materials that may not be readily available from commercial sources and that are useful for preparing various compounds of the present invention as described in the previous schemes. In particular, it illustrates general methodologies for benzaldehyde analogues that utilize an appropriate aldehyde protected aromatic Br or I reagent, whereas the Br or I can be displaced using cross coupling or other aromatic Br or I facilitated derivatizations widely known to those skilled in the art and that yield benzaldehyde starting materials useful for preparing various compounds of the present invention as described in previous schemes. When Z is OH, the hydroxyl group can be protected with various protecting groups known to those skilled in the art as needed to efficiently execute the synthetic procedures depicted. The protecting group can subsequently be removed with known de-protecting reagents. These are meant to be general synthetic methods that are readily known and practiced by those skilled in the art, and are not meant to be limiting in scope.

Scheme XIIIA
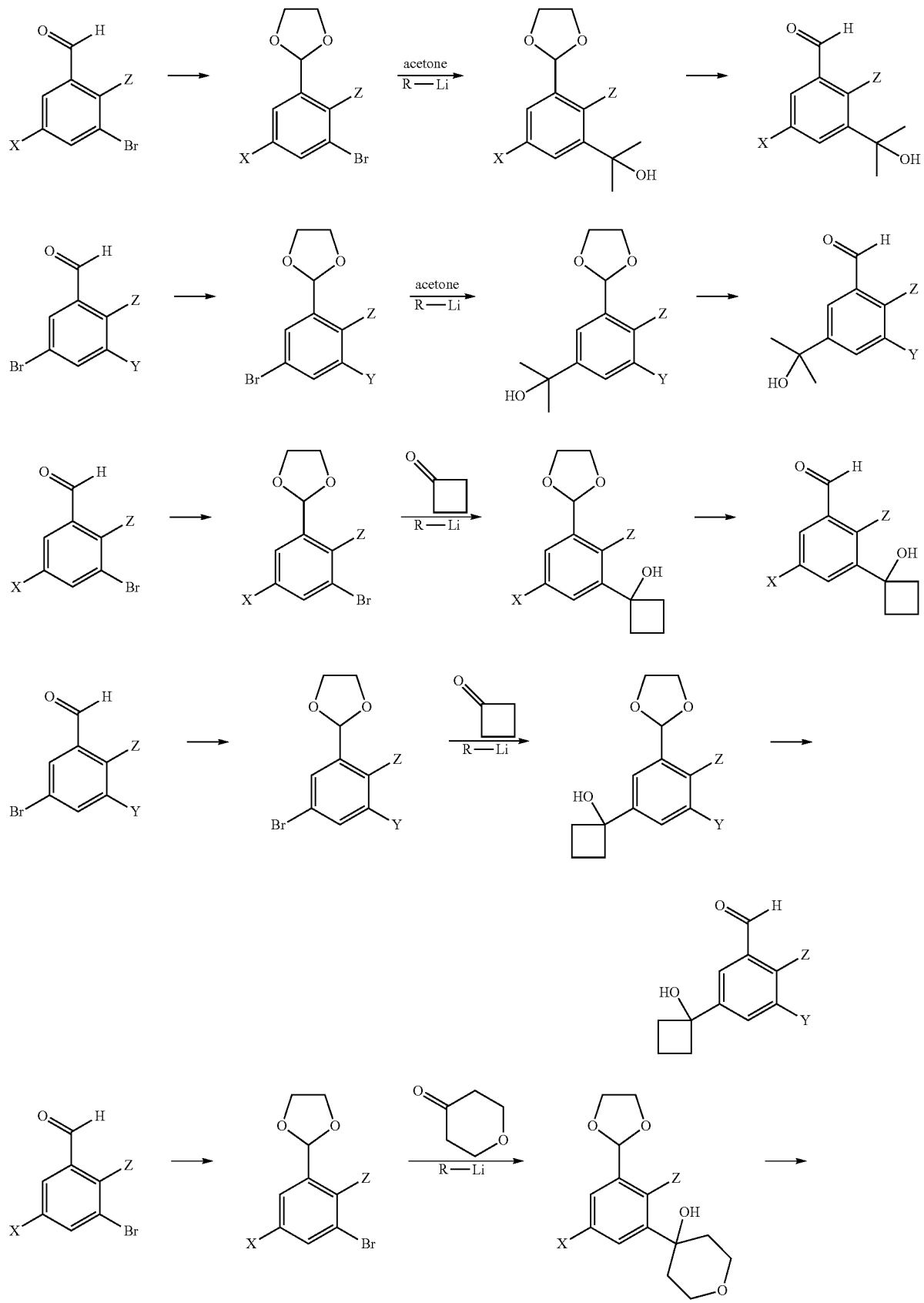

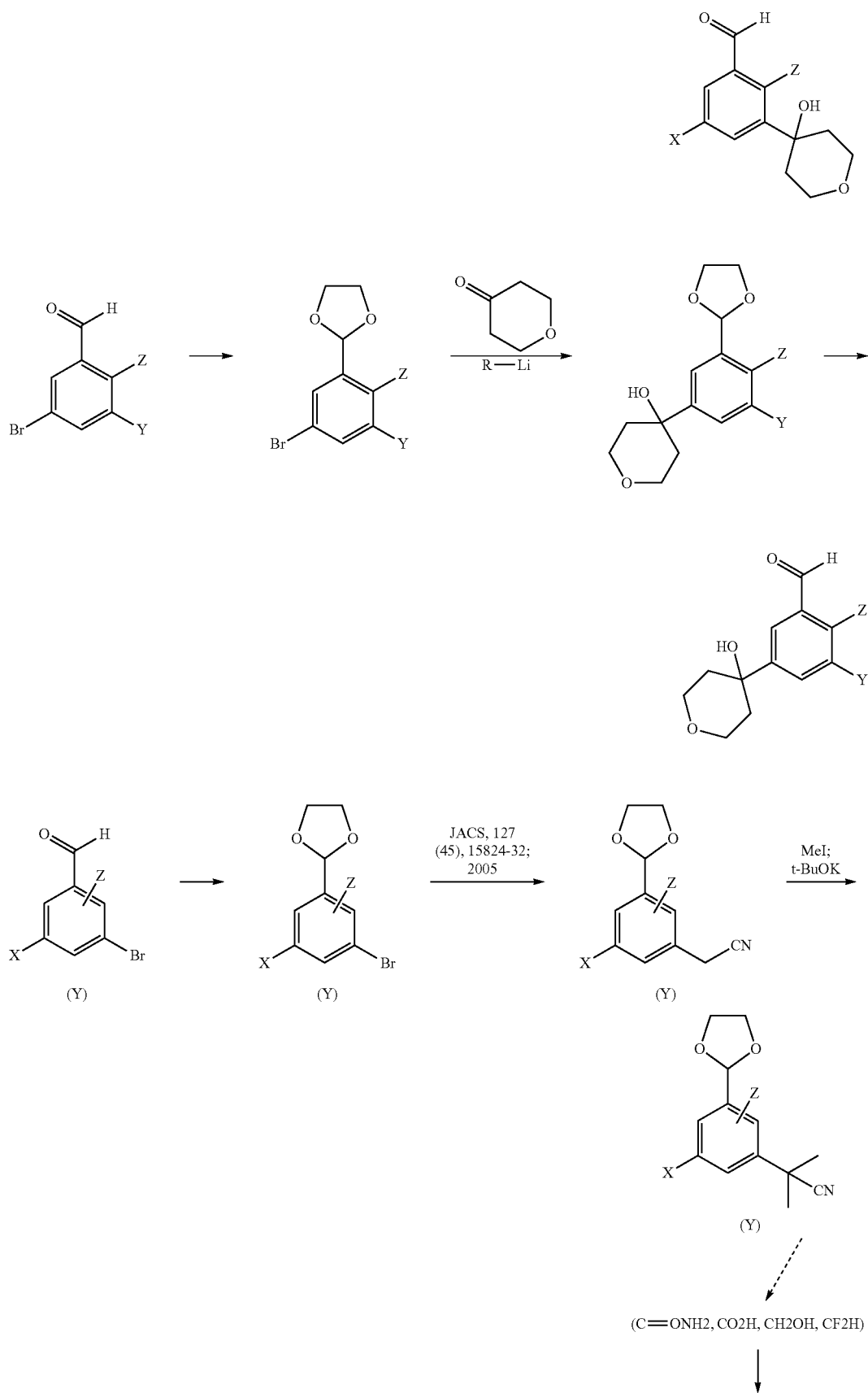
-continued
(C=ONH2, CO2H, CH2OH, CF2H)

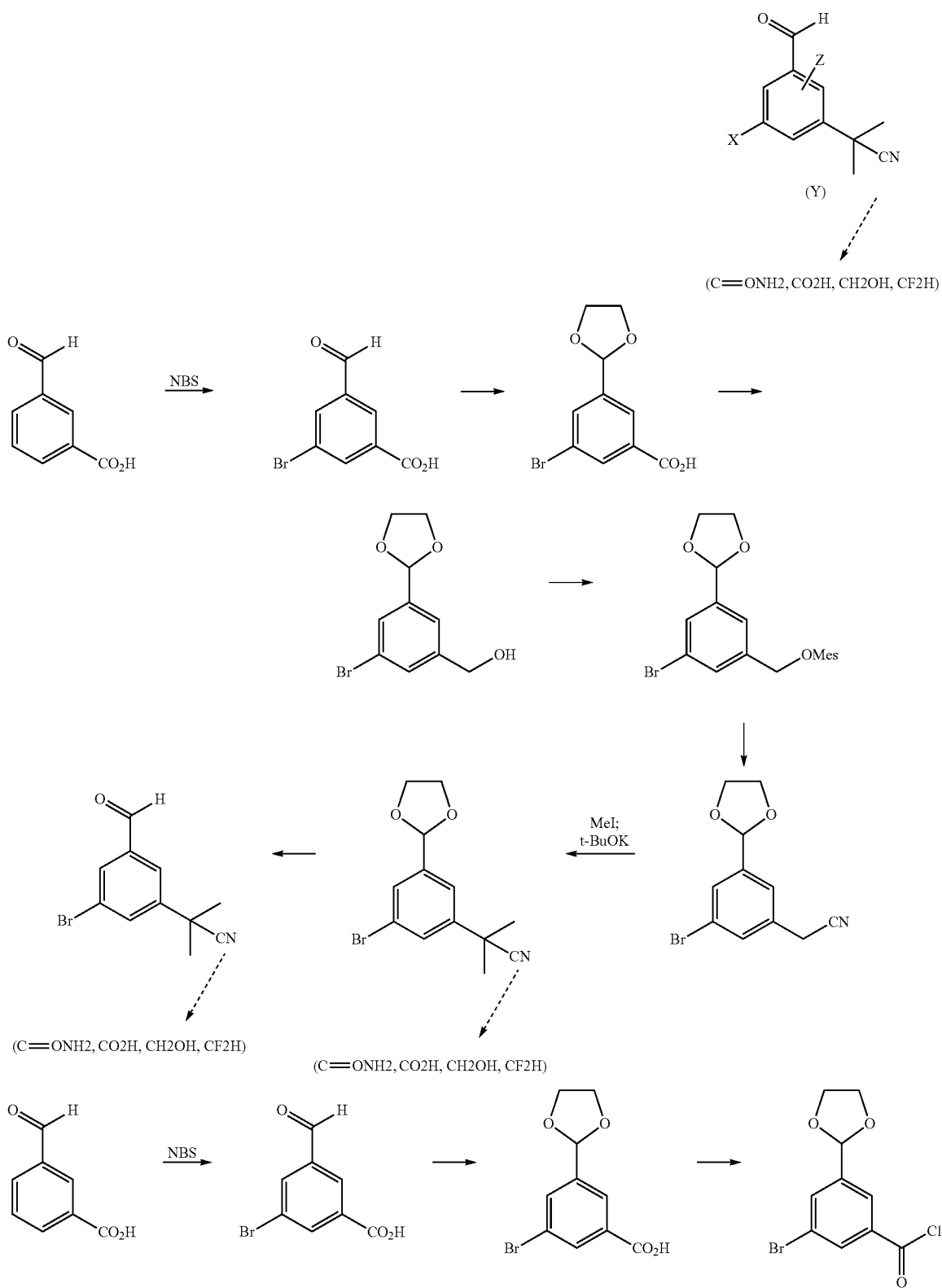

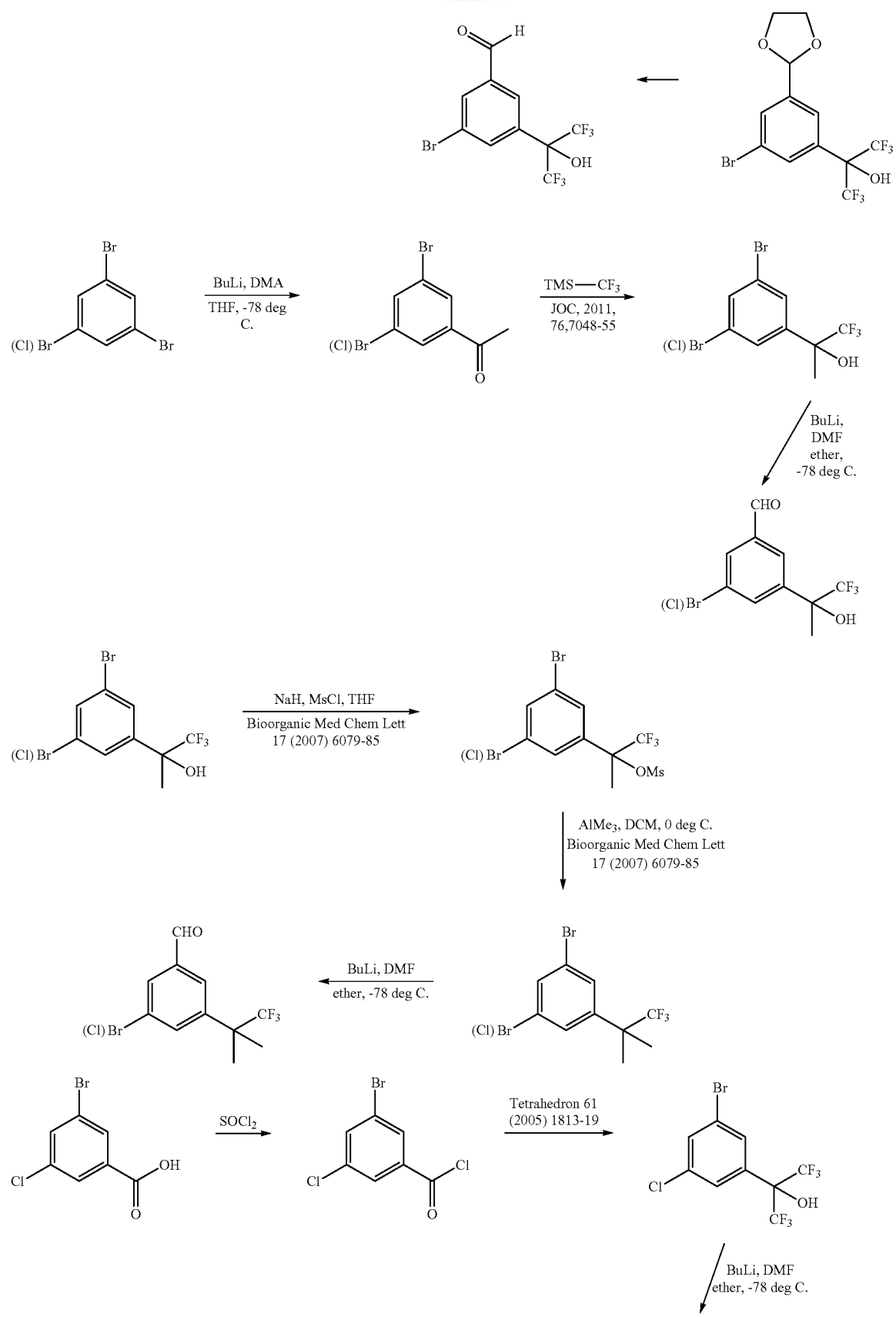

-continued

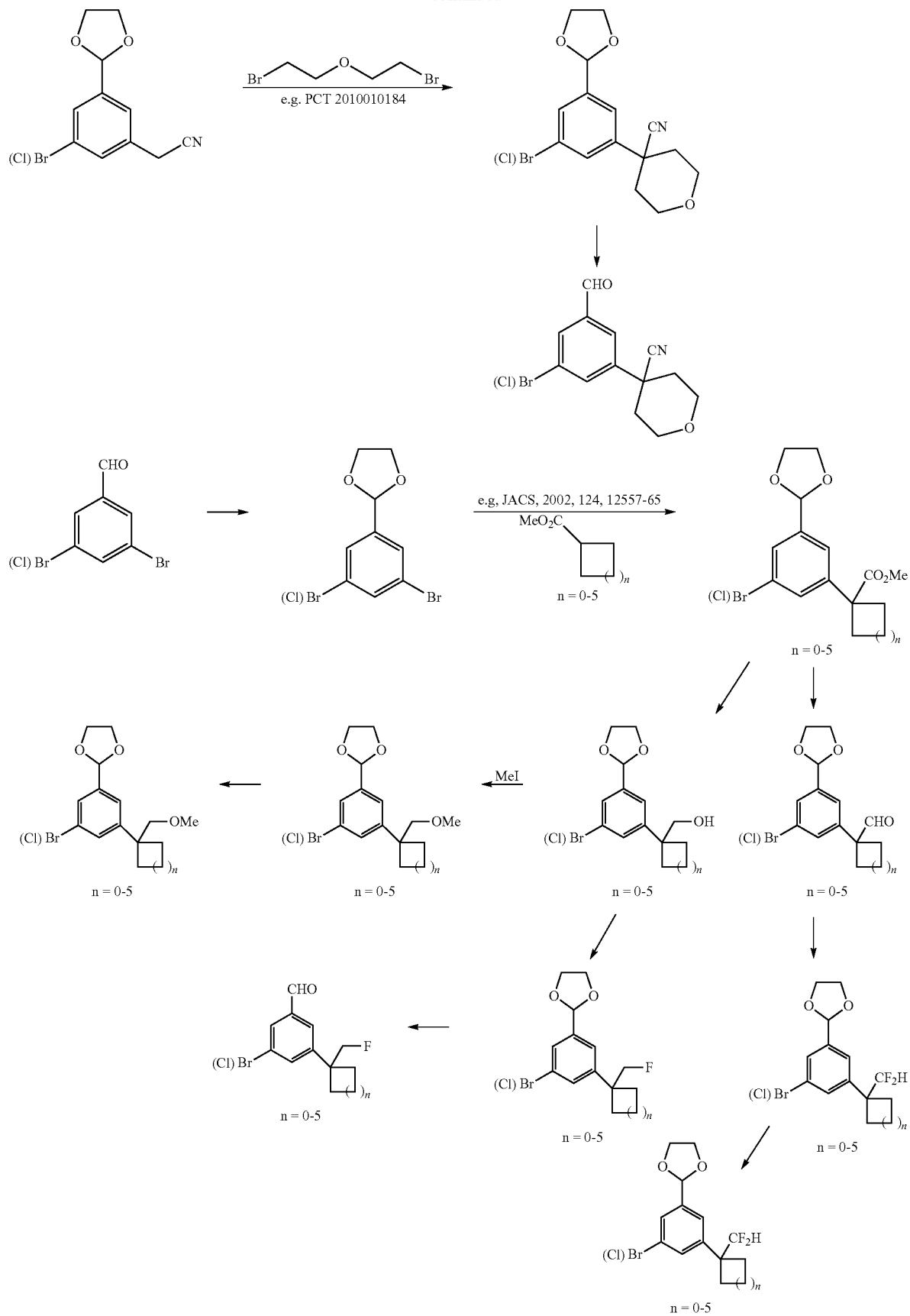

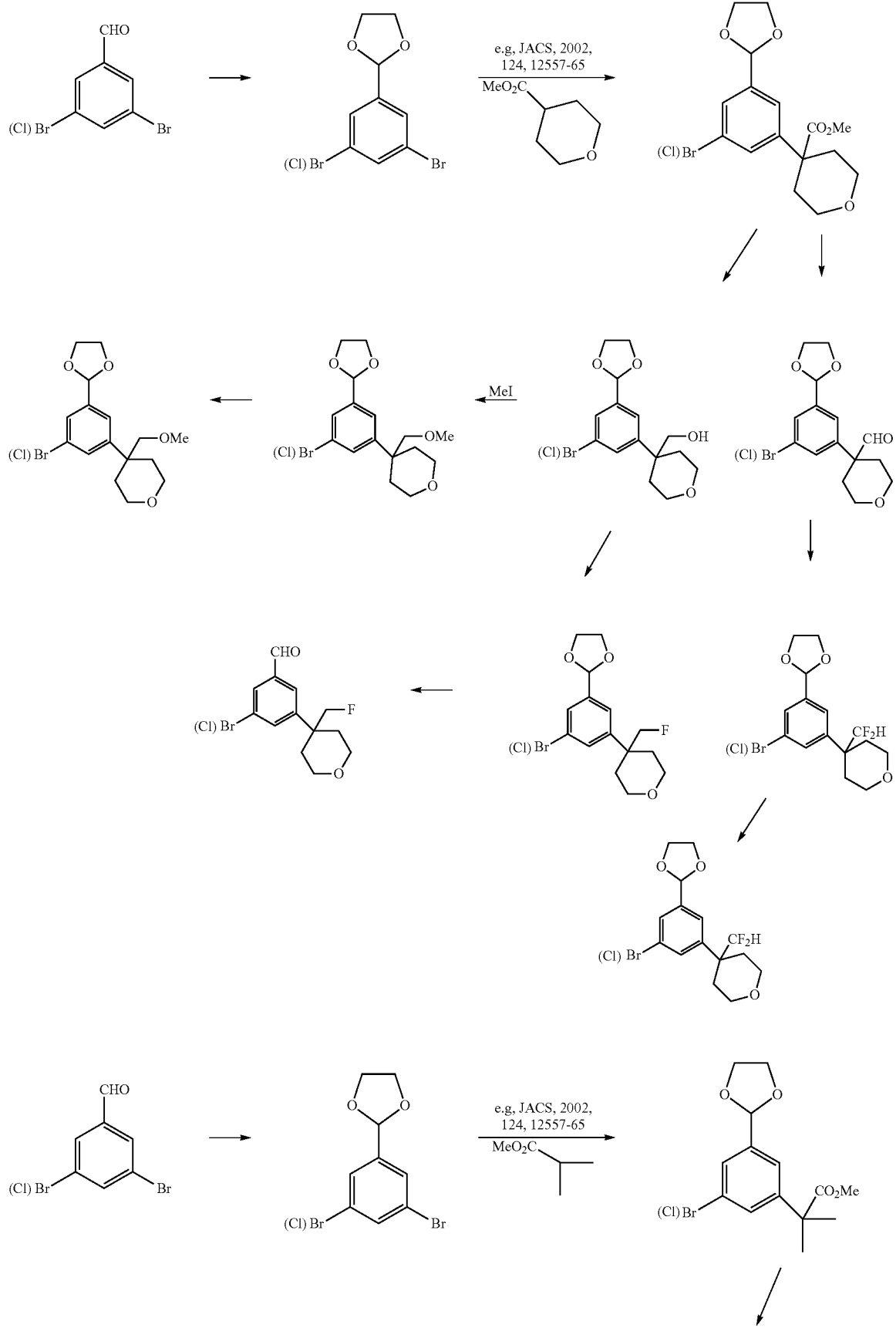

93
-continued
94
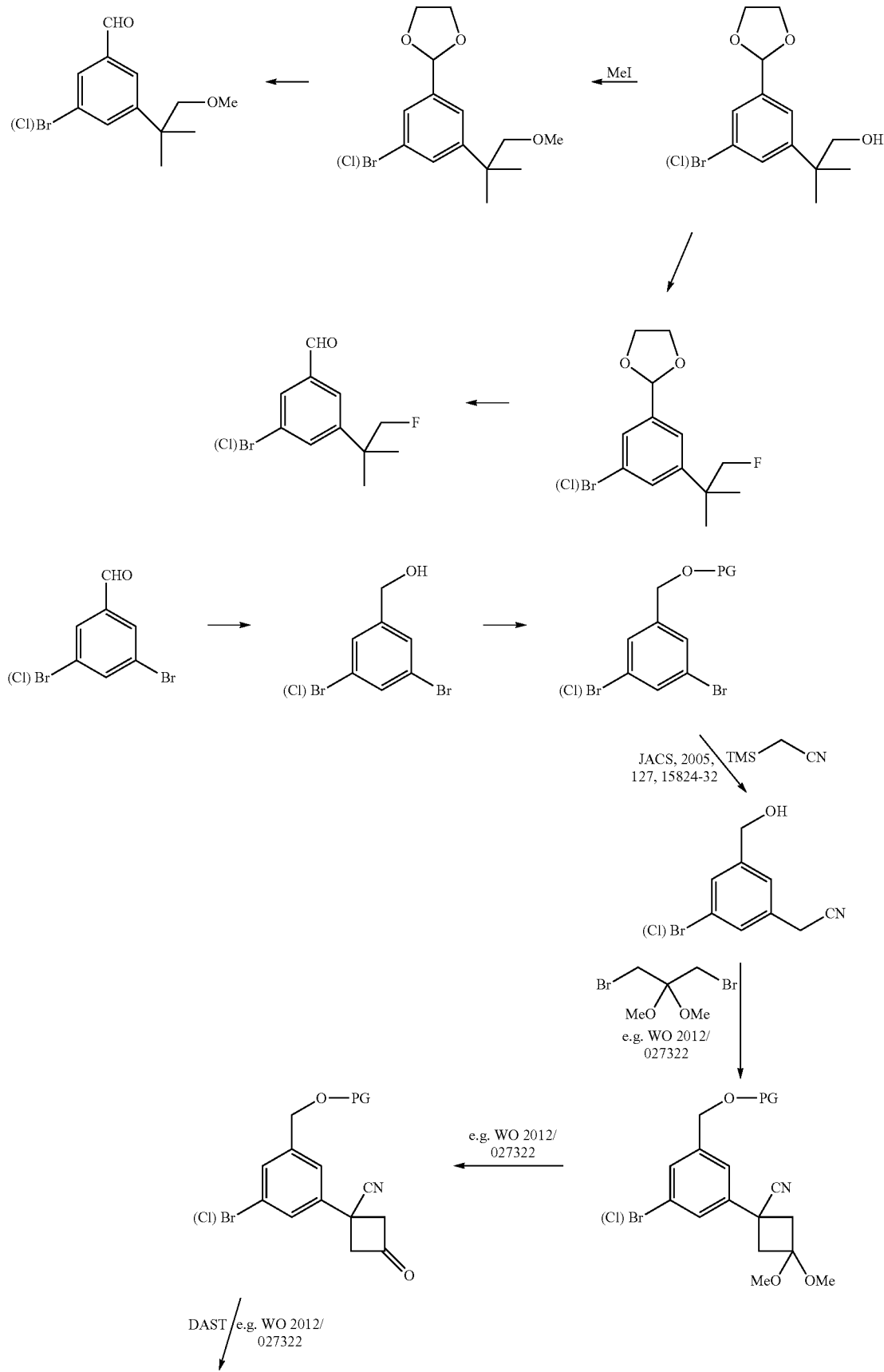

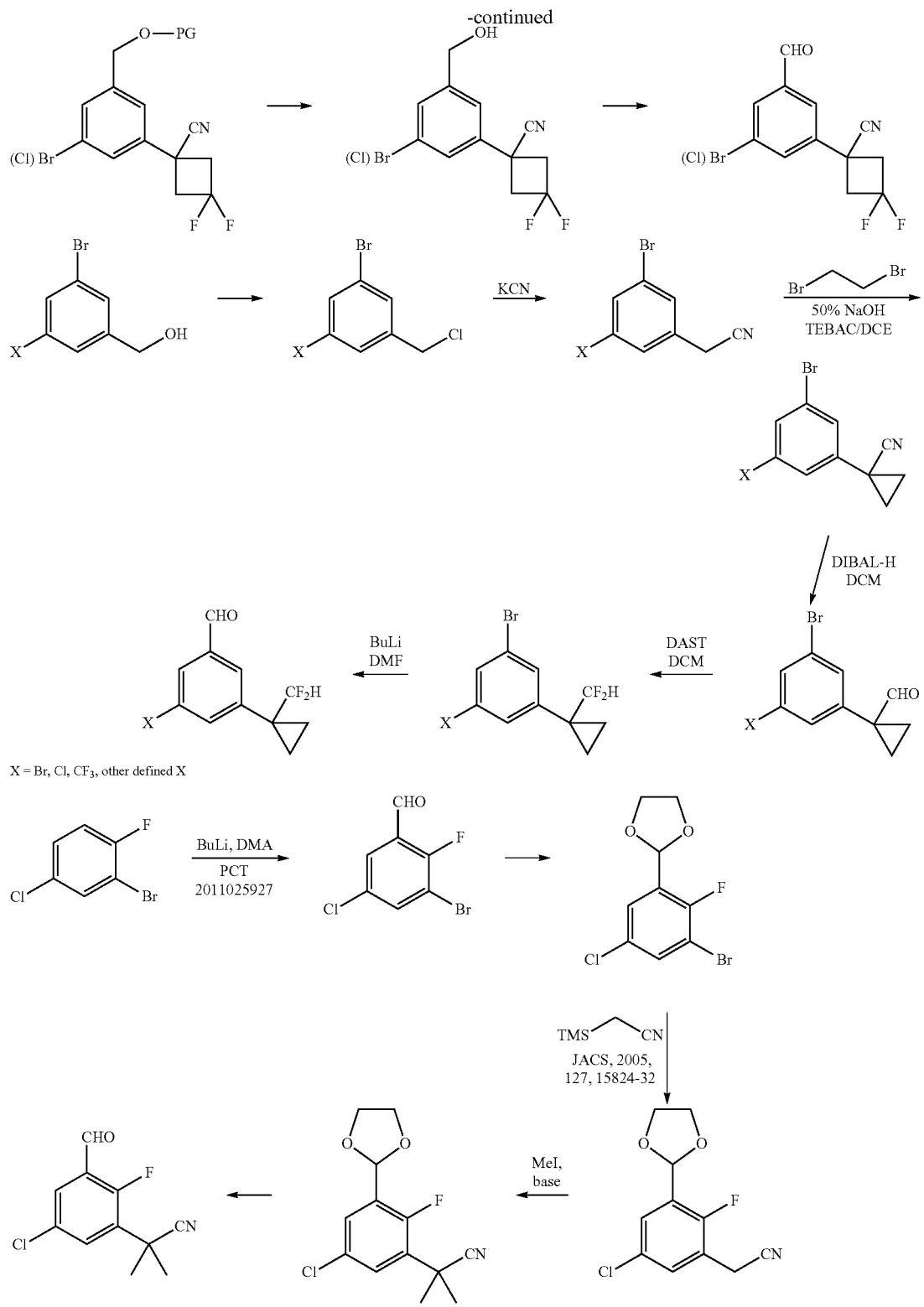

All references listed in Scheme XIIIA are incorporated herein by reference.

Scheme XIIIA further illustrates general synthetic methodologies for benzaldehyde starting materials that may not be readily available from commercial sources and that are useful for preparing various compounds of the present invention as described in the previous schemes. When Z is OH, the hydroxyl group can be protected with various protecting groups known to those skilled in the art as needed to efficiently execute the synthetic procedures depicted. The protecting group can subsequently be removed with known deprotecting reagents. See, for example, Greene & Wuts (1999), which is incorporated herein by reference. Furthermore, a trifluoromethyl or other amenable group as defined for X in the general formula can be substituted for the substituent depicted as (Cl)Br— in the above schemes. These schemes are meant to illustrate methods for generating targeted benzaldehydes that can be used to synthesize compounds claimed herein, but that are not commercially available. They are not intended to be limiting in nature and can be further adapted and modified in ways that are known to those skilled in the art.

Scheme XIV

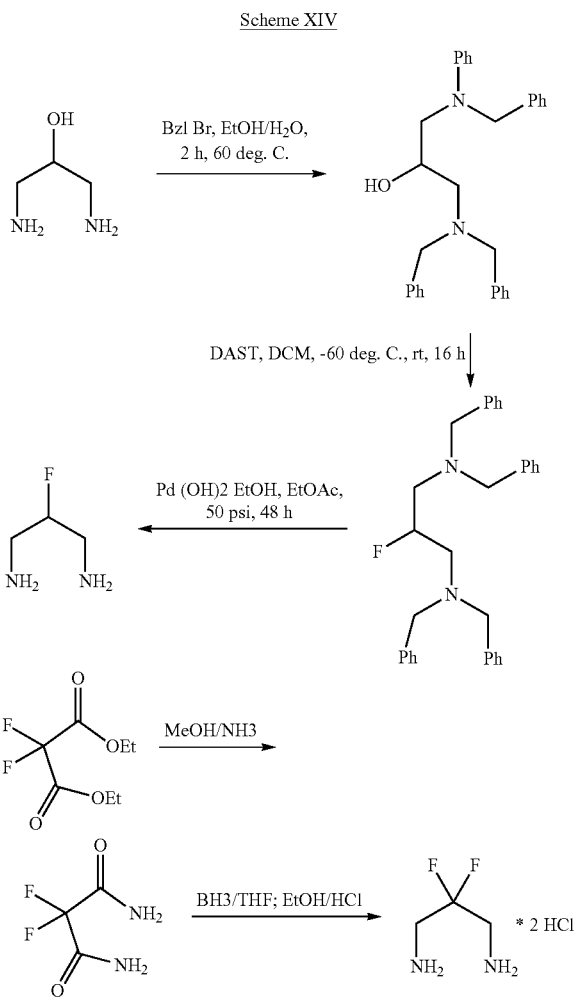

Scheme XIV illustrates general synthetic methodologies for the synthesis of diamine intermediates useful for preparing the tetrahydropyrimidinobenzoic acid portion of Formula I of the present invention as described in Scheme I and where A=H and B=F, or when A and B both=F.

Scheme XV

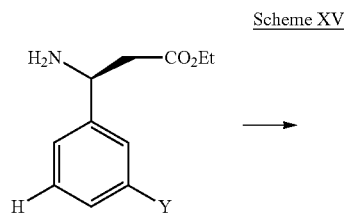

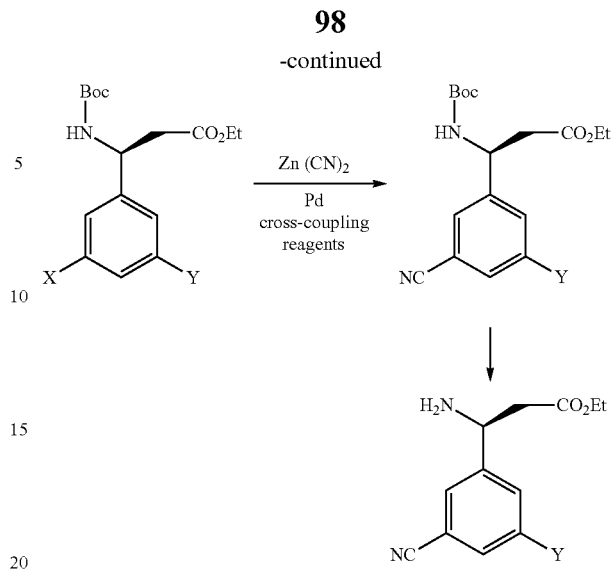

X = Br, Cl,

Scheme XV illustrates a convenient synthetic method for the introduction of a cyano substituent in the synthesis of beta amino ester reagents wherein X is cyano as defined in the general formula and Y can be multiple amenable substituents as defined in the general formula and characterized in the above schemes and subsequent examples. This scheme illustrates one method for synthesizing compounds where X is cyano and is not intended to be limiting in nature and can be further adapted and modified in ways that are known to those skilled in the art.

All these methods described above can be further modified and optimized using the principles and techniques taught in U.S. Pat. Nos. 6,013,651 and 6,028,223, which are incorporated herein by reference, as well as the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Non-limiting examples of compounds which may be made by and used in the methods described herein are listed in Table A (below):

TABLE A

Examples of Beta Amino Acid Derivatives

| W | A |
|---|---|

TABLE A-continued
Examples of Beta Amino Acid Derivatives
| W | A |
|---|---|
| 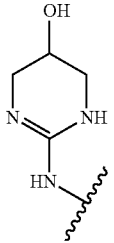 | C—OH |
| 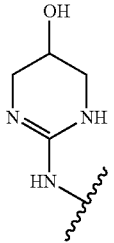 | N |
| 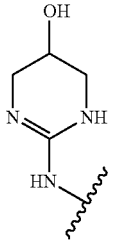 | C—H |
| 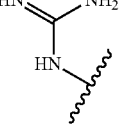 | C—OH |
| 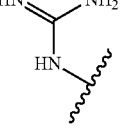 | N |
| 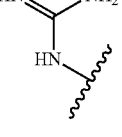 | C—H |
| 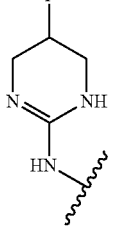 | C—OH |
TABLE A-continued
Examples of Beta Amino Acid Derivatives
| W | A |
|---|---|
| 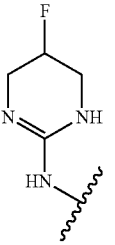 | N |
| 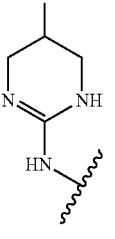 | C—H |
| 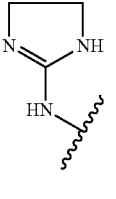 | C—OH |
| 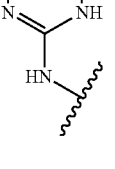 | N |
| 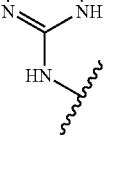 | C—H |
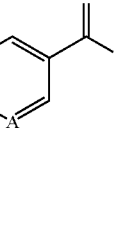

TABLE A-continued

Examples of Beta Amino Acid Derivatives

| W | A |
|---|---|
| 5-hydroxy-tetrahydropyrimidin-2-yl-amino | N |
| 5-hydroxy-tetrahydropyrimidin-2-yl-amino | C—H |
| guanidino | C—OH |
| guanidino | N |
| guanidino | C—H |
| 5-fluoro-tetrahydropyrimidin-2-yl-amino | C—OH |
| 5-fluoro-tetrahydropyrimidin-2-yl-amino | N |
| 5-fluoro-tetrahydropyrimidin-2-yl-amino | C—H |
| 4,5-dihydro-1H-imidazol-2-yl-amino | C—OH |
| 4,5-dihydro-1H-imidazol-2-yl-amino | N |
| 4,5-dihydro-1H-imidazol-2-yl-amino | C—H |
| 5-hydroxy-tetrahydropyrimidin-2-yl-amino | C—OH |

General structure:
W-[pyridine/benzene ring with A]-C(O)-NH-CH₂-C(O)-NH-CH(CO₂H)-[3-CF₃-5-tBu-phenyl]

TABLE A-continued

Examples of Beta Amino Acid Derivatives

| W | A |
|---|---|
| 5-hydroxy-tetrahydropyrimidin-2-yl-amino | N |
| 5-hydroxy-tetrahydropyrimidin-2-yl-amino | C—H |
| guanidino (HN=C(NH2)–NH–) | C—OH |
| guanidino | N |
| guanidino | C—H |
| 5-fluoro-tetrahydropyrimidin-2-yl-amino | C—OH |
| 5-fluoro-tetrahydropyrimidin-2-yl-amino | N |
| 5-fluoro-tetrahydropyrimidin-2-yl-amino | C—H |
| 4,5-dihydro-1H-imidazol-2-yl-amino | C—OH |
| 4,5-dihydro-1H-imidazol-2-yl-amino | N |
| 4,5-dihydro-1H-imidazol-2-yl-amino | C—H |
| 5-hydroxy-tetrahydropyrimidin-2-yl-amino | C—OH |

TABLE A-continued

Examples of Beta Amino Acid Derivatives

| W | A |
|---|---|
| (5-hydroxy-tetrahydropyrimidin-2-yl)amino | N |
| (5-hydroxy-tetrahydropyrimidin-2-yl)amino | C—H |
| guanidino (HN=C(NH2)–NH–) | C—OH |
| guanidino | N |
| guanidino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | N |

TABLE A-continued
Examples of Beta Amino Acid Derivatives
| W | A |
|---|---|
| 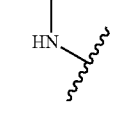 | C—H |
| 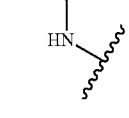 | C—OH |
| 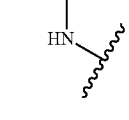 | N |
| 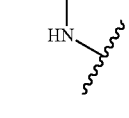 | C—H |
| 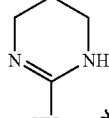 | C—OH |
| 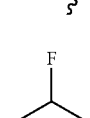 | N |
| 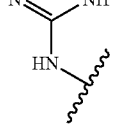 | C—H |
| 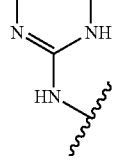 | C—OH |
| 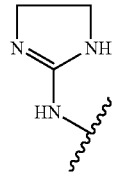 | N |
| 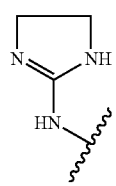 | C—H |
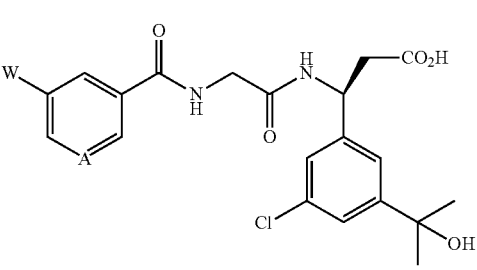
| W | A |
|---|---|
| 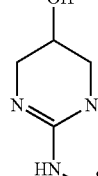 | C—OH |
| 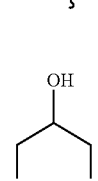 | N |

TABLE A-continued
Examples of Beta Amino Acid Derivatives
| W | A |
|---|---|
| 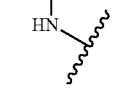 | C—H |
| 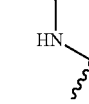 | C—OH |
| 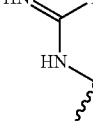 | N |
| 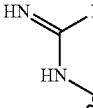 | C—H |
| 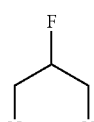 | C—OH |
| 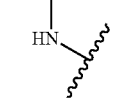 | N |
| 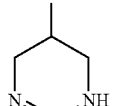 | C—H |
TABLE A-continued
Examples of Beta Amino Acid Derivatives
| W | A |
|---|---|
| | C—OH |
| | N |
| | C—H |
| | C—OH |
| | N |

TABLE A-continued
Examples of Beta Amino Acid Derivatives
| W | A |
|---|---|
| 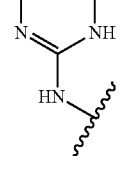 | C—H |
| 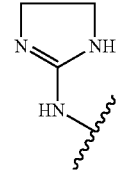 | C—OH |
| 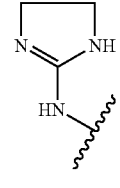 | N |
| 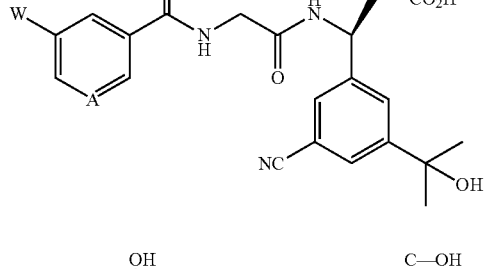 | C—H |
| 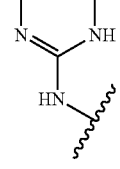 | C—OH |
| 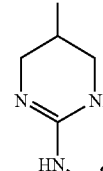 | N |
| (F-substituted tetrahydropyrimidine) | C—H |
TABLE A-continued
Examples of Beta Amino Acid Derivatives
| W | A |
|---|---|
| (imidazoline) | C—OH |
| (imidazoline) | N |
| (imidazoline) | C—H |
| (full structure shown) | |
| (hydroxy tetrahydropyrimidine) | C—OH |
| (hydroxy tetrahydropyrimidine) | N |

TABLE A-continued
Examples of Beta Amino Acid Derivatives
| W | A |
|---|---|
| 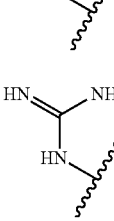 | C—H |
| 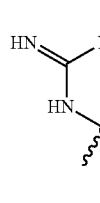 | C—OH |
| 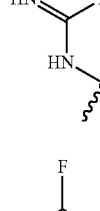 | N |
| 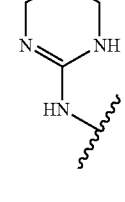 | C—H |
| 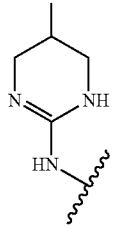 | C—OH |
| 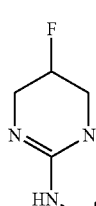 | N |
|  | C—H |
TABLE A-continued
Examples of Beta Amino Acid Derivatives
| W | A |
|---|---|
|  | C—OH |
|  | N |
|  | C—H |
|  | |
|  | C—OH |
|  | N |

TABLE A-continued

Examples of Beta Amino Acid Derivatives

| W | A |
|---|---|
| (5-hydroxy-tetrahydropyrimidin-2-yl)amino | C—H |
| guanidino | C—OH |
| guanidino | N |
| guanidino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | N |
| (5-hydroxy-tetrahydropyrimidin-2-yl)amino | C—H |
| guanidino | C—OH |

TABLE A-continued
Examples of Beta Amino Acid Derivatives
| W | A |
|---|---|
| 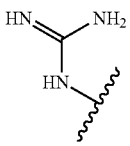 | N |
| 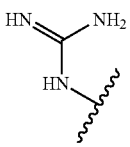 | C—H |
| 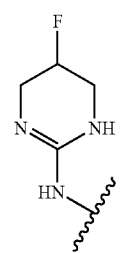 | C—OH |
| 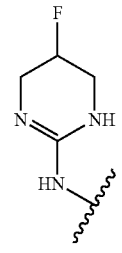 | N |
| 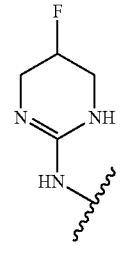 | C—H |
| 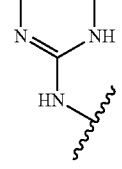 | C—OH |
| 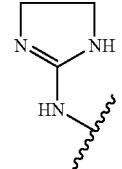 | N |
TABLE A-continued
Examples of Beta Amino Acid Derivatives
| W | A |
|---|---|
| 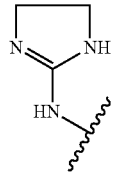 | C—H |
| 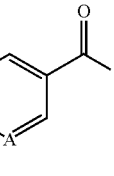 | |
| 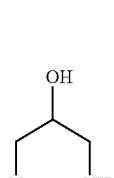 | C—OH |
| 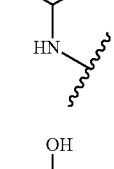 | N |
| 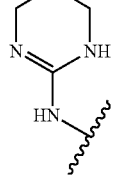 | C—H |
| 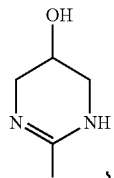 | C—OH |
| 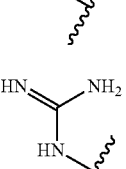 | N |
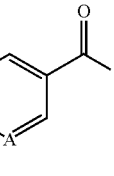

TABLE A-continued

Examples of Beta Amino Acid Derivatives

| W | A |
|---|---|
| (guanidine-HN-) | C—H |
| (5-fluoro-tetrahydropyrimidin-2-yl-NH-) | C—OH |
| (5-fluoro-tetrahydropyrimidin-2-yl-NH-) | N |
| (5-fluoro-tetrahydropyrimidin-2-yl-NH-) | C—H |
| (4,5-dihydroimidazol-2-yl-NH-) | C—OH |
| (4,5-dihydroimidazol-2-yl-NH-) | N |
| (4,5-dihydroimidazol-2-yl-NH-) | C—H |
| (5-hydroxy-tetrahydropyrimidin-2-yl-NH-) | C—OH |
| (5-hydroxy-tetrahydropyrimidin-2-yl-NH-) | N |
| (5-hydroxy-tetrahydropyrimidin-2-yl-NH-) | C—H |
| (guanidine-HN-) | C—OH |
| (guanidine-HN-) | N |
| (guanidine-HN-) | C—H |

General structure:

W—(3-pyridyl with A)—C(O)NH—CH₂—C(O)NH—CH(CO₂H)—[3-bromo-5-(2-cyano-propan-2-yl)phenyl]

TABLE A-continued
Examples of Beta Amino Acid Derivatives
| W | A |
|---|---|
| 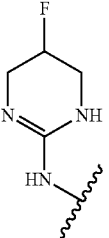 | C—OH |
| 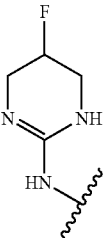 | N |
| 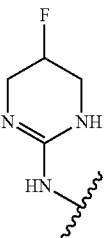 | C—H |
| 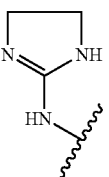 | C—OH |
| 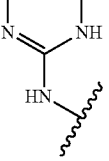 | N |
| 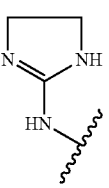 | C—H |
TABLE A-continued
Examples of Beta Amino Acid Derivatives
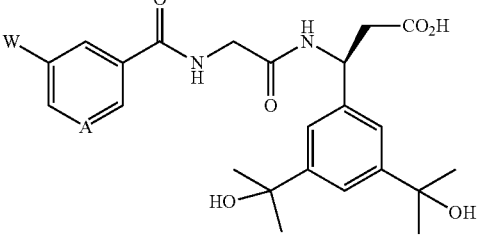
| W | A |
|---|---|
| 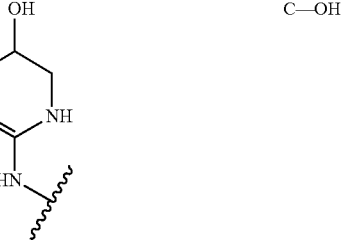 | C—OH |
| 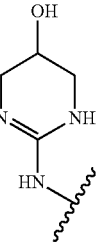 | N |
| 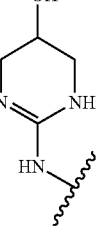 | C—H |
| 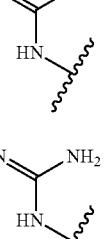 | C—OH |
| 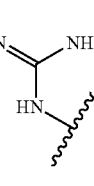 | N |
| 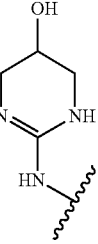 | C—H |

TABLE A-continued

Examples of Beta Amino Acid Derivatives

[Structure showing general formula with W-C(O)-NH-CH2-C(O)-NH-CH(CO2H)- attached to aryl group bearing tert-butyl and C(CH3)2OH substituents, with A in pyridine ring]

| W | A |
|---|---|
| 5-fluoro-tetrahydropyrimidin-2-yl-amino | C—OH |
| 5-fluoro-tetrahydropyrimidin-2-yl-amino | N |
| 5-fluoro-tetrahydropyrimidin-2-yl-amino | C—H |
| 4,5-dihydro-1H-imidazol-2-yl-amino | C—OH |
| 4,5-dihydro-1H-imidazol-2-yl-amino | N |
| 4,5-dihydro-1H-imidazol-2-yl-amino | C—H |
| 5-hydroxy-tetrahydropyrimidin-2-yl-amino | C—OH |
| 5-hydroxy-tetrahydropyrimidin-2-yl-amino | N |
| 5-hydroxy-tetrahydropyrimidin-2-yl-amino | C—H |
| guanidino | C—OH |
| guanidino | N |
| guanidino | C—H |

TABLE A-continued
Examples of Beta Amino Acid Derivatives
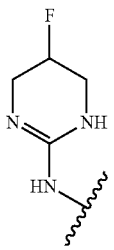
| W | A |
|---|---|
| 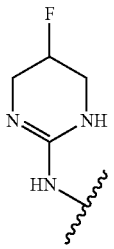 | C—OH |
| 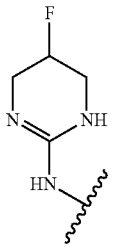 | N |
| 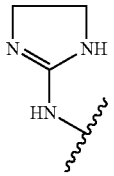 | C—H |
| 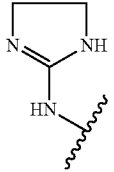 | C—OH |
| 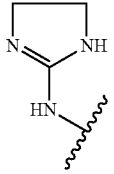 | N |
| 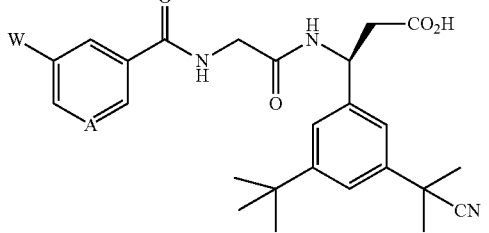 | C—H |
| 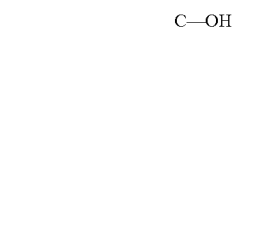 | C—OH |
| 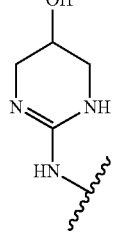 | N |
| 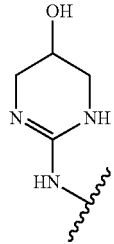 | C—H |
| 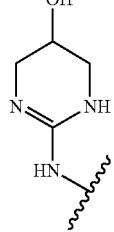 | C—OH |
| 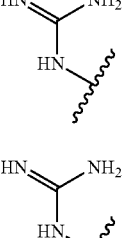 | N |
| 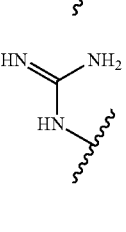 | C—H |

TABLE A-continued
Examples of Beta Amino Acid Derivatives
| W | A |
|---|---|
| 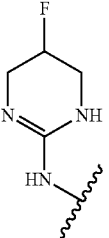 | C—OH |
| 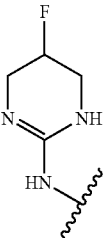 | N |
| 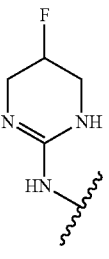 | C—H |
| 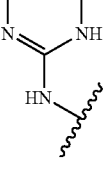 | C—OH |
| 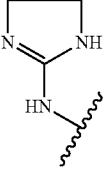 | N |
| 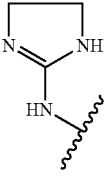 | C—H |
| 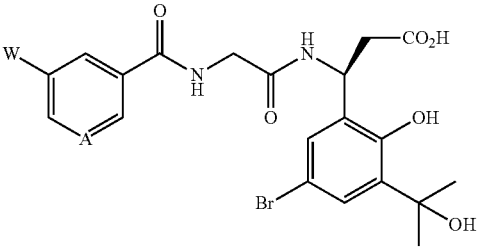 | |
| 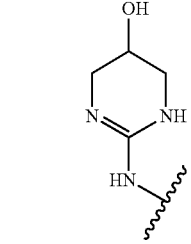 | C—OH |
| 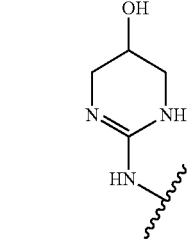 | N |
| 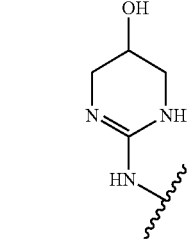 | C—H |
| 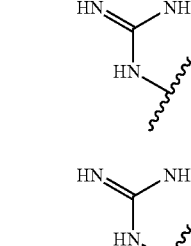 | C—OH |
| 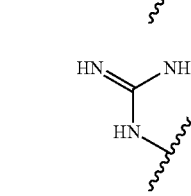 | N |
|  | C—H |

TABLE A-continued
Examples of Beta Amino Acid Derivatives
| W | A |
|---|---|
| 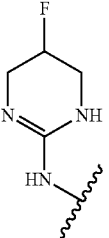 | C—OH |
| 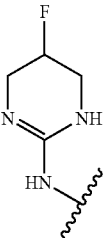 | N |
| 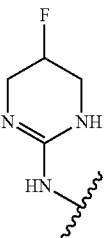 | C—H |
| 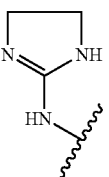 | C—OH |
| 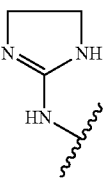 | N |
| 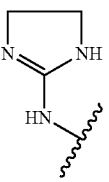 | C—H |
TABLE A-continued
Examples of Beta Amino Acid Derivatives
| W | A |
|---|---|
| 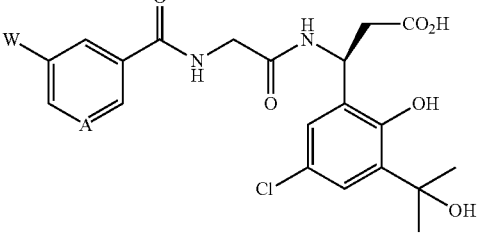 | |
| 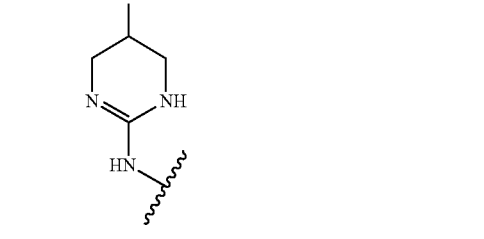 | C—OH |
| 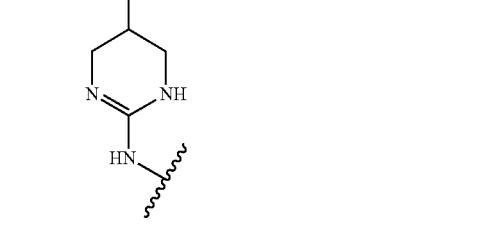 | N |
| 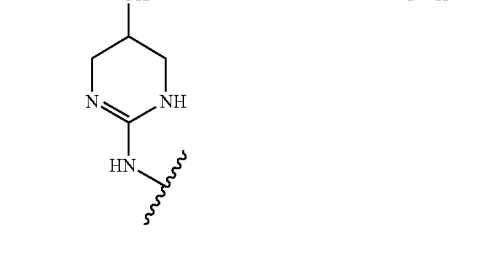 | C—H |
| 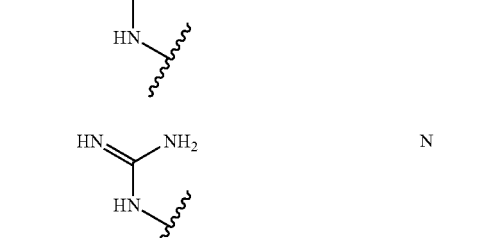 | C—OH |
| 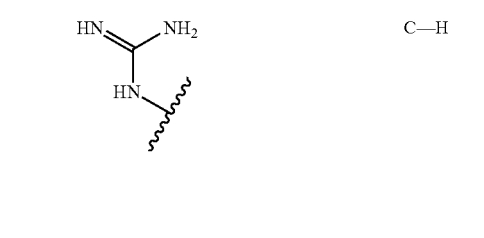 | N |
| 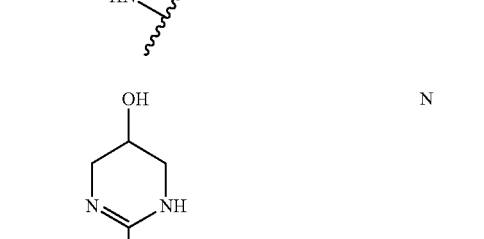 | C—H |

TABLE A-continued
Examples of Beta Amino Acid Derivatives
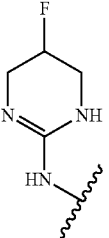
| W | A |
|---|---|
| 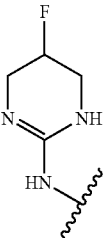 | C—OH |
| 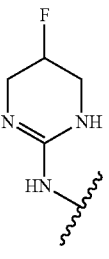 | N |
| 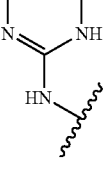 | C—H |
| 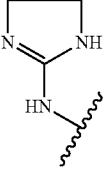 | C—OH |
| 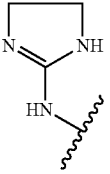 | N |
| 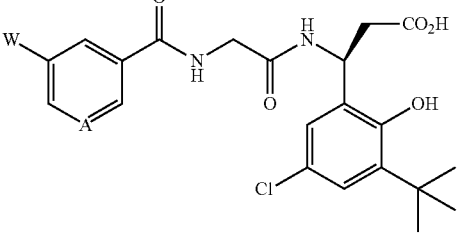 | C—H |
| 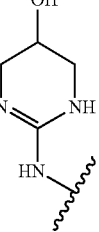 | C—OH |
| 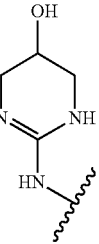 | N |
| 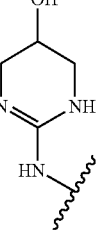 | C—H |
| 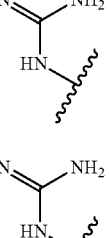 | C—OH |
| 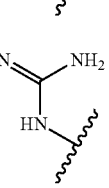 | N |
| | C—H |

TABLE A-continued
Examples of Beta Amino Acid Derivatives
| W | A |
|---|---|
| 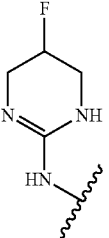 | C—OH |
| 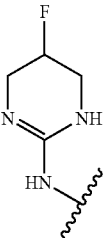 | N |
| 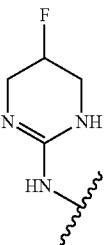 | C—H |
| 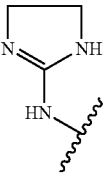 | C—OH |
| 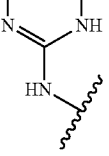 | N |
| 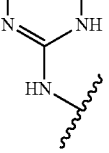 | C—H |
TABLE A-continued
Examples of Beta Amino Acid Derivatives
| W | A |
|---|---|
| 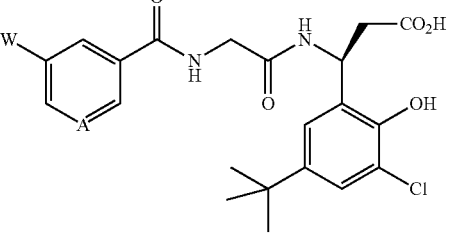 | |
| 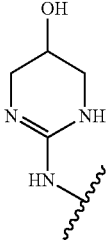 | C—OH |
| 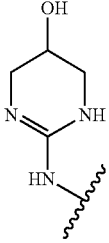 | N |
| 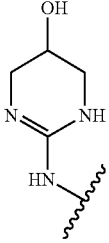 | C—H |
| 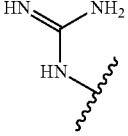 | C—OH |
| 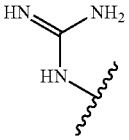 | N |
| 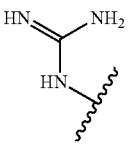 | C—H |

TABLE A-continued
Examples of Beta Amino Acid Derivatives
| W | A |
|---|---|
| 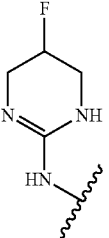 | C—OH |
| 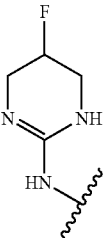 | N |
| 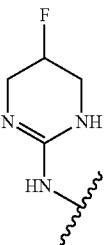 | C—H |
| 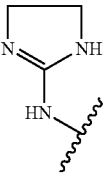 | C—OH |
| 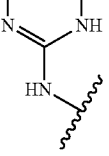 | N |
| 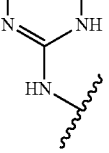 | C—H |
TABLE A-continued
Examples of Beta Amino Acid Derivatives
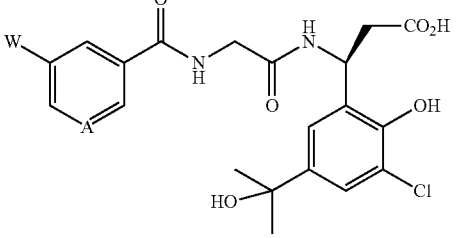
| W | A |
|---|---|
| 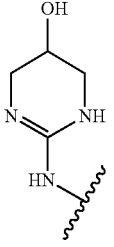 | C—OH |
| 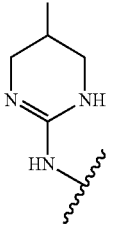 | N |
| 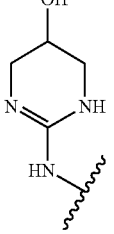 | C—H |
| 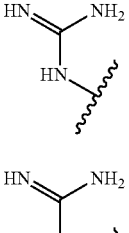 | C—OH |
| 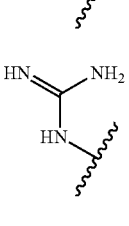 | N |
| 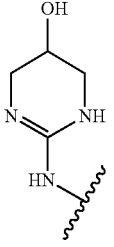 | C—H |

TABLE A-continued

Examples of Beta Amino Acid Derivatives

| W | A |
|---|---|
| 5-fluoro-tetrahydropyrimidin-2-yl-amino | C—OH |
| 5-fluoro-tetrahydropyrimidin-2-yl-amino | N |
| 5-fluoro-tetrahydropyrimidin-2-yl-amino | C—H |
| 4,5-dihydro-1H-imidazol-2-yl-amino | C—OH |
| 4,5-dihydro-1H-imidazol-2-yl-amino | N |
| 4,5-dihydro-1H-imidazol-2-yl-amino | C—H |

General structure:

W—C(=O)—NH—CH₂—C(=O)—NH—CH(CO₂H)—[aryl(OH, Br, C(CH₃)₂OH)], with A in the pyridine-like ring.

| W | A |
|---|---|
| 5-hydroxy-tetrahydropyrimidin-2-yl-amino | C—OH |
| 5-hydroxy-tetrahydropyrimidin-2-yl-amino | N |
| 5-hydroxy-tetrahydropyrimidin-2-yl-amino | C—H |
| guanidino (HN=C(NH₂)—NH—) | C—OH |
| guanidino (HN=C(NH₂)—NH—) | N |
| guanidino (HN=C(NH₂)—NH—) | C—H |

TABLE A-continued

Examples of Beta Amino Acid Derivatives

| W | A |
|---|---|
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | N |
| (5-hydroxy-tetrahydropyrimidin-2-yl)amino | C—H |
| guanidino | C—OH |
| guanidino | N |
| guanidino | C—H |
| (5-fluoro-tetrahydropyrimidin-2-yl)amino | C—OH |

General structure:

W—C(=O)—NH—CH2—C(=O)—NH—CH(CO2H)—[3-bromo-5-tert-butyl-2-hydroxyphenyl], with aryl ring containing A position.

TABLE A-continued
Examples of Beta Amino Acid Derivatives
| W | A |
|---|---|
| 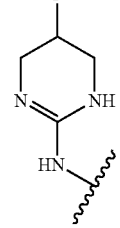 | N |
| 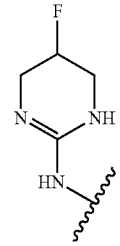 | C—H |
| 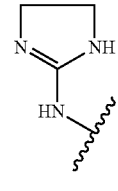 | C—OH |
| 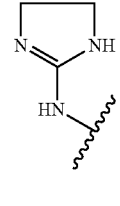 | N |
| 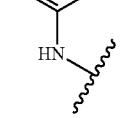 | C—H |
| 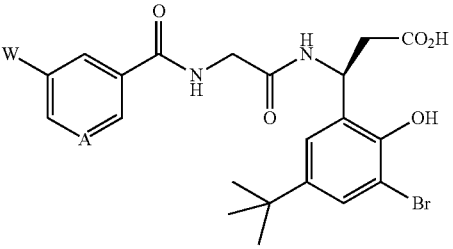 | |
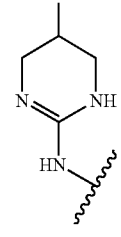
TABLE A-continued
Examples of Beta Amino Acid Derivatives
| W | A |
|---|---|
| 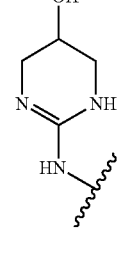 | N |
| 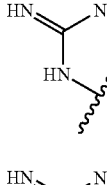 | C—H |
| 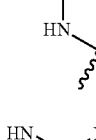 | C—OH |
| 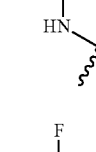 | N |
| 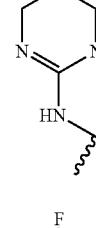 | C—H |
| 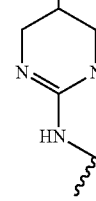 | C—OH |
| 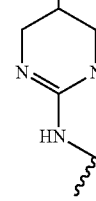 | N |

TABLE A-continued
Examples of Beta Amino Acid Derivatives
| W | A |
|---|---|
| 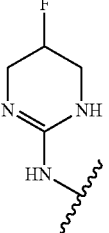 | C—H |
| 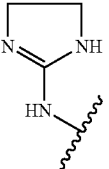 | C—OH |
| 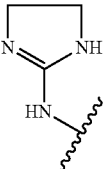 | N |
| 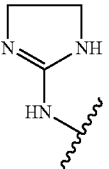 | C—H |
| 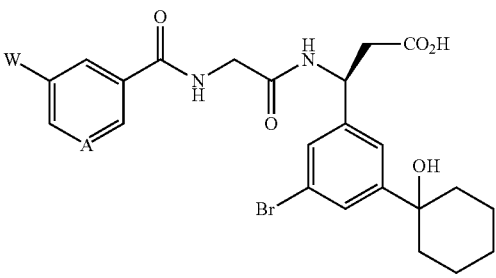 | C—OH |
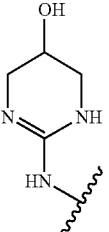
TABLE A-continued
Examples of Beta Amino Acid Derivatives
| W | A |
|---|---|
| 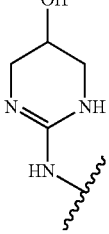 | N |
| 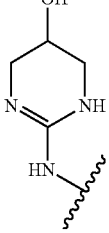 | C—H |
| 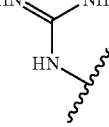 | C—OH |
| 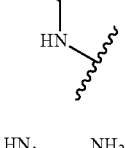 | N |
|  | C—H |
| 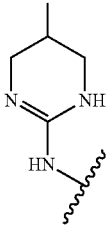 | C—OH |
| 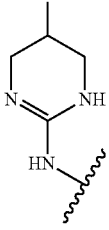 | N |

TABLE A-continued
Examples of Beta Amino Acid Derivatives
| W | A |
|---|---|
| 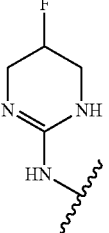 | C—H |
| 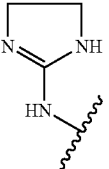 | C—OH |
| 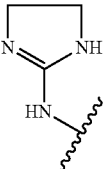 | N |
| 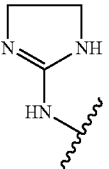 | C—H |
| 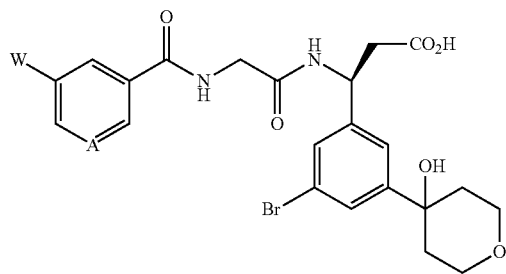 | C—OH |
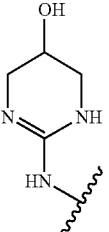
TABLE A-continued
Examples of Beta Amino Acid Derivatives
| W | A |
|---|---|
| 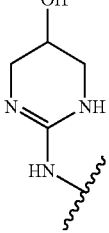 | N |
| 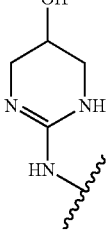 | C—H |
| 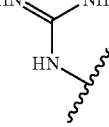 | C—OH |
| 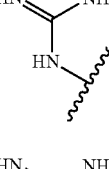 | N |
| 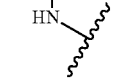 | C—H |
| 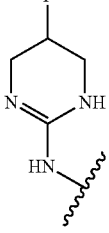 | C—OH |
| 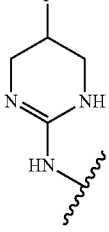 | N |

TABLE A-continued

Examples of Beta Amino Acid Derivatives

| W | A |
|---|---|
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| guanidino | C—OH |
| guanidino | N |
| guanidino | C—H |
| (5-fluoro-tetrahydropyrimidin-2-yl)amino | C—OH |
| (5-fluoro-tetrahydropyrimidin-2-yl)amino | N |

General structure:

W-(3-position of pyridine/benzene ring with A at 5-position)—C(O)NH—CH₂—C(O)NH—CH(CH₂CO₂H)—[3-chloro-5-(4-hydroxy-tetrahydropyran-4-yl)phenyl]

TABLE A-continued
Examples of Beta Amino Acid Derivatives
| W | A |
|---|---|
| 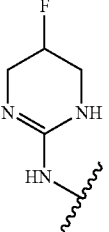 | C—H |
| 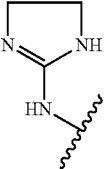 | C—OH |
| 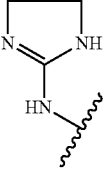 | N |
| 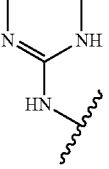 | C—H |
| 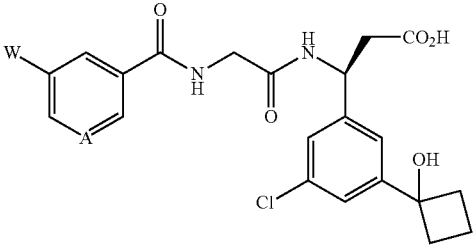 | C—OH |
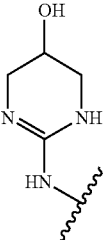
TABLE A-continued
Examples of Beta Amino Acid Derivatives
| W | A |
|---|---|
| 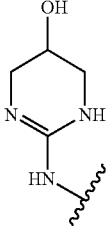 | N |
| 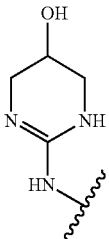 | C—H |
| 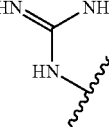 | C—OH |
| 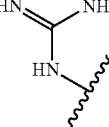 | N |
| 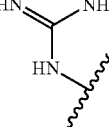 | C—H |
| 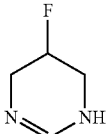 | C—OH |
| 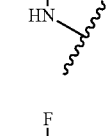 | N |

TABLE A-continued
Examples of Beta Amino Acid Derivatives
| W | A |
|---|---|
| 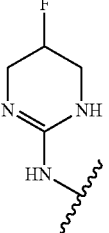 | C—H |
| 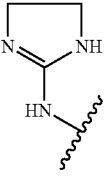 | C—OH |
| 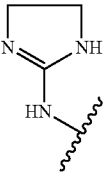 | N |
| 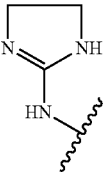 | C—H |
| 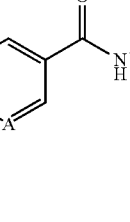 | |
| 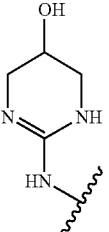 | C—OH |
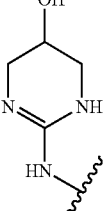
TABLE A-continued
Examples of Beta Amino Acid Derivatives
| W | A |
|---|---|
| 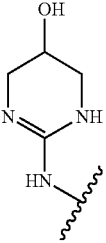 | N |
| 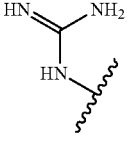 | C—H |
| 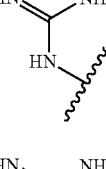 | C—OH |
| 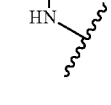 | N |
| 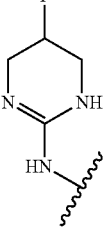 | C—H |
| 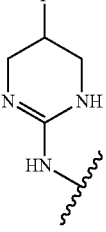 | C—OH |
| | N |

TABLE A-continued
Examples of Beta Amino Acid Derivatives
| W | A |
|---|---|
| 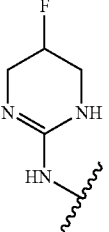 | C—H |
| 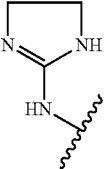 | C—OH |
| 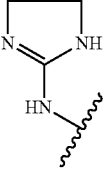 | N |
| 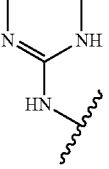 | C—H |
| 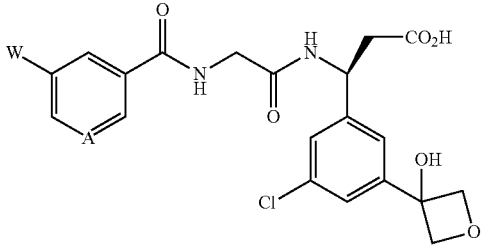 | C—OH |
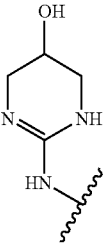
TABLE A-continued
Examples of Beta Amino Acid Derivatives
| W | A |
|---|---|
| 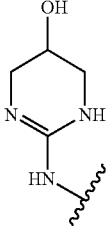 | N |
| 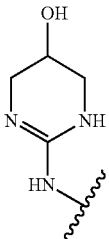 | C—H |
| 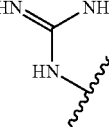 | C—OH |
| 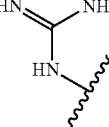 | N |
| 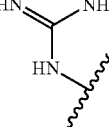 | C—H |
| 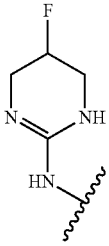 [SMILES: *NC1=NCC(F)CN1] | C—OH |
| 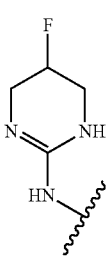 [SMILES: *NC1=NCC(F)CN1] | N |

TABLE A-continued
Examples of Beta Amino Acid Derivatives
| W | A |
|---|---|
| 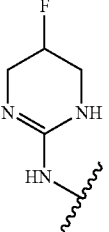 | C—H |
| 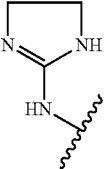 | C—OH |
| 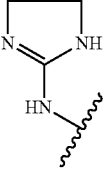 | N |
| 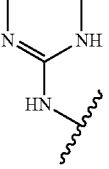 | C—H |
| 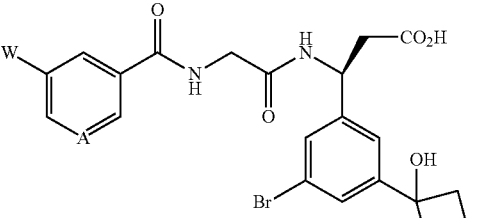 | C—OH |
| 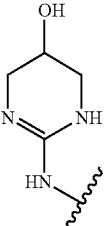 | N |
| 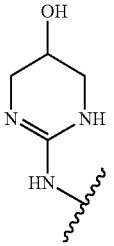 | C—H |
| 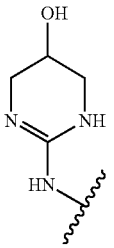 | C—OH |
| 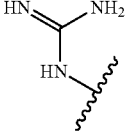 | N |
| 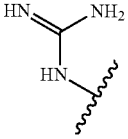 | C—H |
| 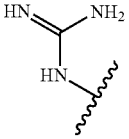 | C—OH |
| 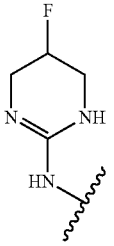 [SMILES: *NC1=NCC(F)CN1] | N |
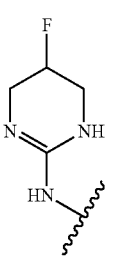 [SMILES: *NC1=NCC(F)CN1]

TABLE A-continued

Examples of Beta Amino Acid Derivatives

| W | A |
|---|---|
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| guanidino | C—OH |
| guanidino | N |
| guanidino | C—H |
| (5-fluoro-tetrahydropyrimidin-2-yl)amino | C—OH |
| (5-fluoro-tetrahydropyrimidin-2-yl)amino | N |

TABLE A-continued
Examples of Beta Amino Acid Derivatives
| W | A |
|---|---|
| 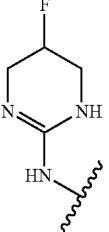 | C—H |
| 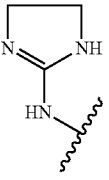 | C—OH |
| 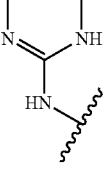 | N |
| 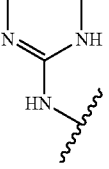 | C—H |
| 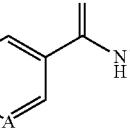 | C—OH |
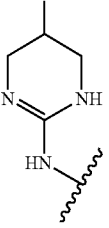
TABLE A-continued
Examples of Beta Amino Acid Derivatives
| W | A |
|---|---|
| 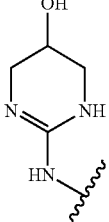 | N |
| 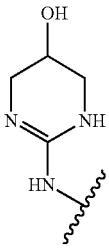 | C—H |
| 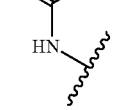 | C—OH |
| 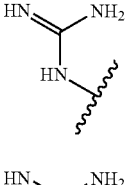 | N |
| 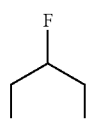 | C—H |
| 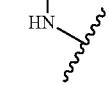 | C—OH |
| 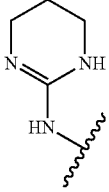 | N |

TABLE A-continued
Examples of Beta Amino Acid Derivatives
| W | A |
|---|---|
| 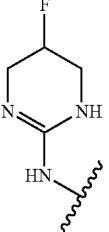 | C—H |
| 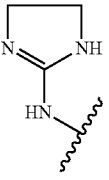 | C—OH |
| 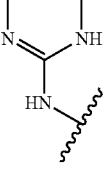 | N |
| 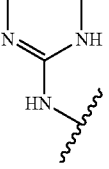 | C—H |
| 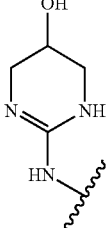 | C—OH |
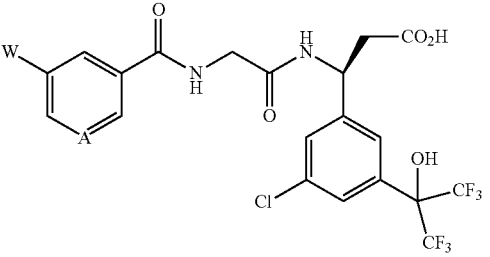
TABLE A-continued
Examples of Beta Amino Acid Derivatives
| W | A |
|---|---|
| 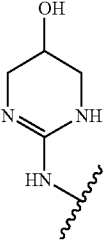 | N |
| 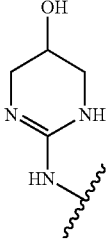 | C—H |
| 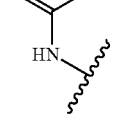 | C—OH |
| 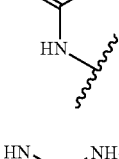 | N |
| 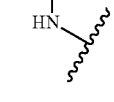 | C—H |
| 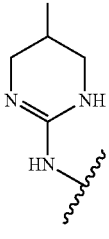 | C—OH |
| 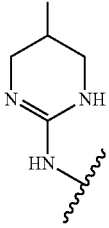 | N |

TABLE A-continued

Examples of Beta Amino Acid Derivatives

| W | A |
|---|---|
| 5-fluoro-tetrahydropyrimidin-2-yl-amino | C—H |
| 4,5-dihydro-1H-imidazol-2-yl-amino | C—OH |
| 4,5-dihydro-1H-imidazol-2-yl-amino | N |
| 4,5-dihydro-1H-imidazol-2-yl-amino | C—H |
| 5-hydroxy-tetrahydropyrimidin-2-yl-amino | C—OH |
| 5-hydroxy-tetrahydropyrimidin-2-yl-amino | N |
| 5-hydroxy-tetrahydropyrimidin-2-yl-amino | C—H |
| guanidino | C—OH |
| guanidino | N |
| guanidino | C—H |
| 5-fluoro-tetrahydropyrimidin-2-yl-amino | C—OH |
| 5-fluoro-tetrahydropyrimidin-2-yl-amino | N |

General structure shown:

W—(phenyl with A)—C(=O)—NH—CH₂—C(=O)—NH—CH(CO₂H)—(3-chloro-5-(2,4-dimethyl-3-hydroxypentan-3-yl)phenyl)

TABLE A-continued

Examples of Beta Amino Acid Derivatives

| W | A |
|---|---|
| 5-fluoro-tetrahydropyrimidin-2-ylamino | C—H |
| 4,5-dihydro-1H-imidazol-2-ylamino | C—OH |
| 4,5-dihydro-1H-imidazol-2-ylamino | N |
| 4,5-dihydro-1H-imidazol-2-ylamino | C—H |
| 5-hydroxy-tetrahydropyrimidin-2-ylamino | C—OH |

General structure:

W—(benzamide)—NH—CH2—C(O)—NH—CH(CO2H)—(3-bromo-5-(2,4-dimethyl-3-hydroxypentan-3-yl)phenyl), with A on the W-bearing ring.

TABLE A-continued

Examples of Beta Amino Acid Derivatives

| W | A |
|---|---|
| 5-hydroxy-tetrahydropyrimidin-2-ylamino | N |
| 5-hydroxy-tetrahydropyrimidin-2-ylamino | C—H |
| guanidino | C—OH |
| guanidino | N |
| guanidino | C—H |
| 5-fluoro-tetrahydropyrimidin-2-ylamino | C—OH |
| 5-fluoro-tetrahydropyrimidin-2-ylamino | N |

TABLE A-continued

Examples of Beta Amino Acid Derivatives

| W | A |
|---|---|
| (5-fluoro-tetrahydropyrimidin-2-yl)amino | C—H |
| (4,5-dihydro-1H-imidazol-2-yl)amino | C—OH |
| (4,5-dihydro-1H-imidazol-2-yl)amino | N |
| (4,5-dihydro-1H-imidazol-2-yl)amino | C—H |
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| guanidino | C—OH |
| guanidino | N |
| guanidino | C—H |
| (5-fluoro-tetrahydropyrimidin-2-yl)amino | C—OH |
| (5-fluoro-tetrahydropyrimidin-2-yl)amino | N |

TABLE A-continued
Examples of Beta Amino Acid Derivatives
| W | A |
|---|---|
| 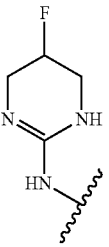 | C—H |
| 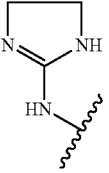 | C—OH |
| 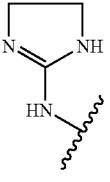 | N |
| 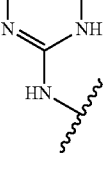 | C—H |
| 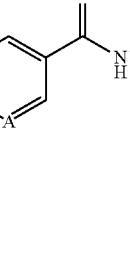 | |
| 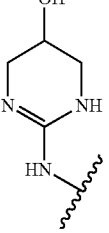 | C—OH |
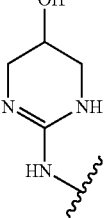
TABLE A-continued
Examples of Beta Amino Acid Derivatives
| W | A |
|---|---|
| 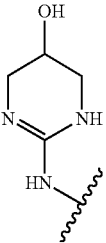 | N |
| 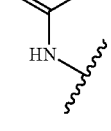 | C—H |
| 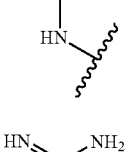 | C—OH |
| 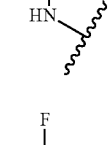 | N |
| 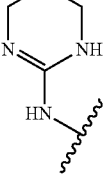 | C—H |
| 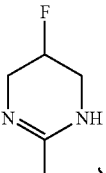 | C—OH |
| 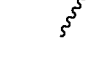 | N |

TABLE A-continued
Examples of Beta Amino Acid Derivatives
| W | A |
|---|---|
| 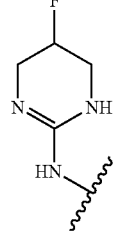 | C—H |
| 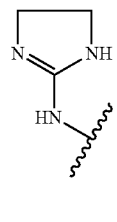 | C—OH |
| 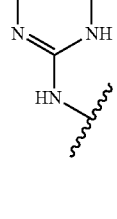 | N |
| 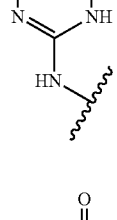 | C—H |
| 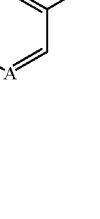 | |
| 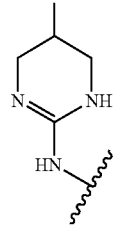 | C—OH |
| 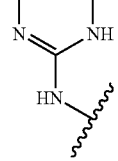 | N |
| 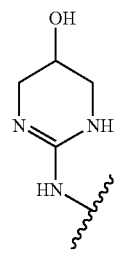 | C—H |
| 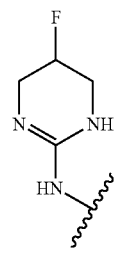 | C—OH |
| 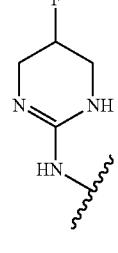 | N |
| 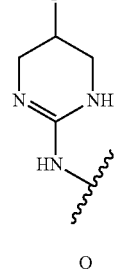 | C—H |
| 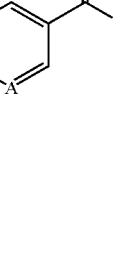 | |
|  | |

TABLE A-continued

Examples of Beta Amino Acid Derivatives

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

General structure:

W—C(=O)—NH—CH₂—C(=O)—NH—CH(CO₂H)—[3-chloro-5-(1,1,1-trifluoro-2-hydroxyprop-2-yl)phenyl], with A in the pyridine-type ring attached to W

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |

TABLE A-continued
Examples of Beta Amino Acid Derivatives
| W | A |
|---|---|
| 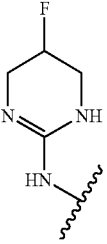 | C—H |
| 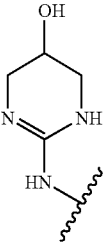 | C—OH |
| 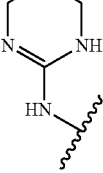 | N |
| 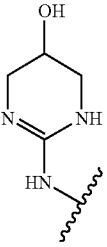 | C—H |
| 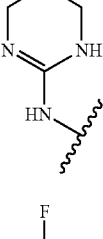 | C—OH |
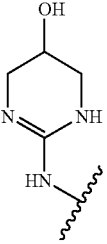
TABLE A-continued
Examples of Beta Amino Acid Derivatives
| W | A |
|---|---|
| 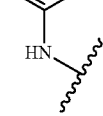 | N |
| 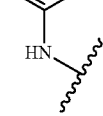 | C—H |
| 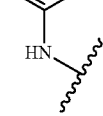 | C—OH |
| 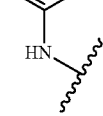 | N |
| 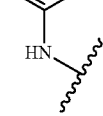 | C—H |
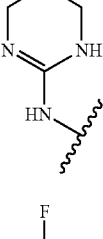

TABLE A-continued
Examples of Beta Amino Acid Derivatives
| W | A |
|---|---|
| 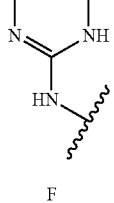 | C—OH |
| | N |
| | C—H |
| 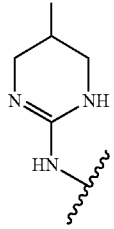 | |
| 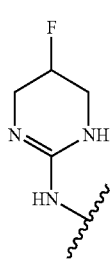 | C—OH |
| | N |
TABLE A-continued
Examples of Beta Amino Acid Derivatives
| W | A |
|---|---|
| 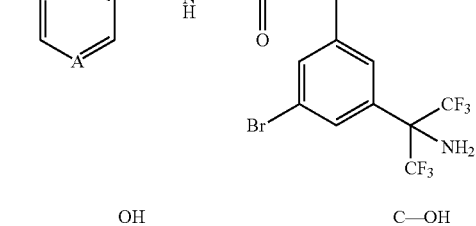 | C—H |
| | C—OH |
| | N |
| | C—H |
| 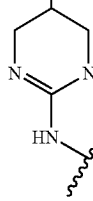 | |
| 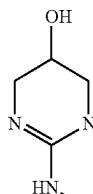 | C—OH |

TABLE A-continued

Examples of Beta Amino Acid Derivatives

| W | A |
|---|---|
| 5-hydroxy-tetrahydropyrimidin-2-ylamino (via HN) | N |
| 5-hydroxy-tetrahydropyrimidin-2-ylamino (via HN) | C—H |
| 5-fluoro-tetrahydropyrimidin-2-ylamino (via HN) | C—OH |
| 5-fluoro-tetrahydropyrimidin-2-ylamino (via HN) | N |
| 5-fluoro-tetrahydropyrimidin-2-ylamino (via HN) | C—H |

TABLE A-continued

Examples of Beta Amino Acid Derivatives

| W | A |
|---|---|
| 5-hydroxy-tetrahydropyrimidin-2-ylamino (via HN) | C—OH |
| 5-hydroxy-tetrahydropyrimidin-2-ylamino (via HN) | N |
| 5-hydroxy-tetrahydropyrimidin-2-ylamino (via HN) | C—H |
| 5-fluoro-tetrahydropyrimidin-2-ylamino (via HN) | C—OH |
| 5-fluoro-tetrahydropyrimidin-2-ylamino (via HN) | N |
| 5-fluoro-tetrahydropyrimidin-2-ylamino (via HN) | C—H |

TABLE A-continued
Examples of Beta Amino Acid Derivatives
| W | A |
|---|---|
| 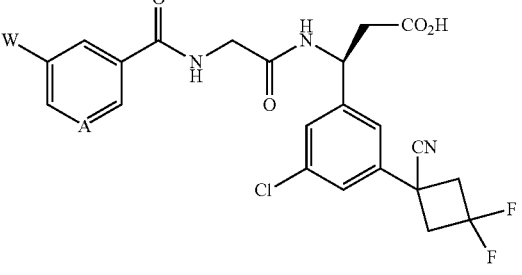 |  |
|  | C—OH |
|  | N |
|  | C—H |
|  | C—OH |
|  | N |
|  | C—H |
|  |  |
|  | C—OH |
|  | N |
|  | C—H |

TABLE A-continued

Examples of Beta Amino Acid Derivatives

| W | A |
|---|---|
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |
| (5-hydroxy-tetrahydropyrimidin-2-ylamino) | C—OH |
| (5-hydroxy-tetrahydropyrimidin-2-ylamino) | N |
| (5-hydroxy-tetrahydropyrimidin-2-ylamino) | C—H |
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |

Structure (chloro-cyano-tetrahydropyran substituted phenyl beta-amino acid derivative with W-aryl-A carbonyl glycinamide):

W–[aryl(A)]–C(O)–NH–CH$_2$–C(O)–NH–CH(CO$_2$H)–[3-chloro-5-(4-cyano-tetrahydropyran-4-yl)phenyl]

Structure (bromo analog):

W–[aryl(A)]–C(O)–NH–CH$_2$–C(O)–NH–CH(CO$_2$H)–[3-bromo-5-(4-cyano-tetrahydropyran-4-yl)phenyl]

TABLE A-continued

Examples of Beta Amino Acid Derivatives

TABLE A-continued

Examples of Beta Amino Acid Derivatives

| W | A |
|---|---|
| (5-fluoro-tetrahydropyrimidin-2-yl)amine | C—H |
| (5-hydroxy-tetrahydropyrimidin-2-yl)amine | C—OH |
| (5-hydroxy-tetrahydropyrimidin-2-yl)amine | N |
| (5-hydroxy-tetrahydropyrimidin-2-yl)amine | C—H |
| (5-fluoro-tetrahydropyrimidin-2-yl)amine | C—OH |
| (5-fluoro-tetrahydropyrimidin-2-yl)amine | N |
| (5-fluoro-tetrahydropyrimidin-2-yl)amine | C—H |
| (5-hydroxy-tetrahydropyrimidin-2-yl)amine | C—OH |
| (5-hydroxy-tetrahydropyrimidin-2-yl)amine | N |

TABLE A-continued

Examples of Beta Amino Acid Derivatives

| W | A |
|---|---|
| (tetrahydropyrimidine with 5-OH, 2-NH-) | C—H |
| (tetrahydropyrimidine with 5-F, 2-NH-) | C—OH |
| (tetrahydropyrimidine with 5-F, 2-NH-) | N |
| (tetrahydropyrimidine with 5-F, 2-NH-) | C—H |

TABLE A-continued

Examples of Beta Amino Acid Derivatives

| W | A |
|---|---|
| (tetrahydropyrimidine with 5-OH, 2-NH-) | C—OH |
| (tetrahydropyrimidine with 5-OH, 2-NH-) | N |
| (tetrahydropyrimidine with 5-OH, 2-NH-) | C—H |
| (tetrahydropyrimidine with 5-F, 2-NH-) | C—OH |
| (tetrahydropyrimidine with 5-F, 2-NH-) | N |
| (tetrahydropyrimidine with 5-F, 2-NH-) | C—H |

TABLE A-continued
Examples of Beta Amino Acid Derivatives
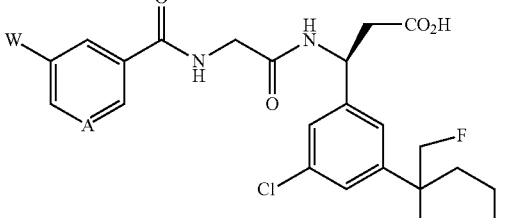
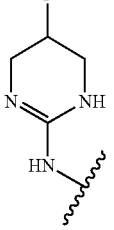

TABLE A-continued

Examples of Beta Amino Acid Derivatives

| W | A |
|---|---|
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |
| (5-hydroxy-tetrahydropyrimidin-2-ylamino) | C—OH |
| (5-hydroxy-tetrahydropyrimidin-2-ylamino) | N |
| (5-hydroxy-tetrahydropyrimidin-2-ylamino) | C—H |
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |

Structure (chloro/CF2H tetrahydropyran derivative):
W-aryl-C(=O)-NH-CH2-C(=O)-NH-CH(CO2H)-aryl(Cl, CF2H-tetrahydropyran)

Structure (bromo/CF2H tetrahydropyran derivative):
W-aryl-C(=O)-NH-CH2-C(=O)-NH-CH(CO2H)-aryl(Br, CF2H-tetrahydropyran)

TABLE A-continued

Examples of Beta Amino Acid Derivatives

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

Examples of Beta Amino Acid Derivatives

General structure: W–C(=O)–NH–CH₂–C(=O)–NH–CH(CO₂H)–Ar, where Ar = 3-chloro-5-(1-methoxymethyl-cyclobutyl)phenyl, and the W-bearing ring is a pyridine-type ring with variable A position.

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |

TABLE A-continued

Examples of Beta Amino Acid Derivatives

| W | A |
|---|---|
| 5-fluoro-tetrahydropyrimidin-2-ylamino | C—H |
| (core structure with Br, OMe, cyclobutyl) | |
| 5-hydroxy-tetrahydropyrimidin-2-ylamino | C—OH |
| 5-hydroxy-tetrahydropyrimidin-2-ylamino | N |
| 5-hydroxy-tetrahydropyrimidin-2-ylamino | C—H |
| 5-fluoro-tetrahydropyrimidin-2-ylamino | C—OH |

TABLE A-continued

Examples of Beta Amino Acid Derivatives

| W | A |
|---|---|
| 5-fluoro-tetrahydropyrimidin-2-ylamino | N |
| 5-fluoro-tetrahydropyrimidin-2-ylamino | C—H |
| (core structure with Cl, OH, cyclobutyl) | |
| 5-hydroxy-tetrahydropyrimidin-2-ylamino | C—OH |
| 5-hydroxy-tetrahydropyrimidin-2-ylamino | N |
| 5-hydroxy-tetrahydropyrimidin-2-ylamino | C—H |

TABLE A-continued

Examples of Beta Amino Acid Derivatives

| W | A |
|---|---|
| 5-F tetrahydropyrimidin-2-yl-amino | C—OH |
| 5-F tetrahydropyrimidin-2-yl-amino | N |
| 5-F tetrahydropyrimidin-2-yl-amino | C—H |
| 5-OH tetrahydropyrimidin-2-yl-amino | C—OH |
| 5-OH tetrahydropyrimidin-2-yl-amino | N |
| 5-OH tetrahydropyrimidin-2-yl-amino | C—H |
| 5-F tetrahydropyrimidin-2-yl-amino | C—OH |
| 5-F tetrahydropyrimidin-2-yl-amino | N |
| 5-F tetrahydropyrimidin-2-yl-amino | C—H |
| 5-OH tetrahydropyrimidin-2-yl-amino | C—OH |

Structure (bottom of column 199): W-substituted benzamide-NH-CH2-C(=O)-NH-CH(CO2H)-[3-bromo-5-(1-hydroxymethylcyclobutyl)phenyl]

Structure (bottom of column 200): W-substituted benzamide-NH-CH2-C(=O)-NH-CH(CO2H)-[3-chloro-5-(1-difluoromethylcyclobutyl)phenyl]

TABLE A-continued
Examples of Beta Amino Acid Derivatives
| W | A |
|---|---|
| 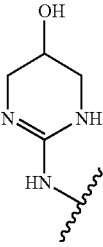 | N |
| 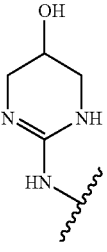 | C—H |
| 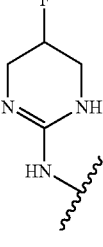 | C—OH |
| 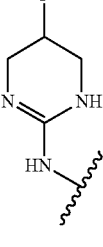 | N |
| 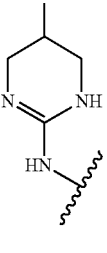 | C—H |
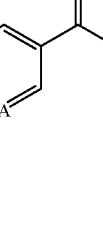
TABLE A-continued
Examples of Beta Amino Acid Derivatives
| W | A |
|---|---|
|  | C—OH |
| 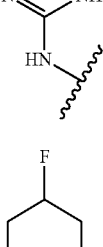 | N |
| 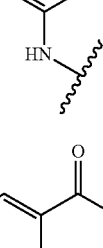 | C—H |
|  | C—OH |
|  | N |
| 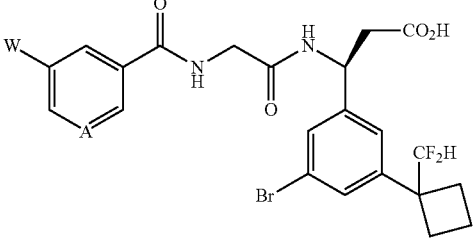 | C—H |

TABLE A-continued
Examples of Beta Amino Acid Derivatives
| W | A |
|---|---|
| 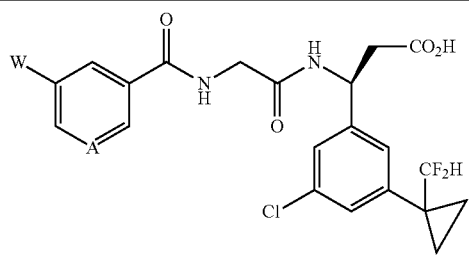 | |
| 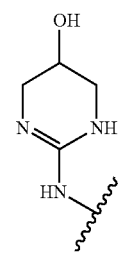 | C—OH |
| 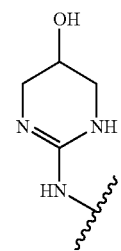 | N |
| 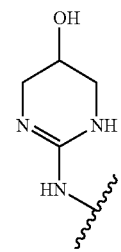 | C—H |
| 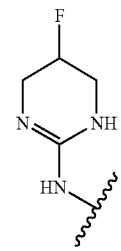 | C—OH |
| 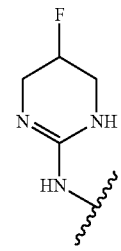 | N |
TABLE A-continued
Examples of Beta Amino Acid Derivatives
| W | A |
|---|---|
| 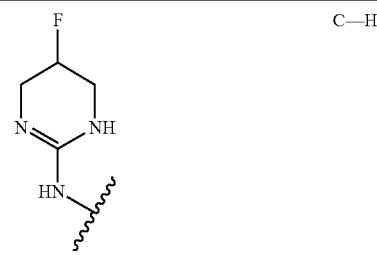 | C—H |
| 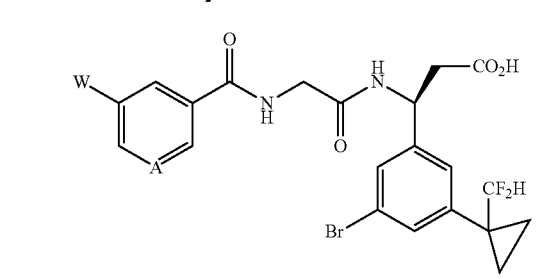 | |
| 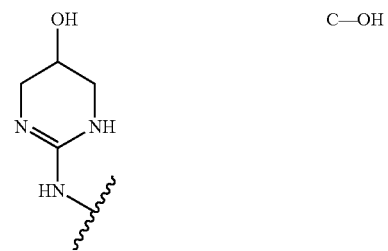 | C—OH |
| 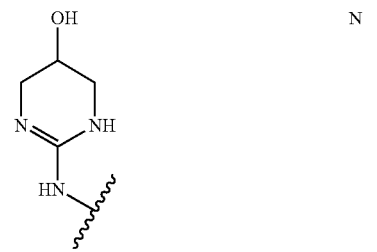 | N |
| 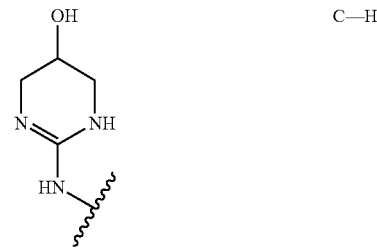 | C—H |
| 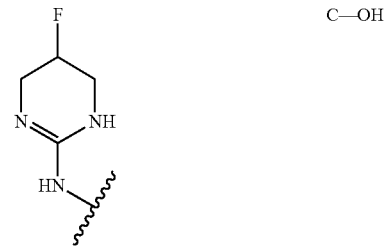 | C—OH |

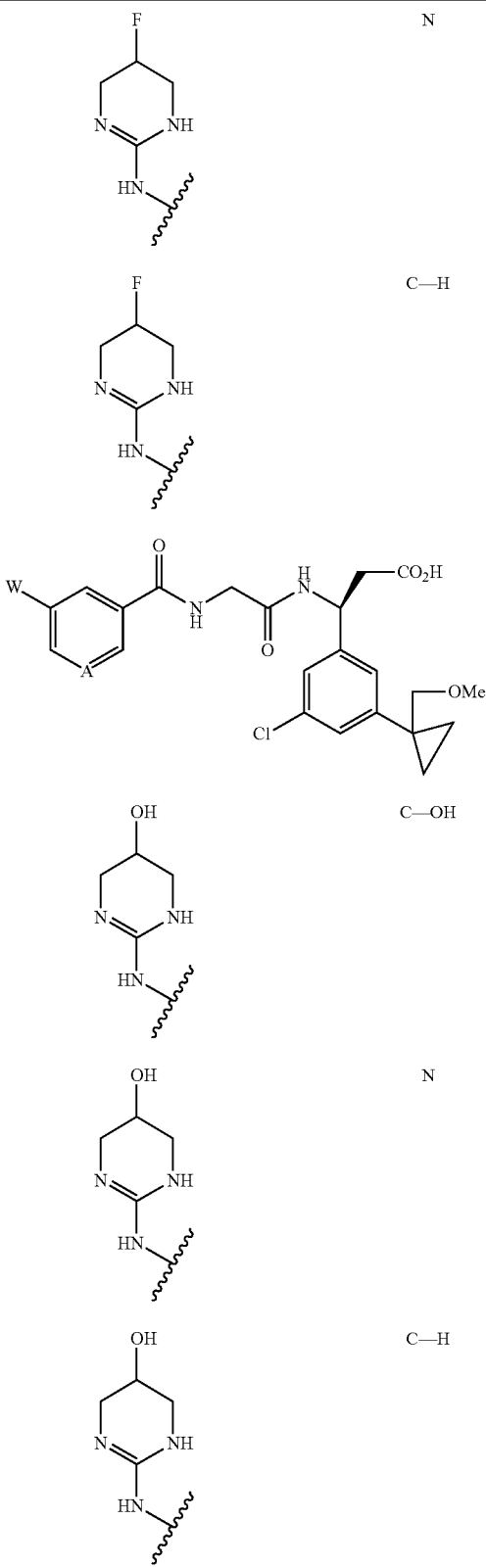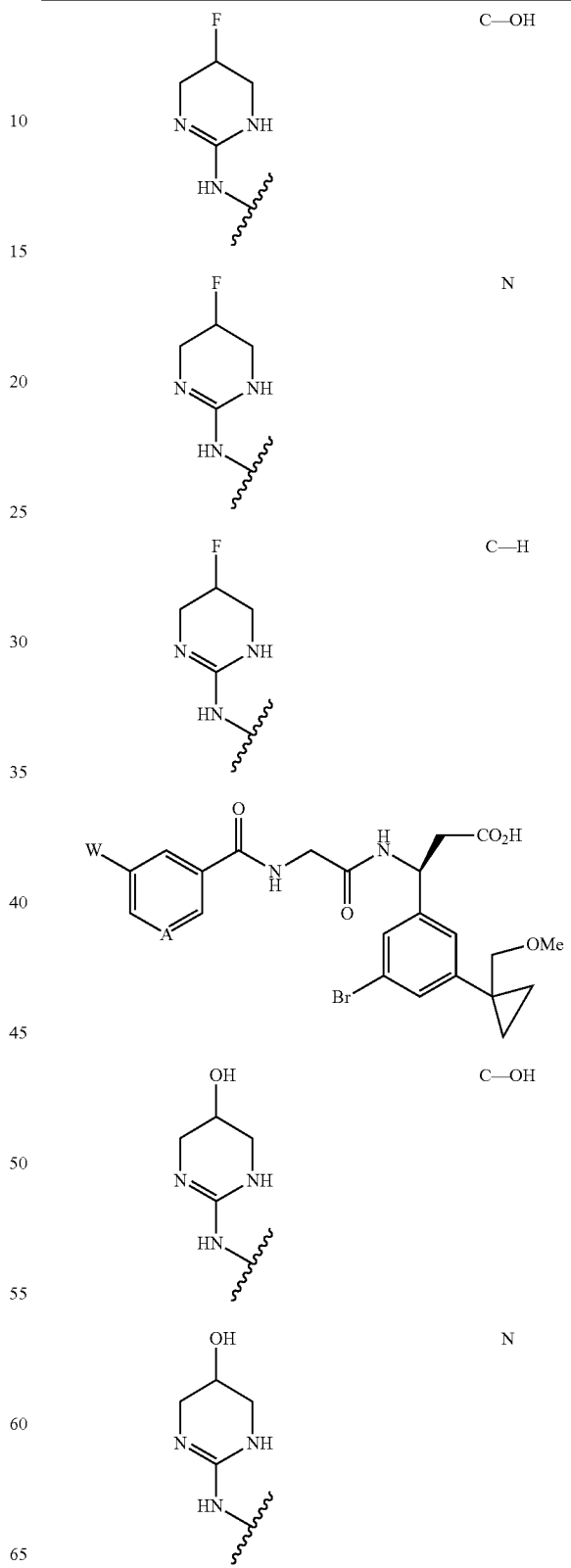

TABLE A-continued

Examples of Beta Amino Acid Derivatives

| W | A |
|---|---|
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

Structure with W, A, Cl, CO2H, cyclopropyl-CH2OH substituents

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

Structure with W, A, Br, CO2H, cyclopropyl-CH2OH substituents

TABLE A-continued

Examples of Beta Amino Acid Derivatives

| W | A |
|---|---|

(structure: 5-hydroxy-tetrahydropyrimidin-2-ylamino) | C—OH
(structure: 5-hydroxy-tetrahydropyrimidin-2-ylamino) | N
(structure: 5-hydroxy-tetrahydropyrimidin-2-ylamino) | C—H
(structure: 5-fluoro-tetrahydropyrimidin-2-ylamino) | C—OH
(structure: 5-fluoro-tetrahydropyrimidin-2-ylamino) | N
(structure: 5-fluoro-tetrahydropyrimidin-2-ylamino) | C—H TABLE A-continued Examples of Beta Amino Acid Derivatives General structure:

W—(pyridine/benzene with A)—C(=O)—NH—CH$_2$—C(=O)—NH—CH(CO$_2$H)—(3-chloro-5-(1-(fluoromethyl)cyclopropyl)phenyl)

| W | A |
|---|---|

(structure: 5-hydroxy-tetrahydropyrimidin-2-ylamino) | C—OH
(structure: 5-hydroxy-tetrahydropyrimidin-2-ylamino) | N
(structure: 5-hydroxy-tetrahydropyrimidin-2-ylamino) | C—H
(structure: 5-fluoro-tetrahydropyrimidin-2-ylamino) | C—OH
(structure: 5-fluoro-tetrahydropyrimidin-2-ylamino) | N TABLE A-continued Examples of Beta Amino Acid Derivatives

| W | A |
|---|---|
| (5-fluoro-tetrahydropyrimidin-2-yl-amino) | C—H |
| (5-hydroxy-tetrahydropyrimidin-2-yl-amino) | C—OH |
| (5-hydroxy-tetrahydropyrimidin-2-yl-amino) | N |
| (5-hydroxy-tetrahydropyrimidin-2-yl-amino) | C—H |
| (5-fluoro-tetrahydropyrimidin-2-yl-amino) | C—OH |

Core structure (211): W-substituted benzamide-NH-CH₂-C(O)-NH-CH(CO₂H)-aryl with 3-Br and 5-(1-(fluoromethyl)cyclopropyl) substituents on the aryl.

TABLE A-continued

Examples of Beta Amino Acid Derivatives

| W | A |
|---|---|
| (5-fluoro-tetrahydropyrimidin-2-yl-amino) | N |
| (5-fluoro-tetrahydropyrimidin-2-yl-amino) | C—H |
| (5-hydroxy-tetrahydropyrimidin-2-yl-amino) | C—OH |
| (5-hydroxy-tetrahydropyrimidin-2-yl-amino) | N |
| (5-hydroxy-tetrahydropyrimidin-2-yl-amino) | C—H |

Core structure (212): W-substituted benzamide-NH-CH₂-C(O)-NH-CH(CO₂H)-aryl with 3-Cl and 5-(1-cyanocyclopropyl) substituents on the aryl.

TABLE A-continued

Examples of Beta Amino Acid Derivatives

| W | A |
|---|---|
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |
| Structure: W-phenyl-C(O)-NH-CH2-C(O)-NH-CH(CH2CO2H)-phenyl(3-Br, 5-(1-cyanocyclopropyl)) | |
| (5-hydroxy-tetrahydropyrimidin-2-ylamino) | C—OH |
| (5-hydroxy-tetrahydropyrimidin-2-ylamino) | N |
| (5-hydroxy-tetrahydropyrimidin-2-ylamino) | C—H |
| (5-fluoro-tetrahydropyrimidin-2-ylamino) | C—OH |
| (5-fluoro-tetrahydropyrimidin-2-ylamino) | N |
| (5-fluoro-tetrahydropyrimidin-2-ylamino) | C—H |
| Structure: W-phenyl-C(O)-NH-CH2-C(O)-NH-CH(CH2CO2H)-phenyl(3-Cl, 5-(2-hydroxy-1,1-dimethylethyl)) | |
| (5-hydroxy-tetrahydropyrimidin-2-ylamino) | C—OH |

TABLE A-continued

Examples of Beta Amino Acid Derivatives

| W | A |
|---|---|
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

| W | A |
|---|---|
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

TABLE A-continued
Examples of Beta Amino Acid Derivatives
| W | A |
|---|---|
| 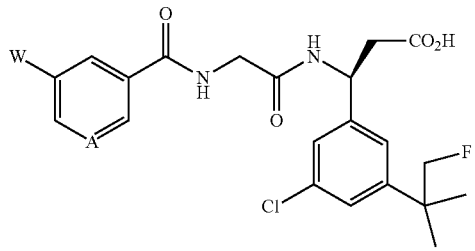 | |
| 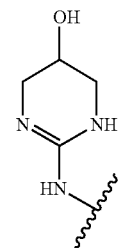 | C—OH |
| 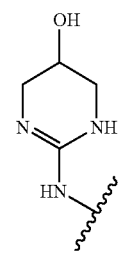 | N |
| 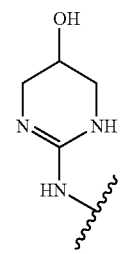 | C—H |
| 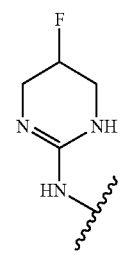 | C—OH |
| 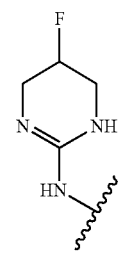 | N |
TABLE A-continued
Examples of Beta Amino Acid Derivatives
| W | A |
|---|---|
| 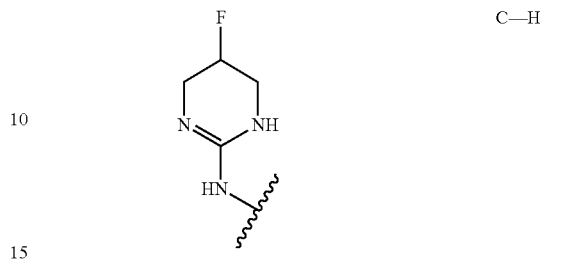 | C—H |
| 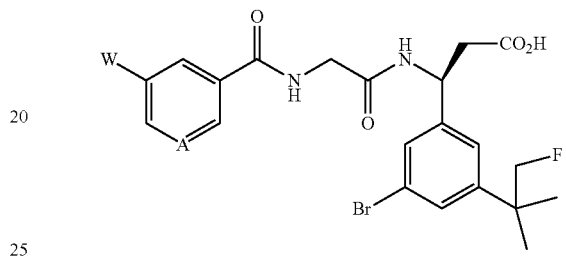 | |
| 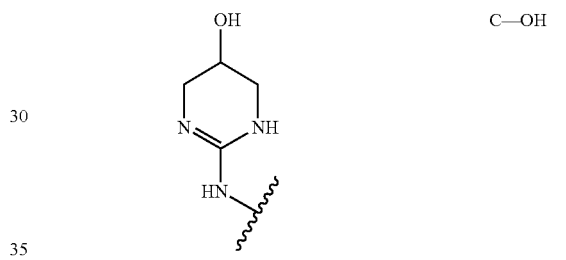 | C—OH |
| 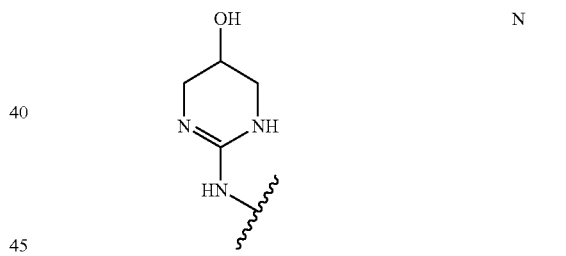 | N |
| 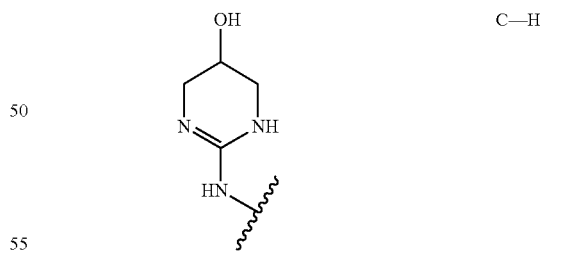 | C—H |
| 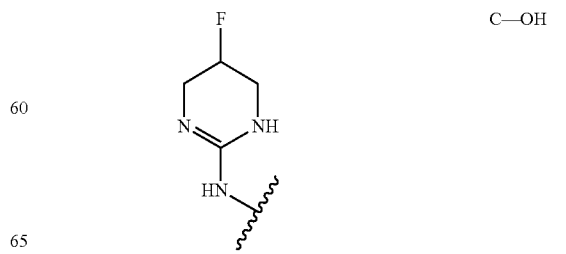 | C—OH |

TABLE A-continued
Examples of Beta Amino Acid Derivatives
| W | A |
|---|---|
| 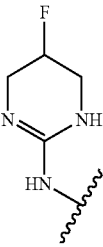 | N |
| 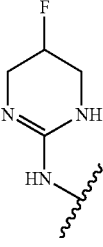 | C—H |
| 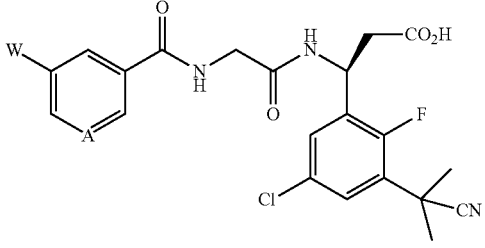 | |
| 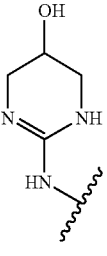 | C—OH |
| 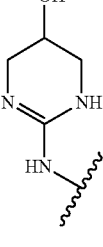 | N |
| 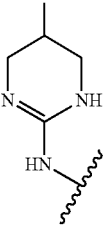 | C—H |
TABLE A-continued
Examples of Beta Amino Acid Derivatives
| W | A |
|---|---|
| 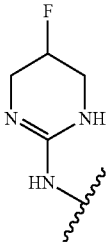 | C—OH |
| 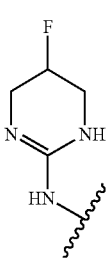 | N |
| 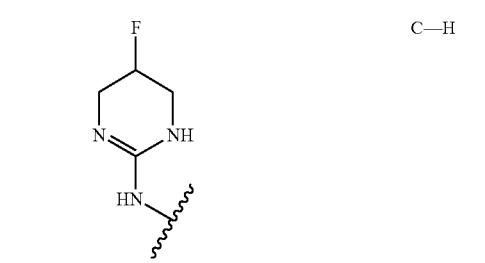 | C—H |
| 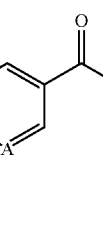 | |
| 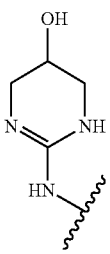 | C—OH |
| 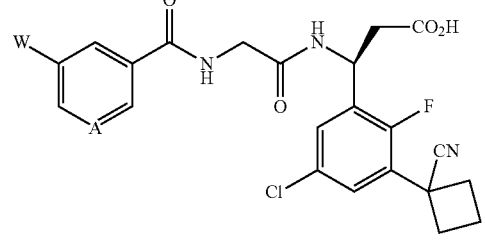 | N |

TABLE A-continued

Examples of Beta Amino Acid Derivatives

| W | A |
|---|---|
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |
| (5-hydroxy-tetrahydropyrimidin-2-yl)amino | C—OH |
| (5-hydroxy-tetrahydropyrimidin-2-yl)amino | N |
| (5-hydroxy-tetrahydropyrimidin-2-yl)amino | C—H |
| (5-fluoro-tetrahydropyrimidin-2-yl)amino | C—OH |
| (5-fluoro-tetrahydropyrimidin-2-yl)amino | N |
| (5-fluoro-tetrahydropyrimidin-2-yl)amino | C—H |

TABLE A-continued

Examples of Beta Amino Acid Derivatives

| W | A |
|---|---|
| (piperidine with OH, N=C-NH, HN-) | C—OH |
| (piperidine with OH, N=C-NH, HN-) | N |
| (piperidine with OH, N=C-NH, HN-) | C—H |
| (piperidine with F, N=C-NH, HN-) | C—OH |
| (piperidine with F, N=C-NH, HN-) | N |
| (piperidine with F, N=C-NH, HN-) | C—H |

Compounds employed in methods of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. The (S)-enantiomer of the beta amino acid portion of formula I is the preferred enantiomer. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration, as defined by the IUPAC 1974 Recommendations. For example, mixtures of stereoisomers may be separated using the techniques taught in the Examples section below, as well as modifications thereof. Tautomeric forms are also included as well as pharmaceutically acceptable salts of such isomers and tautomers.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (Methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. Biological Activity

It is another object of the invention to provide pharmaceutical compositions comprising compounds described above. Such compounds and compositions are useful in inhibiting or antagonizing integrins, and therefore in another embodiment, the present invention relates to a method of inhibiting or antagonizing the α5β1 integrin in particular, and additionally inhibiting or antagonizing the αvβ6 and αvβ8 integrins. Such compounds and compositions may be used to inhibit or antagonize additional integrins, such as αvβ3, αvβ5 and αvβ1 (herein defined as related integrins). The invention further involves treating or inhibiting pathological conditions associated therewith such as angiogenesis, including tumor angiogenesis, fibrosis and fibrotic diseases such as pulmonary fibrosis, renal, cardiac, and liver fibrosis, scleroderma, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. Further, such pharmaceutical agents are useful as immune system modulators via inhibition of TGF-β activation resulting from inhibiting or antagonizing the targeted integrins. Such immune modulation affects the immune activity and functions of T regulatory and T effector cells, and as such can be useful in the treatment of immune related pathologies, including autoimmune diseases such as multiple sclerosis, as well as in the treatment of tumors and infectious pathogens.

IV. Therapeutic Methods

The present invention relates to the fields of pharmaceuticals, medicine and cell biology. More specifically, it relates to pharmaceutical agents (compounds) which are useful as integrin receptor antagonists, with particularly exceptional biological activity as antagonists of the integrin α5b1, and additionally as exceptional antagonists of the integrins avb6 and avb8. As such, these compounds are useful in pharmaceutical compositions and in methods for treating conditions mediated by such integrins by inhibiting or antagonizing these integrins.

Certain compounds of the invention may combine α5β1 antagonism with antagonism of other RGD-binding integrins. Such mixed antagonists may be especially useful in treating or preventing diseases in which more than one integrin promotes aberrant angiogenesis. They may also be useful when a second disease process, which is either co-dependent or independent of angiogenesis, is mediated by RGD integrins that can be simultaneously affected with the anti-angiogenic antagonist. In particular, tumors are critically dependent on the formation of new blood vessels to sustain growth beyond a few millimeters in diameter. Aberrant angiogenesis in the retina is a characteristic of many blinding disorders such as wet age-related macular degeneration, vitreoretinopathies, retinopathy of prematurity, and diabetic retinopathy. Angiogenesis has been associated with progression of pulmonary and liver fibrosis, and with growth of the synovial pannus in rheumatoid arthritis.

The integrins αvβ3 and αvβ5 have been implicated in promoting angiogenesis (Avraamides et al., 2008), so that their antagonism in addition to α5β1 may be predicted to provide superior blockade of this process. Integrin αvβ3 is also known to play a role in tumor cell metastasis, and in the elevated bone resorption associated with osteoporosis and some cancers. The antagonists of the invention possess varying activity against at least five integrins that have been reported to bind the latent cytokine TGFβ complex in vitro: αvβ1, αvβ3, αvβ5, αvβ6, and αvβ8. See (Asano et al., 2005; Mu et al., 2002; Munger et al., 1999; Wipff et al., 2007; and Munger et al., 1998), which are incorporated herein by reference. TGFβ is frequently co-expressed with the angiogenic cytokine VEGF and induces its synthesis (Ferrari et al., 2006). Aside from having vascular regulatory activity, TGFβ is a powerful inducer of fibrosis in many tissues such as lung, liver, kidney, and skin (Nishimura, 2009). Virtually all TGFβ is secreted from cells in a complex which contains the latency associated peptide (LAP). The integrins αvβ3, αvβ5, and αvβ6, interact with the RGD motif contained within LAP, producing a conformational change in the complex which allows TGFβ to bind cellular receptors that activate pro-fibrotic pathways. Integrin αvβ8 also activates TGFβ in an RGD-dependent manner, but utilizes a protease-dependent mechanism distinct from the other integrins.

Latent TGFβ is ubiquitously present in tissues, and is activated by integrins in a spatially and temporally restricted manner. Therefore, upregulation of the epithelial integrin αvβ6 in the lungs or liver may promote localized collagen deposition and scarring, as has been observed in patients with idiopathic pulmonary fibrosis (Horan et al., 2008) or hepatic fibrosis (Popov et al., 2008). Similarly, αvβ5, and to a lesser extent αvβ3, are present on mesenchymal cells and are able to activate mesenchymal TGFβ (Wipff et al., 2007; Scotton et al., 2009). Integrin αvβ8 is expressed on subsets of epithelial, neural, immune, and mesenchymal cell types. In the skin, the TGFβ activation that accompanies the wound healing process mediates matrix deposition and promotes the formation of scars. Compounds of this invention, by virtue of their ability to simultaneously inhibit several TGFβ-activating integrins, have potential for greater efficacy in treatment of fibrosis than any previously described compounds having more restricted inhibitory profiles. Furthermore, these compounds which have exceptional α5β1 potency, have unique potential for benefit in diseases characterized by both aberrant angiogenic and fibrotic pathologies TGFβ is an important inducer of the formation of FoxP3$^+$ regulatory T cells (T$_{reg}$) (Yoshimura, 2011). Therefore, compounds of the present invention that inhibit the activation of TGFβ may reduce T$_{reg}$ activity, and in turn relieve immune suppression in disease states such as cancer, when administered alone or in combination with existing therapies. Mitigation of T$_{reg}$ activity with such compounds also has the potential to enhance the activity of vaccines which are intended to prevent or treat cancer and infectious diseases. TGFβ, in the presence of IL-6, promotes the conversion of naïve T cells to TH17 cells (Yoshimura, 2011). These cells promote a variety of autoimmune diseases. It has been reported that mice lacking all αvβ8 expression on dendritic cells have near complete protection from experimental autoimmune encephalitis, a model of multiple sclerosis (Melton et al., 2010). Therefore, compounds of the present invention that inhibit the activation of TGFβ may reduce Th17 activity, and be useful in preventing or treating autoimmune disease when administered alone or in combination with existing therapies.

Antagonism of the integrin αIIbβ3 (also known as the fibrinogen receptor), is known to block platelet aggregation as part of the blood coagulation process. Hence, to avoid increased bleeding when treating conditions or disease states mediated by integrin α5β1 and other integrins, it would be beneficial to utilize compounds which selectively spare αIIbβ3. A role for αvβ5 in normal maintenance of the retina has also been described (Nandrot et al., 2006). Therefore, in some uses of compounds, it may be desirable to spare αvβ5 inhibition.

As discussed above, integrins are a family of integral cytoplasmic membrane proteins that mediate cell interactions with other cells and with the extracellular matrix (ECM). They also play a role in cell signaling and thereby regulate cellular shape, motility, and the cell cycle. Not only do integrins perform "outside-in" signaling typical of receptors, but they also operate an "inside-out" mode. Thus, they transduce information from the ECM to the cell as well as reveal the status of the cell to the outside, allowing rapid and flexible responses to changes in the environment, for example to allow blood coagulation by platelets.

There are many types of integrin, and many cells have multiple types on their surface. Integrins are of vital importance to all animals and have been found in all animals investigated, from sponges to mammals. As such compounds which target integrins have found numerous uses in different animals including companion animals, livestock animals, zoo animals as well as wild animals. Integrins have been extensively studied in humans. Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

When released into the cell membrane, newly synthesized integrin dimers are speculated to be found in the same "bent" conformation revealed by the structural studies described above. One school of thought claims that this bent form prevents them from interacting with their ligands, although bent forms can predominate in high-resolution EM structures of integrin bound to an ECM ligands. Therefore, integrin dimers must apparently not be 'unbent' in order to prime them and allow their binding to the ECM. In cells, the priming is accomplished by a protein named Talin, which binds to the β tail of the integrin dimer and changes its conformation. Moreover, talin proteins are able to dimerize and thus are thought to intervene in the clustering of integrin dimers which leads to the formation of a focal adhesion. Recently, the Kindlin-1 and Kindlin-2 proteins have also been found to interact with integrin and activate it.

Each integrin is formed by the non-covalent heterodimerization of alpha and beta glycoprotein subunits, the combination of which conveys distinct biological activities such as cell attachment, migration, proliferation, differentiation, and survival. Currently, 24 integrins have been described in mammals that are formed by pairing of 18 α subunits and 8 β subunits:

TABLE 1

| \multicolumn{4}{c}{Integrins} | | | |
| --- | --- | --- | --- |
| Gene | Protein | Synonym | Type |
| ITGA1 | CD49a | VLA1 | Alpha |
| ITGA2 | CD49b | VLA2 | Alpha |
| ITGA3 | CD49c | VLA3 | Alpha |
| ITGA4 | CD49d | VLA4 | Alpha |
| ITGA5 | CD49e | VLA5 | Alpha |
| ITGA6 | CD49f | VLA6 | Alpha |
| ITGA7 | ITGA7 | FLJ25220 | Alpha |
| ITGA8 | ITGA8 | | Alpha |
| ITGA9 | ITGA9 | RLC | Alpha |
| ITGA10 | ITGA10 | | Alpha |
| ITGA11 | ITGA11 | HsT18964 | Alpha |
| ITGAD | CD11D | FLJ39841 | Alpha |
| ITGAE | CD103 | HUMINAE | Alpha |
| ITGAL | CD11a | LFA1A | Alpha |
| ITGAM | CD11b | MAC-1 | Alpha |
| ITGAV | CD51 | VNRA, MSK8 | Alpha |
| ITGAW | ITGAW | | Alpha |
| ITGAX | CD11c | | Alpha |

TABLE 1-continued

Integrins

| Gene | Protein | Synonym | Type |
|---|---|---|---|
| ITGB1 | CD29 | FNRB, MSK12, MDF2 | Beta |
| ITGB2 | CD18 | LFA-1, MAC-1, MFI7 | Beta |
| ITGB3 | CD61 | GP3A, GPIIIa | Beta |
| ITGB4 | CD104 | | Beta |
| ITGB5 | ITGB5 | FLJ26658 | Beta |
| ITGB6 | ITGB6 | | Beta |
| ITGB7 | ITGB7 | | Beta |
| ITGB8 | ITGB8 | | Beta |

In addition, variants of some of the subunits are formed by differential splicing; for example, four variants of the beta-1 subunit exist. Through different combinations of these α and β subunits, some 24 unique integrins are generated, although the number varies according to different studies.

Integrin subunits span the plasma membrane and in general have very short cytoplasmic domains of about 40-70 amino acids. The exception is the beta-4 subunit, which has a cytoplasmic domain of 1088 amino acids, one of the largest known cytoplasmic domains of any membrane protein. Outside the cell plasma membrane, the α and β chains lie close together along a length of about 23 nm; the final 5 nm N-termini of each chain forms a ligand-binding region for the extracellular matrix (ECM).

The molecular mass of the integrin subunits can vary from 90 kDa to 160 kDa. Beta subunits have four cysteine-rich repeated sequences. Both α and β subunits bind several divalent cations. The role of divalent cations in the α subunit is unknown, but may stabilize the folds of the protein. The cations in the β subunits are more interesting: they are directly involved in coordinating at least some of the ligands that integrins bind.

There are various ways of categorizing the integrins. For example, a subset of the α chains has an additional structural element (or "domain") inserted toward the N-terminal, the alpha-A domain (so called because it has a similar structure to the A-domains found in the protein von Willebrand factor; it is also termed the α-I domain). Integrins carrying this domain either bind to collagens (e.g., integrins α1β1, and α2β1), or act as cell-cell adhesion molecules (integrins of the β2 family). This α-I domain is the binding site for ligands of such integrins. Those integrins that don't carry this inserted domain also have an A-domain in their ligand binding site, but this A-domain is found on the β subunit.

In both cases, the A-domains carry up to three divalent cation binding sites. One is permanently occupied in physiological concentrations of divalent cations, and carries either a calcium or magnesium ion, the principal divalent cations in blood at median concentrations of 1.4 mM (calcium) and 0.8 mM (Magnesium). The other two sites become occupied by cations when ligands bind—at least for those ligands involving an acidic amino acid in their interaction sites. An acidic amino acid features in the integrin-interaction site of many ECM proteins, for example as part of the amino acid sequence Arginine-Glycine-Aspartic acid ("RGD").

The invention also relates to a method of inhibiting or antagonizing the α5β1 integrin in particular, as well as αvβ6 and αvβ8 and related integrins. More specifically, it relates to a method of inhibiting pathological conditions associated therewith such as angiogenesis, including tumor angiogenesis, fibrosis and fibrotic diseases such as pulmonary, renal, cardiac and liver fibrosis, scarring, such as retinal, corneal and dermal scarring, retinopathy, including diabetic retinopathy and macular degeneration, vitreoretinopathy, including retinopathy of prematurity (ROP) and familial exudative vitreoretinopathy (FEVR), osteoporosis, humoral hypercalcemia of malignancy, Paget's disease, tumor metastasis, solid tumor growth (neoplasia), arthritis, including rheumatoid arthritis, periodontal disease, psoriasis, smooth muscle cell migration and restenosis, autoimmune disease, such as multiple sclerosis, and infectious pathogens by administering a therapeutically effective amount of a compound described above to achieve such inhibition together with a pharmaceutically acceptable carrier.

For the selective inhibition or antagonism of α5b1, avb6, avb8 and related integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitoneally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by inhibiting or antagonizing the α5b1, avb6, avb8 and related cell surface integrin receptors, which method comprises administering a therapeutically effective amount of a compound selected from the class of compounds described above, wherein one or more compounds is administered in association with one or more nontoxic, pharmaceutically acceptable carriers and/or diluents and/or adjuvants (collectively referred to herein as "carrier" materials) and if desired other active ingredients. More specifically, the present invention provides a method for inhibition of the α5b1, avb6, avb8 and related cell surface integrin receptors. Most preferably the present invention provides a method for inhibiting angiogenesis, including tumor angiogenesis, inhibiting and treating fibrosis and fibrotic diseases such as pulmonary fibrosis and liver fibrosis, inhibiting and treating scarring, such as retinal, corneal and dermal scarring, inhibiting and treating retinopathy, including diabetic retinopathy and macular degeneration, inhibiting and treating vitreoretinopathy, including retinopathy of prematurity (ROP) and familial exudative vitreoretinopathy (FEVR), inhibiting bone resorption, treating osteoporosis, treating humoral hypercalcemia of malignancy, treating Paget's disease, inhibiting tumor metastasis, inhibiting solid tumor growth (neoplasia), treating arthritis, including rheumatoid arthritis, treating periodontal disease, treating psoriasis, inhibiting smooth muscle cell migration and restenosis, treating autoimmune disease, such as multiple sclerosis, and inhibiting and treating infectious pathogens Based upon standard laboratory experimental techniques and procedures well known and appreciated by those skilled in the art, as well as comparisons with compounds of known usefulness, the compounds described above can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

As stated previously, the compounds of the invention can be used in a variety of biological, prophylactic or therapeutic areas. It is contemplated that these compounds are useful in prevention or treatment of any disease state or condition wherein the α5b1, avb6, avb8 and related integrins plays a role.

V. Pharmaceutical Formulations and Routes of Administration

For administration to an animal especially a mammal in need of such treatment, the compounds in a therapeutically effective amount are ordinarily combined with one or more excipients appropriate to the indicated route of administration. The compounds of the present invention are contemplated to be formulated in a manner ameniable to treatment of a veterinary patient as well as a human patient. In some embodiments, the veterinary patient may be a companion animal, livestock animals, zoo animals, and wild animals The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art and may be adapted to the type of animal being treated.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions may be suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (Mg/kg)} = \text{Animal dose (Mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an antiinfective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Instrumentation and General Methods.

Analytical HPLC analyses were performed on an Agilent 1100 system and LC-MS analyses were conducted on Agilent 1100 Series LC/MSD system. Chemical ionization mass spectra (CI) were recorded, at 70 eV ionizing voltage, on a Hewlett-Packard 5973 CI quadrupole mass spectrometer connected to a Hewlett-Packard 6890 gas chromatograph fitted with a Agilent Tech 12 m×0.2 mm×0.33 µm DB-1 (cross linked methyl silicone) column. NMR spectra were recorded on a Bruker Avance-III/400 MHz spectrometer equipped with a Broad Band NMR probe. The signal of the deuterated solvent was used as an internal reference.

Example A

Preparation of 3-Hydroxy-5-((5-hydroxy-1,4,5,6-tetrahydropyrimidin-2-yl)aminobenzoic acid

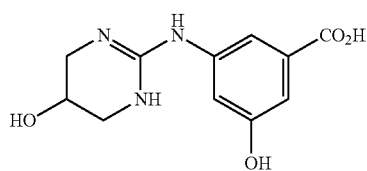 [SMILES: O=C(O)c1cc(O)cc(NC2=NCC(O)CN2)c1]

3-Hydroxy-5-((5-hydroxy-1,4,5,6-tetrahydropyrimidin-2-yl)aminobenzoic acid was synthesized according to literature procedures (see *Organic Process Research & Development*, 8:571-575, 2004, which is incorporated herein by reference).

Example B

Preparation of 2-(3-Hydroxy-5-((5-hydroxy-1,4,5,6-tetrahydropyrimidin-2-yl)amino)benzamido) acetic acid

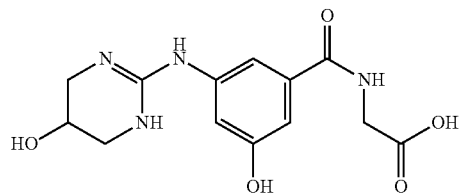 [SMILES: O=C(O)CNC(=O)c1cc(O)cc(NC2=NCC(O)CN2)c1]

2-(3-Hydroxy-5-((5-hydroxy-1,4,5,6-tetrahydropyrimidin-2-yl)amino)benzamido)acetic acid was prepared according to the following procedure:

Coupling of 3-hydroxy-5-((5-hydroxy-1,4,5,6-tetrahydropyrimidin-2-yl)aminobenzoic acid with glycine ethyl ester

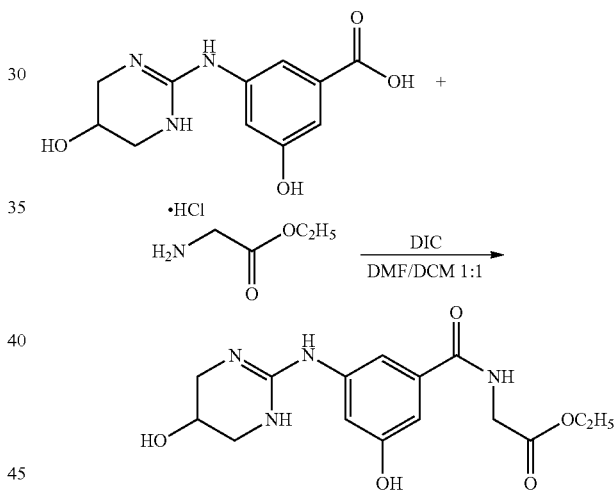

To a suspension of 3-hydroxy-5-((5-hydroxy-1,4,5,6-tetrahydropyrimidin-2-yl)aminobenzoic acid (9.013 g, 35.87 mmol) in a 1:1 mixture of DMF (50.0 mL) and DCM (50.0 mL) was added glycine ethyl ester hydrochloride (5.02 g, 35.95 mmol) and the mixture was stirred at room temperature under nitrogen atmosphere. Neat N,N'-diisopropylcarbodiimide (6.75 mL, 43.60 mmol) was added to above reaction mixture and the mixture was stirred at room temperature overnight to give a colorless suspension. The crude reaction mixture was used as such for the hydrolysis of the above ester.

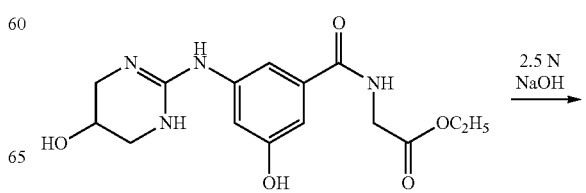

-continued

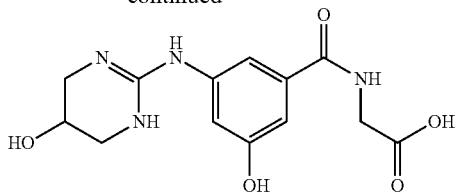

The above crude reaction mixture was cooled to 10° C. (ice-bath) and a 2.5 N NaOH solution (90.0 mL) was added slowly with stirring, the solution temperature was kept below 20° C., to give a pale yellow solution/suspension. The reaction mixture was stirred at room temperature for 1.5 h. The reaction mixture was acidified with 5N HCl with stirring to pH 5 to give a colorless precipitate and the mixture was stirred at room temperature for another 15 min and filtered to give a colorless solid. The solid was washed with water (1×25 mL) and then with acetonitrile (1×25 mL). The solid was dried in-vacuo to give a colorless powder (9.686 g, yield 88%).

$^1$H NMR (400 MHz, $D_2O$): δ 3.37 (dd, J=12.7 and 3.1 Hz, 2H), 3.50 (dd, J=12.7 and 2.8 Hz, 2H), 4.17 (s, 2H), 4.37 (M, 1H), 6.97 (t, J=2.01 Hz, 1H), 7.17-7.26 (m, 2H). $^1$H NMR spectrum of the sample was consistent with the suggested structure of the product.

Example C

Preparation of 5-Guanidino Benzoic Acid

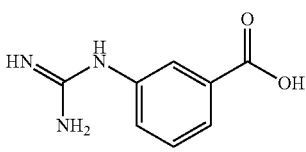 [SMILES: N=C(N)Nc1cccc(C(=O)O)c1]

5-guanidino benzoic acid was prepared according to the following procedure:

Step 1

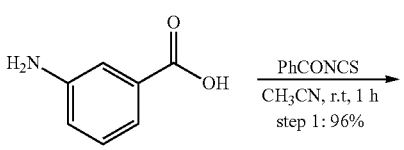

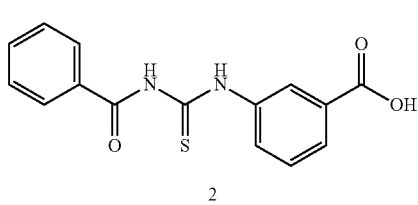

A mixture of compound 1 (50 g, 0.36 mol) and benzoyl-isothiocyanate (65.5 g, 0.40 mol) in $CH_3CN$ (1.0 L) was stirred at room temperature for 1 h. TLC showed no starting material left. The precipitate was filtered and washed with $CH_3CN$, dried to afford Compound 2 (104 g, 96%) as a light yellow solid.

TLC information: (DCM/MeOH=10/1)
Material: $R_f$=0.1
Product: $R_f$=0.2
$^1$H NMR: 400 MHz DMSO δ 12.63 (s, 1H), 11.64 (s, 1H), 8.31 (s, 1H), 8.00-7.98 (d, J=7.06 Hz, 2H), 7.90-7.83 (M, 2H), 7.67-7.65 (M, 1H), 7.57-7.53 (M, 3H).

Step 2

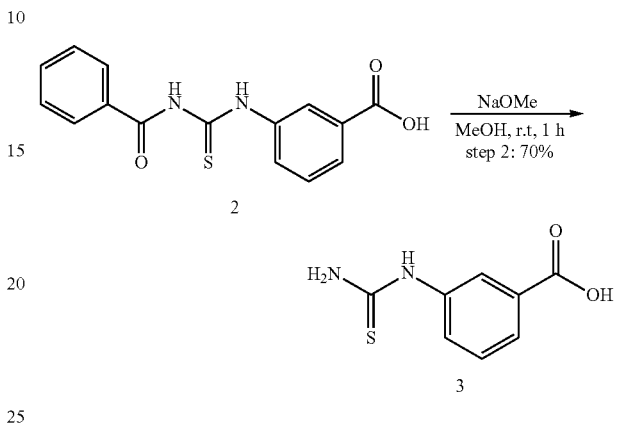

Into a stirred solution of compound 2 (83 g, 0.28 mol) in anhydrous $CH_3OH$ (500 ml) was added NaOMe (16.44 g, 0.30 mol) slowly at room temperature. A clear solution resulted in 10 min, and the reaction mixture was stirred for 1 h. The solvent was removed and the residue was triturated with t-BuOMe to leave a light yellow powder. The powder was diluted with $H_2O$, acidified to pH=2-3. The yellow solid formed was filtered, dried to afford Compound 3 (38 g, 70%).

TLC information: (DCM/$CH_3OH$=20/1+$CH_3COOH$)
Material: $R_f$=0.5
Product: $R_f$=0.3
$^1$H NMR: 400 MHz DMSO
δ 12.98 (s, 1H), 9.83 (s, 1H), 8.02 (s, 1H), 7.69-7.66 (M, 2H), 7.45-7.41 (M, 1H).

Step 3

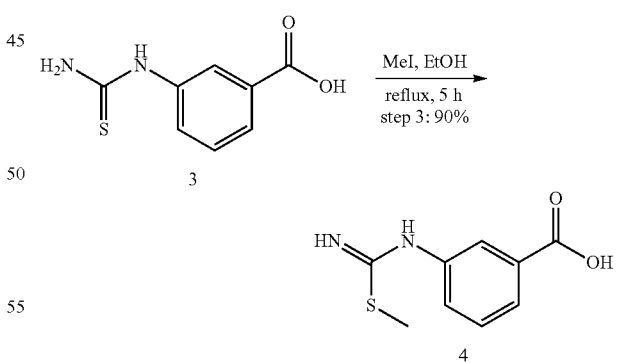

Into a stirred solution of compound 3 (15 g, 0.076 mol) in EtOH (80 ml) was added $CH_3I$ (11.4 g, 0.08 mol) slowly at room temperature. The reaction mixture was heated to reflux and stirred for 5 h. TLC showed no starting material left. The solvent was removed, Compound 4 (14.5 g, 90%) was obtained as a yellow oil.

TLC information: (DCM/$CH_3OH$=20/1+$CH_3COOH$)
Material: $R_f$=0.3
Product: $R_f$=0.2

Step 4

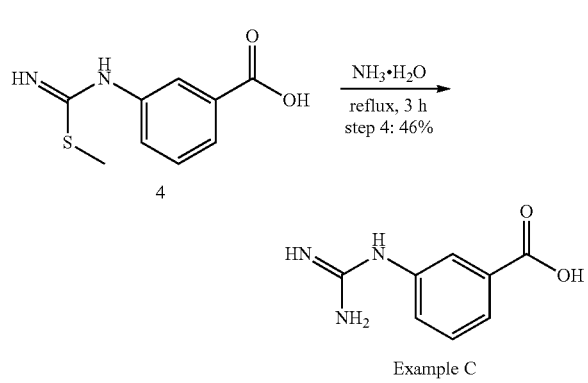

Example C

A mixture of compound 4 (14.5 g, 0.069 mol) in NH₄OH (100 ml) was heated to reflux and stirred for 3 h. The solid formed was filtered and dried. 5-guanidino benzoic acid (Example C) (5.68 g, 46%) was obtained as a white solid.

LC/MS (M+H=180.1) is consistent for the desired product.

$^1$H NMR: 400 MHz DMSO δ 12.71-12.67 (M, 1H), 8.16 (s, 3H), 7.74-7.72 (M, 2H), 7.40-7.31 (M, 2H).

Example D

Preparation of 3-[(4,5-dihydro-Boc-1H-imidazol-2-yl)amino]-benzoic acid

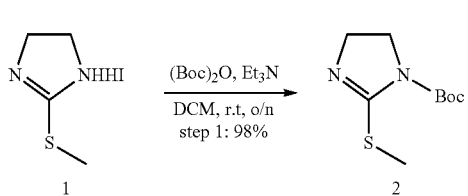

3-[(4,5-dihydro-Boc-1H-imidazol-2-yl)amino]-benzoic acid was prepared according to the following procedure:

Step 1

Into a stirred solution of compound 1 (23.0 g, 0.094 mol) and Et₃N (20.0 g, 0.198 mol) was added (Boc)₂O (20.5 g, 0.0942 mol) at room temperature and the reaction mixture was stirred overnight. The solvent was removed and the residue was purified by flash column chromatography (PE: EA=10:1) to get Compound 2 (20 g, 98%) as a colorless oil.

TLC information: (PE/EA=5/1)
Material: $R_f$=0.1
Product: $R_f$=0.4

$^1$H NMR: WH00398-025-1A 400 MHz CDCl₃
δ 3.84-3.82 (M, 4H), 2.38 (s, 3H), 1.50 (s, 9H).

Step 2

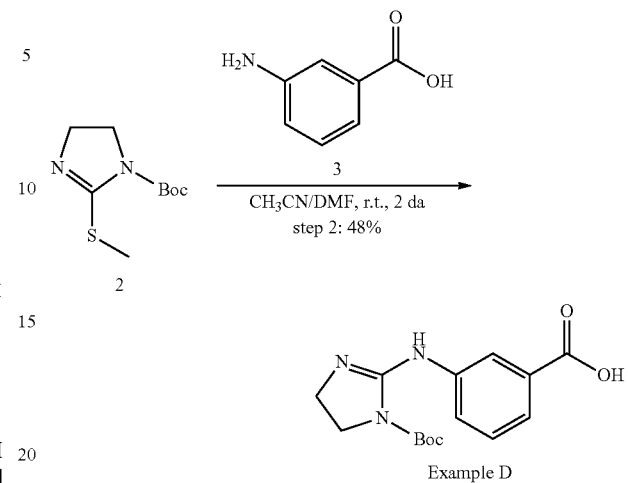

Example D

A solution of compound 2 (11.6 g, 0.054 mol) and compound 3 (7.0 g, 0.05 mol) in CH₃CN/DMF (50 ml/20 ml) was stirred at room temperature for 2 d. The solid formed was filtered and dried. Example D (7.28 g, 48%) was obtained as a white solid.

LC/MS (M+H=306) is consistent for the desired product.

$^1$H NMR: WH00398-037-1A 400 MHz CH₃OD

δ 7.94-7.87 (M, 2H), 7.51-7.43 (M, 2H), 4.12-4.08 (M, 2H), 3.72-3.67 (M, 2H), 1.61 (s, 9H).

Example E

Preparation of 3-[(4,5-dihydro-1H-imidazol-2-yl)amino]-5-hydroxy benzoic acid

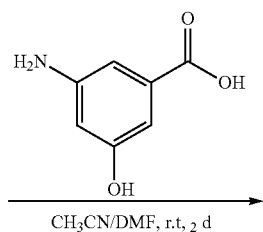

3-[(4,5-dihydro-1H-imidazol-2-yl)amino]-5-hydroxy benzoic acid was prepared according to the following procedure:

(compound 2 from example D)

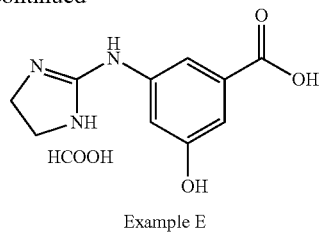

Example E

A solution of compound 2 from Example D (15.5 g, 0.072 mol) and 3-amino-5-hydroxy benzoic acid (10 g, 0.065 mol) in $CH_3CN/DMF$ (50 ml/20 ml) was stirred at room temperature for 2 d. The solid formed was filtered, dried. Then the solid was purified by Prep-HPLC to give Example E (2.1 g, 10%), obtained as a white solid.

LC/MS (M+H=222) is consistent for the desired product.

$^1H$ NMR: A000018723 WH00292-035-SLU-DMF-1J DMSO-$d_6$ 400 MHz

δ13.089 (s, 1H), 10.726 (s, 1H), 10.251 (s, 1H), 8.540 (s, 1H), 7.248-7.227 (M, 2H), 7.687-6.876 (M, 1H), 3.677 (s, 4H).

Example F

Preparation of 5-Guanidino Nicotinic Acid

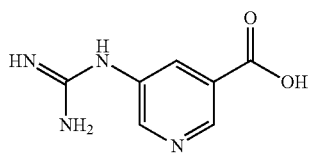 [SMILES: N=C(N)Nc1cncc(C(=O)O)c1]

5-guanidino nicotinic acid was prepared according to the following procedure:

Step 1

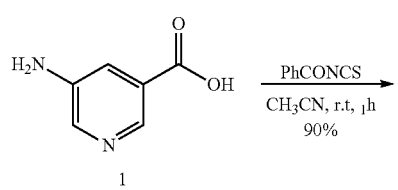

A mixture of compound 1 (40 g, 0.3 mol) and benzoyl-isothiocyanate (95 g, 0.58 mol) in $CH_3CN$ (2.0 L) was stirred at room temperature for 12 h. TLC showed no starting material left. The precipitate was filtered and washed with $CH_3CN$, dried to afford Compound 2 (80 g, 90%) as a light yellow solid.
TLC information: (DCM/MeOH=10/1)
Material: $R_f$=0.1
Product: $R_f$=0.2

Step 2

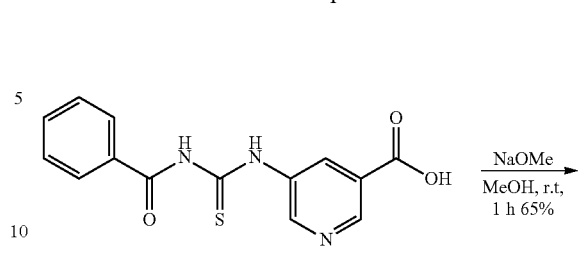

Into a stirred solution of compound 2 (80 g, 0.27 mol) in anhydrous $CH_3OH$ (500 ml) was added NaOMe (28.5 g, 0.53 mol) slowly at room temperature. A clear solution resulted in 20 min, and the reaction mixture was stirred for 1 h. The solvent was removed and the residue was triturated with t-BuOMe to leave a light yellow powder. The powder was diluted with $H_2O$, acidified to pH=2-3. The yellow solid formed was filtered, dried to afford Compound 3 (33.7 g, 65%).

TLC information: (DCM/$CH_3OH$=20/1+$CH_3COOH$)
Material: $R_f$=0.5
Product: $R_f$=0.3

Step 3

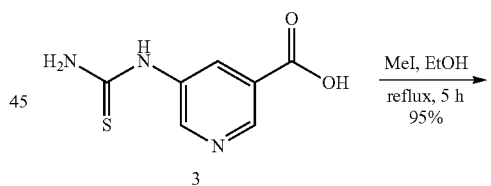

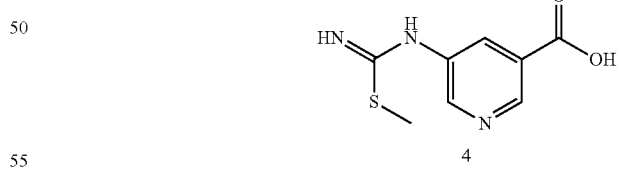

Into a stirred solution of compound 3 (33.7 g, 0.17 mol) in DMF (200 ml) was added $CH_3I$ (24.3 g, 0.17 mol) slowly at room temperature. The reaction mixture was stirred at RT for 1 h. TLC showed no starting material left. The solvent was removed, and Compound 4 (34.3 g, 95%) was obtained as a yellow oil.

TLC information: (DCM/$CH_3OH$=20/1+$CH_3COOH$)
Material: $R_f$=0.3
Product: $R_f$=0.2

Step 4

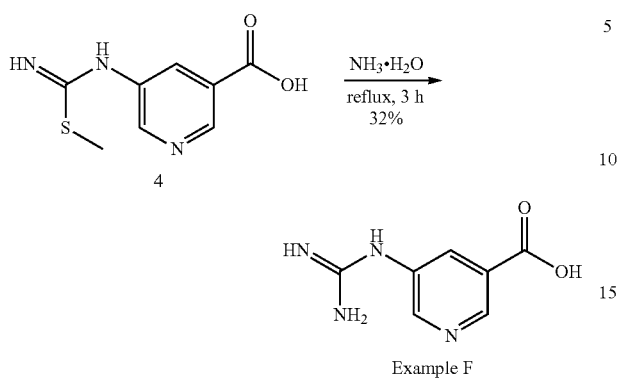

Example F

A mixture of compound 4 (18.8 g, 0.089 mol) in NH$_4$OH (100 ml) was heated to reflux and stirred for 5 h. The solid formed was filtered and dried. Example F (5.14 g, 32%) was obtained as a white solid.

LC/MS (M+H=181) is consistent for the desired product.
$^1$H NMR: A000017761 WH00398-043-1 DMSO-d$_6$ 400 MHz δ 12.602 (s, 1H), 8.851 (s, 1H), 8.597 (s, 1H), 8.322 (s, 3H), 7.978 (s, 1H).

Example G

Preparation of 5-((5-hydroxy-1,4,5,6-tetrahydropyrimidin-2-yl)amino nicotinic acid

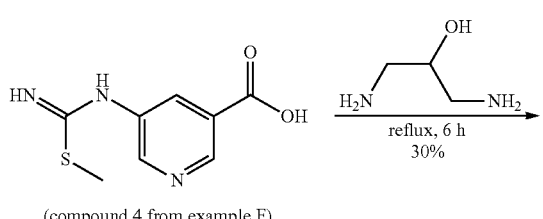

5-((5-hydroxy-1,4,5,6-tetrahydropyrimidin-2-yl)amino nicotinic acid was prepared according to the following procedure:

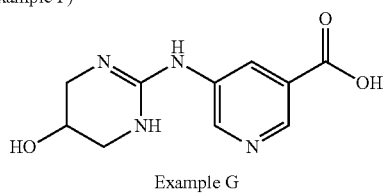

Example G

A mixture of compound 4 from example F (15.5 g, 0.074 mol) and the hydroxy diamino propane (20 g, 0.22 mol) in DMF (100 ml) was heated to reflux and stirred for 5 h. The solid formed was filtered and dried. Example G (5.2 g, 30%) was obtained as a white solid.

LC/MS (M+H=237) is consistent for the desired product.
$^1$H NMR: B000004008 wh00398-050-1C DMSO-d$_6$ 400 MHz δ 13.053 (s, 1H), 9.881 (s, 2H), 8.783 (s, 1H), 8.630 (s, 1H), 7.897 (s, 1H), 5.492 (s, 1H), 4.112 (s, 1H), 3.410 (s, 2H), 3.228-3.190 (M, 2H).

Example H

Preparation of (S)-3-(2-Amino-acetylamino)-3-(3-bromo-5-tert-butyl-phenyl)-propionic acid ethyl ester hydrochloride salt

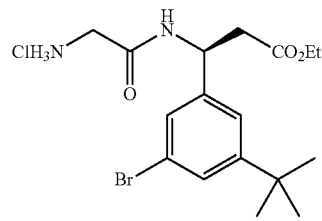

(S)-3-(2-Amino-acetylamino)-3-(3-bromo-5-tert-butyl-phenyl)-propionic acid ethyl ester hydrochloride salt was prepared according to the following procedure:

Step-1: Preparation of 3-Bromo-5-tert-butyl-benzaldehyde

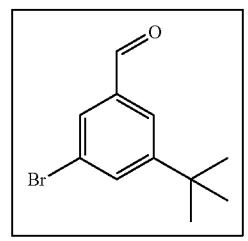

1,3-Dibromo-5-tert-butylbenzene (50 g, 0.17 mol) was dissolved in anhydrous ether (200 mL) in a dried flask under nitrogen. The reaction mixture was cooled to −78° C. and stirred under nitrogen atmosphere. A 2.46 M solution of n-BuLi in hexanes (171.2 mL, 0.171 mol) was added dropwise to the above solution and the reaction mixture was stirred at −78° C. for 30 minute after complete addition of n-BuLi. After 30 minute of stirring at −78° C., the reaction mixture was warmed to −30° C. DMF (16 mL, 0.2 mol) was added to the above reaction mixture dropwise, keeping the reaction mixture below −20° C. After addition of DMF, the reaction mixture was warmed slowly to 0° C. (30 minute) and then stirring was continued overnight to obtain a yellow-orange solution. The reaction mixture was poured into 400 mL of chilled 10% aqueous HCl and the mixture was stirred for 15 minutes. The ether layer was separated, washed with water (2×250 mL), dried over anhydrous Na$_2$SO$_4$, filtered and evaporated in vacuo to give the product as a pale yellow viscous liquid. The crude product was dissolved in dichloromethane (250 mL) and passed through a small pad of silica gel (250 g). Evaporation of the solvent in vacuo gave the product as a pale yellow viscous liquid (41.2 g).

Step-2: Preparation of 3-Amino-3-(3-bromo-5-tert-butyl-phenyl)-propionic acid

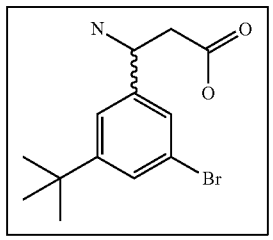 [SMILES: CC(C)(C)c1cc(Br)cc(C(N)CC(=O)O)c1]

A suspension of 3-bromo-5-tert-butylbenzaldehyde (41.5 g, 0.17 mol), malonic acid (21.5 g, 0.20 mol) and ammonium acetate (26.6 g, 0.34 mol) in isopropanol (350 mL) was heated at reflux under nitrogen for 14 h to afford a thick colorless solid. The solid was filtered hot, washed with hot isopropanol (2×100 mL) and dried in vacuo to give the desired racemic product as a colorless solid (37.8 g).

Step-3: Preparation of 3-Amino-3-(3-bromo-5-tert-butyl-phenyl)-propionic acid ethyl ester hydrochloride salt

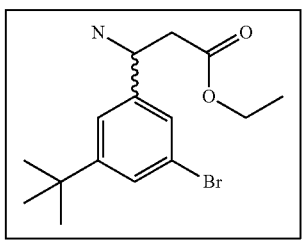 [SMILES: CCOC(=O)CC(N)c1cc(Br)cc(C(C)(C)C)c1]

Absolute ethanol (300 ml, saturated with anhydrous HCl gas) was added to 3-amino-3-(3-bromo-5-tert-butylphenyl)-propionic acid (35 g, 0.12 mol) and the reaction mixture was heated to reflux for 1.5 h to give a pale yellow solution. The solvent was removed in vacuo to give a colorless solid. The solid was washed with diethyl ether and hexane (2×100 mL). After the solvent layer was decanted off, the residue was dried in vacuo to give the racemic amino ester hydrochloride salt as a cream solid (30 g).

Step-4: Preparation of (S)-3-Amino-3-(3-bromo-5-tert-butyl-phenyl)-propionic acid

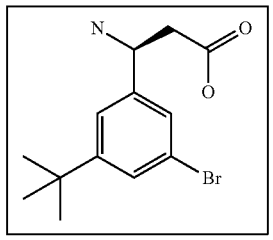 [SMILES: CC(C)(C)c1cc(Br)cc([C@@H](N)CC(=O)O)c1]

A suspension of ethyl 3-amino-3-(3-bromo-5-tert-butylphenyl)-propionate hydrochloride (125 g, 0.38 mol) in water (500 mL) was basified with 2.5 N NaOH (pH ~12) by drop-wise addition to give a creamy oily residue. The pH of the aqueous layer was adjusted to pH=8.2 by the addition of 50 mM $KH_2PO_4$ solution. Amano lipase PS (75 g) was added to above reaction mixture and the reaction mixture was stirred overnight at room temperature. The reaction mixture was filtered and the solid was washed with ethyl acetate to give a colorless solid of the resolved (S)-acid (37 g).

Step-5: Preparation of (S)-3-Amino-3-(3-bromo-5-tert-butyl-phenyl)-propionic acid ethyl ester

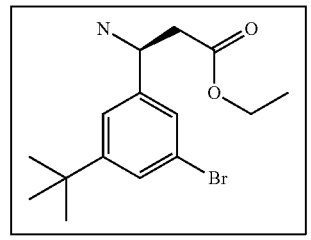 [SMILES: CCOC(=O)C[C@H](N)c1cc(Br)cc(C(C)(C)C)c1]

Absolute ethanol (500 mL, saturated with anhydrous HCl gas) was added to (S)-3-amino-3-(3-bromo-5-tert-butylphenyl)-propionic acid (37 g, 0.12 mol) and the reaction mixture was heated at reflux for 2 h to give a colorless solution. The solvent was removed in vacuo to give a cream-yellow foamy solid. The solid was washed with diethyl ether/hexane and the dried to give a yellow foamy solid (41 g).

Step-6: Preparation of (S)-3-(3-Bromo-5-tert-butyl-phenyl)-3-(2-tert-butoxycarbonylamino-acetylamino)-propionic acid ethyl ester

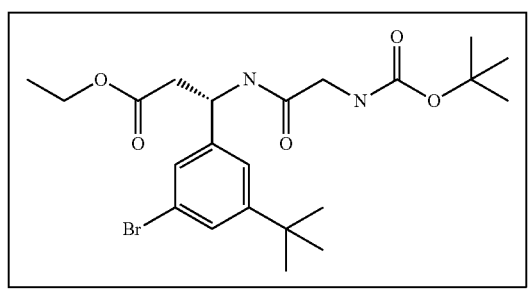 [SMILES: CCOC(=O)C[C@H](NC(=O)CNC(=O)OC(C)(C)C)c1cc(Br)cc(C(C)(C)C)c1]

To a suspension of EDCl.HCl (50 g, 0.25 mol) and HOBt (67.5 g, 0.5 mol) in anhydrous DMF (100 ml) Boc-Gly (32.8 gm, 0.18 mol) and amino ester (41 g, 0.12 mol) were added at 0° C. under nitrogen and the reaction mixture was stirred for 16 h at RT. Reaction was monitored by TLC and completion of the reaction, mixture was quenched with ice, extracted with ethyl acetate (3×250 ml). The organic layer was washed successively with water and brine. The organic layer was dried over anhydrous sodium sulfate and concentrated under vacuum to give crude product. The crude product was then purified by flash chromatography using basic alumina (eluted with 50% ethyl acetate in hexane) to give the pure product (28 g, 46%) as a pale orange sticky liquid.

Step-7: Preparation of (S)-3-(2-Amino-acetylamino)-3-(3-bromo-5-tert-butyl-phenyl)-propionic acid ethyl ester hydrochloride salt

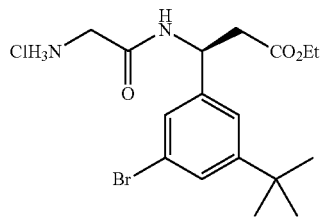

To an ice-cold solution of Boc-ester (28 g, 0.25 mmol) in anhydrous dioxane (100 ml) was passed anhydrous HCl-gas for 30 minute. Then refluxed the reaction mixture for 4 h. Reaction was monitored by TLC and after completion of the reaction mixture was concentrated under vacuum to give the pure product (24 g, 98.6%) as off white solid.

Example I

Preparation of (S)-3-(2-Amino-acetylamino)-3-(3-cyano-5-tert-butyl-phenyl)-propionic acid ethyl ester hydrochloride salt

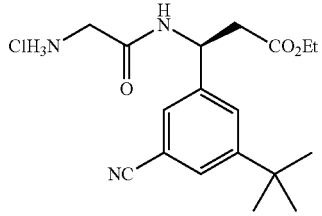

(S)-3-(2-Amino-acetylamino)-3-(3-cyano-5-tert-butyl-phenyl)-propionic acid ethyl ester hydrochloride salt was prepared according to the following procedure:

Step-1: Preparation of (S)-3-(3-Bromo-5-tert-butyl-phenyl)-3-(2-tert-butoxycarbonylamino-acetylamino)-propionic acid ethyl ester

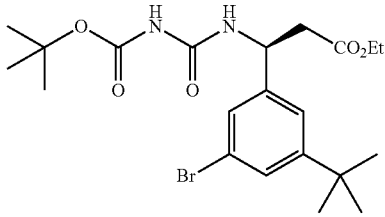 [SMILES: CCOC(=O)C[C@H](NC(=O)NC(=O)OC(C)(C)C)c1cc(Br)cc(C(C)(C)C)c1]

To a solution of the product from example H (2 gm, 5.204 mmol) in 1,4-Dioxane (20 ml) was added saturated aq. NaHCO₃ solution (2.5 ml) and stirred for 5 min at RT. Boc-anhydride (1.36 ml, 6.245 mmol) was then added to it at 0 C and the reaction mixture was allowed to stir at room temperature for 2 hrs. Reaction mixture was concentrated, dissolved in EtOAc (60 ml) and washed with water (60 ml), dried over Na₂SO₄, filtered and concentrated under reduced pressure to obtain the crude which was purified by silica gel (100-200 mesh) column chromatography eluting with 10% EtOAc to afford the desired compound (1.7 g) as a colorless liquid.

Step-2: Preparation of (S)-3-(3-cyano-5-tert-butyl-phenyl)-3-(2-tert-butoxycarbonylamino-acetylamino)-propionic acid ethyl ester

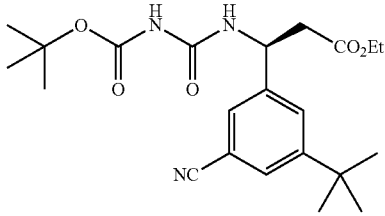 [SMILES: CCOC(=O)C[C@H](NC(=O)NC(=O)OC(C)(C)C)c1cc(C#N)cc(C(C)(C)C)c1]

The product from step 1 (250 mg, 0.515 mmol), and Zn (6.7 mg, 0.103 mmol) were taken in DMF (5 ml) and the resulting suspension was degassed with argon for 10 mins. Zn(CN)₂ (60.4 mg, 0.515 mmol) followed by Pd(OAc)₂ (11.56 mg, 0.052 mmol) and Di-ter-butyl-phosphino-1,1-binapthyl (20.52 mg, 0.052 mmol) were added to it and further degassed with argon for 15 min. After 3 hrs stifling at 110° C., reaction mass was cooled to room temperature, 2N NH₄OH solution (20 mL) was added to it. Resulting mixture was extracted with EtOAc (50 ml×2). Combined organic layer was dried over Na₂SO₄, evaporated to dryness and purified by silica gel column chromatography to afford the desired compound (100 mg).

Step-3: Preparation of (S)-3-(2-Amino-acetylamino)-3-(3-tert-butyl-5-cyano-phenyl)-propionic acid ethyl ester hydrochloride salt

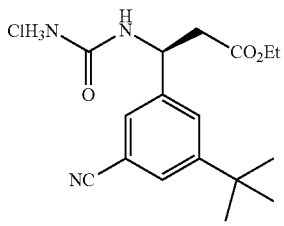

The product from step 2 (100 mg, 0.232 mmol) was treated with 4N Dioxane-HCl (2 mL) at 0° C. for 2 hrs. Reaction mixture was concentrated and the residue was triturated with pentane (2×5 mL) to afford the desired compound as the HCl salt (150 mg) as an off-white sticky solid.

Example J

Preparation of 3-Amino-3-[3-(1-hydroxy-1-methyl-ethyl)-5-trifluoromethyl-phenyl]-propionic acid ethyl ester hydrochloride salt

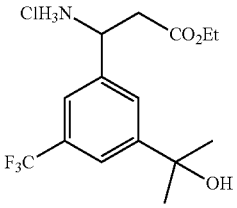

3-Amino-3-[3-(1-hydroxy-1-methyl-ethyl)-5-trifluoromethyl-phenyl]-propionic acid ethyl ester hydrochloride salt was prepared according to the following procedure:

Step-1: Preparation of 2-(3-bromo-5-trifluoromethyl-phenyl)-[1,3]dioxolane

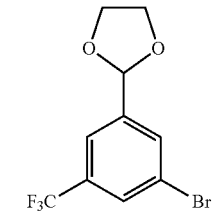

A mixture of 3-bromo-5-trifluoromethyl benzaldehyde (10 gm, 39.523 mmol), ethylene glycol (6.63 ml, 118.568 mmol) and PTSA.H$_2$O (150 mg, 0.79 mmol) in anhydrous toluene (60 ml) was heated to reflux under Dean-stark conditions for 6 h. The reaction mixture was diluted with EtOAc (100 ml) and washed with water (150 ml) and brine solution (150 ml). Organic layer was dried over Na$_2$SO$_4$, filtered and evaporated in vacuum to afford 11 g crude as a colorless liquid which was purified by column chromatography (100-200 silica gel mesh), eluted with 5% EtOAc in Hexane to afford the desired compound (10 g) as a colorless liquid.

Step-2: Preparation of 2-(3-trifluoromethyl-5-[1,3] dioxolan-2-yl-phenyl)-propan-2-ol

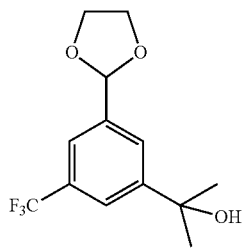 [SMILES: CC(C)(O)c1cc(C2OCCO2)cc(C(F)(F)F)c1]

To a solution of the compound from step 1 (5 gm, 16.831 mmol) in dry diethyl ether (70 mL) was added drop wise n-BuLi (2.17 M, 16.8 mL, 48.81 mmol) at −78° C. to give a yellow color suspension. The reaction mixture was stirred for 50 min at −78° C. Acetone (3.9 mL, 67.324 mmol) was added drop wise at −78° C. and continued stifling for 1 hr. After completion of the reaction, the mixture was quenched with a saturated NH$_4$Cl solution (100 mL). Reaction mixture was diluted with diethyl ether (50 mL) and the organic layer was separated, dried over Na$_2$SO$_4$, filtered and concentrated to afford a crude pale yellow liquid (7 gm). The crude compound was purified by silica gel (100-200 mesh) column chromatography, eluting with 15% EtOAc in Hexane, the collected fractions were concentrated under reduced pressure to afford the desired compound (4 gm) as a colorless liquid.

Step-3: Preparation of 3-(1-Hydroxy-1-methyl-ethyl)-5-trifluoromethyl-benzaldehyde

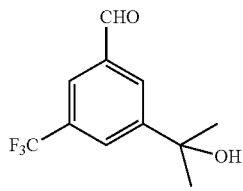 [SMILES: CC(C)(O)c1cc(C=O)cc(C(F)(F)F)c1]

To a solution of the compound from step 2 (1 g, 3.62 mmol) in acetone (10 mL) was added PTSA.H$_2$O (275 mg, 1.448 mmol) and the reaction mixture was stirred at 25° C. to give orange red solution for 4 hrs. After completion of the reaction, the mixture was concentrated, diluted with EtOAc (30 mL) and washed with saturated aq. NaHCO$_3$ solution (30 ml). Organic layer was dried over Na$_2$SO$_4$, filtered and concentrated under reduced pressure to afford 900 mg of crude compound which was purified by silica gel (100-200 mesh) column chromatography by eluting with 10% EtOAc in hexane afford the desired compound (450 mg) as pale yellow sticky solid.

Step-4: Preparation of 3-Amino-3-[3-(1-hydroxy-1-methyl-ethyl)-5-trifluoromethyl-phenyl]-propionic acid ethyl ester hydrochloride salt

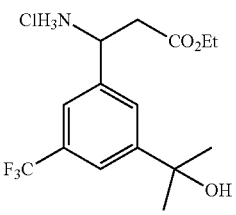

A mixture of the compound from step 3 (2.2 g, 11.891 mmol), Mono ethyl malonate (3.1 mL, 26.278 mmol) and ammonium formate (3.9 g, 61.95 mmol) in Ethanol (20 mL) was heated at 50° C. for 4 hrs. After completion of the reaction, the mixture was dissolved in DCM (75 mL) and filtered; the filtrate was concentrated under reduced pressure to obtain crude (2.5 g) as pale yellow liquid. Obtained crude was treated with 4N Dioxane-HCl (10 mL) for 10 min at 0° C. Resulting mixture was concentrated and triturated with 50% Et$_2$O/Pentane, crude salt thus obtained was dissolved in water (50 ml) and washed with Et$_2$O (20 mL×2), aqueous part was basified with solid NaHCO$_3$ and extracted with EtOAc (50 mL×2). Combined organic part was dried over Na$_2$SO$_4$, filtered and evaporated to afford free amino ester (970 mg) as a colorless liquid. This compound was further treated with 4N Dioxane-HCl (5 mL) at 0° C. for 15 min. Resulting mixture was evaporated, triturated with 50% Et$_2$O/Pentane and dried under vacuum to afford the desired compound as a racemic mixture (950 mg) as sticky solid.

Example K

Preparation of (S)-Ethyl 3-amino-3-(3-chloro-5-(1-methoxy-2-methylpropan-2-yl)phenyl)propanoate hydrochloride

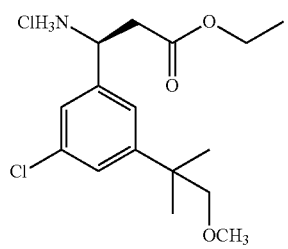

(S)-Ethyl-3-amino-3-(3-chloro-5-(1-methoxy-2-methyl-propan-2-yl)phenyl)propanoate hydrochloride was prepared according to the following procedure:

Step 1

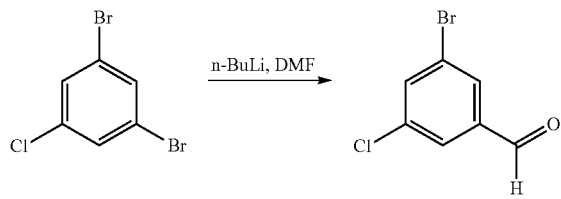 [SMILES: Clc1cc(Br)cc(Br)c1 ; O=Cc1cc(Cl)cc(Br)c1]

3,5-di-bromo-chlorobenzene (27 g, 100 mmol) was dissolved in anhydrous isopropyl ether (300.0 mL) in a dried flask under nitrogen. The reaction mixture was cooled to −78° C. and stirred under nitrogen atmosphere. A 2.6M solution of n-BuLi in hexanes (40 mL, 100 mmol) was added dropwise to the above solution and the reaction mixture was stirred at −78° C. for 30 min after complete addition of n-BuLi. After 30 min of stifling at −78° C., DMF (7.5 g, 100 mmol) was added to above reaction mixture dropwise, keeping the reaction mixture below −78° C. The reaction mixture was added 80 mL of NH$_4$Cl and the reaction mixture was stirred for 15 min. The ether layer was separated, washed with water (2×250 mL), dried over anhydrous NaSO$_4$, filtered and evaporated in vacuo, The product was purified by silica-gel flash chromatography to give the desired product (16 g, 67%).

Step 2

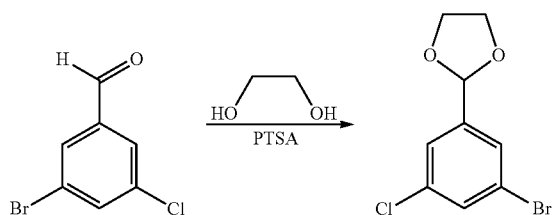

A mixture of the product from step 1 (10 g, 46 mmol) and ethane-1,2-diol (8.5 g, 137 mmol), PTSA (0.18 g, 0.92 mmol) were dissolved in anhydrous toluene (200.0 mL) in a dried flask under nitrogen. Then, reflux, TLC traced, TLC showed the reaction finished. Saturated NaHCO$_3$ solution (100 mL) was added, then the toluene layer was separated, dried over anhydrous NaSO$_4$, filtered and evaporated in vacuo to give the desired product (14 g, quant) as a yellow oil.

Step 3

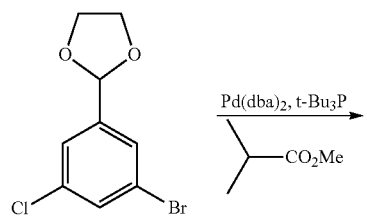

-continued

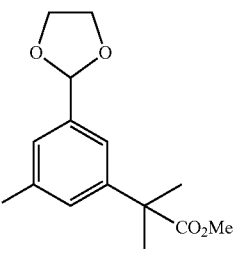

To a solution of dicyclohexylamine (8 mL, 15 mmol) in toluene at −20° C. under argon is added dropwise a 2.5 N solution of nBuLi in hexane (6 mL, 15 mmol). After 15 min at 0° C., methyl isobutyrate (2.1 g, 13 mmol) is added dropwise to the reaction mixture, which is allowed to warm to 25° C. and stirred for 5 min at 25° C. Then, the product from step 2 (3 g, 11 mmol), Pd$_2$(dba)$_3$ (0.20 g, 0.22 mmol) and P(tBu)$_3$ (0.083 g, 0.22 mmol) are added and the reaction mixture is stirred for 1 h. The reaction mixture is quenched with 1 N HCl in Et$_2$O to precipitate the dicyclohexylamine as HCl salt. The reaction mixture is filtered and concentrated. The desired compound is obtained after purification by flash-chromatography on silica gel to give the desired product (2.3 g, 70%).

Step 4

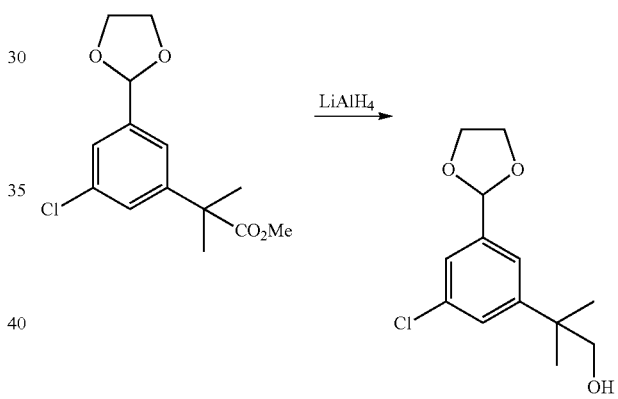

To a solution of LiAlH$_4$ (0.4 g, 8.8 mmol) in THF (10 mL) is added dropwise a solution of the product from step 3 (2.3 g, 8 mmol) dissolved in THF (30 mL). The reaction mixture is stirred for 30 min at 25° C. The reaction mixture is quenched with saturated aq. potassium sodium tartrate and was filtered through a pad of Celite. The organic layer is washed with brine, dried over Na$_2$SO$_4$, filtered and concentrated. The crude desired product (2.1 g, crude) is used as such in the next reaction.

Step 5

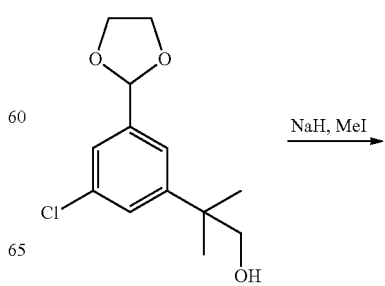

253
-continued

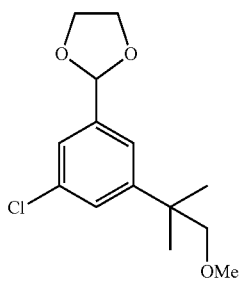

To a solution of the crude product from step 4 (2.1 g, 8 mmol) in THF (20 mL) at 25° C. under argon was added NaH (0.64 g, 16 mmol). After 10 min stirring at 25° C., MeI (2.5 g, 16 mmol) was added and the solution was stirred at 80° C. for 1 h. 20 mL H₂O was added, the mixture was extracted with EtOAc. The organic layers are washed with water and brine, dried over Na₂SO₄, filtered and concentrated. The crude desired product (2.2 g, crude) is used as such in the next reaction.

Step 6

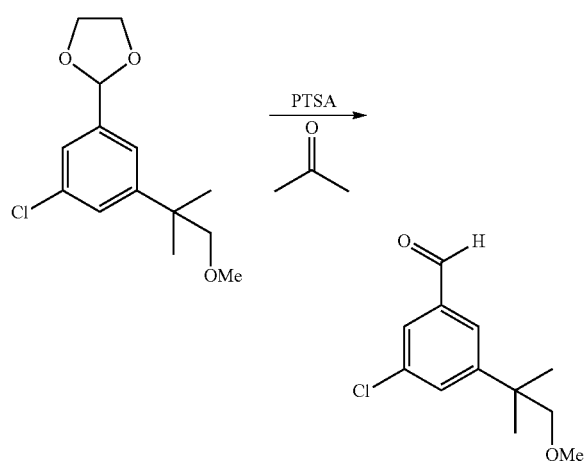

The product from step 5 (2.2 g, 8 mmol) and PTS (0.3 g, 1.6 mmol) were dissolved in anhydrous acetone (100.0 mL) in a dried flask under nitrogen. Then, RT stirred, TLC traced, TLC showed the reaction finished. A satd. NaHCO₃ soln. (10 mL) was added, EtOAc (100 mL×2) extraction, dried over anhydrous Na₂SO₄, filtered and evaporated in vacuo to give the desired crude product. (1.7 g, crude) The crude products was used as such in the next reaction.

Step 7

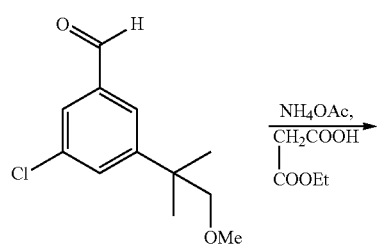

254
-continued

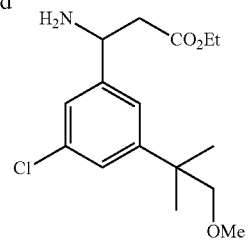

The crude product from step 6 (2.2 g, 8 mmol), mono-ethyl malonate (5.2 g, 40 mmol) and ammonium acetate (5.6 g, 80 mmol) in anhydrous ethanol (50.0 mL) was heated at reflux for 7 h to give a pale yellow solution. The reaction mixture was cooled to room temperature and the solvent was evaporated in vacuo to give a yellow viscous liquid. The residue was partitioned between aqueous saturated NaHCO₃ solution (100 mL) and ethyl acetate (100 mL), and the organic layer was removed, dried over anhydrous sodium sulfate, filtered and evaporated in vacuo. The product was purified by Silica-gel flash chromatography to give the desired product (0.4 g, 15%) as a racemate.

¹H NMR: WH00420-070-01 400 Hz CDCl₃

δ 7.20-7.30 (M, 3H), 4.35-4.40 (M, 1H), 4.23-4.30 (q, 2H), 3.37 (s, 1H), 3.31 (s, 1H), 2.26-264 (M, 2H), 1.30 (s, 6H), 1.25-1.27 (t, 3H)

Step 8

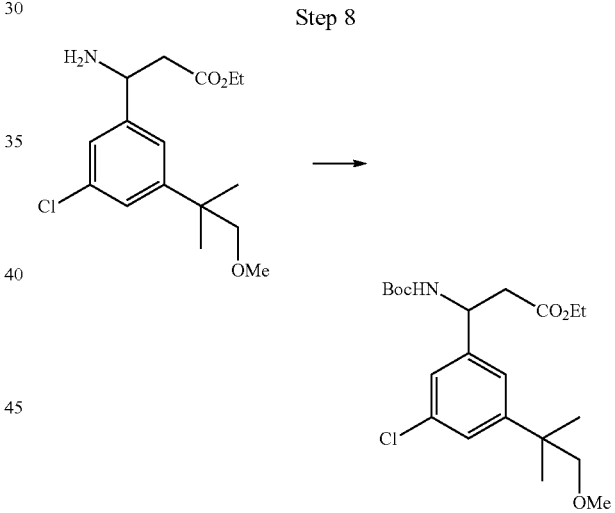

To a solution of the product from step 7 (0.2 g, 0.59 mol), was added 2,6-dimethylpyridine (62.7 mg, 0.59 mmol) and Boc₂O (0.2 g, 0.59 mol) in DCM (10 mL). The mixture was stirred at room temperature for 10 h. To the reaction mixture was added 1M HCl (15 mL), the aqueous layer was extracted with DCM (10 mL×3), the organic layer was washed with brine then dried over Na₂SO₄ and concentrated. The product was purified by Silica-gel flash chromatography to give the desired BOC protected product (0.25 g, 96%) as a yellow solid.

Step 9

The racemic BOC protected product from step 8 was separated by SFC to give the individual (S) and (R) BOC enantiomers

Step 10

Steps 1 to 9 were repeated to yield additional amounts of each of the desired BOC enantiomers, then:

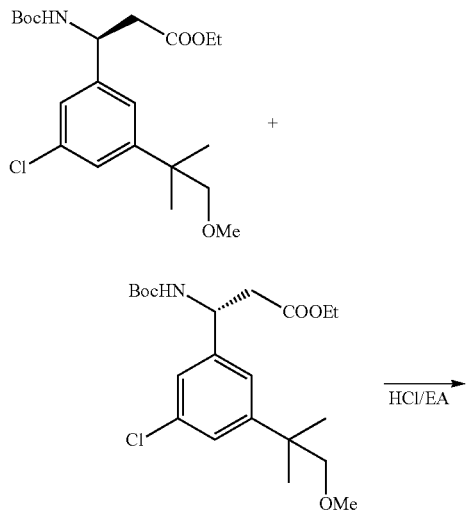

To a solution of each separated BOC enantiomer above (1.7 g each), in ethyl acetate was added HCl/EA (10 mL). After 1 hr, TLC showed the reactions were completed. The solvents were evaporated in-vacuo to give 1 gram of each of the desired enantiomers. The desired (S)-enantiomer was identified analytically by (S)-selective enzymatic resolution with Amano Lipase PS (selective hydrolysis of the (S) enantiomer).

Example L

Preparation of (S)-Ethyl 3-amino-3-(3-chloro-5-(4-(Methoxymethyl)tetrahydro-2H-pyran-4-yl)phenyl)propanoate hydrochloride

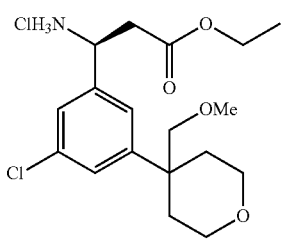

(S)-Ethyl 3-amino-3-(3-chloro-5-(4-(Methoxymethyl)tetrahydro-2H-pyran-4-yl)phenyl)propanoate hydrochloride was prepared according to the following procedure:

Step 1

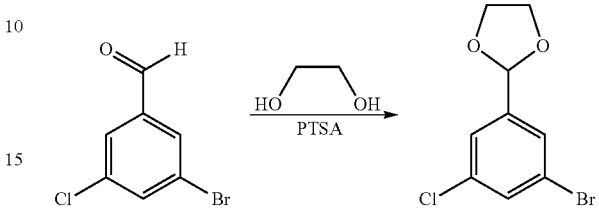

A mixture of 3-bromo-5-chlorobenzaldehyde (10 g, 46 mmol) and ethane-1,2-diol (8.5 g, 137 mmol), PTS (0.18 g, 0.92 mmol) were dissolved in anhydrous toluene (200.0 mL) in a dried flask under nitrogen. Then, reflux, TLC traced, TLC showed the reaction finished. A saturated $NaHCO_3$ soln. (100 mL) was added. The toluene layer was separated, dried over anhydrous $Na_2SO_4$, filtered and evaporated in vacuo to give the desired product (14 g, quant) as a yellow oil.

Step 2

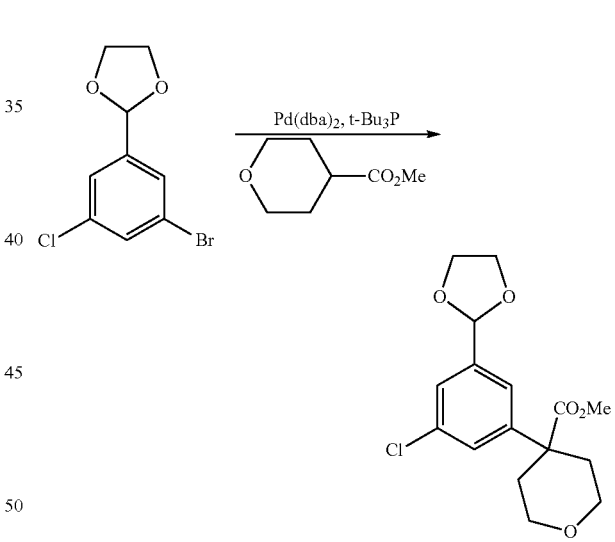

To a solution of dicyclohexylamine (8 mL, 15 mmol) in toluene at −20° C. under argon is added dropwise a 2.5 N solution of n-BuLi in hexane (6 mL, 15 mmol). After 15 min at 0° C., methyl tetrahydro-2H-pyran-4-carboxylate (1.8 g, 13 mmol) is added dropwise to the reaction mixture, which is allowed to warm to 25° C. and stirred 5 min at 25° C. Then, the product from step 1 (3 g, 11 mmol), $Pd_2(dba)_3$ (0.20 g, 0.22 mmol) and $P(t-Bu)_3$ (0.083 g, 0.22 mmol) are added and the reaction mixture is stirred for 1 h. The reaction mixture was quenched with 1 N HCl in $Et_2O$ to precipitate the dicyclohexylamine as HCl salt. The reaction mixture is filtered and concentrated. The desired compound is obtained after purification by flash-chromatography on silica gel to give the desired product (2.3 g, 70%).

Step 3

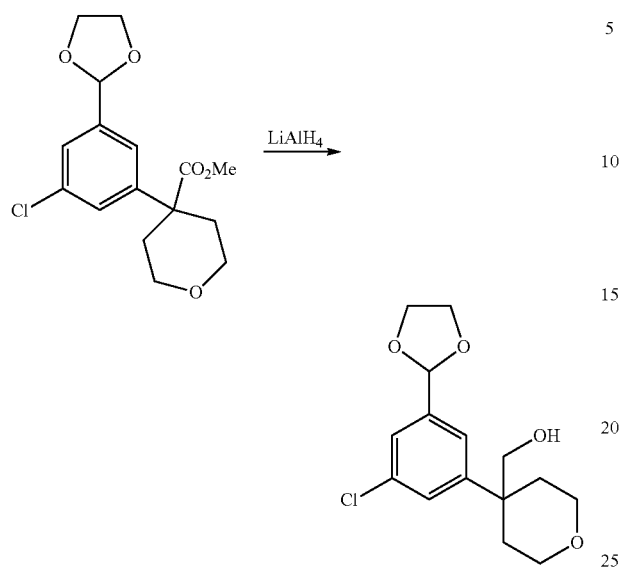

To a solution of LiAlH₄ (0.4 g, 8.8 mmol) in THF (5 mL) is added dropwise a solution of the product from step 3 (2.6 g, 8 mmol) dissolved in THF (2.0 mL). The reaction mixture is stirred for 30 min at 25° C. The reaction mixture is quenched with saturated aq. potassium sodium tartrate and was filtered through a pad of Celite. The organic layer is washed with brine, dried over Na₂SO₄, filtered and concentrated. The crude desired product (3 g, crude) is used as such in the next reaction.

Step 4

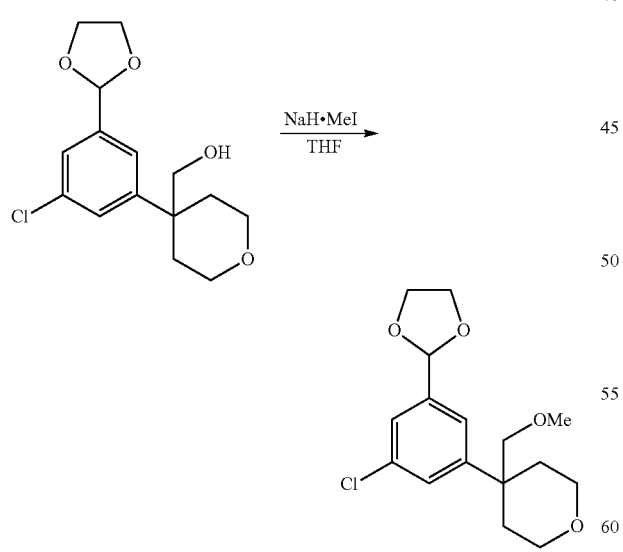

To a solution of the crude product from step 3 (19 g, 63 mmol) in THF (10 mL) at 25° C. under argon is added NaH. After 10 min stirring at 25° C., MeI is added and solution is stirred at 80° C. for 1 h. The reaction mixture is extracted with EtOAc. The organic layers are washed with water and brine, dried over Na₂SO₄, filtered and concentrated. The crude desired product (20 g, crude) is used as such in the next reaction.

Step 5

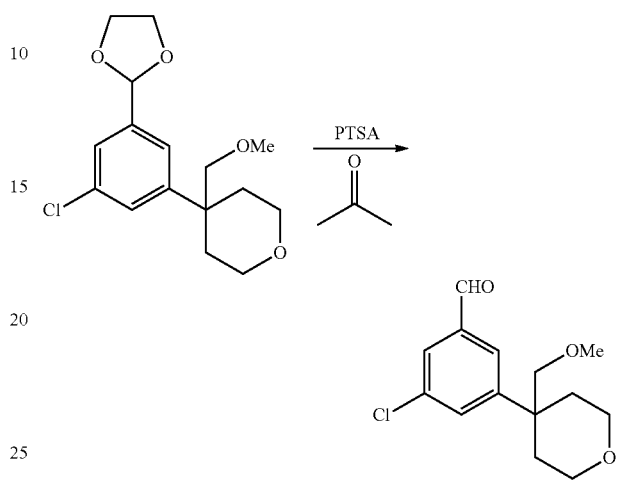

The crude product from step 4 (20 g, 63 mmol) and PTS (2.3 g, 12 mmol) were dissolved in anhydrous acetone (200.0 mL) in a dried flask under nitrogen and stirred at RT for several hours. TLC showed the reaction was finished. Saturated NaHCO₃ soln. (50 mL) was added, the mixture was extracted with EtOAc (200 mL×2), dried over anhydrous Na₂SO₄, filtered and evaporated in vacuo to give the desired product (17 g, (quant).

Step 6

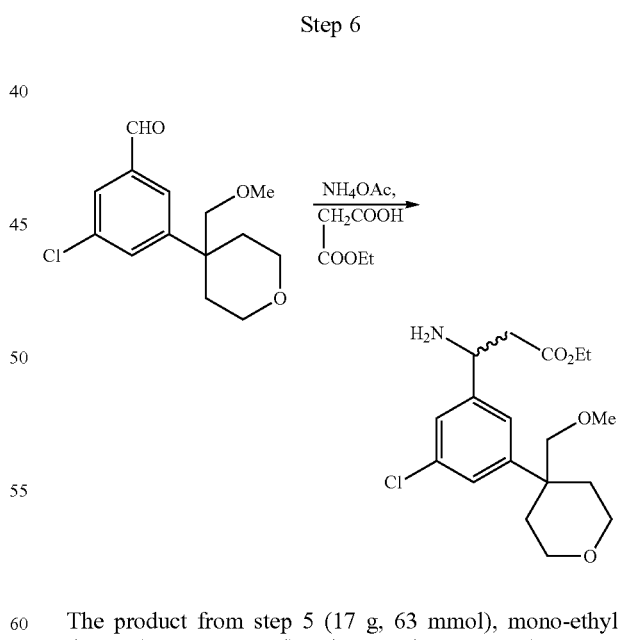

The product from step 5 (17 g, 63 mmol), mono-ethyl malonate (16 g, 126 mmol) and ammonium acetate (24 g, 315 mmol) in anhydrous ethanol (50.0 mL) were heated at reflux for 7 h to give a pale yellow solution. The reaction mixture was cooled to room temperature and the solvent was evaporated in vacuo to give a yellow viscous liquid. The residue was partitioned between aqueous saturated NaHCO₃ solution (100 mL) and ethyl acetate (100 mL). The organic layer was removed, dried over anhydrous sodium sulfate, filtered and evaporated in vacuo. The product was purified by Silica-gel flash chromatography to give the desired product (3.5 g, 17%) as a racemate.

Step 7

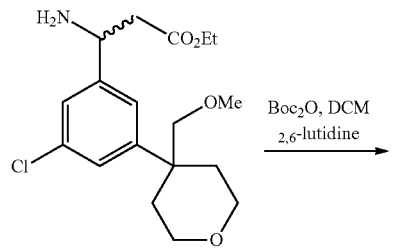

To a solution of the racemate product from step 6 (3.5 g, 10 mmol) in DCM (10 mL) was added 2,6-dimethylpyridine (0.7 g, 10 mmol) and Boc₂O (1.95 g, 10 mol). The mixture was stirred at room temperature for 10 h. To the reaction mixture was added 1M HCl (15 mL), the aqueous layer was extracted with DCM (10 mL×3), the organic layer was washed with brine then dried over Na₂SO₄ and concentrated. The product was purified by silica-gel flash chromatography to give the desired BOC protected racemic product (4.3 g, 96%) as a yellow solid.

Step 8

The racemic BOC protected product from step 7 was separated by SFC to give the individual (S) and (R) BOC enantiomers (~1 gram each enantiomer).

Step 9

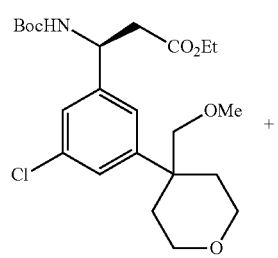

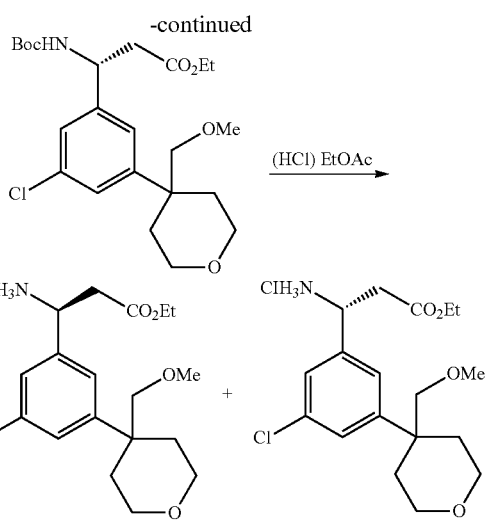

To a solution of 1 g of each BOC protected enantiomer in ethyl acetate from step 8 was added HCl/EA (10 mL). After 1 h, TLC showed the reaction was completed. The solvents were evaporated in-vacuo to give ~800 mg of each of the desired enantiomers. The desired (S)-enantiomer was identified analytically by (S)-selective enzymatic resolution with Amano Lipase PS (selective hydrolysis of the (S) enantiomer).

Example M

Preparation of (S)-Ethyl 3-amino-3-(3-chloro-5-(4-(fluoromethyl)tetrahydro-2H-pyran-4-yl)phenyl)propanoate hydrochloride

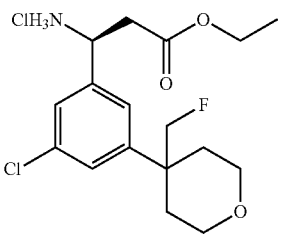

(S)-Ethyl 3-amino-3-(3-chloro-5-(4-fluoromethyl)tetrahydro-2H-pyran-4-yl)phenyl)propanoate hydrochloride was prepared according to the following procedure:

Step 1

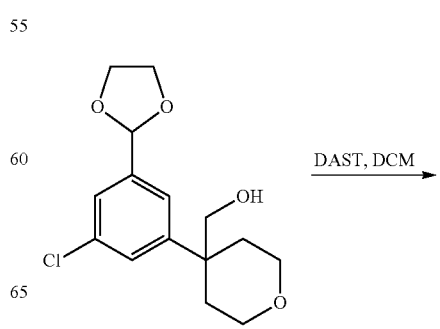

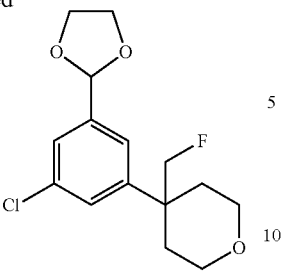

To a solution of the product from Example L, step 3 (15 g, mmol) in DCM (300 mL) at −60° C. under argon is added DAST (24 g, 150 mmol). After 1 hour stirring, at −60° C., water was added and solution is stirred at 20° C. for 1 h. The reaction mixture is extracted with DCM. The organic layers were washed with water and brine, dried over Na$_2$SO$_4$, filtered and concentrated. The crude desired product (12 g, crude) is used as such in the next reaction.

Step 2

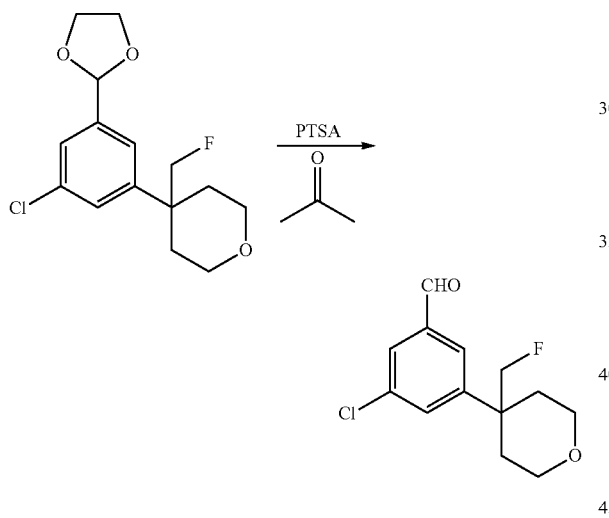

The product from step 1 (12 g, 40 mmol) and PTS (2.3 g, 12 mmol) were dissolved in anhydrous acetone (120.0 mL) in a dried flask under nitrogen and stirred at RT for several hours. TLC showed the reaction was finished. Saturated NaHCO$_3$ soln., 50 mL, was added and the mixture was extracted with EtOAc (200 ml×2), dried over anhydrous Na$_2$SO$_4$, filtered and evaporated in vacuo to give the crude desired product (2.3 g, 18.7% yield).

Step 3

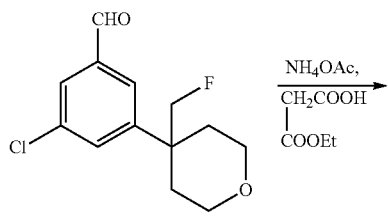

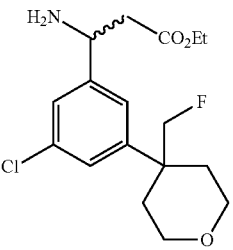

The product from step 2 (2.3 g, 8.9 mmol), mono-ethyl malonate (5.2 g, 40 mmol) and ammonium acetate (5.6 g, 80 mmol) in anhydrous ethanol (50.0 mL) was heated at reflux for 7 h to give a pale yellow solution. The reaction mixture was cooled to room temperature and the solvent was evaporated in vacuo to give a yellow viscous liquid. The residue was partitioned between aqueous saturated NaHCO$_3$ solution (100 mL) and ethyl acetate (100 mL). The organic layer was removed, dried over anhydrous sodium sulfate, filtered and evaporated in vacuo. The product was purified by Silica-gel flash chromatography to give the desired product (0.7 g).

Step 4

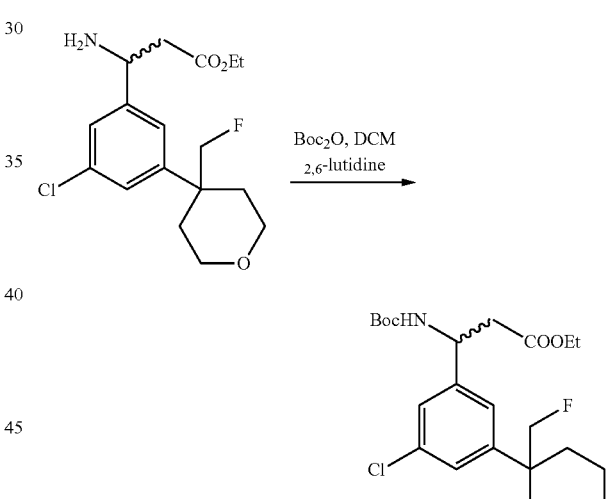

A solution of the product from step 3 (0.7 g, 2 mol), 2,6-dimethylpyridine (0.3 g, 3 mmol) and Boc$_2$O (0.65 g, 3 mol) in DCM (10 mL) was stirred at room temperature for 10 h. To the reaction mixture was added 1M HCl (15 mL), the aqueous layer was extracted with DCM (10 mL×3), the organic layer was washed with brine then dried over Na$_2$SO$_4$ and concentrated. The product was purified by silica-gel flash chromatography to give the desired BOC protected racemic product (0.3 g, 33%) as a yellow solid.

Step 5

The racemic BOC protected product from step 4 was separated by SFC to give the individual (S) and (R) BOC enantiomers (~110 mg each enantiomer).

Step 6

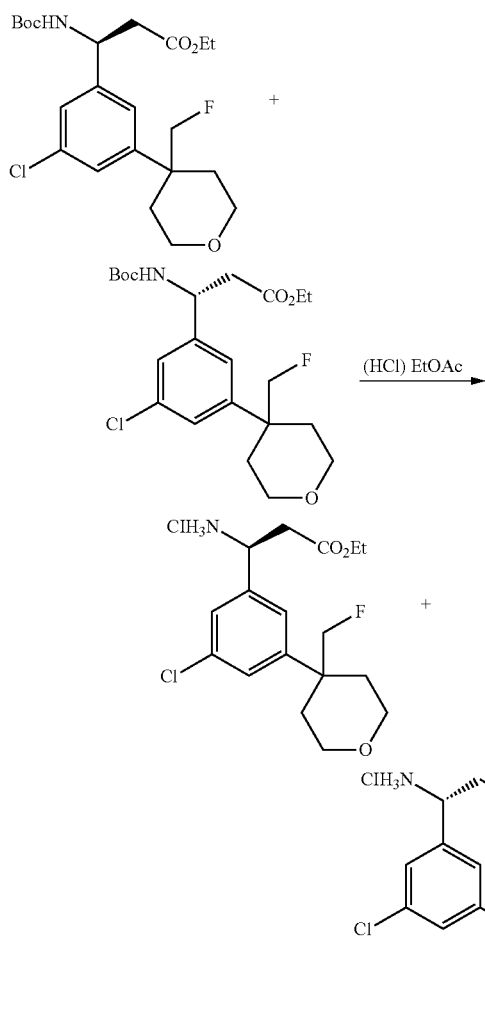

To a solution of 110 mg of each BOC protected enantiomer in ethyl acetate from step 5 was added HCl/ethyl acetate (10 mL). After 1 h, TLC showed the reaction was completed. The solvents were evaporated in vacuo to give ~75 mg of each of the desired enantiomers (76%). The desired (S)-enantiomer was identified analytically by (S)-selective enzymatic resolution with Amano Lipase PS (selective hydrolysis of the (S) enantiomer).

Example N

Preparation of rac-ethyl 3-amino-3-(3-chloro-5-(1-cyanocyclobutyl)phenyl)propanoate

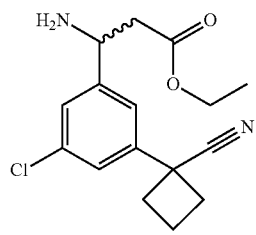 [SMILES: CCOC(=O)CC(N)c1cc(Cl)cc(C2(C#N)CCC2)c1]

rac-ethyl 3-amino-3-(3-chloro-5-(1-cyanocyclobutyl)phenyl)propanoate was prepared according to the following procedure:

Step 1

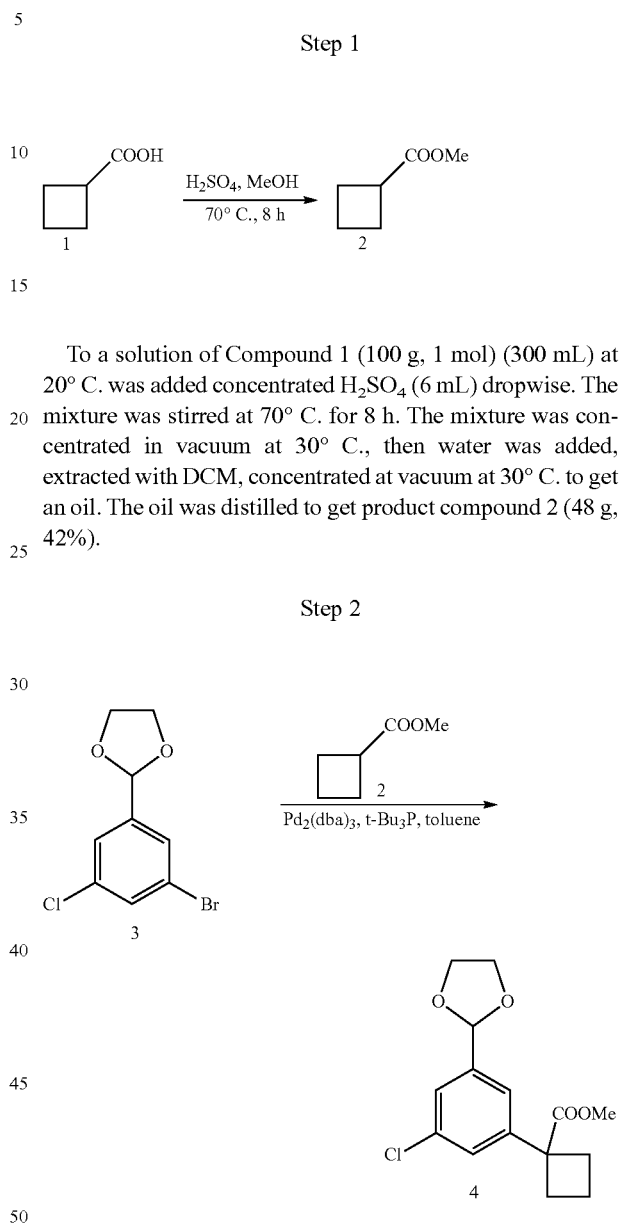

To a solution of Compound 1 (100 g, 1 mol) (300 mL) at 20° C. was added concentrated $H_2SO_4$ (6 mL) dropwise. The mixture was stirred at 70° C. for 8 h. The mixture was concentrated in vacuum at 30° C., then water was added, extracted with DCM, concentrated at vacuum at 30° C. to get an oil. The oil was distilled to get product compound 2 (48 g, 42%).

Step 2

To a solution of dicyclohexylamine (8 mL, 15 mmol) in toluene at −20° C. under argon is added dropwise a 2.5 N solution of n-BuLi in hexane (6 mL, 15 mmol). After 15 min at 0° C., compound 2 (1.5 g, 13 mmol) is added dropwise to the reaction mixture, which is allowed to warm to 25° C. and stirred 15 min at 25° C. Then, compound 3 (see Example K, step 2) (3 g, 11 mmol), $Pd_2(dba)_3$ (0.20 g, 0.22 mmol) and $P(t-Bu)_3$ (0.083 g, 0.22 mmol) are added and the reaction mixture is stirred for 1 h. The reaction mixture was quenched with 1 N HCl in $Et_2O$ to precipitate the dicyclohexylamine as HCl salt. The reaction mixture is filtered and concentrated. The title compound is obtained after purification by flash-chromatography on silica gel to give the product compound 4 (2 g, 53%).

Step 3

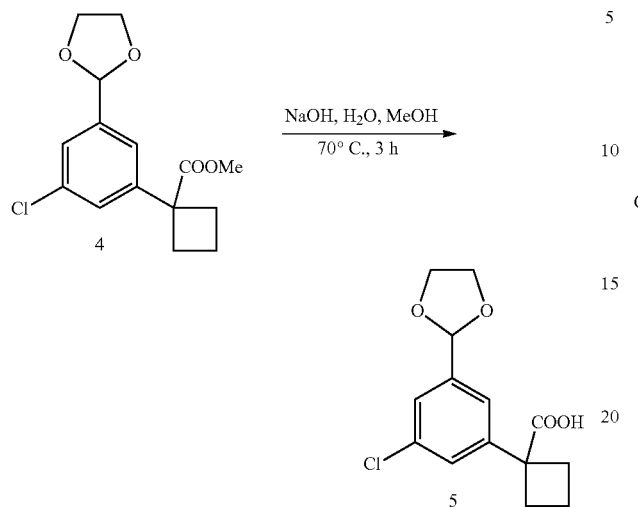

To a solution of compound 4 (2 g, 6 mmol) in MeOH (20 mL) was added NaOH a.q (1 N, 30 mL), the mixture was stirred at 80° C. for 3 h. The solution was concentrated. Then, ethyl acetate and $H_2O$ were added, the water phase was separated. 1N HCl was added adjust to pH 2-4. Ethyl acetate was added. The organic phase was separated, dried and concentrated to give the product compound 5 (1.2 g, 70%).

Step 4

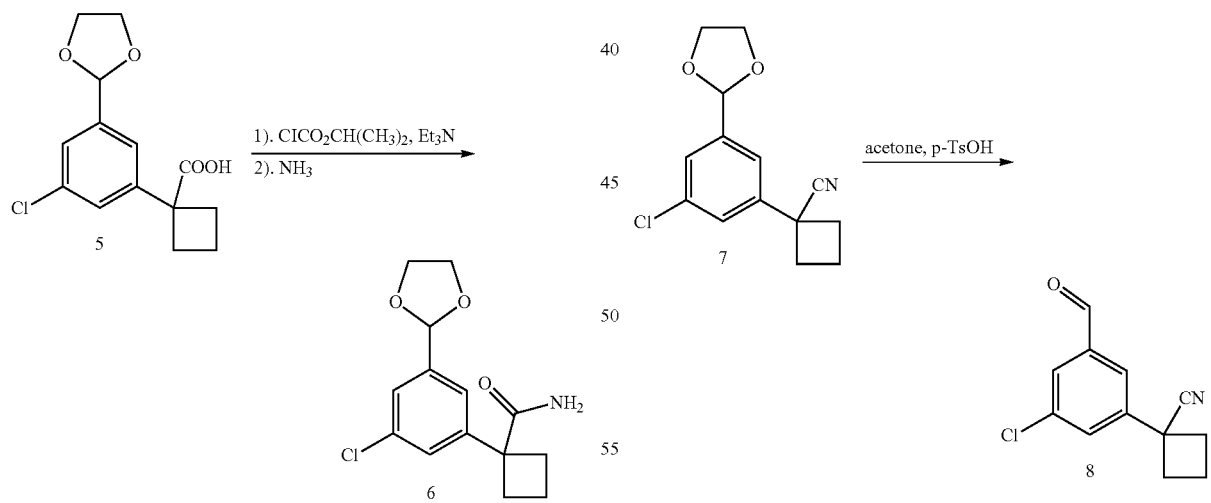

Compound 5 (1.2 g, 4.2 mmol) and $Et_3N$ (0.76 g, 7.6 mmol) were dissolved in anhydrous THF (20 mL). ClCOOt-Bu (0.78 g, 5.8 mmol) was added dropwise at 0° C. in a dried flask under nitrogen. The mixture was stirred at RT for 2 hours. TLC showed the reaction was finished. $NH_3$/THF (100 mL) was then added, and the mixture was stirred at RT for 2 hours. The mixture was concentrated to give the product compound 6 (1.8 g, quant).

Step 5

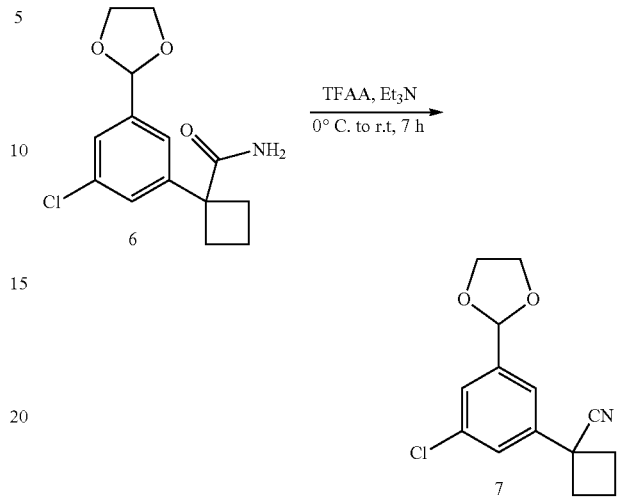

Compound 6 (1.2 g, 4.2 mmol) and $Et_3N$ (0.76 g, 7.6 mmol) were dissolved in anhydrous DCM (20 mL). TFAA (1.6 g, 7.6 mmol) was added dropwise at 0° C. in a dried flask under nitrogen. Then, the mixture was stirred at RT for 4 hours. TLC showed the reaction was finished. The mixture was washed with 1N HCl (30 mL×2), dried over anhydrous $Na_2SO_4$, filtered and evaporated in vacuo to give compound 7 (1.2 g, quant).

Step 6

Compound 7 (1.2 g, 4.5 mmol) and PTSA (0.2 g, 1 mmol) were dissolved in anhydrous acetone (20 mL) in a dried flask under nitrogen and stirred at RT for 14 hours. TLC showed the reaction was finished. Saturated $NaHCO_3$ (50 mL) was added, the mixture was extracted with EtOAc (200 mL×2), dried over anhydrous $NaSO_4$, filtered and evaporated in vacuo to give the product. The title compound is obtained after purification by flash-chromatography on silica gel to give the product compound 8 (0.6 g, 61%).

Step 7

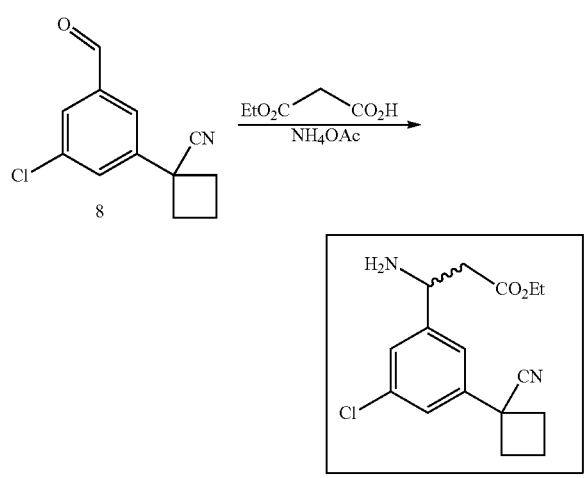

Compound 8 (7 g, 32 mmol), mono-ethyl malonate (6.9 g, 52 mmol) and ammonium acetate (10 g, 130 mmol) in anhydrous ethanol (100.0 mL) was heated at 80° C. for 7 h to give a pale yellow solution. The reaction mixture was cooled to room temperature and the solvent was evaporated in vacuo to give a yellow viscous liquid. The residue was partitioned between aqueous saturated NaHCO$_3$ solution (100 mL) and ethyl acetate (100 mL); the organic layer was removed, dried over anhydrous sodium sulfate, filtered and evaporated in vacuo. The product was purified by silica-gel flash chromatography to give the desired product (2.1 g, 22%)

Example O

Preparation of rac-ethyl 3-amino-3-(3-chloro-5-(4-cyanotetrahydro-2H-pyran-4-yl)phenyl) propanoate

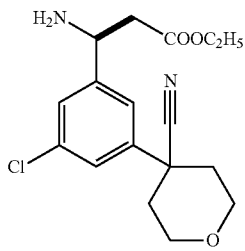

rac-ethyl 3-amino-3-(3-chloro-5-(4-cyanotetrahydro-2H-pyran-4-yl)phenyl) propanoate was prepared according to the following procedure:

Step 1

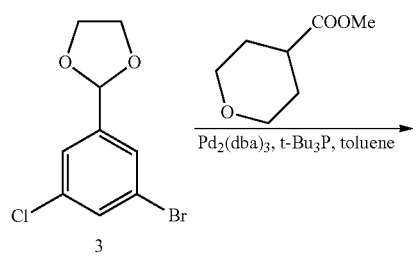

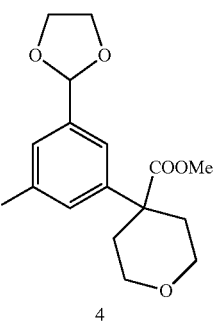

To a solution of dicyclohexylamine (8 mL, 15 mmol) in toluene at −20° C. under argon is added dropwise a 2.5 N solution of n-BuLi in hexane (6 mL, 15 mmol). After 15 min at 0° C., methyl tetrahydro-2H-pyran-4-carboxylate (1.8 g, 13 mmol) is added dropwise to the reaction mixture, which is then allowed to warm to 25° C. and then stirred for 5 min at 25° C. Then, compound 3 (see Example K, step 2) (3 g, 11 mmol), Pd$_2$(dba)$_3$ (0.20 g, 0.22 mmol) and P(t-Bu)$_3$ (0.083 g, 0.22 mmol) are added and the reaction mixture is stirred for 1 h. The reaction mixture was quenched with 1 N HCl in Et$_2$O to precipitate the dicyclohexylamine as HCl salt. The reaction mixture is filtered and concentrated. The desired compound is obtained after purification by flash-chromatography on silica gel to give the product compound 4 (2 g, 56%).

Step 2

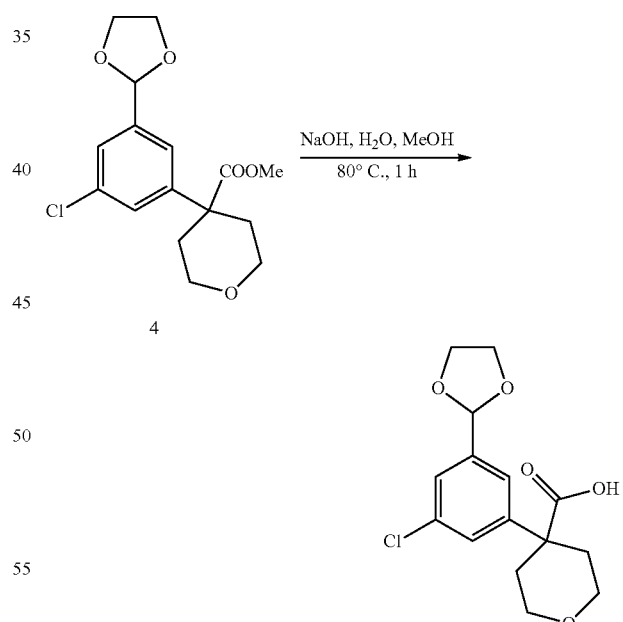

To a solution of compound 4 (2 g, 6 mmol) in MeOH (20 mL) was added NaOH aq (1 N, 30 mL). The mixture was stirred at 80° C. for 3 h. The solution was concentrated. Then, ethyl acetate and H$_2$O were added, the water phase was separated. 1N HCl was added adjust to pH 2-4. Ethyl acetate was added. The organic phase was separated, dried and concentrated to give the product compound 5 (1.2 g, 63%).

Step 3

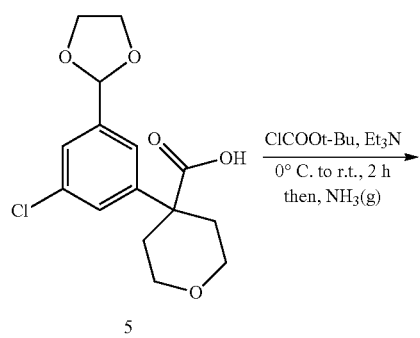

Compound 5 (1.2 g, 3.8 mmol) and Et₃N (0.76 g, 7.6 mmol) were dissolved in anhydrous THF (20 mL). ClCOOt-Bu (0.78 g, 5.8 mmol) was added dropwise at 0° C. in a dried flask under nitrogen. The mixture was stirred at RT for 2 hours. TLC showed the reaction was finished. NH₃/THF (100 mL) was then added, and the mixture was stirred at RT for 2 hours. The mixture was concentrated to give the product compound 6 (1.8 g, quant).

Step 4

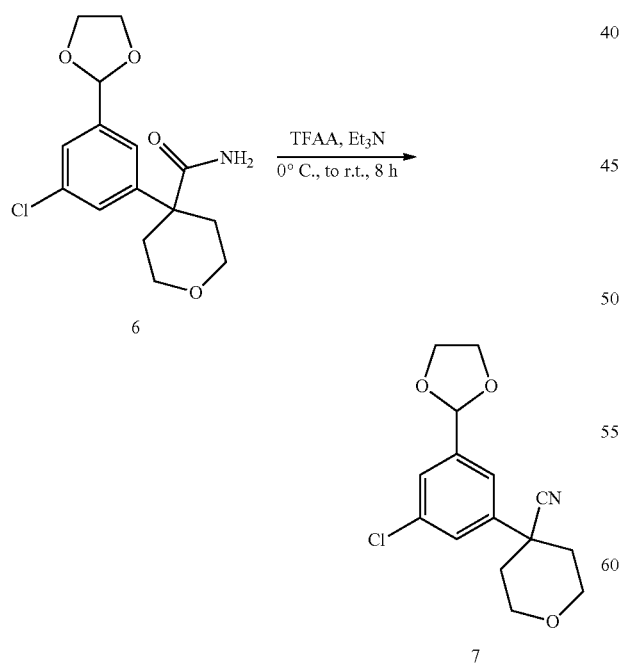

Compound 6 (1.2 g, 3.8 mmol) and Et₃N (0.76 g, 7.6 mmol) were dissolved in anhydrous DCM (20 mL). TFAA (1.6 g, 7.6 mmol) was added dropwise at 0° C. in a dried flask under nitrogen. Then, the mixture was stirred at RT for 4 hours. TLC showed the reaction was finished. The mixture was washed with 1N HCl (30 mL×2), dried over anhydrous Na₂SO₄, filtered and evaporated in vacuo to give compound 7 (1.2 g, quant).

Step 5

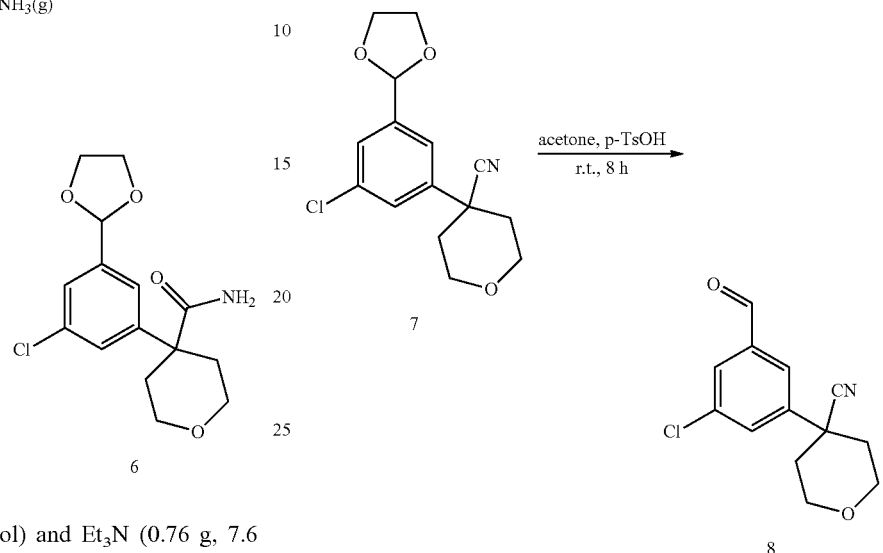

Compound 7 (1.2 g, 4 mmol) and PTSA (0.2 g, 1 mmol) were dissolved in anhydrous acetone (20 mL) in a dried flask under nitrogen and stirred at RT for 14 hours. TLC showed the reaction was finished. Saturated NaHCO₃ (50 mL) was added, the mixture was extracted with EtOAc (200 mL×2), dried over anhydrous NaSO₄, filtered and evaporated in vacuo to give the product. The title compound is obtained after purification by flash-chromatography on silica gel to give the product compound 8 (0.6 g, 61%).

Step 6

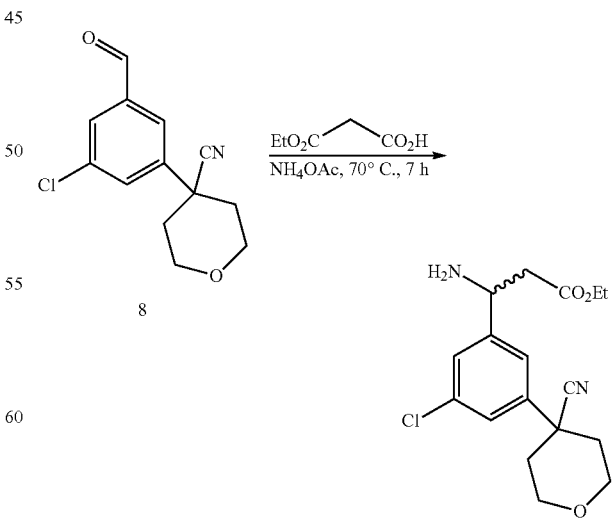

Compound 8 (7 g, 28 mmol), mono-ethyl malonate (6.9 g, 52 mmol) and ammonium acetate (10 g, 130 mmol) in anhydrous ethanol (100.0 mL) was heated at 80° C. for 7 h to give a pale yellow solution. The reaction mixture was cooled to room temperature and the solvent was evaporated in vacuo to give a yellow viscous liquid. The residue was partitioned between aqueous saturated NaHCO$_3$ solution (100 mL) and ethyl acetate (100 mL); the organic layer was removed, dried over anhydrous sodium sulfate, filtered and evaporated in vacuo. The product was purified by silica-gel flash chromatography to give the desired product (2.1 g, 22%)

Example P

Preparation of rac-ethyl 3-amino-3-(3-chloro-5-(1,1,1-trifluoro-2-hydroxypropan-2-yl)phenyl) propanoate

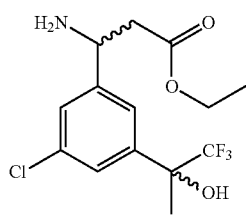 [SMILES: CCOC(=O)CC(N)c1cc(Cl)cc(C(C)(O)C(F)(F)F)c1]

rac-ethyl 3-amino-3-(3-chloro-5-(1,1,1-trifluoro-2-hydroxypropan-2-yl)phenyl) propanoate was prepared according to the following procedure:

Step 1

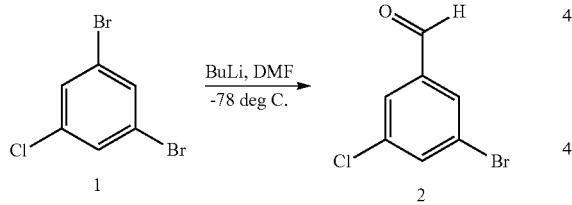

Compound 1 (90 g, 0.333 mol) was dissolved in anhydrous isopropyl ether (500 mL) in a dried flask under nitrogen. The reaction mixture was cooled to −78° C. and stirred under nitrogen atmosphere. A 2.5 M solution of n-BuLi in hexanes (133.3 mL, 0.333 mol) was added dropwise to the above solution and the reaction mixture was stirred at −78° C. for 30 min after complete addition of n-BuLi. After 30 min of stirring at −78° C., anhydrous DMF (24.3 g, 0.333 mol) was added to above reaction mixture dropwise, keeping the reaction mixture below −60° C. After addition of anhydrous DMF is complete, the reaction mixture was stirred at −70° C. for (30 min) and then the reaction mixture was poured into 400 mL of aqueous NH$_4$Cl and the reaction mixture was stirred for 15 min. The isopropyl ether was separated, dried over anhydrous MgSO$_4$, filtered and evaporated in vacuo to give the compound 2 (43 g, 58%) as a white solid.

Step 2

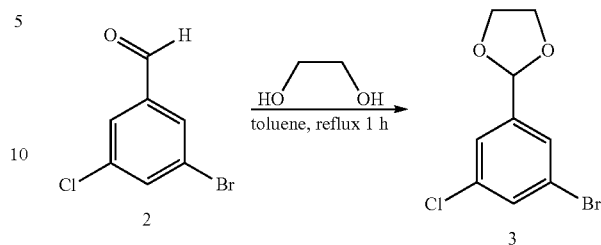

Compound 2 (10 g, 46 mmol), ethane-1,2-diol (8.5 g, 137 mmol), and PTSA (0.18 g, 0.92 mmol) were dissolved in anhydrous toluene (200.0 mL) in a dried flask under nitrogen. The reaction was stirred under reflux until TLC showed the reaction finished. Saturated NaHCO$_3$ (100 mL) was add, the toluene layer was separated, dried over anhydrous NaSO$_4$, filtered and evaporated in vacuo to give the product compound 3 (14 g, quant) as a yellow oil.

Step 3

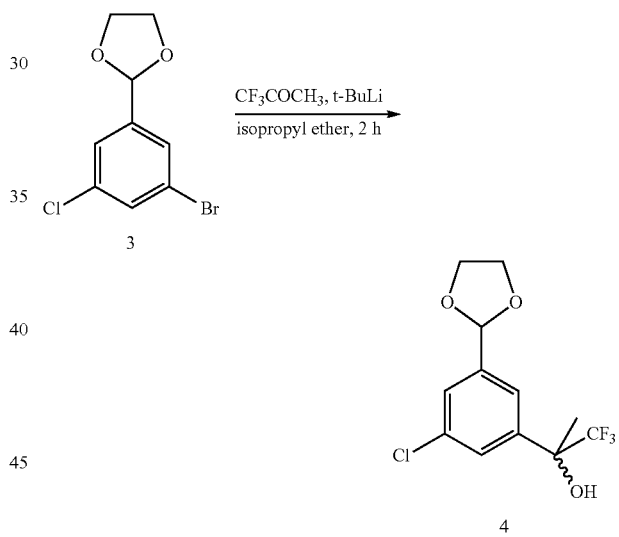

Compound 3 (4.3 g, 16.2 mmol) was dissolved in anhydrous isopropyl ether (50.0 mL) in a dried flask under nitrogen. The reaction mixture was cooled to −78° C. and stirred under nitrogen atmosphere. A 1.3 M solution of t-BuLi in hexanes (12.5 mL, 16.2 mmol) was added dropwise to the above solution and the reaction mixture was stirred at −78° C. for 30 min after complete addition of n-BuLi. After 30 min of stifling at −78° C., the reaction mixture was warmed to −30° C. 1,1,1-trifluoro acetone (2.2 g, 20.0 mmol) was added to above reaction mixture dropwise, keeping the reaction mixture below −30° C. After addition is complete, the reaction mixture was warmed slowly to −30° C. (30 min) and then stirring at room temperature. The reaction mixture was poured into 40 mL of aqueous NH$_4$Cl and the reaction mixture was stirred for 15 min. The isopropyl ether was separated, dried over anhydrous MgSO$_4$, filtered and evaporated in vacuo to give the compound 4 (4.0 g, crude) as a pale yellow viscous liquid.

Step 4

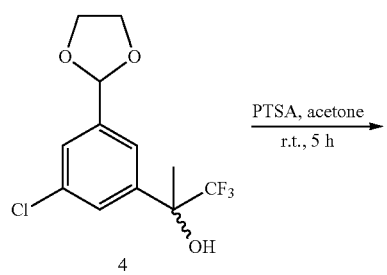

Compound 4 (4.0 g, 14 mmol) and PTSA (0.5 g, 2.8 mmol) were dissolved in anhydrous acetone (100.0 mL) in a dried flask under nitrogen. The reaction was stirred at R.T. until TLC showed the reaction finished. Saturated NaHCO$_3$ solution (100 mL) was added and this was extracted with ethyl acetate (100 mL×2), dried over anhydrous NaSO$_4$, filtered and evaporated in vacuo to give the product compound 5 (3.2 g, crude).

Step 5

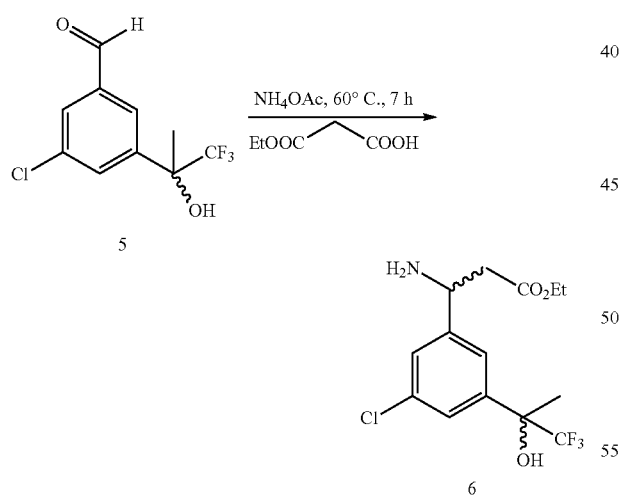

A solution of compound 5 (22 g, 0.087 mol), mono-ethyl malonate (35.1 g, 0.266 mmol) and ammonium acetate (33.5 g, 0.435 mol) in EtOH (50 mL) was heated at 70° C. under nitrogen. TLC showed the reaction was completed. Saturated NaHCO$_3$ (100 mL) was added, extracted with ethyl acetate (100 mL×2), and dried over anhydrous NaSO$_4$, filtered and evaporated in vacuo. The product was purified by silica-gel flash chromatography to give the desired product compound 6 (3.7 g, 12.5%)

Example Q

Preparation of rac-ethyl 3-amino-3-(3-chloro-5-(1,1,1-trifluoro-2-methylpropan-2-yl)phenyl)propanoate

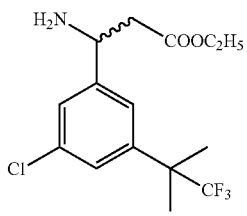

rac-ethyl 3-amino-3-(3-chloro-5-(1,1,1-trifluoro-2-methylpropan-2-yl)phenyl)propanoate was prepared according to the following procedure:

Step 1

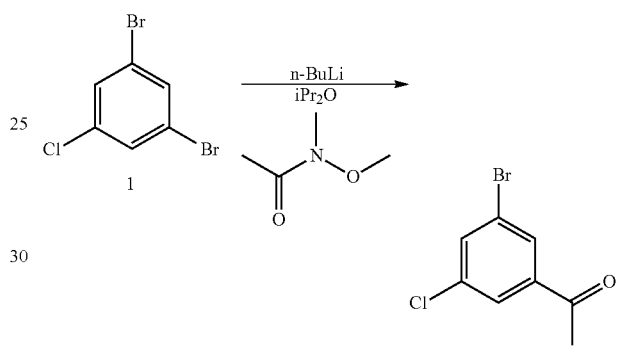

Compound 1 (30 g, 100 mmol) was dissolved in anhydrous i-Pr$_2$O (300.0 mL) in a dried flask under nitrogen. The reaction mixture was cooled to −78° C. and stirred under nitrogen atmosphere. A 2.5 M solution of n-BuLi in hexanes (40 mL, 100 mmol) was added dropwise to the above solution and the reaction mixture was stirred at −78° C. for 30 min after complete addition of n-BuLi. N-methoxy-N-methylacetamide (12 g, 120.0 mmol) was added to the above reaction mixture, while keeping the reaction mixture below −78° C. After addition of N-methoxy-N-methylacetamide was completed, the reaction mixture was warmed slowly to room temperature for 30 min. The reaction mixture was poured into 40 mL of aqueous NH$_4$Cl and the reaction mixture was stirred for 15 min. The organic phase was separated, dried over anhydrous MgSO$_4$, filtered and evaporated in vacuo to give the compound 2 (25 g, crude) as a pale yellow viscous liquid.

Step 2

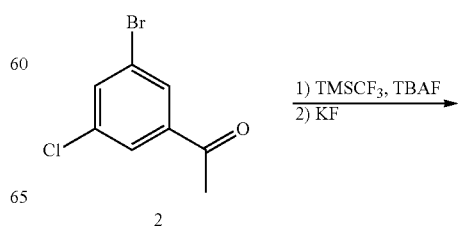

-continued

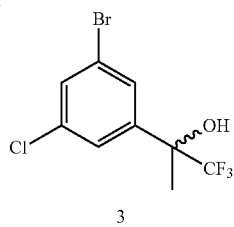

3

To a mixture of compound 2 (25 g, 100 mmol) and TMSCF₃ (14.2 g, 100 mmol) in THF (200 mL) was added TBAF (0.25 g, 1 mmol) at 0° C. The mixture was stirred at 0° C. for 1 h. The solution was concentrated. Then, MeOH (200 mL) and KF (10 g) were added. The mixture was stirred at RT for 3 h. The mixture was concentrated. Ethyl acetate and H₂O were added. The organic phase was separated, dried and concentrated to give the product compound 3 (25 g, crude).

Step 3

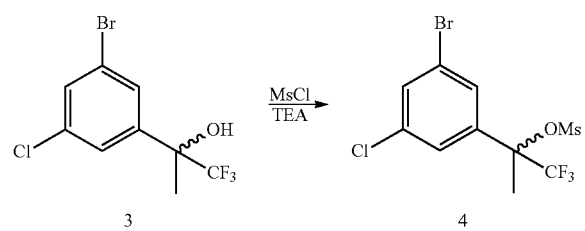 [SMILES: "MsCl" ; CC(O)(c1cc(Cl)cc(Br)c1)C(F)(F)F ; "TEA" ; CC(OS(C)(=O)=O)(c1cc(Cl)cc(Br)c1)C(F)(F)F]

A mixture of compound 3 (50 g, 0.167 mol) and TEA (50 g, 0.5 mol) was dissolved in DCM (500.0 mL) in a dried flask under nitrogen. The reaction mixture was cooled to –0° C. and stirred under a nitrogen atmosphere. MsCl (22.8 g, 0.2 mol) was added dropwise to the above solution and the reaction mixture was stirred at 20° C. for 3 h after complete reaction. The reaction mixture was extracted with DCM, washed with water. The organic phase was separated, dried over anhydrous MgSO₄, filtered and evaporated in vacuo to give the compound 4 (64 g, crude) as a liquid.

Step 4

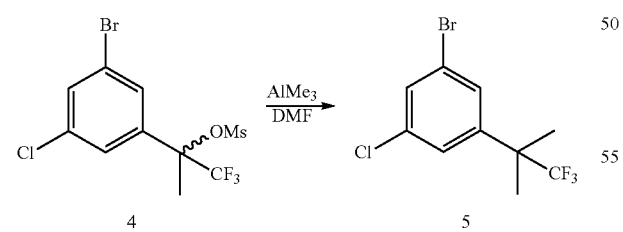

Compound 4 (30 g, 0.079 mol) was dissolved in anhydrous DCM (300.0 mL) in a dried flask under nitrogen. The reaction mixture was cooled to –78° C. and stirred under nitrogen atmosphere. A 2.0 M solution of AlMe₃ in toluene (80 mL, 0.16 mmol) was added dropwise to the above solution and the reaction mixture was stirred at 25° C. for 8 h. The reaction mixture was poured into 1 L of aqueous NH₄Cl and the reaction mixture was stirred for 15 min. The organic phase was separated, dried over anhydrous MgSO₄, and purified by silica gel column to give the compound 5 (20 g, crude) as a liquid.

Step 5

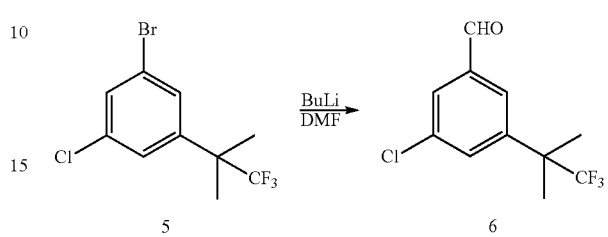

Compound 5 (10 g, 30 mmol) was dissolved in anhydrous i-Pr₂O (100.0 mL) in a dried flask under nitrogen. The reaction mixture was cooled to –78° C. and stirred under a nitrogen atmosphere. A 2.5 M solution of n-BuLi in hexanes (24 mL, 60 mmol) was added dropwise to the above solution and the reaction mixture was stirred at –78° C. for 30 min after complete addition of n-BuLi. DMF (2.8 g, 36 mmol) was added to above reaction mixture, keeping the reaction mixture below –78° C. After addition of DMF was completed, the reaction mixture was warmed slowly to room temperature for 30 min. The reaction mixture was poured into 40 mL of aqueous NH₄Cl and the reaction mixture was stirred for 15 min. The organic phase was separated, dried over anhydrous MgSO₄, filtered and evaporated in vacuo to give compound 6 (10 g, crude) as a liquid.

Step 6

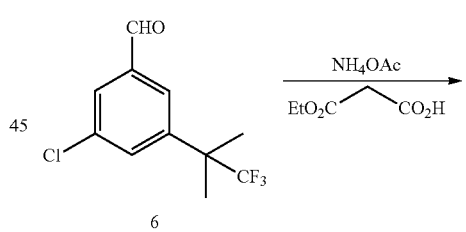

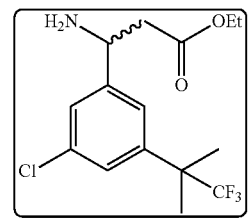

Compound 6 (8 g, 32 mmol), mono-ethyl malonate (9.2 g, 70 mmol) and ammonium acetate (14 g, 181 mmol) in anhydrous ethanol (200.0 mL) was heated at 80° C. for 7 h. The reaction mixture was cooled to room temperature and the solvent was evaporated in vacuo to give a yellow viscous liquid. The residue was partitioned between aqueous saturated NaHCO₃ solution (100 mL) and ethyl acetate (100 mL); the organic layer was removed, dried over anhydrous sodium sulfate, filtered and evaporated in vacuo. The product was purified by silica-gel flash chromatography to give the desired product (1.4 g, 13%).

Example R

Preparation of rac-ethyl 3-amino-3-(3-(1,1,1-trifluoro-2-hydroxypropan-2-yl)-5-(trifluoromethyl)phenyl)propanoate rac-ethyl 3-amino-3-(3-(1,1,1-trifluoro-2-hydroxypropan-2-yl)-5-(trifluoromethyl)phenyl)propanoate was prepared according to the following procedure:

Step 1

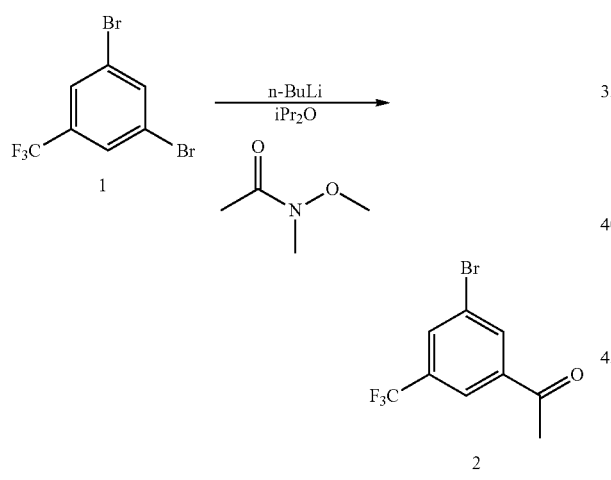

Compound 1 (30 g, 100 mmol) was dissolved in anhydrous i-Pr$_2$O (300.0 mL) in a dried flask under nitrogen. The reaction mixture was cooled to −78° C. and stirred under nitrogen atmosphere. A 2.5 M solution of n-BuLi in hexanes (40 mL, 100 mmol) was added dropwise to the above solution and the reaction mixture was stirred at −78° C. for 30 min after complete addition of n-BuLi. N-methoxy-N-methylacetamide (12 g, 120.0 mmol) was added to above reaction mixture, while keeping the reaction mixture below −78° C. After addition of N-methoxy-N-methylacetamide was completed, the reaction mixture was warmed slowly to room temperature for 30 min. The reaction mixture was poured into 40 mL of aqueous NH$_4$Cl and the reaction mixture was stirred for 15 min. The organic phase was separated, dried over anhydrous MgSO$_4$, filtered and evaporated in vacuo to give compound 2 (25 g, crude) as a pale yellow viscous liquid.

Step 2

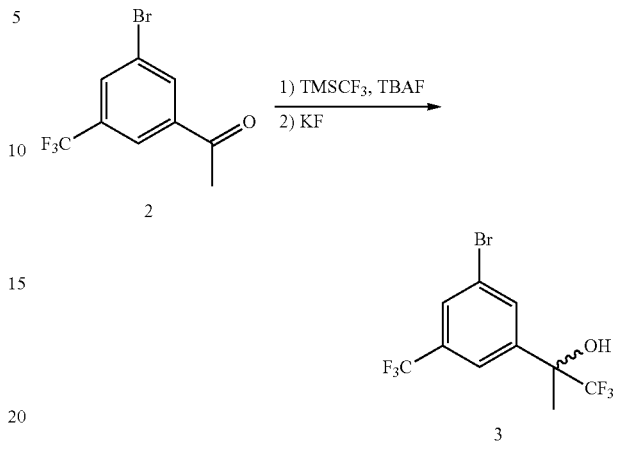

To a mixture of compound 2 (25 g, 94 mmol) and TMSCF$_3$ (14.2 g, 100 mmol) in THF (200 mL) was added TBAF (0.25 g, 1 mmol) at 0° C. The mixture was stirred at 0° C. for 1 h. The solution was concentrated, Then, MeOH (200 mL) and KF (10 g) were added, and the mixture was stirred at RT for 3 h. The mixture was concentrated. Ethyl acetate and H$_2$O were added. The organic phase was separated, dried and concentrated to give the product compound 3 (25 g, crude).

Step 3

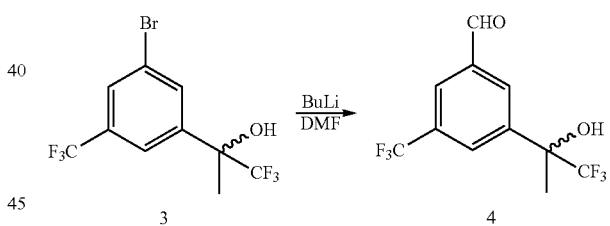

Compound 3 (10 g, 30 mmol) was dissolved in anhydrous i-Pr$_2$O (100.0 mL) in a dried flask under nitrogen. The reaction mixture was cooled to −78° C. and stirred under nitrogen atmosphere. A 2.5 M solution of n-BuLi in hexanes (24 mL, 60 mmol) was added dropwise to the above solution and the reaction mixture was stirred at −78° C. for 30 min after complete addition of n-BuLi. DMF (2.8 g, 36 mmol) was added to above reaction mixture, keeping the reaction mixture below −78° C. After addition of DMF was completed, the reaction mixture was warmed slowly to room temperature for 30 min. The reaction mixture was poured into 40 mL of aqueous NH$_4$Cl and the reaction mixture was stirred for 15 min. The organic phase was separated, dried over anhydrous MgSO$_4$, filtered and evaporated in vacuo to give compound 4 (10 g, crude) as a liquid.

Step 4

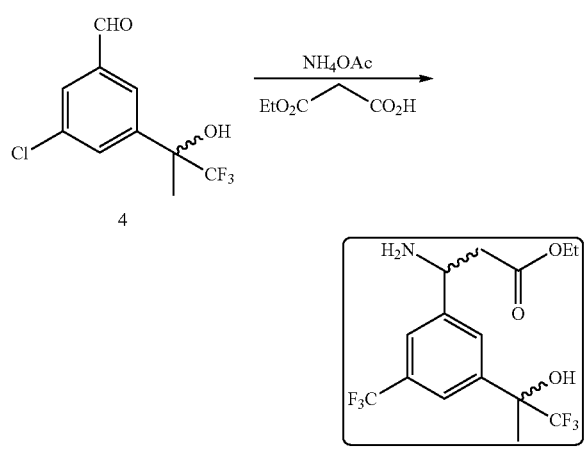

Compound 4 (10 g, 35 mmol), mono-ethyl malonate (9.2 g, 70 mmol) and ammonium acetate (14 g, 181 mmol) in anhydrous ethanol (200.0 mL) was heated at 80° C. for 7 h. The reaction mixture was cooled to room temperature and the solvent was evaporated in vacuo to give a yellow viscous liquid. The residue was partitioned between aqueous saturated NaHCO$_3$ solution (100 mL) and ethyl acetate (100 mL); the organic layer was removed, dried over anhydrous sodium sulfate, filtered and evaporated in vacuo. The product was purified by silica gel flash chromatography to give the desired product (2.8 g, 21%)

Example S

Preparation of rac-ethyl 3-amino-3-(3-bromo-5-(1-(difluoromethyl)cyclopropyl)-phenyl)propanoate

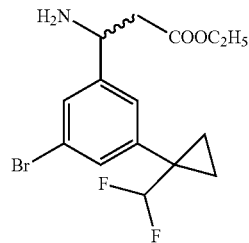

rac-ethyl 3-amino-3-(3-bromo-5-(1-(difluoromethyl)cyclopropyl)phenyl)propanoate was prepared according to the following procedure:

Step 1

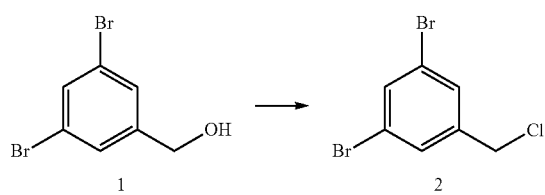 [SMILES: OCc1cc(Br)cc(Br)c1 ; ClCc1cc(Br)cc(Br)c1]

1,3-Dibromo-benzyl alcohol (1) (20 g, 75.2 mmol) was dissolved in anhydrous DCM (200 mL) in a dried flask under nitrogen. The reaction mixture was cooled to 0° C. and stirred under nitrogen atmosphere. DIPEA (25.8 mL, 150.4 mmol) was added drop wise to the above solution, after 10 minutes of stifling at 0° C., mesyl chloride (8.7 mL, 112.8 mmol) was added drop-wise to the above reaction mixture. Finally, the reaction mixture was allowed to stir at RT for 2 hrs. Reaction mixture was diluted with DCM, washed with water (100 mL) followed by NaHCO$_3$ solution and brine, dried over anhydrous Na$_2$SO$_4$, filtered and evaporated to dryness to give 21 gm of crude product (2) as a brown liquid which was carried forward to the next step as such.

Step 2

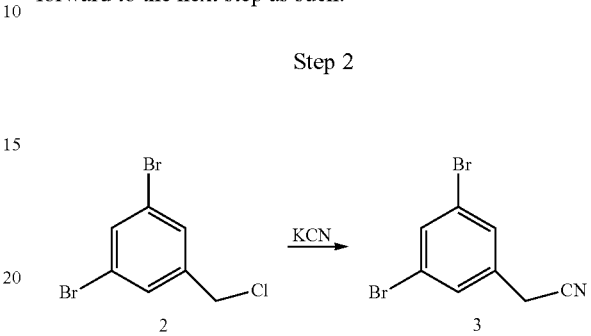

A suspension of 1,3-Dibromo-5-chloromethyl-benzene (2) (21.0 g, 73.9 mmol), KCN (24.1 g, 369.7 mmol) and 18-Crown-6 (1.95 g, 7.40 mmol) in acetonitrile (250 mL) was stirred for overnight at rt. The reaction mixture was concentrated under reduced pressure. The resulting residue was taken in water and extracted with DCM (3×150 mL), organic layer was dried over sodium sulfate concentrated under reduced pressure to afford 25 gm of crude 3 which was purified by column chromatography [silica gel (100-200) and 0.5% ethyl acetate/hexane as eluent] to get 14.5 gm of compound 3 as off white solid.

Step 3

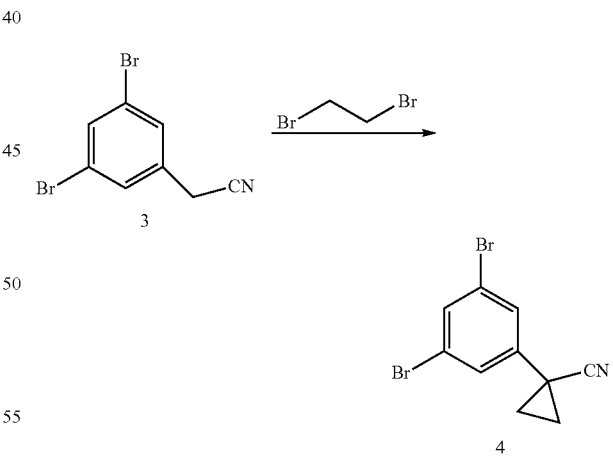

To a stirred solution of Benzyl triethyl ammonium chloride (TEBAC) (0.35 gm, 1.55 mmol) in 50% NaOH (50 mL) was added to a (3,5-Dibromo-phenyl)-acetonitrile (3) (8.5 gm, 30.9 mmol), 1,2-dibromoethane (7.9 mL, 91.5 mmol) solution at 0° C. The resulting mixture was stirred for 5 hrs at rt. The reaction mixture was poured into ice water and extracted with ethyl acetate (3×75 mL). Organic layer was dried over sodium sulfate and concentrated under reduced pressure to afford 10 gm of crude product. Column chromatography

[silica (100-200 mesh) and 0.5% ethyl acetate/HA as eluent] rendered 6 gm of compound 4 as off white solid.

[silica (100-200 mesh) and 0.5% ethyl acetate in hexane as eluent] to afford 4.5 gm of compound 6 as white solid.

Step 4

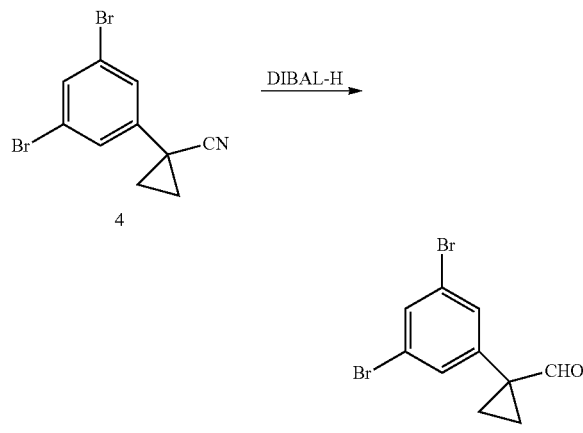

Step 6

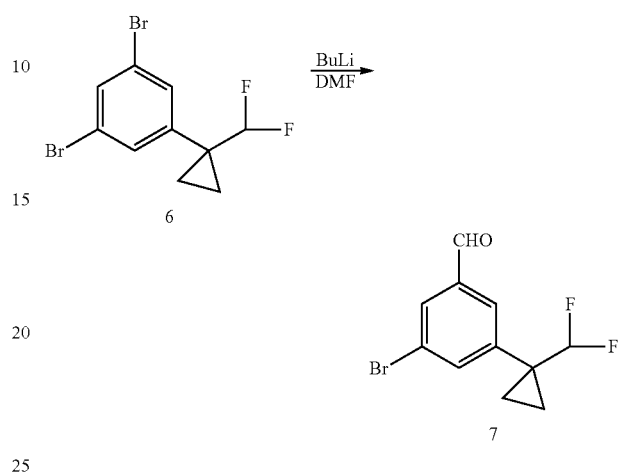

To a stirred solution of 1-(3,5-Dibromo-phenyl)-cyclopropanecarbonitrile (4) (6.8 gm, 22.6 mmol) in DCM (250 ml) was added DiBAl—H (16.9 ml, 25.9 mmol, 25% in toluene) at −78° C. The resulting mixture was stirred for 1 hr at −78° C. The reaction mixture was quenched with 2N HCl and extracted with DCM (3×200 mL). Organic layer was washed with saturated NaHCO₃ solution, followed by brine, dried over sodium sulfate and concentrated under reduced pressure to afford 5.6 gm of crude compound 5 as off white solid.

To a stirred solution of 1,3-Dibromo-5-(1-difluoromethyl-cyclopropyl)-benzene (6) (6 gm, 18.4 mmol) in THF (90 mL) was added n-BuLi (8.4 mL, 18.4 mmol) drop wise at −78° C. The resulting mixture was stirred for 10 mins at −78° C. and quenched with DMF (2.1 mL, 27.6 mmol) at −78 C, and stirred for 10 mins. Sat. NH₄Cl was added to the reaction mixture and extracted with ethyl acetate (3×70 ml). Organic layer was dried over sodium sulfate and concentrated under reduced pressure to afford 6.2 gm of crude product as pale brown solid. Column chromatography [silica gel (100-200) and 0.2% ethyl acetate/HA as eluent] rendered 3.8 gm of compound 7 as white solid.

Step 5

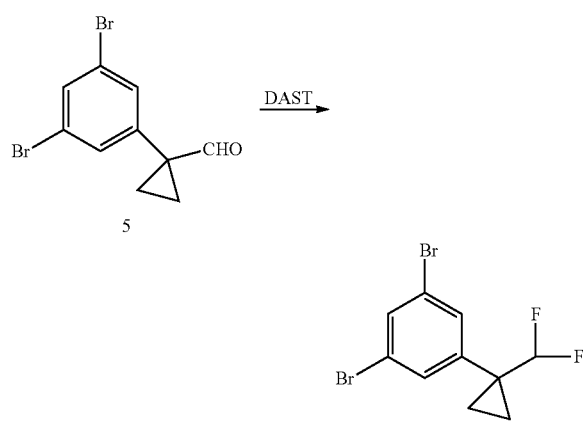

Step 7

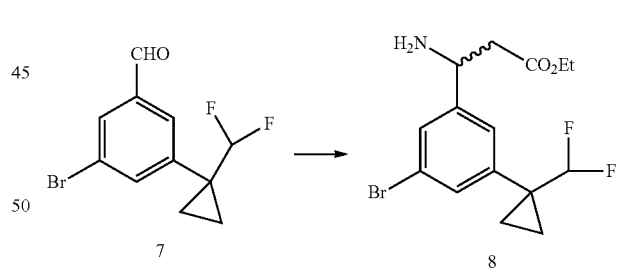

To a stirred solution of 1-(3,5-Dibromo-phenyl)-cyclopropanecarbaldehyde (5) (5.6 gm, 18.4 mmol) in DCM (80 ml) DAST (9.7 mL, 73.7 mmol) was added slowly at 0° C. The resulting mixture was stirred for 2 hrs at rt. The reaction mixture was diluted with DCM (150 mL) and washed with water. Organic layer was dried over sodium sulfate and concentrated under reduced pressure to afford 5.8 gm of crude product which was purified by column chromatography To a stirred solution of (7) (3.8 gm, 13.8 mmol) in EtOH (35 mL) was added malonic acid (2.9 gm, 27.6 mmol), HCOONH₄ (1.8 gm, 27.6 mmol) and heated to reflux for 6 hrs. Reaction was cooled to RT and concentrated under reduced pressure to afford 4.3 gm of crude intermediate. 4.3 g of the above crude intermediate was refluxed in ethanolic HCl (40 mL) for 1 hr. The reaction mixture was concentrated under reduced pressure and the resulting residue was dissolved in water and neutralized with saturated NaHCO₃ solution, extracted with ethyl acetate (4×75 mL), the organic layer was dried over sodium sulfate and concentrated under reduced pressure to afford 4.5 gm of crude product which was purified by column chromatography [silica (100-200 mesh)

and 0.5% MeOH in DCM as eluent] to afford 1.3 gm of desired compound 8 as pale brown liquid.

Example 1

Preparation of (3S)-3-(3-bromo-5-(tert-butyl)-2-hydroxyphenyl)-3-(2-(3-hydroxy-5-((5-hydroxy-1,4,5,6-tetrahydropyrimidin-2-yl)amino)benzamido)acetamido)propanoic acid

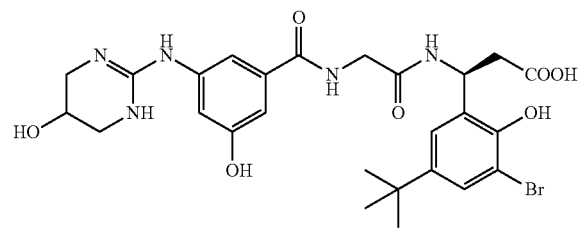 [SMILES: CC(C)(C)c1cc(Br)c(O)c([C@H](CC(=O)O)NC(=O)CNC(=O)c2cc(O)cc(NC3=NCC(O)CN3)c2)c1]

Preparation of (S)-ethyl 3-amino-3-(3-bromo-5-(tert-butyl)-2-hydroxyphenyl)propionate. p-toluene-4-sulfonic acid

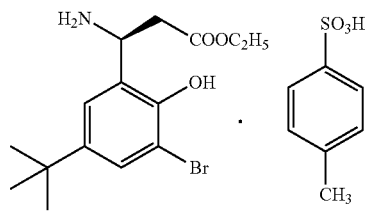

The following Scheme describes a synthesis of the β-amino acid: (S)-ethyl 3-amino-3-(3-bromo-5-(tert-butyl)-2-hydroxyphenyl)propionate-pTSA salt which will be used to synthesize the above compound (Example 1):

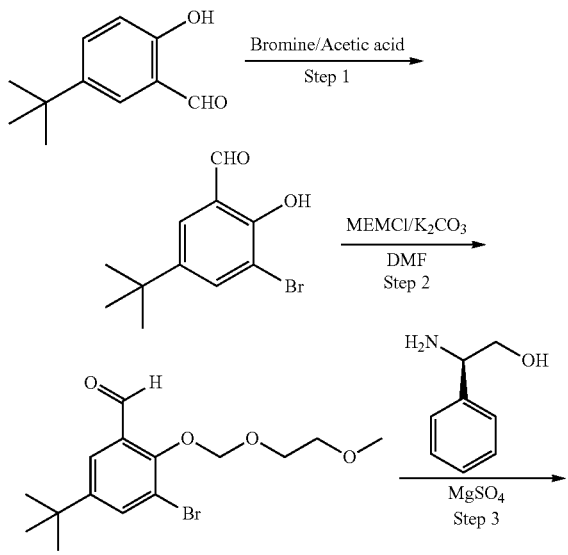

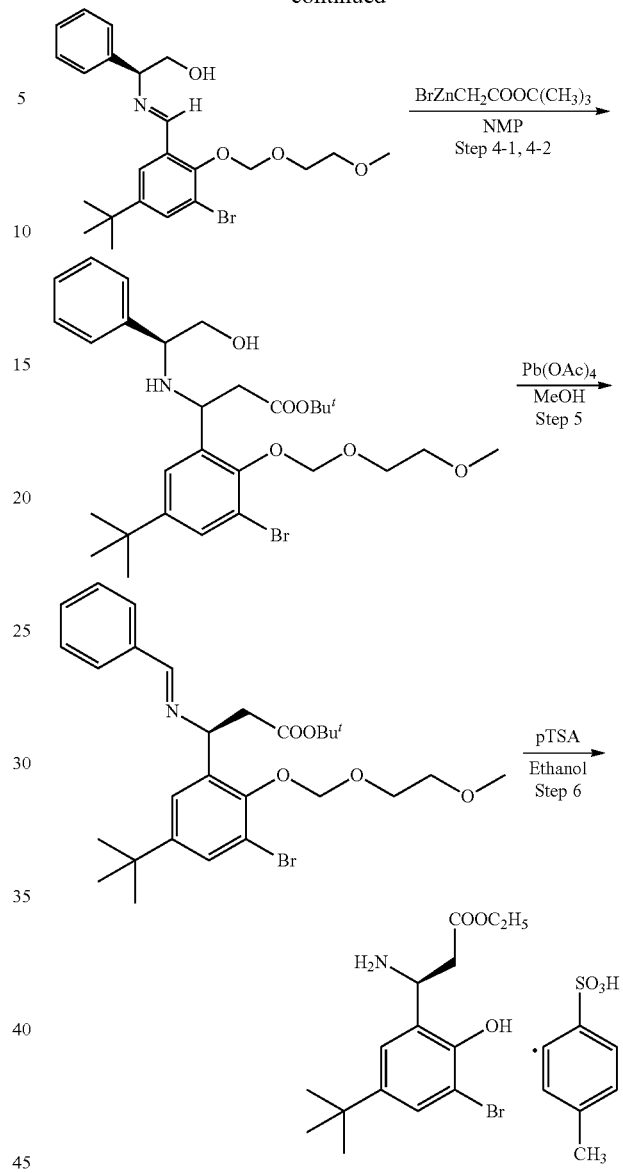

Step 1

Preparation of 3-bromo-5-tert-butylsalicylaldehyde

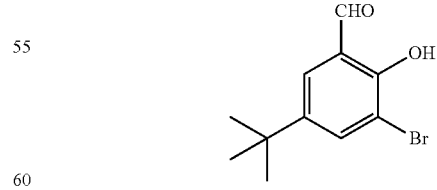

To a stirred solution of 5-tert-butylsalicylaldehyde (3.03 g, 16.97 mmol) in acetic acid (3.5 mL) was added a solution of bromine (0.90 mL, 17.56 mmol) in acetic acid (8.5 mL) dropwise within 15 min. The reaction mixture was stirred at room temperature for 3 h at 50° C. and was monitored by TLC (EA/heptane:1:4) and analytical HPLC analysis. Analytical HPLC analysis of the reaction mixture after 2.5 h shows the desired product ~68% and the unreacted starting material ~32%. A second batch of bromine (0.15 mL) in acetic acid (3 mL) was added and the reaction mixture was stirred at 50° C. for another 15 h. Analytical HPLC analysis of the reaction mixture after overnight stirring shows the desired product ~96% and still shows the starting material ~4%. The reaction mixture was diluted with dichloromethane (50 mL) and the organic layer was washed with 39% sodium bisulfite solution (1×10 mL), water, saturated NaHCO$_3$ and brine. The organic layer was dried over anhydrous sodium sulfate, filtered and evaporated in vacuo to give the crude desired product as a pale yellow crystalline solid (4.6150 g). Purification of the crude product by Silica-gel flash chromatography on silica gel column and elution with 0-5% ethyl acetate in n-heptane afforded the desired product as a pale yellow crystalline solid (4.07 g, 93% yield). $^1$H NMR (400 MHz, CDCl$_3$): δ 1.33 (s, 9H, t-Bu-), 7.49 (s, 1H, H-4), 7.81 (d, 1H, H-6), 9.85 (s, 1H, —CHO), 11.41 (s, 1H, —OH). $^1$H NMR of the isolated product was identical with that of a previously reported sample of the product (Girsch et al., 2008) LC-MS analysis of the product in negative mode shows the desired product's mass: m/z 255 ($^{79Br}$M$^+$–H) and m/z 257 ($^{81Br}$M$^+$–H). GC-MS analysis of the product in CI mode (Methane) shows the desired product's mass: m/z 256 ($^{79Br}$M$^+$) and m/z 258 ($^{81Br}$M$^+$).

Step 2

Preparation of 3-bromo-5-tert-butyl-2-[(2-methoxyethoxy)methoxy]benzaldehyde

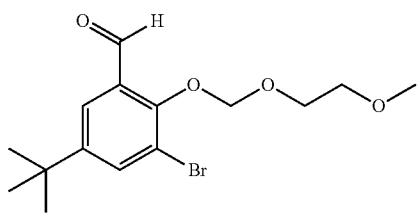 [SMILES: COCCOCOc1c(Br)cc(C(C)(C)C)cc1C=O]

A mixture of 3-bromo-5-(tert-butyl)-2-hydroxybenzaldehyde (3.99 g, 15.51 mmol) and anhydrous potassium carbonate (2.36 g, 17.10 mmol) in anhydrous DMF (20.0 mL) was stirred under nitrogen in a water bath (20° C.) to give an orange-yellow suspension. After stirring for 20 min, 2-methoxyethoxymethyl chloride (2.00 mL, 17.66 mmol, technical grade) was added drop wise (30 min) to above suspension while maintaining an internal temperature of 20° C. The reaction mixture was stirred at room temperature for 2.5 h to give a yellow-orange suspension. The reaction mixture was poured into ice-water (150 mL) and stirred at room temperature to give a yellow oily liquid, no solid formation was observed. After 30 min of stirring, the reaction mixture was extracted with dichloromethane (2×100 mL). The organic layer was removed, washed with water (1×50 mL) and dried over anhydrous magnesium sulfate, filtered and evaporated in vacuo to give a very pure product as an orange viscous liquid (5.40 g). $^1$H NMR (400 MHz; CDCl$_3$): δ 1.29 (s, 9H, (CH$_3$)$_3$C—), 3.33 (s, 3H, CH$_3$—O—), 3.53 (M, 2H, —CH$_2$—CH$_2$—O—), 3.98 (M, 2H, —CH$_2$—CH$_2$—O—), 5.25 (s, 2H, —O—CH$_2$—O—), 7.79 (s, 2H, H-4 and H-6), 10.28 (s, 1H, —CHO). The $^1$H NMR spectrum of the sample was consistent with the suggested structure of the product.

Step 3

Preparation of (S,E)-2-((3-bromo-5-(tert-butyl)-2-(2-methoxyethoxy) methoxy)benzylidene)amino)-2-phenylethanol

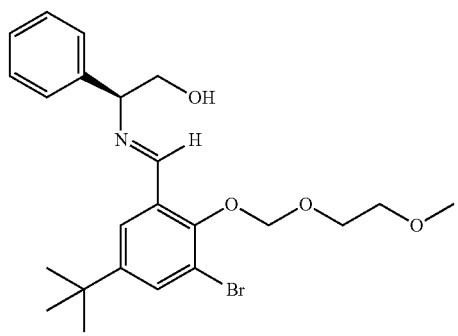 [SMILES: COCCOCOc1c(Br)cc(C(C)(C)C)cc1/C=N/[C@H](CO)c1ccccc1]

(S)-(+)-2-Phenylglycinol (2.14 g, 15.63 mmol) was added to a solution of 3-bromo-5-(tert-butyl-2-[(2-methoxyethoxy)methoxy]benzaldehyde (5.38 g, 15.58 mmol) in anhydrous THF (25.0 mL) at room temperature and the reaction mixture was stirred at room temperature to give an orange solution. After stirring at room temperature for 1 h, anhydrous magnesium sulfate (4.00 g) was added and the reaction mixture was stirred for another 2 h to give an orange solution. After stifling for an additional 2 h at room temperature, the reaction mixture was filtered on a fritted filter and the cake was washed with THF (1×15 mL). The filtrate and washings were evaporated in vacuo to afford a yellow viscous liquid containing the desired imine (7.83 g). LC-MS analysis of the crude product shows the desired product's mass: m/z 464 (M$^+$H) and m/z 486 (M$^+$Na). $^1$H NMR (400 MHz, CDCl$_3$): $^1$H NMR spectrum of the sample was consistent with the suggested structure of the product.

Step 4

Preparation of (S)-tert-butyl 3-(3-bromo-5-(tert-butyl)-2-((2-methoxyethoxy)methoxy)phenyl)-3-(S)-2-hydroxy-1-phenylethyl)amino)propanoate

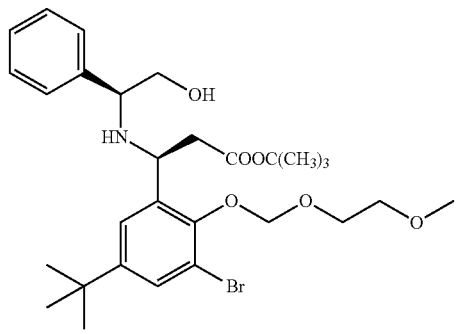

Step 4.1

Preparation of tert-butoxycarbonylmethylzinc bromide (Reformatsky Reagent)

Zinc metal (3.84 g, 58.80 mmol) and anhydrous THF (30 mL) were placed in a 150 mL flask that was fitted with a condenser under nitrogen atmosphere. With magnetic stirring, 1,2-dibromoethane (152 µL, 1.76 mmol) was added and the suspension of zinc in THF was heated to reflux (65-70° C.) for 1 h at this temperature. The reaction mixture was cooled to 50° C. before charging the tert-butyl bromoacetate (9.0 mL, 60.95 mmol) dropwise by a syringe in the following sequence: 2.0 mL, 2.0 mL and 2.0 mL. The reaction mixture was heated with stifling under nitrogen atmosphere. The reaction mixture was warmed to 58° C. and within a few minutes of heating at 58° C. (15-20 min), an exotherm was observed and the reaction mixture starting to boiling, zinc started to disappear. The reaction mixture was charged with remaining tert-butyl bromoacetate (3.00 mL) after that exotherm allowed to subside, a colorless solid started to precipitate and increased with time. The reaction mixture was heated for another 1 h at 60° C. with stirring to give a pale yellow-green solution. After 1 h, the reaction mixture was cooled to room temperature and then at 0° C. to give a colorless precipitate. The reaction mixture was stored in a freezer (−20° C.) overnight under nitrogen atmosphere. A colorless to white crystalline solid with pale yellow-green mother liquor was observed. The solvent was removed by a double-tipped cannula to give a colorless to dirty white solid, still contains the residual THF (2-3 mL). The solid precipitate was triturated with anhydrous THF (10 mL) and the THF wash was removed by a cannula to give a cream cake. The crude tert-butoxycarbonylmethylzinc bromide will be used as such in the next step.

Step 4.2

Preparation of (S)-tert-butyl 3-(3-bromo-5-(tert-butyl)-2-((2-methoxyethoxy)methoxy)phenyl)-3-((S)-2-hydroxy-1-phenylethyl)amino)propanoate

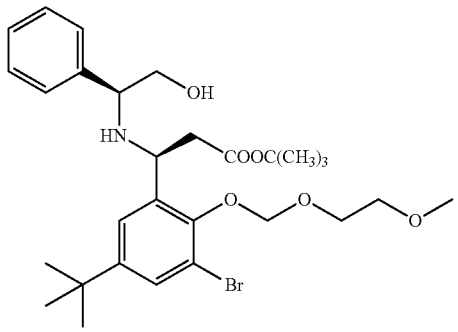

Solid Reformatsky reagent: BrZnCH$_2$COOC(CH$_3$)$^t_3$.THF from Step #4-1 was dissolved in anhydrous 1-methyl-2-pyrrolidinone (NMP) (12.0 mL) at −10-15° C. (ice/salt bath) under nitrogen to give a pale yellow solution. The crude imine from Step #3 (7.82 g, 16.84 mmol) was dissolved in anhydrous NMP (15.0 mL) under nitrogen atmosphere separately. The solution of the imine in NMP (12.0 mL) was added slowly to a solution of the Reformatsky reagent in NMP at −15° C. in 30 min under nitrogen atmosphere. The reaction mixture was first let stirred at −10° C. for 2 h and then at −5° C. for another 1 h. The reaction mixture was cooled to −10° C. (salt/ice bath). A mixture of conc. HCl (1.0 mL) in 100 mL of a saturated ammonium chloride solution was added slowly to above cold reaction mixture in 10 min and the reaction mixture was stirred at 0° C. (ice-bath) to give a yellow-orange solution. After stirring the reaction mixture for 15 min at 0° C., the reaction mixture was warmed to room temperature. MTBE (80 mL) was added and the reaction mixture was stirred at room temperature for 30 min. Stirring was stopped and the layers were separated. The aqueous layer was extracted with MTBE (20 mL). The two organic layers were combined and washed successively with a saturated solution of NH$_4$Cl (25 mL), water (25 mL) and saturated sodium chloride solution (25 mL). The organic layer was dried with anhydrous MgSO$_4$, filtered and evaporated in vacuo to afford an orange viscous liquid (9.82 g). LC-MS analysis of the liquid shows the desired product's mass: m/z 580 ($^{79Br}$M+H) and m/z 582 ($^{81Br}$M+H). $^1$H NMR (400 MHz, CDCl$_3$): $^1$H NMR spectrum of the sample was consistent with the suggested structure of the product. The above crude product will be used as such for the next step.

Step 5

Preparation of (S,E)-tert-butyl 3-(benzylideneamino)-3-(3-bromo-5-(tert-butyl)-2-((2-methoxyethoxy)methoxy)phenyl)propanoate

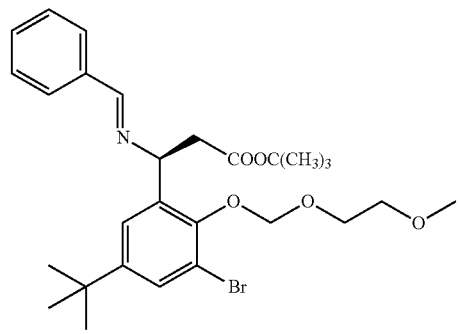

Lead tetraacetate (7.48 g, 16.88 mmol) was added in one portion to a solution of the crude ester from Step #4 (9.80 g, 16.88 mmol) in anhydrous methanol (100 mL) at 0° C. (ice-bath). The solution turned from orange-yellow to red-orange before going back to yellow-orange. The reaction mixture was stirred at 0° C. for 3 h to give an orange solution. After stifling for another ½ h, 15% NaOH solution in water (15 mL) was added to the reaction mixture while maintaining the temperature below 5° C. Most of the methanol was removed under reduced pressure on a rotary evaporator (~135 mL) to give a thick cream-orange residue. An additional portion of 15% aqueous NaOH solution (80 mL) was added and the reaction mixture was extracted with ethyl acetate (3×100 mL). The organic layer was washed with water (1×100 mL) and a saturated NaCl solution (1×50 mL). The organic layer was removed, dried over anhydrous MgSO$_4$ and the filtered over Celite. The filtrate was evaporated in vacuo to afford an orange viscous liquid containing the desired product (9.050 g). The above crude product will be used as such for the reaction with p-toluenesulfonic acid.

Step 6

Preparation of (S)-ethyl 3-amino-3-(3-bromo-5-(tert-butyl)-2-hydroxyphenyl)propionate p-toluene-4-sulfonic acid

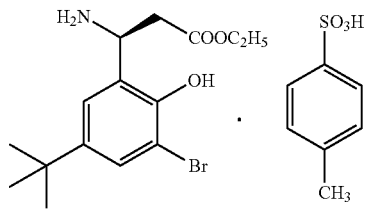

p-Toluenesulfonic acid monohydrate was added to a solution of crude ester from step #5 (9.05 g, 16.50 mmol) in absolute ethanol (25.0 mL). The reaction mixture was heated under refluxing conditions under nitrogen atmosphere to give an orange red-brown solution. The heating was discontinued after 7 h and the reaction mixture was cooled to room temperature. The solvent was evaporated in vacuo to afford a dark orange-brown viscous liquid. The crude product was dissolved in THF (20.0 mL) and diluted slowly with heptane (50.0 mL) to give a dirty orange-brown gummy residue. This mixture was stored in a freezer (−20° C.) overnight. A dirty cream gummy solid precipitated in a yellow-orange heptane mother liquor. The heptane layer was decanted off and the residue was triturated with heptane (10 mL). The heptane layer was removed and combined with the decanted heptane layer. A colorless precipitate started to deposit in the combined heptane layer and the amount of the solid increased significantly after standing at room temperature for 30 min. The precipitated solid was filtered, washed with heptane and dried in vacuo to afford a white solid (6.24 g). LC-MS analysis of the above crude product shows the desired product's mass: m/z 344 ($^{79Br}$M+H) and m/z 346 ($^{81Br}$M+H), Calcd for $C_{15}H_{22}BrNO_3$: 344.24, Calcd for p-TSA salt $C_{15}H_{22}BrNO_3 \cdot C_7H_8O_3S$: 516.44. $^1$H NMR (400 MHz, DMSO-$d_6$): δ 1.13 (t, J=7.10 Hz, 3H, $CH_3CH_2$—), 1.36 (s, 6H, $(CH_3)_2C$—), 2.30 (S, 3H, 4-$CH_3$-(pTSA)), 2.95 (ABq, $J_{AB}$=16.42 and 7.42 Hz and $J_{AB}$=16.42 and 6.72 Hz, 2H, —$CH_2$—$COOC_2H_5$), 4.05 (q, J=7.10 Hz, 2H, $CH_3CH_2$—), 5.01 (apptq/m, J=6.20 Hz, 1H, —NH—CH—$CH_2$—COO—), 7.12 (d, J=8.40 Hz, 2H, pTSA-H-3 & H-5), 7.30 (d, J=2.44 Hz, 1H), 7.47 (s, 1H), 7.48 (d, J=6.00 Hz, 2H, pTSA H-2 & H-6), 8.26 (brs, 2H, —$NH_2$), 9.02 (brs, 1H, —OH). $^1$H NMR spectrum of the sample was consistent with the suggested structure of the product.

Preparation of (S)-ethyl 3-(3-bromo-5-(tert-butyl)-2-hydroxyphenyl)-3-(2-((tert-butoxycarbonyl)amino)acetamido)propanoate

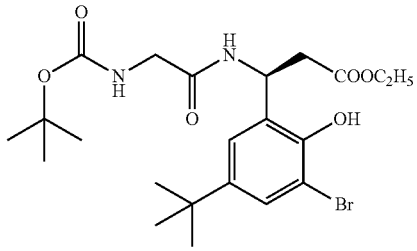

To a solution of a mixture of the (S)-ethyl 3-amino-3-(3-bromo-5-(tert-butyl)-2-hydroxyphenyl)propanoate-p-TSA salt (2.71 g, 5.26 mmol) and N-t-Boc-glycine hydroxysuccinimide ester (1.45 g, 5.30 mmol) in anhydrous DMF (25 mL) was added triethylamine (900 µL, 6.46 mmol) and the reaction mixture was stirred at room temperature under nitrogen atmosphere overnight. The solvent was evaporated in vacuo to afford an orange viscous liquid. The residue was partitioned between ethyl acetate (50 mL), water (50 mL) and a saturated $NaHCO_3$ solution (50 mL). The ethyl acetate layer was removed, washed with water (1×50 mL), dried over anhydrous $Na_2SO_4$, filtered and evaporated in-vacuo to afford a cream foamy solid (2.383 g). The crude product will be used as such for the deprotection of the t-Boc-group.

Preparation of (S)-ethyl 3-(2-aminoacetamido)-3-(3-bromo-5-(tert-butyl)-2-hydroxyphenyl)propanoate, Hydrochloride salt

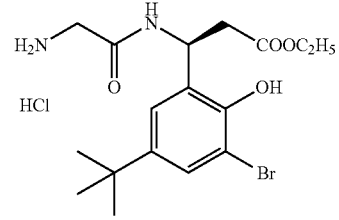

4M HCl in 1,4-dioxane (7.0 mL) was added to a solution of a crude sample of (S)-ethyl-3-(3-bromo-5-(tert-butyl)-2-hydroxyphenyl)-3-(2-((tert-butoxycarbonyl)amino)acetamido)propanoate (2.38 g, 4.75 mmol) in 1,4-dioxane (6.0 mL) at 0° C. (ice-bath) and the reaction mixture was stirred at 0° C. for 30 min and then at room temperature for 30 min. The reaction mixture was then heated at 50° C. for 2.5 h under nitrogen atmosphere to give a yellow-orange suspension. The solvent was evaporated in-vacuo to afford a dirty yellow-orange foamy solid. Acetonitrile (25 mL) was added to the solid, stirred for 5 min to give a cream-yellow suspension and evaporated in vacuo to afford a dirty yellow-foamy solid. The foamy solid was redissolved in acetonitrile (25 mL) to give a dirty yellow suspension, filtered to remove a colorless insoluble solid. The filtrate was evaporated in vacuo to afford a yellow-orange viscous liquid. The liquid was triturated with a mixture of ethyl acetate/heptane to give a dirty cream precipitate; the solvent was removed in vacuo to afford a dirty cream solid (2.00 g). LC/MS analysis of the product shows the desired product's mass: m/z 401 ($^{79Br}$M+H) and m/z 403 ($^{81Br}$M+H), Calcd for $C_{17}H_{25}BrN_2O_4$: 401.29. $^1$H NMR (400 MHz, DMSO-$d_6$): δ 1.12 (t, J=7.11 Hz, 3H, $CH_3$—$CH_2$—), 1.23 (s, 9H, $(CH_3)_3C$—), 2.76 (ABq, J=15.50 and 9.20 Hz and J=15.50 and 5.56 Hz, 2H, —$CH_2$—$COOC_2H_5$), 3.57 (brs, 2H, $NH_2$—$CH_2$—C=O), 4.03 (q, J=7.07 Hz, $CH_3$—$CH_2$—), 5.56 (brm, 1H, —$NH_2$—CH—), 7.25 (d, J=2.30 Hz, 1H), 7.36 (d, J=2.30 Hz, 1H), 7.96 (brs, 2H, $NH_2$—), 8.87 (d, J=8.46 Hz, 1H), 9.15 (brs, 1H, —OH). $^1$H NMR spectrum of the sample was consistent with the suggested structure of the product.

291

Preparation of (3S)-ethyl 3-(3-bromo-5-(tert-butyl)-2-hydroxyphenyl)-3-(2-(3-hydroxy-5-((5-hydroxy-1,4,5,6-tetrahydropyrimidin-2-yl)amino)benzamido)acetamido)propanoate

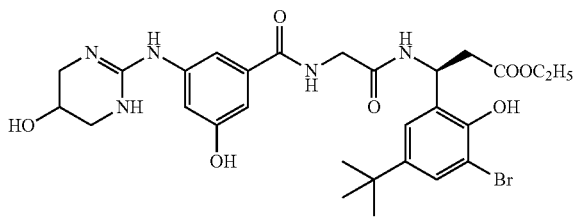

To a mixture of (S)-ethyl 3-(2-aminoacetamido)-3-(3-bromo-5-(tert-butyl)-2-hydroxyphenyl)propanoate HCl salt (1.12 g, 0.995 mmol), 3-hydroxy-5-((5-hydroxy-1,4,5,6-tetrahydropyrimidin-2-yl)amino)benzoic acid (Example A) (0.60 g, 2.41 mmol) and 1-hydroxybenzotriazole hydrate (74.0 mg, 0.48 mmol) in anhydrous DMF (7.0 mL) and DCM (7.0 mL) was added N,N'-diisopropylcarbodiimide (445 µL, 2.86 mmol) and the reaction mixture was stirred at room temperature under nitrogen atmosphere overnight. The solvent was evaporated on a rotary evaporator to give a colorless gummy residue. The residue was dissolved in acetonitrile (25 mL), stirred for 5 min and filtered to remove the precipitated urea (~300 mg). Evaporation of the filtrate in vacuo gave an almost colorless gummy/viscous residue (1.39 g). LC/MS analysis of the crude product shows the desired product's mass: m/z 635 ($^{79Br}$M+H) and m/z 637 ($^{81Br}$M+H), Calcd for $C_{28}H_{36}BrN_5O_7$: 634.519. The crude product will be used as such for the saponification with lithium hydroxide.

Preparation of (3S)-3-(3-bromo-5-(tert-butyl)-2-hydroxyphenyl)-3-(2-(3-hydroxy-5-((5-hydroxy-1,4,5,6-tetrahydropyrimidin-2-yl)amino)benzamido)acetamido)propanoic acid

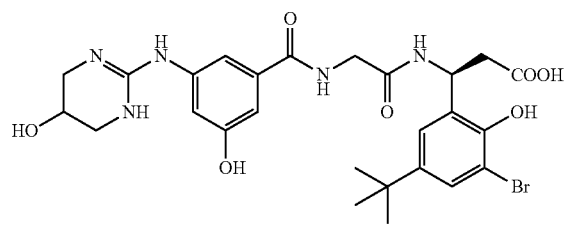 [SMILES: CC(C)(C)c1cc(Br)c(O)c([C@H](CC(=O)O)NC(=O)CNC(=O)c2cc(O)cc(NC3=NCC(O)CN3)c2)c1]

To a suspension of crude (3S)-ethyl 3-(3-bromo-5-(tert-butyl)-2-hydroxyphenyl)-3-(2-(3-hydroxy-5-((5-hydroxy-1,4,5,6-tetrahydropyrimidin-2-yl)amino)benzamido)acetamido)propanoate (1.389 g, 2.19 mmol) in a 1:1 mixture of acetonitrile/water (10.0 mL) was added lithium hydroxide monohydrate (0.735 g, 17.51 mmol) at room temperature and the reaction mixture was stirred at room temperature for 3 h to afford a pale yellow solution. Acetonitrile was evaporated on a rotary evaporator to give a pale yellow aqueous residue. The residue was extracted with dichloromethane (2×25 mL) to remove HOBt and DIPU. The aqueous layer was neutralized with TFA (3.0 mL in 5.0 mL CH$_3$CN) and the mixture was evaporated in vacuo to give a pale viscous residue. The crude product was purified by reverse-phase HPLC on Biotage SP1 system using a gradient 10-40% CH$_3$CN in water containing 0.05% TFA to afford a colorless glassy solid. The purified product was dissolved in water containing a few drops of acetonitrile and lyophilized to afford a colorless powder (778.0 mg). LC/MS analysis of the purified product shows the desired product's mass: m/z 606 ($^{79Br}$M+H) and m/z 608 ($^{81Br}$M+H), Calc'd for $C_{26}H_{32}BrN_5O_7$: 606.466. $^1$H NMR (400 MHz, DMSO-d$_6$): δ 1.25 (s, 9H, (CH$_3$)$_3$C—), 2.70 (ABq, J$_{AB}$=16.00 and 8.73 Hz and J$_{AB}$=15.95 and 5.45 Hz, 2H, —CH$_2$—COOH), 3.17 (d, J=12.0 Hz, 2H), 3.35 (d, J=11.0 Hz, 2H), 3.89 (d, J=6.0 Hz, 2H), 4.09 (M, 1H), 5.45 (brm, 1H, —NH—CH—CH$_2$—COOH), 6.75 (brt/m, J=2.02 Hz, 1H), 7.13 (dt, 2H), 7.26 (d, J=2.30 Hz, 1H), 7.34 (d, J=2.32 Hz, 1H), 8.60 (d, J=8.26 Hz, 1H), 8.64 (t, J=5.85 Hz, 1H), 9.31 (s, 1H), 9.60 (s, 1H), 10.02 (brs, 1H), 12.27 (brs, 1H, —COOH). $^1$H NMR spectrum of the sample was consistent with the suggested structure of the product.

Example 2

Preparation of (3S)-3-(5-bromo-3-(tert-butyl)-2-hydroxyphenyl)-3-(2-(3-hydroxy-5-((5-hydroxy-1,4,5,6-tetrahydropyrimidin-2-yl)amino)benzamido)acetamido)propanoic acid

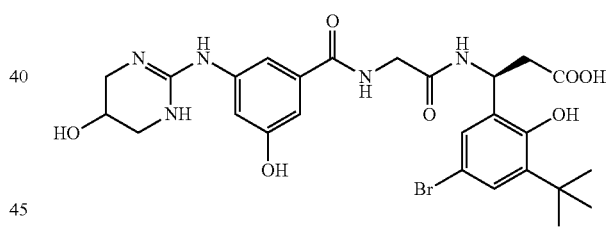

Preparation of (S)-ethyl 3-amino-3-(5-bromo-3-(tert-butyl)-2-hydroxyphenyl)propionate. p-toluene-4-sulfonic acid

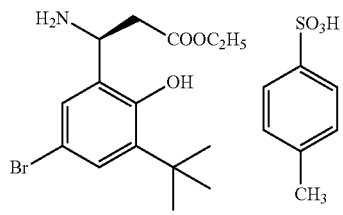

The following Scheme describes a synthesis of the β-amino acid: (S)-ethyl 3-amino-3-(5-bromo-3-(tert-butyl)-

2-hydroxyphenyl)propionate-pTSA salt which will be used to synthesize the above compound (Example 2).

Preparation of (S)-ethyl 3-amino-3-(5-bromo-3-(tert-butyl)-2-hydroxyphenyl)propionate-p-toluene-4-sulfonic acid

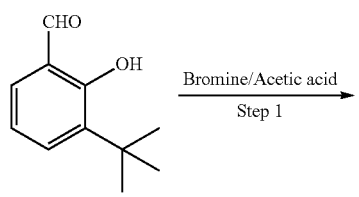

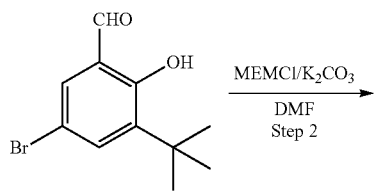

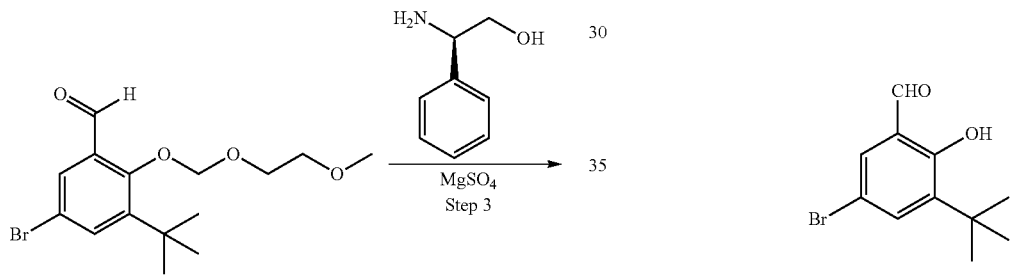

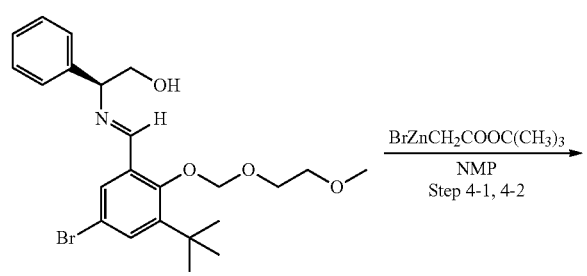

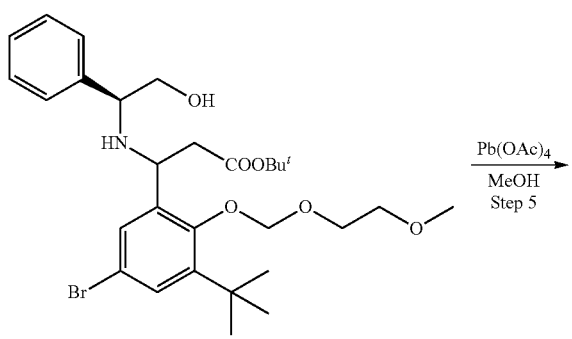

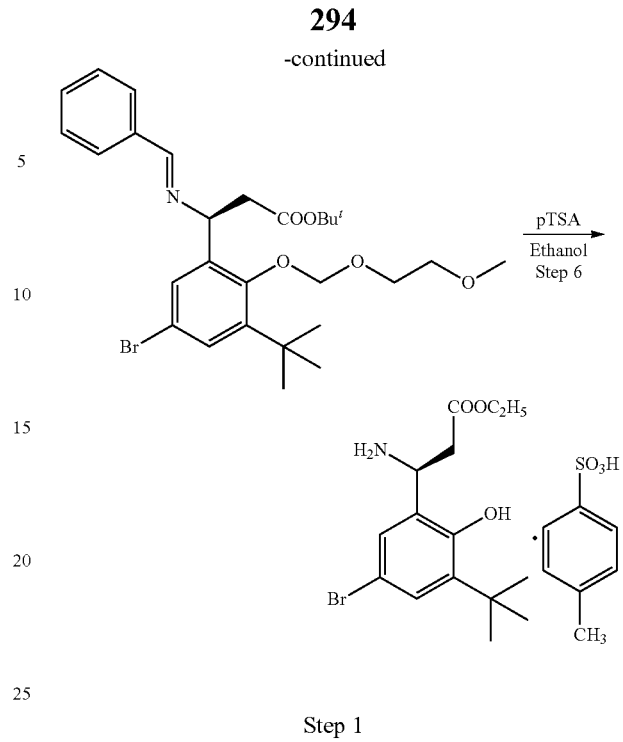

Step 1

Preparation of 5-bromo-3-tert-butylsalicylaldehyde

To a stirred solution of 3-tert-butylsalicylaldehyde (5.13 g, 28.8 mmol) in acetic acid (15 mL) was added a solution of bromine (1.65 mL, 32.25 mmol) in acetic acid (7.0 mL) dropwise within 20 min. The reaction mixture was stirred at room temperature for 3 h. Analytical HPLC analysis after 3 h shows the desired product ~72% and the unreacted starting material ~28%. A second batch of bromine (0.5 mL) in acetic acid (3 mL) was added and the reaction mixture was stirred at room temperature for another 3 h. Analytical HPLC analysis of the reaction mixture after 3 h (6 h total) shows the desired product ~85% and still shows the starting material ~15%. After 6 h of stifling, the reaction mixture was diluted with dichloromethane (50 mL) and the organic layer was washed with 39% sodium bisulfite solution (1×10 mL), water, saturated $NaHCO_3$ and brine. The organic layer was dried over anhydrous sodium sulfate, filtered and evaporated in vacuo to give the desired product as a pale yellow crystalline solid (7.2421 g). Purification by silica-gel flash chromatography on silica gel column and elution with 0-5% ethyl acetate in n-heptane afforded the desired product as a pale yellow crystalline solid (4.792 g, 64% yield). LC-MS analysis of the product in negative mode shows the desired product's mass: m/z 255 ($^{79Br}M^+$–H) and m/z 257 ($^{81Br}M^+$–H). GC-MS analysis of the product in CI mode (Methane) shows the desired product's mass: m/z 256 ($^{91Br}M^+$) and m/z 258 ($^{81Br}M^+$), calc'd. for $C_{11}H_{13}BrO_2$: 257.124. $^1$H NMR (400 MHz, $CDCl_3$): δ 1.39 (s, 9H, t-Bu-), 7.50 (s, 1H, H-4), 7.56 (s, 1H, H-6), 9.79 (s, 1H, —CHO), 11.70 (s, 1H, —OH). $^1$H NMR of the isolated product was identical with that of a previously reported sample of the product (Girsch et al., 2007).

Step 2

Preparation of 5-bromo-3-tert-butyl-2-[(2-methoxyethoxy)methoxy]benzaldehyde

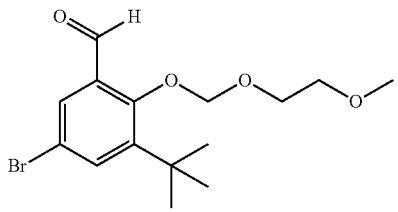 [SMILES: COCCOCOc1c(C=O)cc(Br)cc1C(C)(C)C]

A mixture of 5-bromo-3-(tert-butyl)-2-hydroxybenzaldehyde (4.74 g, 18.42 mmol) and anhydrous potassium carbonate (2.83 g, 20.45 mmol) in anhydrous DMF (20.0 mL) was stirred under nitrogen in a water bath (20° C.) to give an orange-yellow suspension. After stirring for 20 min, 2-methoxyethoxymethyl chloride (2.40 mL, 21.19 mmol, technical grade) was added drop wise (20 min) to above suspension while maintaining an internal temperature of 20° C. The reaction mixture was stirred at room temperature for 3 h to give a canary yellow suspension. The reaction mixture was poured into ice-water (150 mL) and stirred at room temperature to give a yellow oily liquid, no solid formation was observed. After 30 min of stirring, the reaction mixture was extracted with dichloromethane (2×75 mL). The organic layer was removed, washed with water (1×50 mL) and dried over anhydrous magnesium sulfate, filtered and evaporated in-vacuo to give a pale yellow viscous liquid (6.7832 g). No purification was necessary and the crude product (purity >97%) was used directly in the next Step #3.

Step 3

Preparation of (S,E)-2-((5-bromo-3-(tert-butyl)-2-((2-methoxyethoxy) methoxy)benzylidene)amino)-2-phenylethanol

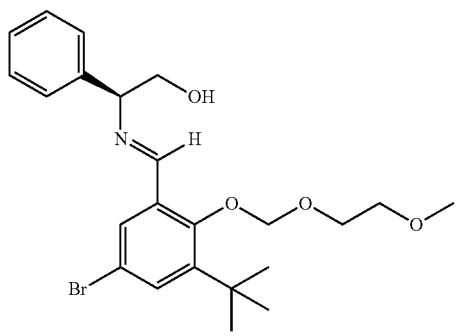 [SMILES: COCCOCOc1c(/C=N/[C@H](CO)c2ccccc2)cc(Br)cc1C(C)(C)C]

(S)-(+)-2-Phenylglycinol (2.71 g, 19.73 mmol) was added to a solution of 5-bromo-3-(tert-butyl-2-[(2-methoxyethoxy) methoxy]benzaldehyde (6.78 g, 19.64 mmol) in anhydrous THF (25.0 mL) at room temperature and the reaction mixture was stirred at room temperature to give an orange solution. After stirring at room temperature for 1 h, anhydrous magnesium sulfate (5.00 g) was added and the reaction mixture was stirred for another 2 h to give an orange solution. LC-MS analysis of the reaction mixture after 2 h shows the desired product's mass: m/z 464 ($^{79Br}$M+H) and m/z 466 ($^{81Br}$M+H). The reaction mixture was let stirred at room temperature for another 1 h and filtered on a fritted filter and the cake was washed with THF (3×25 mL). The filtrate and washings were evaporated in vacuo to afford a yellow viscous liquid containing the desired imine (9.40 g). $^1$H NMR spectrum of the sample was consistent with the suggested structure of the product. No purification was necessary and the crude product (purity >95%) was used directly in the next Step #4.

Step 4

Preparation of (S)-tert-butyl 3-(5-bromo-3-(tert-butyl)-2-((2-methoxyethoxy)methoxy)phenyl)-3-((S)-2-hydroxy-1-phenylethyl)amino)propanoate

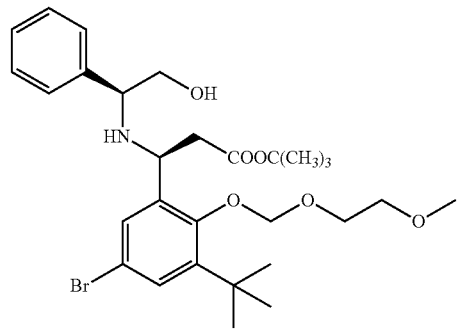

Step 4.1

Preparation of tert-butoxycarbonylmethylzinc bromide (Reformatsky Reagent)

BrZnCH$_2$COOC(CH$_3$)$_3$

Zinc metal (3.44 g, 52.60 mmol) and anhydrous THF (30 mL) were placed in a 150 mL flask that was fitted with a condenser under nitrogen atmosphere. With magnetic stirring, 1,2-dibromoethane (150 µL, 1.76 mmol) was added and the suspension of zinc in THF was heated to reflux (65-70° C.) for 1 h at this temperature. The reaction mixture was cooled to 50° C. before charging the tert-butyl bromoacetate (7.80 mL, 52.80 mmol) dropwise by a syringe in the following sequence: 2.0 mL and 2.0 mL. The reaction mixture was heated with stifling under nitrogen atmosphere. The reaction mixture was warmed to 58° C. and within a few minutes of heating at 58° C. (15-20 min), an exotherm was observed and the reaction mixture starting to boiling, zinc started to disappear. The reaction mixture was charged with remaining tert-butyl bromoacetate (3.80 mL) after that exotherm allowed to subside, a colorless solid started to precipitate and increased with time. The reaction mixture was heated for another 1 h at 60° C. with stirring to give a pale yellow-green solution. After 1 h, the reaction mixture was cooled to room temperature and then at 0° C. to give a colorless precipitate. The reaction mixture was stored in a freezer (−20° C.) overnight under nitrogen atmosphere. A colorless to white crystalline solid with a pale yellow-green mother liquor. The solvent was removed by a double-tipped cannula to give a colorless to dirty white solid, still contains the residual THF (2-3 mL). The solid precipitate was triturated with anhydrous THF (10 mL) and the THF wash was removed by a cannula to give a cream cake. The crude tert-butoxycarbonylmethylzinc bromide will be used as such in the next step.

Step 4.2

Preparation of (S)-tert-butyl 3-(5-bromo-3-(tert-butyl)-2-((2-methoxyethoxy)methoxy)phenyl)-3-((S)-2-hydroxy-1-phenylethyl)amino)propanoate

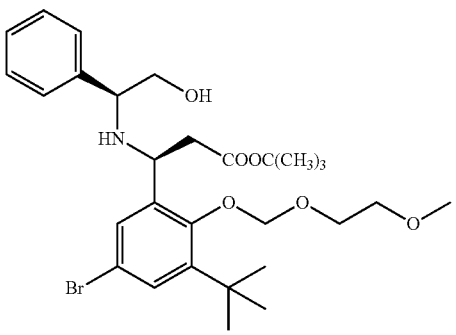

Solid Reformatsky reagent: BrZnCH$_2$COOC(CH$_3$)$^t_3$·THF (52.0 mmol) from the Step #4-1 was dissolved in anhydrous 1-methyl-2-pyrrolidinone (NMP) (12.0 mL) at −10 to −15° C. (ice/salt bath) under nitrogen to give a pale yellow solution. The crude imine from Step #3 (9.40 g, 20.24 mmol) was dissolved in anhydrous NMP (15.0 mL) under nitrogen atmosphere separately. The solution of the imine in NMP was added slowly to a solution of the Reformatsky reagent in NMP at −15° C. in 30 min under nitrogen atmosphere. The reaction mixture was first let stirred at −10° C. for 2 h and then at −5° C. for another 1 h. The reaction mixture was cooled to −10° C. (salt/ice bath). A mixture of conc. HCl (1.0 mL) in 100 mL of a saturated ammonium chloride solution was added slowly to above cold reaction mixture in 10 min and the reaction mixture was stirred at 0° C. (ice-bath) to give a yellow-orange solution. After stirring the reaction mixture for 15 min at 0° C., the reaction mixture was warmed to room temperature. MTBE (80 mL) was added and the reaction mixture was stirred at room temperature for 30 min. Stirring was stopped and the layers were separated. The aqueous layer was extracted with MTBE (20 mL). The two organic layers were combined and washed successively with a saturated solution of NH$_4$Cl (25 mL), water (25 mL) and saturated sodium chloride solution (25 mL). The organic layer was dried with anhydrous MgSO$_4$, filtered and evaporated in vacuo to afford an orange viscous liquid (6.80 g). LC-MS analysis of the liquid shows the desired product's mass: m/z 580 ($^{79Br}$M+H) and m/z 582 ($^{81Br}$M+H), Calcd for C$_{28}$H$_{38}$BrNO$_5$: 548.509. The above crude product will be used as such for the next Step #5.

Step 5

Preparation of (S,E)-tert-butyl 3-(benzylidene-amino)-3-(5-bromo-3-(tert-butyl)-2-(2-methoxy-ethoxy)methoxy)phenyl)propanoate

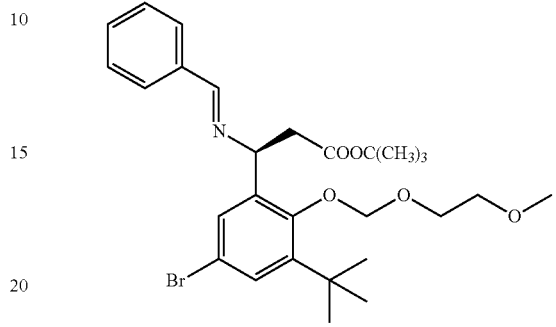

Lead tetraacetate (5.20 g, 11.75 mmol) was added in one portion to a solution of the crude ester from Step #4 (6.80 g, 6.80 mmol) in anhydrous methanol (100 mL) at 0° C. (ice-bath). The solution turned from orange-yellow to red-orange before going back to yellow-orange. The reaction mixture was stirred at 0° C. for 3 h to give an orange solution. After stifling for another ½ h, 15% NaOH solution in water (15 mL) was added to the reaction mixture while maintaining the temperature below 5° C. Most of the methanol was removed under reduced pressure on a rotary evaporator (~135 mL) to give a thick cream-orange residue. An additional portion of 15% aqueous NaOH solution (80 mL) was added and the reaction mixture was extracted with ethyl acetate (3×100 mL). The organic layer was washed with water (1×100 mL) and a saturated NaCl solution (1×50 mL). The organic layer was removed, dried over anhydrous MgSO$_4$ and the filtered over Celite. The filtrate was evaporated in vacuo to afford an orange viscous liquid containing the desired product (5.4038 g). The above crude product will be used as such for the reaction with p-toluenesulfonic acid in the next Step #6.

Step 6

Preparation of (S)-ethyl 3-amino-3-(5-bromo-3-(tert-butyl)-2-hydroxyphenyl)propionate p-toluene-4-sulfonic acid

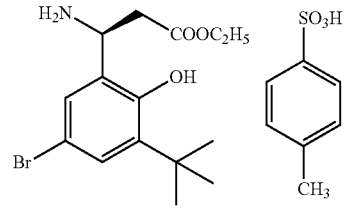

p-Toluenesulfonic acid monohydrate was added to a solution of crude ester from the Step #5 (5.40 g, 9.84 mmol) in absolute ethanol (25.0 mL). The reaction mixture was heated under refluxing conditions under nitrogen atmosphere to give an orange red-brown solution. The heating was discontinued after 7 h and the reaction mixture was cooled to room temperature. The solvent was evaporated in vacuo to afford a dark orange-brown viscous liquid. The crude product was dissolved in THF (10.0 mL) and diluted slowly with heptane (50.0 mL) to give a creamish brown suspension. This mixture was stored in a freezer (−20° C.) overnight. A dirty cream gummy solid precipitated in a yellow-orange heptane mother liquor. The heptane layer was decanted off and the residue was dried in vacuo to give a dirty beige foamy solid (4.56 g). A second crop of the product was also obtained from the heptane layers as a colorless solid (290.0 mg). LC-MS analysis of the above crude product shows the desired product's mass: m/z 344 ($^{79Br}$M+H) and m/z 346 ($^{81Br}$M+H), Calcd for $C_{15}H_{22}BrNO_3$: 344.24, Calcd for p-TSA salt $C_{15}H_{22}BrNO_3 \cdot C_7H_8O_3S$: 516.44. $^1$H NMR (400 MHz, DMSO-$d_6$): δ 1.13 (t, J=7.10 Hz, 3H, $CH_3CH_2$—), 1.36 (s, 6H, $(CH_3)_2C$—), 2.30 (S, 3H, 4-$CH_3$—(pTSA)), 2.95 (ABq, $J_{AB}$=16.42 and 7.42 Hz and $J_{AB}$=16.42 and 6.72 Hz, 2H, —$CH_2$—$COOC_2H_5$), 4.05 (q, J=7.10 Hz, 2H, $CH_3CH_2$—), 5.01 (apptq/m, J=6.20 Hz, 1H, —NH—$CH_2$—COO—), 7.12 (d, J=8.40 Hz, 2H, pTSA-H-3 & H-5), 7.30 (d, J=2.44 Hz, 1H), 7.47 (s, 1H), 7.48 (d, J=6.00 Hz, 2H, pTSA H-2 & H-6), 8.26 (brs, 2H, —$NH_2$), 9.02 (brs, 1H, —OH). $^1$H NMR spectrum of the sample was consistent with the suggested structure of the product.

Preparation of (S)-ethyl 3-(5-bromo-3-(tert-butyl)-2-hydroxyphenyl)-3-(2-((tert-butoxycarbonyl)amino)acetamido)propanoate

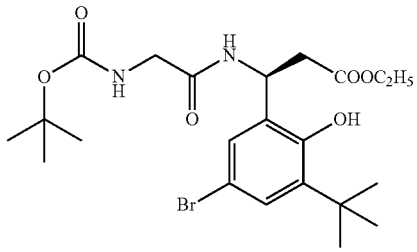

To a solution of a mixture of the (S)-ethyl 3-amino-3-(5-bromo-3-(tert-butyl)-2-hydroxyphenyl)propanoate-p-TSA salt (1.10 g, 2.90 mmol) and N-t-Boc-glycine hydroxysuccinimide ester (0.80 g, 2.95 mmol) in anhydrous DMF (20 mL) was added triethylamine (485 µL, 3.48 mmol) and the reaction mixture was stirred at room temperature under nitrogen atmosphere overnight. The solvent was evaporated in vacuo to afford an orange viscous liquid. The residue was partitioned between ethyl acetate (50 mL), water (50 mL) and a saturated $NaHCO_3$ solution (50 mL). The ethyl acetate layer was removed, washed with water (1×50 mL), dried over anhydrous $Na_2SO_4$, filtered and evaporated in vacuo to afford a pinkish-cream foamy solid (1.435 g). The crude product will be used as such for the deprotection of the t-Boc-group.

Preparation of (S)-ethyl 3-(2-aminoacetamido)-3-(5-bromo-3-(tert-butyl)-2-hydroxyphenyl)propanoate, Hydrochloride salt

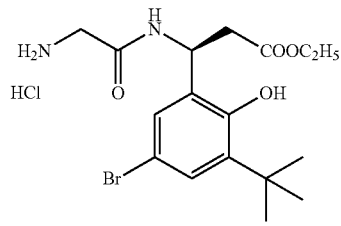

4M HCl in 1,4-dioxane (3.0 mL) was added to a solution of a crude sample of (S)-ethyl 3-(5-bromo-3-(tert-butyl)-2-hydroxyphenyl)-3-(2-((tert-butoxycarbonyl)amino)acetamido)propanoate (0.922 g, 1.84 mmol) in 1,4-dioxane (3.0 mL) at 0° C. (ice-bath) and the reaction mixture was stirred at 0° C. for 30 min and then at room temperature for 30 min. The reaction mixture was then heated at 50° C. for 2.5 h under nitrogen atmosphere to give a yellow-orange suspension. The solvent was evaporated in-vacuo to afford a dirty yellow-orange foamy solid. Acetonitrile (25 mL) was added to the solid, stirred for 5 min to give a cream-yellow suspension and evaporated in vacuo to afford a dirty cream solid (0.935 g). LC/MS analysis of the product shows the desired product's mass: m/z 402 ($^{79Br}$M+H) and m/z 404 ($^{81Br}$M+H), Calcd for $C_{17}H_{25}BrN_2O_4$: 401.29.

Preparation of (3S)-ethyl 3-(5-bromo-3-(tert-butyl)-2-hydroxyphenyl)-3-(2-(3-hydroxy-5-((5-hydroxy-1,4,5,6-tetrahydropyrimidin-2-yl)amino)benzamido)acetamido) propanoate

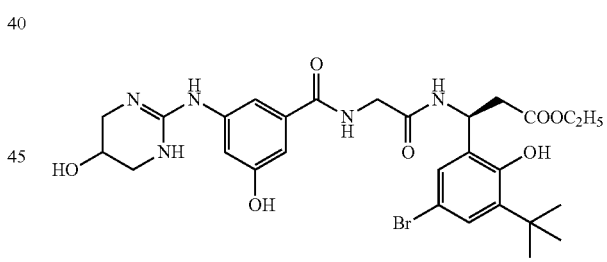

To a mixture of (S)-ethyl 3-(2-aminoacetamido)-3-(5-bromo-3-(tert-butyl)-2-hydroxyphenyl)propanoate (0.607 g, 0.986 mmol), 3-hydroxy-5-((5-hydroxy-1,4,5,6-tetrahydropyrimidin-2-yl)amino)benzoic acid (Example A) (0.330 g, 1.313 mmol) and 1-hydroxybenzotriazole hydrate (40.2 mg, 0.26 mmol) in anhydrous DMF (5.0 mL) and DCM (5.0 mL) was added N,N'-diisopropylcarbodiimide (240 µL, 1.55 mmol) and the reaction mixture was stirred at room temperature under nitrogen atmosphere overnight. The solvent was evaporated on a rotary evaporator to give a colorless gummy residue. The residue was dissolved in acetonitrile (15 mL), stirred for 5 min and filtered to remove the precipitated urea. Evaporation of the filtrate in vacuo gave an almost colorless gummy/viscous residue (0.855 g). The crude product will be used as such for the saponification with lithium hydroxide in the next step.

301

Preparation of (3S)-3-(5-bromo-3-(tert-butyl)-2-hydroxyphenyl)-3-(2-(3-hydroxy-5-((5-hydroxy-1,4,5,6-tetrahydropyrimidin-2-yl)amino)benzamido)acetamido)propanoic acid

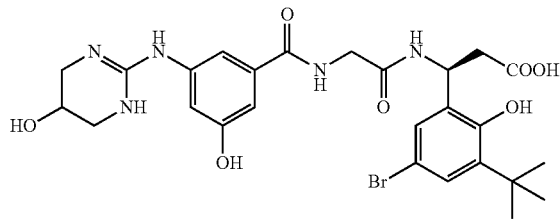 [SMILES: CC(C)(C)c1cc(Br)cc([C@H](CC(=O)O)NC(=O)CNC(=O)c2cc(O)cc(NC3=NCC(O)CN3)c2)c1O]

To a suspension of crude (3S)-ethyl 3-(5-bromo-3-(tert-butyl)-2-hydroxyphenyl)-3-(2-(3-hydroxy-5-((5-hydroxy-1,4,5,6-tetrahydropyrimidin-2-yl)amino)benzamido)acetamido) propanoate (0.758 g, 1.195 mmol) in a 1:1 mixture of acetonitrile/water (6.0 mL) was added lithium hydroxide monohydrate (0.401 g, 9.56 mmol) at room temperature and the reaction mixture was stirred at room temperature for 2.5 h to afford a pale yellow solution. Acetonitrile was evaporated on a rot-vap to give a pale yellow aqueous residue. The residue was diluted with water (10 mL) and filtered to remove precipitated urea. The aqueous layer was neutralized with TFA (1.0 mL in 5.0 mL CH$_3$CN) and the mixture was evaporated in vacuo to give a pale yellow-cream foamy solid. The crude product was purified by reverse-phase HPLC using a gradient 10-40% CH$_3$CN in water containing 0.05% TFA to afford a colorless glassy solid. The purified product was dissolved in water containing a few drops of acetonitrile and lyophilized to afford a colorless powder (407.0 mg). LC/MS analysis of the purified product shows the desired product's mass: m/z 606 ($^{79Br}$M+H) and m/z 608 ($^{81Br}$M+H), Calcd for C$_{26}$H$_{32}$BrN$_5$O$_7$: 606.466. $^1$H NMR spectrum of the sample was consistent with the suggested structure of the product.

Example 3

Preparation of (3S)-3-(3-bromo-5-(2-hydroxypropan-2-yl)phenyl)-3-(2-(3-hydroxy-5-((5-hydroxy-1,4,5,6-tetrahydropyrimidin-2-yl)amino)benzamido) acetamido)propanoic acid

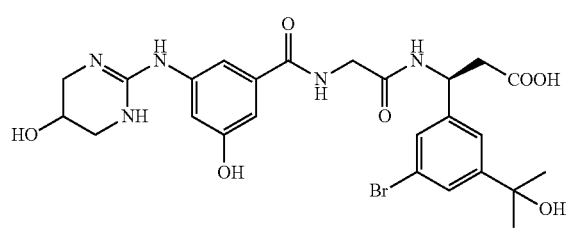

302

Preparation of (S)-ethyl 3-amino-3-(3-bromo-5-(2-hydroxypropan-2-yl)phenyl)propanoate

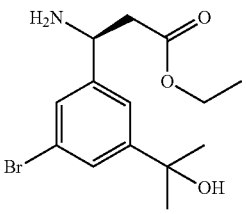

The following Scheme describes a synthesis of the β-amino acid: (S)-ethyl 3-amino-3-(3-bromo-5-(2-hydroxypropan-2-yl)phenyl)propionate which will be used to synthesize the above compound (Example 3).

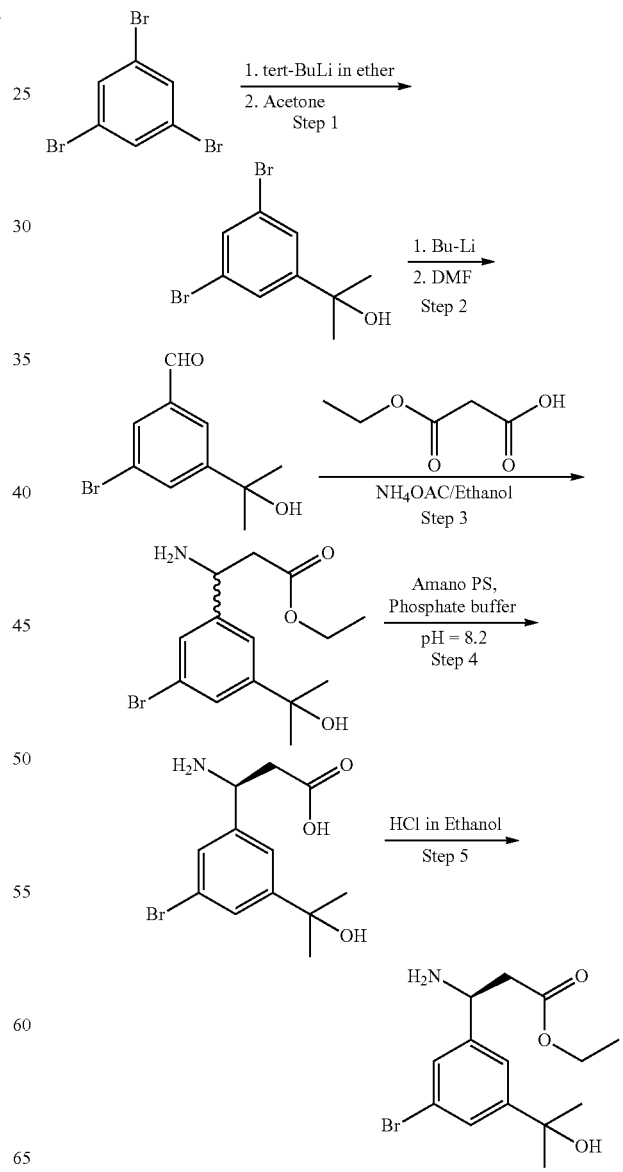

Step 1

Preparation of 1,3-Dibromo-5-{(1-hydroxy-1-methyl)ethyl}-benzene

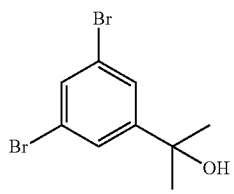

To a solution/suspension of 1,3,5-tribromobenzene (5.03 g, 15.96 mmol) in anhydrous diethyl ether (75.0 mL) was slowly added a 1.70 M solution of tert-butyllithium in pentane (19.25 mL, 32.70 mmol) at −78° C. (dry ice-acetone bath) in 15 min to give a purple solution/suspension. The reaction mixture was warmed to −30° C. and stirred at that temperature for 2 h. Dry acetone (1.25 mL, 17.0 mmol) was added to the solution to give a brown-purple solution and the reaction mixture was stirred at −30° C. for another 3 h. The reaction mixture was quenched with a saturated aqueous solution of NH$_4$Cl (35.0 mL) at −30° C. and warmed to room temperature before diluted with diethyl ether (50 mL). The organic layer was separated, washed with water, dried over anhydrous MgSO$_4$, filtered and evaporated in vacuo to afford a dark orange-red viscous liquid (4.50 g). The crude product was purified by Silica-gel flash chromatography on Biotage SP1 system using a Varian SF-40-120 g Super Flash silica gel column and elution with 10-90% diethyl ether in n-heptane. Evaporation of the pure fractions mixture in vacuo afforded the desired product as a tan crystalline solid (2.50 g). GC/MS analysis of the solid shows the desired product's mass: m/z 292 ($^{79Br,79Br}$M$^+$) m/z 294 ($^{79Br,81Br}$M$^+$) and m/z 296 ($^{81Br,81Br}$M$^+$), Calcd for C$_9$H$_{10}$Br$_2$O: 293.98. $^1$H NMR (400 MHz, CDCl$_3$): δ 1.53 (s, 6H, (CH$_3$)$_2$C—OH), 1.71 (brs, 1H, (CH$_3$)$_2$C—OH), 7.52 (d, J=1.75 Hz, 1H, H-2), 7.54 (d, J=1.75 Hz, 2H, H-4 and H-6). $^1$H NMR spectrum of the sample was consistent with the suggested structure of the product.

Step 2

Preparation of 3-bromo-5-(2-hydroxypropan-2-yl)benzaldehyde

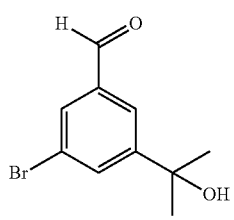

2-(3,5-dibromophenyl)propan-2-ol (2.50 g, 8.50 mmol) from step #1 was dissolved in anhydrous diethyl ether (20 mL) in a dried flask under nitrogen. The reaction mixture was cooled to −78° C. (Dry ice-acetone bath) and stirred under nitrogen atmosphere. A 1.6 M solution of n-butyllithium in hexanes (11.0 mL, 17.60 mmol) was added dropwise to the above solution at −78° C. and the reaction mixture was stirred at −78° C. for 30 min after complete addition of n-BuLi to give a red-brown solution. After 30 min of stifling at −78° C., the reaction mixture was warmed to −30° C. to give a light pink suspension. DMF (800 μL, 10.33 mmol) was added to above reaction mixture dropwise, keeping the reaction mixture below −20° C. (5 min). After addition of DMF is complete, the reaction mixture was warmed slowly to 0° C. (ice-bath) (30 min) to give a pale pink suspension. The reaction mixture was stirred at room temperature under nitrogen atm. Although the reaction was done in 30 min but the reaction mixture was let stirred at room temperature overnight under nitrogen to give a pale pink suspension, the reaction mixture was poured into 50 mL of chilled 10% aqueous HCl and the mixture was stirred for 15 min. The ether layer was separated and then washed with water (1×25 mL), dried over anhydrous Na$_2$SO$_4$, filtered and evaporated on the rot-yap to give a dirty orange crystalline solid (2.18 g). Purification of the crude product by Silica-gel flash chromatography on silica gel column and elution with 5-40% ethyl acetate in n-heptane afforded the desired product as a dirty yellow solid (1.054 g). GC-MS analysis (CI mode/methane) of the product shows the desired product's mass: m/z 242 ($^{79Br}$M$^+$) and m/z 244 ($^{81Br}$M$^+$), Calcd for C$_{10}$H$_{11}$BrO$_2$: 243.097. $^1$H NMR (400 MHz, CDCl$_3$): δ 1.59 (s, 6H, (CH$_3$)$_2$C—OH), 1.81 (brs, 1H, (CH$_3$)$_2$C—OH), 7.86 (dd, J=1.80 and 1.50 Hz, 1H), 7.89 (appt, J=1.70 Hz, 1H), 7.91 (appt, J=1.80 Hz, 1H), 9.94 (s, 1H, —CHO). $^1$H NMR spectrum of the sample was consistent with the suggested structure of the product.

Step 3

Preparation of ethyl 3-amino-3-(3-bromo-5-(2-hydroxypropan-2-yl)phenyl)propanoate

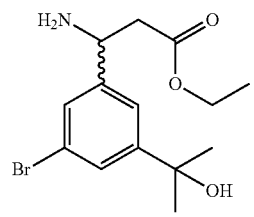 [SMILES: CCOC(=O)CC(N)c1cc(Br)cc(C(C)(C)O)c1]

A solution of 3-bromo-5-(2-hydroxypropan-2-yl)benzaldehyde (1.04 g, 4.28 mmol) mono-ethyl malonate (1.25 g, 9.46 mmol) and ammonium acetate (1.72 g, 22.30 mmol) in anhydrous ethanol (70.0 mL) was heated at reflux for 7 h to give a pale yellow solution. The reaction mixture was cooled to room temperature and the solvent was evaporated in vacuo to give a yellow viscous liquid. The residue was partitioned between aqueous saturated NaHCO$_3$ solution (25 mL) and ethyl acetate (25 mL), the organic layer was removed, dried over anhydrous sodium sulfate, filtered and evaporated in vacuo to give a yellow viscous liquid of the amino ester (1.60 g). LC-MS analysis of the crude product shows the desired product's mass: m/z 330 ($^{79Br}$M$^+$) and m/z 332 ($^{81Br}$M$^+$), Calcd for C$_{14}$H$_{20}$BrNO$_3$: 330.21.

Step 4

Preparation of (S)-3-amino-3-(3-bromo-5-(2-hydroxypropan-2-yl)phenyl)propanoic acid

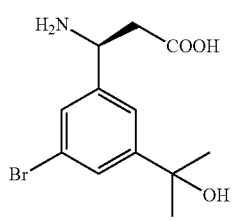 [SMILES: CC(C)(O)c1cc(Br)cc([C@@H](N)CC(=O)O)c1]

Enzymatic Resolution of the Racemic Mixture.

A suspension of the crude product from Step #3 (270.0 mg, 0.82 mmol) in 50 mM $KH_2PO_4$ solution (40.0 mL) was stirred at room temperature and the pH of the aqueous layer was adjusted to pH 8.20 by the addition of 1.0 N NaOH solution. Amano PS was added to above suspension and the reaction mixture was stirred at room temperature overnight. A slightly turbid solution with a few small yellow-orange colored beads was obtained after overnight stifling. No solid or precipitate was obtained, the desired (S)-acid might be soluble in the above aqueous system. The above mixture was diluted with MTBE (15 mL) and reaction mixture was stirred at room temperature for 15 min to extract the (R)-ester. Evaporation of the aqueous layer in vacuo afforded a cream solid containing the (S)-acid as well as Amano Lipase and Phosphate buffer salt (735.0 mg).). LC-MS analysis of the crude residue shows the desired (S)-acid's mass: m/z 302 ($^{79Br}M^+$) and m/z 304 ($^{81Br}M^+$), Calcd for $C_{12}H_{16}BrNO_3$:302.16. The above crude residue will be used as such for the preparation of the (S)-ester.

Step 5

Preparation of (S)-ethyl 3-amino-3-(3-bromo-5-(2-hydroxypropan-2-yl)phenyl)propanoate

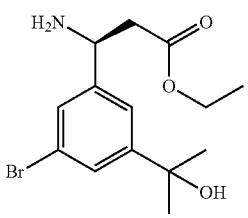

The crude residue containing the (S)-acid as well as Amano Lipase and Phosphate buffer salt from Step #3 was suspended in abs. ethanol saturated with dry HCl gas (10 mL) and the reaction mixture was heated at reflux for 2 h to give a dirty pink-yellow suspension. The reaction mixture was diluted with acetonitrile (50 mL), filtered and evaporated in vacuo to give a dirty yellow-brown oily residue. The residue was treated with an aq. $NaHCO_3$ solution (25 mL) and extracted with MTBE (2×25 mL). Evaporation of the solvent in vacuo gave a yellow-brown gummy residue and the residue was purified by reverse-phase HPLC with a gradient 10-40% $CH_3CN$ in water containing 0.05% TFA to give the desired product after lyophilization as a colorless lyophilized solid (18.4 mg). LC/MS analysis of the purified product shows the desired product's mass: m/z 330 ($^{79Br}M+H$) and m/z 332 ($^{81Br}M+H$). $^1H$ NMR (400 MHz, DMSO-$d_6$): δ 1.10 (t, J=7.10 Hz, 3H, $CH_3CH_2$—), 1.42 (s, 6H, $(CH_3)_2C$—), 3.00 (ABq, $J_{AB}$=16.15 and 8.15 Hz and $J_{AB}$=16.15 and 6.40 Hz, 2H, —$CH_2$—$COOC_2H_5$), 4.03 (dq, J=7.10 and 1.0 Hz, 2H, $CH_3CH_2$—), 4.65 (appt, J=7.16 Hz, 1H, —NH—CH—$CH_2$—COO—), 5.30 (s, 1H, $(CH_3)_2$—C—OH), 7.57 (appt, J=1.60 Hz, 2H), 7.67 (appt, J=1.60 Hz, 1H), 8.42 (brs, 2H, —$NH_2$). $^1H$ NMR spectrum of the sample was consistent with the suggested structure of the product.

Step 6

Preparation of (3S)-3-(3-bromo-5-(2-hydroxypropan-2-yl)phenyl)-3-(2-(3-hydroxy-5-((5-hydroxy-1,4,5,6-tetrahydropyrimidin-2-yl)amino)benzamido) acetamido) propanoic acid

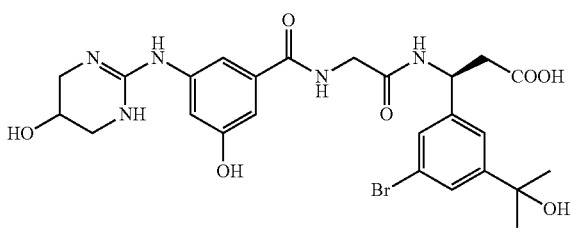 [SMILES: CC(C)(O)c1cc(Br)cc([C@H](CC(=O)O)NC(=O)CNC(=O)c2cc(O)cc(NC3=NCC(O)CN3)c2)c1]

A mixture of 2-(3-hydroxy-5-((5-hydroxy-1,4,5,6-tetrahydropyrimidin-2-yl)amino)benzamido)acetic acid (Example B) (20.13 mg, 0.065 mmol), (S)-ethyl 3-amino-3-(3-bromo-5-(2-hydroxypropan-2-yl)phenyl)propanoate hydrochloride (19.60 mg, 0.059 mmol) was dissolved in DMF (1.0 mL) and dichloromethane (1.0 mL) to give a cream suspension. Solid 1-hydroxybenzatriazole hydrate (2.0 mg, 0.013 mmol) was added to above reaction mixture and the reaction mixture was stirred under nitrogen atmosphere for 10 min. N,N'-diisopropylcarbodiimide (12 μL) was added and the reaction mixture was stirred at room temperature overnight under nitrogen atmosphere. The solvent was evaporated in-vacuo to give a pale yellow viscous gummy residue. The residue was dissolved in acetonitrile (10 mL), stirred for 5 min and filtered to remove the precipitated urea. Evaporation of the filtrate in vacuo gave a yellow-orange gummy residue of the product: (3S)-ethyl 3-(3-bromo-5-(2-hydroxypropan-2-yl)phenyl)-3-(2-(3-hydroxy-5-((5-hydroxy-1,4,5,6-tetrahydropyrimidin-2-yl)amino)benzamido) acetamido)propanoate (30.0 mg).

To a solution of the above product in a mixture of a 1:1 mixture of acetonitrile/water was added lithium hydroxide monohydrate (20.0 mg) at room temperature and the reaction mixture was stirred at room temperature for 1.5 h. The mixture was neutralized with TFA (100 μL in 1.0 mL $CH_3CN$) and the mixture was evaporated in-vacuo to give a pale residue. The crude above product was purified by reverse-phase HPLC with a gradient 10-40% $CH_3CN$ in water containing 0.05% TFA to give the desired product, after lyophilization, as a colorless lyophilized solid (22.0 mg). LC/MS analysis of the product shows the desired product's mass: m/z 592 ($^{79Br}M^+$) and m/z 594 ($^{81Br}M^+$), calcd for $C_{25}H_{30}BrN_5O_7$: 592.43. $^1H$ NMR (400 MHz, DMSO-$d_6$): δ 1.39 (s, 12H, 2×$(CH_3)_2C$—OH), 2.69 (d, J=7.81 Hz, 2H, —$CH_2$—COOH), 3.15 (d, J=12.23 Hz, 2H), 3.33 (d, J=12.06 Hz, 2H), 3.86 (d, J=5.84 Hz, 2H), 4.07 (appt/m, 1H), 5.17 (brm/q, 1H, —NH—CH—$CH_2$—COOH), 6.74 (brt/m, 1H), 7.11 (dt, J=10.4 Hz, 2H), 7.34 (appt/m, 1H), 7.39 (appt/m, 1H), 7.50 (appt/m, 1H), 8.14 (brs, 2H), 8.51 (d, J=8.20 Hz, 1H), 8.62 (brt, J=7.35 Hz, 1H), 9.69 (s, 1H), 10.01 (brs, 1H), 12.38 (brs, 1H, —COOH). ¹H NMR spectrum of the sample was consistent with the suggested structure of the product.

Example 4

Preparation of (3S)-3-(3-chloro-5-(2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid

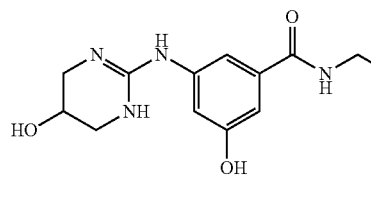

Preparation of (S)-ethyl 3-amino-3-(3-chloro-5-(2-hydroxypropan-2-yl)phenyl)propanoate

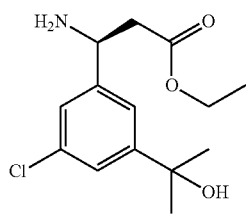 [SMILES: CCOC(=O)C[C@H](N)c1cc(Cl)cc(C(C)(C)O)c1]

The following Scheme describes a synthesis of the β-amino acid (S)-ethyl 3-amino-3-(3-chloro-5-(2-hydroxypropan-2-yl)phenyl)propionate

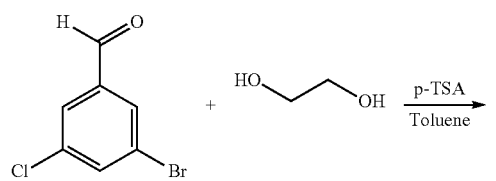

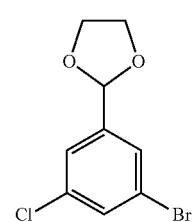

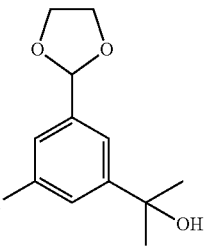

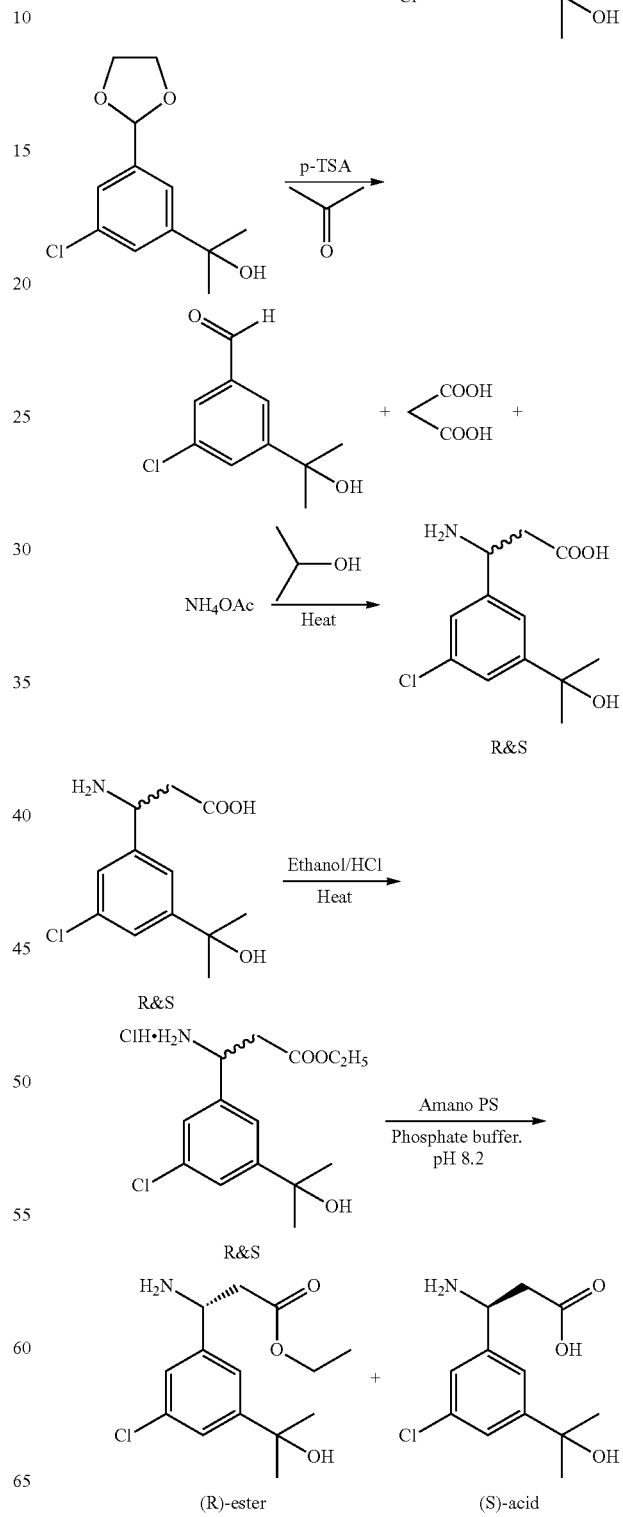

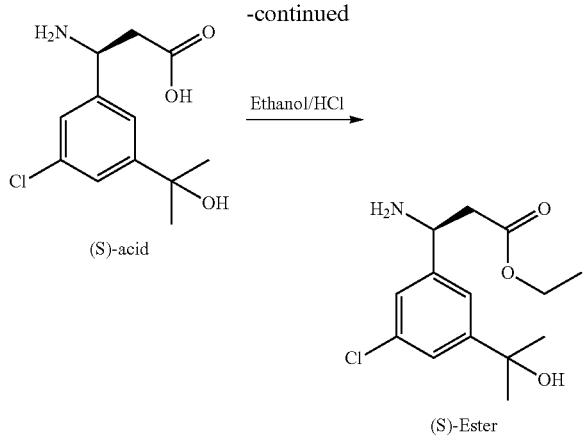

(S)-acid → (S)-Ester (Ethanol/HCl)

Step 1

Preparation of 2-(3-bromo-5-chlorophenyl)-1,3-dioxolane

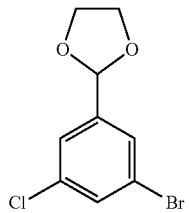 [SMILES: Clc1cc(Br)cc(C2OCCO2)c1]

A mixture of 3-bromo-5-chlorobenzaldehyde (5.00 g, 22.80 mmol), ethylene glycol (3.82 mL, 68.90 mmol) and p-toluenesulfonic acid hydrate (88.0 mg, 0.45 mmol) in anhydrous toluene was heated at reflux under Dean-Stark conditions for 6 h. The reaction mixture was cooled to room temperature and diluted with ethyl acetate (50 mL). The ethyl acetate layer was washed with a saturated $NaHCO_3$ solution (25 mL). The organic layer was removed and washed with water (1×25 mL) and dried with anhydrous $MgSO_4$, filtered and evaporated in-vacuo to give an almost colorless viscous liquid (6.05 g). GC-MS analysis (CI mode/methane) analysis of the liquid shows the desired product's mass: m/z 262 ($^{79Br,35Cl}M^+$) and m/z 264 ($^{81Br,37Cl}M^+$), Calcd for $C_9H_8BrClO_2$: 263.51. $^1H$ NMR (400 MHz, $CDCl_3$): δ 3.98-4.04 (M, 2H, —$CH_2$—O—), 4.04-4.10 (M, 2H, —$CH_2$—O—), 5.69 (s, 1H, O—CH—O), 7.39 (M, 1H), 7.47-7.51 (M, 2H). $^1H$ NMR spectrum of the liquid was consistent with the suggested structure of the product.

Step 2

Preparation of 2-(3-chloro-5-(1,3-dioxolan-2-yl)phenyl)propan-2-ol

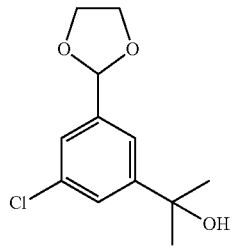 [SMILES: CC(C)(O)c1cc(Cl)cc(C2OCCO2)c1]

To a solution of 2-(3-bromo-5-chlorophenyl)-1,3-dioxolane (3.34 g, 12.68 mmol) in anhydrous diethyl ether (40 mL) in a dried flask was slowly added a 1.70 M solution of tert-butyl lithium in pentane (15.0 mL, 25.50 mmol) at −78° C. under nitrogen to give a pinkish-yellow suspension. The reaction mixture was stirred at −78° C. for 45 min under nitrogen atmosphere. After 45 min, the reaction mixture was warmed to −30° C. and stirred at that temperature for 2 h. Acetone (2.0 mL, 25.35 mmol) was added drop wise to the above solution and the reaction mixture stirred at −30° C. for another 3 h. The reaction mixture was quenched with a saturated $NH_4Cl$ solution (20 mL) at −30° C. and the reaction mixture was warmed slowly to room temperature (30 min) and then diluted with diethyl ether (25.0 mL). The ether layer was separated and then washed with water (1×25 mL), dried over anhydrous $Na_2SO_4$, filtered and evaporated on the rotyap to give a pale yellow viscous liquid (5.45 g from two runs). GC-MS analysis (EI mode) of the product shows the desired product's mass: m/z 241 ($^{35Cl}M+$) and m/z 243 ($^{37Cl}M+$), Calcd for $C_{12}H_{15}BrClO_3$: 242.67. LC-MS analysis of the crude product shows the desired product's mass: m/z 243 ($^{35Cl}M+H$), m/z 245 ($^{37Cl}M+H$), m/z 225 ($^{35Cl}M+H-H_2O$), m/z 227 ($^{37Cl}M+H-H_2O$). $^1H$ NMR (400 MHz, $CDCl_3$): δ 1.54 (s, 6H, $(CH_3)_2C$—OH), 3.90-4.25 (M, 4H, 2×—$CH_2$—O—), 5.75 (s, 1H, O—CH-0), 7.34 (s, 1H), 7.43 (d, 2H). $^1H$ NMR spectrum of the sample was consistent with the suggested structure of the product.

Step 3

Preparation of 3-chloro-5-(2-hydroxypropan-2-yl)benzaldehyde

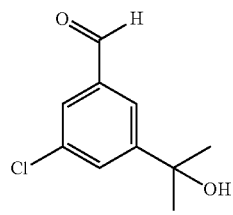

To a solution of 2-(3-chloro-5-(1,3-dioxolan-2-yl)phenyl)propan-2-ol (5.45 g, 22.46 mmol) in acetone (50 mL) was added p-toluenesulfonic acid hydrate (0.85 g, 4.47 mmol) and the reaction mixture was stirred at room temperature for 1 h to give an orange-red solution. The solvent was evaporated in vacuo to give an orange-brown residue. The residue was partitioned between aqueous saturated $NaHCO_3$ solution (25 mL) and ethyl acetate (50 mL), the organic layer was removed, washed with brine (1×25 mL), dried over anhydrous sodium sulfate, filtered and evaporated in-vacuo to give an orange-red viscous liquid (4.75 g). Purification of the crude product by Silica-gel flash chromatography on silica gel column and elution with 5-40% ethyl acetate in n-hexane afforded the desired product as a cream crystalline solid (2.35 g). $^1H$ NMR (400 MHz, $CDCl_3$): δ 1.59 (s, 6H, $(CH_3)_2C$—OH), 1.76 (brs, 1H, $(CH_3)_2C$—OH), 7.71 (dd, J=1.80 Hz, 1H), 7.75 (appt, J=1.80 Hz, 1H), 7.85 (appt/dd, J=1.40 Hz, 1H), 9.96 (s, 1H, —CHO). $^1H$ NMR spectrum of the solid was consistent with the suggested structure of the product.

Step 4

Preparation of racemic 3-amino-3-(3-chloro-5-(2-hydroxypropan-2-yl)phenyl)propionic acid

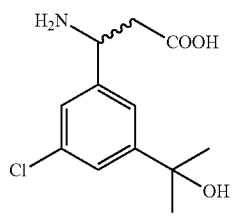 [SMILES: CC(C)(O)c1cc(Cl)cc(C(N)CC(=O)O)c1]

A suspension of 3-chloro-5-(2-hydroxypropan-2-yl)benzaldehyde (2.35 g, 11.83 mmol), malonic acid (1.50 g, 14.41 mmol) and ammonium acetate (1.85 g, 24.00 mmol) in isopropanol (30.0 mL) was heated at reflux under nitrogen atmosphere for 4 h to afford a colorless suspension in a yellow-orange solution. The hot reaction mixture was filtered and the solid was washed with hot isopropanol (2×25 mL) and discarded. The filtrate was evaporated in vacuo to afford a mixture of the desired acid (40%) and the byproduct: 3-(3-chloro-5-(2-hydroxypropan-2-yl)phenyl)acrylic acid (60%) as a cream yellow foamy solid. The solid was recrystallized several times (×5) from ethyl acetate to afford the pure desired product, free from the byproduct impurity, as a colorless solid (632.8 mg). LC-MS analysis of the solid shows the desired product's mass: m/z 258 ($^{35Cl}$M+H), m/z 260 ($^{37Cl}$M+H), m/z 240 ($^{35Cl}$M+H–H$_2$O) and m/z 242 ($^{37Cl}$M+H–H$_2$O); Calcd for $C_{12}H_{16}ClNO_3$: 257.71. $^1$H NMR (400 MHz, DMSO-d$_6$): δ 1.42 (s, 6H, (CH$_3$)$_2$C—), 2.30 (dd, J=8.0 and 6.0 Hz, 2H, —CH$_2$—COOH), 4.21 (appt, J=7.0 Hz, 1H, —NH—CH—CH$_2$—COOH), 6.33 (s, 1H, (CH$_3$)$_2$—C—OH), 7.31 (appt, J=1.60 Hz, 1H), 7.38 (appt, J=1.70 Hz, 1H), 7.42 ((d, J=9.0 Hz, 1H). $^1$H NMR spectrum of the sample was consistent with the suggested structure of the product.

Step 5

Preparation of racemic ethyl 3-amino-3-(3-chloro-5-(2-hydroxypropan-2-yl)phenyl)propanoate hydrochloride

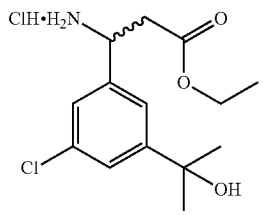

Absolute ethanol saturated with anhydrous HCl gas (5 mL) was added to 3-amino-3-(3-chloro-5-(2-hydroxypropan-2-yl)phenyl)propionic acid (632.0 mg, 2.45 mmol) and the reaction mixture was heated at reflux for 2 h to give a colorless solution. The solvent was removed in vacuo to give a colorless solid. The solid was slurried with diethyl ether and heptane (2×25 mL). After the solvent layer was decanted off, the residue was dried in vacuo to give the racemic β-amino ester hydrochloride salt as a colorless foamy solid (746 mg). LC-MS analysis of the solid shows the desired product's mass: m/z 286 ($^{35Cl}$M+H), m/z 288 ($^{37Cl}$M+H), m/z 268 ($^{35Cl}$M+H–H$_2$O) and m/z 270 ($^{37Cl}$M+H–H$_2$O); Calcd for $C_{14}H_{20}ClNO_3$: 285.77.

Step 6

Preparation of (S)-3-amino-3-(3-chloro-5-(2-hydroxypropan-2-yl)phenyl)propanoic acid

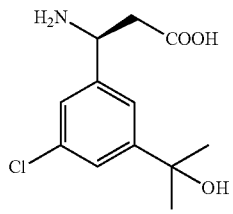 [SMILES: CC(C)(O)c1cc(Cl)cc([C@@H](N)CC(=O)O)c1]

Enzymatic Resolution of the Racemic Mixture:

A suspension of the crude product from step #5 (270.0 mg, 0.82 mmol) in 50 mM KH$_2$PO$_4$ solution (40.0 mL) was stirred at room temperature and the pH of the aqueous layer was adjusted to pH 8.20 by the addition of 1.0 N NaOH solution. Amano PS was added to above suspension and the reaction mixture was stirred at room temperature overnight. A slightly turbid solution with a few small yellow-orange colored beads was obtained after overnight stifling. No solid or precipitate was obtained, the desired (S)-acid might be soluble in the above aqueous system. The above mixture was diluted with MTBE (15 mL) and reaction mixture was stirred at room temperature for 15 min to extract the (R)-ester. Evaporation of the aqueous layer in-vacuo afforded a cream solid containing the (S)-acid as well as Amano Lipase and Phosphate buffer salt (735.0 mg).). LC-MS analysis of the crude residue shows the desired (S)-acid's mass: m/z 302 ($^{79Br}$M+) and m/z 304 ($^{81Br}$M+), Calcd for $C_{12}H_{16}BrNO_3$:302.16. The above crude residue will be used as such for the preparation of the (S)-ester.

Step 7

Preparation of (S)-ethyl 3-amino-3-(3-chloro-5-(2-hydroxypropan-2-yl)phenyl)propanoate hydrochloride

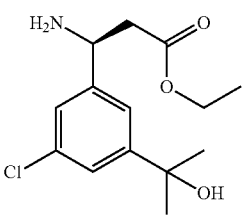 [SMILES: CCOC(=O)C[C@H](N)c1cc(Cl)cc(C(C)(C)O)c1]

The crude residue containing the (S)-acid as well as Amano Lipase and Phosphate buffer salt from Step #6 was suspended in abs. ethanol saturated with dry HCl gas (5 mL) and the reaction mixture was stirred at room temperature for 2 h to give a colorless solution. Analytical HPLC analysis of the reaction mixture shows the desired product as well as a trace of the byproduct: ethyl 3-(3-chloro-5-(2-hydroxypropan-2- yl)phenyl) acrylate. Evaporation of the solvent in vacuo gave a colorless residue which was purified by reverse-phase HPLC with a gradient 10-45% CH$_3$CN in water containing 0.05% TFA to give the desired product, after lyophilization as a colorless foamy solid (170.0 mg) (TFA salt). LC/MS analysis of the purified product shows the desired product's mass: m/z 286 ($^{35Cl}$M+H), m/z 288 ($^{37Cl}$M+H), m/z 268 ($^{35Cl}$M+H–H$_2$O) and m/z 270 ($^{37Cl}$M+H–H$_2$O); Calcd for C$_{14}$H$_{20}$ClNO$_3$: 285.77. The isolated product was stirred in absolute ethanol saturated with anhydrous HCl gas (5.0 mL) for 30 min and evaporated in vacuo to afford a colorless foamy solid (147.40 mg). The HCl salt will be used as such for the coupling reaction.

Preparation of (3S)-3-(3-chloro-5-(2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid

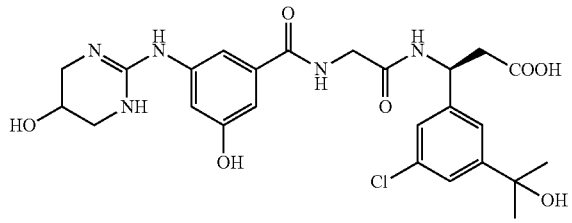 [SMILES: CC(C)(O)c1cc(Cl)cc([C@H](CC(=O)O)NC(=O)CNC(=O)c2cc(O)cc(NC3=NCC(O)CN3)c2)c1]

Step 1

Preparation of (3S)-ethyl 3-(3-chloro-5-(2-hydroxypropan-2-yl)phenyl)-3-(2-(3-hydroxy-5-((5-hydroxy-1,4,5,6-tetrahydropyrimidin-2-yl)amino)benzamido)acetamido)propanoate

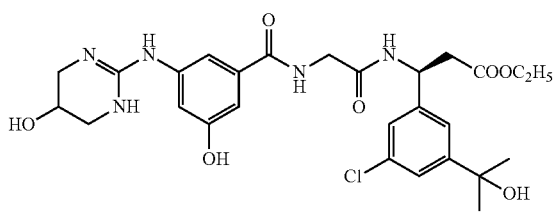

A mixture of 2-(3-hydroxy-5-((5-hydroxy-1,4,5,6-tetrahydropyrimidin-2-yl)amino)benzamido) acetic acid (Example B) (151.0 mg, 49 mmol) and (S)-ethyl 3-amino-3-(3-chloro-5-(2-hydroxypropan-2-yl)phenyl)propanoate hydrochloride (147.40 mg, 0.46 mmol) was dissolved in DMF (2.0 mL) and dichloromethane (2.0 mL) to give a colorless suspension. Solid 1-hydroxybenzotriazole hydrate (14 mg, 0.10 mmol) was added to above reaction mixture and the reaction mixture was stirred under nitrogen atmosphere for 10 min. N,N'-diisopropylcarbodiimide (205 µL, 1.33 mmol) was added and the reaction mixture was stirred at room temperature under nitrogen atmosphere overnight. The solvent was evaporated in vacuo to give a cream gummy residue of the product: (3S)-ethyl 3-(3-chloro-5-(2-hydroxypropan-2-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 576 ($^{35Cl}$M+H) and m/z 576 ($^{37Cl}$M+H). The crude residue will be used as such for the saponification (step #2).

Step 2

Preparation of (3S)-3-(3-chloro-5-(2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid

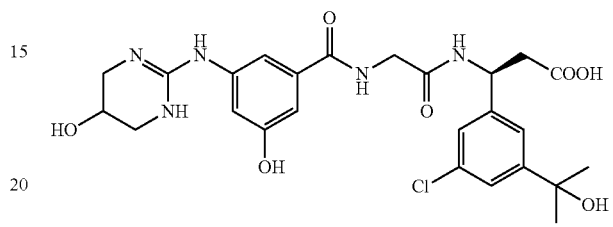

To a solution of the crude product (0.46 mmol) from step #1 in a mixture of a 1:1 mixture of acetonitrile/water (4 mL) was added lithium hydroxide monohydrate (145 mg, 3.46 mmol)) at room temperature and the reaction mixture was stirred at room temperature for 1.5 h. The mixture was neutralized with TFA (250 µL in 1.0 mL CH$_3$CN) and the mixture was evaporated in vacuo to give a pale residue. The above crude product was purified by reverse-phase HPLC with a gradient 10-45% CH$_3$CN in water containing 0.05% TFA to give the desired product (Example 4), after lyophilization, as a colorless lyophilized solid (160.0 mg). LC/MS analysis of the product shows the desired product's mass: m/z 548 ($^{35Cl}$M+H) and m/z 550 ($^{37Cl}$M+H), Calcd for C$_{25}$H$_{30}$ClN$_5$O$_7$: 547.99. $^1$H NMR (400 MHz, DMSO-d$_6$): δ 1.40 (s, 6H, (CH$_3$)$_2$C—OH), 2.70 (d, J=7.30 Hz, 2H, —CH$_2$—COOH), 3.16 (d, J=12.20 Hz, 2H), 3.33 (d, J=11.75 Hz, 2H), 3.86 (d, J=5.68 Hz, 2H), 4.08 (appt/m, 1H), 5.18 (q, J=7.30 Hz, 1H, —NH—CH—CH$_2$—COOH), 6.74 (brt/m, 1H), 7.12 (dt, J=9.70 Hz, 2H), 7.22 (appt/m, 1H), 7.37 (appt/m, 2H), 8.18 (brs, 2H), 8.55 (d, J=8.20 Hz, 1H), 8.65 (brt, J=5.80 Hz, 1H), 9.73 (s, 1H), 10.08 (brs, 1H), 12.30 (brs, 1H, —COOH). $^1$H NMR spectrum of the solid was consistent with the suggested structure of the product.

Example 5

Preparation of (S)-3-(3-bromo-5-(tert-butyl)phenyl)-3-(2-(3-guanidinobenzamido)acetamido) propanoic acid

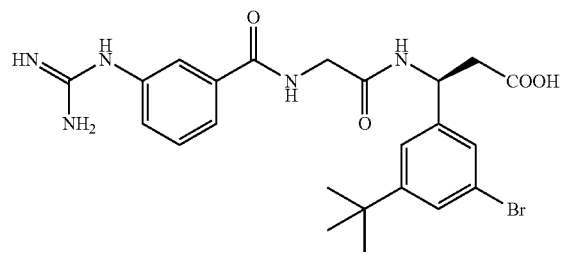 [SMILES: CC(C)(C)c1cc(Br)cc([C@H](CC(=O)O)NC(=O)CNC(=O)c2cccc(NC(=N)N)c2)c1]

Step 1

Preparation of (S)-ethyl 3-(3-bromo-5-(tert-butyl) phenyl)-3-(2-(3-guanidinobenzamido) propanoate

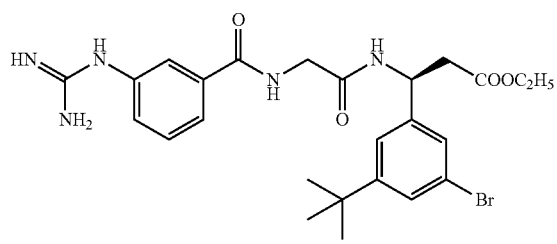

A mixture of 3-guanidinobenzoic acid (Example C) (179.5 mg, 1.00 mmol), (S)-ethyl 3-(2-aminoacetamido)-3-(3-bromo-5-tert-butyl)phenyl)propanoate hydrochloride (Example H) (439.5 mg, 1.00 mmol) and 1-hydroxybenzotriazole hydrate (31.2 mg, 0.20 mmol) was dissolved in DMF (4 mL) and dichloromethane (4 mL) and stirred at room temperature under nitrogen atmosphere for 10 min to give a colorless suspension. N,N'-diisopropylcarbodiimide (205 uL, 1.33 mmol) was added and the reaction mixture was stirred at room temperature under nitrogen atmosphere overnight. The solvent was evaporated in vacuo to give a yellow viscous residue of the intermediate product: (S)-ethyl 3-(3-bromo-5-(tert-butyl)phenyl)-3-(2-(3-guanidinobenzamido) acetamido) propanoate. LC-MS analysis of the crude residue shows the desired product's mass: m/z 546 ($^{79Br}$M+H), m/z 548 ($^{81Br}$M+H); m/z 568 ($^{79Br}$M+Na) and m/z 570 ($^{81Br}$M+Na); Calcd for $C_{25}H_{32}BrN_5O_4$: 546.46. The crude residue will be used as such for the saponification (step #2).

Step 2

Preparation of (S)-3-(3-bromo-5-(tert-butyl)phenyl)-3-(2-(3-guanidinobenzamido)acetamido) propanoic acid

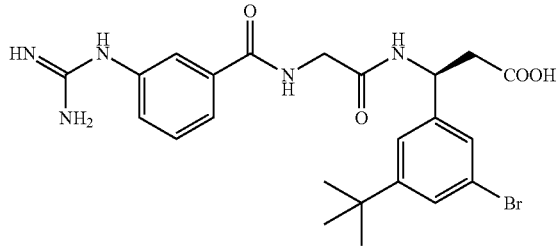 [SMILES: CC(C)(C)c1cc(Br)cc([C@H](CC(=O)O)NC(=O)CNC(=O)c2cccc(NC(=N)N)c2)c1]

To a suspension of the crude (S)-ethyl 3-(3-bromo-5-(tert-butyl)phenyl)-3-(2-(3-guanidinobenzamido) acetamido) propanoate (1.00 mmol) from step #1 in a mixture of a 1:1 mixture of acetonitrile/water (6 mL) was added lithium hydroxide monohydrate (245.6 mg, 5.85 mmol) and the reaction mixture was stirred at room temperature overnight. The reaction mixture was neutralized with TFA (1 mL in 3 mL CH$_3$CN) and the mixture was evaporated in vacuo to give a cream residue. The crude product was purified by reverse-phase HPLC with a gradient 10-60% CH$_3$CN in water containing 0.05% TFA to give the desired product (Example 5), after lyophilization, as a colorless lyophilized solid (510.2 mg). LC/MS analysis of the product shows the desired product's mass: m/z 518 ($^{79Br}$M+H), m/z 520 ($^{81Br}$M+H); m/z 540 ($^{79Br}$M+Na), and m/z 542 ($^{81Br}$M+Na); Calcd for $C_{23}H_{28}BrN_5O_4$: 518.40. $^1$H NMR (400 MHz, DMSO-d$_6$): δ 1.26 (s, 9H, (CH$_3$)$_3$C—), 2.70 (d, J=7.30 Hz, 2H, —CH$_2$—COOH), 3.90 (d, J=5.80 Hz, 2H), 5.19 (q, J=7.53 Hz, 1H, —NH—CH—CH$_2$—COOH), 7.34 (br appt, 1H), 7.36 (br appt, 1H), 7.39 (br appt, 1H), 7.49 (brs, 2H), 7.54 (t, J=7.8 Hz, 1H), 7.72 (br appt, 1H), 7.79 (d, J=7.90 Hz, 1H), 8.54 (d, J=8.3 Hz, 1H), 8.79 (br appt, 1H), 9.81 (brs, 1H), 12.33 (brs, 1H, —COOH). $^1$H NMR spectrum of the sample was consistent with the suggested structure of the product.

Example 6

Preparation of (S)-3-(3-bromo-5-(tert-butyl)phenyl)-3-(2-(5-guanidinonicotinamido)acetamido) propanoic acid

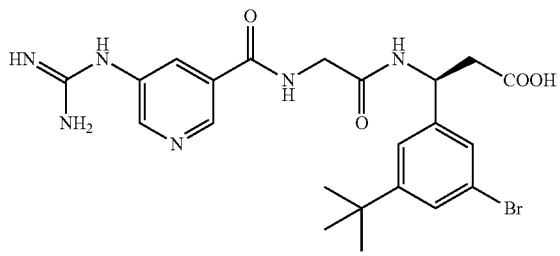 [SMILES: CC(C)(C)c1cc(Br)cc([C@H](CC(=O)O)NC(=O)CNC(=O)c2cncc(NC(=N)N)c2)c1]

Step 1

Preparation of (S)-ethyl 3-(3-bromo-5-(tert-butyl) phenyl)-3-(2-(5-guanidinonicotinamido)acetamido) propanoate

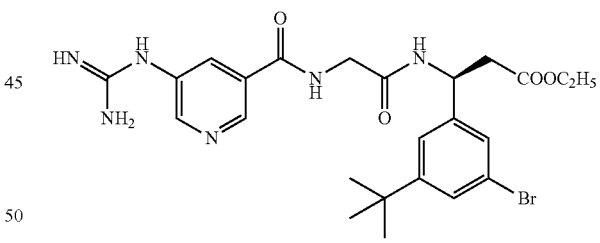

A mixture of 3-guanidinonicotinic acid (Example F) (181.0 mg, 1.00 mmol), (S)-ethyl 3-(2-aminoacetamido)-3-(3-bromo-5-tert-butyl)phenyl)propanoate hydrochloride (Example H) (437.8 mg, 1.00 mmol) and 1-hydroxybenzotriazole hydrate (32 mg, 0.21 mmol) was dissolved in DMF (4 mL) and dichloromethane (4 mL) and stirred at room temperature under nitrogen atmosphere for 10 min to give a colorless suspension. N,N'-diisopropylcarbodiimide (205 uL, 1.33 mmol) was added and the reaction mixture was stirred at room temperature under nitrogen atmosphere overnight. The solvent was evaporated in vacuo to give a yellow to cream crystalline residue. The residue was suspended/dissolved in acetonitrile to give a colorless crystalline precipitate of the urea, filtered and the filtrate was evaporated in vacuo to afford a pale yellow gummy solid of the intermediate product:

(S)-ethyl 3-(3-bromo-5-(tert-butyl)phenyl)-3-(2-(5-guanidinonicotinamido)acetamido) propanoate. LC-MS analysis of the crude residue shows the desired product's mass: m/z 547 ($^{79Br}$M+H), m/z 549 ($^{81Br}$M+H); m/z 569 ($^{79Br}$M+Na), and m/z 571 ($^{81Br}$M+Na); Calcd for $C_{24}H_{31}BrN_6O_4$: 547.44. The crude residue will be used as such for the saponification (step #2).

Step 2

Preparation of (S)-3-(3-bromo-5-(tert-butyl)phenyl)-3-(2-(5-guanidinonicotinamido)acetamido) propanoic acid

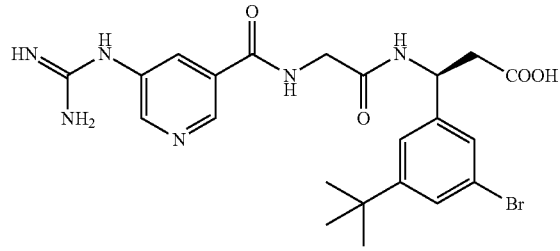 [SMILES: CC(C)(C)c1cc(Br)cc([C@H](CC(=O)O)NC(=O)CNC(=O)c2cncc(NC(=N)N)c2)c1]

To a suspension of the crude (S)-ethyl 3-(3-bromo-5-(tert-butyl)phenyl)-3-(2-(5-guanidinonicotinamido) acetamido) propanoate (1.00 mmol) from step #1 in a mixture of a 1:1 mixture of acetonitrile/water (6 mL) was added lithium hydroxide monohydrate (255 mg, 6.1 mmol) and the reaction mixture was stirred at room temperature overnight. The reaction mixture was neutralized with TFA (1 mL in 3 mL $CH_3CN$) and the mixture was evaporated in-vacuo to give a pale yellow residue. The crude product was purified by reverse-phase HPLC with a gradient 10-60% $CH_3CN$ in water containing 0.05% TFA to give the desired product (Example 6), after lyophilization, as a colorless lyophilized solid (541.0 mg). LC/MS analysis of the product shows the desired product's mass: m/z 519 ($^{79Br}$M+H), m/z 521 ($^{81Br}$M+H); m/z 541 ($^{79Br}$M+Na), and m/z 543 ($^{81Br}$M+Na); Calcd for $C_{22}H_{27}BrN_6O_4$: 519.39. $^1$H NMR (400 MHz, DMSO-$d_6$): δ 1.26 (s, 9H, $(CH_3)_3C$—), 2.70 (d, J=7.20 Hz, 2H, —$CH_2$—COOH), 3.93 (d, J=5.80 Hz, 2H), 5.20 (q, J=7.00 Hz, 1H, —NH—CH—$CH_2$—COOH), 7.34 (br appt, 1H), 7.36 (br appt, 1H), 7.39 (br appt, 1H), 7.75 (brs, 3H), 7.54 (t, J=7.8 Hz, 1H), 8.08 (appt, J=2.0 Hz, 1H), 8.56 (d, J=8.3 Hz, 1H), 8.62 (d, J=2.3 Hz, 1H), 8.93 (d, J=1.7 Hz, 1H), 9.03 (brt, J=5.8 Hz, 1H), 10.09 (brs, 1H), 12.30 (brs, 1H, —COOH). $^1$H NMR spectrum of the sample was consistent with the suggested structure of the product.

Example 7

Preparation of (S)-3-(3-bromo-5-(tert-butyl)phenyl)-3-(2-(3-((4,5-dihydro-1H-imidazol-2-yl)amino)benzamido)acetamido)propanoic acid

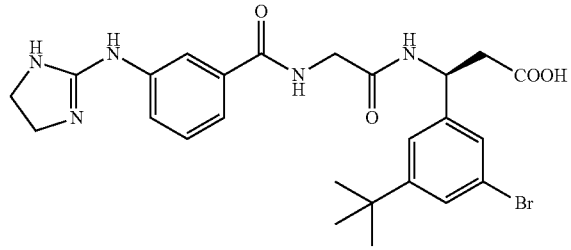 [SMILES: CC(C)(C)c1cc(Br)cc([C@H](CC(=O)O)NC(=O)CNC(=O)c2cccc(NC3=NCCN3)c2)c1]

Step 1

Preparation of (S)-tert-butyl 2-((3-((2-(1-(3-bromo-5-(tert-butyl)phenyl)-3-ethoxy-3-oxopropyl)amino)-2-oxoethyl)carbamoyl)phenyl)amino)-4,5-dihydro-1H-imidazole-1-carboxylate

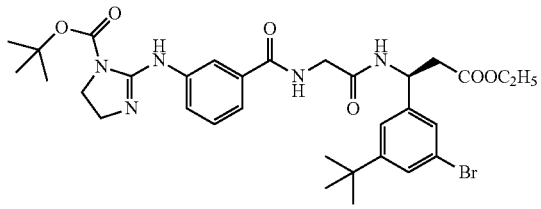

A mixture of 3-((1-tert-butoxycarbonyl)-4,5-dihydro-1H-imidazol-2-yl)amino)benzoic acid (Example D) (305.8 mg, 1.00 mmol), (S)-ethyl 3-(2-aminoacetamido)-3-(3-bromo-5-tert-butyl)phenyl)propanoate hydrochloride (Example H) (437.8 mg, 1.00 mmol) and 1-hydroxybenzotriazole hydrate (32 mg, 0.21 mmol) was dissolved in DMF (4 mL) and dichloromethane (4 mL) and stirred at room temperature under nitrogen atmosphere for 10 min to give a colorless suspension. N,N'-diisopropylcarbodiimide (205 uL, 1.33 mmol) was added and the reaction mixture was stirred at room temperature under nitrogen atmosphere overnight. The solvent was evaporated in vacuo to give a colorless gummy residue. The residue was suspended/dissolved in acetonitrile (10 mL) to give a colorless crystalline precipitate of the urea, filtered and the filtrate was evaporated in-vacuo to afford a pale yellow gummy solid of the intermediate product: (S)-tert-butyl 2-((3-((2-((1-(3-bromo-5-(tert-butyl)phenyl)-3-ethoxy-3-oxopropyl)amino)-2-oxoethyl)carbamoyl)phenyl)amino)-4,5-dihydro-1H-imidazole-1-carboxylate. LC-MS analysis of the crude residue shows the desired product's mass: m/z 672 ($^{79Br}$M+H), m/z 674 ($^{81Br}$M+H); m/z 694 ($^{79Br}$M+Na), and m/z 696 ($^{81Br}$M+Na); Calcd for $C_{32}H_{42}BrN_5O_6$: 672.61 The crude residue will be used as such for the saponification (step #2).

Step 2

Preparation of (S)-3-(3-bromo-5-(tert-butyl)phenyl)-3-(2-(3-O-(tert-butoxycarbonyl)-4,5-dihydro-1H-imidazol-2-yl)amino)benzamido)acetamido)propanoic acid

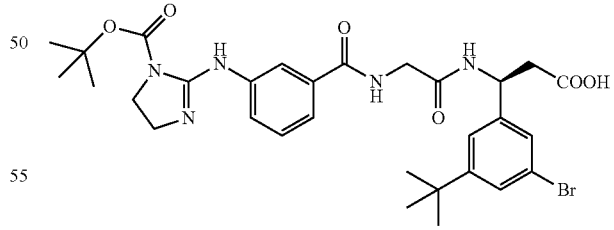

To a suspension of the crude (S)-tert-butyl 2-((3-((2-((1-(3-bromo-5-(tert-butyl)phenyl)-3-ethoxy-3-oxopropyl)amino)-2-oxoethyl)carbamoyl)phenyl)amino)-4,5-dihydro-1H-imidazole-1-carboxylate (1.00 mmol) from step #1 in a mixture of a 1:1 mixture of acetonitrile/water (6 mL) was added lithium hydroxide monohydrate (248 mg, 5.91 mmol) and the reaction mixture was stirred at room temperature overnight. The reaction mixture was neutralized with TFA (1 mL in 3 mL $CH_3CN$) and the mixture was evaporated in-vacuo to give a cream foamy residue of the intermediate product: (S)-3-(3-bromo-5-(tert-butyl)phenyl)-3-(2-(3-((1-(tert-butoxycarbonyl)-4,5-dihydro-1H-imidazol-2-yl)amino)benzamido)acetamido)propanoic acid. LC/MS analysis of the crude product shows the desired product's mass: m/z 644 ($^{79Br}$M+H), and m/z 646 ($^{81Br}$M+H); Calcd for $C_{30}H_{38}BrN_5O_6$: 644.56. The crude residue will be used as such for the deprotection of the Boc-group (step #3).

Step 3

Preparation of (S)-3-(3-bromo-5-(tert-butyl)phenyl)-3-(2-(3-((4,5-dihydro-1H-imidazol-2-yl)amino)benzamido)acetamido)propanoic acid

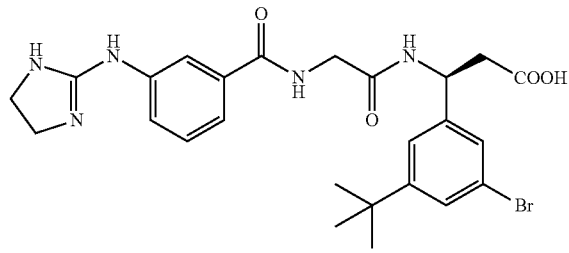 [SMILES: CC(C)(C)c1cc(Br)cc([C@H](CC(=O)O)NC(=O)CNC(=O)c2cccc(NC3=NCCN3)c2)c1]

The crude (S)-3-(3-bromo-5-(tert-butyl)phenyl)-3-(2-(3-((1-(tert-butoxycarbonyl)-4,5-dihydro-1H-imidazol-2-yl)amino)benzamido)acetamido)propanoic acid from Step #2 was dissolved in 20% TFA in acetonitrile (10 mL) and the reaction mixture was stirred at room temperature overnight to give a colorless solution. The solvent was evaporated in vacuo to give a colorless viscous residue. The crude product was purified by reverse-phase HPLC with a gradient 10-70% $CH_3CN$ in water containing 0.05% TFA to give the desired product (Example 7), after lyophilization, as a colorless lyophilized solid (364 mg). LC/MS analysis of the product shows the desired product's mass: m/z 544 ($^{79Br}$M+H), and m/z 546 ($^{81Br}$M+H); Calcd for $C_{25}H_{30}BrN_5O_4$: 544.44. $^1$H NMR (400 MHz, DMSO-$d_6$): δ 1.27 (s, 9H, $(CH_3)_3C$—), 2.71 (d, J=7.30 Hz, 2H, —$CH_2$—COOH), 3.68 (brs, 3H), 3.92 (d, J=5.80 Hz, 2H), 5.20 (q, J=7.5 Hz, 1H, —NH—CH—$CH_2$—COOH), 7.36 (brd, J=9.8 Hz, 2H), 7.41 (brd/m, 2H), 7.55 (t, J=7.8 Hz, 1H), 7.73 (brs, 1H), 7.79 (d, J=7.8 Hz, 1H), 8.46 (s, 2H), 1H), 8.55 (d, J=7.30 Hz, 1H), 8.80 (appt, J=5.80 Hz, 1H), 10.62 (s, 1H), 12.37 (brs, 1H, —COOH). $^1$H NMR spectrum of the sample was consistent with the suggested structure of the product.

Example 8

Preparation of (3S)-3-(3-bromo-5-(tert-butyl)phenyl)-3-(2-(5-((5-hydroxy-1,4,5,6-tetrahydropyrimidin-2-yl)amino)nicotinamido)acetamido)propanoic acid

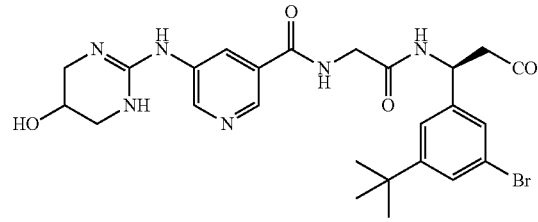

Step 1

Preparation of (3S)-ethyl 3-(3-bromo-5-(tert-butyl)phenyl)-3-(2-(5-((5-hydroxy-1,4,5,6-tetrahydropyrimidin-2-yl)amino)nicotinamido)acetamido)propanoate

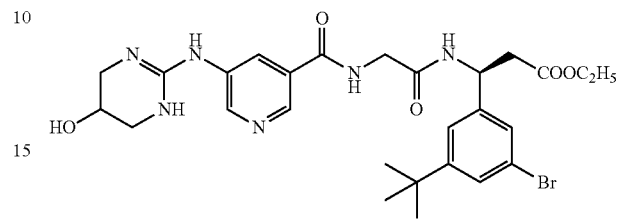

A mixture of 5-((5-hydroxy-1,4,5,6-tetrahydropyrimidin-2-yl)nicotinic acid (Example G) (236.8 mg, 1.00 mmol), (S)-ethyl 3-(2-aminoacetamido)-3-(3-bromo-5-tert-butyl)phenyl) propanoate hydrochloride (Example H) (434.7 mg, 1.00 mmol) and 1-hydroxybenzotriazole hydrate (32 mg, 0.21 mmol) was dissolved in DMF (4 mL) and dichloromethane (4 mL) and stirred at room temperature under nitrogen atmosphere for 10 min to give a colorless suspension. N,N'-diisopropylcarbodiimide (205 µL, 1.33 mmol) was added and the reaction mixture was stirred at room temperature under nitrogen atmosphere overnight. The solvent was evaporated in-vacuo to give a yellow crystalline/gummy residue. The residue was suspended/dissolved in acetonitrile (10 mL) to give a colorless crystalline precipitate of the urea, filtered and the filtrate was evaporated in vacuo to afford a yellow gummy solid of the intermediate product: (3S)-ethyl 3-(3-bromo-5-(tert-butyl)phenyl)-3-(2-(5-((5-hydroxy-1,4,5,6-tetrahydropyrimidin-2-yl)amino)nicotinamido) propanoate. LC-MS analysis of the crude residue shows the desired product's mass: m/z 603 ($^{79Br}$M+H), m/z 605 ($^{81Br}$M+H); m/z 625 ($^{79Br}$M+Na), and m/z 627 ($^{81Br}$M+Na); Calcd for $C_{27}H_{35}BrN_6O_6$: 603.51 The crude residue will be used as such for the saponification (step #2).

Step 2

Preparation of (3S)-3-(3-bromo-5-(tert-butyl)phenyl)-3-(2-(5-((5-hydroxy-1,4,5,6-tetrahydropyrimidin-2-yl)amino)nicotinamido)acetamido)propanoic acid

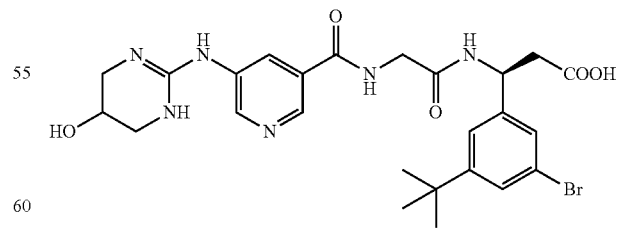

To a suspension of the crude (3S)-ethyl 3-(3-bromo-5-(tert-butyl)phenyl)-3-(2-(5-((5-hydroxy-1,4,5,6-tetrahydropyrimidin-2-yl)amino)nicotinamido) propanoate (1.00 mmol) from step #1 in a mixture of a 1:1 mixture of acetonitrile/water (6 mL) was added lithium hydroxide monohydrate (247 mg, 5.88 mmol) and the reaction mixture was stirred at room temperature overnight. The reaction mixture was neutralized with TFA (1 mL in 3 mL CH$_3$CN) and the mixture was evaporated in-vacuo to give a pale yellow residue. The crude product was purified by reverse-phase HPLC with a gradient 10-70% CH$_3$CN in water containing 0.05% TFA to give the desired product (Example 8), after lyophilization, as a colorless lyophilized solid (611.6 mg). LC/MS analysis of the product shows the desired product's mass: m/z 575 ($^{79Br}$M+H), m/z 577 ($^{81Br}$M+H); and m/z 541 ($^{79Br}$M+Na); Calcd for C$_{25}$H$_{31}$BrN$_6$O$_5$: 575.45. $^1$H NMR (400 MHz, DMSO-d$_6$): δ 1.26 (s, (CH$_3$)$_3$C—), 2.70 (d, J=7.2 Hz, 2H, —CH$_2$—COOH), 3.17 (dt, J=12.4 Hz, 2H), 3.35 (brd, J=12.4 Hz, 2H), 3.93 (d, J=5.80 Hz, 2H), 4.10 (appt/m, 1H), 5.19 (q, J=7.5 Hz, 1H, —NH—CH—CH$_2$—COOH), 7.34 (s/appt, 1H), 7.40 (s/appt, 1H), 8.02 (s/appt, 1H), 8.56 (brs, 2H), 8.90 (d, J=1.60 Hz, 1H), 9.02 (t, J=5.8 Hz, 1H), 9.87 (s, 1H), 12.38 (brs, 1H, —COOH). $^1$H NMR spectrum of the sample was consistent with the suggested structure of the product.

Example 9

Preparation of (S)-3-(3-bromo-5-(tert-butyl)phenyl)-3-(2-(3-((4,5-dihydro-1H-imidazol-2-yl)amino)-5-hydroxybenzamido)acetamido)propanoic

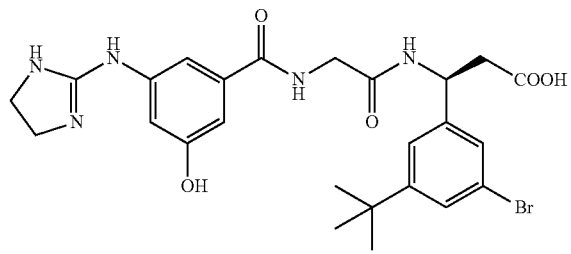 [SMILES: CC(C)(C)c1cc(Br)cc([C@H](CC(=O)O)NC(=O)CNC(=O)c2cc(O)cc(NC3=NCCN3)c2)c1]

Step 1

Preparation of (S)-ethyl 3-(3-bromo-5-(tert-butyl)phenyl)-3-(2-(3-((4,5-dihydro-1H-imidazol-2-yl)amino)-5-hydroxybenzamido)acetamido)propanoate

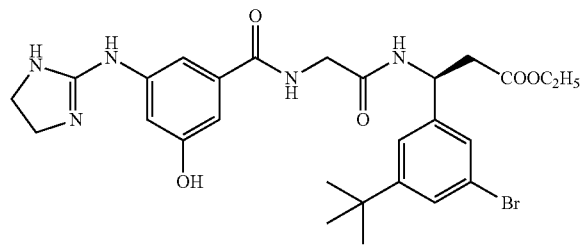

A mixture of 3-((4,5-dihydro-1H-imidazol-2-yl)amino)-5-hydroxybenzoic acid formic acid salt (Example E) (268.7 mg, 1.00 mmol), (S)-ethyl 3-(2-aminoacetamido)-3-(3-bromo-5-tert-butyl)phenyl)propanoate hydrochloride (Example H) (437.8 mg, 1.00 mmol) and 1-hydroxybenzotriazole hydrate (32 mg, 0.21 mmol) was dissolved in DMF (4 mL) and dichloromethane (4 mL) and stirred at room temperature under nitrogen atmosphere for 10 min to give a colorless suspension. N,N'-diisopropylcarbodiimide (205 μL, 1.33 mmol) was added and the reaction mixture was stirred at room temperature under nitrogen atmosphere overnight. The solvent was evaporated in vacuo to give a pale yellow gummy residue. The residue was suspended/dissolved in acetonitrile (10 mL) to give a colorless crystalline precipitate of the urea, filtered and the filtrate was evaporated in vacuo to afford a pale yellow gummy solid of the intermediate product: (S)-ethyl 3-(3-bromo-5-(tert-butyl)phenyl)-3-(2-(3-((4,5-dihydro-1H-imidazol-2-yl)amino)-5-hydroxybenzamido) acetamido)propanoate. LC-MS analysis of the crude residue shows the desired product's mass: m/z 588 ($^{79Br}$M+H), m/z 590 ($^{81Br}$M+H); m/z 610 ($^{79Br}$M+Na), and m/z 612 ($^{81Br}$M+Na); Calcd for C$_{27}$H$_{34}$BrN$_5$O$_5$: 588.49. The crude product was purified by reverse-phase HPLC with a gradient 10-70% CH$_3$CN in water containing 0.05% TFA to give the desired product as a colorless foamy solid (300 mg) which will be used as such for the saponification (step #2).

Step 2

Preparation of (S)-3-(3-bromo-5-(tert-butyl)phenyl)-3-(2-(3-((4,5-dihydro-1H-imidazol-2-yl)amino)-5-hydroxybenzamido)acetamido)propanoic acid

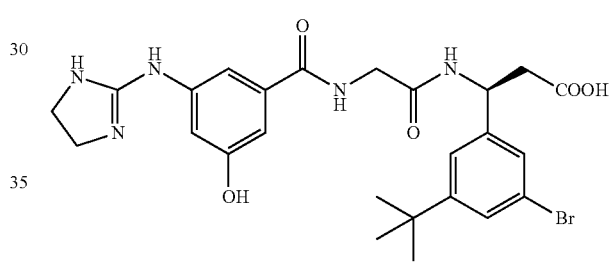

To a suspension of the purified (S)-ethyl 3-(3-bromo-5-(tert-butyl)phenyl)-3-(2-(3-((4,5-dihydro-1H-imidazol-2-yl)amino)-5-hydroxybenzamido) acetamido)propanoate (0.51 mmol) intermediate from step #1 in a mixture of a 1:1 mixture of acetonitrile/water (6 mL) was added lithium hydroxide monohydrate (190 mg, 4.53 mmol) and the reaction mixture was stirred at room temperature overnight. The reaction mixture was neutralized with TFA (1 mL TFA in 4 mL CH$_3$CN) and the solvent was evaporated in-vacuo to give a cream foamy residue. The crude product was purified by reverse-phase HPLC with a gradient 10-70% CH$_3$CN in water containing 0.05% TFA to give the desired product (Example 9), after lyophilization, as a colorless lyophilized solid (83.0 mg). LC/MS analysis of the product shows the desired product's mass: m/z 560 ($^{79Br}$M+H), and m/z 562 ($^{81Br}$M+H); Calcd for C$_{25}$H$_{30}$BrN$_5$O$_5$: 560.44.

$^1$H NMR (400 MHz, DMSO-d$_6$): δ 1.26 (s, 9H, (CH$_3$)$_3$C—), 2.70 (d, J=7.40 Hz, 2H, —CH$_2$—COOH), 3.66 (s, 4H, —CH$_2$—CH$_2$—), 3.87 (d, J=5.92 Hz, 2H), 5.18 (q, J=5.92 Hz, 1H, —NH—CH—CH$_2$—COOH), 6.78 (t/, J=2.08 Hz, 1H), 7.13 (t, J=1.64 Hz, 1H), 7.16 (t, J=1.82 Hz, 1H), 7.34 (t J=1.48 Hz, 1H), 7.36 (t, J=1.47 Hz, 1H), 7.40 (t, J=1.75 Hz, 1H), 8.41 (s, 2H), 8.52 (d, J=8.25 Hz, 1H), 8.64 (t, J=5.95 Hz, 1H), 10.07 (brs, 1H), 10.54 (s, 1H), 12.35 (brs, 1H, —COOH). $^1$H NMR spectrum of the sample was consistent with the suggested structure of the product.

Example 10

Preparation of (S)-3-(3,5-di-tert-butylphenyl)-3-(2-(5-guanidinonicotinamido)acetamido)propanoic acid

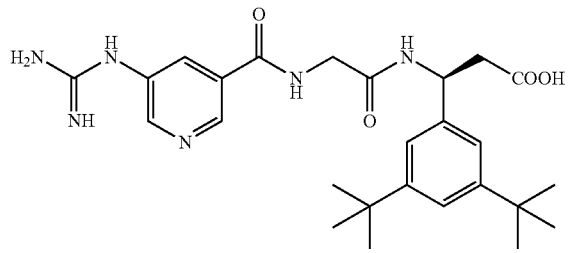 [SMILES: CC(C)(C)c1cc([C@H](CC(=O)O)NC(=O)CNC(=O)c2cncc(NC(=N)N)c2)cc(C(C)(C)C)c1]

Step 1

Preparation of 3-amino-3-(3,5-di-tert-butylphenyl)propionic acid

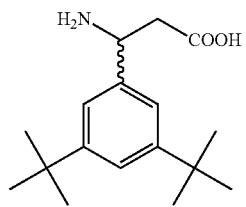 [SMILES: CC(C)(C)c1cc(C(N)CC(=O)O)cc(C(C)(C)C)c1]

A mixture 3,5-di-tert-butylbenzaldehyde (0.996 g, 4.56 mmol), malonic acid (0.572 g, 5.50 mmol) and ammonium acetate (0.710 g, 9.21 mmol) in isopropanol (30 mL) was heated at reflux under nitrogen for 5 h to afford a colorless solid. The solid was filtered and washed with hot isopropanol (30 mL). The residue was dried in vacuo to give the desired racemic product as a colorless solid (0.340 g).

Step 2

Preparation of ethyl 3-amino-3-(3,5-di-tert-butylphenyl)propionate hydrochloride

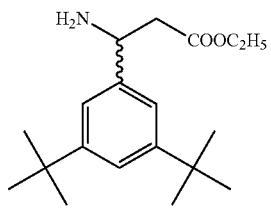

Absolute ethanol saturated with anhydrous HCl gas (100 mL) was added to 3-amino-3-(3,5-di-tert-butylphenyl)propionic acid (2.558 g, 9.22 mmol) and the reaction mixture was heated at reflux for 2 h to give a colorless solution. The solvent was removed in vacuo to give a colorless gummy solid. The solid was slurried a couple of times with diethyl ether. After the solvent was decanted off, the residue was dried in vacuo to give the racemic β-amino ester hydrochloride salt as a colorless solid (2.48 g).

Step 3

Preparation of (S)-ethyl 3-amino-3-(3,5-di-tert-butylphenyl)propionate hydrochloride

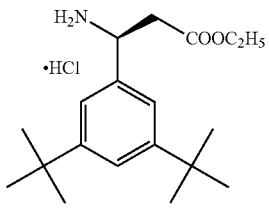

Enzymatic Resolution of the Racemic Mixture:

A suspension of ethyl 3-amino-3-(3,5-di-tert-butylphenyl)propionate hydrochloride (1.0 g, 2.92 mmol) in water (5.0 mL) was basified with 2.5N NaOH (pH ~12) by drop wise addition to give a cream colored oily residue. The pH of the aqueous layer was adjusted to pH 8.32 by the addition of 50 mM $KH_2PO_4$ solution. Amano lipase PS (1.20 g) was added to above reaction mixture and the reaction mixture was stirred at room temperature overnight. The reaction mixture was filtered after 23 h and the solid was washed with acetone to give a colorless solid of the resolved (S)-acid (376.5 mg).

Absolute ethanol saturated with anhydrous HCl gas (50 mL) was added to (S)-3-amino-3-(3,5-di-tert-butylphenyl)propionic acid (0.916 g, 3.30 mmol) and the reaction mixture was heated at reflux for 2 h to give a colorless solution. The solvent was removed in vacuo to give a colorless gummy solid. The solid was slurried a couple of times with diethyl ether. After the solvent was decanted off, the residue was dried in vacuo to give the desired (S)-β-amino ester hydrochloride salt as a colorless solid (1.19 g).

Step 4

Preparation of (S)-ethyl 3-(2-((tert-butoxycarbonyl)amino)acetamido)-3-(3,5-di-tert-butylphenyl)propanoate

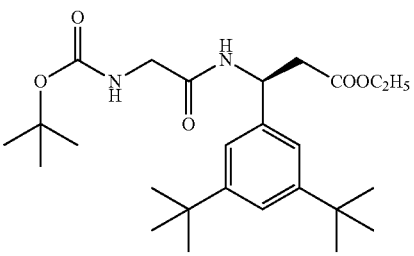

To a solution of a mixture of (S)-ethyl 3-amino-3-(3,5-di-tert-butylphenyl)propionate hydrochloride (112.0 mg, 0.33 mmol) and Boc-Gly-Osu (95.0 mg, 0.35 mmol) in anhydrous DMF was added triethylamine (62 μL, 0.45 mmol) and the reaction mixture was stirred at room temperature under nitrogen atmosphere overnight to give a colorless solution. The solvent was evaporated in-vacuo and the residue was partitioned between ethyl acetate (25 mL), water (25 mL) and saturated NaHCO$_3$ solution (10 mL). The organic layer was removed, washed with water (1×10 mL), dried over anhydrous Na$_2$SO$_4$, filtered and evaporated in vacuo to afford a cream foamy solid (163.4 mg). LC-MS analysis of the solid shows the desired product's mass: m/z 463 (M+H) and m/.z 485 (M+Na); Calcd for C$_{26}$H$_{42}$N$_2$O$_5$: 462.62. The above product will be used as such for the Boc-deprotection. (step #5).

Step 5

Preparation of (S)-ethyl 3-(2-aminoacetamido)-3-(3,5-di-tert-butylphenyl)propanoate hydrochloride

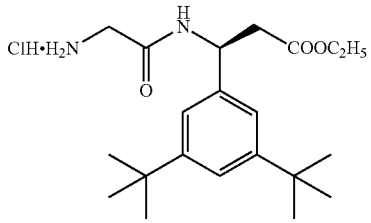

To a solution of S)-ethyl 3-(2-((tert-butoxycarbonyl)amino)acetamido)-3-(3,5-di-tert-butylphenyl)propanoate (163.4 mg, 0.35 mmol) in 1,4-dioxane (2 mL) was added 4.0 M HCl solution in 1,4-dioxane and the reaction mixture was stirred at room temperature for 1 h. Evaporation of the solvent in vacuo and the crystallization of the residue from ethyl acetate/hexanes mixture afforded a colorless foamy solid (153.0 mg). LC-MS analysis of the solid shows the desired product's mass: m/z 363 (M+H) and m/z 725 (2M+H); Calcd for C$_{21}$H$_{34}$N$_2$O$_3$: 362.51.

Step 6

Preparation of (S)-ethyl 3-(3,5-di-tert-butylphenyl)-3-(2-(5-guanidinonicotinamido)acetamido) propanoate

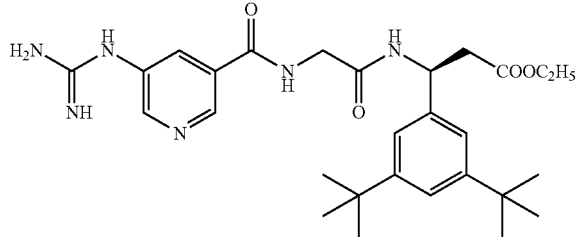

A mixture of 5-guanidinonicotinic acid (Example F) (70.8 mg, 0.39 mmol), (S)-ethyl 3-(2-aminoacetamido)-3-(3,5-di-tert-butyl)phenyl)propanoate hydrochloride (from step 5) (153.0 mg, 0.38 mmol) and 1-hydroxybenzotriazole hydrate (12.2 mg, 0.08 mmol) was dissolved in DMF (3 mL) and dichloromethane (3 mL) and stirred at room temperature under nitrogen atmosphere for 5 min to give a cream suspension. To above suspension, neat N,N'-diisopropylcarbodiimide (80 µL, 0.52 mmol) was added and the reaction mixture was stirred at room temperature under nitrogen atmosphere overnight. The solvent was evaporated in vacuo to give a cream gummy residue of the intermediate product: (S)-ethyl 3-(3,5-di-tert-butylphenyl)-3-(2-(5-guanidinonicotinamido) acetamido) propanoate. LC-MS analysis of the crude residue shows the desired product's mass: m/z 525 (M+H), and m/z 547 (M+Na); Calcd for C$_{28}$H$_{40}$N$_6$O$_4$: 524.66. The crude product will be used as such for the saponification (step #7).

Step 7

Preparation of (S)-3-(3,5-di-tert-butylphenyl)-3-(2-(5-guanidinonicotinamido)acetamido)propanoic acid

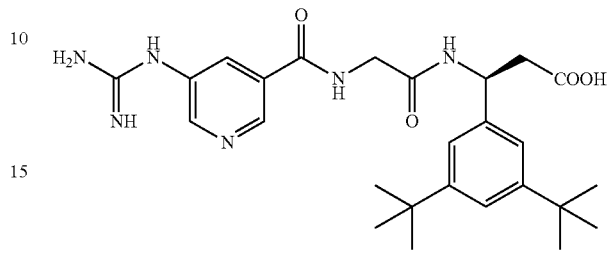

To a suspension of (S)-ethyl 3-(3,5-di-tert-butylphenyl)-3-(2-(5-guanidinonicotinamido) acetamido) propanoate (0.39 mmol) from step #6 in a mixture of a 1:1 mixture of acetonitrile/water (6 mL) was added lithium hydroxide monohydrate (83 mg, 1.98 mmol) and the reaction mixture was stirred at room temperature overnight. The solvent was evaporated in vacuo to afford a pale yellow crystalline-gummy residue. The residue was dissolved in water (20 mL) and extracted with dichloromethane (2×25 mL) to remove N,N'-diisopropylurea (DIPU). The aqueous layer was neutralized with TFA (1 mL TFA in 3 mL CH$_3$CN) and evaporated in vacuo to give a cream gummy residue. The crude product was purified by reverse-phase HPLC with a gradient 10-80% CH$_3$CN in water containing 0.05% TFA to give the desired product (Example 10), after lyophilization, as a colorless lyophilized solid (122.3 mg). LC-MS analysis shows the desired product's mass: m/z 497 (M+H) and m/z 993 (2M+H); Calcd for C$_{26}$H$_{36}$N$_6$O$_4$: 496.60.

$^1$H NMR (400 MHz, DMSO-d$_6$): δ 1.27 (s, 18H, 2×(CH$_3$)$_3$C—), 2.68 (d, J=7.60 Hz, 2H, —CH$_2$—COOH), 3.93 (d, J=7.40 Hz, 2H), 5.24 (q, J=7.45 Hz, 1H, —NH—CH—CH$_2$—COOH), 7.17 (d, J=1.67 Hz, 2H), 7.26 (appt, J=1.75 Hz, 1H), 7.69 (s, 4H), 8.07 (appt, J=2.20 Hz, 1H), 8.53 (d, J=8.64 Hz, 1H), 8.61 (d, J=2.46 Hz, 1H), 8.93 (d, J=1.80 Hz, 1H), 9.00 (t, J=5.80 Hz, 1H), 9.96 (s, 1H), 12.26 (brs, 1H, —COOH). $^1$H NMR spectrum of the sample was consistent with the suggested structure of the product.

Example 11

Preparation of (3S)-3-(3-bromo-5-(2-cyanopropan-2-yl)phenyl)-3-(2-(3-hydroxy-5-((5-hydroxy-1,4,5,6-tetrahydropyrimidin-2-yl)amino)benzamido)acetamido)propanoic acid

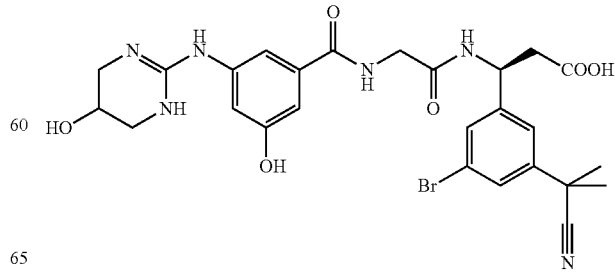

327
Step 1
Preparation of (S)-Ethyl 3-amino-3-(3-bromo-5-(2-cyanopropan-2-yl)phenyl)propanoate hydrochloride
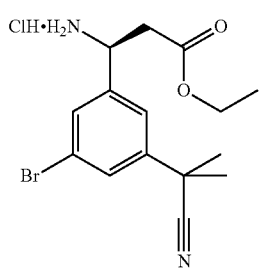
The following Scheme describes the synthesis of (S)-ethyl 3-amino-3-(3-bromo-5-(2-cyanopropan-2-yl)phenyl)propionate which will be used in the synthesis of Example 11:
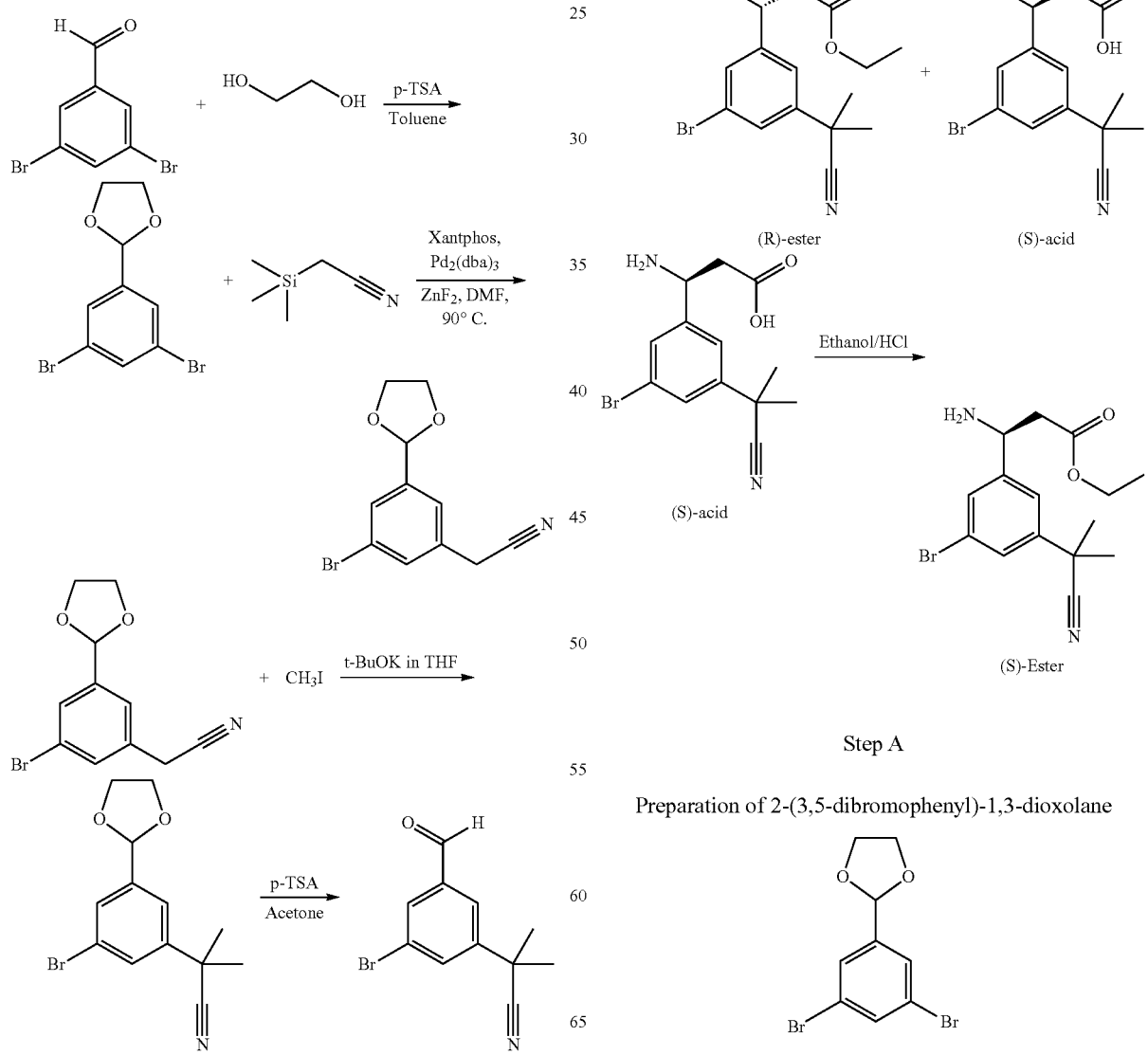
328
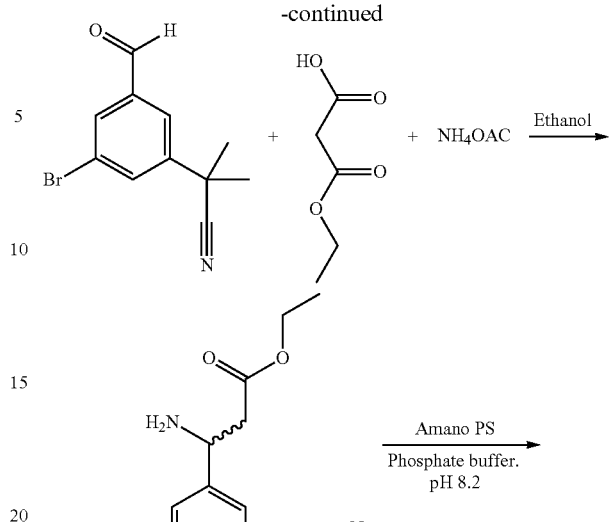
Step A
Preparation of 2-(3,5-dibromophenyl)-1,3-dioxolane
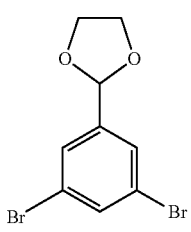

A mixture of 3,5-dibromobenzaldehyde (5.37 g, 20.37 mmol), ethylene glycol (3.40 mL, 61.10 mmol) and p-toluenesulfonic acid monohydrate (78 mg, 0.41 mmol) in anhydrous toluene (30 mL) was heated at reflux under Dean-Stark conditions for 5 h. The reaction mixture was cooled to room temperature and diluted with ethyl acetate (25 mL). The ethyl acetate layer was washed with a saturated NaHCO$_3$ solution (25 mL). The organic layer was removed and washed with water (1×25 mL) and dried with anhydrous MgSO$_4$, filtered and evaporated in vacuo to give a colorless viscous liquid (6.27 g). GC-MS (Cl/methane) analysis of the liquid shows the desired product's mass: m/z 306 ($^{79Br,79Br}$M$^+$), m/z 308 ($^{79Br,81Br}$M$^+$), and m/z 310 ($^{81Br,81Br}$M$^+$); Calcd for C$_9$H$_8$Br$_2$O$_2$: 307.96. $^1$H NMR (400 MHz, CDl$_3$): δ 3.97-4.10 (M, 4H, 2×—CH$_2$—O—), 5.74 (s, 1H, O—CH-0), 7.53 (d, J=1.80 Hz, 2H), 7.63 (appt, J=1.80 Hz, 1H). $^1$H NMR spectrum of the liquid was consistent with the suggested structure of the product.

Step B

Preparation of 2-(3-bromo-5-(1,3-dioxolan-2-yl)phenyl)acetonitrile

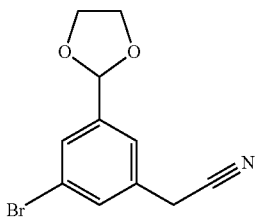

To a screw-capped vial containing 2-(3,5-dibromophenyl)-1,3-dioxolane (4.g, 12.99 mmol), Xantphos (0.15 g, 0.26 mmol), Pd$_2$(dba)$_3$ in anhydrous DMF (5.0 mL) was added trimethylsilyl acetonitrile (2.20 mL, 16.07 mmol) and the reaction mixture was degassed with nitrogen for 15 min to give an orange-red suspension. To the above mixture was added ZnF$_2$ under nitrogen atmosphere and the vial sealed with a cap containing a PTFE/silicone septum under nitrogen. The heterogeneous mixture was heated with stirring at 90° C. in an oil bath to give an olive green suspension. The reaction mixture was let stirred at 90° C. for 22 h to give a dark brown suspension/solution. The reaction mixture cooled to room temperature and diluted with diethyl ether (100 mL). The resulting solution was washed with water (2×75 mL). The organic layer was removed and evaporated in vacuo and the residue was dissolved in ethyl acetate (50 mL), dried over anhydrous Na$_2$SO$_4$, filtered and evaporated in vacuo to afford an orange-red viscous liquid (3.65 g). Purification of the crude product by Silica-gel flash chromatography on silica gel column and elution with 10-80% ethyl acetate in hexanes afforded the desired product as a pale yellow viscous liquid (1.95 g). LC-MS analysis of the liquid shows the desired product's mass: m/z 268 ($^{79Br}$M+H), m/z 270 ($^{81Br}$M+H), m/z 290 ($^{79Br}$M+Na), and m/z 292 ($^{81Br}$M+Na); GC-MS (EI mode) analysis also shows the desired product's mass: m/z 266 ($^{79Br}$M$^+$) and m/z 268 ($^{81Br}$M$^+$), Calcd for C$_{11}$H$_{10}$BrNO$_2$: 268.11. $^1$H NMR (400 MHz, CDCl$_3$): δ 3.72 (s, 2H, —CH$_2$CN), 3.98-4.05 (M, 2H, —CH$_2$—O—), 4.06-4.13 (M, 2H, —CH$_2$—O—), 5.75 (s, 1H, O—CH—O), 7.36 (s, 1H), 7.47 (s, 1H), 7.58 (s, 1H). $^1$H NMR spectrum of the liquid was consistent with the suggested structure of the product.

Step C

Preparation of 2-(3-bromo-5-(1,3-dioxolan-2-yl)phenyl)-2-methylpropanenitrile

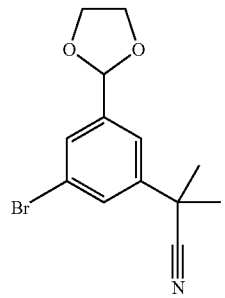 [SMILES: Br ; Cc1cc(C2OCCO2)cc(C(C)(C)C#N)c1]

To a 1.0 M solution of potassium tert-butoxide in THF (18 mL, 18 mmol) at −50° C. was added a solution of a mixture of 2-(3-bromo-5-(1,3-dioxolan-2-yl)phenyl)acetonitrile (1.92 g, 7.16 mmol) and iodomethane (1.40 mL, 22.49 mmol) in THF (10 mL) under nitrogen atmosphere over a period of 50-60 min. The cooling bath was removed after 1 h and the reaction mixture was allowed to warm to room temperature and the reaction mixture was stirred at room temperature for 2 h to give a light beige suspension. The reaction mixture was quenched with water (50 mL) to give an orange-brown solution. THF (~25 mL) was removed in-vacuo and the aqueous phase was extracted with ethyl acetate (3×25 mL). The combined organic layers were washed with water (1×50 mL), brine (1×25 mL) and dried over anhydrous Na$_2$SO$_4$, filtered and evaporated in-vacuo to afford an orange brown viscous liquid (1.9836 g). LC-MS analysis of the liquid shows the desired product's mass: m/z 296 ($^{79Br}$M+H), m/z 298 ($^{81Br}$M+H), m/z 318 ($^{79Br}$M+Na), and m/z 320 ($^{81Br}$M+Na); Calcd for C$_{13}$H$_{14}$BrNO$_2$: 296.16. The crude product will be used as such for the next step.

Step D

Preparation of 2-(3-bromo-5-formylphenyl)-2-methylpropanenitrile

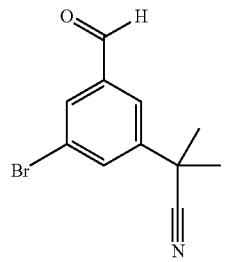

To a solution of 2-(3-bromo-5-(1,3-dioxolan-2-yl)phenyl)-2-methylpropanenitrile (1.9836 g, 6.70 mmol) in acetone (25 mL) was added p-toluenesulfonic acid hydrate (0.26 g, 1.36 mmol) and the reaction mixture was stirred at room temperature overnight to give an orange-red solution. The solvent was evaporated in vacuo to give an orange-brown residue. The residue was partitioned between aqueous saturated NaHCO₃ solution (25 mL) and ethyl acetate (50 mL), the organic layer was removed, washed with brine (1×25 mL), dried over anhydrous sodium sulfate, filtered and evaporated in vacuo to give an orange viscous liquid (2.08 g). Purification of the crude product by silica-gel flash chromatography on silica gel column and elution with 5-40% ethyl acetate in n-hexane afforded the desired product as a pale yellow crystalline solid (0.89 g). LC-MS analysis of the solid shows the desired product's mass: m/z 252 ($^{79Br}$M+H), m/z 254 ($^{81Br}$M+H); Calcd for $C_{11}H_{10}BrNO$: 252.11

Step E

Preparation of racemic ethyl 3-amino-3-(3-bromo-5-(2-cyanopropan-2-yl)phenyl)propanoate

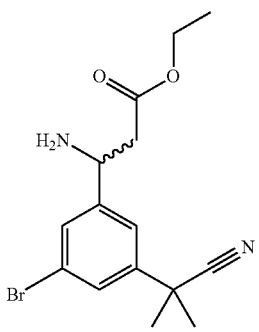 [SMILES: Br ; CCOC(=O)CC(N)c1cc(C)cc(C(C)(C)C#N)c1]

A solution of 2-(3-bromo-5-formylphenyl)-2-methylpropanenitrile (0.884 g, 3.51 mmol), mono-ethyl malonate (1.107 g, 8.38 mmol) and ammonium acetate (1.49 g, 19.33 mmol) in anhydrous ethanol (50 mL) was heated at reflux for 8 h to give a pale yellow solution. The reaction mixture was cooled to room temperature and the solvent was evaporated in-vacuo to give a yellow viscous liquid. The residue was partitioned between aqueous saturated NaHCO₃ solution (25 mL) and ethyl acetate (50 mL), the organic layer was removed, dried over anhydrous sodium sulfate, filtered and evaporated in vacuo to give a yellow viscous liquid of the amino ester (1.18 g). LC-MS analysis of the crude product shows the desired product's mass: m/z 339 ($^{79Br}$M+H), m/z 341 ($^{81Br}$M+H), m/z 361 ($^{79Br}$M+Na), and m/z 363 ($^{81Br}$M+Na); Calcd for $C_{15}H_{19}BrNO2O_2$: 339.23, LC-MS also shows the byproduct: (E)-ethyl 3-(3-bromo-5-(2-cyanopropan-2-yl) phenyl)acrylate's mass: m/z 322 ($^{79Br}$M+H), and m/z 324 ($^{81Br}$M+H); Calcd for $C_{15}H_{16}BrNO_2$: 322.20. The crude product was purified by reverse-phase HPLC with a gradient 10-50% CH₃CN in water containing 0.05% TFA to give the desired product as a colorless glassy solid. The solid was dissolved in absolute ethanol saturated with anhydrous HCl gas (5 mL) and the reaction mixture was stirred for 2 h and evaporated in vacuo to afford a colorless crystalline/foamy solid (0.4212 g) (HCl salt).

Step F

Preparation of (S)-3-amino-3-(3-bromo-5-(2-cyanopropan-2-yl)phenyl)propanoic acid

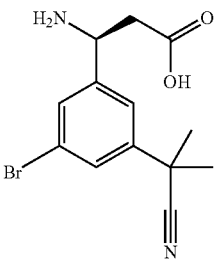 [SMILES: Br ; Cc1cc([C@@H](N)CC(=O)O)cc(C(C)(C)C#N)c1]

Enzymatic Resolution of the Racemic Mixture:

A suspension of the product from the above step E (421.2 mg, 1.12 mmol) in 50 mM KH₂PO₄ solution (40.0 mL) was stirred at room temperature and the pH of the aqueous layer was adjusted to pH 8.20 by the addition of 1.0 N NaOH solution. Amano Lipase PS (523 mg, excess) was added to above suspension and the reaction mixture was stirred at room temperature overnight. A slightly turbid solution was obtained after stirring for 3 days. No solid or precipitate was obtained, the desired (S)-acid might be soluble in the above aqueous system. The above mixture was diluted with MTBE (2×25 mL) and reaction mixture was stirred at room temperature for 15 min to extract the (R)-ester. Evaporation of the aqueous layer in vacuo afforded a cream solid containing the (S)-acid as well as Amano Lipase and Phosphate buffer salt. LC-MS analysis of the crude residue shows the desired (S)-acid's mass: m/z 311 ($^{79Br}$M+H), m/z 313 ($^{81Br}$M+H), m/z 333 ($^{79Br}$M+Na), and m/z 335 ($^{81Br}$M+Na); Calcd for $C_{15}H_{19}BrN2O_2$:311.17. The crude product was purified by reverse-phase HPLC with a gradient 10-40% CH₃CN in water containing 0.05% TFA to give the desired product as a colorless foamy solid (0.253 g). (TFA salt).

Step G

Preparation of (S)-ethyl 3-amino-3-(3-bromo-5-(2-cyanopropan-2-yl)phenyl)propanoate

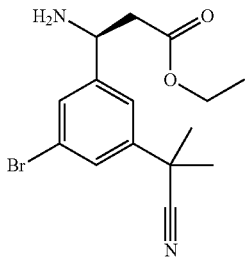 [SMILES: CCOC(=O)C[C@H](N)c1cc(Br)cc(C(C)(C)C#N)c1]

The product from step F was dissolved in abs. ethanol saturated with dry HCl gas (5 mL) and the reaction mixture was heated at reflux for 2 h to give a colorless solution. Evaporation of the solvent in vacuo gave a colorless glassy/ viscous liquid. The residue was triturated with diethyl ether (10 mL) and evaporated in vacuo to afford a colorless foamy solid (221 mg). (HCl salt) LC/MS analysis of the solid shows the desired product's mass: m/z 339 ($^{79Br}$M+H), m/z 341 ($^{81Br}$M+H), m/z 361 ($^{79Br}$M+Na), and m/z 363 ($^{81Br}$M+Na); Calcd for $C_{15}H_{19}BrN_2O_2$: 339.23.

Step 2

Preparation of (3S)-ethyl 3-(3-bromo-5-(2-cyanopropan-2-yl)phenyl)-3-(2-(3-hydroxy-5-((5-hydroxy-1,4,5,6-tetrahydropyrimidin-2-yl)amino)benzamido)acetamido)propanoate

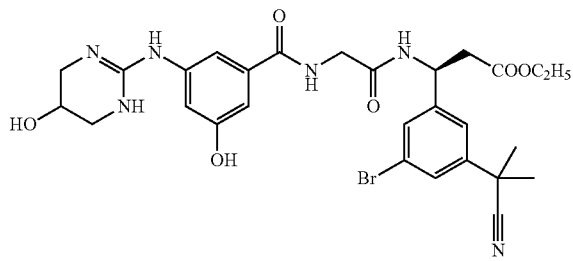

A mixture of 2-(3-hydroxy-5-((5-hydroxy-1,4,5,6-tetrahydropyrimidin-2-yl)amino)benzamido)acetic acid (Example B) (120.8 mg, 0.39 mmol), (S)-ethyl 3-amino-3-(3-bromo-5-(2-cyanopropan-2-yl)phenyl)propanoate hydrochloride (from step #1, step G) (145 mg, 0.039 mmol) and 1-hydroxybenzotriazole hydrate (13 mg, 0.85 mmol) was dissolved in DMF (3.0 mL) and dichloromethane (3.0 mL) and stirred at room temperature under nitrogen atmosphere for 10 min to give a colorless suspension. N,N'-diisopropylcarbodiimide (80 μL, 0.52 mmol) was added and the reaction mixture was stirred at room temperature under nitrogen atmosphere overnight. The solvent was evaporated in vacuo to give a cream residue of the intermediate product: (3S)-ethyl 3-(3-bromo-5-(2-cyanopropan-2-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 629 ($^{79Br}$M+H) and m/z 631 ($^{81Br}$M+H); Calcd for $C_{28}H_{33}BrN_6O_6$: 629.50 The crude residue will be used as such for the saponification (step #3).

Step 3

Preparation of (3S)-3-(3-bromo-5-(2-cyanopropan-2-yl)phenyl)-3-(2-(3-hydroxy-5-((5-hydroxy-1,4,5,6-tetrahydropyrimidin-2-yl)amino)benzamido)acetamido)propanoic acid

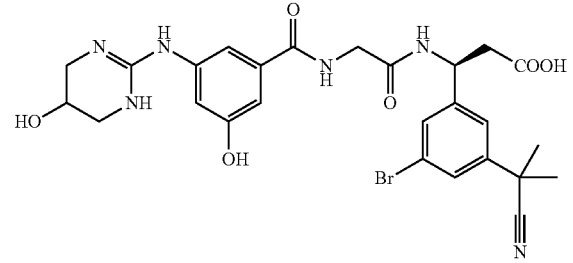 [SMILES: CC(C)(C#N)c1cc(Br)cc([C@H](CC(=O)O)NC(=O)CNC(=O)c2cc(O)cc(NC3=NCC(O)CN3)c2)c1]

To a suspension of (3S)-ethyl 3-(3-bromo-5-(2-cyanopropan-2-yl)phenyl)-3-(2-(3-hydroxy-5-((5-hydroxy-1,4,5,6-tetrahydropyrimidin-2-yl)amino)benzamido)acetamido)propanoate (~0.39 mmol) (from step #2) in a mixture of a 1:1 mixture of acetonitrile/water (6 mL) was added lithium hydroxide monohydrate (84 mg, 2.0 mmol) and the reaction mixture was stirred at room temperature overnight. The solvent was evaporated in vacuo and the residue was dissolved in water (25 mL) and extracted with dichloromethane (2×25 mL) to remove to remove the urea. The aqueous layer was neutralized with TFA (1 mL in 3 mL $CH_3CN$) and the mixture was evaporated in-vacuo to give a colorless residue. The crude product was purified by reverse-phase HPLC with a gradient 10-50% $CH_3CN$ in water containing 0.05% TFA to give the desired product (Example 11), after lyophilization, as a colorless lyophilized solid (184.0 mg). LC/MS analysis of the product shows the desired product's mass: m/z 601 ($^{79Br}$M+H), m/z 603 ($^{81Br}$M+H); m/z 623 ($^{79Br}$M+Na) and m/z 625 ($^{81Br}$M+Na); Calcd for $C_{26}H_{29}BrN_6O_6$: 601.45.

$^1$H NMR (400 MHz, DMSO-$d_6$): δ 1.70 (s, 6H, $(CH_3)_2$C—), 2.74 (d, J=7.20 Hz, 2H, —$CH_2$—COOH), 3.17 t(brd, 2H), 3.35 (brdt, 2H), 3.88 (d, J=5.70 Hz, 2H), 4.09 (appt, 1H), 5.21 (q, J=7.46 Hz, 1H, —NH—CH—$CH_2$—COOH), 5.44 (brs, 1H), 6.75 (s, 1H), 7.12 (s, 1H), 7.15 (s, 1H), 7.50 (s, 1H), 7.54 (s, 1H), 7.58 (s, 1H), 8.09 (brs, 2H), 8.58 (d, J=8.10 Hz, 1H), 8.65 (brt, J=5.80 Hz, 1H), 9.58 (s, 1H), 10.01 (brs, 1H), 12.43 (brs, 1H, —COOH). $^1$H NMR spectrum of the solid was consistent with the suggested structure of the product.

Example 12

Preparation of (3S)-3-(3-(tert-butyl)-5-cyanophenyl)-3-(2-(3-hydroxy-5-((5-hydroxy-1,4,5,6-tetrahydropyrimidin-2-yl)amino)benzamido)acetamido)propanoic acid

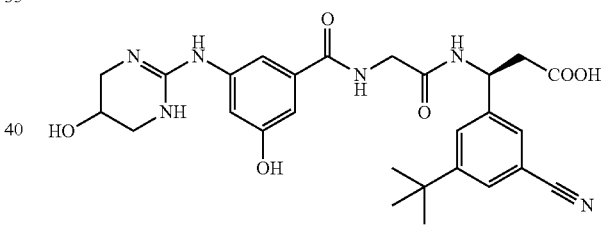

Step 1

Preparation of (3S)-ethyl 3-(3-(tert-butyl)-5-cyanophenyl)-3-(2-(3-hydroxy-5-((5-hydroxy-1,4,5,6-tetrahydropyrimidin-2-yl)amino)benzamido)acetamido)propanoate

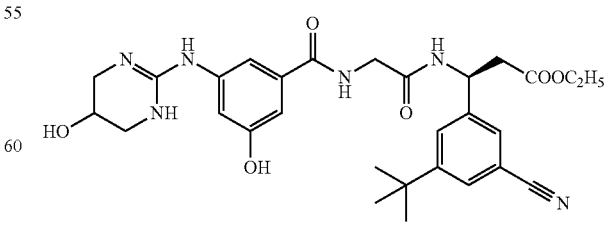

A mixture of 3-Hydroxy-5-((5-hydroxy-1,4,5,6-tetrahydropyrimidin-2-yl)aminobenzoic acid (Example A), (152.6 mg, 0.61 mmol), (S)-ethyl 3-(2-aminoacetamido)-3-(3-(tert-butyl)-5-cyanophenyl)propanoate hydrochloride (Example I) (223.5 mg, 0.61 mmol) and 1-hydroxybenzotriazole hydrate (19.6 mg, 0.128 mmol) was dissolved in DMF (4 mL) and dichloromethane (4 mL) and stirred at room temperature under nitrogen atmosphere for 10 min to give a colorless suspension. N,N'-diisopropylcarbodiimide (125 μL, 0.81 mmol) was added and the reaction mixture was stirred at room temperature under nitrogen atmosphere overnight. The solvent was evaporated in vacuo to give a yellow viscous residue of the intermediate product: (3S)-ethyl 3-(3-(tert-butyl)-5-cyanophenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 565 (M+H); Calcd for $C_{29}H_{36}N_6O_6$:564.63 The crude residue will be used as such for the saponification (step #2).

Step 2

Preparation of (3S)-3-(3-(tert-butyl)-5-cyanophenyl)-3-(2-(3-hydroxy-5-((5-hydroxy-1,4,5,6-tetrahydropyrimidin-2-yl)amino)benzamido)acetamido)propanoic acid

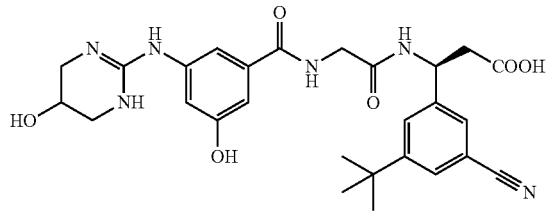 [SMILES: CC(C)(C)c1cc(C#N)cc([C@H](CC(=O)O)NC(=O)CNC(=O)c2cc(O)cc(NC3=NCC(O)CN3)c2)c1]

To a suspension of the crude (3S)-ethyl 3-(3-(tert-butyl)-5-cyanophenyl)-3-(2-(3-hydroxy-5-((5-hydroxy-1,4,5,6-tetrahydropyrimidin-2-yl)amino)benzamido)acetamido)propanoate (~0.61 mmol) from step #1 in a mixture of a 1:1 mixture of acetonitrile/water (6 mL) was added lithium hydroxide monohydrate (130 mg, 3.1 mmol) and the reaction mixture was stirred at room temperature for 2 h. The solvent was evaporated in-vacuo and the residue was dissolved in water (10 mL) and extracted with dichloromethane (2×25 mL) to remove the urea. The aqueous layer was neutralized with TFA (1 mL in 3 mL $CH_3CN$) and the mixture was evaporated in-vacuo to give a colorless residue. The crude product was purified by reverse-phase HPLC with a gradient 10-60% $CH_3CN$ in water containing 0.05% TFA to give the desired product (Example 12), after lyophilization, as a colorless lyophilized solid (258.5 mg). LC/MS analysis of the product shows the desired product's mass: m/z 537 (M+H), Calcd for $C_{27}H_{32}N_6O_6$:536.58 product's mass: m/z 537 (M+H), Calcd for $C_{27}H_{32}N_6O_6$:536.58.

$^1$H NMR (400 MHz, DMSO-d$_6$): δ 1.29 (s, 9H, (CH$_3$)$_3$C—), 2.74 (d, J=7.30 Hz, 2H, —CH$_2$—COOH), 3.16 (brd, J=12.20 Hz, 2H), 3.33 (brd, J=11.70 Hz, 2H), 3.88 (d, J=5.80 Hz, 2H), 4.09 (appt/m, 1H), 5.23 (q, J=7.43 Hz, 1H, —NH—CH—CH$_2$—COOH), 6.75 (brt/m, 1H), 7.11 (appt, 1H), 7.14 (appt, 1H), 7.60 (brs, 1H), 7.72 (brs, 2H), 8.08 (s, 2H), 8.56 (d, J=8.20 Hz, 1H), 8.64 (t, J=5.80 Hz, 1H), 9.55 (s, 1H), 10.00 (brs, 1H), 12.38 (brs, 1H, —COOH). $^1$H NMR spectrum of the product was consistent with the suggested structure of the product.

Example 13

Preparation of (3S)-3-(2-(3-hydroxy-5-((5-hydroxy-1,4,5,6-tetrahydropyrimidin-2-yl)amino)benzamido)acetamido)-3-(3-(2-hydroxypropan-2-yl)-5-(trifluoromethyl)phenyl)propanoic acid

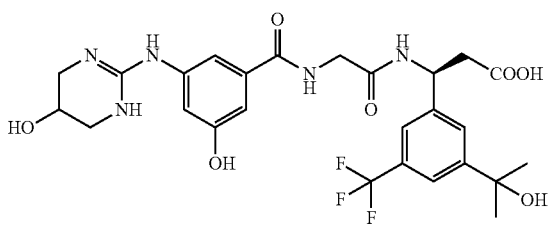 [SMILES: CC(C)(O)c1cc([C@H](CC(=O)O)NC(=O)CNC(=O)c2cc(O)cc(NC3=NCC(O)CN3)c2)cc(C(F)(F)F)c1]

Step 1

Preparation of (S)-3-amino-3-(3-(2-hydroxypropan-2-yl)-5-(trifluoromethyl)phenyl)propanoic acid

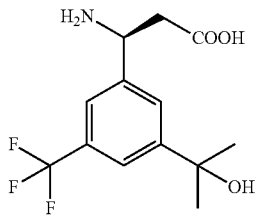 [SMILES: CC(C)(O)c1cc([C@@H](N)CC(=O)O)cc(C(F)(F)F)c1]

Enzymatic Resolution of Example J:

A suspension of racemic ethyl 3-amino-3-(3-(2-hydroxypropan-2-yl)-5-(trifluoromethyl)phenyl)propanoate hydrochloride (Example J) (540.4 mg, 1.52 mmol) in water (2.0 mL) was basified with 2.5 N NaOH solution (pH 12) by drop wise addition to give a dirty pink oily residue. The pH of the aqueous phase was adjusted to pH 8.20 by the addition of 50 mom KH$_2$PO$_4$ solution (40.0 mL). Amano Lipase PS (607.6 mg) was added to the above suspension and the reaction mixture was stirred at room temperature for 63 h to give a pale pink suspension. The reaction mixture was diluted with methyl t-butyl ether (MTBE) (50 mL) and the reaction mixture was stirred at room temperature for 30 min. After 30 min, the organic layer containing the (R)-ester was separated. Evaporation of the aqueous layer in vacuo afforded a cream gummy solid containing the (S)-acid as well as Amano Lipase and Phosphate buffer salt. LC-MS analysis of the crude residue shows the desired (S)-acid's mass: m/z 292 (M+H), m/z 314 (M+Na), and m/z 274 (M+H–H$_2$O); Calcd for $C_{13}H_{16}F_3NO_3$: 291.27. The crude product was purified by reverse-phase HPLC with a gradient 10-40% CH$_3$CN in water containing 0.05% TFA to give the desired product, after lyophilization, as a colorless lyophilized solid (324 mg) (TFA salt).

Step 2

Preparation of (S)-ethyl 3-amino-3-(3-trifluoromethyl-5-(2-hydroxypropan-2-yl)phenyl)propionate hydrochloride

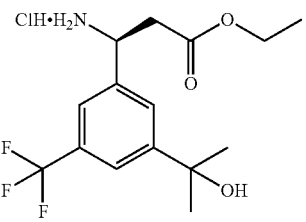

The product from step #1 (324 mg) was dissolved in absolute ethanol saturated with anhydrous HCl gas (10 mL) and the reaction mixture was stirred at room temperature for 2 h and the solvent was evaporated in vacuo to afford a colorless foamy solid of the product: (S)-ethyl 3-amino-3-(3-trifluoromethyl-5-(2-hydroxypropan-2-yl)phenyl)propionate hydrochloride (289 mg). LC-MS analysis of the solid shows the desired (S)-ester's mass: m/z 320 (M+H), and m/z 342 (M+Na); Calcd for $C_{15}H_{20}F_3NO_3$: 319.22. The solid will be used as such for the coupling reaction (step #3).

Step 3

Preparation of (3S)-ethyl 3-(2-(3-hydroxy-5-((5-hydroxy-1,4,5,6-tetrahydropyrimidin-2-yl)amino)benzamido)acetamido)-3-(3-(2-hydroxypropan-2-yl)-5-(trifluoromethyl)phenyl)propanoate

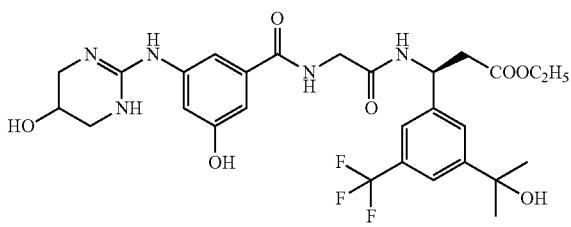

A mixture of 2-(3-hydroxy-5-((5-hydroxy-1,4,5,6-tetrahydropyrimidin-2-yl)amino)benzamido)acetic acid (Example B) (251 mg, 0.81 mmol), (S)-ethyl 3-amino-3-(3-trifluoromethyl-5-(2-hydroxypropan-2-yl)phenyl)propionate hydrochloride (from step #2) (289 mg, 0.81 mmol) and 1-hydroxybenzotriazole hydrate (25 mg, 0.16 mmol) was dissolved in DMF (3 mL) and dichloromethane (3 mL) and stirred at room temperature under nitrogen atmosphere for 10 min to give a cream suspension. N,N'-diisopropylcarbodiimide (166 μL, 1.08 mmol) was added and the reaction mixture was stirred at room temperature under nitrogen atmosphere overnight. The solvent was evaporated in-vacuo to give a cream viscous residue of the intermediate product: (3S)-ethyl 3-(2-(3-hydroxy-5-((5-hydroxy-1,4,5,6-tetrahydropyrimidin-2-yl)amino)benzamido)acetamido)-3-(3-(2-hydroxypropan-2-yl)-5-(trifluoromethyl)phenyl)propanoate. LC-MS analysis of the crude residue shows the desired product's mass: m/z 610 (M+H), and m/z 632 (M+Na); Calcd for $C_{28}H_{34}F_3N_5O_7$: 609.59. The crude residue will be used as such for the saponification (step #4).

Step 4

Preparation of (3S)-3-(2-(3-hydroxy-5-((5-hydroxy-1,4,5,6-tetrahydropyrimidin-2-yl)amino)benzamido)acetamido)-3-(3-(2-hydroxypropan-2-yl)-5-(trifluoromethyl)phenyl)propanoic acid

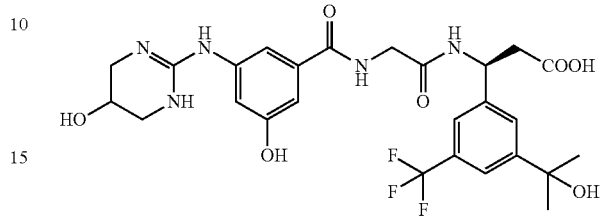

To a suspension of (3S)-ethyl 3-(2-(3-hydroxy-5-((5-hydroxy-1,4,5,6-tetrahydropyrimidin-2-yl)amino)benzamido)acetamido)-3-(3-(2-hydroxypropan-2-yl)-5-(trifluoromethyl)phenyl)propanoate (0.70 mmol) from step #3 in a mixture of a 1:1 mixture of acetonitrile/water (6 mL) was added lithium hydroxide monohydrate (170 mg, 4.05 mmol) and the reaction mixture was stirred at room temperature for 2 h. The solvent was evaporated in vacuo to afford a pale yellow gummy residue. The residue was dissolved in water (20 mL) and extracted with dichloromethane (2×25 mL) to remove N,N'-diisopropylurea. The aqueous layer was neutralized with TFA (1 mL TFA in 3 mL $CH_3CN$) and evaporated in-vacuo to give a cream gummy residue. The crude product was purified by reverse-phase HPLC with a gradient 10-50% $CH_3CN$ in water containing 0.05% TFA to give the desired product (Example 13), after lyophilization, as a colorless lyophilized solid (147 mg). LC-MS analysis of the solid shows the desired product's mass: m/z 582 (M+H); Calcd for $C_{26}H_{30}F_3N_5O_7$: 581.54.

$^1$H NMR (400 MHz, DMSO-$d_6$): δ 1.44 (s, 6H, $(CH_3)_2C$—OH), 2.75 (d, J=7.70 Hz, 2H, —$CH_2$—COOH), 3.16 (dt, J=12.10 and 3.40 Hz, 2H), 3.33 (dd, J=12.10 and 2.50 Hz, 2H), 3.87 (d, J=9.60 Hz, 2H), 4.08 (appt, 1H), 5.27 (q, J=7.50 Hz, 1H, —NH—CH—$CH_2$—COOH), 6.74 (t, J=2.0 Hz, 1H), 7.12 (dt, J=12.0 and 1.5 Hz, 2H), 7.52 (s, 1H), 7.69 (brd, J=8.70 Hz, 2H), 8.10 (brs, 2H), 8.60 (d, J=8.20 Hz, 1H), 8.63 (brt, J=8.14 Hz, 1H), 9.62 (s, 1H), 10.03 (brs, 1H), 12.37 (brs, 1H, —COOH). $^1$H NMR spectrum of the sample was consistent with the suggested structure of the product.

Example 14

Preparation of (3S)-3-(3-chloro-5-(1-methoxy-2-methylpropan-2-yl)phenyl)-3-(2-(3-hydroxy-5-((5-hydroxy-1,4,5,6-tetrahydropyrimidin-2-yl)amino)benzamido)acetamido)propanoic acid

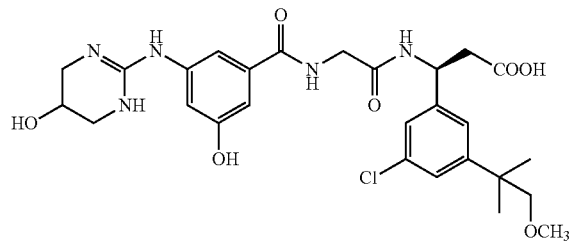 [SMILES: COCC(C)(C)c1cc(Cl)cc([C@H](CC(=O)O)NC(=O)CNC(=O)c2cc(O)cc(NC3=NCC(O)CN3)c2)c1]

Step 1

Preparation of (3S)-ethyl 3-(3-chloro-5-(1-methoxy-2-methylpropan-2-yl)phenyl)-3-(2-(3-hydroxy-5-((5-hydroxy-1,4,5,6-tetrahydropyrimidin-2-yl)amino)benzamido)acetamido)propanoate

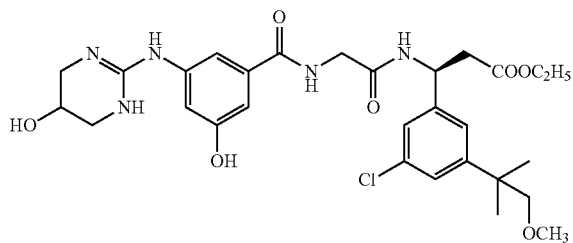

A mixture of 2-(3-hydroxy-5-((5-hydroxy-1,4,5,6-tetrahydropyrimidin-2-yl)amino)benzamido)acetic acid (Example B) (343.5 mg, 1.11 mmol), (S)-ethyl 3-amino-3-(3-chloro-5-(1-methoxy-2-methylpropan-2-yl)phenyl)propanoate hydrochloride (Example K) (385.2 mg, 1.11 mmol) and 1-hydroxybenzotriazole hydrate (35 mg, 0.23 mmol) was dissolved in DMF (3 mL) and dichloromethane (3 mL) and stirred at room temperature under nitrogen atmosphere for 10 min to give a cream suspension. Neat N,N'-diisopropylcarbodiimide (180 µL, 1.16 mmol) was added and the reaction mixture was stirred at room temperature under nitrogen atmosphere overnight. The solvent was evaporated in vacuo to give a dirty cream gummy residue of the intermediate product: (3S)-ethyl 3-(3-chloro-5-(1-methoxy-2-methylpropan-2-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 604 ($^{35Cl}$M+H), m/z 606 ($^{37Cl}$M+H); m/z 626 ($^{35Cl}$M+Na), and m/z 628 ($^{37Cl}$M+Na); Calcd for $C_{29}H_{38}ClN_5O_7$: 604.09. The crude residue will be used as such for the saponification (step #2).

Step 2

Preparation of (3S)-3-(3-chloro-5-(1-methoxy-2-methylpropan-2-yl)phenyl)-3-(2-(3-hydroxy-5-((5-hydroxy-1,4,5,6-tetrahydropyrimidin-2-yl)amino)benzamido)acetamido)propanoic acid

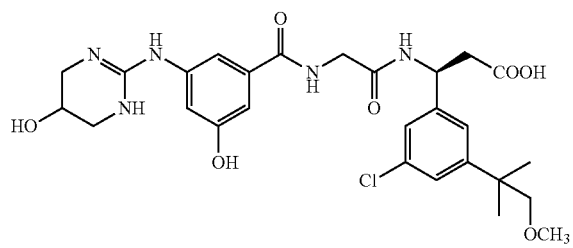 [SMILES: COCC(C)(C)c1cc(Cl)cc([C@H](CC(=O)O)NC(=O)CNC(=O)c2cc(O)cc(NC3=NCC(O)CN3)c2)c1]

To a suspension of (3S)-ethyl 3-(3-chloro-5-(1-methoxy-2-methylpropan-2-yl)phenyl)-3-(2-(3-hydroxy-5-((5-hydroxy-1,4,5,6-tetrahydropyrimidin-2-yl)amino)benzamido)acetamido)propanoate (1.11 mmol) from step #1 in a mixture of a 1:1 mixture of acetonitrile/water (8 mL) was added lithium hydroxide monohydrate (234 mg, 5.58 mmol) and the reaction mixture was stirred at room temperature for 2.5 h. The solvent was evaporated in vacuo to afford a pale yellow crystalline-gummy residue. The residue was dissolved in water (20 mL) and extracted with dichloromethane (2×25 mL) to remove the N,N'-diisopropylurea. The aqueous layer was neutralized with TFA (1 mL TFA in 3 mL CH$_3$CN) and evaporated in vacuo to give a pale yellow viscous residue. The crude product was purified by reverse-phase HPLC with a gradient 10-60% CH$_3$CN in water containing 0.05% TFA to give the desired product (Example 14), after lyophilization, as a colorless lyophilized solid (352.0 mg). LC-MS analysis of the solid shows the desired product's mass: m/z 576 ($^{35Cl}$M+H), m/z 578 ($^{37Cl}$M+H); m/z 598 ($^{35Cl}$M+Na), and m/z 600 ($^{37Cl}$M+H); Calcd for $C_{27}H_{34}ClN_5O_7$: 576.04.

$^1$H NMR (400 MHz, DMSO-d$_6$): δ 1.22 (s, 6H, —(CH$_3$)$_2$—CH$_2$—OCH$_3$), 2.70 (d, J=7.20 Hz, 2H, —CH$_2$—COOH), 3.14 (appt, J=3.90 Hz, 1H), 3.17 (appt, J=3.50 Hz, 1H), 3.21 (s, 3H, —OCH$_3$), 3.34 (brd, 2H), 3.87 (d, J=5.80 Hz, 2H), 4.08 (appt, J=3.0 Hz, 1H), 5.19 (q, J=7.50 Hz, 1H, —NH—CH—CH$_2$—COOH), 6.74 (t, J=2.06 Hz, 1H), 7.11 (appt, J=1.80 Hz, 1H), 7.14 (appt, J=1.80 Hz, 1H), 7.21 (appt, J=1.50 Hz, 1H), 7.24 (appt, J=1.80 Hz, 1H), 7.29 (appt, J=1.40 Hz, 1H), 8.09 (s, 2H), 8.51 (d, J=8.38 Hz, 1H), 8.61 (t, J=5.80 Hz, 1H), 9.58 (s, 1H), 10.00 (brs, 1H), 12.33 (brs, 1H, —COOH). $^1$H NMR spectrum of the sample was consistent with the suggested structure of the product.

Example 15

Preparation of (3S)-3-(3-chloro-5-(1-hydroxy-2-methylpropan-2-yl)phenyl)-3-(2-(3-hydroxy-5-((5-hydroxy-1,4,5,6-tetrahydropyrimidin-2-yl)amino)benzamido)acetamido)propanoic acid

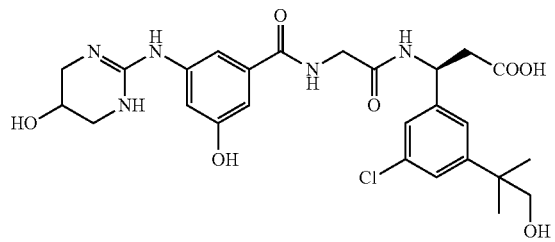 [SMILES: CC(C)(CO)c1cc(Cl)cc([C@H](CC(=O)O)NC(=O)CNC(=O)c2cc(O)cc(NC3=NCC(O)CN3)c2)c1]

To a solution of (3S)-3-(3-chloro-5-(1-methoxy-2-methylpropan-2-yl)phenyl)-3-(2-(3-hydroxy-5-((5-hydroxy-1,4,5,6-tetrahydropyrimidine-2-yl)amino)benzamido)propanoic acid TFA salt (Example 14) (138.4 mg, 0.20 mmol) in anhydrous dichloromethane (2.0 mL) was added a solution of 15-crown-5 (267.0 mg, 1.212 mmol) saturated with sodium iodide in dichloromethane (7.0 mL) at room temperature and the reaction mixture was cooled to −30° C. (dry ice/CH$_3$CN) and a 1.0 M BBr$_3$ solution in dichloromethane (650 µL, 0.65 mmol) was added and the reaction mixture stirred at −30° C. for 2 h to give an orange suspension. After 2 hr the reaction mixture was allowed to warm slowly to room temperature and stirred at room temperature overnight to give an orange-cream suspension. The suspension was filtered, washed with dichloromethane (2×10 mL) and dried in vacuo to give a yellow-cream residue. The crude product was purified by reverse-phase HPLC with a gradient 10-60% CH$_3$CN in water containing 0.05% TFA to give the desired product (Example 15), after lyophilization, as a colorless lyophilized solid (126.4 mg). LC/MS analysis of the product shows the desired product's mass: m/z 562 ($^{35Cl}$M+H), m/z 564 ($^{37Cl}$M+H), m/z 584 ($^{35Cl}$M+Na), and m/z 586 ($^{37Cl}$M+Na), Calcd for $C_{26}H_{32}ClN_5O_7$: 562.01.

$^1$H NMR (400 MHz, DMSO-d$_6$): δ 1.20 (s, 6H, —(CH$_3$)$_2$—CH$_2$—OH), 2.70 (d, J=7.30 Hz, 2H, —CH$_2$—COOH), 3.16 (appdt, J=12.15 Hz and J=3.50 Hz, 2H), 3.33 (brd, J=12.25 Hz, 2H), 3.87 (d, J=6.00 Hz, 2H), 4.08 (appt, J=3.10 Hz, 1H), 5.19 (q, J=7.64 Hz, 1H, —NH—CH—CH$_2$—COOH), 5.42 (brs, 1H), 6.74 (t, J=2.06 Hz, 1H), 7.11 (appt, J=1.60 Hz, 1H), 7.13 (appt, J=1.80 Hz, 1H), 7.20 (appt, J=1.54 Hz, 1H), 7.25 (appt, J=1.80 Hz, 1H), 7.28 (appt, J=1.40 Hz, 1H), 8.10 (s, 2H), 8.51 (d, J=8.45 Hz, 1H), 8.61 (t, J=5.90 Hz, 1H), 9.60 (s, 1H), 10.00 (brs, 1H), 12.31 (brs, 1H, —COOH). $^1$H NMR spectrum of the sample was consistent with the suggested structure of the product.

Example 16

Preparation of (3S)-3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

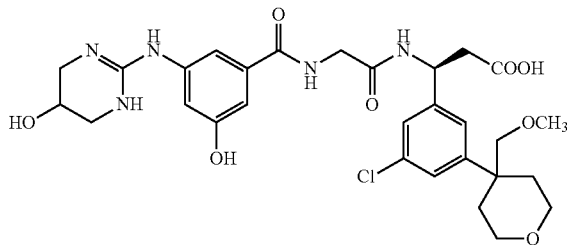 [SMILES: COCC1(c2cc(Cl)cc([C@H](CC(=O)O)NC(=O)CNC(=O)c3cc(O)cc(NC4=NCC(O)CN4)c3)c2)CCOCC1]

Step 1

Preparation of (3S)-ethyl 3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate

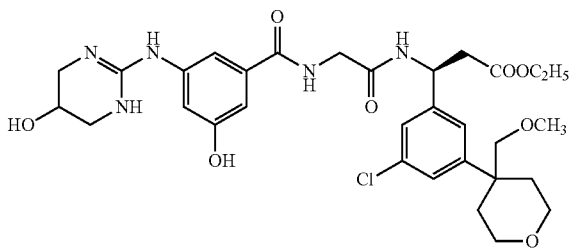

A mixture of 2-(3-hydroxy-5-((5-hydroxy-1,4,5,6-tetrahydropyrimidin-2-yl)amino)benzamido)acetic acid (Example B) (277.0 mg, 0.90 mmol), (S)-ethyl 3-amino-3-(3-chloro-5-(4-(Methoxymethyl)tetrahydro-2H-pyran-4-yl)phenyl)propanoate hydrochloride (Example L) (342.1 mg, 0.87 mmol) and 1-hydroxybenzotriazole hydrate (28 mg, 0.18 mmol) was dissolved in DMF (3 mL) and dichloromethane (3 mL) and stirred at room temperature under nitrogen atmosphere for 10 min to give a cream suspension. N,N'-diisopropylcarbodiimide (180 uL, 1.16 mmol) was added and the reaction mixture was stirred at room temperature under nitrogen atmosphere overnight. The solvent was evaporated in-vacuo to give an orange-cream viscous residue of the intermediate product: (3S)-ethyl 3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 646 ($^{35Cl}$M+H), and m/z 648 ($^{37Cl}$M+H); Calcd for $C_{31}H_{40}ClN_5O_8$: 646.13. The crude residue will be used as such for the saponification (step #2).

Step 2

Preparation of (3S)-3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

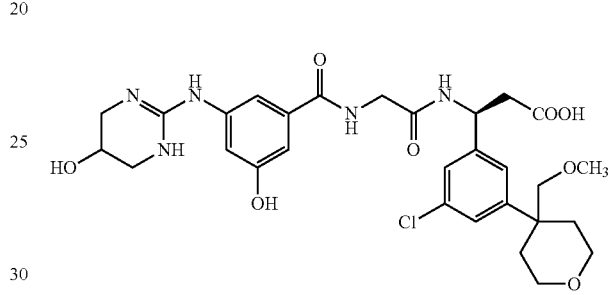

To a suspension of (3S)-ethyl 3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate (0.87 mmol) from step #1 in a mixture of a 1:1 mixture of acetonitrile/water (8 mL) was added lithium hydroxide monohydrate (184 mg, 4.38 mmol) and the reaction mixture was stirred at room temperature overnight. The solvent was evaporated in vacuo to afford a dirty yellow crystalline-gummy residue. The residue was dissolved in water (20 mL) and extracted with dichloromethane (2×25 mL) to remove the N,N'-diisopropylurea. The aqueous layer was neutralized with TFA (1 mL TFA in 3 mL CH$_3$CN) and evaporated in vacuo to give a yellow-orange viscous residue. The crude product was purified by reverse-phase HPLC with a gradient 10-60% CH$_3$CN in water containing 0.05% TFA to give the desired product (Example 16), after lyophilization, as a colorless lyophilized solid (343.3 mg). LC-MS analysis of the solid shows the desired product's mass: m/z 618 ($^{35Cl}$M+H), and m/z 620 ($^{37Cl}$M+H); Calcd for $C_{29}H_{36}ClN_5O_8$: 618.08.

$^1$H NMR (400 MHz, DMSO-d$_6$): δ 1.80-1.90 (M, 2H, —CH$_2$—(C═)—CH$_2$—), 1.94-2.04 (M, 2H, —CH$_2$—(C═)—CH$_2$—), 2.71 (d, J=7.20 Hz, 2H, —CH$_2$—COOH), 3.12 (s, 3H, —OCH$_3$), 3.13-3.20 (dt/m, 2H), 3.28-3.42 (dt/m, 4H), 3.62-3.72 (dt/m, 2H), 3.87 (d, J=6.00 Hz, 2H), 4.08 (appt, J=3.16 Hz, 1H), 5.21 (q, J=7.50 Hz, 1H, —NH—CH—CH$_2$—COOH), 5.45 (brs, 1H), 6.75 (appt, J=2.05 Hz, 1H), 7.11 (appt, J=1.64 Hz, 1H), 7.14 (appt, J=1.80 Hz, 1H), 7.25 (d, J=1.40 Hz, 2H), 7.29 (appt, 1H), 8.14 (s, 2H), 8.52 (d, J=8.30 Hz, 1H), 8.64 (appt, J=5.90 Hz, 1H), 9.67 (s, 1H), 10.03 (brs, 1H), 12.34 (brs, 1H, —COOH). $^1$H NMR spectrum of the sample was consistent with the suggested structure of the product.

Example 17

Preparation of (3S)-3-(3-chloro-5-(4-(hydroxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

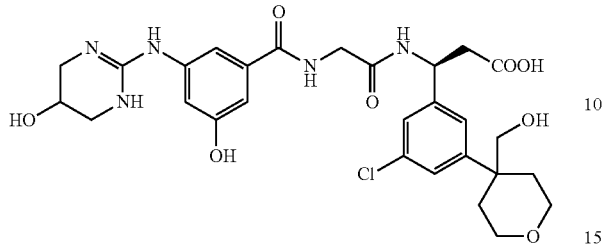

To a solution of (3S)-3-(3-chloro-5-(4-(Methoxymethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid TFA salt (Example 16) (85.5 mg, 0.117 mmol) in anhydrous dichloromethane (2.0 mL) was added a solution of 15-crown-5 (155.0 mg, 0.702 mmol) saturated with sodium iodide in dichloromethane (6.0 mL) at room temperature and the reaction mixture was cooled to −30° C. (dry-ice/CH$_3$CN) and a 1.0 M BBr$_3$ solution in dichloromethane (350 µL, 0.35 mmol) was added and the reaction mixture stirred at −30° C. for 2 h to give an orange suspension. After 2 hr the reaction mixture was allowed to warm slowly to room temperature and stirred at room temperature overnight to give an orange-cream suspension. The suspension was filtered, washed with dichloromethane (2×10 mL) and dried in vacuo to give a yellow-cream solid. The crude product was purified by reverse-phase HPLC with a gradient 10-50% CH$_3$CN in water containing 0.05% TFA to give the desired product (Example 17), after lyophilization, as a colorless lyophilized solid (64.5 mg). LC/MS analysis of the product shows the desired product's mass: m/z 604 ($^{35Cl}$M+H), m/z 606 ($^{37Cl}$M+H), m/z 626 ($^{35Cl}$M+Na), and m/z 628 ($^{37Cl}$M+Na), Calcd for C$_{28}$H$_{34}$ClN$_5$O$_8$:604.05.

$^1$H NMR (400 MHz, DMSO-d$_6$): δ 1.75-1.90 (M, 2H, —CH$_2$—(C=)—CH$_2$—), 1.90-2.00 (M, 2H, —CH$_2$—(C=)—CH$_2$—), 2.70 (d, J=7.30 Hz, 2H, —CH$_2$—COOH), 3.12-3.20 (dt/m, 4H), 3.25-3.37 (dt/m, 2H), 3.62-3.72 (dt/m, 2H), 3.86 (d, J=5.80 Hz, 2H), 4.08 (appt, J=3.30 Hz, 1H), 5.21 (q, J=7.50 Hz, 1H, —NH—CH—CH$_2$—COOH), 5.46 (brs, 1H), 6.75 (appt, J=1.80 Hz, 1H), 7.11 (appt, J=1.50 Hz, 1H), 7.14 (appt, J=1.75 Hz, 1H), 7.23 (s, 2H), 7.26 (s, 1H), 8.10 (brs, 2H), 8.51 (d, J=8.50 Hz, 1H), 8.62 (appt, J=5.80 Hz, 1H), 9.59 (s, 1H), 10.00 (brs, 1H), 12.32 (brs, 1H, —COOH). $^1$H NMR spectrum of the sample was consistent with the suggested structure of the product.

Example 18

Preparation of (3S)-3-(3-(tert-butyl)-5-(pyridin-3-yl)phenyl)-3-(2-(3-hydroxy-5-((5-hydroxy-1,4,5,6-tetrahydropyrimidin-2-yl)amino)benzamido)acetamido)propanoic acid

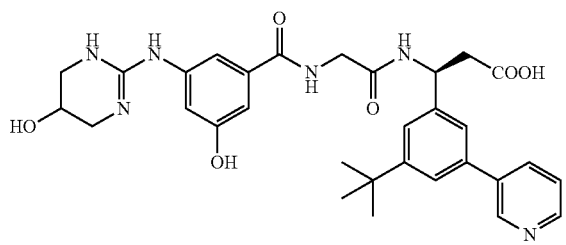 [SMILES: CC(C)(C)c1cc(-c2cccnc2)cc([C@H](CC(=O)O)NC(=O)CNC(=O)c2cc(O)cc(NC3=NCC(O)CN3)c2)c1]

Step 1

Preparation of (S)-ethyl 3-(3-bromo-5-(tert-butyl)phenyl)-3-(2-((tert-butoxycarbonyl)amino) acetamido)propanoate

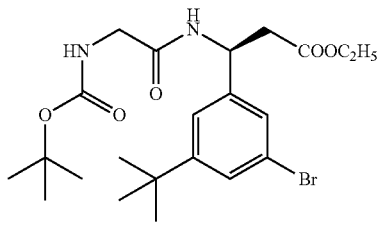

To a solution of (S)-ethyl 3-(2-aminoacetamido)-3-(3-bromo-5-(tert-butyl)phenyl)propanoate hydrochloride (Example H) (1.50 g, 3.56 mmol) in anhydrous dichloromethane (20 mL) was added triethylamine (1.0 mL, 7.18 mmol) at room temperature under nitrogen atmosphere. After stirring the reaction mixture for 5 min, di-tert-butyl dicarbonate was added and the reaction mixture was stirred at room temperature overnight. The solvent was evaporated in vacuo to afford a colorless viscous/foamy residue of the intermediate: (S)-ethyl 3-(3-bromo-5-(tert-butyl)phenyl)-3-(2-((tert-butoxycarbonyl)amino)acetamido)propanoate. LC-MS analysis of the residue shows the desired product's mass: m/z 507 ($^{79Br}$M+Na), m/z 509 ($^{81Br}$M+Na), m/z 429 ($^{79Br}$M+H-t-Bu-), m/z 431 ($^{81Br}$M+H-t-Bu-), m/z 385 ($^{79Br}$M+H-t-Boc-), and m/z 387 ($^{81Br}$M+H-t-Boc-); Calcd for C$_{22}$H$_{33}$BrN$_2$O$_5$: 485.41. Several attempts to crystallize the intermediate with ethyl acetate/hexanes or heptane afforded a colorless gummy solid (1.769 g). The gummy solid will be used as such for the Suzuki couplings (step #2).

Step 2

Preparation of (S)-ethyl 3-(2-((tert-butoxycarbonyl)amino)acetamido)-3-(3-(tert-butyl)-5-(pyridin-3-yl)phenyl)propanoate

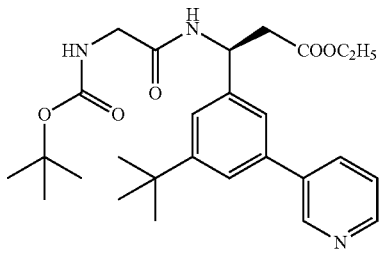

To a stirred mixture of (S)-ethyl 3-(3-bromo-5-(tert-butyl)phenyl)-3-(2-((tert-butoxycarbonyl)amino) acetamido)propanoate (from step #1) (268 mg, 0.55 mmol), pyridine-3-boronic acid (137 mg, 1.12 mmol) and Pd(PPh$_3$)$_4$ (65 mg, 0.056 mmol) in anhydrous DMF (2.5 mL) was added a degassed solution of Cs$_2$CO$_3$ (360 mg, 1.11 mmol) in water (1.5 mL) under nitrogen atmosphere and the reaction mixture was heated at 80° C. under nitrogen atmosphere for 2 h to give a gray suspension. The reaction mixture was evaporated in-vacuo and the residue was dissolved in water (25 mL) and the mixture was extracted with ethyl acetate (2×25 mL). The organic layer was separated, dried over anhydrous Na₂SO₄, filtered, and evaporated in vacuo to give an almost colorless gummy residue of the intermediate product: (S)-ethyl 3-(2-((tert-butoxycarbonyl)amino)acetamido)-3-(3-(tert-butyl)-5-(pyridin-3-yl)phenyl)propanoate (276 mg). LC-MS analysis of the residue shows the desired product's mass: m/z 484 (M+H), m/z 506 (M+Na), m/z 989 (2M+Na); Calcd for $C_{27}H_{37}N_3O_5$: 483.60. The crude residue will be used as such for the saponification (step #3).

Step 3

Preparation of (S)-ethyl 3-(2-aminoacetamido)-3-(3-(tert-butyl)-5-(pyridin-3-yl)phenyl)propanoate hydrochloride

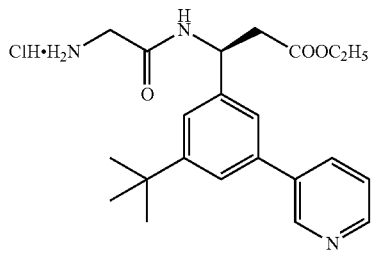

To a solution of (S)-ethyl 3-(2-((tert-butoxycarbonyl)amino)acetamido)-3-(3-(tert-butyl)-5-(pyridin-3-yl)phenyl)propanoate (from step #2) (272 mg, 0.56 mmol) in dichloromethane (2.0 mL) was added a 20% solution of TFA in dichloromethane (5.0 mL) at room temperature and the reaction mixture was stirred at room temperature for 2 h. The solvent was evaporated in vacuo to afford a pale yellow gummy residue. LC-MS analysis of the solid shows the desired product's mass: m/z 384 (M+H), m/z 767 (2M+H), and m/z 789 (2M+Na); Calcd for $C_{22}H_{29}N_3O_3$: 383.48. The residue was triturated with heptane (3×10 mL) and the heptane layers were decanted off to remove PPh₃O. The residue after heptane extractions was dissolved in absolute ethanol saturated with anhydrous HCl gas (10.0 mL), heated at reflux for 30 min and after cooling to room temperature, the solvent was evaporated in vacuo to afford a dirty cream solid of the product: (S)-ethyl 3-(2-aminoacetamido)-3-(3-(tert-butyl)-5-(pyridin-3-yl)phenyl)propanoate hydrochloride (244.2 mg). The solid will be used as such for the coupling reaction (step #4).

Step 4

Preparation of (3S)-ethyl 3-(3-(tert-butyl)-5-(pyridin-3-yl)phenyl)-3-(2-(3-hydroxy-5-((5-hydroxy-1,4,5,6-tetrahydropyrimidin-2-yl)amino)benzamido)acetamido)propanoate

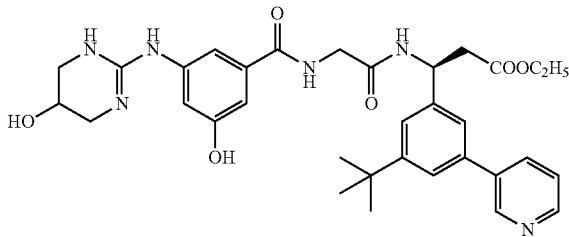

A mixture of 3-hydroxy-5-((5-hydroxy-1,4,5,6-tetrahydropyrimidin-2-yl)aminobenzoic acid (Example A) (186 mg, 0.74 mmol), (S)-ethyl 3-(2-aminoacetamido)-3-(3-(tert-butyl)-5-(pyridin-3-yl)phenyl)propanoate hydrochloride (from step #3) (311 mg, 0.74 mmol) and 1-hydroxybenzotriazole hydrate (23 mg, 0.15 mmol) was dissolved in DMF (3 mL) and dichloromethane (3 mL) and stirred at room temperature under nitrogen atmosphere for 10 min to give a colorless suspension. N,N'-diisopropylcarbodiimide (125 μL, 0.81 mmol) was added and the reaction mixture was stirred at room temperature under nitrogen atmosphere overnight. The solvent was evaporated in vacuo to give a yellow cream gummy residue of the intermediate product: (3S)-ethyl 3-(3-(tert-butyl)-5-(pyridin-3-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 617 (M+H) and m/z 309 (M/2+H); Calcd for $C_{33}H_{40}N_6O_6$: 616.71 The crude residue will be used as such for the saponification with lithium hydroxide (step #5).

Step 5

Preparation of (3S)-3-(3-(tert-butyl)-5-(pyridin-3-yl)phenyl)-3-(2-(3-hydroxy-5-((5-hydroxy-1,4,5,6-tetrahydropyrimidin-2-yl)amino)benzamido)acetamido)propanoic acid

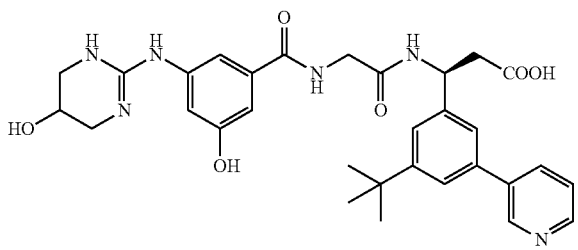 [SMILES: CC(C)(C)c1cc(-c2cccnc2)cc([C@H](CC(=O)O)NC(=O)CNC(=O)c2cc(O)cc(NC3=NCC(O)CN3)c2)c1]

To a suspension of (3S)-ethyl 3-(3-(tert-butyl)-5-(pyridin-3-yl)phenyl)-3-(2-(3-hydroxy-5-((5-hydroxy-1,4,5,6-tetrahydropyrimidin-2-yl)amino)benzamido)acetamido)propanoate (from step #4) (74 mmol) in a 1:1 mixture of acetonitrile/water (6 mL) was added lithium hydroxide monohydrate (156 mg, 3.72 mmol) and the reaction mixture was stirred at room temperature overnight. The solvent was evaporated in-vacuo and the residue was dissolved in water (10 mL) and extracted with dichloromethane (2×25 mL) to remove the urea. The aqueous layer was neutralized with TFA (1 mL in 3 mL CH₃CN) and the mixture was evaporated in vacuo to give a pale yellow-orange viscous residue. The crude product was purified by reverse-phase HPLC with a gradient 10-60% CH₃CN in water containing 0.05% TFA to give the desired product (Example 18), after lyophilization, as a colorless lyophilized solid (198.7 mg). LC/MS analysis of the product shows the desired product's mass: m/z 589 (M+H), and m/z 295 (M/2+H); Calcd for $C_{31}H_{36}N_6O_6$: 588.65.

¹H NMR (400 MHz, DMSO-d₆): δ 1.34 (s, 9H, (CH₃)₃C—), 2.77 (d, J=7.00 Hz, 2H, —CH₂—COOH), 3.15.50 (dt, J=12.50 Hz and 3.50 Hz, 2H), 3.33 (d, J=12.20 Hz, 2H), 4.08 (t, J=3.50 Hz, 1H), 5.31 (q, J=7.60 Hz, 1H, —NH—CH—CH₂—COOH), 6.75 (t, J=2.05 Hz, 1H), 7.12 (t, J=1.62 Hz, 1H), 7.14 (t, J=1.82 Hz, 1H), 7.45 (t, J=1.37 Hz, 1H), 7.53 (t, J=1.45 Hz, 1H), 7.60 (t, J=1.69 Hz, 1H), 7.69 (dd, J=8.05 Hz and 5.0 Hz, 1H), 8.13 (s, 2H), 8.35 (dt, J=8.05 Hz and J=1.8 Hz, 1H), 8.55 (brd, J=8.40 Hz, 1H), 8.66 (t, J=6.10 Hz, 1H), 8.69 (dd, J=5.10 Hz and J=1.4 Hz, 1H), 9.03 (d, J=2.0 Hz, 1H), 9.66 (s, 1H), 10.01 (brs, 1H), 12.36 (brs, 1H, —COOH). $^1$H NMR spectrum of the solid was consistent with the suggested structure of the product.

Example 19

Preparation of (3S)-3-(3-(tert-butyl)-5-(pyrimidin-5-yl)phenyl)-3-(2-(3-hydroxy-5-((5-hydroxy-1,4,5,6-tetrahydropyrimidin-2-yl)amino)benzamido)acetamido)propanoic acid

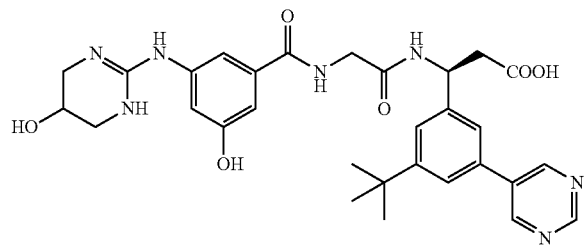 [SMILES: CC(C)(C)c1cc(-c2cncnc2)cc([C@H](CC(=O)O)NC(=O)CNC(=O)c2cc(O)cc(NC3=NCC(O)CN3)c2)c1]

Step 1

Preparation of (S)-ethyl 3-(2-((tert-butoxycarbonyl)amino)acetamido)-3-(3-(tert-butyl)-5-(pyrimidin-5-yl)phenyl)propanoate

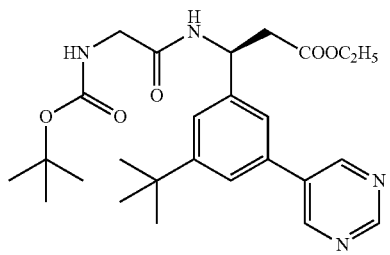

To a stirred mixture of (S)-ethyl 3-(3-bromo-5-(tert-butyl)phenyl)-3-(2-((tert-butoxycarbonyl)amino) acetamido)propanoate (Example 18, step #1) (314 mg, 0.65 mmol), pyrimidine-5-boronic acid (161 mg, 1.30 mmol) and Pd(PPh$_3$)$_4$ (81 mg, 0.07 mmol) in anhydrous DMF (2.5 mL) was added a degassed solution of Cs$_2$CO$_3$ (424 mg, 1.30 mmol) in water (1.5 mL) under nitrogen atmosphere and the reaction mixture was heated at 80° C. under nitrogen atmosphere for 2 h to give a black-brown suspension. The reaction mixture was evaporated in vacuo and the residue was dissolved in water (25 mL) and the mixture was extracted with ethyl acetate (2×25 mL). The organic layer was separated, dried over anhydrous Na$_2$SO$_4$, filtered, and evaporated in vacuo to give an orange-yellow gummy residue of the intermediate product: (S)-ethyl 3-(2-((tert-butoxycarbonyl)amino)acetamido)-3-(3-(tert-butyl)-5-(pyrimidin-5-yl)phenyl)propanoate (273 mg). LC-MS analysis of the residue shows the desired product's mass: m/z 992 (2M+Na); m/z 485 (M+H), m/z 507 (M+Na), m/z 429 (M+H-t-Bu-), and m/z 385 (M+H-t-Boc-); Calcd for C$_{26}$H$_{36}$N$_4$O$_5$: 484.59. The crude residue will be used as such for the saponification (step #2).

Step 2

Preparation of (S)-ethyl 3-(2-aminoacetamido)-3-(3-(tert-butyl)-5-(pyrimidin-5-yl)phenyl)propanoate hydrochloride

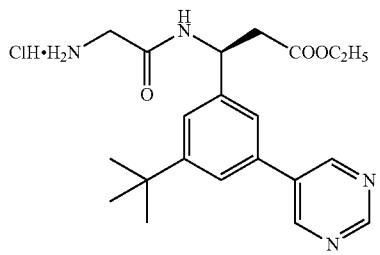

To a solution of (S)-ethyl 3-(2-((tert-butoxycarbonyl)amino)acetamido)-3-(3-(tert-butyl)-5-(pyrimidin-5-yl)phenyl)propanoate (from step #1) (266 mg, 0.55 mmol) in dichloromethane (2.0 mL) was added a 20% solution of TFA in dichloromethane (5.0 mL) at room temperature and the reaction mixture was stirred at room temperature for 2 h. The solvent was evaporated in vacuo to afford a pale orange gummy residue. LC-MS analysis of the solid shows the desired product's mass: m/z 385 (M+H), m/z 407 (M+Na), m/z 769 (2M+H), and m/z 791 (2M+Na); Calcd for C$_{21}$H$_{28}$N$_4$O$_3$: 384.47. The residue was triturated with heptane (3×10 mL) and the heptane layers were decanted off to remove PPh$_3$O. The residue after three heptane extractions was dissolved in absolute ethanol saturated with anhydrous HCl gas (10.0 mL), heated at reflux for 30 min and after cooling to room temperature, the solvent was evaporated in vacuo to afford a yellow-cream microcrystalline solid of the product: (S)-ethyl 3-(2-aminoacetamido)-3-(3-(tert-butyl)-5-(pyrimidin-5-yl)phenyl)propanoate hydrochloride (176.4 mg). The solid will be used as such for the coupling reaction (step #3).

Step 3

Preparation of (3S)-ethyl 3-(3-(tert-butyl)-5-(pyrimidin-5-yl)phenyl)-3-(2-(3-hydroxy-5-((5-hydroxy-1,4,5,6-tetrahydropyrimidin-2-yl)amino)benzamido)acetamido)propanoate

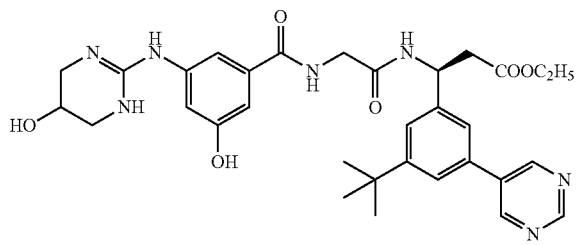

A mixture of 3-hydroxy-5-((5-hydroxy-1,4,5,6-tetrahydropyrimidin-2-yl)aminobenzoic acid (Example A) (45 mg, 0.18 mmol), (S)-ethyl 3-(2-aminoacetamido)-3-(3-(tert-butyl)-5-(pyrimidin-5-yl)phenyl)propanoate hydrochloride (from step #2) (75.4 mg, 0.18 mmol) and 1-hydroxybenzotriazole hydrate (6 mg, 0.039 mmol) was dissolved in DMF (2 mL) and dichloromethane (2 mL) and stirred at room temperature under nitrogen atmosphere for 10 min to give a pale yellow solution. Neat N,N'-diisopropylcarbodiimide (40 µL, 0.26 mmol) was added and the reaction mixture was stirred at room temperature under nitrogen atmosphere overnight. The solvent was evaporated in-vacuo to give a yellow cream gummy residue of the intermediate product: (3S)-ethyl 3-(3-(tert-butyl)-5-(pyrimidin-5-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 618 (M+H), m/z 640 (M+Na), and m/z 309 (M/2+H); Calcd for $C_{32}H_{39}N_7O_6$: 617.70 The crude residue will be used as such for the saponification with lithium hydroxide (step #4).

Step 4

Preparation of (3S)-3-(3-(tert-butyl)-5-(pyrimidin-5-yl)phenyl)-3-(2-(3-hydroxy-5-((5-hydroxy-1,4,5,6-tetrahydropyrimidin-2-yl)amino)benzamido)acetamido)propanoic acid

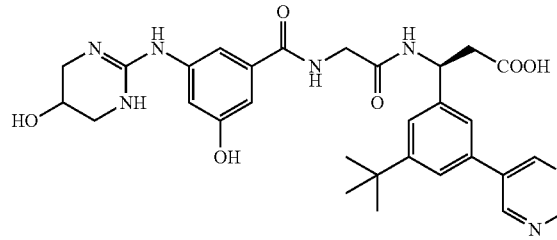

To a suspension of (3S)-ethyl 3-(3-(tert-butyl)-5-(pyrimidin-5-yl)phenyl)-3-(2-(3-hydroxy-5-((5-hydroxy-1,4,5,6-tetrahydropyrimidin-2-yl)amino)benzamido)acetamido)propanoate (from step #3) (0.18 mmol) in a 1:1 mixture of acetonitrile/water (6 mL) was added lithium hydroxide monohydrate (38 mg, 0.91 mmol) and the reaction mixture was stirred at room temperature for 3.5 h. The solvent was evaporated in vacuo and the residue was dissolved in water (20 mL) and extracted with dichloromethane (2×25 mL) to remove the urea. The aqueous layer was neutralized with TFA (1 mL in 3 mL $CH_3CN$) and the mixture was evaporated in vacuo to give a pale yellow-orange viscous residue. The crude product was purified by reverse-phase HPLC with a gradient 10-60% $CH_3CN$ in water containing 0.05% TFA to give the desired product (Example 19), after lyophilization, as a colorless lyophilized solid (128.4 mg). LC/MS analysis of the product shows the desired product's mass: m/z 590 (M+H), and m/z 295 (M/2+H); Calcd for $C_{30}H_{35}N_7O_6$: 589.64.

$^1$H NMR (400 MHz, DMSO-$d_6$): δ 1.34 (s, 9H, $(CH_3)_3$C—), 2.77 (d, J=7.50 Hz, 2H, —$CH_2$—COOH), 3.10-3.20 (brdt, 2H), 3.28-3.38 (brdt, 2H), 4.08 (t, J=3.33 Hz, 1H), 5.31 (q, J=7.55 Hz, 1H, —NH—CH—$CH_2$—COOH), 6.74 (t, J=2.05 Hz, 1H), 7.13 (t, J=1.66 Hz, 1H), 7.14 (t, J=1.82 Hz, 1H), 7.47 (t, J=1.45 Hz, 1H), 7.57 (t, J=1.40 Hz, 1H), 7.64 (t, J=1.68 Hz, 1H), 8.15 (brs, 2H), 8.54 (d, J=8.40 Hz, 1H), 8.67 (t, J=6.05 Hz, 1H), 9.17 (s, 1H), 9.19 (s, 1H), 9.70 (s, 1H), 10.03 (brs, 1H), 12.08 (brs, 1H, —COOH). $^1$H NMR spectrum of the solid was consistent with the suggested structure of the product.

Example 20

Preparation of (3S)-3-(3-chloro-5-(4-(fluoromethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

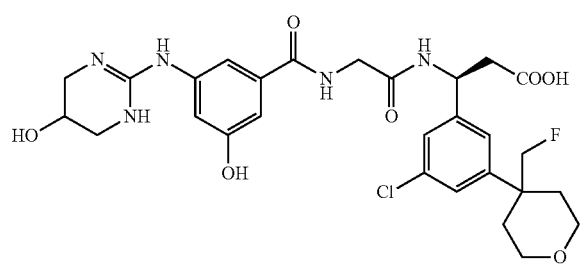 [SMILES: O=C(O)C[C@H](NC(=O)CNC(=O)c1cc(O)cc(NC2=NCC(O)CN2)c1)c1cc(Cl)cc(C2(CF)CCOCC2)c1]

Step 1

Preparation of (3S)-ethyl 3-(3-chloro-5-(4-(fluoromethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate

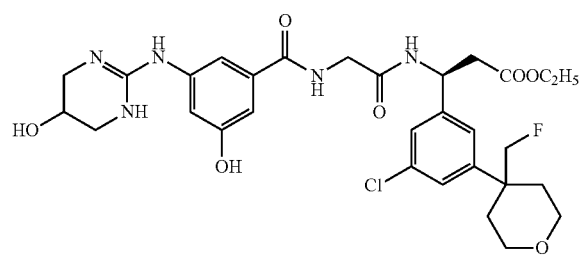

A mixture of 2-(3-hydroxy-5-((5-hydroxy-1,4,5,6-tetrahydropyrimidin-2-yl)amino)benzamido)acetic acid (Example B) (45.0 mg, 0.146 mmol), (S)-ethyl 3-amino-3-(3-chloro-5-(4-(fluoromethyl)tetrahydro-2H-pyran-4-yl)phenyl)propanoate hydrochloride (Example M) (55.5 mg, 0.146 mmol) and 1-hydroxybenzotriazole hydrate (5 mg, 0.033 mmol) was dissolved in DMF (2 mL) and dichloromethane (2 mL) and stirred at room temperature under nitrogen atmosphere for 10 min to give a cream suspension. N,N'-diisopropylcarbodiimide (35 µL, 0.226 mmol) was added and the reaction mixture was stirred at room temperature under nitrogen atmosphere overnight. The solvent was evaporated in vacuo to give a cream gummy residue of the intermediate product: (3S)-ethyl 3-(3-chloro-5-(4-(fluoromethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate. LC-MS analysis of the crude residue shows the desired product's mass: m/z 634 ($^{35Cl}$M+H), m/z 636 ($^{37Cl}$M+H), m/z 656 ($^{35Cl}$M+Na), and m/z 658 ($^{37Cl}$M+Na); Calcd for $C_{30}H_{37}ClFN_5O_7$: 634.10. The crude residue will be used as such for the saponification (step #2)

Step 2

Preparation of (3S)-3-(3-chloro-5-(4-(fluoromethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

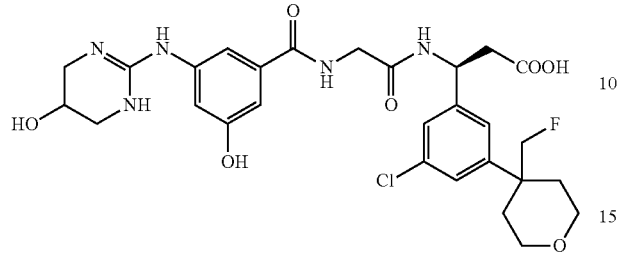

To a suspension of (3S)-ethyl 3-(3-chloro-5-(4-(fluoromethyl)tetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate (from step #1) (0.146 mmol) in a mixture of a 1:1 mixture of acetonitrile/water (6 mL) was added lithium hydroxide monohydrate (32 mg, 0.763 mmol) and the reaction mixture was stirred at room temperature for 4 h. The solvent was evaporated in vacuo to afford a cream crystalline-gummy residue. The residue was dissolved in water (20 mL) and extracted with dichloromethane (2×25 mL) to remove the N,N'-diisopropylurea. The aqueous layer was neutralized with TFA (1 mL TFA in 3 mL CH$_3$CN) and evaporated in-vacuo to give a yellow-orange viscous residue. The crude product was purified by reverse-phase HPLC with a gradient 10-60% CH$_3$CN in water containing 0.05% TFA to give the desired product (Example 20), after lyophilization, as a colorless lyophilized solid (50.5 mg). LC-MS analysis of the solid shows the desired product's mass: m/z 606 ($^{35Cl}$M+H), and m/z 608 ($^{37Cl}$M+H); Calcd for C$_{28}$H$_{33}$ClFN$_5$O$_7$: 606.04.

$^1$H NMR (400 MHz, DMSO-d$_6$): δ 1.48-1.68 (M, 2H, —CH$_2$—(C═)—CH$_2$—), 1.68-1.82 (M, 2H, —CH$_2$—(C═)—CH$_2$—), 2.65-2.78 (M, 2H), 2.88-3.02 (M, 2H), 3.16 (dt, J=12.36 Hz and 3.80 Hz, 2H), 3.34 (brd, J=12.00 Hz, 2H), 3.42-3.54 (dt/m, 2H), 3.66-3.75 (dt/m, 2H), 3.86 (d, J=5.90 Hz, 2H), 4.08 (appt, J=3.30 Hz, 1H), 5.16 (q, J=7.40 Hz, 1H, —NH—CH—CH$_2$—COOH), 5.54 (brs, 1H), 6.75 (t, J=2.06 Hz, 1H), 7.11 (t, J=1.65 Hz, 1H), 7.13 (t, J=1.84 Hz, 1H), 7.15 (d, J=5.50 Hz, 1H), 7.29 (t, J=1.66 Hz, 1H), 8.15 (s, 2H), 8.38 (brs, 1H), 8.51 (d, J=8.15 Hz, 1H), 8.61 (t, J=5.83 Hz, 1H), 9.69 (s, 1H), 10.03 (brs, 1H), 12.33 (brs, 1H, —COOH). $^1$H NMR spectrum of the sample was consistent with the suggested structure of the product.

Example 21

Preparation of (3S)-3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoic acid

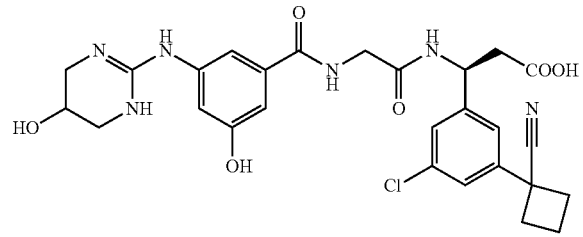 [SMILES: N#CC1(c2cc(Cl)cc([C@H](CC(=O)O)NC(=O)CNC(=O)c3cc(O)cc(NC4=NCC(O)CN4)c3)c2)CCC1]

Step 1

Preparation of (S)-ethyl 3-amino-3-(3-chloro-5-(1-cyanocyclobutyl)phenyl)propanoate hydrochloride

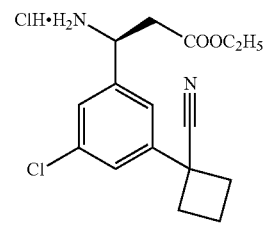

Part A

Preparation of (S)-3-amino-3-(3-chloro-5-(1-cyanocyclobutyl)phenyl)propanoic acid by enzymatic Lipase catalyzed hydrolysis of the racemic mixture

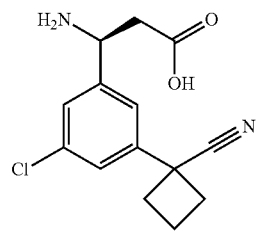 [SMILES: N#CC1(c2cc(Cl)cc([C@@H](N)CC(=O)O)c2)CCC1]

A suspension of rac-ethyl 3-amino-3-(3-chloro-5-(1-cyanocyclobutyl)phenyl)propanoate (Example N) (911.4 mg, 2.971 mmol) was stirred in 50 mM KH$_2$PO$_4$ solution (35 mL). The pH of the aqueous phase was adjusted to pH 8.25 by the addition of 1N NaOH solution and 50 mM KH$_2$PO$_4$ solution. Amano Lipase PS (981.5 mg) was added and the reaction mixture was stirred at room temperature under nitrogen atmosphere. The reaction mixture after stifling for 5 days was diluted with MTBE (25 mL) and the mixture was stirred at room temperature for 15 min. The aqueous and MTBE layers were separated; the aqueous layer was extracted with MTBE (1×25 mL). The combined MTBE layer was dried over anhydrous Na$_2$SO$_4$, filtered and evaporated in vacuo to afford a pale yellow viscous liquid (477.3 mg). LC-MS analysis of the liquid shows the (R)-ethyl 3-amino-3-(3-chloro-5-(1-cyanocyclobutyl)phenyl)propanoate's mass: m/z 307 ($^{35Cl}$M+H), m/z 309 ($^{37Cl}$M+H), m/z 329 ($^{35Cl}$M+Na) and m/z 331 ($^{37Cl}$M+Na); Calcd for C$_{16}$H$_{19}$ClN$_2$O$_2$: 306.79. The aqueous layer after MTBE extractions was evaporated in vacuo to afford a colorless to cream gummy residue (1.9965 g) containing the (S)—COOH, Amano Lipase-PS and the phosphate buffer. LC-MS analysis of the crude residue shows the desired product: (S)-3-amino-3-(3-chloro-5-(1-cyanocyclobutyl)phenyl)propanoic acid's mass: m/z 279 ($^{35Cl}$M+H), m/z 281 ($^{37Cl}$M+H), m/z 301 ($^{35Cl}$M+Na) and m/z 303 ($^{37Cl}$M+Na), m/z 557 ($^{35Cl,35Cl}$2M+Na), m/z 559 ($^{35Cl,37Cl}$2M+Na,) and m/z 561 ($^{37Cl,37Cl}$2M+Na); Calcd for $C_{14}H_{15}ClN_2O_2$: 278.73. The crude residue is used as such for the esterification with absolute ethyl alcohol saturated with anhydrous HCl gas (step B).

Part B

Preparation of (S)-ethyl 3-amino-3-(3-chloro-5-(1-cyanocyclobutyl)phenyl)propanoate hydrochloride

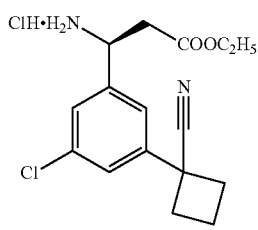

To a suspension of the residue from Step A above containing (S)-3-amino-3-(3-chloro-5-(1-cyanocyclobutyl)phenyl)propanoic acid (~1.485 mml, crude residue), Amano Lipase-PS and the phosphate buffer in absolute ethyl alcohol (5 mL) was added absolute ethanol saturated with anhydrous HCl gas (15 mL) and the reaction mixture was heated at reflux under nitrogen for 2 h to give a light brown solution containing a colorless suspension. The solvent was evaporated in vacuo to give a brown viscous liquid of the crude product (1.9965 g). The crude product was purified by reverse-phase preparative HPLC on a Biotage 40+M (100 g) C18HS column and a gradient 10-60% acetonitrile in water containing 0.05% TFA. The pure fractions were mixed together and evaporated in vacuo to afford a pale yellow viscous residue. The residue was dissolved in absolute ethyl alcohol saturated with anhydrous HCl gas (5 mL), stirred at room temperature for 5 min and evaporated in vacuo to afford a pale yellow viscous residue, triturated with diethyl ether (5 mL) and evaporated in vacuo to afford a cream foamy solid (345.2 mg). LC-MS analysis of the solid shows the desired (S)-ethyl 3-amino-3-(3-chloro-5-(1-cyanocyclobutyl)phenyl) propanoate's mass: m/z 307 ($^{35Cl}$M+H), m/z 309 ($^{37Cl}$M+H), m/z 329 ($^{35Cl}$M+Na) and m/z 331 ($^{37Cl}$M+Na); Calcd for $C_{16}H_{19}ClN_2O_2$:306.79

Step 2

Preparation of (3S)-ethyl 3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoate

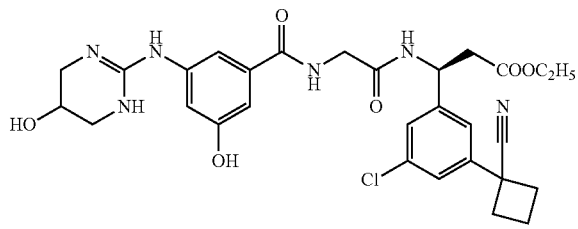

A mixture of 2-(3-hydroxy-5-((5-hydroxy-1,4,5,6-tetrahydropyrimidin-2-yl)amino)benzamido)acetic acid (Example B) (314.5 mg, 1.02 mmol), ethyl (S)-3-amino-3-(3-chloro-5-(1-cyanocyclobutyl)phenyl)propanoate hydrochloride salt (from step 1 above) (345.15 mg, 1.006 mmol) and 1-hydroxybenzotriazole hydrate (31.2 mg, 0.204 mmol) was dissolved in a mixture of DMF/DCM (1:1) (8 mL) and stirred at room temperature under nitrogen atmosphere for 10 min to give a cream suspension. N,N'-diisopropylcarbodiimde (225 μL, 1.453 mmol) was added to the above suspension and the reaction mixture was stirred at room temperature under nitrogen atmosphere overnight (19 h). The solvent was evaporated in vacuo to give a yellow-orange gummy residue. LC-MS analysis of the gummy residue shows the desired product: (3S)-ethyl 3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoate's mass: m/z 597 ($^{35Cl}$M+H), m/z 599 ($^{37Cl}$M+H), m/z 619 ($^{35Cl}$M+Na) and m/z 621 ($^{37Cl}$M+Na); Calcd for $C_{29}H_{33}ClN_6O_6$: 597.06. The crude residue is used as such for the saponification with lithium hydroxide monohydrate (Step 3).

Step 3

Preparation of (3S)-3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoic acid

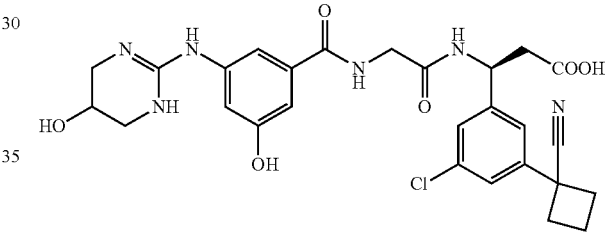

To a suspension of (3S)-ethyl 3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoate (from step 2 above) (1.006 mmol, crude residue) in a mixture of acetonitrile/water (1:1) (6 mL) was added lithium hydroxide monohydrate (212 mg, 5.052 mmol) and the reaction mixture was stirred at room temperature overnight (16 h). The solvent was evaporated in vacuo to afford a yellow-orange viscous residue. The residue was dissolved in water (25 mL) and stirred with dichloromethane (50 mL). The DCM layer was removed and discarded after analyzed by LC-MS, shows the DIPU, byproducts and baseline impurities only. The aqueous layer was acidified with TFA (1 mL in 3 mL ACN) and evaporated in vacuo to afford a pale viscous residue. The crude residue was purified by reverse-phase preparative HPLC on a Biotage 40+M (100 g) C18HS column and a gradient 10-60% acetonitrile in water containing 0.05% TFA. The pure fractions were mixed together and evaporated in vacuo to give the desired product, after lyophilization, as a colorless lyophilized powder (305 mg). LC-MS analysis of the solid shows the desired product: (3S)-3-(3-chloro-5-(1-cyanocyclobutyl)phenyl)-3-(2-(3-hydroxy-5-((5-hydroxy-1,4,5,6-tetrahydropyrimidin-2-yl)amino)benzamido)acetamido)propanoic acid's mass: m/z 569 ($^{35Cl}$M+H) and m/z 571 ($^{37Cl}$M+H); Calcd for $C_{27}H_{29}ClN_6O_6$: 569.01

$^1$H NMR (400 MHz, DMSO-$d_6$): δ 1.94-2.06 (M, 1H), 2.20-2.34 (dp, J=11.3, 8.8 Hz, 1H), 2.55-2.80 (M, 6H), 3.16 (dt, J=12.3, 3.6 Hz, 2H), 3.28-3.38 (dd/m, 2H), 3.87 (d, J=5.8

Hz, 2H), 4.09 (q, J=3.3 Hz, 1H), 5.21 (q, J=7.5, 1H), 5.43 (brs, 1H), 6.74 (t, J=2.1 Hz, 1H), 7.12 (dt, J=12.0 and 1.5 Hz, 2H), 7.40 (dt, J=2.1, 1.2 Hz, 3H), 8.12 (brs, 2H), 8.57 (d, J=8.20 Hz, 1H), 8.65 (brt, J=8.2 Hz, 1H), 9.64 (s, 1H), 10.02 (brs, 1H), 12.38 (brs, 1H). $^1$H NMR spectrum of the sample was consistent with the structure of the desired titled product.

Example 22

Preparation of (3S)-3-(3-chloro-5-(4-cyanotetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

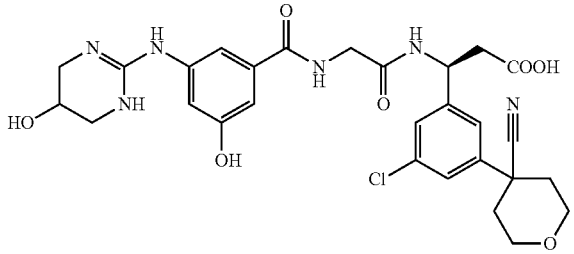 [SMILES: N#CC1(c2cc(Cl)cc([C@H](CC(=O)O)NC(=O)CNC(=O)c3cc(O)cc(NC4=NCC(O)CN4)c3)c2)CCOCC1]

Step 1

Preparation of ethyl (S)-3-amino-3-(3-chloro-5-(4-cyanotetrahydro-2H-pyran-4-yl)phenyl)propanoate hydrochloride

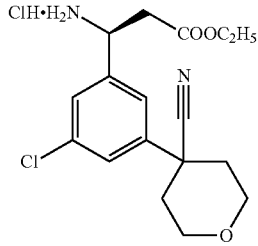

Part A

Preparation of (S)-3-amino-3-(3-chloro-5-(4-cyanotetrahydro-2H-pyran-4-yl)phenyl)propanoic acid by enzymatic Lipase catalyzed hydrolysis of the racemic mixture

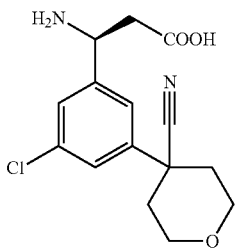 [SMILES: N#CC1(c2cc(Cl)cc([C@@H](N)CC(=O)O)c2)CCOCC1]

A suspension of rac-ethyl 3-amino-3-(3-chloro-5-(4-cyanotetrahydro-2H-pyran-4-yl)phenyl)propanoate (Example O) (943.4 mg, 2.801 mmol) was stirred in 50 mM $KH_2PO_4$ solution (35 mL) and the pH of the aqueous phase was adjusted to pH 8.32 by the addition of 1N NaOH solution and 50 mM $KH_2PO_4$ solution. Amano Lipase PS (1.0276 g) was added and the reaction mixture was stirred at room temperature for 5 days. The reaction mixture was diluted with MTBE (25 mL) and the mixture was stirred at room temperature for 15 min. The aqueous and MTBE layers were separated; the aqueous layer was extracted with MTBE (1×25 mL). The MTBE layer was dried over anhydrous $Na_2SO_4$, filtered and evaporated in vacuo to afford a pale yellow viscous liquid (530.6 mg). LC-MS analysis of the liquid shows the (R)-ethyl 3-amino-3-(3-chloro-5-(4-cyanotetrahydro-2H-pyran-4-yl)phenyl)propanoate's mass: m/z 337 ($^{35Cl}$M+H), m/z 339 ($^{37Cl}$M+H), m/z 359 ($^{35Cl}$M+Na) and m/z 361 ($^{37Cl}$M+Na); Calcd for $C_{17}H_{21}ClN_2O_3$:336.81.

Evaporation of the aqueous layer after MTBE extractions in vacuo to afford a colorless to cream flaky/gummy residue (1.8270 g) containing the (S)—COOH, Amano Lipase-PS and the phosphate buffer. LC-MS analysis of the residue shows the (S)-3-amino-3-(3-chloro-5-(4-cyanotetrahydro-2H-pyran-4-yl) phenyl)propanoic acid's mass: m/z 309 ($^{35Cl}$M+H), m/z 311 ($^{37Cl}$M+H), m/z 331 ($^{35Cl}$M+Na) and m/z 333 ($^{37Cl}$M+Na), m/z 617 ($^{35Cl,35Cl}$2M+Na), m/z 619 ($^{35Cl,37Cl}$2M+Na) and m/z 621 ($^{37Cl,37Cl}$2M+Na). The above crude residue will be used as such for the esterification to synthesize: ethyl (S)-3-amino-3-(3-chloro-5-(4-cyanotetrahydro-2H-pyran-4-yl)phenyl)propanoate hydrochloride (Step B).

Part B

Preparation of ethyl (S)-3-amino-3-(3-chloro-5-(4-cyanotetrahydro-2H-pyran-4-yl)phenyl)propanoate hydrochloride

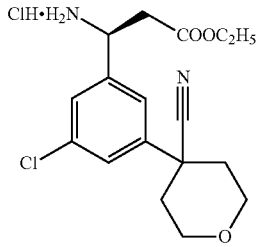

To a suspension of the crude product from step A above containing the (S)—COOH (1.4 mmol), Amano Lipase-PS and the phosphate buffer in absolute ethyl alcohol (5 mL) was added absolute ethanol saturated with anhydrous HCl gas and the reaction mixture was heated at reflux under nitrogen for 6 h to give a light brown solution containing a colorless suspension. The reaction mixture cooled to room temperature and filtered to remove insoluble suspension. The filtrate was evaporated in vacuo to give a brown viscous liquid (2.054 g). The above crude product was purified by reverse-phase preparative HPLC on a Biotage 40+M (100 g) C18HS column and a gradient 10-60% acetonitrile in water containing 0.05% TFA to afford the desired product as a pale yellow viscous residue. The residue was dissolved in absolute ethyl alcohol saturated with anhydrous HCl gas (5 mL), stirred at room temperature for 5 min and evaporated in vacuo to afford a pale yellow viscous residue, triturated with diethyl ether (5 mL) and evaporated in vacuo to afford a pale pink foamy solid (314.3 mg). LC-MS analysis of the foamy solid shows the desired product: (S)-ethyl-3-amino-3-(3-chloro-5-(4-cyanotetrahydro-2H-pyran-4-yl)phenyl)propanoate's mass: m/z 337 ($^{35Cl}$M+H), m/z 339 ($^{37Cl}$M+H), m/z 359 ($^{35Cl}$M+Na) and m/z 361 ($^{37Cl}$M+Na); Calcd for $C_{17}H_{21}ClN_2O_3$: 336.81.

Step 2

Preparation of (3S)-ethyl 3-(3-chloro-5-(4-cyanotetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate

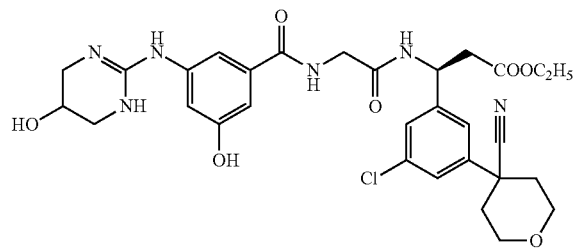

A mixture of 2-(3-hydroxy-5-((5-hydroxy-1,4,5,6-tetrahydropyrimidin-2-yl)amino)benzamido)acetic acid (Example B) (264.7 mg, 0.859 mmol), (S)-ethyl-3-amino-3-(3-chloro-5-(4-cyanotetrahydro-2H-pyran-4-yl)phenyl)propanoate hydrochloride salt (from step 1 above) (314.3 mg, 0.842 mmol) and 1-hydroxybenzotriazole hydrate (27.4 mg, 0.179 mmol) was dissolved in a mixture of DMF/DCM (1:1) (8 mL) and stirred at room temperature under nitrogen atmosphere for 10 min to give a cream suspension. Neat N,N'-diisopropylcarbodiimide (175 µL, 1.13 mmol) was added to the above suspension and the reaction mixture was stirred at room temperature under nitrogen atmosphere overnight. The solvent was evaporated in vacuo to give a pale yellow-cream gummy residue. LC-MS analysis of the crude residue shows the desired product: (3S)-ethyl 3-(3-chloro-5-(4-cyanotetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate's mass: m/z 627 ($^{35Cl}$M+H) and m/z 629 ($^{37Cl}$M+H); Calcd for $C_{30}H_{35}ClN_6O_7$: 627.09. The crude residue is used as such for the saponification with lithium hydroxide monohydrate (Step 3).

Step 3

Preparation of (3S)-3-(3-chloro-5-(4-cyanotetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoic acid

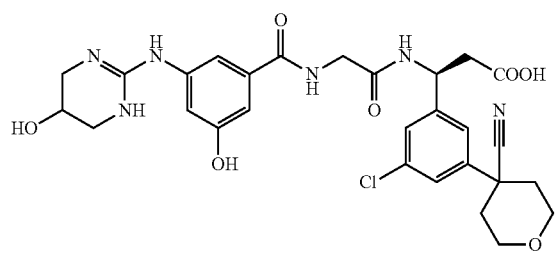 [SMILES: N#CC1(c2cc(Cl)cc([C@H](CC(=O)O)NC(=O)CNC(=O)c3cc(O)cc(NC4=NCC(O)CN4)c3)c2)CCOCC1]

To a suspension of (3S)-ethyl 3-(3-chloro-5-(4-cyanotetrahydro-2H-pyran-4-yl)phenyl)-3-(2-(3-hydroxy-5-((5-hydroxy-1,4,5,6-tetrahydropyrimidin-2-yl)amino)benzamido)acetamido)propanoate (from step 2 above) (0.842 mmol, crude residue) in a mixture of acetonitrile/water (1:1) (6 mL) was added lithium hydroxide monohydrate (180.0 mg, 4.289 mmol) and the reaction mixture was stirred at room temperature overnight. The solvent was evaporated in vacuo to afford a yellow-orange viscous residue. The residue was dissolved in water (25 mL) and stirred with dichloromethane (50 mL). The aqueous layer was separated and acidified with TFA (1 mL in 3 mL ACN) and evaporated in vacuo to afford a pale orange viscous residue. The crude residue was purified by reverse-phase preparative HPLC on a Biotage 40+M (100 g) C18HS column and a gradient 10-60% acetonitrile in water containing 0.05% TFA to give the desired product, after lyophilization, as a colorless lyophilized powder (305 mg). LC-MS analysis of the solid shows the desired product's mass: m/z 599 ($^{35Cl}$M+H) and m/z 601 ($^{37Cl}$M+H); Calcd for $C_{28}H_{31}ClN_6O_7$:599.03.

$^1$H NMR (400 MHz, DMSO-d$_6$): δ 2.00-2.18 (M, 4H), 2.70-2.80 (M, 2H), 3.16 (dt, J=12.3, 3.5 Hz, 2H), 3.33 (brd, J=12.7 Hz, 2H), 3.57-3.74 (M, 2H), 3.87 (d, J=5.9 Hz, 2H), 3.96-4.04 (M, 2H), 4.08 (appt, 1H), 5.22 (q, J=7.5 Hz, 1H), 6.75 (t, J=2.1 Hz, 1H), 7.12 (dt, J=12.0 and 1.5 Hz, 2H), 7.43 (t, J=1.5 Hz, 1H), 7.46-7.53 (M, 2H), 8.11 (d, J=3.2 HZ, 2H), 8.57 (d, J=8.1 Hz, 1H), 8.66 (t, J=5.9 Hz, 1H), 9.62 (s, 1H), 10.02 (brs, 1H), 12.39 (brs, 1H). $^1$H NMR spectrum of the sample was consistent with the structure of the desired titled product.

Example 23

Preparation of (3S)-3-(3-chloro-5-(1,1,1-trifluoro-2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid

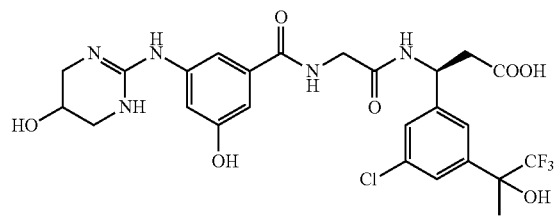 [SMILES: CC(O)(c1cc(Cl)cc([C@H](CC(=O)O)NC(=O)CNC(=O)c2cc(O)cc(NC3=NCC(O)CN3)c2)c1)C(F)(F)F]

Step 1

Preparation of (S)-ethyl 3-amino-3-(3-chloro-5-(1,1,1-trifluoro-2-hydroxypropan-2-yl)phenyl)propanoate hydrochloride

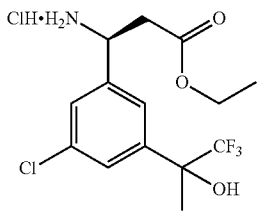

Part A

Preparation of (3S)-3-amino-3-(3-chloro-5-(1,1,1-trifluoro-2-hydroxypropan-2-yl)phenyl)propanoic acid by enzymatic Lipase catalyzed hydrolysis of the racemic mixture

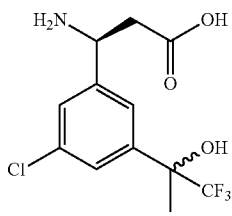 [SMILES: CC(O)(c1cc(Cl)cc([C@@H](N)CC(=O)O)c1)C(F)(F)F]

A suspension of rac-ethyl 3-amino-3-(3-chloro-5-(1,1,1-trifluoro-2-hydroxypropan-2-yl)phenyl)propanoate (Example P) (1121.5 mg, 3.301 mmol) in 50 mM $KH_2PO_4$ solution (40.0 mL) was stirred at room temperature and the pH of the aqueous layer was adjusted to pH 8.34 by the addition of 1.0 N NaOH solution. Amano Lipase (1.20 g) was added to the above suspension and the reaction mixture was stirred at room temperature. After stirring for 6 days at room temperature, the reaction mixture was diluted with MTBE (25 mL) and reaction mixture was stirred at room temperature to extract the (R)-ester. The aqueous and MTBE layers were separated and the aqueous layer containing a colorless suspension/precipitate was extracted with methyl tert-butyl ether (MTBE) (1×25 mL). The combined MTBE layer was washed with water (1×25 mL), dried over anhydrous $Na_2SO_4$, filtered and evaporated in vacuo to afford a yellow-orange viscous liquid (502.0 mg). LC-MS analysis of the liquid shows the (3R)-ethyl 3-amino-3-(3-chloro-5-(1,1,1-trifluoro-2-hydroxypropan-2-yl)phenyl)propanoate's mass: m/z 340 ($^{35Cl}$M+H), m/z 342 ($^{37Cl}$M+H), m/z 362 ($^{35Cl}$M+Na) and m/z 364 ($^{37Cl}$M+Na); Calcd for $C_{14}H_{17}ClF_3NO_3$: 339.74. The aqueous layer was evaporated in vacuo to afford a colorless to cream solid (2.2231 g) containing the (S)—COOH, Amano Lipase-PS and the phosphate buffer. LC-MS analysis of the residue also shows the desired product: (3S)-3-amino-3-(3-chloro-5-(1,1,1-trifluoro-2-hydroxypropan-2-yl)phenyl)propanoic acid's mass: m/z 312 ($^{35Cl}$M+H), m/z 314 ($^{37Cl}$M+H), m/z 334 ($^{35Cl}$M+Na) and m/z 336 ($^{37Cl}$M+Na); Calcd for $C_{12}H_{13}ClF_3NO_3$: 311.68. The above crude residue will be used as such for the esterification with absolute ethyl alcohol saturated with anhydrous HCl gas to synthesize: (3S)-ethyl 3-amino-3-(3-chloro-5-(1,1,1-trifluoro-2-hydroxypropan-2-yl) phenyl)propanoate hydrochloride (Step B).

Part B

Preparation of (S)-ethyl 3-amino-3-(3-chloro-5-(1,1,1-trifluoro-2-hydroxypropan-2-yl)phenyl)propanoate hydrochloride

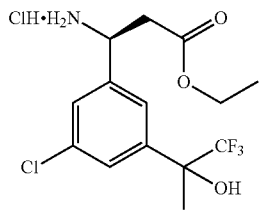

To a suspension of the crude product from step A above containing the (S)-acid, Amano Lipase and Phosphate buffer salt in absolute ethyl alcohol (5 mL) was added absolute ethanol saturated with anhydrous HCl gas (15 mL) and the reaction mixture was heated at reflux under nitrogen to give a brown solution containing a colorless to gray suspension. The reaction mixture cooled to room temperature and filtered to remove insoluble suspension. The filtrate was evaporated in vacuo to give a brown foamy-gummy residue (2.45 g). The crude product was purified by reverse-phase preparative HPLC on a Biotage 40+M (100 g) C18HS column and a gradient 10-60% acetonitrile in water containing 0.05% TFA. The pure fractions were mixed together and evaporated in vacuo to afford a pale yellow foamy-viscous residue (771.0 mg). The residue was dissolved in absolute ethyl alcohol saturated with anhydrous HCl gas (10 mL), heated at reflux for 10 min and evaporated in vacuo to afford a pale yellow viscous residue. The residue was triturated with diethyl ether (10 mL) and evaporated in vacuo to give a cream foamy solid (622.0 mg). LC-MS analysis of the foamy solid shows the desired product: (S)-ethyl 3-amino-3-(3-chloro-5-(1,1,1-trifluoro-2-hydroxypropan-2-yl)phenyl)propanoate's mass: m/z 340 ($^{35Cl}$M+H), m/z 342 ($^{37Cl}$M+H), m/z 362 ($^{35Cl}$M+Na) and m/z 364 ($^{37Cl}$M+Na); Calcd for $C_{14}H_{17}ClF_3NO_3$:339.74.

Step 2

Preparation of (3S)-ethyl 3-(3-chloro-5-(1,1,1-trifluoro-2-hydroxypropan-2-yl)phenyl)-3-(2-(3-hydroxy-5-((5-hydroxy-1,4,5,6-tetrahydropyrimidin-2-yl)amino)benzamido)acetamido)propanoate

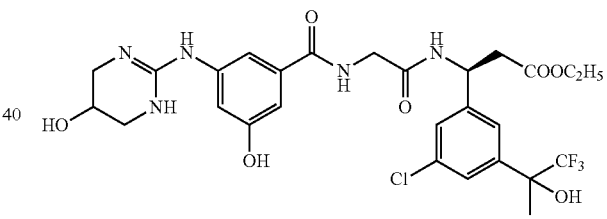

A mixture of 2-(3-hydroxy-5-((5-hydroxy-1,4,5,6-tetrahydropyrimidin-2-yl)amino)benzamido)acetic acid (Example B) (328.3 mg, 1.065 mmol), (3S)-ethyl 3-amino-3-(3-chloro-5-(1,1,1-trifluoro-2-hydroxypropan-2-yl)phenyl)propanoate hydrochloride salt (from step 1 above) (364.2 mg, 0.968 mmol) and 1-hydroxybenzotriazole hydrate (31.5 mg, 0.206 mmol) was dissolved in a mixture of DMF/DCM (1:1) and stirred at room temperature under nitrogen atmosphere for 10 min to give a cream suspension. N,N'-diisopropylcarbodiimde (210 μL, 1.356 mmol) was added to the above suspension and the reaction mixture was stirred at room temperature overnight (19 h) under nitrogen atmosphere. The solvent was evaporated in vacuo to give a yellow-cream gummy residue. LC-MS analysis of the crude residue shows the desired product: (3S)-ethyl 3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido) propanoate's mass: m/z 630 ($^{35Cl}$M+H) and m/z 632 ($^{37Cl}$M+H); Calcd for $C_{27}H_{31}ClF_3N_5O_7$: 630.01. The crude residue is used as such for the saponification with lithium hydroxide monohydrate (Step 3)

Step 3

Preparation of (3S)-3-(3-chloro-5-(1,1,1-trifluoro-2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid

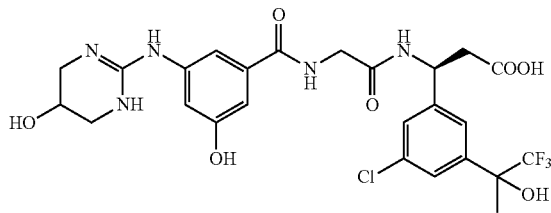

To a suspension of (3S)-ethyl 3-(3-chloro-5-(1,1,1-trifluoro-2-hydroxypropan-2-yl)phenyl)-3-(2-(3-hydroxy-5-((5-hydroxy-1,4,5,6-tetrahydropyrimidin-2-yl)amino)benzamido)acetamido)propanoate (from step 2 above) (0.968 mmol, crude residue) in a mixture of acetonitrile/water (1:1) (8 mL) was added lithium hydroxide monohydrate (203.1 mg, 4.84 mmol) and the reaction mixture was stirred at room temperature overnight (15 h). The solvent was evaporated in vacuo to afford a yellow-orange viscous residue. The residue was dissolved in water (25 mL) and stirred with dichloromethane (50 mL). The DCM layer was removed and discarded after analyzed by LC-MS. The aqueous layer was neutralized with TFA (1 mL in 3 mL ACN) and evaporated in vacuo to afford a pale viscous residue. The crude residue was purified by reverse-phase preparative HPLC on a Biotage 40+M (100 g) C18HS column and a gradient 10-60% acetonitrile in water containing 0.05% TFA to afford the desired product, after lyophilization, as a colorless lyophilized powder (439.2 mg). LC-MS analysis of the solid shows the desired product: (3S)-3-(3-chloro-5-(1,1,1-trifluoro-2-hydroxypropan-2-yl)phenyl)-3-(2-(3-hydroxy-5-((5-hydroxy-1,4,5,6-tetrahydropyrimidin-2-yl)amino)benzamido)acetamido)propanoic acid's mass: m/z 602 ($^{35Cl}$M+H) and m/z 604 ($^{37Cl}$M+H); Calcd for $C_{25}H_{27}ClF_3N_5O_7$: 601.96. $^1$H NMR (400 MHz, DMSO-$d_6$): δ 1.69 (s, 3H), 2.72 (d, J=7.0 Hz, 2H), 3.16 (d, J=12.8 Hz, 2H), 3.33 (d, J=12.7 Hz, 2H), 3.87 (d, J=5.3 Hz, 2H), 4.08 (s, 1H), 5.21 (appq, 1H), 5.45 (brs, 1H), 6.74 (brs, 1H), 6.79 (brs, 1H), 7.12 (dt/m, 2H), 7.41 (s, 1H), 7.49 (brs, 2H), 8.14 (brs, 2H), 8.58 (dd/m, 1H), 8.63 (brt, 1H), 9.67 (brs, 1H), 10.03 (brs, 1H), 12.40 (brs, 1H). $^1$H NMR spectrum of the sample was consistent with the structure of the desired titled product.

Example 24

Preparation of (3S)-3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido)propanoic acid

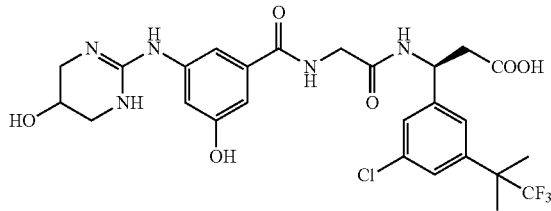 [SMILES: CC(C)(c1cc(Cl)cc([C@H](CC(=O)O)NC(=O)CNC(=O)c2cc(O)cc(NC3=NCC(O)CN3)c2)c1)C(F)(F)F]

Step 1

Preparation of (S)-ethyl 3-amino-3-(3-chloro-5-(1,1,1-trifluoro-2-methylpropan-2-yl)phenyl)propanoate hydrochloride

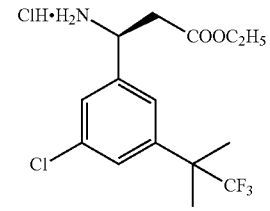

Part A

Preparation of (S)-3-amino-3-(3-chloro-5-(1,1,1-trifluoro-2-methylpropan-2-yl)phenyl)propanoic acid by enzymatic Lipase catalyzed hydrolysis of the racemic mixture

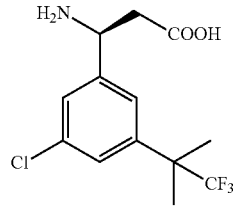 [SMILES: CC(C)(c1cc(Cl)cc([C@@H](N)CC(=O)O)c1)C(F)(F)F]

A suspension of rac-ethyl 3-amino-3-(3-chloro-5-(1,1,1-trifluoro-2-methylpropan-2-yl)phenyl)propanoate (Example Q) (921.7 mg, 2.729 mmol) was stirred in 50 mM $KH_2PO_4$ solution (40 mL). The pH of the aqueous phase was adjusted to pH 8.32 by the addition of 1N NaOH solution and 50 mM $KH_2PO_4$ solution. Amano lipase PS *Burkholderia cepacia* (1.15 g) was added to above reaction mixture and the reaction mixture was stirred at room temperature. The reaction mixture after stifling for 7 days was diluted with MTBE (25 mL), stirred at room temperature for 15 min and the mixture was filtered to remove precipitated solid. The solid was washed with acetone (2×25 mL) and dried in vacuo to afford a white powder (252.8 mg). LC-MS analysis of the solid shows the desired product: (S)-3-amino-3-(3-chloro-5-(1,1,1-trifluoro-2-methylpropan-2-yl)phenyl)propanoic acid's mass: m/z 310 ($^{35Cl}$M+H), m/z 312 ($^{37Cl}$M+H), m/z 332 ($^{35Cl}$M+Na) and m/z 334 ($^{37Cl}$M+Na); Calcd for $C_{13}H_{15}ClF_3NO_2$:309.71. The aqueous and MTBE layers were separated; the aqueous layer was extracted with MTBE (1×25 mL). The combined MTBE layer was dried over anhydrous $Na_2SO_4$, filtered and evaporated in vacuo to afford a pale yellow viscous liquid (465 mg). LC-MS analysis of the liquid shows the (R)-ethyl 3-amino-3-(3-chloro-5-(1,1,1-trifluoro-2-methylpropan-2-yl)phenyl)propanoate's mass: m/z 338 ($^{35Cl}$M+H), m/z 340 ($^{37Cl}$M+H), m/z 360 ($^{35Cl}$M+Na) and m/z 362 ($^{37Cl}$M+Na); Calcd for $C_{15}H_{19}ClF_3NO_2$: 337.77. The aqueous layer after MTBE extractions was evaporated in vacuo to afford a colorless to cream gummy residue (1.9845 g) containing the (S)—COOH, Amano Lipase-PS and the phosphate buffer. The residue was triturated with a mixture of water and acetonitrile to afford a colorless precipitate, filtered, washed with water and acetonitrile and dried in vacuo to afford a colorless microcrystalline solid (146.3 mg, 2$^{nd}$ crop) of the (S)-3-amino-3-(3-chloro-5-(1,1,1-trifluoro-2-methylpropan-2-yl)phenyl) propanoic acid. The filtrate after 2$^{nd}$ crop removal was evaporated in vacuo to afford a colorless gummy residue containing the (S)—COOH, Amano Lipase-PS and the phosphate buffer. The residue was purified by reverse-phase preparative HPLC on a Biotage 40+M (100 g) C18HS column and a gradient 10-60% acetonitrile in water containing 0.05% TFA. The pure fractions were mixed together and evaporated in vacuo to afford a colorless crystalline solid (46.4 mg, 3$^{rd}$ crop).

Part B

Preparation of (S)-ethyl 3-amino-3-(3-chloro-5-(1,1,1-trifluoro-2-methylpropan-2-yl)phenyl)propanoate hydrochloride

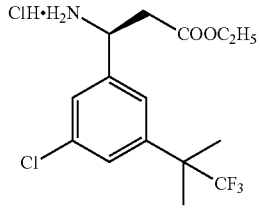

Absolute ethanol saturated with anhydrous HCl gas (10 mL) was added to a suspension of (S)-3-amino-3-(3-chloro-5-(1,1,1-trifluoro-2-methylpropan-2-yl)phenyl)propanoic acid (from step A above) (252.8 mg, 0.816 mmol) in absolute ethyl alcohol (5 mL) and the reaction mixture was heated at reflux for 4 h to give a colorless solution. The solvent was removed in vacuo to give a colorless gummy solid. The solid was slurried a couple of times with diethyl ether (2×5 mL). After the solvent was decanted off, the residue was dried in vacuo to give the desired (S)-ethyl 3-amino-3-(3-chloro-5-(1,1,1-trifluoro-2-methylpropan-2-yl)phenyl)propanoate hydrochloride salt as a cream foamy solid (293.76 mg). LC-MS analysis of the solid shows the desired product's mass: m/z 338 ($^{35Cl}$M+H), m/z 340 ($^{37Cl}$M+H), m/z 360 ($^{35Cl}$M+Na) and m/z 362 ($^{37Cl}$M+Na); Calcd for $C_{15}H_{19}ClF_3NO_2$: 337.77.

Step 2

Preparation of (3S)-ethyl 3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido)propanoate

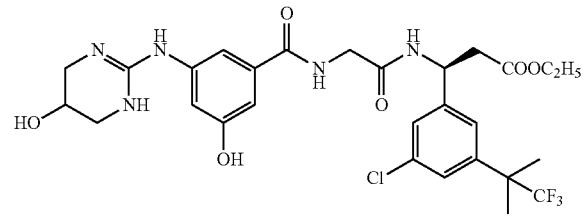

A mixture of 2-(3-hydroxy-5-((5-hydroxy-1,4,5,6-tetrahydropyrimidin-2-yl)amino)benzamido)acetic acid (Example B) (242 mg, 0.785 mmol), (S)-ethyl 3-amino-3-(3-chloro-5-(1,1,1-trifluoro-2-methylpropan-2-yl)phenyl)propanoate hydrochloride salt (from step 1 above) (293.76 mg, 0.785 mmol) and 1-hydroxybenzotriazole hydrate (24.1 mg, 0.157 mmol) was dissolved in a mixture of DMF/DCM (1:1) (8 mL) and stirred at room temperature under nitrogen atmosphere for 10 min to give a cream suspension. N,N'-diisopropylcarbodiimide (170 µL, 1.098 mmol) was added to the above suspension and the reaction mixture was stirred at room temperature under nitrogen atmosphere overnight (19 h). The solvent was evaporated in vacuo to give a pale yellow viscous gummy residue (917.0 mg). LC-MS analysis of the crude residue shows the desired product: (3S)-ethyl 3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido) propanoate's mass: m/z 628 ($^{35Cl}$M+H) and m/z 630 ($^{37Cl}$M+H); Calcd for $C_{28}H_{33}ClF_3N_5O_6$: 628.04. The crude residue will be used as such for the saponification with lithium hydroxide monohydrate. (Step 3).

Step 3

Preparation of (3S)-3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido)propanoic acid

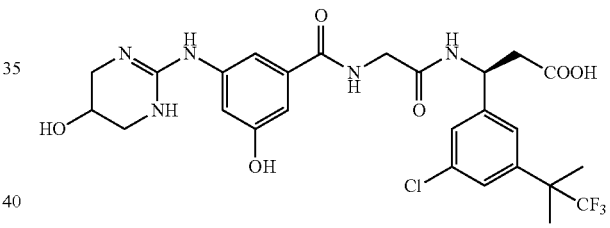

To a suspension of (3S)-ethyl 3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido)propanoate (from step 2 above) (0.785 mmol, crude residue) in a mixture of acetonitrile/water (1:1) (6 mL) was added lithium hydroxide monohydrate (165 mg, 3.932 mmol) and the reaction mixture was stirred at room temperature overnight. The solvent was evaporated in vacuo to afford a yellow-orange viscous residue and the residue was dissolved in water (25 mL) and stirred with dichloromethane (50 mL) for 15 min. The aqueous layer was separated, acidified with TFA (1 mL in 3 mL ACN) and evaporated in vacuo to afford a pale viscous residue. The crude residue was purified by reverse-phase preparative HPLC on a Biotage 40+M (100 g) C18HS column and a gradient 10-60% acetonitrile in water containing 0.05% TFA to afford the desired product, after lyophilization, as a colorless lyophilized powder (277.7 mg). LC-MS analysis of the residue shows the desired product: (3S)-3-(3-chloro-5-(1,1,1-trifluoro-2-methylpropan-2-yl)phenyl)-3-(2-(3-hydroxy-5-((5-hydroxy-1,4,5,6-tetrahydropyrimidin-2-yl)amino)benzamido)acetamido)propanoic acid's mass: m/z 600 ($^{35Cl}$M+H), and m/z 602 ($^{37Cl}$M+H); Calcd for $C_{26}H_{29}ClF_3N_5O_6$: 599.99.

$^1$H NMR (400 MHz, DMSO-d$_6$): δ 1.55 (s, 6H), 2.72 (dd, J=7.9, 3.4 Hz, 2H), 3.16 (d, J=12.6 Hz, 2H), 3.34 (d, J=12.7

Hz, 2H), 3.86 (appt, 2H), 4.08 (s, 1H), 4.08 (s, 1H), 5.22 (q, J=8.2 Hz, 1H), 5.54 (brs, 1H), 6.75 (brs, 1H), 7.12 (dd, J=11.0, 3.2 Hz, 2H), 7.42 (dd, J=11.0, 3.2 Hz, 2H), 7.47 (s, 1H), 8.15 (d, J=3.9 Hz, 2H),), 8.15 (s, 2H), 8.57 (brd, 1H), 8.64 (brm, 1H), 9.68 (s, 1H), 10.03 (s, 1H), 12.38 (brs, 1H, —COOH). $^1$H NMR spectrum of the sample was consistent with the structure of the desired titled product.

Example 25

Preparation of (3S)-3-(2-(3-hydroxy-5-((5-hydroxy-1,4,5,6-tetrahydropyrimidin-2-yl)amino)benzamido)acetamido)-3-(3-(1,1,1-trifluoro-2-hydroxypropan-2-yl)-5-(trifluoromethyl)phenyl)propanoic acid

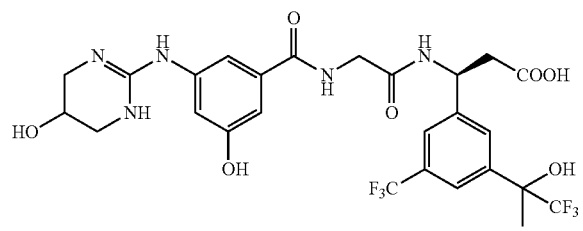 [SMILES: CC(O)(c1cc([C@H](CC(=O)O)NC(=O)CNC(=O)c2cc(O)cc(NC3=NCC(O)CN3)c2)cc(C(F)(F)F)c1)C(F)(F)F]

Step 1

Preparation of (3S)-ethyl 3-amino-3-(3-(1,1,1-trifluoro-2-hydroxypropan-2-yl)-5-(trifluoromethyl)phenyl)propanoate hydrochloride

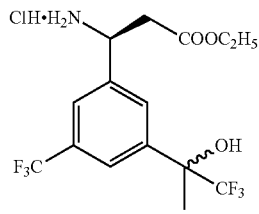

Part A

Preparation of (3S)-3-amino-3-(3-(1,1,1-trifluoro-2-hydroxypropan-2-yl)-5-(trifluoromethyl)phenyl)propanoic acid by enzymatic Lipase catalyzed hydrolysis of the racemic mixture

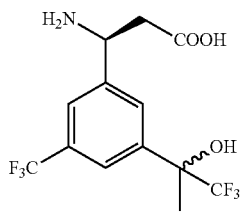 [SMILES: CC(O)(c1cc([C@@H](N)CC(=O)O)cc(C(F)(F)F)c1)C(F)(F)F]

A suspension of rac-ethyl 3-amino-3-(3-(1,1,1-trifluoro-2-hydroxypropan-2-yl)-5-(trifluoromethyl)phenyl)propanoate (Example R) (1.001 g, 2.682 mmol) was stirred in 50 mM KH$_2$PO$_4$ solution (35 mL) and the pH of the aqueous phase was adjusted to pH 8.25 by the addition of 1N NaOH solution and 50 mM KH$_2$PO$_4$ solution. Amano Lipase PS (1.1522 g) was added and the reaction mixture was stirred at room temperature for 6 days to give a slightly turbid solution. The reaction mixture was diluted with MTBE (25 mL) and the mixture was stirred at room temperature for 15 min. The aqueous and MTBE layers were separated and the aqueous layer was extracted with MTBE (1×25 mL). The combined MTBE layer was dried over anhydrous Na$_2$SO$_4$, filtered and evaporated in vacuo to afford a pale yellow viscous liquid (552.2 mg). LC-MS analysis of the liquid shows the (3R)-ethyl 3-amino-3-(3-(1,1,1-trifluoro-2-hydroxypropan-2-yl)-5-(trifluoromethyl)phenyl)propanoate's mass: m/z 374 (M+H) and m/z 396 (M+Na); Calcd for C$_{15}$H$_{17}$F$_6$NO$_3$: 373.29.

Evaporation of the aqueous layer in vacuo afforded a colorless to cream gummy solid (2.2554 g) containing the (S)—COOH as well as Amano Lipase and phosphate buffer salt. LC-MS analysis of the solid shows the desired (3S)-3-amino-3-(3-(1,1,1-trifluoro-2-hydroxypropan-2-yl)-5-(trifluoromethyl)phenyl)propanoic acid's mass: m/z 346 (M+H) and m/z 368 (M+Na); Calcd for C$_{13}$H$_{13}$F$_6$NO$_3$:345.24. The crude solid will be used as such for the synthesis of the beta-amino ester. (Step B).

Part B

Preparation of (3S)-ethyl 3-amino-3-(3-(1,1,1-trifluoro-2-hydroxypropan-2-yl)-5-(trifluoromethyl)phenyl)propanoate hydrochloride

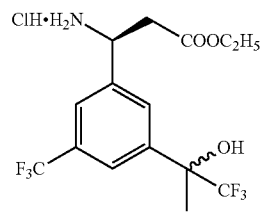

To a suspension of the crude product from Step A above containing the (S)—COOH (~1.34 mmol), Amano Lipase-PS and the phosphate buffer in absolute ethyl alcohol (5 mL) was added absolute ethanol saturated with anhydrous HCl gas (10 mL) and the reaction mixture was heated at reflux under nitrogen for 3 h to give a light brown solution containing a colorless suspension. The reaction mixture cooled to room temperature, filtered and the filtrate was evaporated in vacuo to give a light yellow-brown viscous liquid (2.4556 g). The crude product was purified by reverse-phase preparative HPLC on a Biotage 40+M (100 g) C18HS column and a gradient 10-60% acetonitrile in water containing 0.05% TFA to afford the desired product as a pale yellow viscous liquid. The residue was dissolved in absolute ethyl alcohol saturated with anhydrous HCl gas (5 mL), stirred at room temperature for 5 min and evaporated in vacuo to afford a pale yellow viscous residue, triturated with diethyl ether (5 mL) and evaporated in vacuo to afford a pale pink cream foamy solid (483.4 mg). LC-MS analysis of the solid shows the desired product: (3S)-ethyl 3-amino-3-(3-(1,1,1-trifluoro-2-hydroxypropan-2-yl)-5-(trifluoromethyl)phenyl)propanoate's mass: m/z 374 (M+H) and m/z 396 (M+Na); Calcd for $C_{15}H_{17}F_6NO_3$:373.29.

Step 2

Preparation of (3S)-ethyl 3-(2-(3-hydroxy-5-((5-hydroxy-1,4,5,6-tetrahydropyrimidin-2-yl)amino) benzamido)acetamido)-3-(3-(1,1,1-trifluoro-2-hydroxypropan-2-yl)-5-(trifluoromethyl)phenyl) propanoate

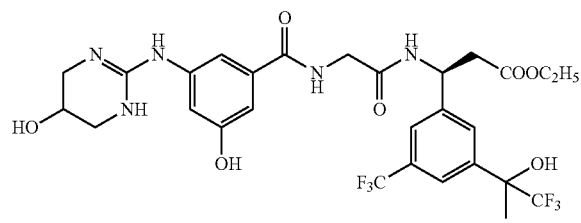

A mixture of 2-(3-hydroxy-5-((5-hydroxy-1,4,5,6-tetrahydropyrimidin-2-yl)amino)benzamido)acetic acid (Example B) (232.4 mg, 0.754 mmol), (3S)-ethyl 3-amino-3-(3-(1,1,1-trifluoro-2-hydroxypropan-2-yl)-5-(trifluoromethyl) phenyl) propanoate hydrochloride salt (from step 1 above) (290.0 mg, 0.708 mmol) and 1-hydroxybenzotriazole hydrate (22.2 mg, 0.145 mmol) was dissolved in a mixture of DMF/DCM (1:1) (8 mL) and stirred at room temperature under nitrogen atmosphere for 10 min to give a cream suspension. N,N'-Diisopropylcarbodiimide (150 μL, 0.969 mmol) was added and the reaction mixture was stirred at room temperature under nitrogen atmosphere overnight. The solvent was evaporated in vacuo to give a pale yellow-cream gummy residue of the intermediate product: (3S)-ethyl 3-(2-(3-hydroxy-5-((5-hydroxy-1,4,5,6-tetrahydropyrimidin-2-yl)amino)benzamido) acetamido)-3-(3-(1,1,1-trifluoro-2-hydroxypropan-2-yl)-5-(trifluoromethyl)phenyl)propanoate. LC-MS analysis of the crude residue shows the desired product's mass: m/z 664 (M+H) and m/z 686 (M+Na); Calcd for $C_{28}H_{31}F_6N_5O_7$: 663.57. The crude residue will be used without further purification for the saponification with LiOH monohydrate (Step 3).

Step 3

Preparation of (3S)-3-(2-(3-hydroxy-5-((5-hydroxy-1,4,5,6-tetrahydropyrimidin-2-yl)amino)benzamido) acetamido)-3-(3-(1,1,1-trifluoro-2-hydroxypropan-2-yl)-5-(trifluoromethyl)phenyl)propanoic acid

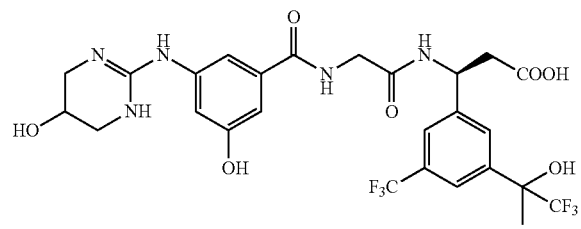 [SMILES: CC(O)(c1cc([C@H](CC(=O)O)NC(=O)CNC(=O)c2cc(O)cc(NC3=NCC(O)CN3)c2)cc(C(F)(F)F)c1)C(F)(F)F]

To a suspension of (3S)-ethyl 3-(2-(3-hydroxy-5-((5-hydroxy-1,4,5,6-tetrahydropyrimidin-2-yl)amino)benzamido) acetamido)-3-(3-(1,1,1-trifluoro-2-hydroxypropan-2-yl)-5-(trifluoromethyl)phenyl)propanoate (from step 2 above) (~708 mmol, crude residue) in a mixture of acetonitrile/water (1:1) (6 mL) was added lithium hydroxide mono hydrate (150 mg, 3.575 mmol) and the reaction mixture was stirred at room temperature overnight. The solvent was evaporated in vacuo to afford a yellow-orange viscous residue. The residue was dissolved in water (25 mL) and stirred with dichloromethane (50 mL) to remove the urea. The aqueous layer was neutralized with TFA (1 mL in 3 mL ACN) and evaporated in vacuo to afford a pale viscous residue. The crude residue was purified by reverse-phase preparative HPLC on a Biotage 40+M (100 g) C18HS column and a gradient 10-60% acetonitrile in water containing 0.05% TFA to give the desired product, after lyophilzation, as a colorless lyophilized powder (287.8 mg). LC-MS analysis of the solid shows the desired product's mass: m/z 636 (M+H); Calcd for $C_{26}H_{27}F_6N_5O_7$: 635.51

$^1$H NMR (400 MHz, DMSO-$d_6$): δ 1.74 (s, 3H), 2.68-2.85 (M, 2H), 3.15 (dt, J=12.2, 3.7 Hz, 2H), 3.33 (d, J=12.6 Hz, 2H), 3.80-3.96 (M, 2H), 4.09 (q, J=3.5 Hz, 1H), 5.29 (q, J=7.2 Hz, 1H), 6.74 (t, J=2.0 Hz, 1H), 6.91 (brs, 1H), 7.10 (brt, 1H), 7.13 (brt, 1H), 7.52 (s, 1H), 7.71 (t, J=1.6 Hz, 1H), 7.81 (dd, J=26.3, 4.6 Hz, 2H), 8.13 (brs, 2H), 8.55-8.75 (M, 2H), 9.65 (s, 1H), 10.02 (brs, 1H), 12.40 (brs, 1H). $^1$H NMR spectrum of the sample was consistent with the structure of the desired titled product.

Example 26

Preparation of (3S)-3-(3-bromo-5-(1-(difluoromethyl)cyclopropyl)phenyl)-3-(2-(3-hydroxy-5-((5-hydroxy-1,4,5,6-tetrahydropyrimidin-2-yl)amino) benzamido)acetamido)propanoic acid

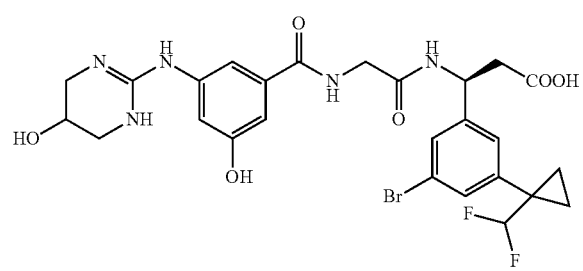 [SMILES: O=C(O)C[C@H](NC(=O)CNC(=O)c1cc(O)cc(NC2=NCC(O)CN2)c1)c1cc(Br)cc(C2(C(F)F)CC2)c1]

Step 1

Preparation of (S)-ethyl 3-amino-3-(3-bromo-5-(1-(difluoromethyl)cyclopropyl)phenyl)propanoate hydrochloride

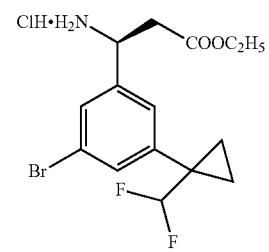

Part A

Preparation of (S)-3-amino-3-(3-bromo-5-(1-(difluoromethyl)cyclopropyl)phenyl)propanoic acid by enzymatic Lipase catalyzed hydrolysis of the racemic mixture

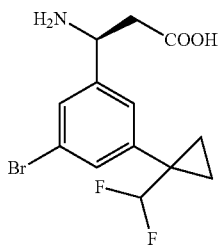 [SMILES: N[C@@H](CC(=O)O)c1cc(Br)cc(C2(C(F)F)CC2)c1]

A suspension of rac-ethyl 3-amino-3-(3-bromo-5-(1-(difluoromethyl)cyclopropyl)phenyl)propanoate (Example S) (1010.2 mg, 2.789 mmol) was stirred in 50 mM $KH_2PO_4$ solution (40 mL). The pH of the aqueous phase was adjusted to pH 8.32 by the addition of 1N NaOH solution and 50 mM $KH_2PO_4$ solution. Amano Lipase PS from *Burkholderiacepacia* (1.2152 g) was added and the reaction mixture was stirred at room temperature for 26 h. The reaction mixture was diluted with MTBE (50 mL) and mixture was stirred at room temperature and the aqueous and MTBE layers were separated. The aqueous layer containing a colorless suspension/precipitate was extracted with MTBE (1×25 mL). The combined MTBE layer was washed with water (1×25 mL), dried over anhydrous $Na_2SO_4$, filtered and evaporated in vacuo to afford a yellow-orange viscous liquid (567 mg). LC-MS analysis of the liquid shows the (R)-ethyl 3-amino-3-(3-bromo-5-(1-(difluoromethyl)cyclopropyl)phenyl)propanoate's mass: m/z 362 ($^{79Br}$M+H), m/z 364 ($^{81Br}$M+H), m/z 384 ($^{79Br}$M+Na) and m/z 386 ($^{81Br}$M+Na); Calcd for $C_{15}H_{18}BrF_2NO_2$: 362.21. The aqueous layer after MTBE extractions was filtered to remove the precipitated (S)—COOH, the solid was washed with water and acetonitrile mixture (1:1) and dried in vacuo to afford a colorless powder (225.5 mg). LC-MS analysis of the solid shows the desired (S)-3-amino-3-(3-bromo-5-(1-(difluoromethyl)cyclopropyl)phenyl) propanoic acid's mass: m/z 334 ($^{79Br}$M+H), m/z 336 ($^{81Br}$M+H), m/z 356 ($^{79Br}$M+Na) and m/z 358 ($^{81Br}$M+Na); Calcd for $C_{13}H_{14}BrF_2NO_2$: 334.16. The above solid will be used as such for the esterification with absolute ethyl alcohol saturated with anhydrous HCl gas. (Step B).

Part B

Preparation of (S)-ethyl 3-amino-3-(3-bromo-5-(1-(difluoromethyl)cyclopropyl)phenyl)propanoate hydrochloride

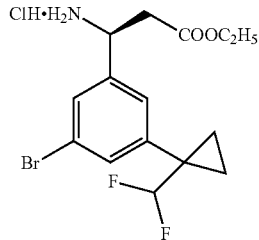

To a solution of (S)-3-amino-3-(3-bromo-5-(1-(difluoromethyl)cyclopropyl)phenyl)propanoic acid (from step A above) (225.5 mg, 0.675 mmol) in absolute ethyl alcohol (3 mL) was added absolute ethanol saturated with anhydrous HCl gas (7 mL) and the reaction mixture was heated at reflux under nitrogen for 3 h to give a colorless solution. The solvent was evaporated in vacuo to give a colorless viscous liquid. The residue was triturated with diethyl ether (10 mL) and the solvent was evaporated in vacuo to give the desired (S)-ethyl 3-amino-3-(3-bromo-5-(1-(difluoromethyl)cyclopropyl) phenyl)propanoate hydrochloride salt as a colorless foamy solid (253.0 mg). LC-MS analysis of the solid shows the desired product's mass: m/z 362 ($^{79Br}$M+H), m/z 364 ($^{81Br}$M+H), m/z 384 ($^{79Br}$M+Na) and m/z 386 ($^{81Br}$M+Na); Calcd for $C_{15}H_{18}BrF_2NO_2$:362.21. The isolated solid will be used as such for the next step.

Step 2

Preparation of (3S)-ethyl 3-(3-bromo-5-(1-(difluoromethyl)cyclopropyl)phenyl)-3-(2-(3-hydroxy-5-((5-hydroxy-1,4,5,6-tetrahydropyrimidin-2-yl)amino)benzamido)acetamido)propanoate

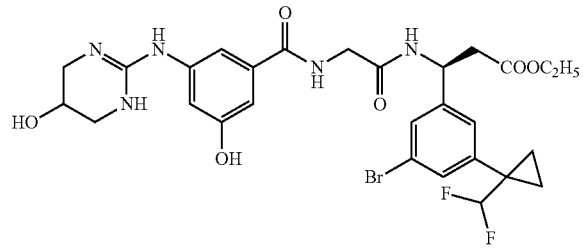

A mixture of 2-(3-hydroxy-5-((5-hydroxy-1,4,5,6-tetrahydropyrimidin-2-yl)amino)benzamido)acetic acid (Example B) (197.22 mg, 0.64 mmol), (S)-ethyl 3-amino-3-(3-bromo-5-(1-(difluoromethyl)cyclopropyl)phenyl)propanoate hydrochloride salt (from step 1 above) (253 mg, 0.635 mmol) and 1-hydroxybenzotriazole hydrate (19.44 mg, 0.127 mmol) was dissolved in a mixture of DMF/DCM (1:1) (8 mL) and stirred at room temperature under nitrogen atmosphere for 10 min to give a cream suspension. N,N'-diisopropylcarbodiimide (142 µL, 0.917 mmol) was added to the above suspension and the reaction mixture was stirred at room temperature overnight (16 h) under nitrogen atmosphere. The solvent was evaporated in vacuo to give a yellow gummy residue of the intermediate product. LC-MS analysis shows the desired product: (3S)-ethyl 3-(3-bromo-5-(1-(difluoromethyl)cyclopropyl)phenyl)-3-(2-(3-hydroxy-5-((5-hydroxy-1,4,5,6-tetrahydropyrimidin-2-yl)amino)benzamido)acetamido)propanoate's mass: m/z 652 ($^{79Br}$M+H), m/z 654 ($^{81Br}$M+H). The crude residue will be used as such for the saponification with lithium hydroxide monohydrate (Step 3).

Step 3

Preparation of (3S)-3-(3-bromo-5-(1-(difluoromethyl)cyclopropyl)phenyl)-3-(2-(3-hydroxy-5-((5-hydroxy-1,4,5,6-tetrahydropyrimidin-2-yl)amino)benzamido)acetamido)propanoic acid

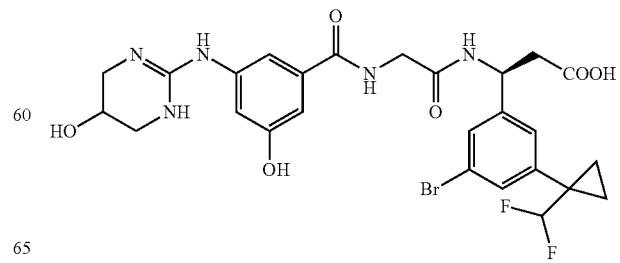

To a suspension of (3S)-ethyl 3-(3-bromo-5-(1-(difluoromethyl)cyclopropyl)phenyl)-3-(2-(3-hydroxy-5-((5-hydroxy-1,4,5,6-tetrahydropyrimidin-2-yl)amino)benzamido)acetamido)propanoate (from step 2 above) (0.635 mmol, crude residue) in a mixture of acetonitrile/water (1:1) (6 mL) was added lithium hydroxide monohydrate (135 mg, 3.217 mmol) and the reaction mixture was stirred at room temperature overnight. The solvent was evaporated in vacuo to afford a pale yellow crystalline residue. The residue was dissolved in water (25 mL) and stirred with dichloromethane (50 mL) to remove the urea. The aqueous layer was neutralized with TFA (1 mL in 3 mL ACN) and evaporated in vacuo to afford a pale yellow viscous residue. The crude residue was purified by reverse-phase preparative HPLC on a Biotage 40+M (100 g) C18HS column and a gradient 10-60% acetonitrile in water containing 0.05% TFA to give the desired product, after lyophilization, as a colorless lyophilized powder (94.0 mg). LC-MS analysis of the product shows the desired product's mass: m/z 624 ($^{79Br}$M+H) and m/z 626 ($^{81Br}$M+H); Calcd for $C_{26}H_{28}BrF_2N_5O_6$: 624.43.

$^1$H NMR (400 MHz, DMSO-$d_6$): δ 1.00 (d, J=8.9 Hz, 2H), 1.12 (q, J=4.2, 3.2 Hz, 2H), 2.70 (d, J=7.2 Hz, 2H), 3.15 (d, J=12.6 Hz, 2H), 3.33 (d, J=12.8 Hz, 2H), 3.85 (d, J=5.8 Hz, 2H), 4.08 (appt, 1H), 5.17 (q, J=7.5 Hz, 1H), 5.45 (brs, 1H), 5.89 (t, J=56.1 Hz, 1H), 6.74 (t, J=2.0 Hz, 1H), 7.12 (dt, J=10.2, 1.6 Hz, 2H), 7.32 (t, J=1.6 Hz, 1H), 7.44 (dt, J=16.9, 1.7 Hz, 1H), 8.13 (d, J=2.4 Hz, 2H), 8.54 (d, J=8.2 Hz, 1H), 8.63 (t, J=5.9 Hz, 1H), 9.65 (s, 1H), 10.03 (brs, 1H), 12.4 (brs, 1H). $^1$H NMR spectrum of the sample was consistent with the structure of the desired titled product.

Example 27

Biological Assay Results

The activity of the compounds of the present invention was tested in the following assays. The results are shown in Table 2.

Solid Phase Receptor Assay for α5β1 Function.

Purified human fibronectin (R&D Systems, 1918-FN) diluted to 2 μg/mL in TBS+ buffer (25 mM Tris 7.4, 137 mM NaCl, 2.7 mM KCl, 1 mM CaCl$_2$, 1 mM MgCl$_2$, 1 mM MnCl$_2$) was added to wells (50 μL/well) of a 96-well half-well transparent microtiter plate (Greiner 675061) and incubated overnight at 4° C. Wells were washed 3 times with 150 μL TBS+ and 150 μl of blocking buffer (TBS+ with 1% bovine serum albumin, Sigma A7906) were added. The plate was incubated for 1 hr at 37° C. and then washed 3× with TBS+ buffer. Recombinant human integrin α5β1 (R&D Systems, 3230-A5) was diluted to 0.1 μg/mL in TBS+/0.1% bovine serum albumin. Compounds were diluted 1:100 into the integrin solution and then 50 μL added to empty wells of the washed fibronectin-coated plate according to a standard template with each sample repeated in triplicate. After incubation for two hours at room temperature, the plate was washed 3× with 150 μL of TBS+ buffer. To each well, 50 μL of biotinylated anti-α5 antibody (R&D Systems, BAF1864) at 0.5 ug/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of room temperature TMB substrate (Sigma, T444) added to each well and the plate incubated for 20 min at room temperature. The reaction was optionally stopped with 25 μL of Stop Solution (Sigma S5689). Plates were read by colorimetric detection at 650 nm wavelength using a Tecan Safire II plate reader. Concentration-response curves were constructed by non-linear regression (best fit) analysis, and IC$_{50}$ values were calculated for each compound.

Solid Phase Receptor Assay for αvβ1 Function.

Purified human fibronectin (R&D Systems, 1918-FN) diluted to 5 μg/mL in TBS+ buffer (25 mM Tris 7.4, 137 mM NaCl, 2.7 mM KCl, 1 mM CaCl$_2$, 1 mM MgCl$_2$, 1 mM MnCl$_2$) was added to wells (50 μL/well) of a 96-well half-well transparent microtiter plate (Greiner 675061) and incubated overnight at 4° C. Wells were washed 3 times with 150 μl TBS+ and 150 μL of blocking buffer (TBS+ with 1% bovine serum albumin, Sigma A7906) were added. The plate was incubated for 1 hr at 37° C. and then washed 3× with TBS+ buffer. Recombinant human integrin αvβ1 (R&D Systems. 6579-AV) was diluted to 2.0 μg/mL in TBS+/0.1% bovine serum albumin. Compounds were diluted 1:100 into the integrin solution and 50 μL added to empty wells of the washed fibronectin-coated plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 1 μg/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma, T4444) added to each well and the plate incubated for 20 min at room temperature. The reaction was optionally stopped with 25 μL of Stop Solution (Sigma S5689). Plates were read by colorimetric detection at 650 nm wavelength using a Tecan Safire II plate reader. Concentration-response curves were constructed by non-linear regression (best fit) analysis, and IC$_{50}$ values were calculated for each compound.

Solid Phase Receptor Assay for αvβ3 Function.

Recombinant human vitronectin (R& D Systems, 2308-VN) diluted to 1 μg/mL in TBS+ buffer (25 mM Tris 7.4, 137 mM NaCl, 2.7 mM KCl, 1 mM CaCl$_2$, 1 mM MgCl$_2$, 1 mM MnCl$_2$) was added to wells (50 μL/well) of a 96-well half-well transparent microtiter plate (Greiner 675061) and incubated overnight at 4° C. Wells were washed 3 times with 150 μL TBS+ and 150 μL of blocking buffer (TBS+ with 1% bovine serum albumin, Sigma A7906) were added. The plate was incubated for 1 hr at 37° C. and then washed 3× with TBS+ buffer. Recombinant human integrin αvβ3 (R&D Systems, 3050-AV) was diluted to 1 μg/mL in TBS+/0.1% bovine serum albumin. Compounds were diluted 1:100 into the integrin solution and then 50 μL added to empty wells of the washed vitronectin-coated plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 0.5 μg/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma, T4444) added to each well and the plate was incubated for 20 min at room temperature. The reaction was optionally stopped with 25 μL of Stop Solution (Sigma, S5689). Plates were read by colorimetric detection at 650 nm wavelength using a Tecan S afire II plate reader. Concentration-response curves were constructed by non-linear regression (best fit) analysis, and $IC_{50}$ values were calculated for each compound.

Solid Phase Receptor Assay for αvβ5 Function.

Recombinant human vitronectin (R& D Systems, 2308-VN) at 0.25 μg/mL in TBS+ buffer (25 mM Tris 7.4, 137 mM NaCl, 2.7 mM KCl, 1 mM $CaCl_2$, 1 mM $MgCl_2$, 1 mM $MnCl_2$) was added to wells (50 μL/well) of a 96-well half-well transparent microtiter plate (Greiner 675061) and incubated overnight at 4° C. Wells were washed 3 times with 150 μL TBS+ and 150 μL of blocking buffer (TBS+ with 1% bovine serum albumin, Sigma A7906) were added. The plate was incubated for 1 hr at 37° C. and then washed 3× with TBS+ buffer. Recombinant human integrin αvβ5 (R&D Systems, 2528-AV) was diluted to 0.1 μg/mL in TBS+/0.1% bovine serum albumin. Compounds were diluted 1:100 into the integrin solution and then 50 μL added to empty wells of the washed vitronectin-coated plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 0.5 μg/mL in TBS+/0.1% BSA at 0.5 μg/mL were added and the plate covered and incubated for 1 hr at room temperature. After washing the plate 3× with 150 μL of TBS+ buffer, 50 μL of streptavidin-conjugated horseradish peroxidase (R&D Systems DY998) diluted in TBS+ blocking buffer were added to the wells and the plate incubated for 20 min at room temperature. The plate was washed 3× with TBS+ buffer followed by 50 μL of TMB substrate (Sigma T4444) added to each well and the plate incubated for 20 min at room temperature. The reaction was optionally stopped with 25 μL of Stop Solution (Sigma S5689). Plates were read by colorimetric detection at 650 nm wavelength using a Tecan Safire II plate reader. Concentration-response curves were constructed by non-linear regression (best fit) analysis, and $IC_{50}$ values were calculated for each compound.

Solid Phase Receptor Assay for αvβ6 Function.

Recombinant human LAP (R&D Systems, 246-LP) diluted to 0.25 μg/mL in TBS+ buffer (25 mM Tris 7.4, 137 mM NaCl, 2.7 mM KCl, 1 mM $CaCl_2$, 1 mM $MgCl_2$, 1 mM $MnCl_2$) was added to wells (50 μL/well) of a 96-well half-well transparent microtiter plate (Greiner 675061) and incubated overnight at 4° C. Wells were washed 3 times with 150 μL TBS+, and 150 μL of blocking buffer (TBS+ with 1% bovine serum albumin, Sigma A7906) were added. The plate was incubated for 1 hr at 37° C., and then washed 3× with TBS+ buffer. Recombinant human integrin αvβ6 (R&D Systems, 3817-AV) was diluted to 0.1 μg/mL in TBS+/0.1% bovine serum albumin. Compounds were diluted 1:100 into the integrin solution and then 50 μL added to empty wells of the washed LAP-coated plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 0.5 μg/mL in TBS+/0.1% BSA were added and the plate was covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma T4444) added to each well and the plate incubated for 20 min at room temperature. The reaction was optionally stopped with 25 μL of Stop Solution (Sigma S5689). Plates were read by colorimetric detection at 650 nm wavelength using a Tecan Safire II plate reader. Concentration-response curves were constructed by non-linear regression (best fit) analysis, and $IC_{50}$ values were calculated for each compound.

Solid Phase Receptor Assay for αvβ8 Function.

Recombinant human LAP protein (R&D Systems, Inc, 246-LP) diluted to 0.5 μg/mL in TBS+ buffer (25 mM Tris 7.4, 137 mM NaCl, 2.7 mM KCl, 1 mM $CaCl_2$, 1 mM $MgCl_2$, 1 mM $MnCl_2$) was added to wells (50 μL/well) of a 96-well half-well transparent microtiter plate (Greiner 675061), and incubated overnight at 4° C. Wells were washed 3 times with 150 μL TBS+ and 150 μL of blocking buffer (TBS+ with 1% bovine serum albumin, Sigma A7906) were added. The plate was incubated for 1 hr at 37° C. and then washed 3× with TBS+. Recombinant human integrin αvβ8 (R&D Systems, 4135-AV) was diluted to 0.1 μg/mL in TBS+/0.1% bovine serum albumin. Compounds were diluted 1:100 into the integrin solution and 50 μL added to empty wells of the washed LAP-coated plate according to a standard template with each sample repeated in triplicate. After incubation for two hours at room temperature, the plate was washed 3× with 150 μL of TBS+. To each well, 50 μL of biotinylated anti-αv antibody (R&D Systems, BAF1219) at 1 μg/mL in TBS+/0.1% BSA were added and the plate was covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ followed by 50 μL of TMB substrate (Sigma T4444) added to each well and the plate incubated for 20 min at room temperature. The reaction was optionally stopped with 25 μL of Stop Solution (Sigma S5689). Plates were read by colorimetric detection at 650 nm wavelength using a Tecan Safire II plate reader. Concentration-response curves were constructed by non-linear regression (best fit) analysis, and $IC_{50}$ values were calculated for each compound.

TABLE 2

Biological Assay Results

| Example | α5β1 SPRA IC50 (nM) | αvβ1 SPRA IC50 (nM) | αvβ3 SPRA IC50 (nM) | αvβ5 SPRA IC50 (nM) | αvβ6 SPRA IC50 (nM) | αvβ8 SPRA IC50 (nM) |
|---|---|---|---|---|---|---|
| 1 | 0.5 | 2.1 | 5.1 | 47 | 0.4 | 0.1 |
| 2 | 0.5 | 2.2 | 1.8 | 1.0 | 0.7 | 0.1 |
| 3 | 0.3 | 2.2 | 2.0 | 0.7 | 0.7 | 0.4 |
| 4 | 0.7 | 1.7 | 2.3 | 0.4 | 0.5 | 0.6 |
| 5 | 0.6 | 3.2 | 2.6 | 1.6 | 0.6 | 0.2 |
| 6 | 1.0 | 4.7 | 3.5 | 2.2 | 0.5 | 0.3 |
| 7 | 0.7 | 2.7 | 1.3 | 0.5 | 0.2 | 0.1 |
| 8 | 0.4 | 3.0 | 1.5 | 0.5 | 0.5 | 0.1 |
| 9 | 0.5 | 2.4 | 2.9 | 1.2 | 0.5 | 0.1 |
| 10 | 0.5 | 2.1 | 172 | 71 | 1.2 | 0.2 |
| 11 | 0.3 | 2.8 | 3.4 | 0.7 | 0.5 | 0.2 |
| 12 | 0.3 | 2.0 | 2.8 | 0.2 | 0.4 | 0.2 |
| 13 | 0.9 | 4.0 | 1.8 | 0.3 | 0.6 | 0.6 |
| 14 | 0.2 | 2.4 | 1.7 | 0.3 | 0.4 | 0.3 |
| 15 | 0.4 | 2.9 | 3.3 | 0.4 | 0.4 | 0.3 |
| 16 | 0.5 | 3.3 | 1.7 | 0.6 | 0.5 | 0.4 |
| 17 | 0.4 | 3.0 | 4.0 | 0.5 | 0.5 | 0.4 |
| 18 | 0.4 | 3.4 | 14.5 | 21 | 0.6 | 0.3 |
| 19 | 0.4 | 4.1 | 8.8 | 21 | 0.7 | 0.4 |
| 20 | 2.4 | 4.9 | 3.7 | 0.5 | 1.4 | 0.5 |
| 21 | 0.3 | NT | NT | 0.4 | 0.3 | NT |
| 22 | 0.3 | NT | NT | 0.4 | 0.3 | NT |

TABLE 2-continued

Biological Assay Results

| Example | α5β1 SPRA IC50 (nM) | αvβ1 SPRA IC50 (nM) | αvβ3 SPRA IC50 (nM) | αvβ5 SPRA IC50 (nM) | αvβ6 SPRA IC50 (nM) | αvβ8 SPRA IC50 (nM) |
|---|---|---|---|---|---|---|
| 23 | 0.3 | NT | NT | 0.5 | 0.4 | NT |
| 24 | 0.3 | NT | NT | 0.3 | 0.4 | NT |
| 25 | 0.4 | NT | NT | 1.3 | 0.4 | NT |
| 26 | 0.1 | NT | NT | 0.5 | 0.1 | NT |

NT = Not Tested

REFERENCES

The following references to the extent that they provide exemplary procedural or other details supplementary to those set forth herein, are specifically incorporated herein by reference.

U.S. Pat. No. 5,840,961
U.S. Pat. No. 6,013,651
U.S. Pat. No. 6,028,223
U.S. Pat. No. 6,414,180
WO 2010/104933
WO 2008/018827
WO 2012/027322
WO 2010/010184
WO 2010/025927
Adachi et al., *Clin. Cancer Res.*, 6(1):96-101, 2000.
Asano et al., *J. Immunol.*, 175(11):7708-7718, 2005.
Avraamides et al., *Nat. Rev. Cancer*, 8(8):604-617, 2008.
Awasthi et al., *J. Org. Chem.*, 70:5387-5397, 2005.
Babadzhanova, et al., *Tetrahedron*, 61(7):1813-1819, 2005.
Bax et al., *J. Biol. Chem.*, 278(36):34605-34616, 2003.
Becker et al., *Tetrahedron*, 39:4189-4192, 1983.
Bhaskar et al., *J. Transl. Med.*, 5:61, 2007.
Blase et al., *Int. J. Cancer*, 60(6):860-866, 1995.
Clark, et al., *Organic Process Research & Development*, 8:51-61, 2004.
Clark, et al., *Organic Process Research & Development*, 8:571-575, 2004.
Collo, *J. Cell Sci.*, 112(Pt 4):569-578, 1999.
Danen et al., *Histopathology*, 24(3):249-256, 1994.
Edward, *Curr. Opin. Oncol.*, 7(2):185-191, 1995.
Engleman et al., *J. Clin. Invest.*, 99(9):2284-2292, 1997.
Faulconbridge et al., *Tetrahedron Lett.*, 41:2679-2681, 2000.
Ferrari et al., *Proc. Natl. Acad. Sci. USA*, 103(46):17260-17265, 2006.
Gao and Brigstock, *Gut*, 55:856-862, 2006.
Girsch et al., *J. Med. Chem.*, 50:1658-1667, 2007.
Girsch et al., *J. Med. Chem.*, 51:6752-6760, 2008.
Greene & Wuts, *Protective Groups in Organic Synthesis*, 3rd Ed., John Wiley, 1999.
*Handbook of Pharmaceutical Salts: Properties, and Use*, Stahl and Wermuth (Eds.), Verlag Helvetica Chimica Acta, 2002.
Herlt, et al., *Austr. J. Chem.*, 34(6):1319-1324, 1981.
Horan et al., *Am. J. Respir. Crit. Care Med.*, 177(1):56-65, 2008.
Huang, et al., *Synlett*, 15:2518-2520, 2009.
Jørgensen, et al., *J. Am. Chem. Soc.*, 124(42):12557-12565, 2002.
Kim et al., *Am. J. Pathol.*, 156(4):1345-1362, 2000.
Kurahashi et al., *J. Am. Chem. Soc.*, 133(21):8307-8316, 2011.
Landis et al., *Organic Process Research & Development*, 6:539-546, 2002.
Li et al., *Invest. Ophthalmol. Vis. Sci.*, 50(12):5988-5996, 2009.
Livant et al., *J. Clin. Invest.*, 105(11):1537-1545, 2000.
Lobert et al., *Dev. Cell*, 19(1):148-159, 2010.
*March's Advanced Organic Chemistry: Reactions, Mechanisms, and Structure*, 2007.
Melton et al., *J. Clin. Invest.*, 120(12):4436-4444, 2010.
Millard et al., *Theranostics*, 1:154-88, 2011.
Mu et al., *Cell Biol.*, 157(3):493-507, 2002.
Munger et al., *Cell.*, 96(3):319-328, 1999.
Munger et al., *Mol. Biol. Cell*, 9:2627-2638, 1998.
Nandrot et al., *Am. J. Physiol. Cell Physiol.*, 290(4):C1256-1262, 2006.
Nishimura, *Am. J. Pathol.*, 175(4):1362-1370, 2009.
Nomura et al., *Chemistry—A Europ. J.*, 13(16):4433-4451, 2007.
Perdih, *Curr. Med. Chem.*, 17(22):2371-2392, 2010.
Popov et al., *J. Hepatol.*, 48(3):453-464, 2008.
Reagan-Shaw et al., *FASEB J.*, 22(3):659-661, 2008
Rico, *Tett. Let.*, 35:6599-6602, 1994.
Scotton et al., *J. Clin. Invest.*, 119(9):2550-2563, 2009.
Suchiro et al., *J. Biochem.*, 128(4):705-710, 2000.
Tanaka and Shishido, *Bioorg. Med. Chem. Lett.*, 17(22):6079-6085, 2007
*Vogel's Textbook of Practical Organic Chemistry*, 5th Ed., p:1040, 1989.
Wan, et al., *J. Org. Chem.*, 76(17):7048-7055, 2011.
Wipff et al., *J. Cell Biol.*, 179(6):1311-1323, 2007.
Wu, et al., *J. Am. Chem. Soc.*, 127(45):15824-15832, 2005.
Yang et al., *Development*, 119(4):1093-1105, 1993.
Yoshimura, *Curr. Top. Microbiol. Immunol.*, 350:127-147, 2011.
Zahn et al., *Arch. Ophthalmol.*, 127(10):1329-1335, 2009.
Zahn et al., *Invest. Ophthalmol. Vis. Sci.*, 51(2):1028-1035, 2010

What is claimed is:

1. A compound of the formula:

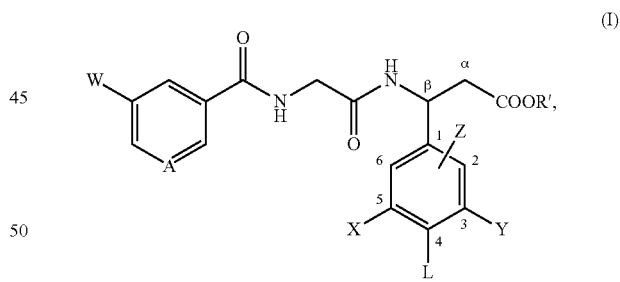

wherein:
W is

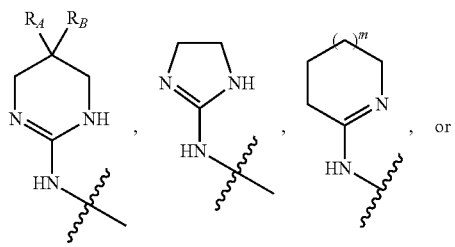

-continued

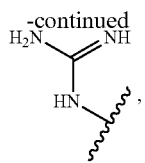

wherein:
R_A is —H or —F;
R_B is —H, —OH, —NH$_2$, —F, —CN, or alkoxy$_{(C≤8)}$, wherein if R_A is —F, then R_B is —H or —F; and
m is 0-3;
A is C—R" or N, wherein:
R" is —H, —OH, —CO$_2$R$_1$, —C(=O)R$_2$, or —N(R$_1$)(C=O)R$_3$, or alkoxy$_{(C≤8)}$, acyloxy$_{(C≤8)}$, alkylamino$_{(C≤8)}$, dialkylamino$_{(C≤8)}$, or a substituted version of any of the groups, wherein:
R$_1$ is —H, alkyl$_{(C≤8)}$ or substituted alkyl$_{(C≤8)}$;
R$_2$ is alkylamino$_{(C≤8)}$, dialkylamino$_{(C≤8)}$, heterocycloalkyl$_{(C≤8)}$, heteroaryl$_{(C≤8)}$, or a substituted version of any of the groups;
R$_3$ is alkyl$_{(C≤8)}$, aryl$_{(C≤8)}$, aralkyl$_{(C≤8)}$, heteroaryl$_{(C≤8)}$, heterocycloalkyl$_{(C≤8)}$, or a substituted version of any of the groups;
R' is —H, alkyl$_{(C≤8)}$ or substituted alkyl$_{(C≤8)}$;
X is:
hydrogen, halo, or cyano;
alkyl$_{(C≤12)}$, alkoxy$_{(C≤12)}$, aryl$_{(C≤12)}$, aralkyl$_{(C≤12)}$, heteroaryl$_{(C≤8)}$, heterocycloalkyl$_{(C≤12)}$, aryloxy$_{(C≤12)}$, acyloxy$_{(C≤12)}$, or a substituted version of any of the groups;
—(CH$_2$)$_{n'}$—CO$_2$-alkyl$_{(C≤6)}$, wherein, n' is 0-3;

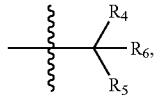

wherein
R$_4$ and R$_5$ are each independently alkyl$_{(C≤8)}$, substituted alkyl$_{(C≤8)}$, or —CH$_2$O-alkyl$_{(C≤8)}$;
R$_6$ is —OH, —CN, —NH$_2$, —CF$_3$, —CF$_2$H, —CH$_2$F, —CO$_2$H, —CO$_2$-alkyl$_{(C≤8)}$, —C(=O)NH$_2$, —CH$_2$OH, —CH$_2$O-alkyl$_{(C≤8)}$, or alkoxy$_{(C≤8)}$, provided that where R$_4$ and R$_5$ are each —CF$_3$, then R$_6$ is —OH, alkoxy$_{(C≤8)}$ or —NH$_2$;

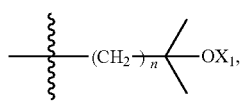

wherein n is 1 or 2 and X$_1$ is —H or alkyl$_{(C≤8)}$; or

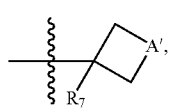

wherein:
A' is a covalent bond, thereby forming a cyclopropane ring, —CF$_2$—, —O—, alkanediyl$_{(C≤6)}$ or alkoxydiyl$_{(C≤8)}$; and R$_7$ is —OH, —CN, —NH$_2$, —CO$_2$H, —CO$_2$-alkyl$_{(C≤8)}$, —C(=O)NH$_2$, —CF$_3$, —CF$_2$H, —CH$_2$F, —CH$_2$OH, —CH$_2$O-alkyl$_{(C≤8)}$, alkyl$_{(C≤8)}$ or alkoxy$_{(C≤8)}$;
Y is:
t-butyl, neopentyl, norbornyl, or adamantyl;

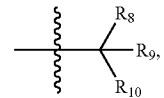

wherein
R$_8$ and R$_9$ are each independently alkyl$_{(C≤8)}$, substituted alkyl$_{(C≤8)}$, or —CH$_2$O-alkyl$_{(C≤8)}$;
R$_{10}$ is —OH, —CN, —NH$_2$, —CF$_3$, —CF$_2$H, —CFH$_2$, —CO$_2$H, —CO$_2$-alkyl$_{(C≤8)}$, —C(=O)NH$_2$, —CH$_2$OH, —CH$_2$O-alkyl$_{(C≤8)}$, or alkoxy$_{(C≤8)}$, provided that where R$_8$ and R$_9$ are each —CF$_3$, then R$_{10}$ is —OH, alkoxy$_{(C≤8)}$ or —NH$_2$;

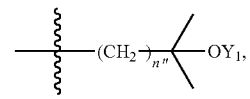

wherein n" is 1 or 2 and Y$_1$ is —H or alkyl$_{(C≤8)}$; or

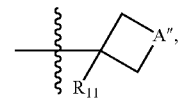

wherein:
A" is a covalent bond, thereby forming a cyclopropane ring, —O—, —CF$_2$—, alkanediyl$_{(C≤6)}$ or alkoxydiyl$_{(C≤8)}$; and
R$_{11}$ is —OH, —CN, —NH$_2$, —CO$_2$H, —CO$_2$-alkyl$_{(C≤8)}$, —C(=O)NH$_2$, —CF$_3$, —CF$_2$H, —CH$_2$F, —CH$_2$OH, —CH$_2$O-alkyl$_{(C≤8)}$, alkyl$_{(C≤8)}$ or alkoxy$_{(C≤8)}$;
L is hydrogen, hydroxy or alkoxy$_{(C≤8)}$; and
Z is hydrogen, fluorine, or hydroxy and is attached to either carbon atom 2 or 6;
provided that if W is

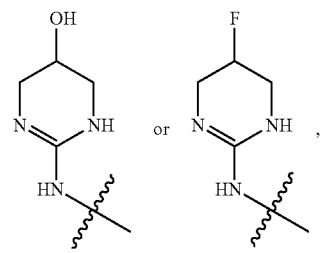 [SMILES: *NC1=NCC(O)CN1 ; *NC1=NCC(F)CN1]

then X and Y are not both each t-butyl; and further provided that if W is

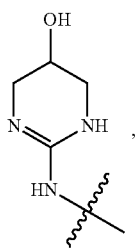

A is C—OH, Z is hydrogen, and X is bromo or iodo, then Y is not t-butyl;
or a pharmaceutically acceptable salt or tautomer thereof.

2. The compound of claim 1, further defined as:

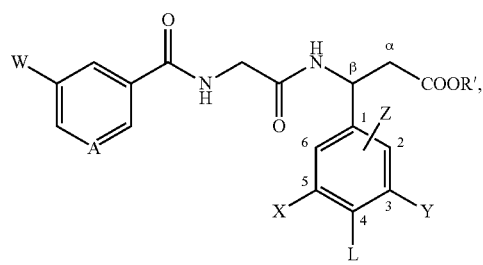

wherein:
W is

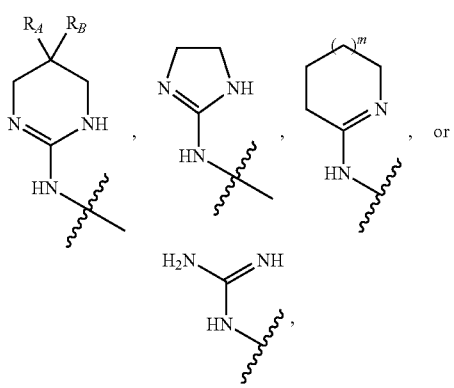

wherein:
$R_A$ is —H or —F;
$R_B$ is —H, —OH, —NH$_2$, —F, —CN, or alkoxy$_{(C \leq 8)}$, wherein if $R_A$ is —F, then $R_B$ is —H or —F; and
m is 0-3;
A is C—R″ or N, wherein:
R″ is —H, —OH, —CO$_2$R$_1$, —C(=O)R$_2$, or —N(R$_1$)(C=O)R$_3$, or alkoxy$_{(C \leq 8)}$, acyloxy$_{(C \leq 8)}$, alkylamino$_{(C \leq 8)}$, dialkylamino$_{(C \leq 8)}$, or a substituted version of any of the groups, wherein:
R$_1$ is —H, alkyl$_{(C \leq 8)}$ or substituted alkyl$_{(C \leq 8)}$;
R$_2$ is alkylamino$_{(C \leq 8)}$, dialkylamino$_{(C \leq 8)}$, heterocycloalkyl$_{(C \leq 8)}$, heteroaryl$_{(C \leq 8)}$, or a substituted version of any of the groups;
R$_3$ is alkyl$_{(C \leq 8)}$, aryl$_{(C \leq 8)}$, aralkyl$_{(C \leq 8)}$, heteroaryl$_{(C \leq 8)}$, heterocycloalkyl$_{(C \leq 8)}$, or a substituted version of any of the groups;
R′ is —H, alkyl$_{(C \leq 8)}$ or substituted alkyl$_{(C \leq 8)}$;

X is:
hydrogen, halo, or cyano;
alkyl$_{(C \leq 12)}$, alkoxy$_{(C \leq 12)}$, aryl$_{(C \leq 12)}$, aralkyl$_{(C \leq 12)}$, heteroaryl$_{(C \leq 8)}$, heterocycloalkyl$_{(C \leq 12)}$, aryloxy$_{(C \leq 12)}$, acyloxy$_{(C \leq 12)}$, or a substituted version of any of the groups;
—(CH$_2$)$_{2'}$—CO$_2$-alkyl$_{(C \leq 6)}$, wherein, n′ is 0-3;

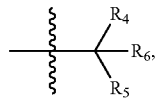

wherein
$R_4$ and $R_5$ are each independently alkyl$_{(C \leq 8)}$ or substituted alkyl$_{(C \leq 8)}$;
$R_6$ is —OH, —CN, —NH$_2$, —CF$_3$, —CF$_2$H, —CO$_2$H, —CO$_2$-alkyl$_{(C \leq 8)}$, —C(=O)NH$_2$, —CH$_2$OH, or alkoxy$_{(C \leq 8)}$, provided that where $R_4$ and $R_5$ are each CF$_3$, then $R_6$ is OH;

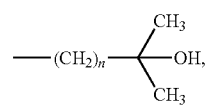

wherein n is 1 or 2; or

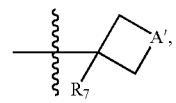

wherein:
A′ is a covalent bond, thereby forming a cyclopropane ring, alkanediyl$_{(C \leq 6)}$ or alkoxydiyl$_{(C \leq 8)}$; and
$R_7$ is —OH, —CN, —NH$_2$, —CO$_2$H, —CO$_2$-alkyl$_{(C \leq 8)}$, —C(=O)NH$_2$, —CF$_3$, —CF$_2$H, or alkoxy$_{(C \leq 8)}$;
Y is:
t-butyl, neopentyl, norbornyl, or adamantyl;

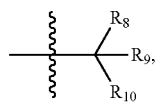

wherein
$R_8$ and $R_9$ are each independently alkyl$_{(C \leq 8)}$ or substituted alkyl$_{(C \leq 8)}$;
$R_{10}$ is —OH, —CN, —NH$_2$, —CF$_3$, —CF$_2$H, —CO$_2$H, —CO$_2$-alkyl$_{(C \leq 8)}$, —C(=O)NH$_2$, —CH$_2$OH, or alkoxy$_{(C \leq 8)}$, provided that where $R_8$ and $R_9$ are each CF$_3$, then $R_{10}$ is OH;

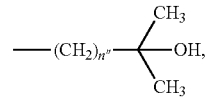

wherein n" is 1 or 2; or

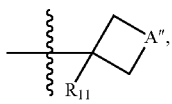

wherein:
A" is a covalent bond, thereby forming a cyclopropane ring, alkanediyl$_{(C\leq 6)}$ or alkoxydiyl$_{(C\leq 8)}$; and
R$_{11}$ is —OH, —CN, —NH$_2$, —CO$_2$H, —CO$_2$-alkyl$_{(C\leq 8)}$, —C(=O)NH$_2$, —CF$_3$, —CF$_2$H, or alkoxy$_{(C\leq 8)}$;
L is hydrogen, hydroxy or alkoxy$_{(C\leq 8)}$; and
Z is hydrogen or hydroxy and is attached to either carbon atom 2 or 6;
provided that if W is

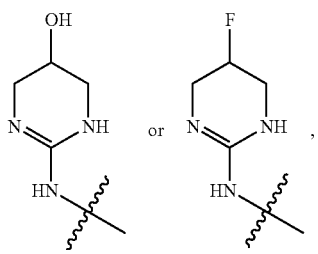

then X and Y are not both each t-butyl; and further provided that if W is

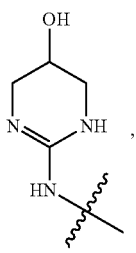

A is C—OH, Z is hydrogen, and X is bromo or iodo, then Y is not t-butyl;
or a pharmaceutically acceptable salt or tautomer thereof.

3. The compound of claim 1, wherein W is

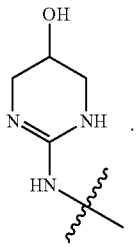

4. The compound of claim 1, wherein A is C—OH.
5. The compound of claim 1, wherein X is halo.
6. The compound of claim 1, wherein X is alkyl$_{(C\leq 8)}$ or substituted alkyl$_{(C\leq 8)}$.
7. The compound of claim 1, wherein X is cyano.

8. The compound of claim 1, wherein X is heteroaryl.
9. The compound of claim 1, wherein L is hydrogen.
10. The compound of claim 1, wherein Y is t-butyl.
11. The compound claim 1, wherein Y is 2-hydroxy-iso-propyl.
12. The compound of claim 1, wherein Y is

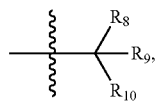

wherein R$_8$ and R$_9$ are each independently alkyl$_{(C\leq 8)}$, substituted alkyl$_{(C\leq 8)}$, or —CH$_2$O-alkyl$_{(C\leq 8)}$; R$_{10}$ is —OH, —CN, —NH$_2$, —CF$_3$, —CF$_2$H, —CFH$_2$, —CO$_2$H, —CO$_2$-alkyl$_{(C\leq 8)}$, —C(=O)NH$_2$, —CH$_2$OH, —CH$_2$O-alkyl$_{(C\leq 8)}$, or alkoxy$_{(C\leq 8)}$, provided that where R$_8$ and R$_9$ are each —CF$_3$, then R$_{10}$ is —OH, alkoxy$_{(C\leq 8)}$ or —NH$_2$.

13. The compound of claim 1, wherein Y is

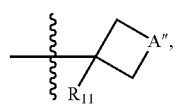

wherein: A" is a covalent bond, thereby form a cyclopropane ring, —O—, —CF$_2$—, alkanediyl$_{(C\leq 6)}$ or alkoxydiyl$_{(C\leq 8)}$; and R$_{11}$ is —OH, —CN, —NH$_2$, —CO$_2$H, —CO$_2$-alkyl$_{(C\leq 8)}$, —C(=O)NH$_2$, —CF$_3$, —CF$_2$H, —CH$_2$F, —CH$_2$OH, —CH$_2$O-alkyl$_{(C\leq 8)}$, alkyl$_{(C\leq 8)}$ or alkoxy$_{(C\leq 8)}$.

14. The compound of claim 1, wherein Z is hydrogen.
15. The compound of claim 1, wherein R' is hydrogen.
16. The compound of claim 1, further defined as:

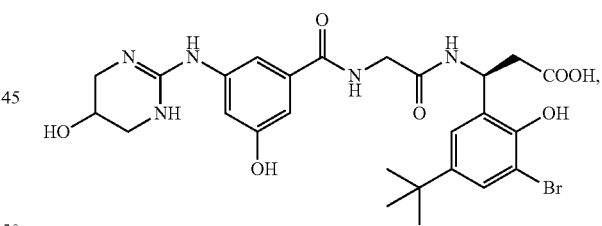

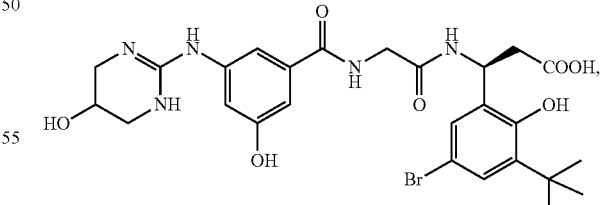

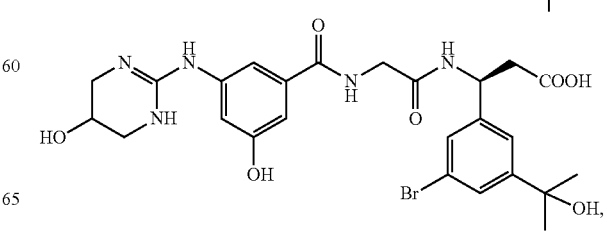

383
-continued
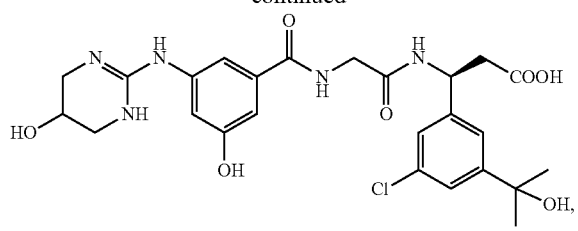
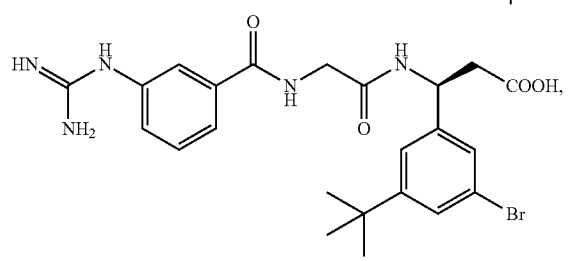
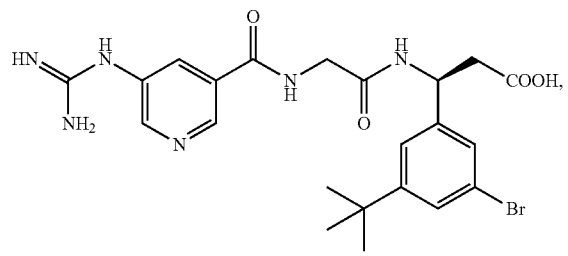
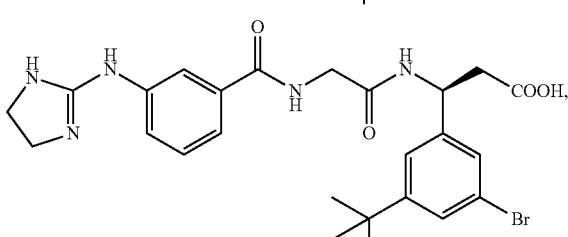
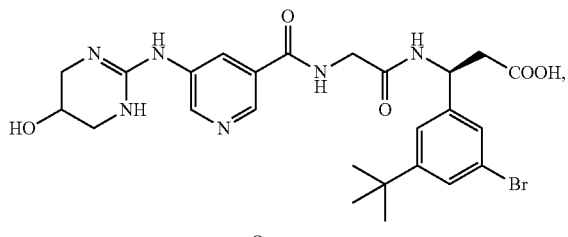
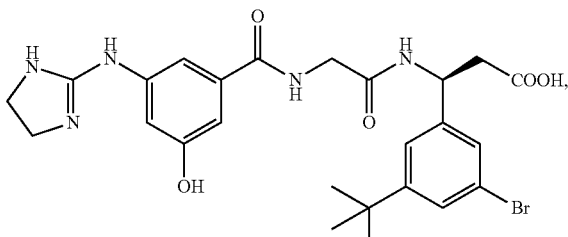
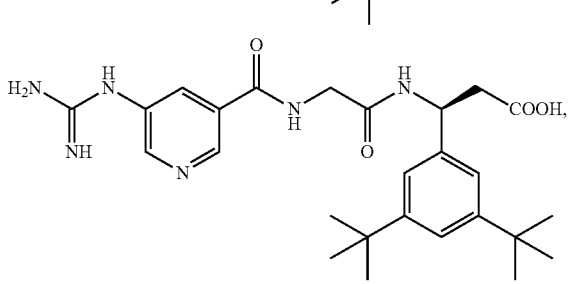
384
-continued
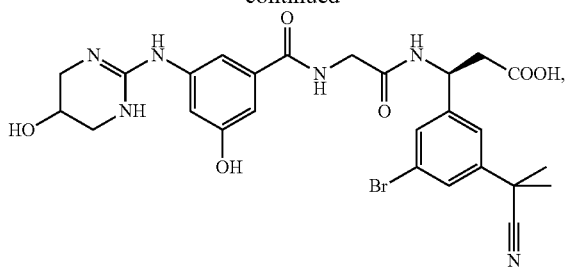
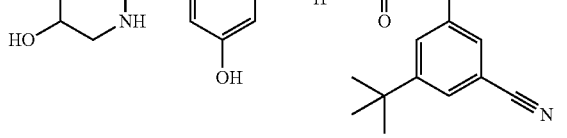
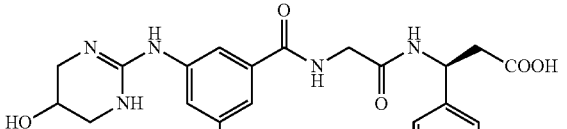
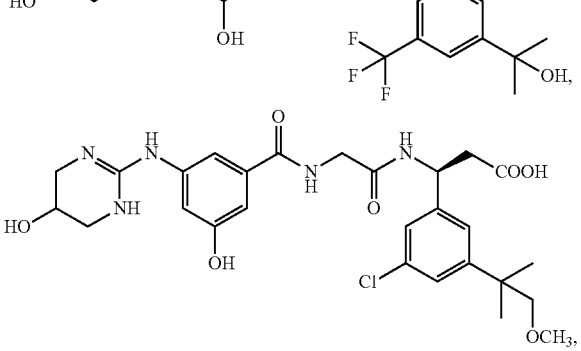
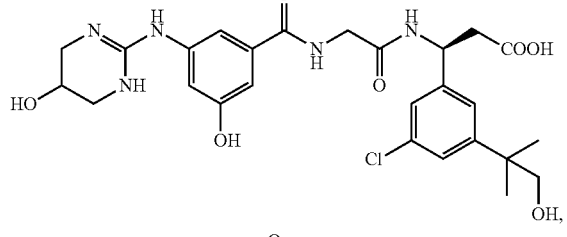
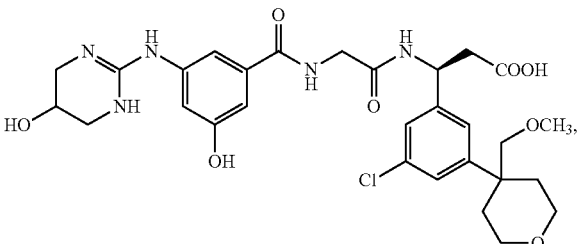
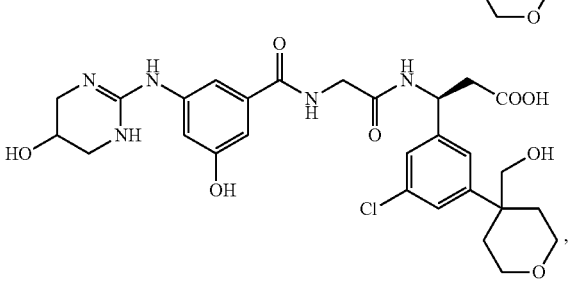

385
-continued
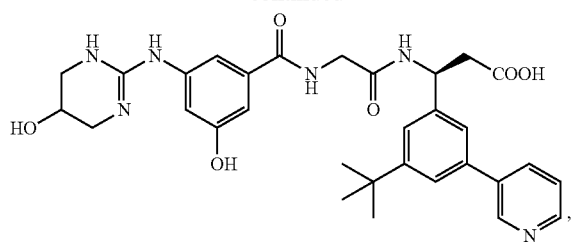
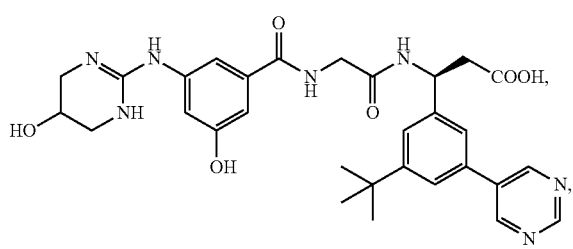
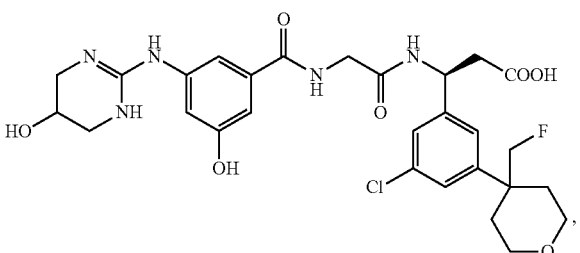
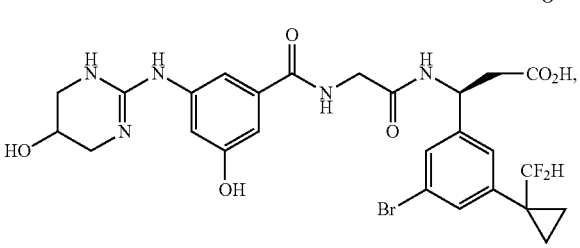
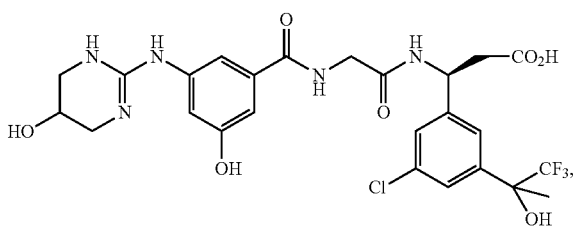
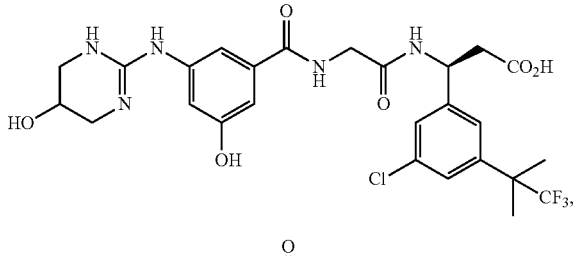
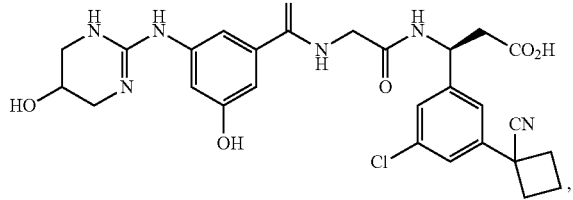
386
-continued
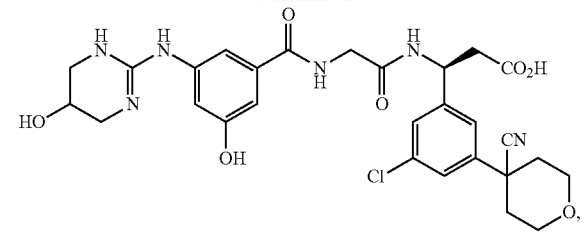
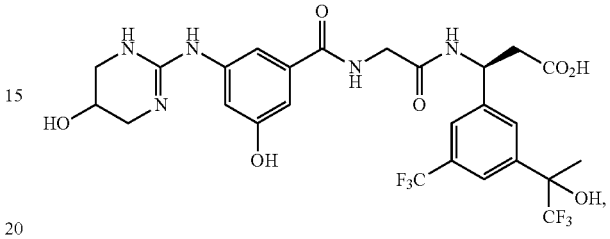
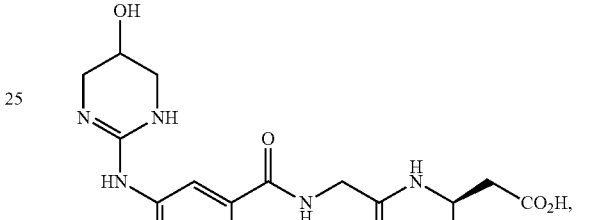
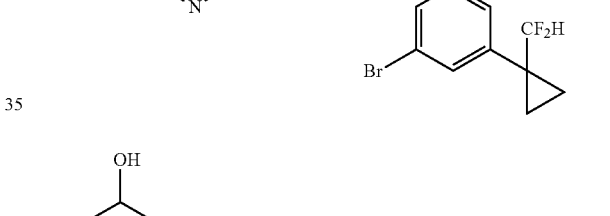
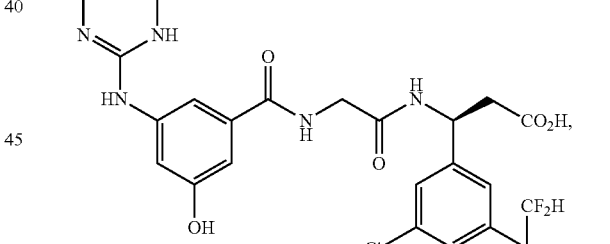
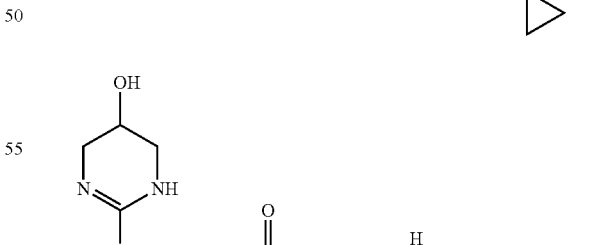
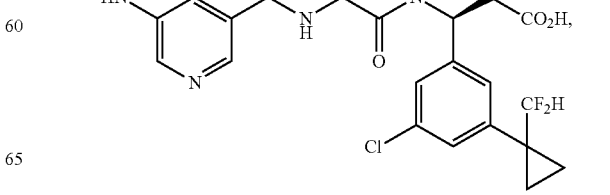

387
-continued
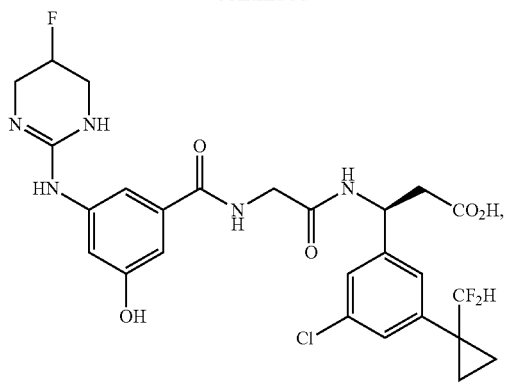
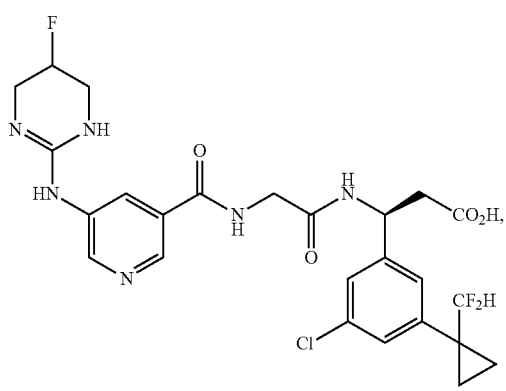
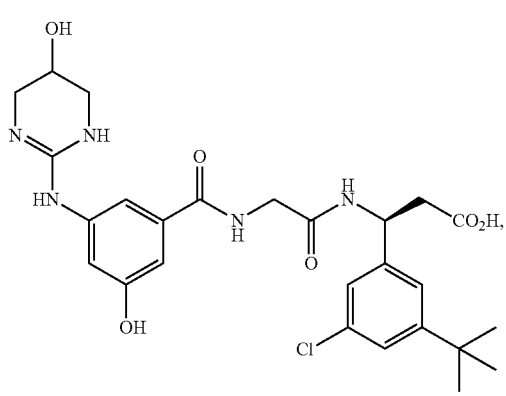
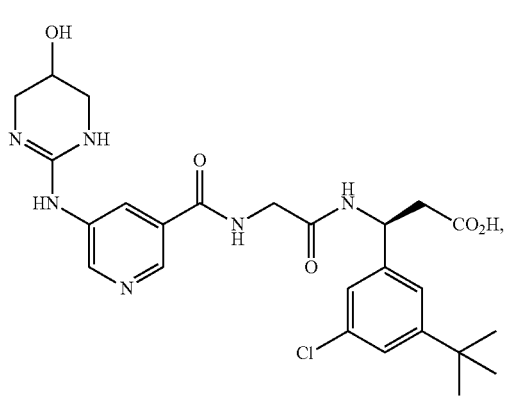
388
-continued
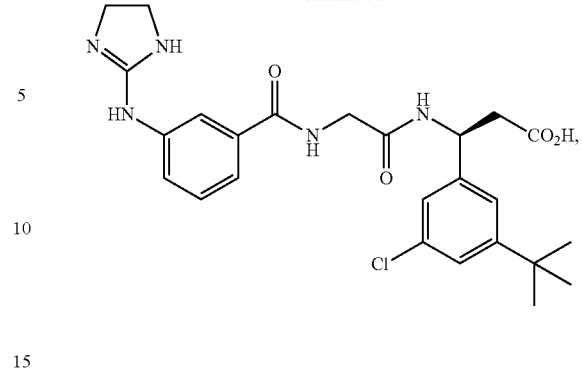
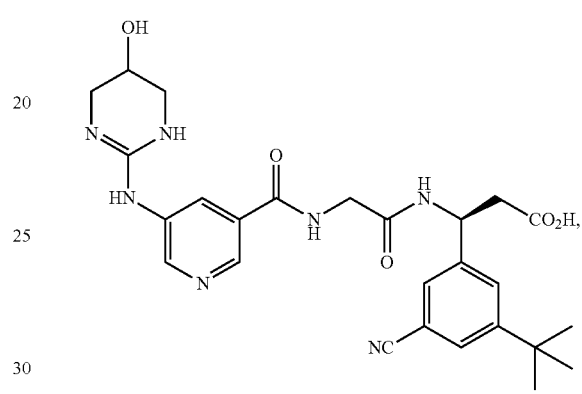
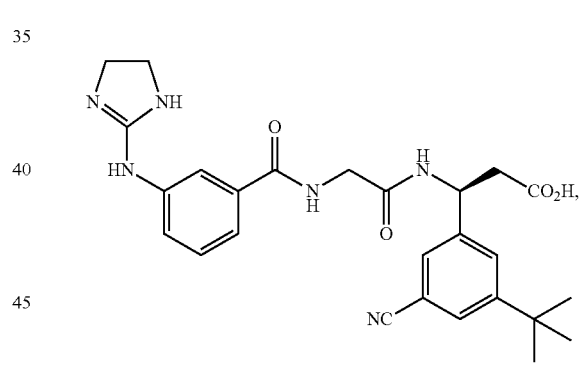
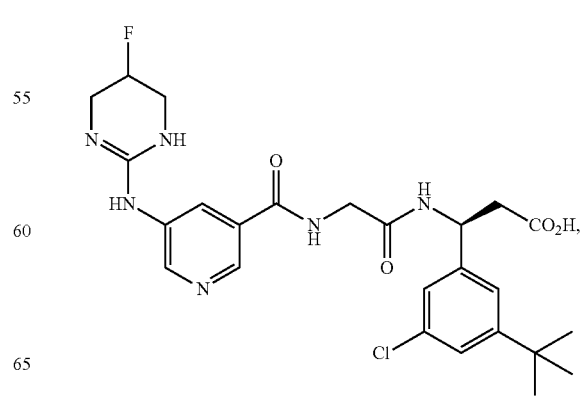

389
-continued
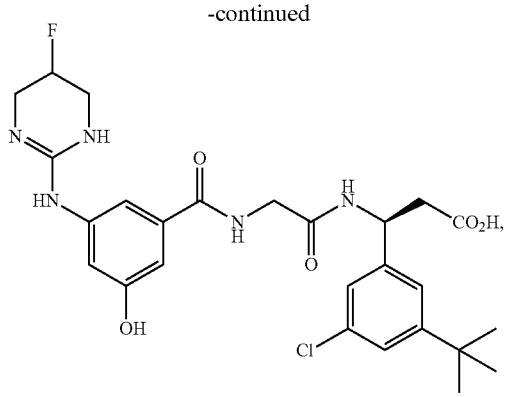
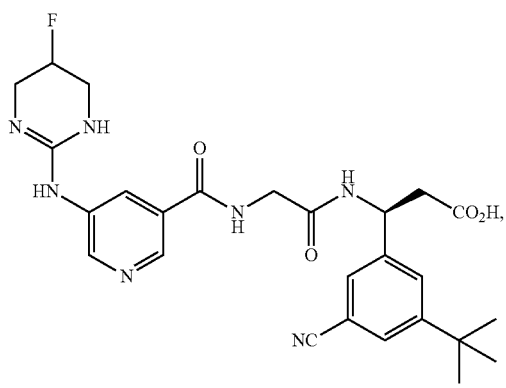
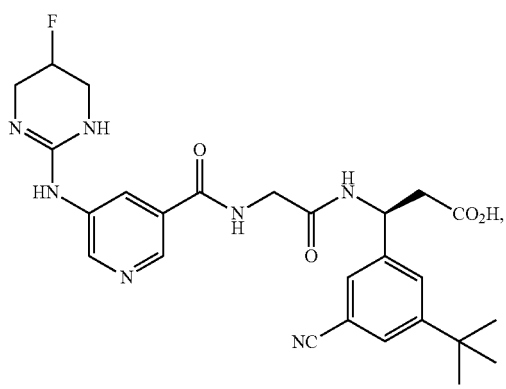
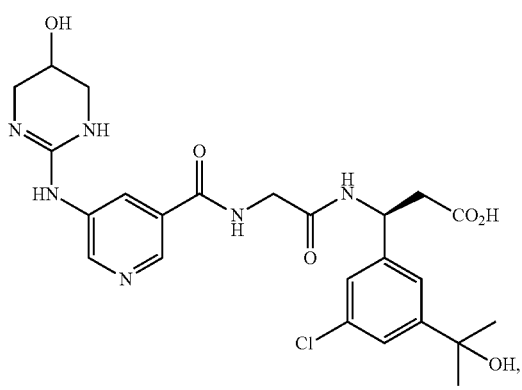
390
-continued
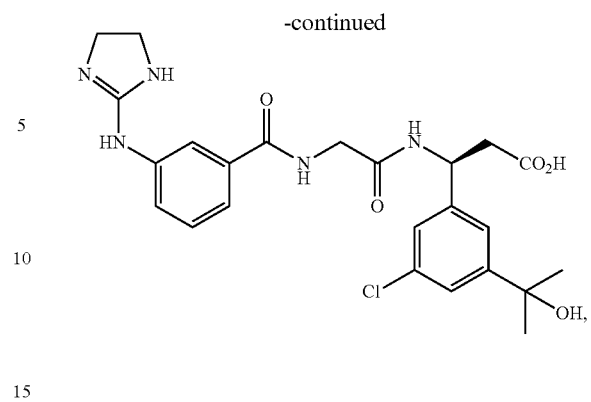
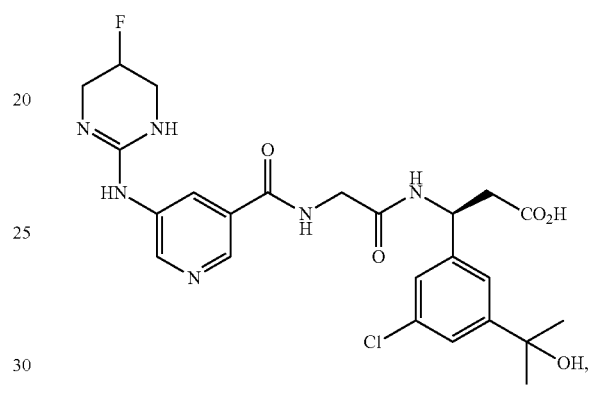
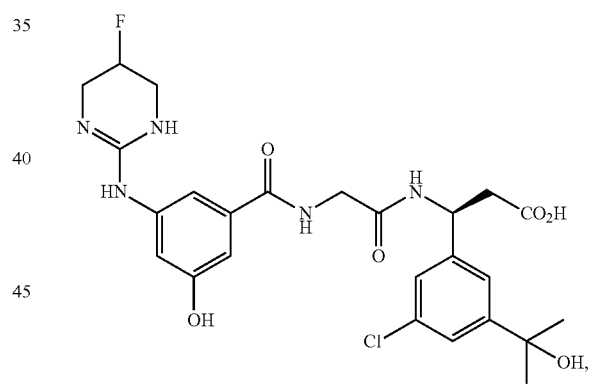
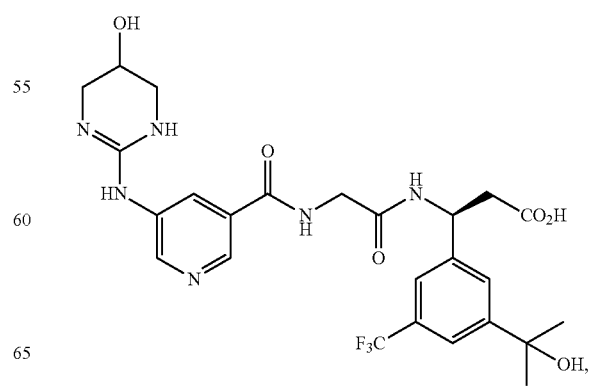

391
-continued
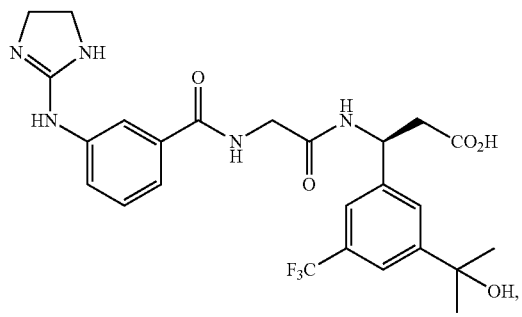
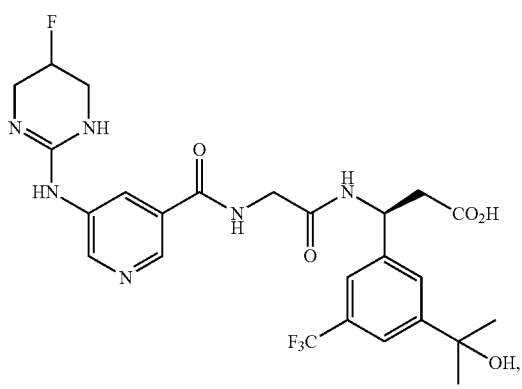
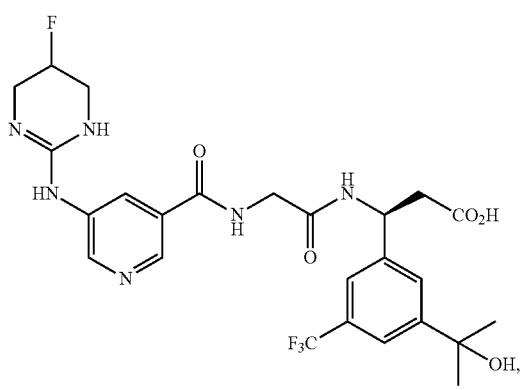
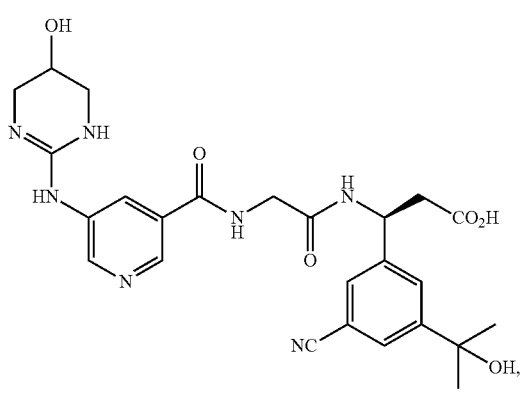
392
-continued
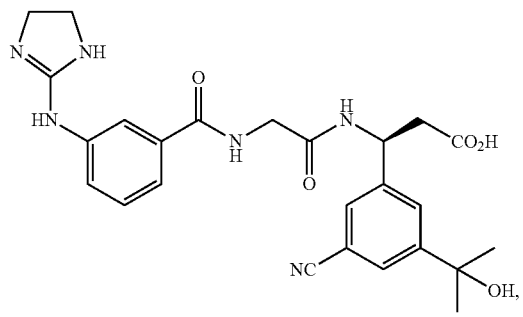
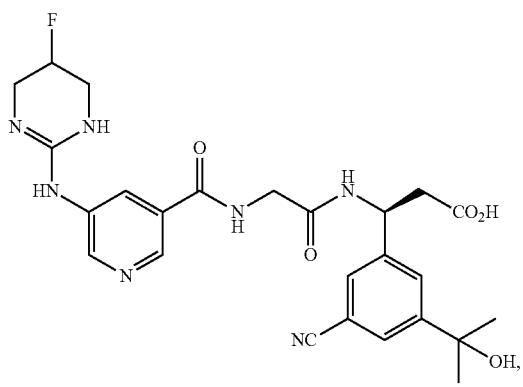
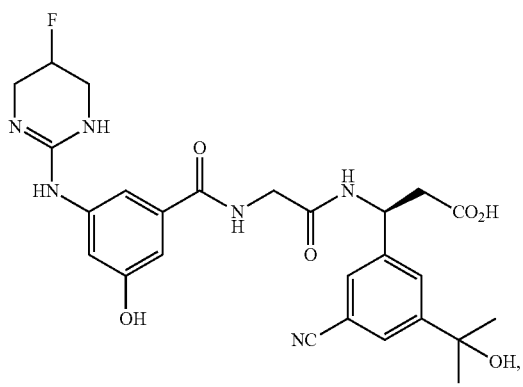
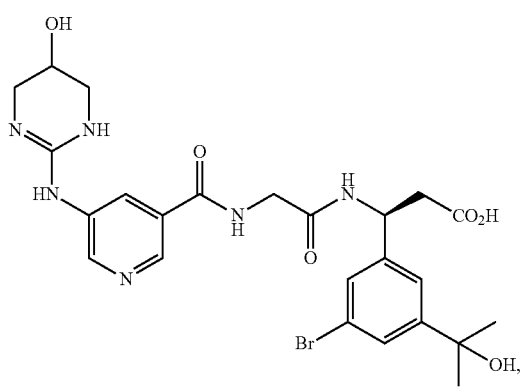

393
-continued
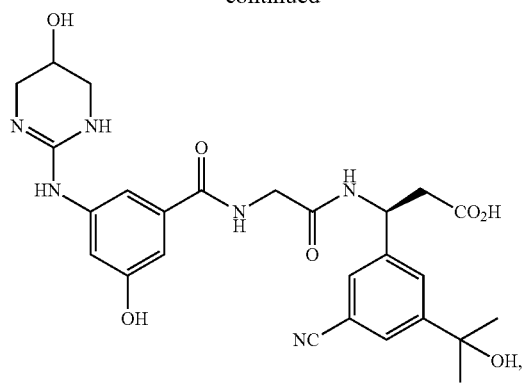
394
-continued
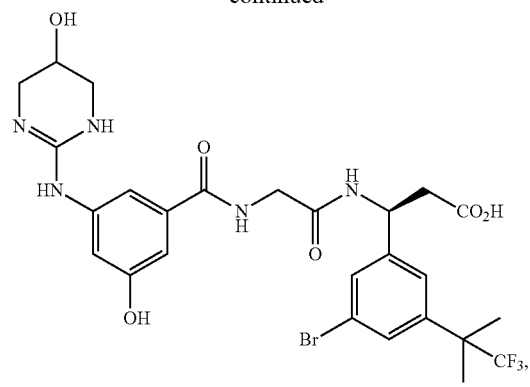
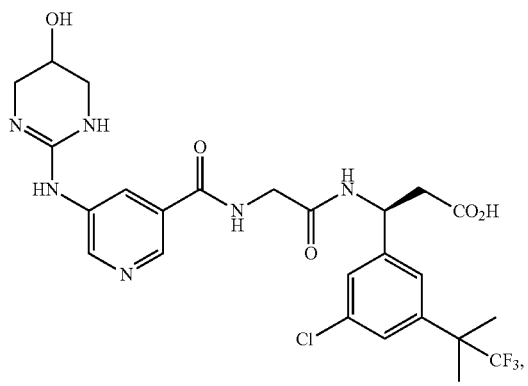
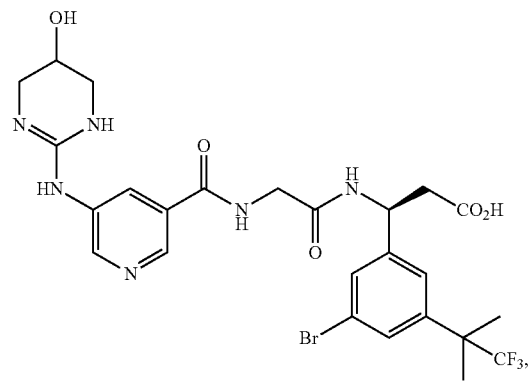
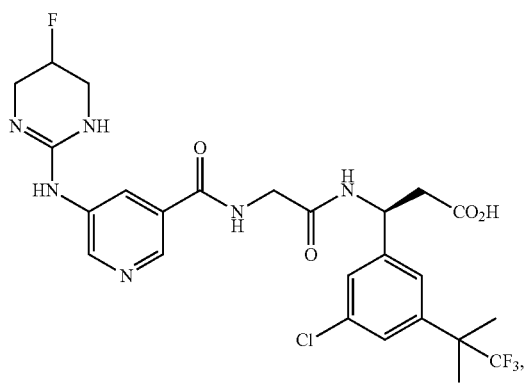
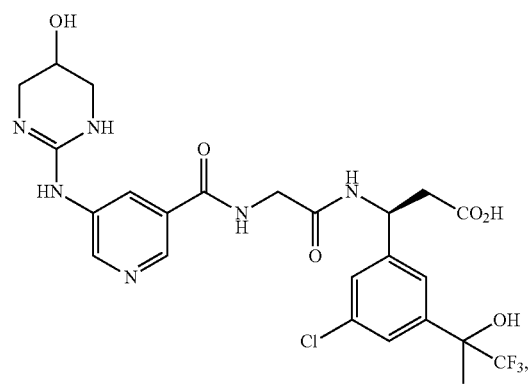

395
-continued
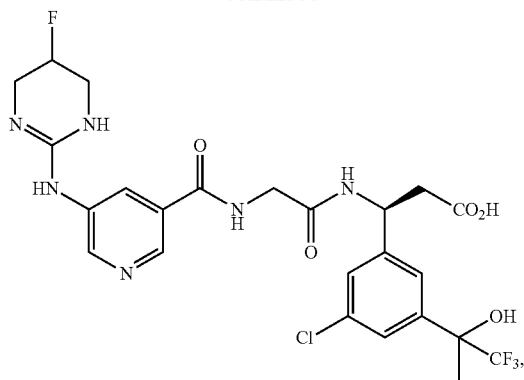
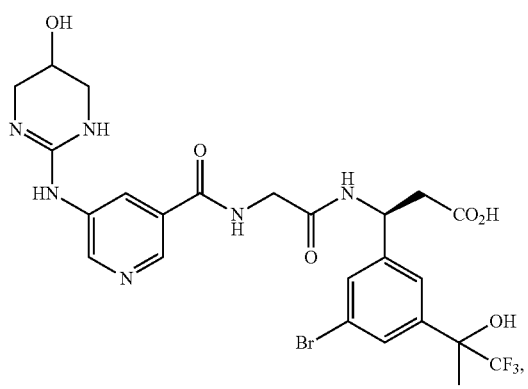
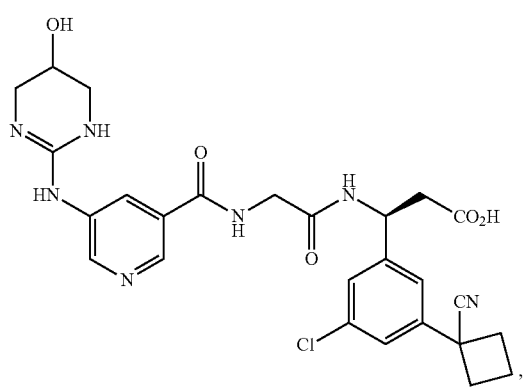
396
-continued
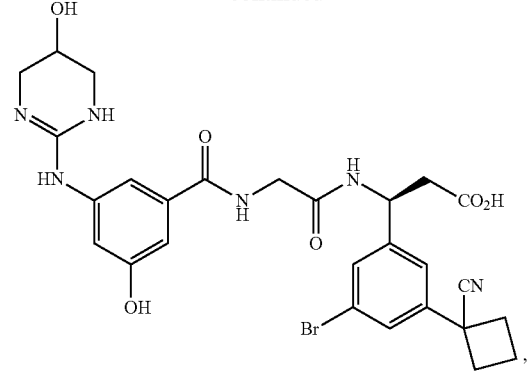
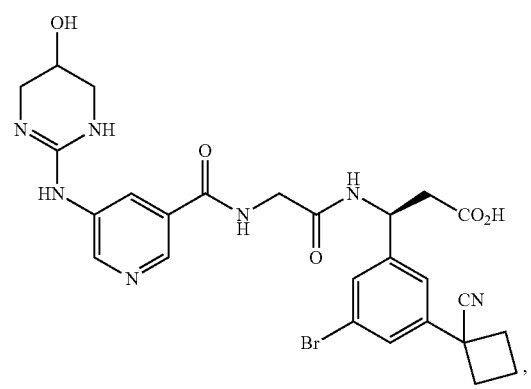
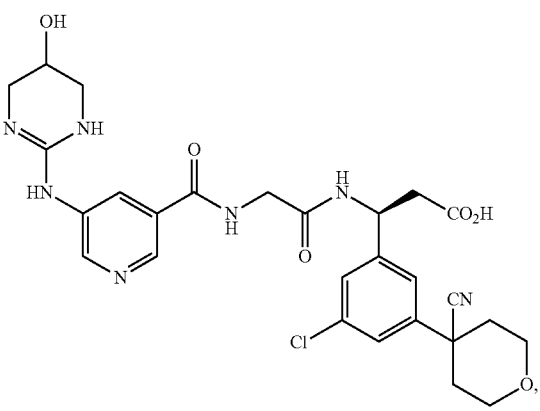

397
-continued
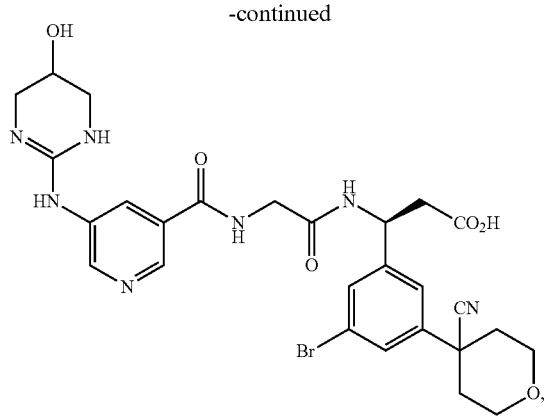
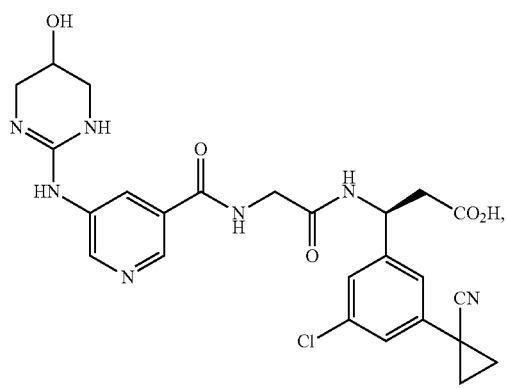
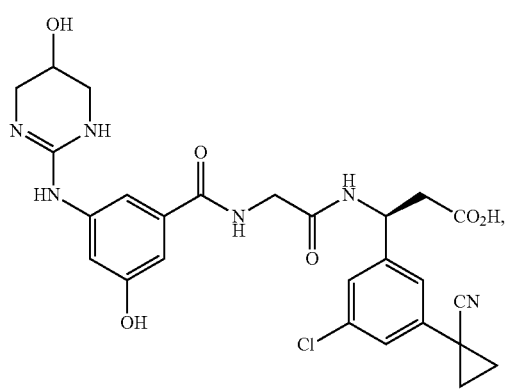
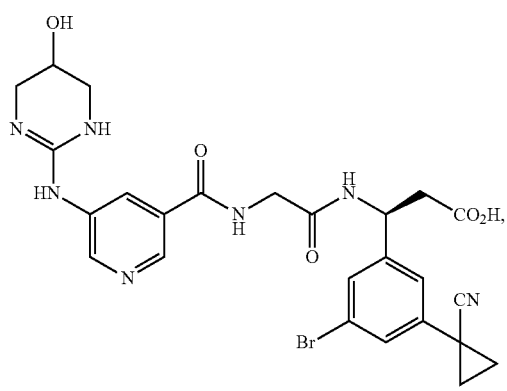
398
-continued
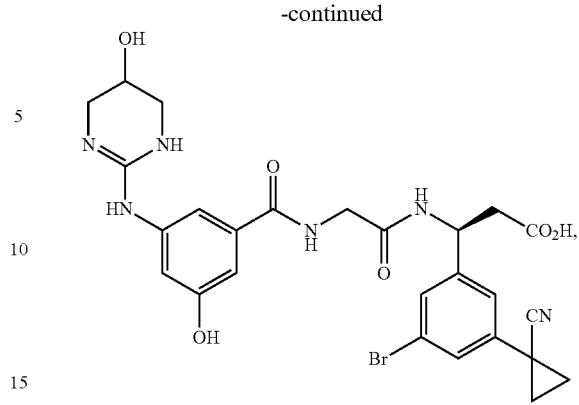
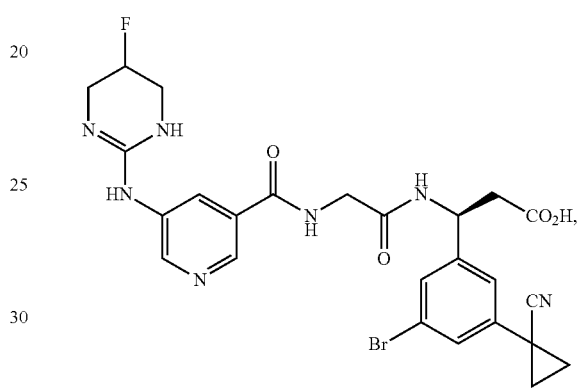
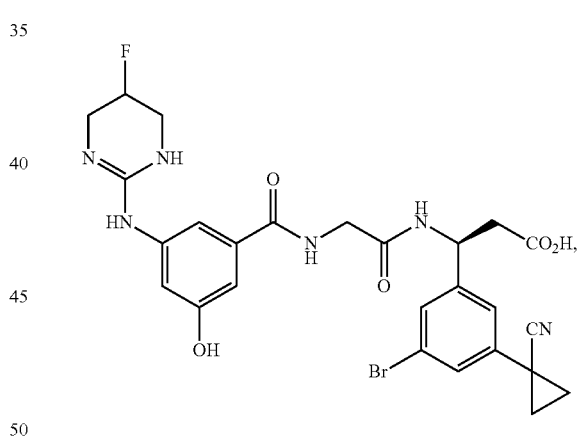
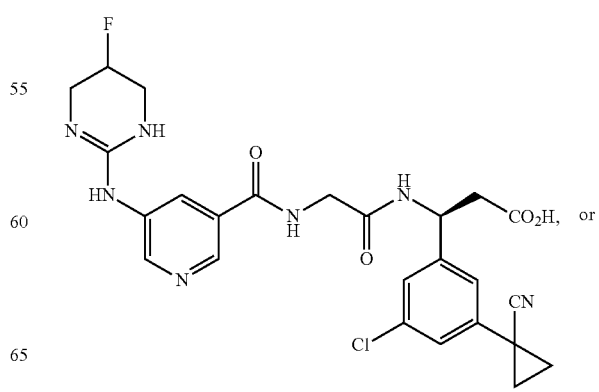 or 399
-continued
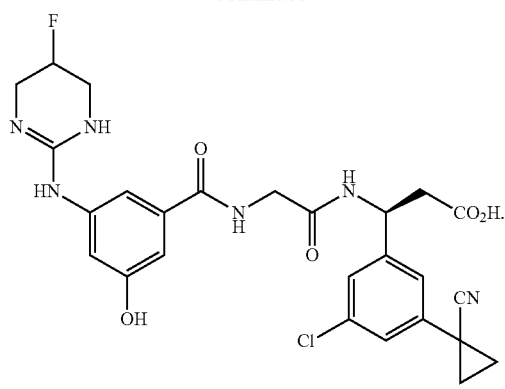
or a pharmaceutically acceptable salt or tautomer thereof.
17. The compound of claim 1, further defined as:
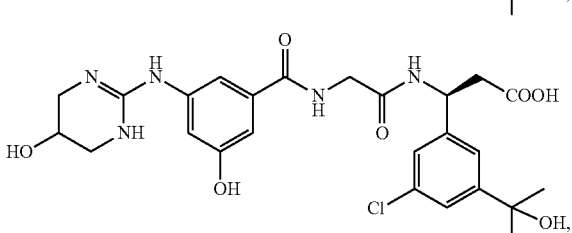
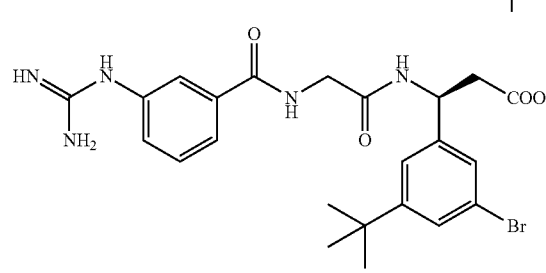
400
-continued
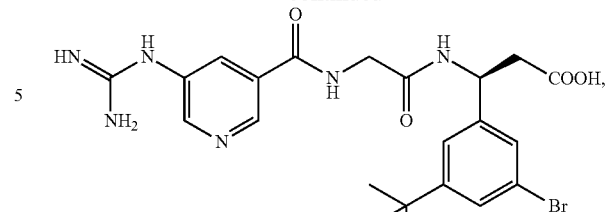
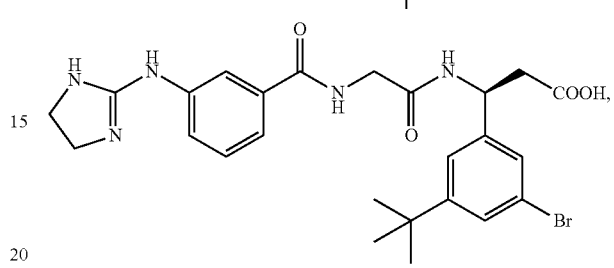
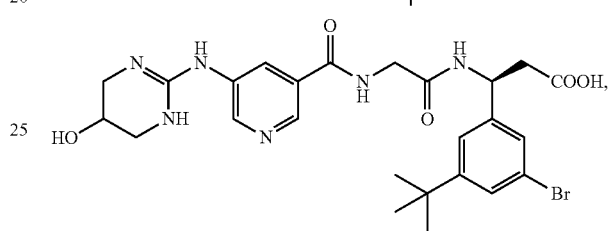
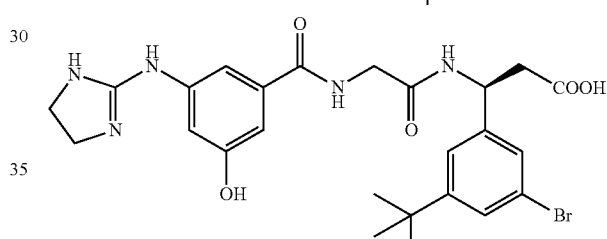
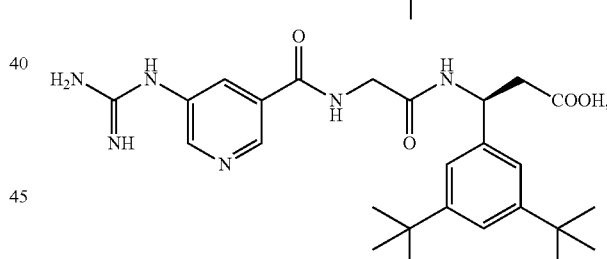
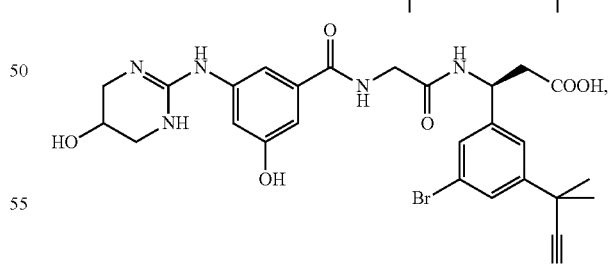
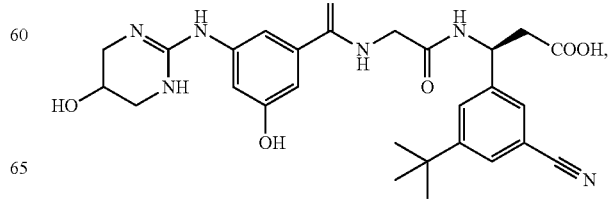

401
-continued
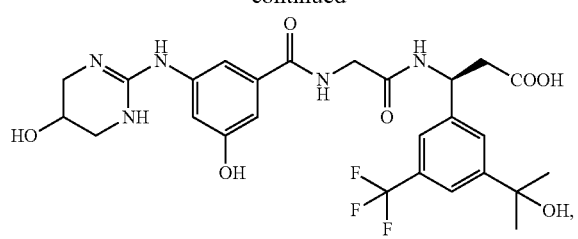
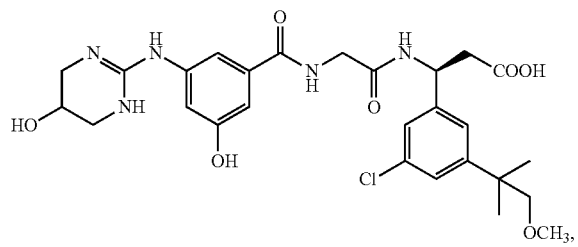
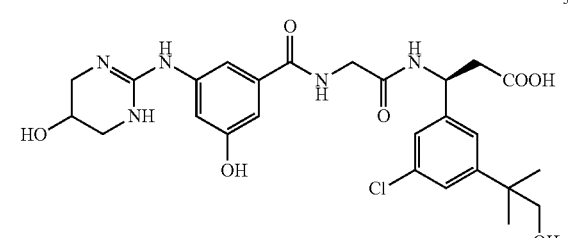
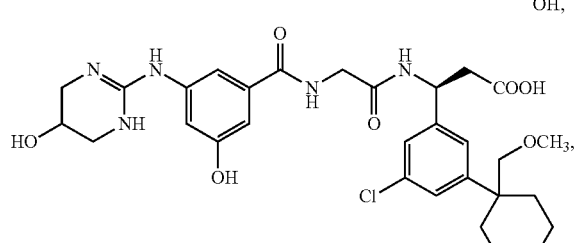
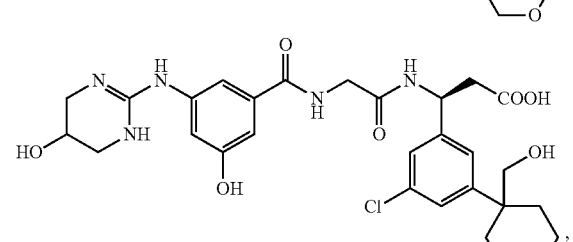
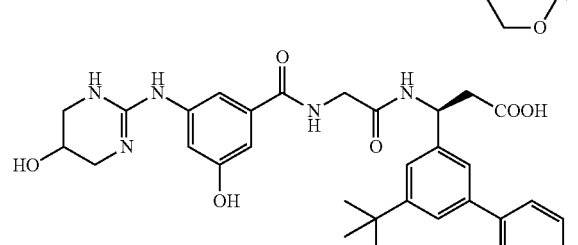
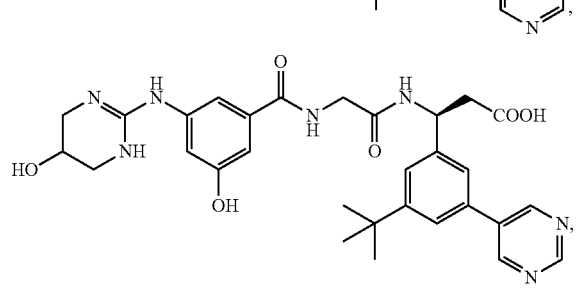
402
-continued
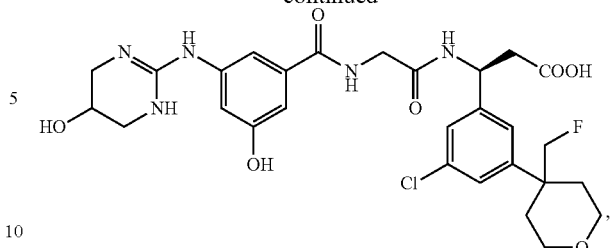
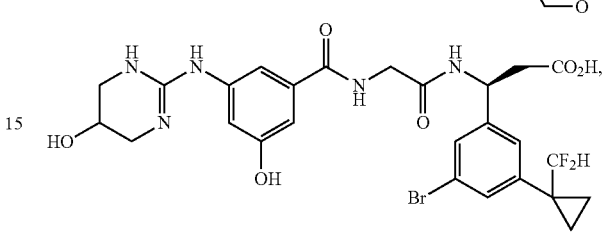
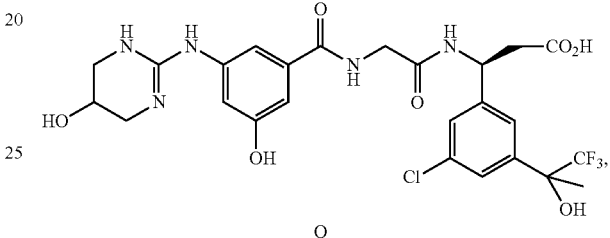
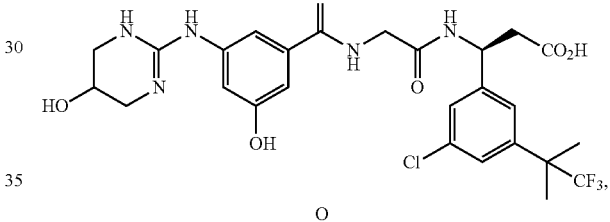
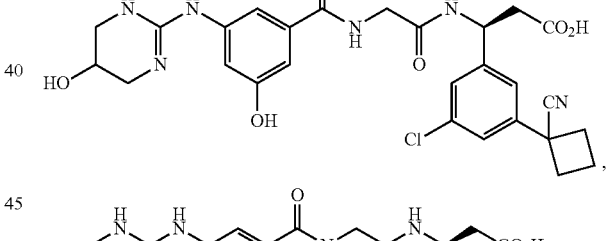
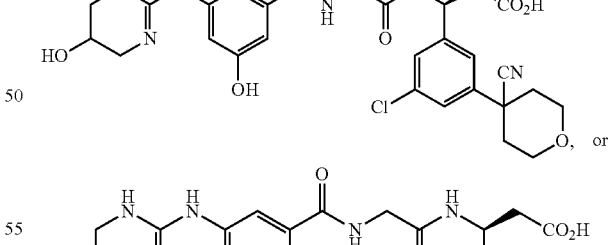
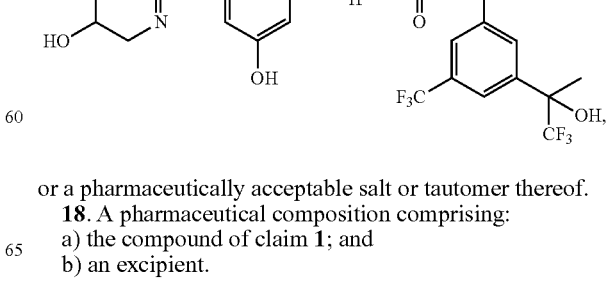
or a pharmaceutically acceptable salt or tautomer thereof.
18. A pharmaceutical composition comprising:
a) the compound of claim 1; and
b) an excipient.
* * * * *

UNITED STATES PATENT AND TRADEMARK OFFICE
CERTIFICATE OF CORRECTION

PATENT NO.        : 9,085,606 B2  Page 1 of 1
APPLICATION NO.   : 13/944599
DATED             : July 21, 2015
INVENTOR(S)       : Peter Ruminski and David Griggs It is certified that error appears in the above-identified patent and that said Letters Patent is hereby corrected as shown below:

In the claims

In claim 2, column 380, line 7, delete "—$(CH_2)_2$'" and insert -- —$(CH_2)_{n'}$ -- therefor.

Signed and Sealed this
Fifth Day of January, 2016

Michelle K. Lee
*Director of the United States Patent and Trademark Office*